US011827634B2

(12) United States Patent
Eccles et al.

(10) Patent No.: US 11,827,634 B2
(45) Date of Patent: *Nov. 28, 2023

(54) SMALL MOLECULE INHIBITORS OF NF-KB INDUCING KINASE

(71) Applicant: Janssen Pharmaceutica NV, Beerse (BE)

(72) Inventors: Wendy Eccles, Erdenheim, PA (US); Michael D. Hack, San Diego, CA (US); William M. Jones, Jenkintown, PA (US); Paul J. Krawczuk, Newtown, PA (US); Alec D. Lebsack, Ladera Ranch, CA (US); Daniel J. Pippel, San Diego, CA (US); Alexander R. Rovira, San Diego, CA (US); Ronald L. Wolin, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/549,057

(22) Filed: Dec. 13, 2021

(65) Prior Publication Data

US 2023/0080834 A1 Mar. 16, 2023

Related U.S. Application Data

(63) Continuation of application No. 16/887,889, filed on May 29, 2020, now Pat. No. 11,254,673.

(60) Provisional application No. 62/907,833, filed on Sep. 30, 2019, provisional application No. 62/855,144, filed on May 31, 2019.

(51) Int. Cl.
*C07D 471/04* (2006.01)
(52) U.S. Cl.
CPC .................. *C07D 471/04* (2013.01)
(58) Field of Classification Search
CPC .................................................. C07D 471/04
USPC .................................................. 514/264.11
See application file for complete search history.

(56) References Cited

U.S. PATENT DOCUMENTS

| | | | |
|---|---|---|---|
| 7,915,009 B2 | 3/2011 | Foxwell et al. | |
| 9,034,866 B2 | 5/2015 | Staben et al. | |
| 9,605,005 B2 | 3/2017 | Blaquiere et al. | |
| 11,254,673 B2 * | 2/2022 | Barbay | C07D 417/10 |
| 11,458,149 B1 | 10/2022 | Castro | |
| 11,643,434 B2 | 5/2023 | Saluturo et al. | |
| 2005/0009859 A1 | 1/2005 | Majid et al. | |
| 2021/0094976 A1 | 4/2021 | Li et al. | |
| 2022/0227749 A1 | 7/2022 | Bruno et al. | |

FOREIGN PATENT DOCUMENTS

| | | |
|---|---|---|
| CL | 202103165 | 9/2022 |
| CL | 202103166 | 9/2022 |
| CL | 202103190 | 9/2022 |
| CL | 202200787 | 10/2022 |
| EP | 3405196 B1 | 12/2019 |
| WO | WO 2006/053277 A2 | 5/2006 |
| WO | 2009/158011 A1 | 12/2009 |
| WO | 2010/042337 A1 | 4/2010 |
| WO | 2012/123522 A1 | 9/2012 |
| WO | 2013/120980 A1 | 8/2013 |
| WO | 2014/174021 A1 | 10/2014 |
| WO | 2015/025025 A1 | 2/2015 |
| WO | 2015/025026 A1 | 2/2015 |
| WO | 2015_044267 A1 | 4/2015 |
| WO | 2015/044269 A1 | 4/2015 |
| WO | 2016/062789 A1 | 4/2016 |
| WO | 2016/062790 A1 | 4/2016 |
| WO | 2016/062791 A1 | 4/2016 |
| WO | 2016/135163 A1 | 9/2016 |
| WO | 2017/125530 A1 | 7/2017 |
| WO | 2017/125534 A1 | 7/2017 |
| WO | 2018/002217 A1 | 1/2018 |
| WO | 2018/002219 A1 | 1/2018 |
| WO | 2018/037058 A1 | 3/2018 |
| WO | 2018/037059 A1 | 3/2018 |
| WO | 2016/062792 A1 | 4/2018 |
| WO | 2019/008011 A1 | 1/2019 |

OTHER PUBLICATIONS

Abu-Amer, Y., "NF-κB signaling and bone resorption", Osteoporos Int, 2013, pp. 2377-2386, vol. 24.
Al-Khawaldeh, et al., "An Alkynylpyrimidine-Based Covalent Inhibitor That Targets a Unique Cysteine in NF-κB-Inducing Kinase", J. Med. Chem., 2021, https://doi.org/10.1021/acs.jmedchem.0c01249.
Arbabi-Ghahroudi, M., "Camelid Single-Domain Antibodies: Historical Perspective and Future Outlook", Front. Immunol., 2017, 8 pages, vol. 8, Article 1589, doi: 10.3389/fimmu.2017.01589.
Aya et al., "NF-kB-inducing kinase controls lymphocyte and osteoclast activities in inflammatory arthritis", J. Clin. Invest., 2005, pp. 1848-1854, vol. 115, No. 7.
Berge, S.M. et al., "Pharmaceutical Salts", J. Pharm. Sci., 1977, pp. 1-19, vol. 66, No. 1.
Blaquiere et al., "Scaffold-Hopping Approach To Discover Potent, Selective, and Efficacious Inhibitors of NF-κB Inducing Kinase", J. Med. Chem., 2018, pp. 6801-6813, vol. 61.

(Continued)

*Primary Examiner* — Niloofar Rahmani
(74) *Attorney, Agent, or Firm* — Guodong Liu

(57) ABSTRACT

The present invention relates to compounds that inhibit NIK and pharmaceutical compositions comprising such compounds and methods of using the same. These compounds and pharmaceutical compositions are envisaged to be useful for preventing or treating diseases such as cancer (such as B-cell malignancies including leukemias, lymphomas and myeloma), inflammatory disorders, autoimmune disorders, immunodermatologic disorders such as palmoplantar pustulosis and hidradenitis suppurativa, and metabolic disorders such as obesity and diabetes.

31 Claims, No Drawings

(56) References Cited

OTHER PUBLICATIONS

Boumpas et al., "A Short Course of BG9588 (Anti-CD40 Ligand Antibody) Improves Serologic Activity and Decreases Hematuria in Patients With Proliferative Lupus Glomerulonephritis", Arthritis & Rheumatism, 2003, pp. 719-727, vol. 48, No. 3.
Brightbill et al., "Conditional Deletion of NF-kB-Inducing Kinase (NIK) in Adult Mice Disrupts Mature B Cell Survival and Activation", The Journal of Immunology, 2015, pp. 953-964, vol. 195, No. 3.
Brightbill et al., "NF-κB inducing kinase is a therapeutic target for systemic lupus erythematosus", Nature Communications, 2018, 14 pages, 9:179, DOI: 10.1038/s41467-017-02672-0.
Brue et al., "Mutations in NFKB2 and potential genetic heterogeneity in patients with DAVID syndrome, having variable endocrine and immune deficiencies", BMC Medical Genetics, 2014, 7 pages, 15:139, DOI 10.1186/s12881-014-0139-9.
Castanedo et al., "Structure-Based Design of Tricyclic NF-κB Inducing Kinase (NIK) Inhibitors That Have High Selectivity over Phosphoinositide-3-kinase (PI3K)", J. Med. Chem., 2017, pp. 627-640, vol. 60.
Cheng et al., "Identification of new NIK inhibitors by discriminatory analysis-based molecular docking and biological evaluation", Arch Pharm Chem Life Sci., 2019, 9 pages, e1800374.
Cheng, et al., "Pharmacological inhibition Of NF-kB-inducing Kinase (NIK) With Small Molecules for the treatment of human disease", Royal Society Of Chemistry, 2021, pp. 552-565, vol. 12.
Elgueta et al., "Molecular mechanism and function of CD40/CD40L engagement in the immune system", Immunological Reviews, 2009, pp. 152-172, vol. 229, No. 1.
Farhat et al., "Immunologic reconstitution following hematopoietic stem cell transplantation despite lymph node paucity in NF-kB-inducing kinase deficiency", J Allergy Clin Immunol, 2019, pp. 1241-1243, vol. 143, No. 3.
Feng, et al., "Structure Based Design of Potent Selective Inhibitors of Protein Kinase D1 (PKD1)", ACS Med. Chem. Lett., 2019, pp. 1260-1265, vol. 10.
González-Murillo et al., "The NFKB Inducing Kinase Modulates Hematopoiesis During Stress", Stem Cells, 2015, pp. 2825-2837, vol. 33.
Groom et al., "Association of BAFF/BLyS overexpression and altered B cell differentiation with Sjögren's syndrome", Journal of Clinical Investigation, 2002, pp. 59-68, vol. 109, No. 1, DOI:10.1172/JCI200214121.
Halkowycz et al., "Biochemical and Cellular Profile of NIK Inhibitors with Long Residence Times", SLAS Discovery, 2021, pp. 676-683, vol. 26, No. 5.
Häcker et al., "NIK Prevents the Development of Hypereosinophilic Syndrome-like Disease in Mice Independent of IKKα Activation", The Journal of Immunology, 2012, pp. 4602-4610, vol. 188.
International Search Report and Written Opinion for International application PCT/EP2020/065024 dated Jul. 23, 2020.
Jie et al., "NIK signaling axis regulates dendritic cell function in intestinal immunity and homeostasis", Nature Immunology, 2018, pp. 1224-1235, vol. 19.
Jin et al., "Regulation of Th17 cell differentiation and EAE induction by MAP3K NIK", Blood, 2009, pp. 6603-6610, vol. 113, No. 26.
Kajiura et al., "NF-kB-Inducing Kinase Establishes Self-Tolerance in a Thymic Stroma-Dependent Manner", The Journal of Immunology, 2004, pp. 2067-2075, vol. 172.
Keung, W. "Discovery of NF-kappa-B-Inducing Kinase (NIK) Inhibitors", Drug Discovery Chemistry Meeting, Inflammation Inhibitors-Small Molecule Approaches for Oral-Based Therapeutics Section, Apr. 25-25, 2017, San Diego, CA, oral presentation, abstract and notes provided.
Kinoshita et al., "Essential Role of IkB Kinase α in Thymic Organogenesis Required for the Establishment of Self-Tolerance", J Immunol, 2006, pp. 3995-4002, vol. 176.
Komiyama et al., "Histopathological and immunohistological analyses in IgA deficient lymphoplasia (aly/aly) mouse", Journal of Oral Science, 2001, pp. 91-96, vol. 43, No. 2.
Krumbholz et al., "BAFF is produced by astrocytes and up-regulated in multiple sclerosis lesions and primary central nervous system lymphoma", Journal of Experimental Medicine, 2005, pp. 195-200, vol. 201, No. 2.
Kwok, L., "Discovery of Novel Inhibitors of NF-kB Inducing Kinase (NIK) from an FBDD approach", 253rd American Chemical Society (ACS) National Meeting & Exposition, Apr. 2-6, 2017, MEDI-116, San Francisco, CA, poster presentation, abstract and notes provided.
Lee et al., "Autosomal-dominant B-cell deficiency with alopecia due to a mutation in NFKB2 that results in nonprocessable p100", Blood, 2014, pp. 2964-2972, vol. 124, No. 19.
Li et al., "Discovery of a Potent and Selective NF-κB-Inducing Kinase (NIK) Inhibitor That Has Anti-inflammatory Effects in Vitro and in Vivo", J. Med. Chem., 2020, pp. 4388-4407, vol. 63.
Li et al., "Inhibiting NF-kB-inducing kinase (NIK): Discovery, structure-based design, synthesis, structure-activity relationship, and co-crystal structures", Bioorganic & Medicinal Chemistry Letters, 2013, pp. 1238-1244, vol. 23.
Lindsley et al., "Combined Immune Deficiency in a Patient with a Novel NFKB2 Mutation", J Clin Immunol, 2014, pp. 910-915, vol. 34, No. 8, doi:10.1007/s10875-014-0095-3.
Liu et al., "Inhibition of Pemphigus Vulgaris by Targeting of the CD40-CD154 Co-Stimulatory Pathway: A Step Toward Antigen-Specific Therapy?", Journal of Investigative Dermatology, 2006, pp. 11-13, vol. 126, No. 1.
Liu et al., "Novel NFKB2 Mutation in Early-Onset CVID", J Clin Immunol, 2014, pp. 686-690, vol. 34.
Maubach et al., "NF-kappaB-inducing kinase in cancer", BBA—Reviews on Cancer, 2019, pp. 40-49, vol. 1871.
Miyawaki et al., "A new mutation, aly, that induces a generalized lack of lymph nodes accompanied by immunodeficiency in mice", Eur. J. Immunol., 1994, pp. 429-434, vol. 24.
Mortier et al., "NF-kB inducing kinase (NIK) inhibitors: Identification of new scaffolds using virtual screening", Bioorganic & Medicinal Chemistry Letters, 2010, pp. 4515-4520, vol. 20.
Mouri et al., "NF-kB-Inducing Kinase in Thymic Stroma Establishes Central Tolerance by Orchestrating Cross-Talk with Not Only Thymocytes but Also Dendritic Cells", The Journal of Immunology, 2014, pp. 4356-4367, vol. 193.
Murray et al., "NF-κB-inducing kinase plays an essential T cell-intrinsic role in graft-versus-host disease and lethal autoimmunity in mice", The Journal of Clinical Investigation, 2011, pp. 4775-4786, vol. 121, No. 12.
Navarra et al., "Efficacy and safety of belimumab in patients with active systemic lupus erythematosus: a randomised, placebo-controlled, phase 3 trial", The Lancet, 2011, pp. 721-731, vol. 377.
Noma et al., "Differential dependence on nuclear factor-kB-inducing kinase among natural killer T-cell subsets in their development", Immunology, 2015, pp. 89-99, 146.
Paulekuhn et al., "Trends in Active Pharmaceutical Ingredient Salt Selection based on Analysis of the Orange Book Database", J. Med. Chem., 2007, pp. 6665-6672, vol. 50.
Rowe et al., "A Cell-Intrinsic Requirement for NF-kB-Inducing Kinase in CD4 and CD8 T Cell Memory", J Immunol, 2013, pp. 3663-3672, vol. 191.
Shen et al., "Importance of Incorporating Protein Flexibility in Molecule Modeling: A Theoretical Study on Type I 1/2 NIK Inhibitors", Frontiers in Pharmacology, 2019, vol. 10, Article 345, doi: 10.3389/fphar.2019.00345.
Shen et al., "Thymic NF-κB-inducing kinase regulates CD4+ T cell-elicited liver injury and fibrosis in mice", Journal of Hepatology, 2017, pp. 100-109, vol. 67.
Shinkura et al., "Alymphoplasia is caused by a point mutation in the mouse gene encoding Nf-κb-inducing kinase", Nature Genetics, 1999, pp. 74-77, vol. 22, No. 1.
Sidiropoulos et al., "Lessons learned from anti-CD40L treatment in systemic lupus erythematosus patients", Lupus, 2004, pp. 391-397, vol. 13, No. 5.

(56) References Cited

OTHER PUBLICATIONS

Song et al., "The discovery of quinoline derivatives, as NF-κB inducing kinase (NIK) inhibitors with anti-inflammatory effects in vitro, low toxicities against T cell growth", Bioorg. Med. Chem., 2021, vol. 29, https://doi.org/10.1016/j.bmc.2020.115856.
Soysa et al., "The Pivotal Role of the Alternative NF-kB Pathway in Maintenance of Basal Bone Homeostasis and Osteoclastogenesis", Journal of Bone and Mineral Research, 2010, pp. 809-818, vol. 25, No. 4.
Sun, Shao-Cong, "Non-canonical NF-κB signaling pathway", Cell Research, 2011, pp. 71-85, vol. 21.
Sun, Shao-Cong, "The non-canonical NF-κ B pathway in immunity and inflammation", Nat Rev Immunol., 2017, pp. 545-558, vol. 17, No. 9.
Takakura et al., "A novel inhibitor of NF-κB-inducing kinase prevents bone loss by inhibiting osteoclastic bone resorption in ovariectomized mice", Bone, 2020, vol. 135, https://doi.org/10.1016/j.bone.2020.115316.
Tamura et al., "Impaired function of dendritic cells in alymphoplasia (aly/aly) mice for expansion of CD25+CD4+ regulatory T cells", Autoimmunity, 2006, pp. 445-453, vol. 39, No. 6.
Tan et al., "Activation of microglial cells by the CD40 pathway: relevance to multiple sclerosis", Journal of Neuroimmunology, 1999, pp. 77-85, vol. 97.
Thu et al., "NF-κB inducing kinase: a key regulator in the immune system and in cancer", Cytokine Growth Factor Rev., 2010, pp. 213-226, vol. 21, No. 4, doi:10.1016/j.cytogfr.2010.06.002.
Valiño-Rivas et al., "NIK as a Druggable Mediator of Tissue Injury", Trends in Molecular Medicine, 2019, pp. 341-360, vol. 25, No. 4.
Willmann et al., "Biallelic loss-of-function mutation in NIK causes a primary immunodeficiency with multifaceted aberrant lymphoid immunity", Nature Communications, 2014, 13 pages, 5:5360, DOI: 10.1038/ncomms6360.
Yamada et al., "Abnormal Immune Function of Hemopoietic Cells from Alymphoplasia (aly) Mice, a Natural Strain with Mutant NF-kB-Inducing Kinase", The Journal of Immunology, 2000, pp. 804-812, vol. 165.
Yang et al., "NIK Stabilization in Osteoclasts Results in Osteoporosis and Enhanced Inflammatory Osteolysis", PLoS One, 2010, 9 pages, vol. 5, No. 11, e15383, doi:10.1371/journal.pone.0015383.
Ye et al., "Discovery of novel indoleaminopyrimidine NIK inhibitors based on molecular docking-based support vector regression (SVR) model", Chemical Physics Letters, 2019, pp. 38-45, vol. 718.
Yin et al., "Defective Lymphotoxin-β Receptor-Induced NF-kB Transcriptional Activity in NIK-Deficient Mice", Science, 2001, pp. 2162-2165, vol. 291.
Zarei et al., "Manipulation of the Alternative NF-kB Pathway in Mice Has Sexually Dimorphic Effects on Bone", JBMR Plus, 2019, pp. 14-22, vol. 3, No. 1.
Zhu et al., "Identification of N-Phenyl-7H-pyrrolo[2,3-d]pyrimidin-4-amine Derivatives as Novel, Potent, and Selective NF-κB Inducing Kinase (NIK) Inhibitors for the Treatment of Psoriasis", J. Med. Chem., 2020, pp. 6748-6773, vol. 63.

\* cited by examiner

SMALL MOLECULE INHIBITORS OF NF-κB INDUCING KINASE

This application is a continuation of U.S. Ser. No. 16/887,889, filed on May 29, 2020, pending, which claims the benefit of U.S. Provisional Application No. 62/855,144, filed on May 31, 2019, and U.S. Provisional Application No. 62/907,833, filed on Sep. 30, 2019.

FIELD OF THE INVENTION

NF-κB-inducing kinase (referred to as NIK, also known as MAP3K14) is a regulator and driver of the non-canonical NIK cascade, and thus represents an attractive target for therapeutic intervention. The present invention relates to compounds that inhibit NIK and pharmaceutical compositions comprising such compounds. These compounds and pharmaceutical compositions are envisaged to be useful for preventing or treating diseases such as cancer (such as B-cell malignancies including leukemias, lymphomas and myeloma), inflammatory disorders, autoimmune disorders, immunodermatologic disorders such as palmoplantar pustulosis and hidradenitis suppurativa, and metabolic disorders such as obesity and diabetes. The present invention also relates to methods of preventing or treating such diseases.

BACKGROUND OF THE INVENTION

NIK is a serine/threonine kinase transcription factor propitiating the expression of various genes involved in immune response disorders, cell proliferation disorders, adhesion, apoptosis, and carcinogenesis. Because of this immune system regulatory role, inhibition of NIK blocks several downstream pathways that produce inflammatory molecules. Clinical validation with biologics has confirmed a key role for several NIK dependent pathways in autoimmune diseases. See, e.g., S. V. Navarra, et al., *The Lancet*, 2011; 377(9767):721-31. NIK-dependent transcriptional activation is a tightly controlled signaling pathway, through sequential events including phosphorylation and protein degradation. In a NIK activation pathway, known as a non-canonical pathway, activation is accomplished by phosphorylating the catalytic complex subunit IKKα, leading to the partial proteolysis of the gene product p100, liberating DNA-binding protein p52 which then heterodimerizes with another DNA-binding protein RelB, translocates to the nucleus and mediates gene expression. The non-canonical pathway is activated by ligands such as CD40 ligands, B-cell activating factor (BAFF), lymphotoxin β receptor ligands, TNF-related weak inducer of apoptosis (TWEAK) cytokine, and receptor activator of nuclear factor kappa-B ligand (RANKL), also known as tumor necrosis factor ligand superfamily member 11 (TNFSF11). NIK has been shown to be required for activation of the pathway by these ligands (S.-C. Sun, *Nat Rev Immunol.* 2017, 17(9), 545-558). Because of its role, NIK expression is tightly regulated. Under normal non-stimulated conditions NIK protein levels are very low. This is due to its interaction with baculoviral-IAP-repeat-containing-3 (BIRC3, also known as CIAP2) and a range of TNF receptor associated factors (TRAF2 and TRAF3), which are ubiquitin ligases and result in degradation of NIK. It is believed that when the non-canonical pathway is stimulated by ligands under pathological/abnormal conditions, the activated receptors now compete for TRAFs, dissociating the TRAF-BIRC3-NIK complexes and thereby increasing the levels of NIK (For a more detailed analysis of this background, see e.g., S.-C. Sun (cited above) and Thu and Richmond, *Cytokine Growth F. R.* 2010, 21, 213-226). As indicated above, NIK plays a role propitiating immune response disorders, cell proliferation disorders, adhesion, apoptosis, and carcinogenesis, so a NIK level increase is undesirable, and one way to mitigate or eliminate the adverse effect associated with such increase is NIK inhibition.

BAFF/BAFF-R is a clinically validated therapeutic target whose inhibition is deemed beneficial for systemic lupus erythematosus (SLE) treatment. Belimumab (anti-BAFF antibody) has been approved to treat serum positive SLE patients (S. V. Navarra, et al., *The Lancet*, 2011; 377(9767): 721-31). CD40L/CD40 pathway plays a key role in T-dependent B cell activation, dendritic cell maturation and tissue inflammation/immunity (R. Elgueta, et al., *Immunol. Rev.* 2009; 229(1):152-72). Anti-CD40L antibody has demonstrated promising efficacy in phase 2 clinical studies in SLE patients (P. I. Sidiropoulos and D. T. Boumpas, *Lupus* 2004 May; 13(5):391-7). Mice lacking NIK (R. Shinkura, et al., *Nature Genetics* 1999; 22(1):74-7; H. D. Brightbill, et al., *J Immunol.* 2015; 195(3):953-64) or conditional knock-out of NIK (H. D. Brightbill, et al., *J Immunol.* 2015; 195(3):953-64) or human patients carrying NIK gene mutations (K. L. Willmann, et al., *Nature Comm.* 2014; 5:5360) showed deficiency in NIK non-canonical activation pathways such as BAFF and CD40L pathway, reduced B lymphocytes in peripheral blood, and lymphoid organs and lower T cell dependent antibody responses supporting NIK as a therapeutic target for SLE.

NIK has been characterized as being "important in the immune and bone-destructive components of inflammatory arthritis and represents a possible therapeutic target for these diseases." K. Aya, et al. (*J. Clin. Invest.* 2005, 115, 1848-1854). Mice lacking functional NIK have no peripheral lymph nodes, defective B and T cells, and impaired receptor activator of NIK ligand-stimulated osteoclastogenesis. K. Aya, et al. (*J. Clin. Invest.* 2005, 115, 1848-1854) investigated the role of NIK in murine models of inflammatory arthritis using NIK–/– mice. Reportedly, the serum transfer arthritis model was initiated by preformed antibodies and required only intact neutrophil and complement systems in recipients. While NIK–/– mice had inflammation equivalent to that of NIK+/+ controls, Ada, et al., (cited above) showed significantly less periarticular osteoclastogenesis and less bone erosion. In contrast, NIK–/– mice were completely resistant to antigen-induced arthritis (AIA), which requires intact antigen presentation and lymphocyte function but not lymph nodes. Additionally, transfer of NIK+/+ splenocytes or T cells to Rag2–/– mice conferred susceptibility to AIA, while transfer of NIK–/– cells did not. NIK–/– mice were also resistant to a genetic, spontaneous form of arthritis, generated in mice expressing both the KRN T cell receptor and H-2g7. Transgenic mice were used with OC-lineage expression of NIK lacking its TRAF3 binding domain (NT3), to demonstrate that constitutive activation of NIK drives enhanced osteoclastogenesis and bone resorption, both in basal conditions and in response to inflammatory stimuli. See Aya, et al., cited above. Furthermore, it has been concluded that "[c]onstitutive activation of NIK drives enhanced osteoclastogenesis and bone resorption, both in basal conditions and in response to inflammatory stimuli." (C. Yang, et al., *PLoS ONE* 2010, 5(11): e15383, doi: 10.1371/journal.pone.0015383).

It has also been hypothesized that manipulating levels of NIK in T cells may have therapeutic value. Decreasing NIK activity in T cells might significantly ameliorate autoimmune responses and alloresponses, like GvHD (Graft-Versus-Host Disease) and transplant rejection, without crippling the immune system as severely as do inhibitors of another NIK activation pathway referred to as canonical pathway (S. E. Murray, et al., "NF-κB-inducing kinase plays an essential T cell-intrinsic role in graft-versus-host disease and lethal autoimmunity in mice" *J. Clin. Invest.* 2011; 121(12): 4775-86) (providing data that is characterized as "suggest[ing] that [NIK] tight regulation is critical for avoiding autoimmunity."). (Canonical NIK activation pathway relies on inducible degradation of IκB kinases, particularly IκBα, leading to nuclear translocation of various NF-κB complexes, predominantly the p50/RelA dimer. The degradation of IκBα is mediated through its phosphorylation by the IκB kinase (IKK), a trimeric complex composed of two catalytic subunits, IKKα and IKKβ, and a regulatory subunit, IKKγ (also named NF-κB essential modulator or NEMO). In a non-canonical NIK activation pathway, the RelB/p52 NF-κB complex is activated using a mechanism that relies on the inducible processing of p100 instead of degradation of IκBα. See, e.g., S.-C. Sun, *Cell Res.* 2011 January; 21(1): 71-85).

NIK is also a promising therapeutic target for other BAFF, CD40L or lymphotoxin β receptor ligands driven autoimmune disorders such as Sjogren's syndrome (J. Groom, et al., *J. Clin. Invest.* 2002; 109(1):59-68); proliferative lupus glomerulonephritis (D. T. Boumpas, et al., *Arthritis & Rheumatism* 2003; 48(3):719-27): multiple sclerosis (J. Tan, et al., *J. Neuroimmunol,* 1999; 97 (1-2):77-85), J. Krumbholz, et al., *J. Exp. Med.* 2005; 201(2):195-200); and pemphigus vulgaris (Z. Liu, et al., *J. Invest. Dermatol.* 2006; 126(1):11-3).

BRIEF SUMMARY OF THE INVENTION

Embodiments of this invention include compounds of Formula (I), and pharmaceutically acceptable salts thereof

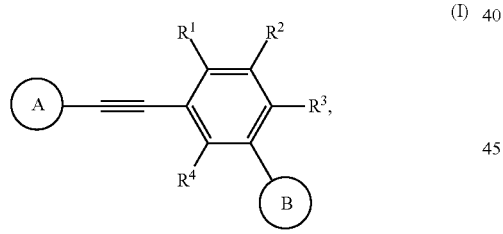

wherein
R¹ is H or —CH₃;
R² is H or —CH₃;
R³ is H, —C₁-C₅alkyl, —OCH₃, or —O—C₁-C₃haloalkyl;
R⁴ is H or —CH₃;
moiety

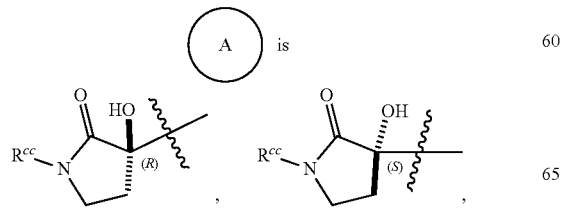

is

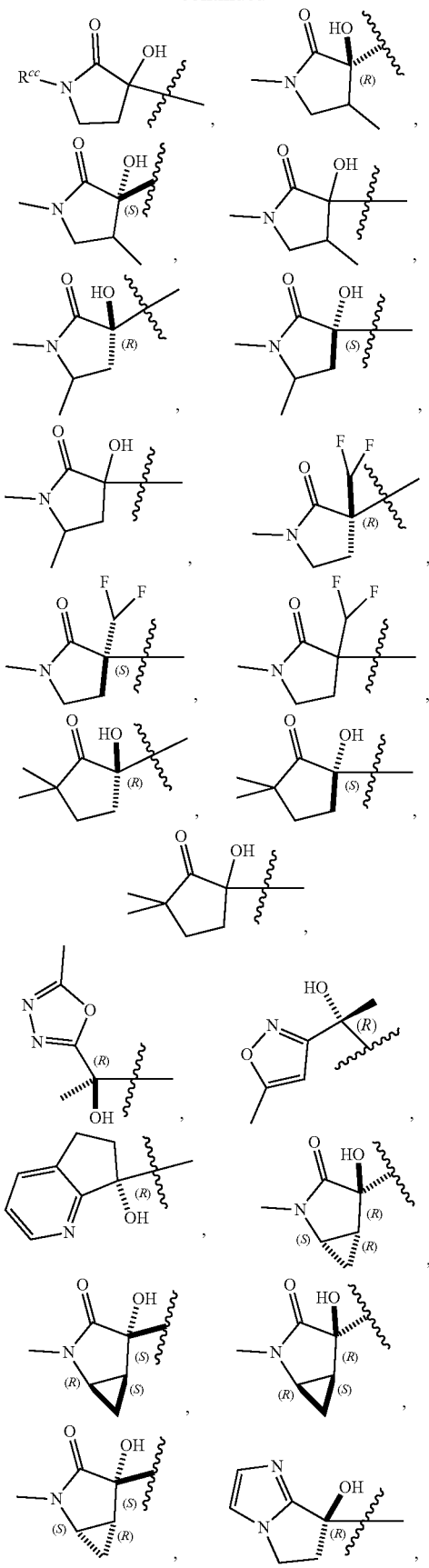

-continued
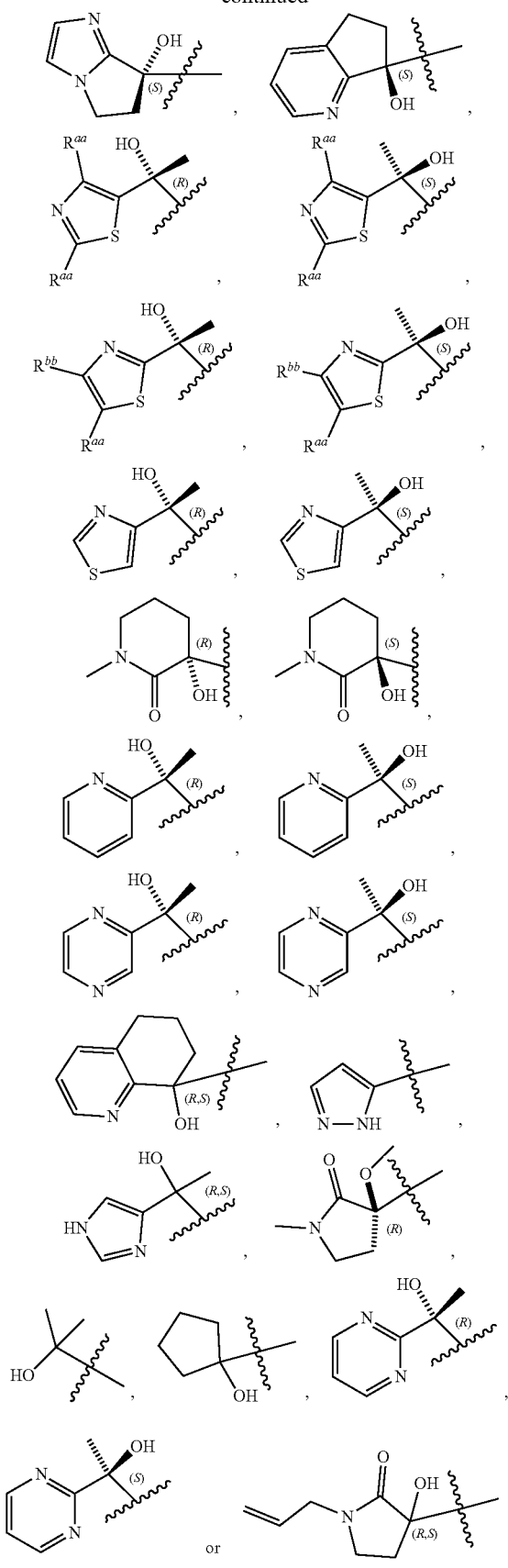
$R^{aa}$ is H or —$CH_3$;
$R^{bb}$ is H, —$CH_3$ or —$CF_3$;
$R^{cc}$ is —$CH_3$, —$CD_3$ or —$CH_2CF_3$;
moiety
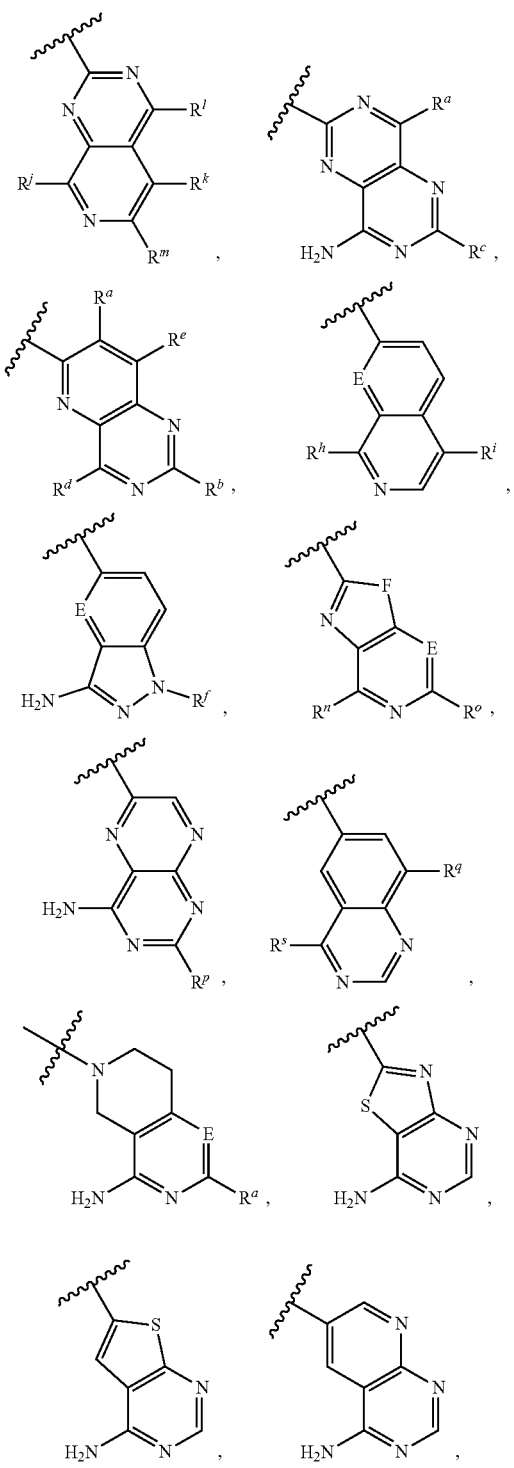

-continued

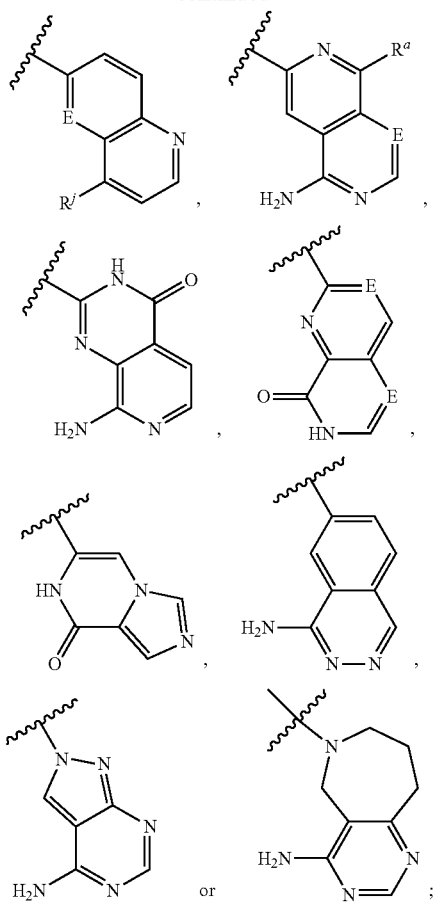

E is N or CH;
F is O, S, NH or NCH$_3$;
R$^a$ is H or —CH$_3$;
R$^b$ is H, D, —OH, F, —C$_1$-C$_5$alkyl, —CH$_2$OCH$_3$, —C$_1$-C$_5$haloalkyl, —NH$_2$, cyclopropyl, or —CH$_2$OH;
R$^c$ is H, D or —CH$_3$;
R$^d$ is H, —CN, —CF$_3$, —C$_1$-C$_5$alkyl, —C$_3$-C$_6$cycloalkyl, —O—C$_1$-C$_3$alkyl, —N(R$^6$)R$^7$, -continued

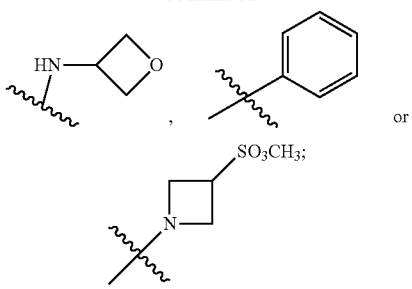

wherein
R$^6$ is H or —C$_1$-C$_3$alkyl;
R$^7$ is H, —C$_1$-C$_3$alkyl, —SO$_2$CH$_3$, —COCH$_3$, —C$_1$-C$_4$haloalkyl or —CH$_2$CN,
or R$^6$ and R$^7$ are taken together with the nitrogen to which they are attached to form
the moiety

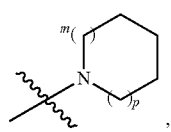

wherein m is 0 or 1, and p is 0 or 1;
R$^8$ is H, F or —C$_1$-C$_3$alkyl;
R$^9$ is H, F or —C$_1$-C$_3$alkyl;
R$^e$ is H, —CD$_3$, Br, —C$_1$-C$_5$alkyl, —C$_3$-C$_6$cycloalkyl,

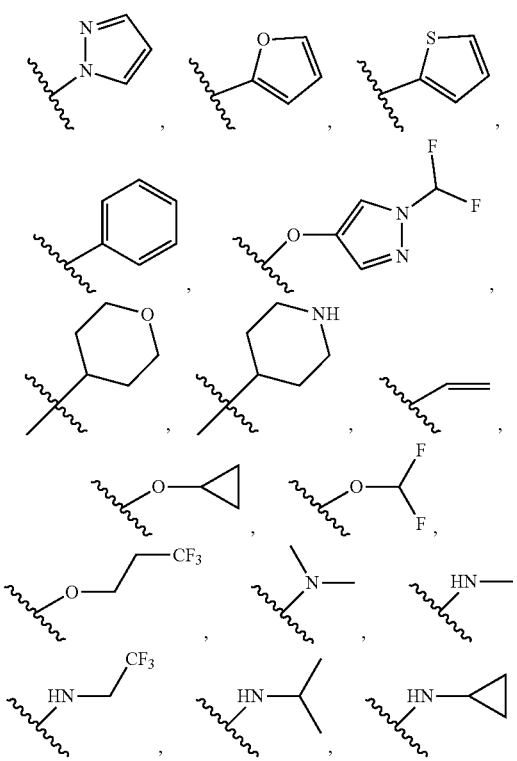

-continued

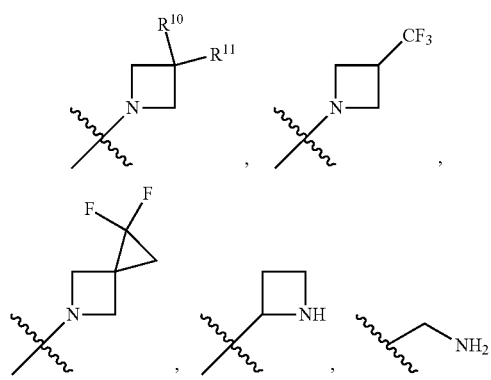

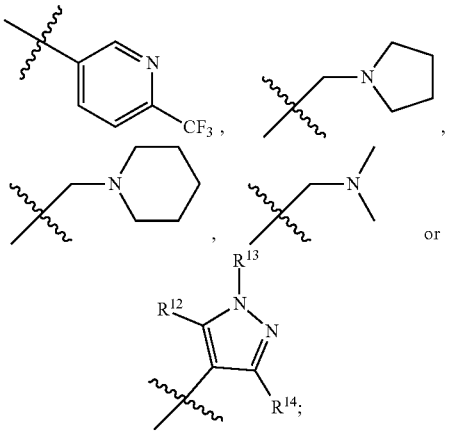

—C$_1$-C$_5$alkyl substituted with 1 to 3 R$^g$ groups, wherein R$^g$ is —NH$_2$, or F;

R$^{10}$ is H or F;

R$^{11}$ is H or F;

R$^f$ is H, —CH$_3$ or

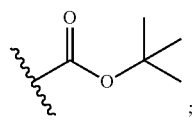 [SMILES: *C(=O)OC(C)(C)C]

R$^h$ is —CH$_3$, —NH$_2$ or

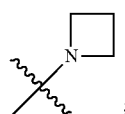

R$^i$ is H, —CH$_3$, —CN, Br,

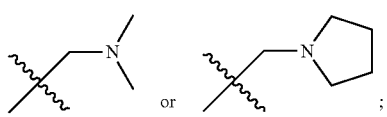

R$^j$ is —NH$_2$ or

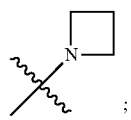 [SMILES: *N1CCC1]

R$^k$ is H, —CF$_3$, I, Cl, Br, —CN, —C$_1$-C$_6$alkyl,

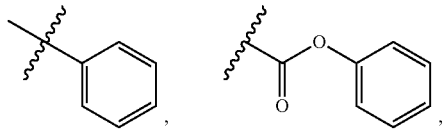

R$^{12}$ is H or —CH$_3$;

R$^{13}$ is H, —CH$_3$, —CH$_2$(C)(CH$_3$)$_2$OH, —(CH$_2$)$_3$CN, or —(CH$_2$)$_2$NH$_2$;

R$^4$ is H or —CH$_3$;

R$^l$ is H, —C$_1$-C$_4$alkyl, —CF$_3$,

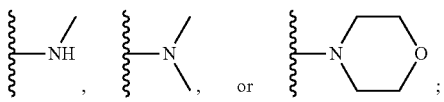

R$^m$ is H or —CH$_3$;

R$^n$ is —NH$_2$;

R$^o$ is H or —CH$_3$;

R$^p$ is H or —CH$_3$;

R$^q$ is H, —CN, F, Cl, —OCH$_3$, —CF$_3$, or —CH$_3$; and

R$^s$ is —NH$_2$ or

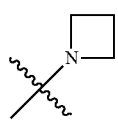

provided that when moiety

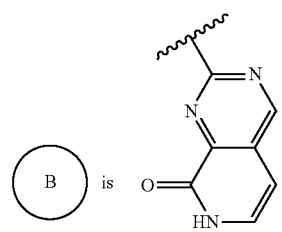

and each R$^1$, R$^2$, R$^3$ and R$^4$ is H, then moiety

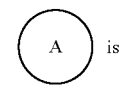

is

-continued

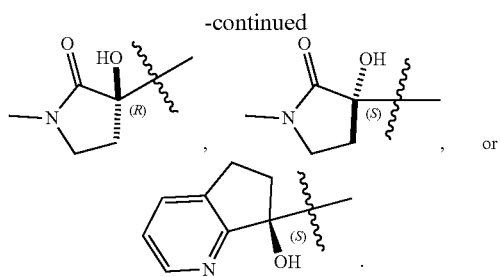

Illustrative embodiments of compounds of Formula (I) are compounds
(R)-3-[2-[3-(8-Aminopyrido[3,4-d]pyrimidin-2-yl)phenyl]ethynyl]-3-hydroxy-1-methyl-pyrrolidin-2-one;
(S)-3-[2-[3-(8-Aminopyrido[3,4-d]pyrimidin-2-yl)phenyl]ethynyl]-3-hydroxy-1-methyl-pyrrolidin-2-one;
(R)-3-[2-[3-(4-Aminopyrido[3,2-d]pyrimidin-6-yl)-4-methyl-phenyl]ethynyl]-3-hydroxy-1-methyl-pyrrolidin-2-one;
(R)-3-((3-(8-Amino-4-methylpyrimido[5,4-d]pyrimidin-2-yl)phenyl)ethynyl)-3-hydroxy-1-methylpyrrolidin-2-one;
(S)-3-((3-(8-Amino-4-methylpyrimido[5,4-d]pyrimidin-2-yl)phenyl)ethynyl)-3-hydroxy-1-methylpyrrolidin-2-one;
(R)-3-((3-(4-Amino-2-methylpyrido[3,2-d]pyrimidin-6-yl)phenyl)ethynyl)-3-hydroxy-1-methylpyrrolidin-2-one;
(S)-3-((3-(4-Amino-2-methylpyrido[3,2-d]pyrimidin-6-yl)phenyl)ethynyl)-3-hydroxy-1-methylpyrrolidin-2-one;
(R)-3-((3-(4-Aminopyrido[3,2-d]pyrimidin-6-yl-2-d)phenyl)ethynyl)-3-hydroxy-1-methylpyrrolidin-2-one;
(S)-3-((3-(4-Aminopyrido[3,2-d]pyrimidin-6-yl-2-d)phenyl)ethynyl)-3-hydroxy-1-methylpyrrolidin-2-one;
(R)-3-((3-(7-Aminothiazolo[5,4-d]pyrimidin-2-yl)-4-methylphenyl)ethynyl)-3-hydroxy-1-methylpyrrolidin-2-one;
(S)-3-((3-(7-Aminothiazolo[5,4-d]pyrimidin-2-yl)-4-methylphenyl)ethynyl)-3-hydroxy-1-methylpyrrolidin-2-one;
(R)-3-((3-(4-Aminopyrido[3,2-d]pyrimidin-6-yl)phenyl)ethynyl)-3-hydroxy-1-methylpyrrolidin-2-one;
(R)-3-[2-[3-(4-Aminopyrimido[5,4-d]pyrimidin-6-yl)phenyl]ethynyl]-3-hydroxy-1-methyl-pyrrolidin-2-one;
(R)-3-((3-(8-Amino-6-methylpyrimido[5,4-d]pyrimidin-2-yl)phenyl)ethynyl)-3-hydroxy-1-methylpyrrolidin-2-one;
(R)-3-[2-[3-(4-Aminopteridin-6-yl)phenyl]ethynyl]-3-hydroxy-1-methyl-pyrrolidin-2-one;
(R)-3-[2-[3-(4-Aminoquinazolin-6-yl)phenyl]ethynyl]-3-hydroxy-1-methyl-pyrrolidin-2-one;
(R)-7-[2-[3-(8-Aminopyrido[3,4-d]pyrimidin-2-yl)phenyl]ethynyl]-5,6-dihydropyrrolo[1,2-a]imidazol-7-ol;
(R)-4-[3-(8-Aminopyrido[3,4-d]pyrimidin-2-yl)phenyl]-2-(5-methyl-1,3,4-oxadiazol-2-yl)but-3-yn-2-ol;
(R)-3-[2-[3-(8-Amino-1,7-naphthyridin-2-yl)phenyl]ethynyl]-3-hydroxy-1-methyl-pyrrolidin-2-one;
(R)-3-((3-(8-Amino-3,4-dihydro-2,7-naphthyridin-2(1H)-yl)phenyl)ethynyl)-3-hydroxy-1-methylpyrrolidin-2-one;
(R)-3-[2-[3-(3-Amino-1-methyl-pyrazolo[4,3-b]pyridin-5-yl)phenyl]ethynyl]-3-hydroxy-1-methyl-pyrrolidin-2-one;
(R)-3-[2-[3-(3-Amino-1H-pyrazolo[4,3-b]pyridin-5-yl)phenyl]ethynyl]-3-hydroxy-1-methyl-pyrrolidin-2-one;
(R)-3-Hydroxy-1-methyl-3-((3-(4-methylpyrido[3,2-d]pyrimidin-6-yl)phenyl)ethynyl)pyrrolidin-2-one;
(R)-3-((3-(4-Ethoxypyrido[3,2-d]pyrimidin-6-yl)phenyl)ethynyl)-3-hydroxy-1-methylpyrrolidin-2-one;
(R)-3-((3-(4-(Dimethylamino)pyrido[3,2-d]pyrimidin-6-yl)phenyl)ethynyl)-3-hydroxy-1-methylpyrrolidin-2-one;
(R)-3-((3-(4-(Azetidin-1-yl)pyrido[3,2-d]pyrimidin-6-yl)phenyl)ethynyl)-3-hydroxy-1-methylpyrrolidin-2-one;
(R)-3-Hydroxy-1-methyl-3-((3-(4-(methylamino)pyrido[3,2-d]pyrimidin-6-yl)phenyl)ethynyl)pyrrolidin-2-one;
(R)-3-((3-(4-Amino-8-methylpyrido[3,2-d]pyrimidin-6-yl)phenyl)ethynyl)-3-hydroxy-1-methylpyrrolidin-2-one;
(R)-3-((3-(4-aminopyrido[3,2-d]pyrimidin-6-yl-2-d)-4-(trifluoromethoxy)phenyl)ethynyl)-3-hydroxy-1-methylpyrrolidin-2-one;
(R)-2-[3-[2-(3-Hydroxy-1-methyl-2-oxo-pyrrolidin-3-yl)ethynyl]phenyl]-7H-pyrido[3,4-d]pyrimidin-8-one;
(S)-2-[3-[2-(3-Hydroxy-1-methyl-2-oxo-pyrrolidin-3-yl)ethynyl]phenyl]-7H-pyrido[3,4-d]pyrimidin-8-one;
(R)-4-[3-(8-Aminopyrido[3,4-d]pyrimidin-2-yl)phenyl]-2-thiazol-2-yl-but-3-yn-2-ol;
1-[2-[3-(8-Aminopyrido[3,4-d]pyrimidin-2-yl)phenyl]ethynyl]cyclopentanol;
(R)-4-[3-(8-Aminopyrido[3,4-d]pyrimidin-2-yl)phenyl]-2-(5-methylisoxazol-3-yl)but-3-yn-2-ol;
4-[3-(8-Aminopyrido[3,4-d]pyrimidin-2-yl)phenyl]-2-methyl-but-3-yn-2-ol;
(R)-3-[2-[3-(1-Amino-7-isoquinolyl)phenyl]ethynyl]-3-hydroxy-1-methyl-pyrrolidin-2-one;
(R)-3-((3-(8-Amino-4-methylpyrido[3,4-d]pyrimidin-2-yl)phenyl)ethynyl)-3-hydroxy-1-methylpyrrolidin-2-one;
(R)-3-((3-(8-Amino-4-(trifluoromethyl)pyrido[3,4-d]pyrimidin-2-yl)phenyl)ethynyl)-3-hydroxy-1-methylpyrrolidin-2-one;
(R)-3-((3-(8-Amino-5-methylpyrido[3,4-d]pyrimidin-2-yl)phenyl)ethynyl)-3-hydroxy-1-methylpyrrolidin-2-one;
(R)-3-((5-(8-Aminopyrido[3,4-d]pyrimidin-2-yl)-2-methylphenyl)ethynyl)-3-hydroxy-1-methylpyrrolidin-2-one;
(R)-3-((3-(8-Aminopyrido[3,4-d]pyrimidin-2-yl)-2-methylphenyl)ethynyl)-3-hydroxy-1-methylpyrrolidin-2-one;
(R)-3-((3-(8-Aminopyrido[3,4-d]pyrimidin-2-yl)-5-methylphenyl)ethynyl)-3-hydroxy-1-methylpyrrolidin-2-one;
(R)-3-((3-(8-Aminopyrido[3,4-d]pyrimidin-2-yl)-4-methylphenyl)ethynyl)-3-hydroxy-1-methylpyrrolidin-2-one;
(R)-3-((3-(8-Amino-6-methylpyrido[3,4-d]pyrimidin-2-yl)phenyl)ethynyl)-3-hydroxy-1-methylpyrrolidin-2-one;
(R)-7-[2-[3-(8-Aminopyrido[3,4-d]pyrimidin-2-yl)phenyl]ethynyl]-5,6-dihydrocyclopenta[b]pyridin-7-ol;
(S)-7-[2-[3-(8-Aminopyrido[3,4-d]pyrimidin-2-yl)phenyl]ethynyl]-5,6-dihydrocyclopenta[b]pyridin-7-ol;
(R)-2-[3-[2-(7-Hydroxy-5,6-dihydrocyclopenta[b]pyridin-7-yl)ethynyl]phenyl]-7H-pyrido[3,4-d]pyrimidin-8-one;
(R)-4-(3-(8-Amino-4-methylpyrido[3,4-d]pyrimidin-2-yl)phenyl)-2-(thiazol-2-yl)but-3-yn-2-ol;
(R)-4-(3-(8-Amino-4-(trifluoromethyl)pyrido[3,4-d]pyrimidin-2-yl)phenyl)-2-(thiazol-2-yl)but-3-yn-2-ol;
(R)-4-(3-(8-Amino-5-methylpyrido[3,4-d]pyrimidin-2-yl)phenyl)-2-(thiazol-2-yl)but-3-yn-2-ol;
(R)-4-(3-(8-Amino-6-methylpyrido[3,4-d]pyrimidin-2-yl)phenyl)-2-(thiazol-2-yl)but-3-yn-2-ol;
(R)-7-[2-[3-(8-Aminopyrido[3,4-d]pyrimidin-2-yl)-5-methyl-phenyl]ethynyl]-5,6-dihydrocyclopenta[b]pyridin-7-ol;
(R)-3-((3-(8-Aminopyrido[3,4-d]pyrimidin-2-yl)-4-methoxyphenyl)ethynyl)-3-hydroxy-1-methylpyrrolidin-2-one;
(R)-3-((3-(8-Aminopyrido[3,4-d]pyrimidin-2-yl)-4-isobutylphenyl)ethynyl)-3-hydroxy-1-methylpyrrolidin-2-one;
(R)-8-Amino-2-(3-((3-hydroxy-1-methyl-2-oxopyrrolidin-3-yl)ethynyl)phenyl)pyrido[3,4-d]pyrimidin-4(3H)-one;

(R)-3-((3-(8-Aminopyrido[3,4-d]pyrimidin-2-yl)-4-(trifluoromethoxy)phenyl)ethynyl)-3-hydroxy-1-methylpyrrolidin-2-one;

(R)-3-((3-(8-Amino-4-morpholinopyrido[3,4-d]pyrimidin-2-yl)phenyl)ethynyl)-3-hydroxy-1-methylpyrrolidin-2-one;

(R)-3-((3-(8-Amino-4-(dimethylamino)pyrido[3,4-d]pyrimidin-2-yl)phenyl)ethynyl)-3-hydroxy-1-methylpyrrolidin-2-one;

(R)-3-[2-[3-(4-Amino-1H-imidazo[4,5-c]pyridin-2-yl)phenyl]ethynyl]-3-hydroxy-1-methyl-pyrrolidin-2-one;

(R)-7-((3-(8-Amino-4-methylpyrido[3,4-d]pyrimidin-2-yl)phenyl)ethynyl)-6,7-dihydro-5H-cyclopenta[b]pyridin-7-ol;

(R)-7-((3-(8-Amino-4-(trifluoromethyl)pyrido[3,4-d]pyrimidin-2-yl)phenyl)ethynyl)-6,7-dihydro-5H-cyclopenta[b]pyridin-7-ol;

(R)-7-((3-(8-Amino-5-methylpyrido[3,4-d]pyrimidin-2-yl)phenyl)ethynyl)-6,7-dihydro-5H-cyclopenta[b]pyridin-7-ol;

(R)-7-((3-(8-Amino-6-methylpyrido[3,4-d]pyrimidin-2-yl)phenyl)ethynyl)-6,7-dihydro-5H-cyclopenta[b]pyridin-7-ol;

(S)-7-[2-[3-(8-Aminopyrido[3,4-d]pyrimidin-2-yl)phenyl]ethynyl]-5,6-dihydropyrrolo[1,2-a]imidazol-7-ol;

(R)-3-[2-[3-(8-Amino-5-methyl-pyrido[3,4-d]pyrimidin-2-yl)-4-methyl-phenyl]ethynyl]-3-hydroxy-1-methyl-pyrrolidin-2-one;

(R)-3-[2-[3-(8-Aminopyrido[3,4-d]pyrimidin-2-yl)phenyl]ethynyl]-3-hydroxy-1-(trideuteriomethyl)pyrrolidin-2-one;

(S)-3-[2-[3-(8-Aminopyrido[3,4-d]pyrimidin-2-yl)phenyl]ethynyl]-3-hydroxy-1-(trideuteriomethyl)pyrrolidin-2-one;

(R)-4-[3-(1-Amino-7-isoquinolyl)-4-methyl-phenyl]-2-thiazol-2-yl-but-3-yn-2-ol;

(R)-4-(3-(8-Aminopyrido[3,4-d]pyrimidin-2-yl)-4-methylphenyl)-2-(thiazol-2-yl)but-3-yn-2-ol;

(R)-3-[2-[3-(1-Amino-7-isoquinolyl)-4-methyl-phenyl]ethynyl]-3-hydroxy-1-(trideuteriomethyl)pyrrolidin-2-one;

(S)-3-[2-[3-(1-Amino-7-isoquinolyl)-4-methyl-phenyl]ethynyl]-3-hydroxy-1-(trideuteriomethyl)pyrrolidin-2-one;

(R)-3-[2-[3-(8-Aminopyrido[3,4-d]pyrimidin-2-yl)phenyl]ethynyl]-3-hydroxy-1-(2,2,2-trifluoroethyl)pyrrolidin-2-one;

(S)-3-[2-[3-(8-Aminopyrido[3,4-d]pyrimidin-2-yl)phenyl]ethynyl]-3-hydroxy-1-(2,2,2-trifluoroethyl)pyrrolidin-2-one;

(R)-4-(3-(8-Aminopyrido[3,4-d]pyrimidin-2-yl)-4-methylphenyl)-2-(5-methyl-1,3,4-oxadiazol-2-yl)but-3-yn-2-ol;

(R)-7-((3-(8-Aminopyrido[3,4-d]pyrimidin-2-yl)-4-methylphenyl)ethynyl)-6,7-dihydro-5H-cyclopenta[b]pyridin-7-ol;

(R)-3-[2-[3-(8-Amino-5-methyl-pyrido[3,4-d]pyrimidin-2-yl)-5-methyl-phenyl]ethynyl]-3-hydroxy-1-methyl-pyrrolidin-2-one;

(R)-3-[2-[3-(1-Amino-7-isoquinolyl)-4-methyl-phenyl]ethynyl]-3-hydroxy-1-(2,2,2-trifluoroethyl)pyrrolidin-2-one;

(R)-4-[3-(1-Amino-7-isoquinolyl)-4-methyl-phenyl]-2-(5-methyl-1,3,4-oxadiazol-2-yl)but-3-yn-2-ol;

(R)-4-[3-(1-Amino-7-isoquinolyl)-4-methyl-phenyl]-2-(5-methylisoxazol-3-yl)but-3-yn-2-ol;

(R)-7-[2-[3-(1-Amino-7-isoquinolyl)-4-methyl-phenyl]ethynyl]-5,6-dihydrocyclopenta[b]pyridin-7-ol;

(R)-7-[2-[3-(1-Amino-7-isoquinolyl)-4-methyl-phenyl]ethynyl]-5,6-dihydropyrrolo[1,2-a]imidazol-7-ol;

(R)-4-(3-(8-Aminopyrido[3,4-d]pyrimidin-2-yl)-4-methylphenyl)-2-(5-methylisoxazol-3-yl)but-3-yn-2-ol;

(R)-3-((3-(8-Amino-4-methylpyrido[3,4-d]pyrimidin-2-yl)phenyl)ethynyl)-3-hydroxy-1-(methyl-d3)pyrrolidin-2-one;

(R)-7-((3-(8-Amino-4-methylpyrido[3,4-d]pyrimidin-2-yl)phenyl)ethynyl)-6,7-dihydro-5H-pyrrolo[1,2-a]imidazol-7-ol;

(R)-3-((3-(8-Amino-4-(methylamino)pyrido[3,4-d]pyrimidin-2-yl)phenyl)ethynyl)-3-hydroxy-1-methylpyrrolidin-2-one;

(R)-7-[2-[3-(8-Amino-5-methyl-pyrido[3,4-d]pyrimidin-2-yl)phenyl]ethynyl]-5,6-dihydropyrrolo[1,2-a]imidazol-7-ol;

(R)-3-[2-[3-(8-Amino-5-methyl-pyrido[3,4-d]pyrimidin-2-yl)phenyl]ethynyl]-3-hydroxy-1-(trideuteromethyl)pyrrolidin-2-one;

(R)-4-[3-(8-Amino-1,7-naphthyridin-2-yl)phenyl]-2-(5-methyl-1,3,4-oxadiazol-2-yl)but-3-yn-2-ol;

(R)-4-[3-(8-Amino-1,7-naphthyridin-2-yl)phenyl]-2-(5-methylisoxazol-3-yl)but-3-yn-2-ol;

(R)-4-[3-(8-Amino-1,7-naphthyridin-2-yl)phenyl]-2-thiazol-2-yl-but-3-yn-2-ol;

(R)-7-[2-[3-(8-Amino-1,7-naphthyridin-2-yl)phenyl]ethynyl]-5,6-dihydropyrrolo[1,2-a]imidazol-7-ol;

(R)-3-[2-[3-(8-Amino-4-methyl-pyrido[3,4-d]pyrimidin-2-yl)phenyl]ethynyl]-3-hydroxy-1-(2,2,2-trifluoroethyl)pyrrolidin-2-one;

(R)-4-(3-(4-Aminopyrido[3,2-d]pyrimidin-6-yl)phenyl)-2-(thiazol-2-yl)but-3-yn-2-ol;

(R)-3-((3-(8-Amino-5-bromopyrido[3,4-d]pyrimidin-2-yl)phenyl)ethynyl)-3-hydroxy-1-methylpyrrolidin-2-one;

(R)-4-(3-(4-Aminopyrido[3,2-d]pyrimidin-6-yl)phenyl)-2-(5-methylisoxazol-3-yl)but-3-yn-2-ol;

(R)-3-[2-[3-(4-Aminophthalazin-6-yl)phenyl]ethynyl]-3-hydroxy-1-methyl-pyrrolidin-2-one;

(R)-4-(3-(4-Aminopyrido[3,2-d]pyrimidin-6-yl)phenyl)-2-(5-methyl-1,3,4-oxadiazol-2-yl)but-3-yn-2-ol;

(R)-3-((3-(8-Amino-4-isopropylpyrido[3,4-d]pyrimidin-2-yl)phenyl)ethynyl)-3-hydroxy-1-methylpyrrolidin-2-one;

(R)-3-[2-[3-[8-Amino-5-(trifluoromethyl)pyrido[3,4-d]pyrimidin-2-yl]phenyl]ethynyl]-3-hydroxy-1-methyl-pyrrolidin-2-one;

(R)-8-Amino-2-(3-((3-hydroxy-1-methyl-2-oxopyrrolidin-3-yl)ethynyl)phenyl)pyrido[3,4-d]pyrimidine-5-carbonitrile;

(R)-3-((3-(7-Aminothiazolo[5,4-d]pyrimidin-2-yl)phenyl)ethynyl)-3-hydroxy-1-methylpyrrolidin-2-one;

(R)-3-((3-(8-Amino-5-iodopyrido[3,4-d]pyrimidin-2-yl)phenyl)ethynyl)-3-hydroxy-1-methylpyrrolidin-2-one;

(R)-3-((3-(8-Amino-5-chloropyrido[3,4-d]pyrimidin-2-yl)phenyl)ethynyl)-3-hydroxy-1-methylpyrrolidin-2-one;

(R)-4-[3-(4-Aminoquinazolin-6-yl)phenyl]-2-(5-methylisoxazol-3-yl)but-3-yn-2-ol;

(R)-4-[3-(4-Aminoquinazolin-6-yl)phenyl]-2-thiazol-2-yl-but-3-yn-2-ol;

(R)-4-[3-(4-Aminoquinazolin-6-yl)phenyl]-2-(5-methyl-1,3,4-oxadiazol-2-yl)but-3-yn-2-ol;

2-(3-((1H-Pyrazol-5-yl)ethynyl)phenyl)-4-methylpyrido[3,4-d]pyrimidin-8-amine;

(R)-4-(3-(4-Aminopyrido[2,3-d]pyrimidin-6-yl)phenyl)-2-(thiazol-2-yl)but-3-yn-2-ol;

(R)-3-((3-(4-Aminopyrido[2,3-d]pyrimidin-6-yl)phenyl)
    ethynyl)-3-hydroxy-1-methylpyrrolidin-2-one;
(R)-3-((3-(4-Amino-8-methylquinazolin-6-yl)phenyl)ethy-
    nyl)-3-hydroxy-1-methylpyrrolidin-2-one;
(R)-3-[2-[3-(4-Aminopyrido[3,4-d]pyrimidin-6-yl)phenyl]
    ethynyl]-3-hydroxy-1-methyl-pyrrolidin-2-one;
(R)-3-[2-[3-(8-Amino-5-bromo-1,7-naphthyridin-2-yl)phe-
    nyl]ethynyl]-3-hydroxy-1-methyl-pyrrolidin-2-one;
(R)-3-[2-[3-(4-Amino-8-fluoro-quinazolin-6-yl)phenyl]
    ethynyl]-3-hydroxy-1-methyl-pyrrolidin-2-one;
(R)-3-((3-(4-Amino-8-methoxyquinazolin-6-yl)phenyl)
    ethynyl)-3-hydroxy-1-methylpyrrolidin-2-one;
(R)-3-((3-(4-Amino-8-(trifluoromethyl)quinazolin-6-yl)
    phenyl)ethynyl)-3-hydroxy-1-methylpyrrolidin-2-one;
(R)-3-((3-(4-Aminothiazolo[4,5-c]pyridin-2-yl)phenyl)
    ethynyl)-3-hydroxy-1-methylpyrrolidin-2-one;
(R)-3-((3-(4-Amino-8-chloroquinazolin-6-yl)phenyl)ethy-
    nyl)-3-hydroxy-1-methylpyrrolidin-2-one;
(R)-8-Amino-2-[3-[2-(3-hydroxy-1-methyl-2-oxo-pyrroli-
    din-3-yl)ethynyl]phenyl]-1,7-naphthyridine-5-carboni-
    trile;
(R)-3-[2-[3-(5-Amino-2,6-naphthyridin-3-yl)phenyl]ethy-
    nyl]-3-hydroxy-1-methyl-pyrrolidin-2-one;
(R)-3-[2-[3-(8-Amino-5-methyl-1,7-naphthyridin-2-yl)phe-
    nyl]ethynyl]-3-hydroxy-1-methyl-pyrrolidin-2-one;
(R)-3-((3-(8-Amino-5-phenylpyrido[3,4-d]pyrimidin-2-yl)
    phenyl)ethynyl)-3-hydroxy-1-methylpyrrolidin-2-one;
(R)-3-[2-[3-[8-Amino-5-(1-methylpyrazol-4-yl)pyrido[3,4-
    d]pyrimidin-2-yl]phenyl]ethynyl]-3-hydroxy-1-methyl-
    pyrrolidin-2-one;
(R)-3-[2-[3-[8-Amino-5-[1-(2-hydroxy-2-methyl-propyl)
    pyrazol-4-yl]pyrido[3,4-d]pyrimidin-2-yl]phenyl]ethy-
    nyl]-3-hydroxy-1-methyl-pyrrolidin-2-one;
(R)-3-[2-[3-[8-Amino-5-(1H-pyrazol-4-yl)pyrido[3,4-d]py-
    rimidin-2-yl]phenyl]ethynyl]-3-hydroxy-1-methyl-pyrro-
    lidin-2-one;
(R)-3-[2-[3-[8-Amino-5-(3,5-dimethyl-1H-pyrazol-4-yl)
    pyrido[3,4-d]pyrimidin-2-yl]phenyl]ethynyl]-3-hydroxy-
    1-methyl-pyrrolidin-2-one;
(R)-4-Amino-6-(3-((3-hydroxy-1-methyl-2-oxopyrrolidin-
    3-yl)ethynyl)phenyl)quinazoline-8-carbonitrile;
(R)-3-[2-[3-[8-Amino-5-(5-methyl-1H-pyrazol-4-yl)pyrido
    [3,4-d]pyrimidin-2-yl]phenyl]ethynyl]-3-hydroxy-1-
    methyl-pyrrolidin-2-one;
(R)-Phenyl 8-amino-2-[3-[2-(3-hydroxy-1-methyl-2-oxo-
    pyrrolidin-3-yl)ethynyl]phenyl]pyrido[3,4-d]pyrimidine-
    5-carboxylate;
(R)-3-((3-(8-Amino-5-ethylpyrido[3,4-d]pyrimidin-2-yl)
    phenyl)ethynyl)-3-hydroxy-1-methylpyrrolidin-2-one;
(R)-3-((3-(8-Amino-5-isobutylpyrido[3,4-d]pyrimidin-2-yl)
    phenyl)ethynyl)-3-hydroxy-1-methylpyrrolidin-2-one;
(R)-2-[2-[3-(4-Aminopyrido[3,2-d]pyrimidin-6-yl)phenyl]
    ethynyl]-2-hydroxy-5,5-dimethyl-cyclopentanone;
(S)-2-[2-[3-(4-Aminopyrido[3,2-d]pyrimidin-6-yl)phenyl]
    ethynyl]-2-hydroxy-5,5-dimethyl-cyclopentanone;
(R)-3-[2-[3-[8-Amino-5-(pyrrolidin-1-ylmethyl)pyrido[3,4-
    d]pyrimidin-2-yl]phenyl]ethynyl]-3-hydroxy-1-methyl-
    pyrrolidin-2-one;
(R)-3-[2-[3-[8-Amino-5-[1-(2-aminoethyl)pyrazol-4-yl]
    pyrido[3,4-d]pyrimidin-2-yl]phenyl]ethynyl]-3-hydroxy-
    1-methyl-pyrrolidin-2-one;
(R)-3-[2-[3-[8-Amino-5-(dimethylaminomethyl)pyrido[3,4-
    d]pyrimidin-2-yl]phenyl]ethynyl]-3-hydroxy-1-methyl-
    pyrrolidin-2-one;
(R)-3-[2-[3-(4-Amino-8-methyl-pyrido[3,4-d]pyrimidin-6-
    yl)phenyl]ethynyl]-3-hydroxy-1-methyl-pyrrolidin-2-
    one;
(R)-4-(3-(8-Aminopyrimido[5,4-d]pyrimidin-2-yl)phenyl)-
    2-(thiazol-2-yl)but-3-yn-2-ol;
(R)-3-((3-(8-Amino-4,5-dimethylpyrido[3,4-d]pyrimidin-2-
    yl)phenyl)ethynyl)-3-hydroxy-1-methylpyrrolidin-2-one;
(R)-3-((3-(4-Aminopyrido[3,2-d]pyrimidin-6-yl)-4-
    methoxyphenyl)ethynyl)-3-hydroxy-1-methylpyrrolidin-
    2-one;
(R)-4-[4-[8-Amino-2-[3-[2-(3-hydroxy-1-methyl-2-oxo-
    pyrrolidin-3-yl)ethynyl]phenyl]pyrido[3,4-d]pyrimidin-
    5-yl]pyrazol-1-yl]butanenitrile;
(R)-3-((3-(4-Aminothieno[2,3-d]pyrimidin-6-yl)phenyl)
    ethynyl)-3-hydroxy-1-methylpyrrolidin-2-one;
(R)-3-((3-(7-Aminooxazolo[5,4-d]pyrimidin-2-yl)phenyl)
    ethynyl)-3-hydroxy-1-methylpyrrolidin-2-one;
(R)-3-((3-(6-Amino-9-methyl-9H-purin-8-yl)phenyl)ethy-
    nyl)-3-hydroxy-1-methylpyrrolidin-2-one;
(R)-7-((3-(8-Aminopyrimido[5,4-d]pyrimidin-2-yl)phenyl)
    ethynyl)-6,7-dihydro-5H-cyclopenta[b]pyridin-7-ol;
(R)-3-[2-[3-[8-Amino-5-(1-piperidylmethyl)pyrido[3,4-d]
    pyrimidin-2-yl]phenyl]ethynyl]-3-hydroxy-1-methyl-
    pyrrolidin-2-one;
(R)-7-[2-[3-(4-Aminopyrimido[5,4-d]pyrimidin-6-yl)phe-
    nyl]ethynyl]-5,6-dihydropyrrolo[1,2-a]imidazol-7-ol;
(R)-3-[2-[3-[8-Amino-5-[6-(trifluoromethyl)-3-pyridyl]
    pyrido[3,4-d]pyrimidin-2-yl]phenyl]ethynyl]-3-hydroxy-
    1-methyl-pyrrolidin-2-one;
(R)-3-[2-[3-(4-Amino-2-methyl-pteridin-6-yl)phenyl]ethy-
    nyl]-3-hydroxy-1-methyl-pyrrolidin-2-one;
(R)-3-((3-(4-Aminopyrido[3,2-d]pyrimidin-6-yl-2-d)-4-
    methylphenyl)ethynyl)-3-hydroxy-1-methylpyrrolidin-2-
    one;
(R)-3-((3-(4-Amino-2-methylpyrido[3,2-d]pyrimidin-6-yl)-
    4-methylphenyl)ethynyl)-3-hydroxy-1-methylpyrrolidin-
    2-one;
(R)-3-((3-(8-Amino-5-neopentylpyrido[3,4-d]pyrimidin-2-
    yl)phenyl)ethynyl)-3-hydroxy-1-methylpyrrolidin-2-one;
(R)-3-((5-(7-Aminothiazolo[5,4-d]pyrimidin-2-yl)-2-meth-
    ylphenyl)ethynyl)-3-hydroxy-1-methylpyrrolidin-2-one;
(R)-3-((3-(7-Aminothiazolo[5,4-d]pyrimidin-2-yl)-5-meth-
    ylphenyl)ethynyl)-3-hydroxy-1-methylpyrrolidin-2-one;
(R)-3-((3-(7-Aminothiazolo[5,4-d]pyrimidin-2-yl)-2-meth-
    ylphenyl)ethynyl)-3-hydroxy-1-methylpyrrolidin-2-one;
(S)-7-((3-(8-Aminopyrimido[5,4-d]pyrimidin-2-yl)phenyl)
    ethynyl)-6,7-dihydro-5H-cyclopenta[b]pyridin-7-ol;
(R)-3-((3-(8-Amino-4,6-dimethylpyrimido[5,4-d]pyrimi-
    din-2-yl)phenyl)ethynyl)-3-hydroxy-1-methylpyrrolidin-
    2-one;
(S)-4-(3-(4-Amino-2-methylpyrido[3,2-d]pyrimidin-6-yl)
    phenyl)-2-(2-methylthiazol-5-yl)but-3-yn-2-ol;
(R)-4-(3-(4-Amino-2-methylpyrido[3,2-d]pyrimidin-6-yl)
    phenyl)-2-(2-methylthiazol-5-yl)but-3-yn-2-ol;
(R)-3-((3-(4-Amino-7,8-dihydropyrido[4,3-d]pyrimidin-6
    (5H)-yl)phenyl)ethynyl)-3-hydroxy-1-methylpyrrolidin-
    2-one;
(R)-3-((3-(4-Aminopyrido[3,2-d]pyrimidin-6-yl-2-d)-4-
    methoxyphenyl)ethynyl)-3-hydroxy-1-methylpyrrolidin-
    2-one;
(R)-3-((3-(4-Amino-2-methylpyrido[3,2-d]pyrimidin-6-yl)-
    4-methoxyphenyl)ethynyl)-3-hydroxy-1-methylpyrroli-
    din-2-one;
(S)-4-(3-(4-Amino-2-methylpyrido[3,2-d]pyrimidin-6-yl)
    phenyl)-2-(4-methylthiazol-5-yl)but-3-yn-2-ol;
(R)-4-(3-(4-Amino-2-methylpyrido[3,2-d]pyrimidin-6-yl)
    phenyl)-2-(4-methylthiazol-5-yl)but-3-yn-2-ol;
(R)-4-(3-(4-Amino-2-methylpyrido[3,2-d]pyrimidin-6-yl)
    phenyl)-2-(thiazol-2-yl)but-3-yn-2-ol;

racemic-8-((3-(4-Amino-2-methylpyrido[3,2-d]pyrimidin-6-yl)phenyl)ethynyl)-5,6,7,8-tetrahydroquinolin-8-ol;
(S)-4-(3-(4-Amino-2-methylpyrido[3,2-d]pyrimidin-6-yl)phenyl)-2-(5-methylthiazol-2-yl)but-3-yn-2-ol;
(R)-4-(3-(4-Amino-2-methylpyrido[3,2-d]pyrimidin-6-yl)phenyl)-2-(5-methylthiazol-2-yl)but-3-yn-2-ol;
(R)-3-((3-(8-Amino-4-methylpyrimido[5,4-d]pyrimidin-2-yl-6-d)phenyl)ethynyl)-3-hydroxy-1-methylpyrrolidin-2-one;
(R)-tert-Butyl 3-amino-5-[3-[2-(3-hydroxy-1-methyl-2-oxo-pyrrolidin-3-yl)ethynyl]phenyl]indazole-1-carboxylate;
(R)-3-((3-(4-Amino-2-(fluoromethyl)pyrido[3,2-d]pyrimidin-6-yl)phenyl)ethynyl)-3-hydroxy-1-methylpyrrolidin-2-one;
(R)-3-[2-[3-[8-Amino-5-(pyrrolidin-1-ylmethyl)-1,7-naphthyridin-2-yl]phenyl]ethynyl]-3-hydroxy-1-methyl-pyrrolidin-2-one;
(R)-3-[2-[3-[8-Amino-5-(dimethylaminomethyl)-1,7-naphthyridin-2-yl]phenyl]ethynyl]-3-hydroxy-1-methyl-pyrrolidin-2-one;
(R)-3-((3-(4-Amino-2-(hydroxymethyl)pyrido[3,2-d]pyrimidin-6-yl)phenyl)ethynyl)-3-hydroxy-1-methylpyrrolidin-2-one;
(R)-3-[2-[3-(3-Amino-1H-indazol-5-yl)phenyl]ethynyl]-3-hydroxy-1-methyl-pyrrolidin-2-one;
(R)-3-((3-(4-Amino-2-cyclopropylpyrido[3,2-d]pyrimidin-6-yl)phenyl)ethynyl)-3-hydroxy-1-methylpyrrolidin-2-one;
(R)-3-((3-(4-Amino-2-(trifluoromethyl)pyrido[3,2-d]pyrimidin-6-yl)phenyl)ethynyl)-3-hydroxy-1-methylpyrrolidin-2-one;
(R)-3-((3-(8-Aminopyrimido[5,4-d]pyrimidin-2-yl)-4-methoxyphenyl)ethynyl)-3-hydroxy-1-methylpyrrolidin-2-one;
(R)-3-((3-(4-Amino-2,7-dimethylpyrido[3,2-d]pyrimidin-6-yl)phenyl)ethynyl)-3-hydroxy-1-methylpyrrolidin-2-one;
(R)-3-((3-(4-Amino-2H-pyrazolo[3,4-d]pyrimidin-2-yl)phenyl)ethynyl)-3-hydroxy-1-methylpyrrolidin-2-one;
(R)-4-(3-(4-Amino-2-methylpyrido[3,2-d]pyrimidin-6-yl)phenyl)-2-(4-methylthiazol-2-yl)but-3-yn-2-ol;
(S)-4-(3-(4-Amino-2-methylpyrido[3,2-d]pyrimidin-6-yl)phenyl)-2-(4-methylthiazol-2-yl)but-3-yn-2-ol;
(R)-3-[2-[3-(7-Amino-5-methyl-thiazolo[5,4-d]pyrimidin-2-yl)-4-methyl-phenyl]ethynyl]-3-hydroxy-1-methyl-pyrrolidin-2-one;
(R)-7-[2-[3-(7-Aminothiazolo[5,4-d]pyrimidin-2-yl)-4-methyl-phenyl]ethynyl]-5,6-dihydropyrrolo[1,2-a]imidazol-7-ol;
(R)-7-[2-[3-(7-Aminothiazolo[5,4-d]pyrimidin-2-yl)-4-methyl-phenyl]ethynyl]-5,6-dihydrocyclopenta[b]pyridin-7-ol;
1-[2-[3-(7-Aminothiazolo[5,4-d]pyrimidin-2-yl)-4-methyl-phenyl]ethynyl]cyclopentanol;
(S)-3-((3-(4-Amino-2-methylpyrido[3,2-d]pyrimidin-6-yl)phenyl)ethynyl)-3-hydroxy-1-methylpiperidin-2-one;
(R)-3-((3-(4-Amino-2-methylpyrido[3,2-d]pyrimidin-6-yl)phenyl)ethynyl)-3-hydroxy-1-methylpiperidin-2-one;
(R)-3-((3-(8-Aminopyrimido[5,4-d]pyrimidin-2-yl)-4-methylphenyl)ethynyl)-3-hydroxy-1-methylpyrrolidin-2-one;
(R)-3-((3-(4-Amino-7-methylpyrido[3,2-d]pyrimidin-6-yl)phenyl)ethynyl)-3-hydroxy-1-methylpyrrolidin-2-one;
(R)-4-[3-(4-Amino-2-methyl-pyrido[3,2-d]pyrimidin-6-yl)phenyl]-2-(2-pyridyl)but-3-yn-2-ol;
(S)-4-[3-(4-Amino-2-methyl-pyrido[3,2-d]pyrimidin-6-yl)phenyl]-2-(2-pyridyl)but-3-yn-2-ol;
(R)-4-(3-(4-Amino-2-methylpyrido[3,2-d]pyrimidin-6-yl)phenyl)-2-(4-(trifluoromethyl)thiazol-2-yl)but-3-yn-2-ol;
(S)-4-(3-(4-Amino-2-methylpyrido[3,2-d]pyrimidin-6-yl)phenyl)-2-(4-(trifluoromethyl)thiazol-2-yl)but-3-yn-2-ol;
(R)-3-((3-(7-Aminothiazolo[5,4-d]pyrimidin-2-yl)-4-methoxyphenyl)ethynyl)-3-hydroxy-1-methylpyrrolidin-2-one;
1-Allyl-3-((3-(4-Amino-2-methylpyrido[3,2-d]pyrimidin-6-yl)phenyl)ethynyl)-3-hydroxypyrrolidin-2-one;
racemic-1-Allyl-3-((3-(4-aminopyrido[3,2-d]pyrimidin-6-yl-2-d)phenyl)ethynyl)-3-hydroxypyrrolidin-2-one;
(R)-4-[3-(4-Amino-2-methyl-pyrido[3,2-d]pyrimidin-6-yl)phenyl]-2-pyrimidin-2-yl-but-3-yn-2-ol;
(S)-4-[3-(4-Amino-2-methyl-pyrido[3,2-d]pyrimidin-6-yl)phenyl]-2-pyrimidin-2-yl-but-3-yn-2-ol;
(S)-3-((3-(4-Aminopyrido[3,2-d]pyrimidin-6-yl-2-d)phenyl)ethynyl)-3-hydroxy-1-methylpiperidin-2-one;
(R)-4-[3-(4-Amino-2-methyl-pyrido[3,2-d]pyrimidin-6-yl)phenyl]-2-pyrazin-2-yl-but-3-yn-2-ol;
(S)-4-[3-(4-Amino-2-methyl-pyrido[3,2-d]pyrimidin-6-yl)phenyl]-2-pyrazin-2-yl-but-3-yn-2-ol;
racemic-4-(3-(4-Amino-2-methylpyrido[3,2-d]pyrimidin-6-yl)phenyl)-2-(1H-imidazol-4-yl)but-3-yn-2-ol;
(R)-3-((3-(2,4-Diaminopyrido[3,2-d]pyrimidin-6-yl)phenyl)ethynyl)-3-hydroxy-1-methylpyrrolidin-2-one;
(R)-3-((3-(4-Aminopyrido[3,2-d]pyrimidin-6-yl)phenyl)ethynyl)-3-(difluoromethyl)-1-methylpyrrolidin-2-one;
(S)-3-((3-(4-Aminopyrido[3,2-d]pyrimidin-6-yl)phenyl)ethynyl)-3-(difluoromethyl)-1-methylpyrrolidin-2-one;
(R)-3-((3-(4-Amino-2-(methoxymethyl)pyrido[3,2-d]pyrimidin-6-yl)phenyl)ethynyl)-3-hydroxy-1-methylpyrrolidin-2-one;
(R)-3-((3-(4-Aminopyrido[3,2-d]pyrimidin-6-yl)phenyl)ethynyl)-3-methoxy-1-methylpyrrolidin-2-one;
(R)-3-((3-(4-Amino-2-(fluoromethyl)pyrido[3,2-d]pyrimidin-6-yl)phenyl)ethynyl)-3-hydroxy-1-(methyl-d3)pyrrolidin-2-one;
(S)-4-[3-(4-Amino-2-methyl-pyrido[3,2-d]pyrimidin-6-yl)phenyl]-2-thiazol-4-yl-but-3-yn-2-ol;
(R)-3-((3-(4-Amino-2-ethylpyrido[3,2-d]pyrimidin-6-yl)phenyl)ethynyl)-3-hydroxy-1-methylpyrrolidin-2-one;
(R)-3-((3-(4-Amino-2-hydroxypyrido[3,2-d]pyrimidin-6-yl)phenyl)ethynyl)-3-hydroxy-1-methylpyrrolidin-2-one;
(R)-4-[3-(4-Amino-2-methyl-pyrido[3,2-d]pyrimidin-6-yl)phenyl]-2-thiazol-4-yl-but-3-yn-2-ol;
(R)-4-(3-(4-Amino-2-methylpyrido[3,2-d]pyrimidin-6-yl)phenyl)-2-(5-methyl-1,3,4-oxadiazol-2-yl)but-3-yn-2-ol;
(R)-3-((3-(7-Aminothiazolo[4,5-d]pyrimidin-2-yl)phenyl)ethynyl)-3-hydroxy-1-methylpyrrolidin-2-one;
(R)-3-((3-(4-Amino-2-methyl-7,8-dihydropyrido[4,3-d]pyrimidin-6(5H)-yl)phenyl)ethynyl)-3-hydroxy-1-methylpyrrolidin-2-one;
(R)-3-[2-[3-(7-Aminothiazolo[5,4-d]pyrimidin-2-yl)-4-methyl-phenyl]ethynyl]-3-hydroxy-1-(trideuteromethyl)pyrrolidin-2-one;
(R)-4-[3-(7-Aminothiazolo[5,4-d]pyrimidin-2-yl)-4-methyl-phenyl]-2-(5-methylisoxazol-3-yl)but-3-yn-2-ol;
(R)-6-[3-[2-(3-Hydroxy-1-methyl-2-oxo-pyrrolidin-3-yl)ethynyl]phenyl]-7H-imidazo[1,5-a]pyrazin-8-one;
(R)-3-((3-(8-Amino-1,5-naphthyridin-2-yl)phenyl)ethynyl)-3-hydroxy-1-methylpyrrolidin-2-one;
(R)-3-((3-(4-Amino-7,8-dihydropyrido[4,3-d]pyrimidin-6(5H)-yl)-4-methylphenyl)ethynyl)-3-hydroxy-1-methylpyrrolidin-2-one;
(R)-6-(3-((3-Hydroxy-1-methyl-2-oxopyrrolidin-3-yl)ethynyl)phenyl)pyrido[3,2-d]pyrimidin-4(3H)-one;

(R)-3-Hydroxy-1-methyl-3-((3-(4-(pyrrolidin-1-yl)pyrido[3,2-d]pyrimidin-6-yl)phenyl)ethynyl)pyrrolidin-2-one;

((R)-3-Hydroxy-1-methyl-3-((3-(pyrido[3,2-d]pyrimidin-6-yl)phenyl)ethynyl)pyrrolidin-2-one;

(R)-3-((3-(4-Amino-5,7,8,9-tetrahydro-6H-pyrimido[5,4-c]azepin-6-yl)phenyl)ethynyl)-3-hydroxy-1-methylpyrrolidin-2-one;

(R)-3-Hydroxy-1-methyl-3-((3-(4-(piperidin-1-yl)pyrido[3,2-d]pyrimidin-6-yl)phenyl)ethynyl)pyrrolidin-2-one;

(R)-3-((3-(4-(3,3-Dimethylazetidin-1-yl)pyrido[3,2-d]pyrimidin-6-yl)phenyl)ethynyl)-3-hydroxy-1-methylpyrrolidin-2-one;

(R)-3-((3-(4-(Ethylamino)pyrido[3,2-d]pyrimidin-6-yl)phenyl)ethynyl)-3-hydroxy-1-methylpyrrolidin-2-one;

(R)-3-Hydroxy-3-((3-(4-(3-hydroxyazetidin-1-yl)pyrido[3,2-d]pyrimidin-6-yl)phenyl)ethynyl)-1-methylpyrrolidin-2-one;

(R)-3-Hydroxy-1-methyl-3-((3-(4-(oxetan-3-ylamino)pyrido[3,2-d]pyrimidin-6-yl)phenyl)ethynyl)pyrrolidin-2-one;

(R)-3-Hydroxy-3-((3-(4-(3-methoxyazetidin-1-yl)pyrido[3,2-d]pyrimidin-6-yl)phenyl)ethynyl)-1-methylpyrrolidin-2-one;

(S)-3-((3-(4-(Azetidin-1-yl)pyrido[3,2-d]pyrimidin-6-yl)phenyl)ethynyl)-3-hydroxy-1-methylpyrrolidin-2-one;

(R)-3-((3-(4-(3,3-Difluoroazetidin-1-yl)pyrido[3,2-d]pyrimidin-6-yl)phenyl)ethynyl)-3-hydroxy-1-methylpyrrolidin-2-one;

(R)-3-((3-(8-(Azetidin-1-yl)-1,7-naphthyridin-2-yl)phenyl)ethynyl)-3-hydroxy-1-methylpyrrolidin-2-one;

(R)-3-((3-(1-(Azetidin-1-yl)isoquinolin-7-yl)phenyl)ethynyl)-3-hydroxy-1-methylpyrrolidin-2-one;

(R)-3-((3-(4-(Azetidin-1-yl)quinolin-6-yl)phenyl)ethynyl)-3-hydroxy-1-methylpyrrolidin-2-one;

(R)-3-((3-(4-(Cyclobutylamino)pyrido[3,2-d]pyrimidin-6-yl)phenyl)ethynyl)-3-hydroxy-1-methylpyrrolidin-2-one;

(R)-3-((3-(4-Amino-2-methylpyrido[3,2-d]pyrimidin-6-yl)-4-(trifluoromethoxy)phenyl)ethynyl)-3-hydroxy-1-methylpyrrolidin-2-one;

(R)—N-(6-(3-((3-Hydroxy-1-methyl-2-oxopyrrolidin-3-yl)ethynyl)phenyl)pyrido[3,2-d]pyrimidin-4-yl)acetamide;

(R)-3-((3-(4-(3-Fluoroazetidin-1-yl)pyrido[3,2-d]pyrimidin-6-yl)phenyl)ethynyl)-3-hydroxy-1-methylpyrrolidin-2-one;

(R)-2-((6-(3-((3-Hydroxy-1-methyl-2-oxopyrrolidin-3-yl)ethynyl)phenyl)pyrido[3,2-d]pyrimidin-4-yl)amino)acetonitrile;

(R)-3-((3-(4-((2,2-Difluoroethyl)amino)pyrido[3,2-d]pyrimidin-6-yl)phenyl)ethynyl)-3-hydroxy-1-methylpyrrolidin-2-one;

(R)-1-(6-(3-((3-Hydroxy-1-methyl-2-oxopyrrolidin-3-yl)ethynyl)phenyl)pyrido[3,2-d]pyrimidin-4-yl)azetidine-3-carbonitrile;

(R)-3-((3-(4-(Azetidin-1-yl)quinazolin-6-yl)phenyl)ethynyl)-3-hydroxy-1-methylpyrrolidin-2-one;

(R)-3-((3-(4-(3-Chloroazetidin-1-yl)pyrido[3,2-d]pyrimidin-6-yl)phenyl)ethynyl)-3-hydroxy-1-methylpyrrolidin-2-one;

(R)-3-Hydroxy-1-methyl-3-((3-(4-(3-(methylsulfonyl)azetidin-1-yl)pyrido[3,2-d]pyrimidin-6-yl)phenyl)ethynyl)pyrrolidin-2-one;

(R)-1-(6-(3-((3-Hydroxy-1-methyl-2-oxopyrrolidin-3-yl)ethynyl)phenyl)pyrido[3,2-d]pyrimidin-4-yl)-N-methylazetidine-3-carboxamide;

(R)-3-((3-(8-(Azetidin-1-yl)pyrido[3,4-d]pyrimidin-2-yl)phenyl)ethynyl)-3-hydroxy-1-methylpyrrolidin-2-one;

(S)-3-((3-(8-(Azetidin-1-yl)pyrido[3,4-d]pyrimidin-2-yl)phenyl)ethynyl)-3-hydroxy-1-methylpyrrolidin-2-one;

(R)-3-((3-(5-Bromo-8-methyl-1,7-naphthyridin-2-yl)phenyl)ethynyl)-3-hydroxy-1-methylpyrrolidin-2-one;

(R)-3-((3-(4,8-Dimethylpyrido[3,2-d]pyrimidin-6-yl)phenyl)ethynyl)-3-hydroxy-1-methylpyrrolidin-2-one;

(R)-2-(3-((3-Hydroxy-1-methyl-2-oxopyrrolidin-3-yl)ethynyl)phenyl)-8-methyl-1,7-naphthyridine-5-carbonitrile;

(R)-3-((3-(5,8-Dimethyl-1,7-naphthyridin-2-yl)phenyl)ethynyl)-3-hydroxy-1-methylpyrrolidin-2-one;

(R)-3-((3-(4-Amino-8-bromopyrido[3,2-d]pyrimidin-6-yl)phenyl)ethynyl)-3-hydroxy-1-methylpyrrolidin-2-one;

(S)-3-((3-(4-Amino-8-bromopyrido[3,2-d]pyrimidin-6-yl)phenyl)ethynyl)-3-hydroxy-1-methylpyrrolidin-2-one;

(R)-3-((3-(4-Amino-8-(tetrahydro-2H-pyran-4-yl)pyrido[3,2-d]pyrimidin-6-yl)phenyl)ethynyl)-3-hydroxy-1-methylpyrrolidin-2-one;

(S)-3-((3-(4-Amino-8-(tetrahydro-2H-pyran-4-yl)pyrido[3,2-d]pyrimidin-6-yl)phenyl)ethynyl)-3-hydroxy-1-methylpyrrolidin-2-one;

(R)-3-Hydroxy-1-methyl-3-((3-(4-phenylpyrido[3,2-d]pyrimidin-6-yl)phenyl)ethynyl)pyrrolidin-2-one;

(R)—N-(6-(3-((3-Hydroxy-1-methyl-2-oxopyrrolidin-3-yl)ethynyl)phenyl)-2-methylpyrido[3,2-d]pyrimidin-4-yl)acetamide;

(R)—N-(6-(3-((3-Hydroxy-1-methyl-2-oxopyrrolidin-3-yl)ethynyl)phenyl)pyrido[3,2-d]pyrimidin-4-yl-2-d)acetamide;

(S)-3-((3-(4-Aminopyrido[3,2-d]pyrimidin-6-yl)-4-methylphenyl)ethynyl)-3-hydroxy-1-methylpyrrolidin-2-one;

(3R,5R)-3-((3-(4-Aminopyrido[3,2-d]pyrimidin-6-yl-2-d)phenyl)ethynyl)-3-hydroxy-1,5-dimethylpyrrolidin-2-one;

(3R,5S)-3-((3-(4-Aminopyrido[3,2-d]pyrimidin-6-yl-2-d)phenyl)ethynyl)-3-hydroxy-1,5-dimethylpyrrolidin-2-one;

(3S,5S)-3-((3-(4-Aminopyrido[3,2-d]pyrimidin-6-yl-2-d)phenyl)ethynyl)-3-hydroxy-1,5-dimethylpyrrolidin-2-one;

(3S,5R)-3-((3-(4-Aminopyrido[3,2-d]pyrimidin-6-yl-2-d)phenyl)ethynyl)-3-hydroxy-1,5-dimethylpyrrolidin-2-one;

(3R,5R)-3-((3-(4-Amino-2-methylpyrido[3,2-d]pyrimidin-6-yl)phenyl)ethynyl)-3-hydroxy-1,5-dimethylpyrrolidin-2-one;

(3S,5S)-3-((3-(4-Amino-2-methylpyrido[3,2-d]pyrimidin-6-yl)phenyl)ethynyl)-3-hydroxy-1,5-dimethylpyrrolidin-2-one;

(3S,5R)-3-((3-(4-Amino-2-methylpyrido[3,2-d]pyrimidin-6-yl)phenyl)ethynyl)-3-hydroxy-1,5-dimethylpyrrolidin-2-one;

(3R,5S)-3-((3-(4-Amino-2-methylpyrido[3,2-d]pyrimidin-6-yl)phenyl)ethynyl)-3-hydroxy-1,5-dimethylpyrrolidin-2-one;

(R)—N-(6-(3-((3-Hydroxy-1-methyl-2-oxopyrrolidin-3-yl)ethynyl)phenyl)pyrido[3,2-d]pyrimidin-4-yl-2-d)methanesulfonamide;

(R)-3-((3-(4-Cyclopropylpyrido[3,2-d]pyrimidin-6-yl)phenyl)ethynyl)-3-hydroxy-1-methylpyrrolidin-2-one;

(R)-3-((3-(4-Aminopyrido[3,2-d]pyrimidin-6-yl)-4-(trifluoromethoxy)phenyl)ethynyl)-3-hydroxy-1-methylpyrrolidin-2-one;

(R)-3-Hydroxy-3-((3-(4-isopropylpyrido[3,2-d]pyrimidin-6-yl)phenyl)ethynyl)-1-methylpyrrolidin-2-one;

(1R,4R,5S)-4-((3-(4-Amino-2-methylpyrido[3,2-d]pyrimidin-6-yl)phenyl)ethynyl)-4-hydroxy-2-methyl-2-azabicyclo[3.1.0]hexan-3-one;

(1S,4S,5R)-4-((3-(4-Amino-2-methylpyrido[3,2-d]pyrimidin-6-yl)phenyl)ethynyl)-4-hydroxy-2-methyl-2-azabicyclo[3.1.0]hexan-3-one;
(1S,4S,5R)-4-((3-(4-Aminopyrido[3,2-d]pyrimidin-6-yl-2-d)phenyl)ethynyl)-4-hydroxy-2-methyl-2-azabicyclo[3.1.0]hexan-3-one;
(1R,4R,5S)-4-((3-(4-Aminopyrido[3,2-d]pyrimidin-6-yl-2-d)phenyl)ethynyl)-4-hydroxy-2-methyl-2-azabicyclo[3.1.0]hexan-3-one;
(R)-3-((3-(4-Amino-8-cyclopentylpyrido[3,2-d]pyrimidin-6-yl-2-d)phenyl)ethynyl)-3-hydroxy-1-methylpyrrolidin-2-one;
(R)-3-Hydroxy-1-methyl-3-((3-(4-(trifluoromethyl)pyrido[3,2-d]pyrimidin-6-yl)phenyl)ethynyl)pyrrolidin-2-one;
(R)-6-(3-((3-Hydroxy-1-methyl-2-oxopyrrolidin-3-yl)ethynyl)phenyl)pyrido[3,2-d]pyrimidine-4-carbonitrile;
(R)-3-Hydroxy-1-methyl-3-((3-(8-methyl-1,7-naphthyridin-2-yl)phenyl)ethynyl)pyrrolidin-2-one;
(1R,4R,5S)-4-((3-(4-amino-8-methylpyrido[3,2-d]pyrimidin-6-yl)phenyl)ethynyl)-4-hydroxy-2-methyl-2-azabicyclo[3.1.0]hexan-3-one;
(R)-3-((3-(4-Amino-8-(aminomethyl)pyrido[3,2-d]pyrimidin-6-yl-2-d)phenyl)ethynyl)-3-hydroxy-1-methylpyrrolidin-2-one;
(R)-3-((3-(4-Amino-8-isopropylpyrido[3,2-d]pyrimidin-6-yl-2-d)phenyl)ethynyl)-3-hydroxy-1-methylpyrrolidin-2-one;
(R)-3-((3-(4-Amino-8-(trifluoromethyl)pyrido[3,2-d]pyrimidin-6-yl)phenyl)ethynyl)-3-hydroxy-1-methylpyrrolidin-2-one;
(R)-3-((3-(4-Amino-2,8-dimethylpyrido[3,2-d]pyrimidin-6-yl)phenyl)ethynyl)-3-hydroxy-1-methylpyrrolidin-2-one;
(R)-3-((3-(4-Amino-8-(methyl-da)pyrido[3,2-d]pyrimidin-6-yl)phenyl)ethynyl)-3-hydroxy-1-methylpyrrolidin-2-one;
(R)-3-((3-(4-Amino-8-(piperidin-4-yl)pyrido[3,2-d]pyrimidin-6-yl-2-d)phenyl)ethynyl)-3-hydroxy-1-methylpyrrolidin-2-one;
(R)-3-((3-(4-Amino-2-fluoropyrido[3,2-d]pyrimidin-6-yl)phenyl)ethynyl)-3-hydroxy-1-methylpyrrolidin-2-one;
(R)-3-((3-(4-Amino-8-(difluoromethyl)pyrido[3,2-d]pyrimidin-6-yl)phenyl)ethynyl)-3-hydroxy-1-methylpyrrolidin-2-one;
(S)-3-((3-(4-Amino-8-(difluoromethyl)pyrido[3,2-d]pyrimidin-6-yl)phenyl)ethynyl)-3-hydroxy-1-methylpyrrolidin-2-one;
(3R,4S*)-3-((3-(4-Amino-2-methylpyrido[3,2-d]pyrimidin-6-yl)phenyl)ethynyl)-3-hydroxy-1,4-dimethylpyrrolidin-2-one;
(3R,4R*)-3-((3-(4-Amino-2-methylpyrido[3,2-d]pyrimidin-6-yl)phenyl)ethynyl)-3-hydroxy-1,4-dimethylpyrrolidin-2-one;
(3S,4S*)-3-((3-(4-Amino-2-methylpyrido[3,2-d]pyrimidin-6-yl)phenyl)ethynyl)-3-hydroxy-1,4-dimethylpyrrolidin-2-one;
(3S,4R*)-3-((3-(4-Amino-2-methylpyrido[3,2-d]pyrimidin-6-yl)phenyl)ethynyl)-3-hydroxy-1,4-dimethylpyrrolidin-2-one;
(R)-3-[2-[3-[4-Amino-8-(dimethylamino)pyrido[3,2-d]pyrimidin-6-yl]phenyl]ethynyl]-3-hydroxy-1-methyl-pyrrolidin-2-one;
(R)-3-[2-[3-[4-Amino-8-(methylamino)pyrido[3,2-d]pyrimidin-6-yl]phenyl]ethynyl]-3-hydroxy-1-methyl-pyrrolidin-2-one;
(R)-3-[2-[3-[4-Amino-8-(isopropylamino)pyrido[3,2-d]pyrimidin-6-yl]phenyl]ethynyl]-3-hydroxy-1-methyl-pyrrolidin-2-one;
(R)-3-[2-[3-[4-Amino-8-(cyclopropylamino)pyrido[3,2-d]pyrimidin-6-yl]phenyl]ethynyl]-3-hydroxy-1-methyl-pyrrolidin-2-one;
(R)-3-[2-[3-[4-Amino-8-(difluoromethoxy)pyrido[3,2-d]pyrimidin-6-yl]phenyl]ethynyl]-3-hydroxy-1-methyl-pyrrolidin-2-one;
(R)-3-[2-[3-[4-Amino-8-(3,3-difluoroazetidin-1-yl)pyrido[3,2-d]pyrimidin-6-yl]phenyl]ethynyl]-3-hydroxy-1-methyl-pyrrolidin-2-one;
(R)-3-[2-[3-(8-Amino-4-methyl-pyrimido[5,4-d]pyrimidin-2-yl)-4-methyl-phenyl]ethynyl]-3-hydroxy-1-methyl-pyrrolidin-2-one;
(R)-3-((3-(4-Amino-8-cyclopropylpyrido[3,2-d]pyrimidin-6-yl)phenyl)ethynyl)-3-hydroxy-1-methylpyrrolidin-2-one;
(R)-3-[2-[3-(4-Amino-8-pyrazol-1-yl-pyrido[3,2-d]pyrimidin-6-yl)phenyl]ethynyl]-3-hydroxy-1-methyl-pyrrolidin-2-one;
(R)-3-[2-[3-[4-Amino-8-(cyclopropoxy)pyrido[3,2-d]pyrimidin-6-yl]phenyl]ethynyl]-3-hydroxy-1-methyl-pyrrolidin-2-one;
(R)-3-[2-[3-[4-Amino-8-[1-(difluoromethyl)pyrazol-4-yl]oxy-pyrido[3,2-d]pyrimidin-6-yl]phenyl]ethynyl]-3-hydroxy-1-methyl-pyrrolidin-2-one;
(R)-3-[2-[3-[4-Amino-8-(3,3,3-trifluoropropoxy)pyrido[3,2-d]pyrimidin-6-yl]phenyl]ethynyl]-3-hydroxy-1-methyl-pyrrolidin-2-one;
(R)-3-[2-[3-[4-Amino-8-(2,2-difluoro-5-azaspiro[2.3]hexan-5-yl)pyrido[3,2-d]pyrimidin-6-yl]phenyl]ethynyl]-3-hydroxy-1-methyl-pyrrolidin-2-one;
(R)-3-((3-(4-Amino-8-ethylpyrido[3,2-d]pyrimidin-6-yl-2-d)phenyl)ethynyl)-3-hydroxy-1-methylpyrrolidin-2-one;
(R)-3-((3-(4-Amino-8-cyclobutylpyrido[3,2-d]pyrimidin-6-yl)phenyl)ethynyl)-3-hydroxy-1-methylpyrrolidin-2-one;
(R)-3-((3-(4-Amino-8-phenylpyrido[3,2-d]pyrimidin-6-yl)phenyl)ethynyl)-3-hydroxy-1-methylpyrrolidin-2-one;
(R)-3-((3-(4-Amino-8-(thiophen-2-yl)pyrido[3,2-d]pyrimidin-6-yl)phenyl)ethynyl)-3-hydroxy-1-methylpyrrolidin-2-one;
(R)-3-((3-(4-Amino-8-(furan-2-yl)pyrido[3,2-d]pyrimidin-6-yl)phenyl)ethynyl)-3-hydroxy-1-methylpyrrolidin-2-one;
(3R)-3-((3-(4-Amino-8-(azetidin-2-yl)pyrido[3,2-d]pyrimidin-6-yl-2-d)phenyl)ethynyl)-3-hydroxy-1-methylpyrrolidin-2-one;
(R)-3-((3-(4-Amino-8-vinylpyrido[3,2-d]pyrimidin-6-yl)phenyl)ethynyl)-3-hydroxy-1-methylpyrrolidin-2-one;
(R)-3-[2-[3-[4-Amino-8-[3-(trifluoromethyl)azetidin-1-yl]pyrido[3,2-d]pyrimidin-6-yl]phenyl]ethynyl]-3-hydroxy-1-methyl-pyrrolidin-2-one;
(R)-3-[2-[3-[4-Amino-8-(azetidin-1-yl)pyrido[3,2-d]pyrimidin-6-yl]phenyl]ethynyl]-3-hydroxy-1-methyl-pyrrolidin-2-one;
(R)-3-((3-(4-Amino-8-((2,2,2-trifluoroethyl)amino)pyrido[3,2-d]pyrimidin-6-yl)phenyl)ethynyl)-3-hydroxy-1-methylpyrrolidin-2-one;
(1R,4R,5S)-4-((3-(7-Aminothiazolo[5,4-d]pyrimidin-2-yl)-4-methylphenyl)ethynyl)-4-hydroxy-2-methyl-2-azabicyclo[3.1.0]hexan-3-one;
(3R,5R)-3-((3-(7-Aminothiazolo[5,4-d]pyrimidin-2-yl)-4-methylphenyl)ethynyl)-3-hydroxy-1,5-dimethylpyrrolidin-2-one; and
pharmaceutically acceptable salts thereof.

Embodiments of the present invention relate to compounds, pharmaceutical compositions containing them, methods of making and purifying them, methods of using them as NIK inhibitors and methods for using them in the treatment of disease states, disorders, and conditions mediated by NIK.

Additional embodiments of the invention are methods of treating a subject suffering from or diagnosed with a disease, disorder, or medical condition mediated by NIK using compounds of the invention.

Additional embodiments, features, and advantages of the invention will be apparent from the following detailed description and through practice of the invention.

DETAILED DESCRIPTION OF THE INVENTION

As used herein, the terms "including", "containing" and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

Unless qualified specifically in particular instances of use, the term "alkyl" refers to a straight- or branched-chain alkyl group having from 1 to 8 carbon atoms in the chain. Examples of alkyl groups include methyl (Me), ethyl (Et), n-propyl, iso-propyl, butyl, iso-butyl, sec-butyl, tert-butyl (tBu), pentyl, iso-pentyl, tert-pentyl, hexyl, iso-hexyl, and groups that in light of the ordinary skill in the art and the teachings provided herein would be considered equivalent to any one of the foregoing examples. "$C_1$-$C_4$alkyl" refers to straight- or branched-chain alkyl group having from 1 to 4 carbon atoms in the chain.

The term "halo" represents chloro, fluoro, bromo, or iodo.

The term "haloalkyl" refers to a straight- or branched-chain alkyl group having from 1 to 6 carbon atoms in the chain optionally substituting one or more H with halo. The term "$C_1$-$C_4$ haloalkyl" as used here refers to a straight- or branched-chain alkyl group having from 1 to 4 carbon atoms in the chain, optionally substituting one or more H with halo. Examples of "haloalkyl" groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl ($CF(CF_3)_2$), and groups that in light of the ordinary skill in the art and the teachings provided herein would be considered equivalent to any one of the foregoing examples.

The term "cycloalkyl" refers to a saturated, monocyclic, fused polycyclic, or spiro polycyclic carbocycle having from 3 to 10 ring atoms per carbocycle. Illustrative examples of cycloalkyl groups include the following entities, in the form of properly bonded moieties, cyclopropyl, cyclobutyl, cyclopentyl, cyclohexyl, cycloheptyl, and cyclooctyl.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the given structural formula as well as certain variations or forms. In particular, compounds of any formula given herein may have asymmetric centers and therefore may exist in different enantiomeric forms. All optical isomers and stereoisomers of the compounds of the general formula, and mixtures thereof, are considered within the scope of such formula. The compounds of this invention may possess one or more asymmetric centers; such compounds can therefore be produced as individual (R)- or (S)-stereoisomers or as mixtures thereof. Thus, any formula given herein is intended to represent a racemate, one or more of its enantiomeric forms, one or more of its diastereomeric forms, and mixtures thereof, unless expressly indicated otherwise.

Certain examples contain chemical structures that comprise (R*) or (S*) terminology. When (R*) or (S*) is used in the name of a compound or in the chemical representation of the compound, it is intended to mean that the compound is a single isomer at that stereocenter, however absolute configuration of that stereocenter has not been established. Thus, a compound designated as (R*) refers to a compound that is a single isomer at that stereocenter with an absolute configuration of either (R) or (S). A compound designated as (S*) refers to a compound that is a single isomer at that stereocenter with an absolute configuration of either (R) or (S). In cases where the absolute stereochemistry has been established, the structures are named using (R) or (S). The use of the term (R, S) or "racemic" in the name of the compound indicates that the compound is a racemate.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number in an enriched form. Examples of isotopes that can be incorporated into compounds of the invention in a form that exceeds natural abundances include isotopes of hydrogen, carbon, nitrogen, and oxygen such as $^2H$ (or D), $^3H$, $^{11}C$, $^{13}C$, $^{14}C$, $^{15}N$, $^{18}O$, and $^{17}O$, respectively. Such isotopically labeled compounds are useful in metabolic studies (for example with $^{14}C$), reaction kinetic studies (with, for example deuterium (i.e., D or $^2H$); or tritium (i.e., T or $^3H$)), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be used for PET or SPECT studies. Further, substitution with heavier isotopes such as deuterium may afford certain therapeutic advantages resulting from greater metabolic stability, for example increased local in vivo half-life or reduced dosage requirements. Isotopically labeled compounds of this invention can generally be prepared by carrying out the procedures disclosed in the schemes or in the examples and preparations described below by substituting a readily available isotopically labeled reagent for a non-isotopically labeled reagent.

When the same plurality of substituents is assigned to various groups, the specific individual substituent assignment to each of such groups is meant to be independently made with respect to the specific individual substituent assignments to the remaining groups. By way of illustration, but not as a limitation, if each of groups Q and R can be H or F, the choice of H or F for Q is made independently of the choice of H or F for R, so the choice of assignment for Q does not determine or condition the choice of assignment for R, or vice-versa, unless it is expressly indicated otherwise. Illustrative claim recitation in this regard would read as "each of Q and R is independently H or F", or "each of Q and R is independently selected from the group consisting of H and F".

"Tautomers" refer to compounds that are interchangeable forms of a particular compound structure, and that vary in the displacement of hydrogen and electrons. Thus, two structures that have an H member in different positions may be in equilibrium while satisfying valency rules. For example, enols and ketones are tautomers because they are rapidly interconverted by treatment with either acid or base. When referring to any formula given herein that comprises at least one tautomer, such given formula is meant to encompass all the related tautomers unless indicated expressly otherwise.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" or "$S^1_{example}$ is $S_1$ or $S_2$, and $S^2_{example}$ is $S_3$ or $S_4$" is accordingly used herein for the sake of brevity, but not by way of limitation. The foregoing first example on substituent terminology, which is stated in generic terms, is meant to illustrate the various substituent assignments described herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" or "$S_{example}$ is $S_1$, $S_2$, or $S_3$" is accordingly used herein for the sake of brevity, but not by way of limitation. The foregoing second example on substituent terminology, which is stated in generic terms, is meant to illustrate the various substituent assignments described herein.

The nomenclature "$C_i$-$C_j$" with j>i, when applied herein to a class of substituents, is meant to refer to embodiments of this invention for which each and every one of the number of carbon members, from i to j including i and j, is independently realized. By way of example, the term $C_1$-$C_3$ refers independently to embodiments that have one carbon member ($C_1$), embodiments that have two carbon members ($C_2$), and embodiments that have three carbon members ($C_3$). For example, the term $C_i$-$C_j$alkyl refers to an aliphatic chain, whether straight or branched, with a total number N of carbon members in the chain that satisfies i≤N≤j, with i>j.

A "pharmaceutically acceptable salt" is a salt of a compound, such as compounds of the present invention, that is non-toxic, biologically tolerable, or otherwise biologically suitable for administration to the subject. See, generally, S. M. Berge, et al., "Pharmaceutical Salts", J. Pharm. Sci. 66, 1-19 (1977); Handbook of Pharmaceutical Salts, Properties, Selection, and Use, Stahl and Wermuth, Eds., Wiley-VCH and VHCA, Zurich, 2002; and G. S. Paulekuhn, et al., "Pharmaceutical ingredient salt selection based on analysis of the Orange Book database", J. Med. Chem. 50, 6665-72 (2007). Compounds of the invention may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of the invention contains at least one basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, and phosphoric acid, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

Embodiments of this invention include compounds of Formula (I), and pharmaceutically acceptable salts thereof

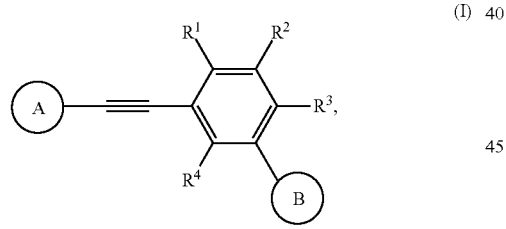
(I)

wherein
R$^1$ is H or —CH$_3$;
R$^2$ is H or —CH$_3$;
R$^3$ is H, —C$_1$-C$_5$alkyl, —OCH$_3$, or —O—C$_1$-C$_3$haloalkyl;
R$^4$ is H or —CH$_3$;
moiety

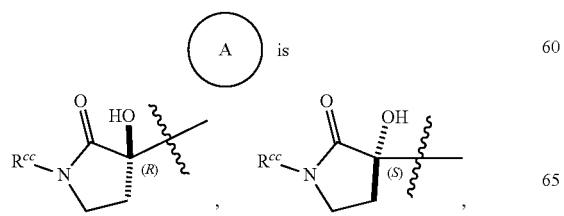
is

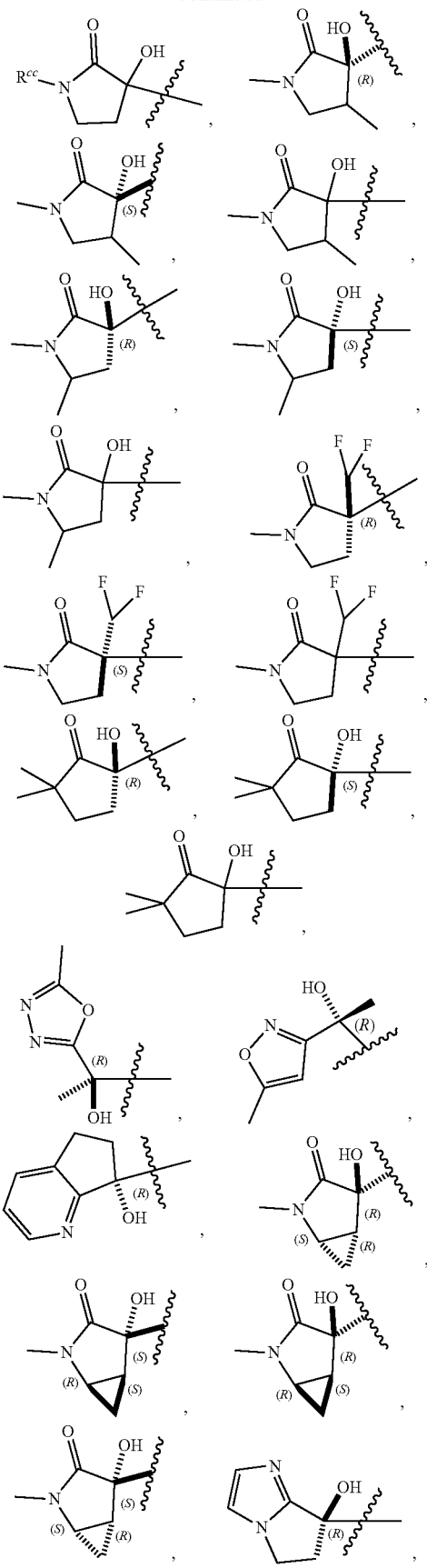

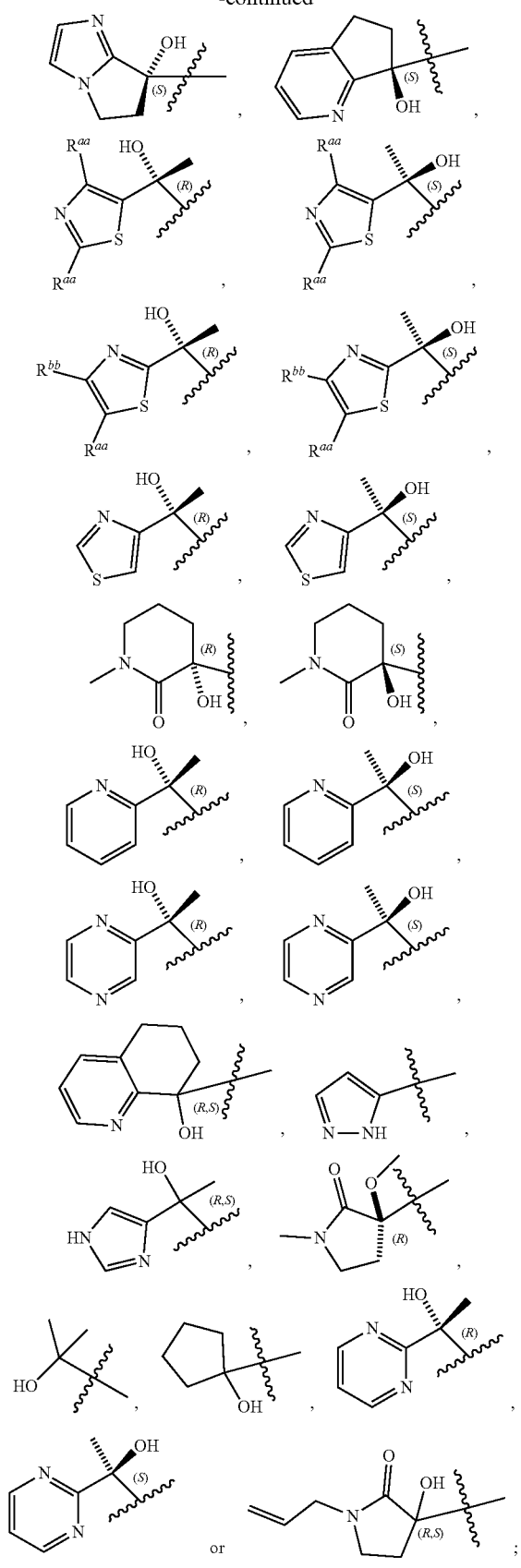
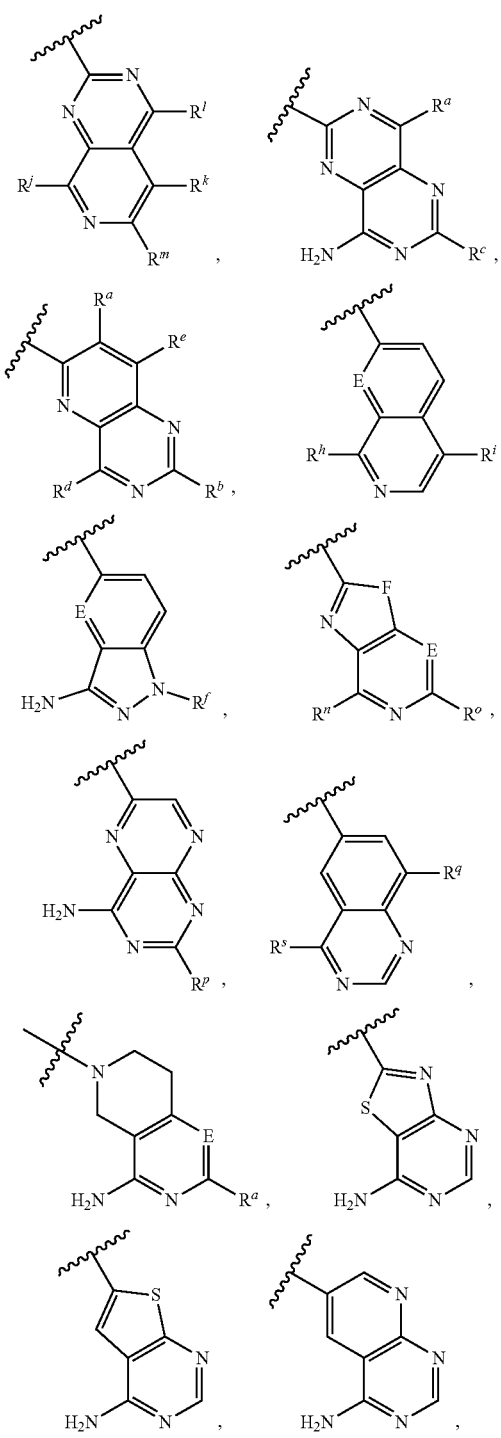
$R^{aa}$ is H or —CH$_3$;
$R^{bb}$ is H, —CH$_3$ or —CF$_3$;
$R^{cc}$ is —CH$_3$, —CD$_3$ or —CH$_2$CF$_3$;
moiety
Ⓑ is -continued

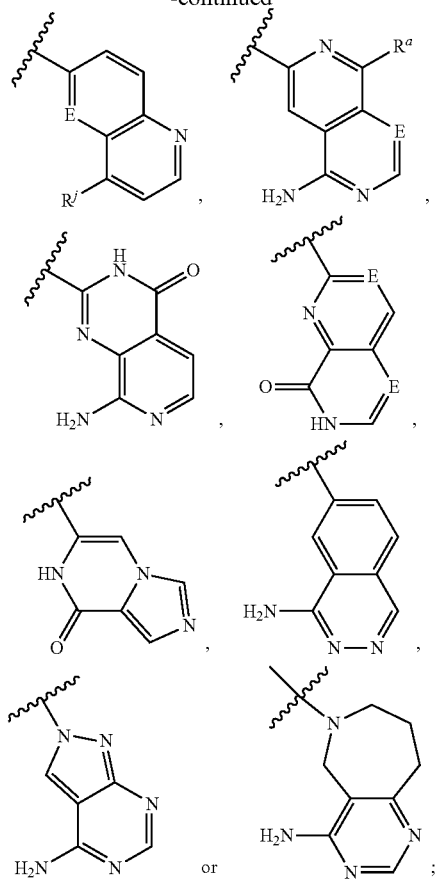

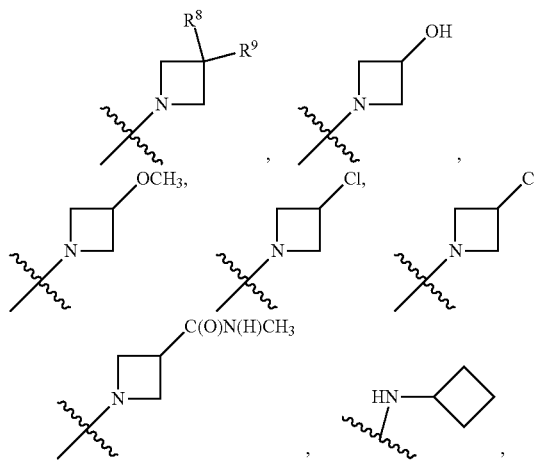

E is N or CH;
F is O, S, NH or NCH$_3$;
R$^a$ is H or —CH$_3$;
R$^b$ is H, D, —OH, F, —C$_1$-C$_5$alkyl, —CH$_2$OCH$_3$, —C$_1$-C$_5$haloalkyl, —NH$_2$, cyclopropyl, or —CH$_2$OH;
R$^c$ is H, D or —CH$_3$;
R$^d$ is H, —CN, —CF$_3$, —C$_1$-C$_5$alkyl, —C$_3$-C$_6$cycloalkyl, —O—C$_1$-C$_3$alkyl, —N(R$^6$)R$^7$, -continued

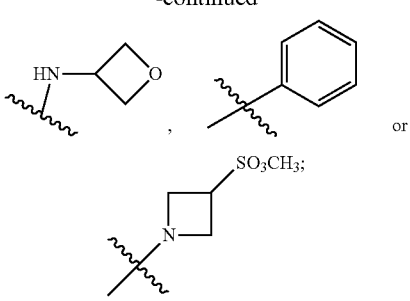

R$^6$ is H or —C$_1$-C$_3$alkyl;
R$^7$ is H, —C$_1$-C$_3$alkyl, —SO$_2$CH$_3$, —COCH$_3$, —C$_1$-C$_4$haloalkyl or CH$_2$CN;
or R$^6$ and R$^7$ are taken together with the nitrogen to which they are attached to form
the moiety

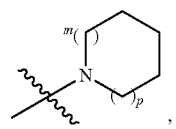

wherein m is 0 or 1, and p is 0 or 1;
R$^8$ is H, F or —C$_1$-C$_3$alkyl;
R$^9$ is H, F or —C$_1$-C$_3$alkyl;
R$^e$ is H, —CD$_3$, Br, —C$_1$-C$_5$alkyl, —C$_3$-C$_5$cycloalkyl,

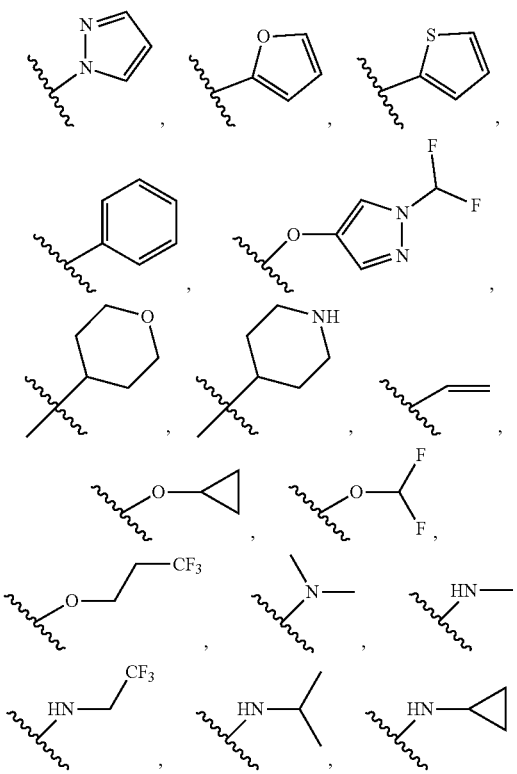

-continued

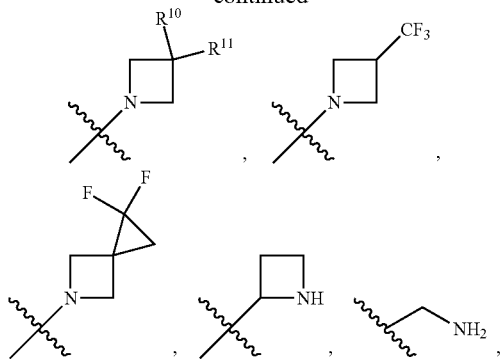

or

—C₁-C₅alkyl substituted with 1 to 3 R^g groups, wherein R^g is —NH₂, or F;

R¹⁰ is H or F;
R¹¹ is H or F;
R is H, —CH₃ or

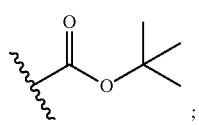

R^h is —CH₃, —NH₂ or

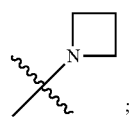

R^i is H, —CH₃, —CN, Br,

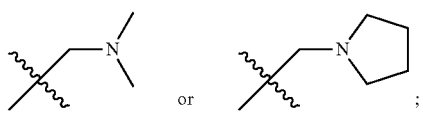

R^j is —NH₂ or

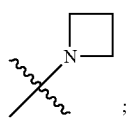

R^k is H, —CF₃, I, Cl, Br, —CN, —C₁-C₆alkyl,

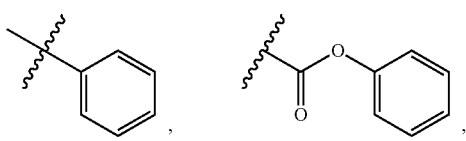

-continued

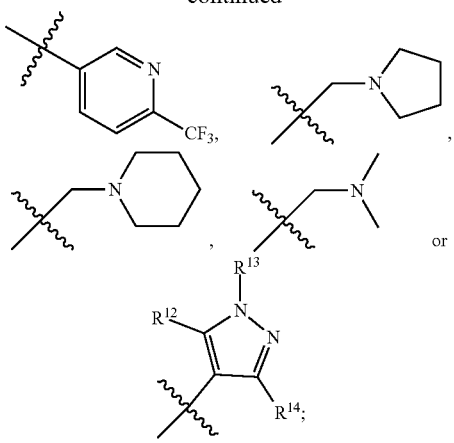

R¹² is H or —CH₃;
R¹³ is H, —CH₃, —CH₂(C)(CH₃)₂OH, —(CH₂)₃CN, or —(CH₂)₂NH₂;
R¹⁴ is H or —CH₃;
R^l is H, —C₁-C₄alkyl, —CF₃,

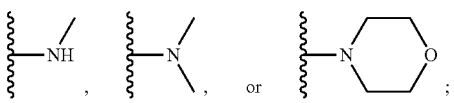

R^m is H or —CH₃;
R^n is —NH₂;
R^o is H or —CH₃;
R^p is H or —CH₃;
R^q is H, —CN, F, Cl, —OCH₃, —CF₃, or —CH₃; and
R^s is —NH₂ or

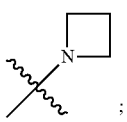

provided that when said moiety

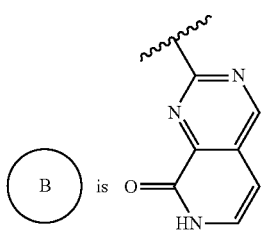

and R¹, R², R³ and R⁴ are H, then said moiety

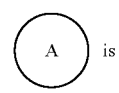 is

-continued
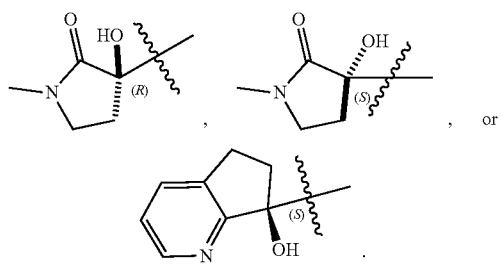
Additional illustrative embodiments of the invention are compounds of Formula (I) and pharmaceutically acceptable salts thereof, wherein
moiety
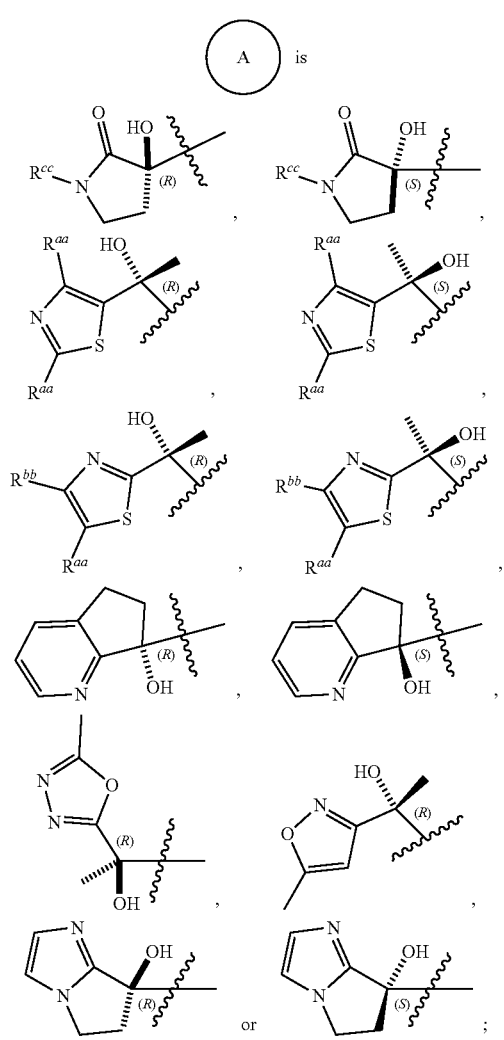
or
;
and moiety
B is
-continued
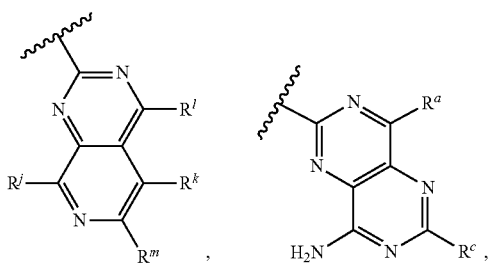

-continued
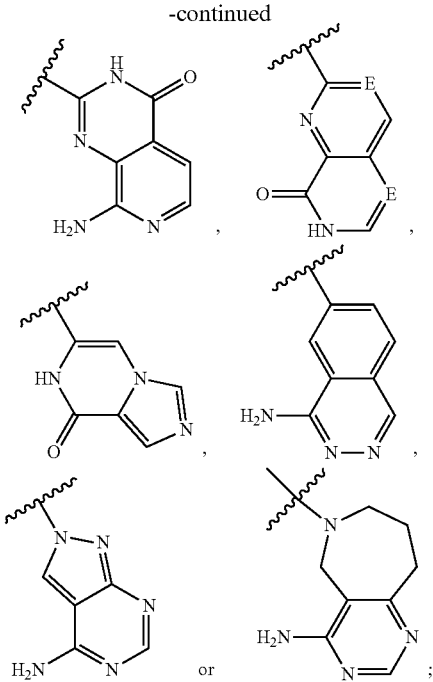
provided that when said moiety
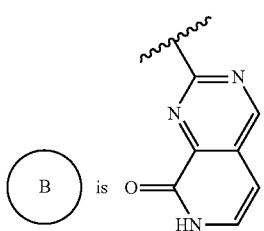
and R[1], R[2], R[3] and R[4] are H, then said moiety
A is
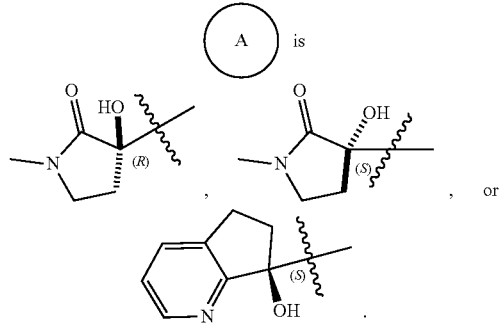
Additional illustrative embodiments of the invention are compounds of Formula (I) and pharmaceutically acceptable salts thereof, wherein
moiety
A is
-continued
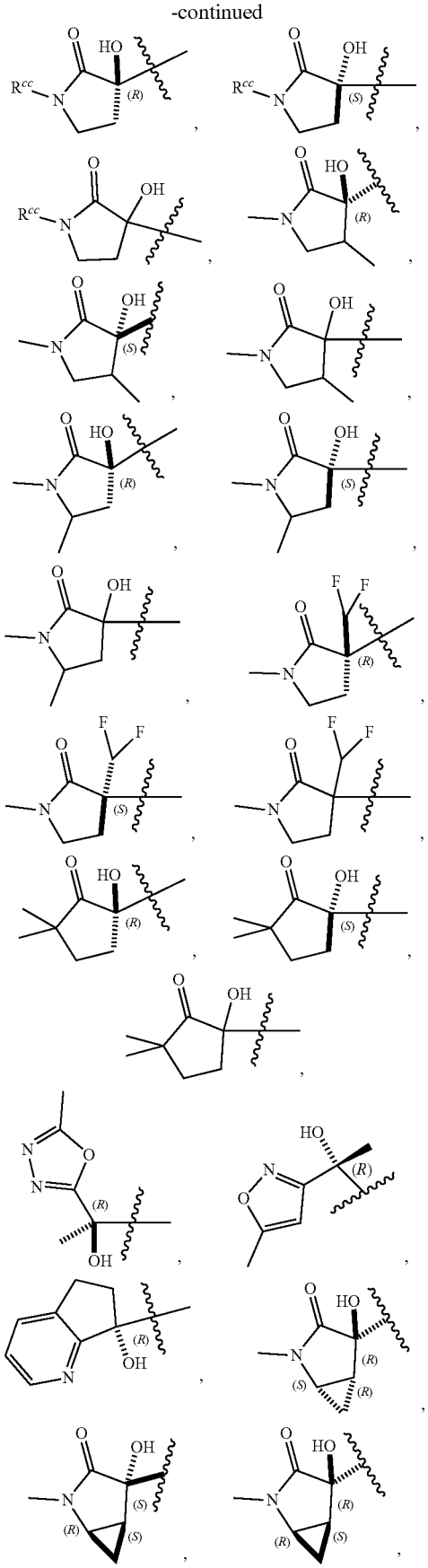

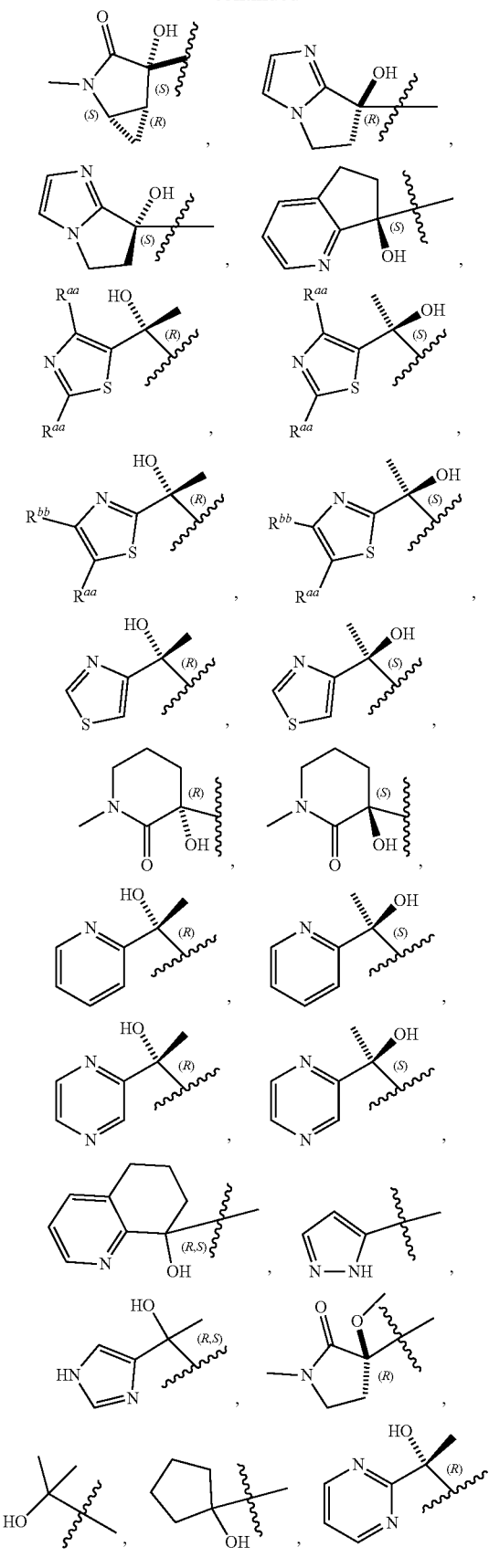
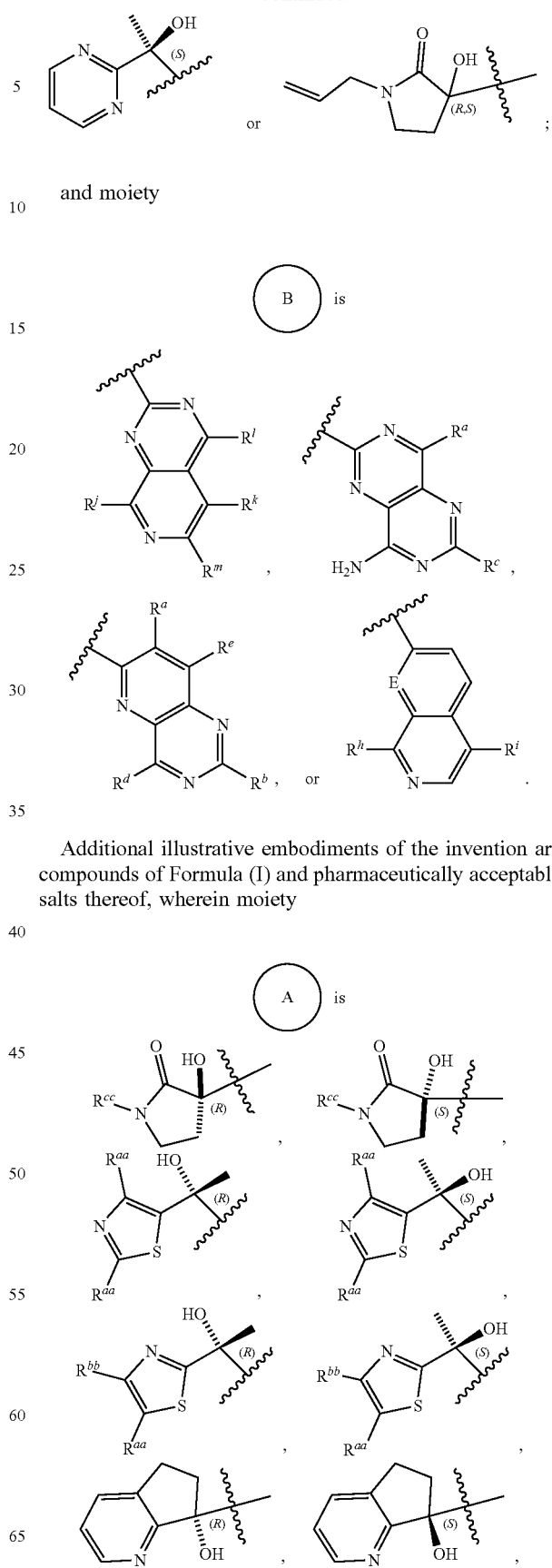
and moiety
B is
Additional illustrative embodiments of the invention are compounds of Formula (I) and pharmaceutically acceptable salts thereof, wherein moiety
A is -continued

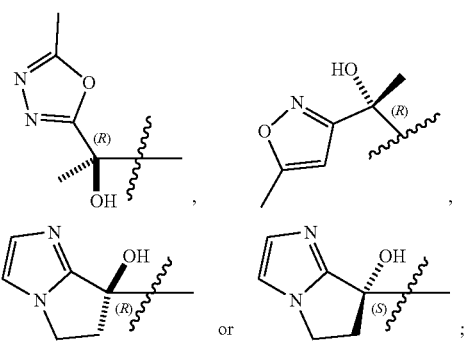

and moiety

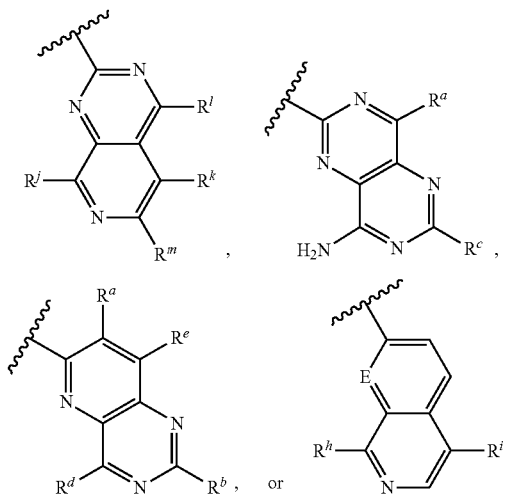

Additional illustrative embodiments of the invention are compounds of Formula (I) and pharmaceutically acceptable salts thereof, wherein moiety

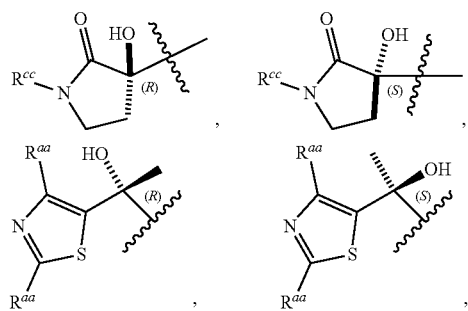

-continued

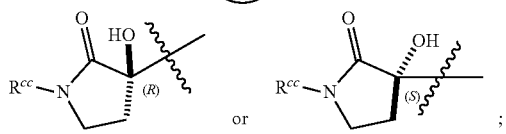

and moiety

B is

[structures]

Additional illustrative embodiments of the invention are compounds of Formula (I) and pharmaceutically acceptable salts thereof, wherein $R^1$ is H; $R^2$ is H; $R^3$ is H; $R^4$ is H;

moiety

A is

[structures]

and
moiety

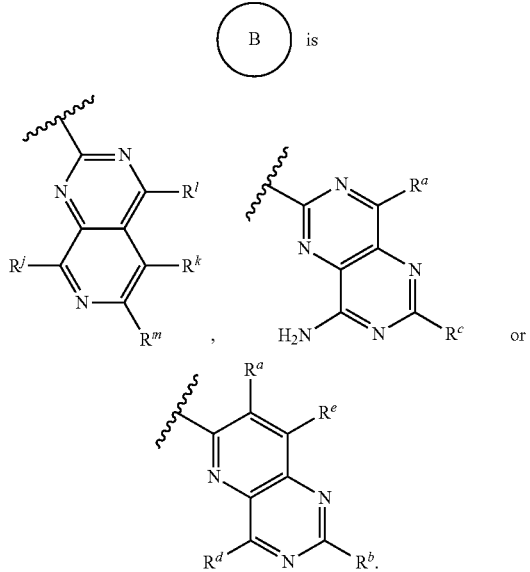

Additional illustrative embodiments of the invention are compounds of Formula (I) and pharmaceutically acceptable salts thereof, wherein $R^1$ is H; $R^2$ is H; $R^3$ is H or —$C_1$-$C_5$alkyl; $R^4$ is H;

moiety

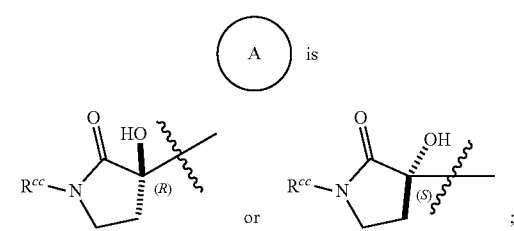

and
moiety

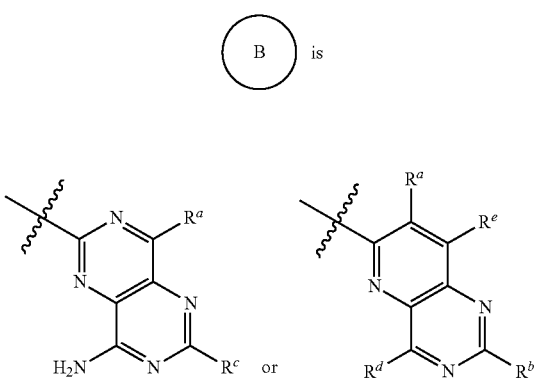

Additional illustrative embodiments of the invention are compounds of Formula (I) and pharmaceutically acceptable salts thereof, wherein
$R^1$ is H; $R^2$ is H; $R^3$ is H or —$C_1$-$C_5$alkyl; $R^4$ is H;
moiety

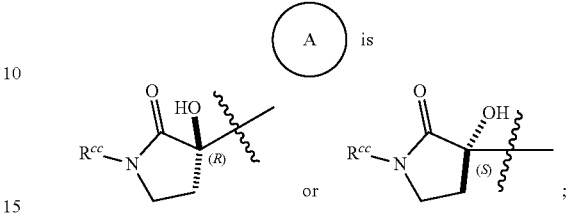

and
moiety

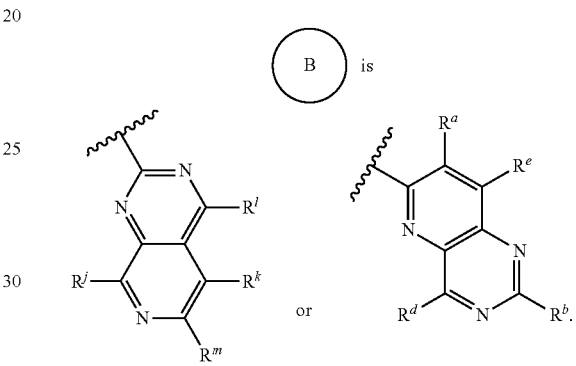

Additional illustrative embodiments of the invention are compounds of Formula (I) and pharmaceutically acceptable salts thereof, wherein
$R^1$ is H; $R^2$ is H; $R^3$ is H; $R^4$ is H;
moiety

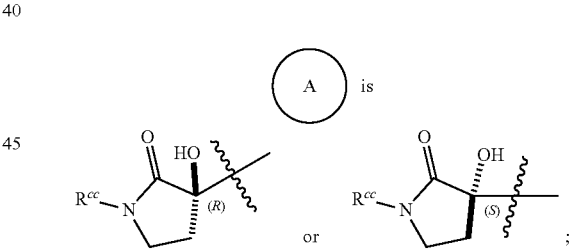

and
moiety

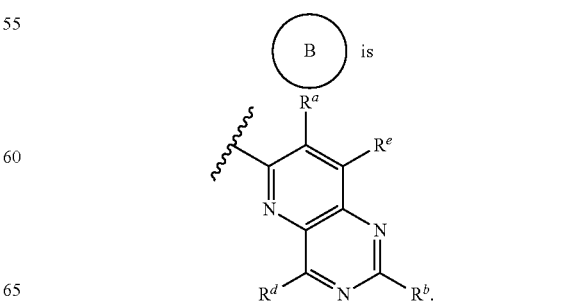

Additional illustrative embodiments of the invention are compounds of Formula (I) and pharmaceutically acceptable salts thereof, wherein
R¹ is H R² is H; R³ is H; R⁴ is H;
moiety

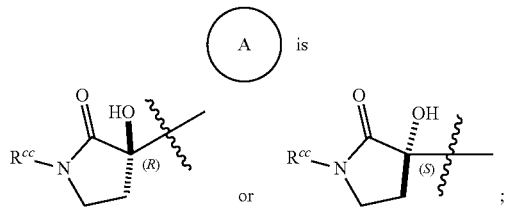

R$^{cc}$ is —CH₃;
moiety

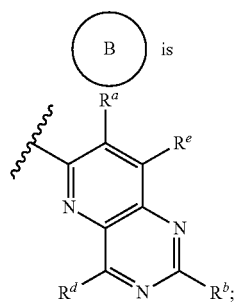

and R$^b$ is —CH₃.

Additional illustrative embodiments of the invention are compounds of Formula (I) and pharmaceutically acceptable salts thereof, wherein
R¹ is H; R² is H; R³ is H; R⁴ is H;
moiety

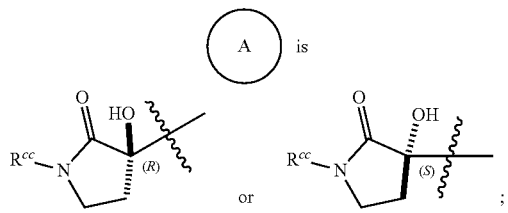

R$^{cc}$ is —CD₃;
moiety

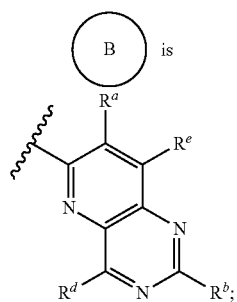

and R$^b$ is —CH₃.

Additional illustrative embodiments of the invention are compounds of Formula (I) and pharmaceutically acceptable salts thereof, wherein moiety

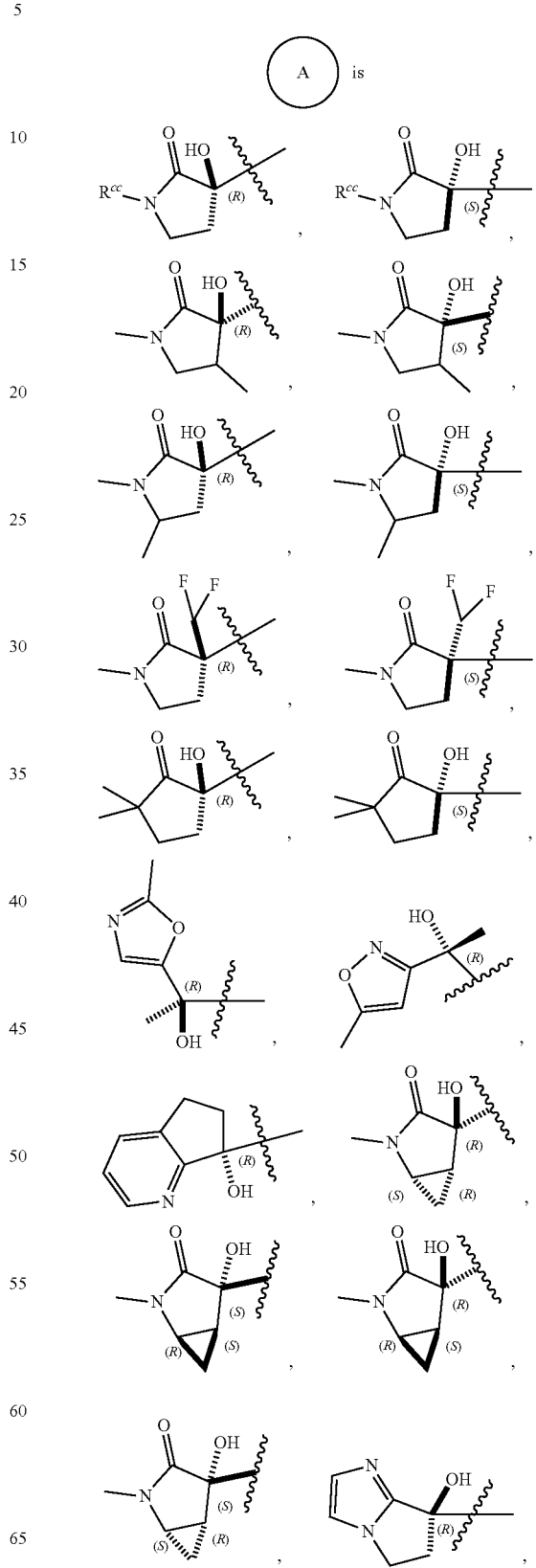

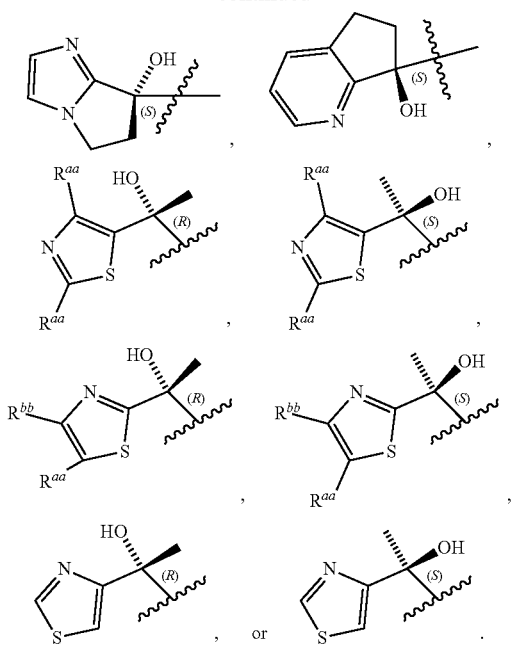
Additional illustrative embodiments of the invention are compounds of Formula (I) and pharmaceutically acceptable salts thereof, wherein moiety Ⓐ is
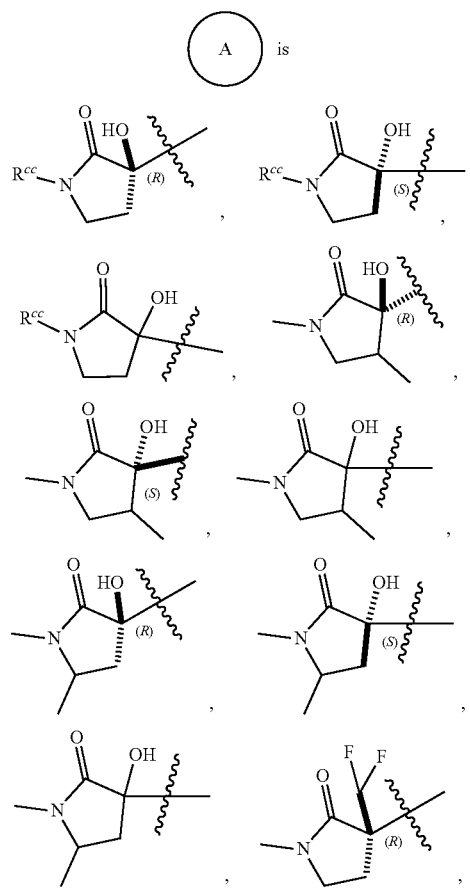
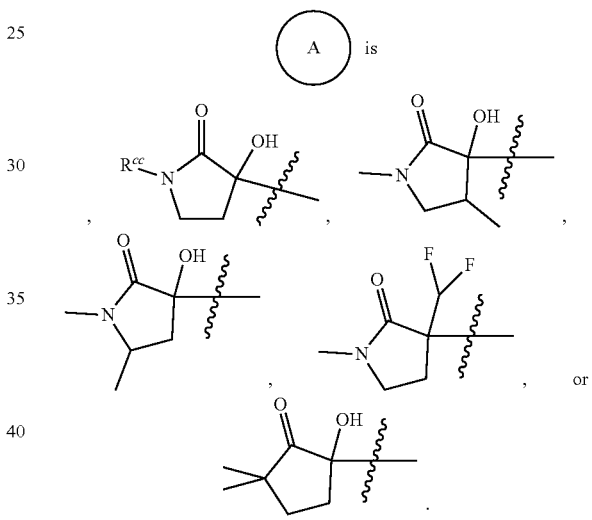
Additional illustrative embodiments of the invention are compounds of Formula (I) and pharmaceutically acceptable salts thereof, wherein moiety Ⓐ is
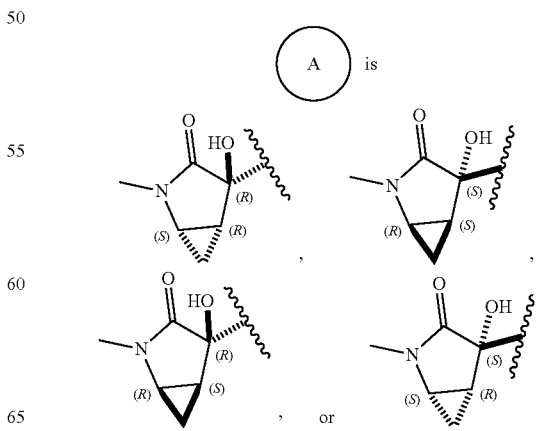

Additional illustrative embodiments of the invention are compounds of Formula (I) and pharmaceutically acceptable salts thereof, wherein moiety

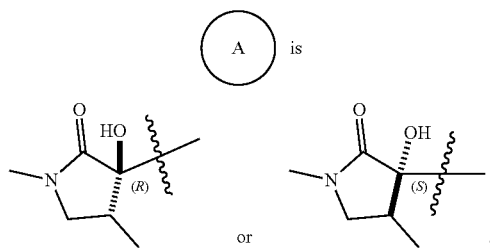

or

Additional illustrative embodiments of the invention are compounds of Formula (I) and pharmaceutically acceptable salts thereof, wherein moiety

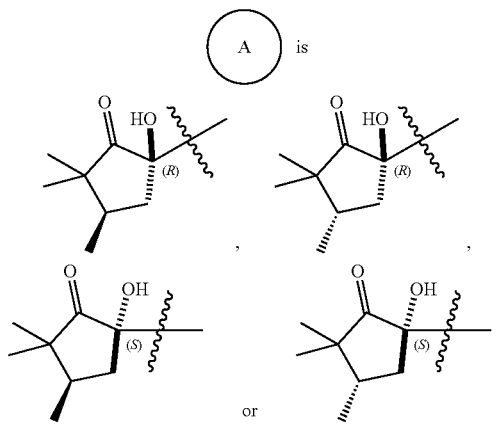

Additional illustrative embodiments of the invention are compounds of Formula (I) and pharmaceutically acceptable salts thereof, wherein moiety

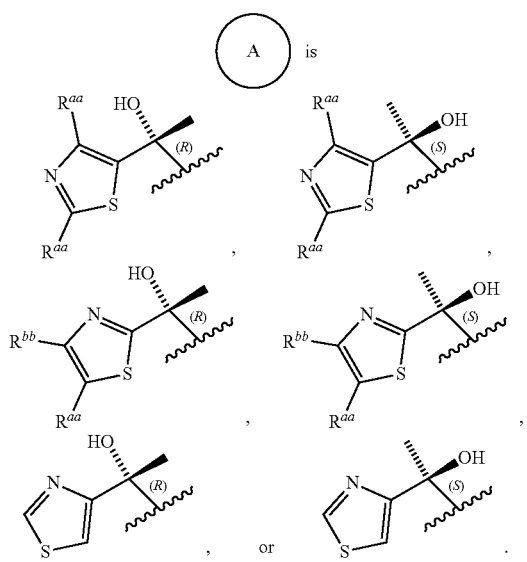

Additional illustrative embodiments of the invention are compounds of Formula (I) and pharmaceutically acceptable salts thereof, wherein moiety

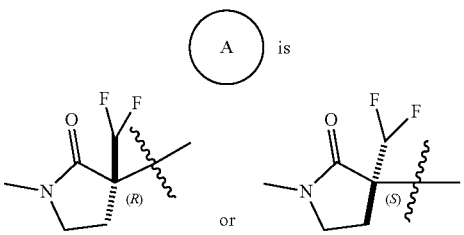

Additional illustrative embodiments of the invention are compounds of Formula (I) and pharmaceutically acceptable salts thereof, wherein moiety

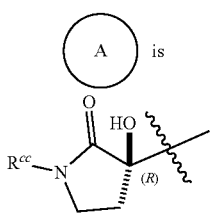

Additional illustrative embodiments of the invention are compounds of Formula (I) and pharmaceutically acceptable salts thereof, wherein moiety

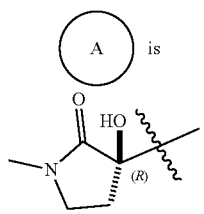

Additional illustrative embodiments of the invention are compounds of Formula (I) and pharmaceutically acceptable salts thereof, wherein moiety

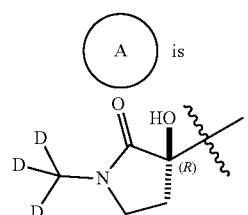

Additional illustrative embodiments of the invention are compounds of Formula (I) and pharmaceutically acceptable salts thereof, wherein moiety -continued

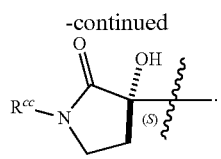

Additional illustrative embodiments of the invention are compounds of Formula (I) and pharmaceutically acceptable salts thereof, wherein moiety

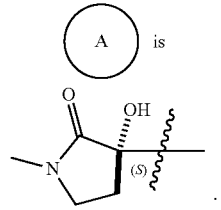 is

Additional illustrative embodiments of the invention are compounds of Formula (I) and pharmaceutically acceptable salts thereof, wherein moiety A is

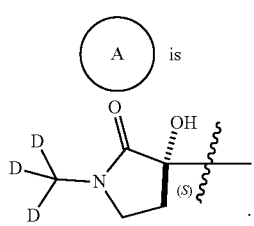

Additional illustrative embodiments of the invention are compounds of Formula (I) and pharmaceutically acceptable salts thereof, wherein moiety A is

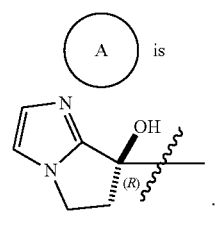

Additional illustrative embodiments of the invention are compounds of Formula (I) and pharmaceutically acceptable salts thereof, wherein moiety A is

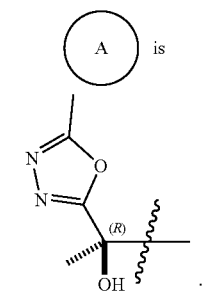

Additional illustrative embodiments of the invention are compounds of Formula (I) and pharmaceutically acceptable salts thereof, wherein moiety B is

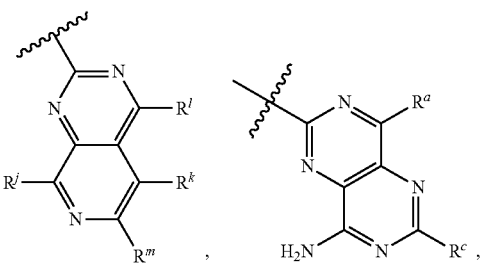

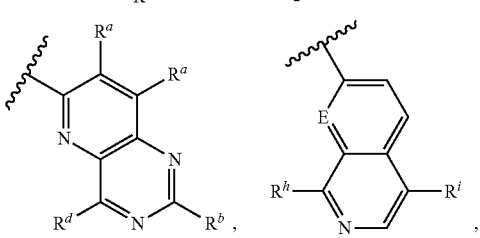

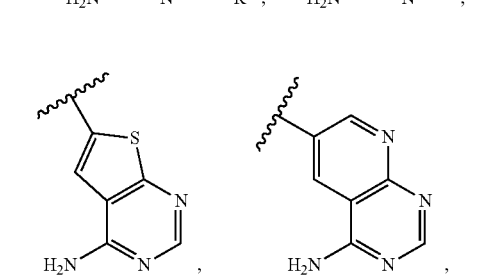

-continued

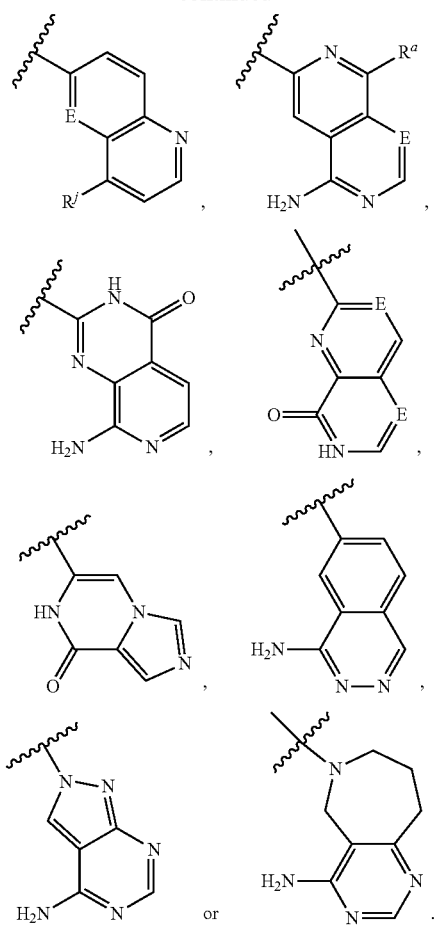

Additional illustrative embodiments of the invention are compounds of Formula (I) and pharmaceutically acceptable salts thereof, wherein moiety B is

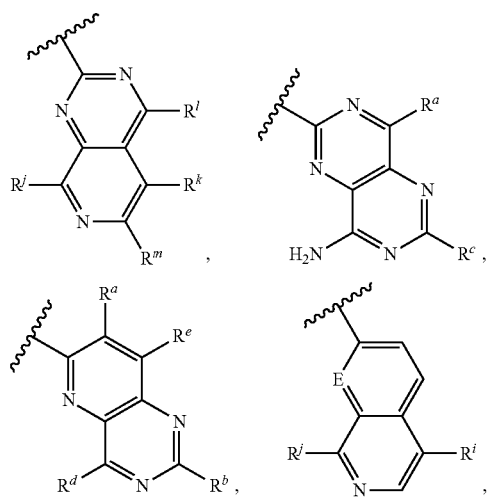

-continued

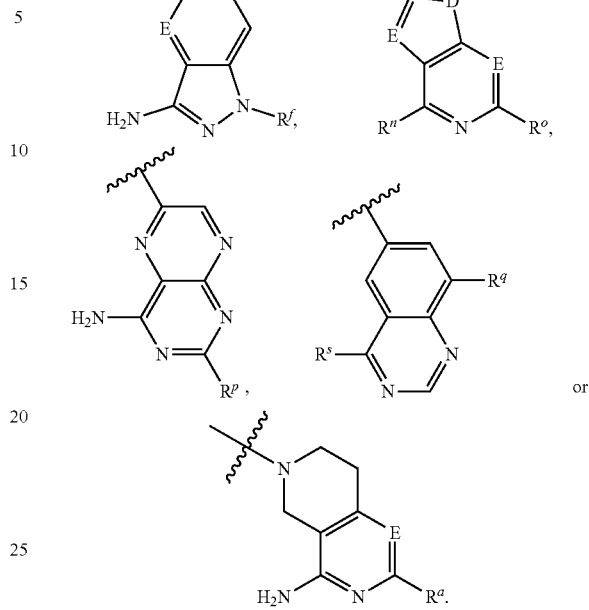

Additional illustrative embodiments of the invention are compounds of Formula (I) and pharmaceutically acceptable salts thereof, wherein moiety B is

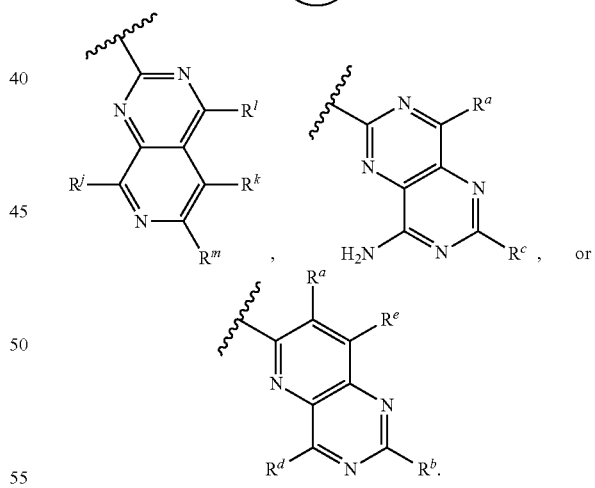

Additional illustrative embodiments of the invention are compounds of Formula (I) and pharmaceutically acceptable salts thereof, wherein moiety B is -continued

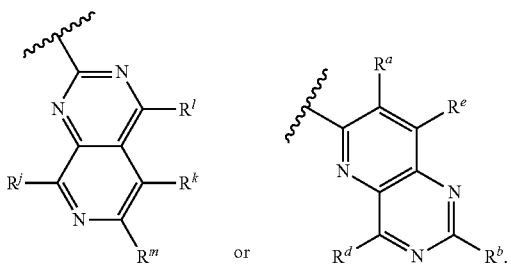

or

Additional illustrative embodiments of the invention are compounds of Formula (I) and pharmaceutically acceptable salts thereof, wherein moiety B is

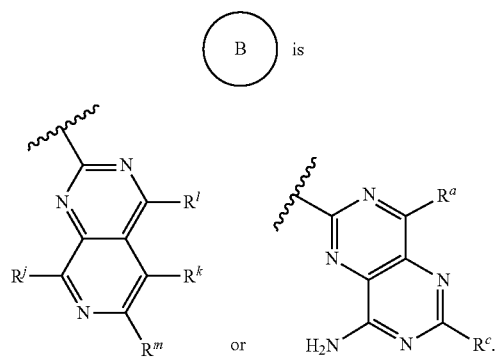

or

Additional illustrative embodiments of the invention are compounds of Formula (I) and pharmaceutically acceptable salts thereof, wherein moiety B is

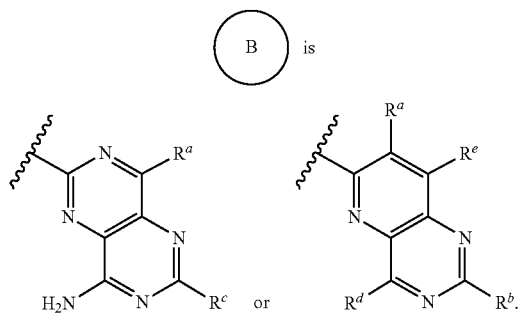

or

Additional illustrative embodiments of the invention are compounds of Formula (I) and pharmaceutically acceptable salts thereof, wherein moiety B is -continued

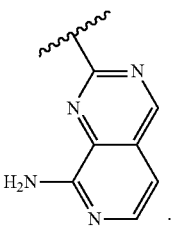

Additional illustrative embodiments of the invention are compounds of Formula (I) and pharmaceutically acceptable salts thereof, wherein moiety B is

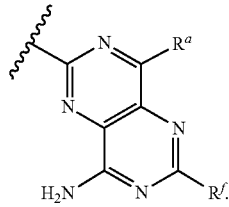

Additional illustrative embodiments of the invention are compounds of Formula (I) and pharmaceutically acceptable salts thereof, wherein moiety B is

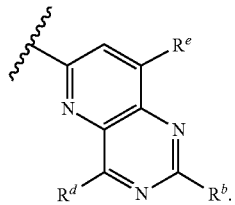

Additional illustrative embodiments of the invention are compounds of Formula (I) and pharmaceutically acceptable salts thereof, wherein moiety B is

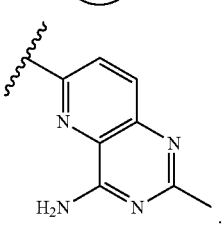

Additional illustrative embodiments of the invention are compounds of Formula (I) and pharmaceutically acceptable salts thereof, wherein moiety

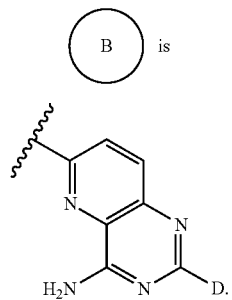 D.

Additional illustrative embodiments of the invention are compounds of Formula (I) and pharmaceutically acceptable salts thereof, wherein moiety

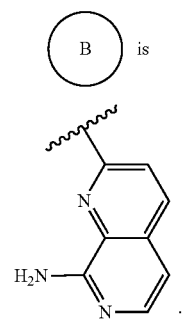

Additional illustrative embodiments of the invention are compounds of Formula (I) and pharmaceutically acceptable salts thereof, wherein moiety

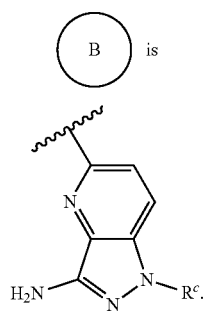

Additional illustrative embodiments of the invention are compounds of Formula (I) and pharmaceutically acceptable salts thereof, wherein moiety

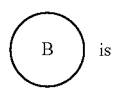

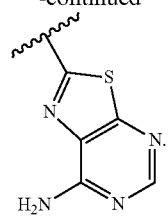

Additional illustrative embodiments of the invention are compounds of Formula (I) and pharmaceutically acceptable salts thereof, wherein moiety

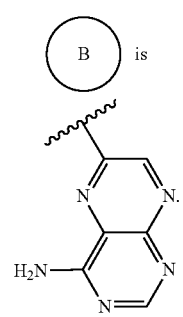

Additional illustrative embodiments of the invention are compounds of Formula (I) and pharmaceutically acceptable salts thereof, wherein moiety

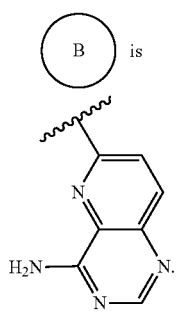

Additional illustrative embodiments of the invention are compounds of Formula (I) and pharmaceutically acceptable salts thereof, wherein moiety

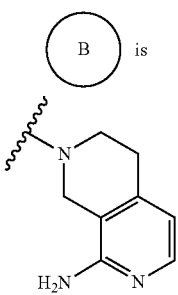

Additional illustrative embodiments of the invention are compounds of Formula (I) and pharmaceutically acceptable salts thereof, wherein moiety A is

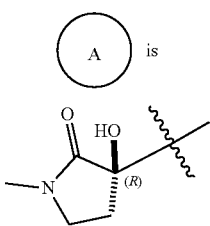

and moiety

B is

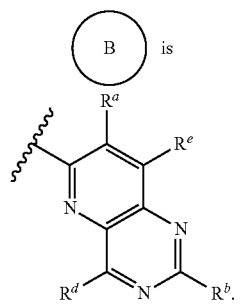

An additional illustrative embodiments of the invention is are compounds of Formula (I) and pharmaceutically acceptable salts thereof, wherein moiety A is

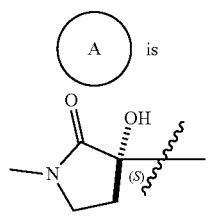

and moiety

B is

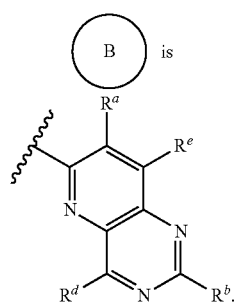

An additional illustrative embodiments of the invention is are compounds of Formula (I) and pharmaceutically acceptable salts thereof, wherein moiety A is

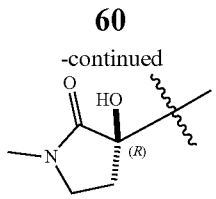

and moiety

B is

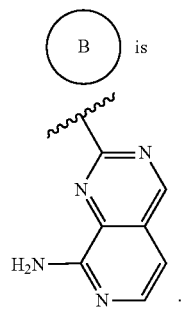

An additional illustrative embodiments of the invention is are compounds of Formula (I) and pharmaceutically acceptable salts thereof, wherein moiety A is

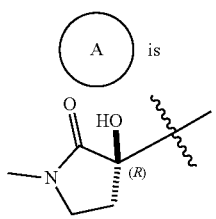

and moiety

B is

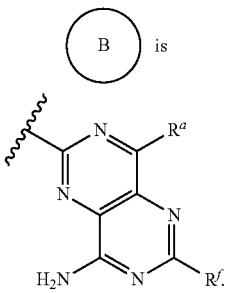

Additional illustrative embodiments of the invention are compounds of Formula I) and pharmaceutically acceptable salts thereof, wherein moiety A is

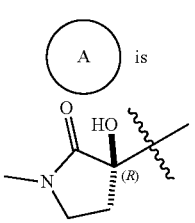

and moiety

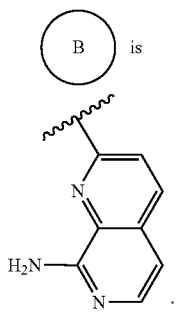

Additional illustrative embodiments of the invention are compounds of Formula (I) and pharmaceutically acceptable salts thereof, wherein moiety

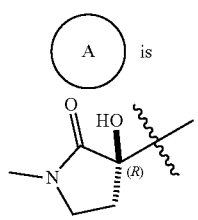

and moiety

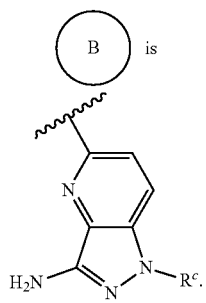

Additional illustrative embodiments of the invention are compounds of Formula (I) and pharmaceutically acceptable salts thereof, wherein moiety

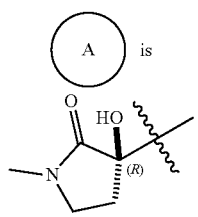

and moiety

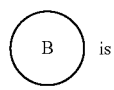

-continued

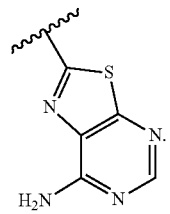

Additional illustrative embodiments of the invention are compounds of Formula (I) and pharmaceutically acceptable salts thereof, wherein moiety

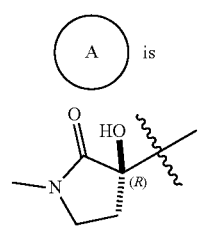

and moiety

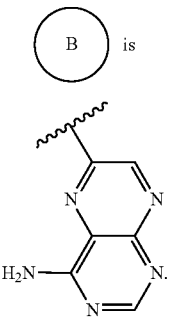

Additional illustrative embodiments of the invention are compounds of Formula (I) and pharmaceutically acceptable salts thereof, wherein moiety

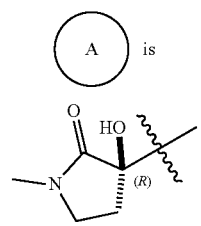

and moiety

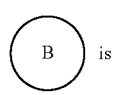

-continued

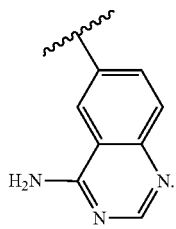

Additional illustrative embodiments of the invention are compounds of Formula (I) and pharmaceutically acceptable salts thereof, wherein moiety

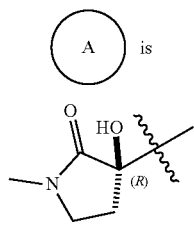 is and moiety

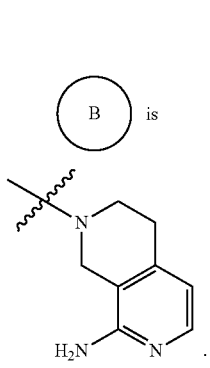 is

Additional illustrative embodiments of the invention are compounds of Formula (I) and pharmaceutically acceptable salts thereof, wherein moiety

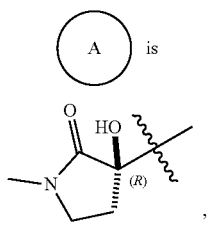 is moiety

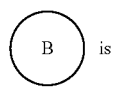 is

-continued

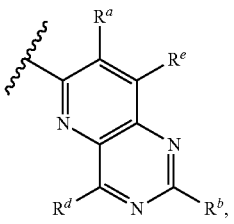

and $R^3$ is H.

Additional illustrative embodiments of the invention are compounds of Formula (I) and pharmaceutically acceptable salts thereof, wherein moiety

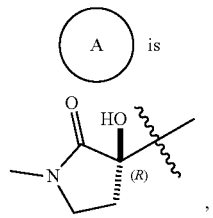 is moiety

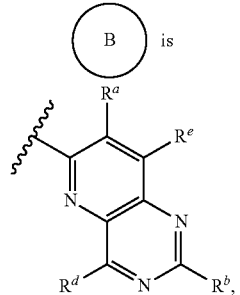 is $R^3$ is H and $R^e$ is H.

Additional illustrative embodiments of the invention are compounds of Formula (I) and pharmaceutically acceptable salts thereof, wherein moiety

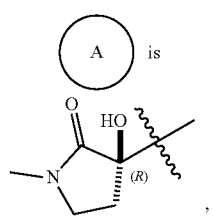 is moiety

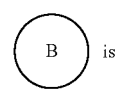 is

65

-continued

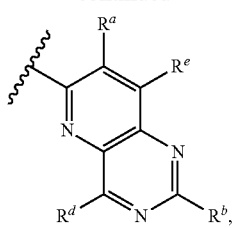

$R^3$ is H, $R^e$ is H and $R^d$ is $N(R^6)R^7$.

Additional illustrative embodiments of the invention are compounds of Formula (I) and pharmaceutically acceptable salts thereof, wherein moiety

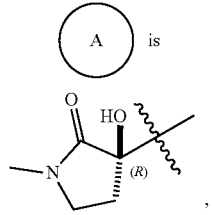

moiety

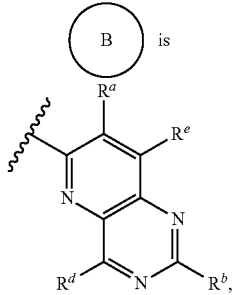

$R^3$ is H, $R^e$ is H, $R^d$ is $N(R^6)R^7$ and $R^b$ is $CH_3$.

Additional illustrative embodiments of the invention are compounds of Formula (I) and pharmaceutically acceptable salts thereof, wherein moiety

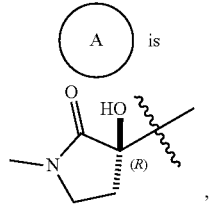

moiety

66

-continued

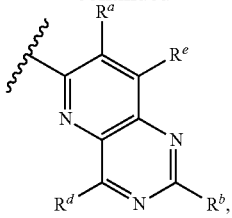

$R^3$ is H, $R^a$ is H, $R^e$ is H, $R^d$ is $N(R^6)R^7$, $R^b$ is $CH_3$, $R^6$ is H or $C_1$-$C_3$alkyl and $R^7$ is H or $C_1$-$C_3$alkyl.

Additional illustrative embodiments of the invention are compounds of Formula (I) and pharmaceutically acceptable salts thereof, wherein moiety

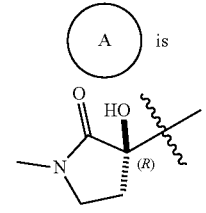

moiety

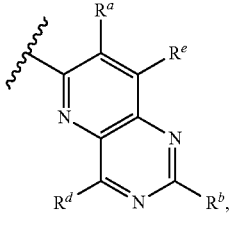

$R^3$ is H, $R^a$ is H, $R^e$ is H, $R^d$ is $N(R^6)R^7$, $R^b$ is $CH_3$, $R^6$ is $C_1$-$C_3$alkyl, and $R^7$ is $C_1$-$C_3$alkyl.

Additional illustrative embodiments of the invention are compounds of Formula (I) and pharmaceutically acceptable salts thereof, wherein moiety

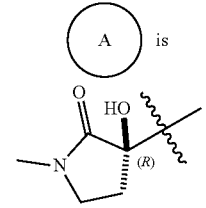

moiety

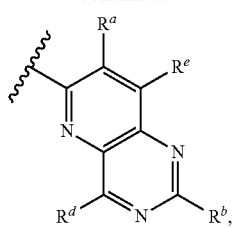

$R^3$ is H, $R^a$ is H, $R^e$ is H, $R^d$ is $N(R^6)R^7$, $R^b$ is $CH_3$, $R^6$ is H and $R^7$ is H.

Additional illustrative embodiments of the invention are compounds of Formula (I) and pharmaceutically acceptable salts thereof, wherein moiety

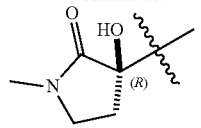 is

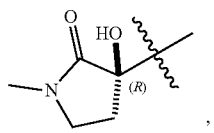

moiety

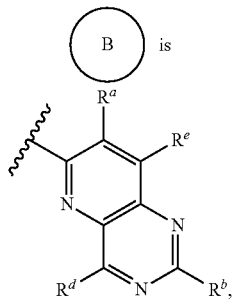

$R^3$ is H, $R^a$ is H, $R^e$ is H, $R^d$ is $N(R^6)R^7$, $R^b$ is $CH_3$, and $R^6$ and $R^7$ are taken together with the nitrogen to which they are attached to form the moiety

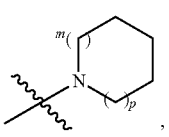

wherein m is 0 or 1, and p is 0 or 1.

Additional illustrative embodiments of the invention are compounds of Formula (I) and pharmaceutically acceptable salts thereof, wherein moiety

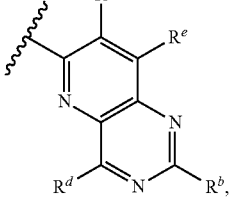

moiety

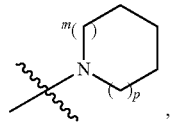 is

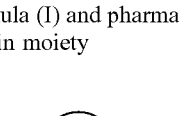

$R^3$ is H, $R^a$ is H, $R^e$ is H, $R^d$ is $N(R^6)R^7$, $R^b$ is $CH_3$, $R^6$ and $R^7$ are taken together with the nitrogen to which they are attached to form the moiety

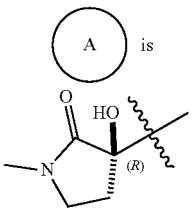

wherein m is 0, and p is 0;

Additional illustrative embodiments of the invention are compounds of Formula (I) and pharmaceutically acceptable salts thereof, wherein moiety A is

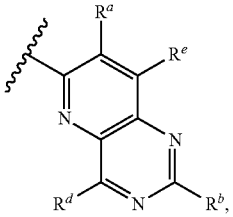

moiety

B is $R^3$ is H, $R^a$ is H, $R^e$ is H, $R^d$ is $N(R^6)R^7$, $R^b$ is $CH_3$, $R^6$ and $R^7$ are taken together with the nitrogen to which they are attached to form the moiety

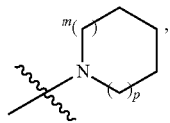

wherein m is 1, and p is 0.

Additional illustrative embodiments of the invention are compounds of Formula (I) and pharmaceutically acceptable salts thereof, wherein moiety

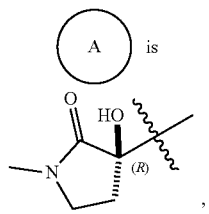

moiety

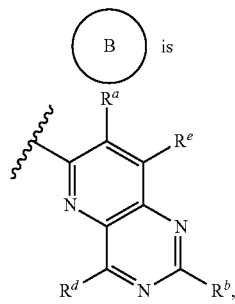

$R^3$ is H, $R^a$ is H, $R^e$ is H, $R^d$ is $N(R^6)R^7$, $R^b$ is $CH_3$, $R^6$ and $R^7$ are taken together with the nitrogen to which they are attached to form the moiety

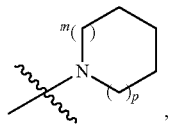

wherein m is 1, and p is 1.

Illustrative embodiments of compounds of Formula (I) are compounds
(R)-3-[2-[3-(8-Aminopyrido[3,4-d]pyrimidin-2-yl)phenyl] ethynyl]-3-hydroxy-1-methyl-pyrrolidin-2-one;
(S)-3-[2-[3-(8-Aminopyrido[3,4-d]pyrimidin-2-yl)phenyl] ethynyl]-3-hydroxy-1-methyl-pyrrolidin-2-one;
(R)-3-[2-[3-(4-Aminopyrido[3,2-d]pyrimidin-6-yl)-4-methyl-phenyl]ethynyl]-3-hydroxy-1-methyl-pyrrolidin-2-one;
(R)-3-((3-(8-Amino-4-methylpyrimido[5,4-d]pyrimidin-2-yl)phenyl)ethynyl)-3-hydroxy-1-methylpyrrolidin-2-one;
(S)-3-((3-(8-Amino-4-methylpyrimido[5,4-d]pyrimidin-2-yl)phenyl)ethynyl)-3-hydroxy-1-methylpyrrolidin-2-one;
(R)-3-((3-(4-Amino-2-methylpyrido[3,2-d]pyrimidin-6-yl)phenyl)ethynyl)-3-hydroxy-1-methylpyrrolidin-2-one;
(S)-3-((3-(4-Amino-2-methylpyrido[3,2-d]pyrimidin-6-yl)phenyl)ethynyl)-3-hydroxy-1-methylpyrrolidin-2-one;
(R)-3-((3-(4-Aminopyrido[3,2-d]pyrimidin-6-yl-2-d)phenyl)ethynyl)-3-hydroxy-1-methylpyrrolidin-2-one;
(S)-3-((3-(4-Aminopyrido[3,2-d]pyrimidin-6-yl-2-d)phenyl)ethynyl)-3-hydroxy-1-methylpyrrolidin-2-one;
(R)-3-((3-(7-Aminothiazolo[5,4-d]pyrimidin-2-yl)-4-methylphenyl)ethynyl)-3-hydroxy-1-methylpyrrolidin-2-one;
(S)-3-((3-(7-Aminothiazolo[5,4-d]pyrimidin-2-yl)-4-methylphenyl)ethynyl)-3-hydroxy-1-methylpyrrolidin-2-one;
(R)-3-((3-(4-Aminopyrido[3,2-d]pyrimidin-6-yl)phenyl) ethynyl)-3-hydroxy-1-methylpyrrolidin-2-one;
(R)-3-[2-[3-(4-Aminopyrimido[5,4-d]pyrimidin-6-yl)phenyl]ethynyl]-3-hydroxy-1-methyl-pyrrolidin-2-one;
(R)-3-((3-(8-Amino-6-methylpyrimido[5,4-d]pyrimidin-2-yl)phenyl)ethynyl)-3-hydroxy-1-methylpyrrolidin-2-one;
(R)-3-[2-[3-(4-Aminopteridin-6-yl)phenyl]ethynyl]-3-hydroxy-1-methyl-pyrrolidin-2-one;
(R)-3-[2-[3-(4-Aminoquinazolin-6-yl)phenyl]ethynyl]-3-hydroxy-1-methyl-pyrrolidin-2-one;
(R)-7-[2-[3-(8-Aminopyrido[3,4-d]pyrimidin-2-yl)phenyl] ethynyl]-5,6-dihydropyrrolo[1,2-a]imidazol-7-ol;
(R)-4-[3-(8-Aminopyrido[3,4-d]pyrimidin-2-yl)phenyl]-2-(5-methyl-1,3,4-oxadiazol-2-yl)but-3-yn-2-ol;
(R)-3-[2-[3-(8-Amino-1,7-naphthyridin-2-yl)phenyl]ethynyl]-3-hydroxy-1-methyl-pyrrolidin-2-one;
(R)-3-((3-(8-Amino-3,4-dihydro-2,7-naphthyridin-2(1H)-yl)phenyl)ethynyl)-3-hydroxy-1-methylpyrrolidin-2-one;
(R)-3-[2-[3-(3-Amino-1-methyl-pyrazolo[4,3-b]pyridin-5-yl)phenyl]ethynyl]-3-hydroxy-1-methyl-pyrrolidin-2-one;
(R)-3-[2-[3-(3-Amino-1H-pyrazolo[4,3-b]pyridin-5-yl)phenyl]ethynyl]-3-hydroxy-1-methyl-pyrrolidin-2-one;
(R)-3-Hydroxy-1-methyl-3-((3-(4-methylpyrido[3,2-d]pyrimidin-6-yl)phenyl)ethynyl)pyrrolidin-2-one;
(R)-3-((3-(4-Ethoxypyrido[3,2-d]pyrimidin-6-yl)phenyl) ethynyl)-3-hydroxy-1-methylpyrrolidin-2-one;
(R)-3-((3-(4-(Dimethylamino)pyrido[3,2-d]pyrimidin-6-yl) phenyl)ethynyl)-3-hydroxy-1-methylpyrrolidin-2-one;
(R)-3-((3-(4-(Azetidin-1-yl)pyrido[3,2-d]pyrimidin-6-yl) phenyl)ethynyl)-3-hydroxy-1-methylpyrrolidin-2-one;
(R)-3-Hydroxy-1-methyl-3-((3-(4-(methylamino)pyrido[3,2-d]pyrimidin-6-yl)phenyl)ethynyl)pyrrolidin-2-one;
(R)-3-((3-(4-Amino-8-methylpyrido[3,2-d]pyrimidin-6-yl) phenyl)ethynyl)-3-hydroxy-1-methylpyrrolidin-2-one;
(R)-3-((3-(4-aminopyrido[3,2-d]pyrimidin-6-yl-2-d)-4-(trifluoromethoxy)phenyl)ethynyl)-3-hydroxy-1-methylpyrrolidin-2-one;
(R)-2-[3-[2-(3-Hydroxy-1-methyl-2-oxo-pyrrolidin-3-yl) ethynyl]phenyl]-7H-pyrido[3,4-d]pyrimidin-8-one;
(S)-2-[3-[2-(3-Hydroxy-1-methyl-2-oxo-pyrrolidin-3-yl) ethynyl]phenyl]-7H-pyrido[3,4-d]pyrimidin-8-one;
(R)-4-[3-(8-Aminopyrido[3,4-d]pyrimidin-2-yl)phenyl]-2-thiazol-2-yl-but-3-yn-2-ol;
1-[2-[3-(8-Aminopyrido[3,4-d]pyrimidin-2-yl)phenyl]ethynyl]cyclopentanol;
(R)-4-[3-(8-Aminopyrido[3,4-d]pyrimidin-2-yl)phenyl]-2-(5-methylisoxazol-3-yl)but-3-yn-2-ol;
4-[3-(8-Aminopyrido[3,4-d]pyrimidin-2-yl)phenyl]-2-methyl-but-3-yn-2-ol;
(R)-3-[2-[3-(1-Amino-7-isoquinolyl)phenyl]ethynyl]-3-hydroxy-1-methyl-pyrrolidin-2-one;
(R)-3-((3-(8-Amino-4-methylpyrido[3,4-d]pyrimidin-2-yl) phenyl)ethynyl)-3-hydroxy-1-methylpyrrolidin-2-one;

(R)-3-((3-(8-Amino-4-(trifluoromethyl)pyrido[3,4-d]pyrimidin-2-yl)phenyl)ethynyl)-3-hydroxy-1-methylpyrrolidin-2-one;
(R)-3-((3-(8-Amino-5-methylpyrido[3,4-d]pyrimidin-2-yl)phenyl)ethynyl)-3-hydroxy-1-methylpyrrolidin-2-one;
(R)-3-((5-(8-Aminopyrido[3,4-d]pyrimidin-2-yl)-2-methylphenyl)ethynyl)-3-hydroxy-1-methylpyrrolidin-2-one;
(R)-3-((3-(8-Aminopyrido[3,4-d]pyrimidin-2-yl)-2-methylphenyl)ethynyl)-3-hydroxy-1-methylpyrrolidin-2-one;
(R)-3-((3-(8-Aminopyrido[3,4-d]pyrimidin-2-yl)-5-methylphenyl)ethynyl)-3-hydroxy-1-methylpyrrolidin-2-one;
(R)-3-((3-(8-Aminopyrido[3,4-d]pyrimidin-2-yl)-4-methylphenyl)ethynyl)-3-hydroxy-1-methylpyrrolidin-2-one;
(R)-3-((3-(8-Amino-6-methylpyrido[3,4-d]pyrimidin-2-yl)phenyl)ethynyl)-3-hydroxy-1-methylpyrrolidin-2-one;
(R)-7-[2-[3-(8-Aminopyrido[3,4-d]pyrimidin-2-yl)phenyl]ethynyl]-5,6-dihydrocyclopenta[b]pyridin-7-ol;
(S)-7-[2-[3-(8-Aminopyrido[3,4-d]pyrimidin-2-yl)phenyl]ethynyl]-5,6-dihydrocyclopenta[b]pyridin-7-ol;
(R)-2-[3-[2-(7-Hydroxy-5,6-dihydrocyclopenta[b]pyridin-7-yl)ethynyl]phenyl]-7H-pyrido[3,4-d]pyrimidin-8-one;
(R)-4-(3-(8-Amino-4-methylpyrido[3,4-d]pyrimidin-2-yl)phenyl)-2-(thiazol-2-yl)but-3-yn-2-ol;
(R)-4-(3-(8-Amino-4-(trifluoromethyl)pyrido[3,4-d]pyrimidin-2-yl)phenyl)-2-(thiazol-2-yl)but-3-yn-2-ol;
(R)-4-(3-(8-Amino-5-methylpyrido[3,4-d]pyrimidin-2-yl)phenyl)-2-(thiazol-2-yl)but-3-yn-2-ol;
(R)-4-(3-(8-Amino-6-methylpyrido[3,4-d]pyrimidin-2-yl)phenyl)-2-(thiazol-2-yl)but-3-yn-2-ol;
(R)-7-[2-[3-(8-Aminopyrido[3,4-d]pyrimidin-2-yl)-5-methyl-phenyl]ethynyl]-5,6-dihydrocyclopenta[b]pyridin-7-ol;
(R)-3-((3-(8-Aminopyrido[3,4-d]pyrimidin-2-yl)-4-methoxyphenyl)ethynyl)-3-hydroxy-1-methylpyrrolidin-2-one;
(R)-3-((3-(8-Aminopyrido[3,4-d]pyrimidin-2-yl)-4-isobutylphenyl)ethynyl)-3-hydroxy-1-methylpyrrolidin-2-one;
(R)-8-Amino-2-(3-((3-hydroxy-1-methyl-2-oxopyrrolidin-3-yl)ethynyl)phenyl)pyrido[3,4-d]pyrimidin-4(3H)-one;
(R)-3-((3-(8-Aminopyrido[3,4-d]pyrimidin-2-yl)-4-(trifluoromethoxy)phenyl)ethynyl)-3-hydroxy-1-methylpyrrolidin-2-one;
(R)-3-((3-(8-Amino-4-morpholinopyrido[3,4-d]pyrimidin-2-yl)phenyl)ethynyl)-3-hydroxy-1-methylpyrrolidin-2-one;
(R)-3-((3-(8-Amino-4-(dimethylamino)pyrido[3,4-d]pyrimidin-2-yl)phenyl)ethynyl)-3-hydroxy-1-methylpyrrolidin-2-one;
(R)-3-[2-[3-(4-Amino-1H-imidazo[4,5-c]pyridin-2-yl)phenyl]ethynyl]-3-hydroxy-1-methyl-pyrrolidin-2-one;
(R)-7-((3-(8-Amino-4-methylpyrido[3,4-d]pyrimidin-2-yl)phenyl)ethynyl)-6,7-dihydro-5H-cyclopenta[b]pyridin-7-ol;
(R)-7-((3-(8-Amino-4-(trifluoromethyl)pyrido[3,4-d]pyrimidin-2-yl)phenyl)ethynyl)-6,7-dihydro-5H-cyclopenta[b]pyridin-7-ol;
(R)-7-((3-(8-Amino-5-methylpyrido[3,4-d]pyrimidin-2-yl)phenyl)ethynyl)-6,7-dihydro-5H-cyclopenta[b]pyridin-7-ol;
(R)-7-((3-(8-Amino-6-methylpyrido[3,4-d]pyrimidin-2-yl)phenyl)ethynyl)-6,7-dihydro-5H-cyclopenta[b]pyridin-7-ol;
(S)-7-[2-[3-(8-Aminopyrido[3,4-d]pyrimidin-2-yl)phenyl]ethynyl]-5,6-dihydropyrrolo[1,2-a]imidazol-7-ol;
(R)-3-[2-[3-(8-Amino-5-methyl-pyrido[3,4-d]pyrimidin-2-yl)-4-methyl-phenyl]ethynyl]-3-hydroxy-1-methyl-pyrrolidin-2-one;
(R)-3-[2-[3-(8-Aminopyrido[3,4-d]pyrimidin-2-yl)phenyl]ethynyl]-3-hydroxy-1-(trideuteriomethyl)pyrrolidin-2-one;
(S)-3-[2-[3-(8-Aminopyrido[3,4-d]pyrimidin-2-yl)phenyl]ethynyl]-3-hydroxy-1-(trideuteriomethyl)pyrrolidin-2-one;
(R)-4-[3-(1-Amino-7-isoquinolyl)-4-methyl-phenyl]-2-thiazol-2-yl-but-3-yn-2-ol;
(R)-4-(3-(8-Aminopyrido[3,4-d]pyrimidin-2-yl)-4-methylphenyl)-2-(thiazol-2-yl)but-3-yn-2-ol;
(R)-3-[2-[3-(1-Amino-7-isoquinolyl)-4-methyl-phenyl]ethynyl]-3-hydroxy-1-(trideuteriomethyl)pyrrolidin-2-one;
(S)-3-[2-[3-(1-Amino-7-isoquinolyl)-4-methyl-phenyl]ethynyl]-3-hydroxy-1-(trideuteriomethyl)pyrrolidin-2-one;
(R)-3-[2-[3-(8-Aminopyrido[3,4-d]pyrimidin-2-yl)phenyl]ethynyl]-3-hydroxy-1-(2,2,2-trifluoroethyl)pyrrolidin-2-one;
(S)-3-[2-[3-(8-Aminopyrido[3,4-d]pyrimidin-2-yl)phenyl]ethynyl]-3-hydroxy-1-(2,2,2-trifluoroethyl)pyrrolidin-2-one;
(R)-4-(3-(8-Aminopyrido[3,4-d]pyrimidin-2-yl)-4-methylphenyl)-2-(5-methyl-1,3,4-oxadiazol-2-yl)but-3-yn-2-ol;
(R)-7-((3-(8-Aminopyrido[3,4-d]pyrimidin-2-yl)-4-methylphenyl)ethynyl)-6,7-dihydro-5H-cyclopenta[b]pyridin-7-ol;
(R)-3-[2-[3-(8-Amino-5-methyl-pyrido[3,4-d]pyrimidin-2-yl)-5-methyl-phenyl]ethynyl]-3-hydroxy-1-methyl-pyrrolidin-2-one;
(R)-3-[2-[3-(1-Amino-7-isoquinolyl)-4-methyl-phenyl]ethynyl]-3-hydroxy-1-(2,2,2-trifluoroethyl)pyrrolidin-2-one;
(R)-4-[3-(1-Amino-7-isoquinolyl)-4-methyl-phenyl]-2-(5-methyl-1,3,4-oxadiazol-2-yl)but-3-yn-2-ol;
(R)-4-[3-(1-Amino-7-isoquinolyl)-4-methyl-phenyl]-2-(5-methylisoxazol-3-yl)but-3-yn-2-ol;
(R)-7-[2-[3-(1-Amino-7-isoquinolyl)-4-methyl-phenyl]ethynyl]-5,6-dihydrocyclopenta[b]pyridin-7-ol;
(R)-7-[2-[3-(1-Amino-7-isoquinolyl)-4-methyl-phenyl]ethynyl]-5,6-dihydropyrrolo[1,2-a]imidazol-7-ol;
(R)-4-(3-(8-Aminopyrido[3,4-d]pyrimidin-2-yl)-4-methylphenyl)-2-(5-methylisoxazol-3-yl)but-3-yn-2-ol;
(R)-3-((3-(8-Amino-4-methylpyrido[3,4-d]pyrimidin-2-yl)phenyl)ethynyl)-3-hydroxy-1-(methyl-d$_3$)pyrrolidin-2-one;
(R)-7-((3-(8-Amino-4-methylpyrido[3,4-d]pyrimidin-2-yl)phenyl)ethynyl)-6,7-dihydro-5H-pyrrolo[1,2-a]imidazol-7-ol;
(R)-3-((3-(8-Amino-4-(methylamino)pyrido[3,4-d]pyrimidin-2-yl)phenyl)ethynyl)-3-hydroxy-1-methylpyrrolidin-2-one;
(R)-7-[2-[3-(8-Amino-5-methyl-pyrido[3,4-d]pyrimidin-2-yl)phenyl]ethynyl]-5,6-dihydropyrrolo[1,2-a]imidazol-7-ol;
(R)-3-[2-[3-(8-Amino-5-methyl-pyrido[3,4-d]pyrimidin-2-yl)phenyl]ethynyl]-3-hydroxy-1-(trideuteriomethyl)pyrrolidin-2-one;
(R)-4-[3-(8-Amino-1,7-naphthyridin-2-yl)phenyl]-2-(5-methyl-1,3,4-oxadiazol-2-yl)but-3-yn-2-ol;
(R)-4-[3-(8-Amino-1,7-naphthyridin-2-yl)phenyl]-2-(5-methylisoxazol-3-yl)but-3-yn-2-ol;

(R)-4-[3-(8-Amino-1,7-naphthyridin-2-yl)phenyl]-2-thiazol-2-yl-but-3-yn-2-ol;
(R)-7-[2-[3-(8-Amino-1,7-naphthyridin-2-yl)phenyl]ethynyl]-5,6-dihydropyrrolo[1,2-a]imidazol-7-ol;
(R)-3-[2-[3-(8-Amino-4-methyl-pyrido[3,4-d]pyrimidin-2-yl)phenyl]ethynyl]-3-hydroxy-1-(2,2,2-trifluoroethyl)pyrrolidin-2-one;
(R)-4-(3-(4-Aminopyrido[3,2-d]pyrimidin-6-yl)phenyl)-2-(thiazol-2-yl)but-3-yn-2-ol;
(R)-3-((3-(8-Amino-5-bromopyrido[3,4-d]pyrimidin-2-yl)phenyl)ethynyl)-3-hydroxy-1-methylpyrrolidin-2-one;
(R)-4-(3-(4-Aminopyrido[3,2-d]pyrimidin-6-yl)phenyl)-2-(5-methylisoxazol-3-yl)but-3-yn-2-ol;
(R)-3-[2-[3-(4-Aminophthalazin-6-yl)phenyl]ethynyl]-3-hydroxy-1-methyl-pyrrolidin-2-one;
(R)-4-(3-(4-Aminopyrido[3,2-d]pyrimidin-6-yl)phenyl)-2-(5-methyl-1,3,4-oxadiazol-2-yl)but-3-yn-2-ol;
(R)-3-((3-(8-Amino-4-isopropylpyrido[3,4-d]pyrimidin-2-yl)phenyl)ethynyl)-3-hydroxy-1-methylpyrrolidin-2-one;
(R)-3-[2-[3-[8-Amino-5-(trifluoromethyl)pyrido[3,4-d]pyrimidin-2-yl]phenyl]ethynyl]-3-hydroxy-1-methyl-pyrrolidin-2-one;
(R)-8-Amino-2-(3-((3-hydroxy-1-methyl-2-oxopyrrolidin-3-yl)ethynyl)phenyl)pyrido[3,4-d]pyrimidine-5-carbonitrile;
(R)-3-((3-(7-Aminothiazolo[5,4-d]pyrimidin-2-yl)phenyl)ethynyl)-3-hydroxy-1-methylpyrrolidin-2-one;
(R)-3-((3-(8-Amino-5-iodopyrido[3,4-d]pyrimidin-2-yl)phenyl)ethynyl)-3-hydroxy-1-methylpyrrolidin-2-one;
(R)-3-((3-(8-Amino-5-chloropyrido[3,4-d]pyrimidin-2-yl)phenyl)ethynyl)-3-hydroxy-1-methylpyrrolidin-2-one;
(R)-4-[3-(4-Aminoquinazolin-6-yl)phenyl]-2-(5-methylisoxazol-3-yl)but-3-yn-2-ol;
(R)-4-[3-(4-Aminoquinazolin-6-yl)phenyl]-2-thiazol-2-yl-but-3-yn-2-ol;
(R)-4-[3-(4-Aminoquinazolin-6-yl)phenyl]-2-(5-methyl-1,3,4-oxadiazol-2-yl)but-3-yn-2-ol;
2-(3-((1H-Pyrazol-5-yl)ethynyl)phenyl)-4-methylpyrido[3,4-d]pyrimidin-8-amine;
(R)-4-(3-(4-Aminopyrido[2,3-d]pyrimidin-6-yl)phenyl)-2-(thiazol-2-yl)but-3-yn-2-ol;
(R)-3-((3-(4-Aminopyrido[2,3-d]pyrimidin-6-yl)phenyl)ethynyl)-3-hydroxy-1-methylpyrrolidin-2-one;
(R)-3-((3-(4-Amino-8-methylquinazolin-6-yl)phenyl)ethynyl)-3-hydroxy-1-methylpyrrolidin-2-one;
(R)-3-[2-[3-(4-Aminopyrido[3,4-d]pyrimidin-6-yl)phenyl]ethynyl]-3-hydroxy-1-methyl-pyrrolidin-2-one;
(R)-3-[2-[3-(8-Amino-5-bromo-1,7-naphthyridin-2-yl)phenyl]ethynyl]-3-hydroxy-1-methyl-pyrrolidin-2-one;
(R)-3-[2-[3-(4-Amino-8-fluoro-quinazolin-6-yl)phenyl]ethynyl]-3-hydroxy-1-methyl-pyrrolidin-2-one;
(R)-3-((3-(4-Amino-8-methoxyquinazolin-6-yl)phenyl)ethynyl)-3-hydroxy-1-methylpyrrolidin-2-one;
(R)-3-((3-(4-Amino-8-(trifluoromethyl)quinazolin-6-yl)phenyl)ethynyl)-3-hydroxy-1-methylpyrrolidin-2-one;
(R)-3-((3-(4-Aminothiazolo[4,5-c]pyridin-2-yl)phenyl)ethynyl)-3-hydroxy-1-methylpyrrolidin-2-one;
(R)-3-((3-(4-Amino-8-chloroquinazolin-6-yl)phenyl)ethynyl)-3-hydroxy-1-methylpyrrolidin-2-one;
(R)-8-Amino-2-[3-[2-(3-hydroxy-1-methyl-2-oxo-pyrrolidin-3-yl)ethynyl]phenyl]-1,7-naphthyridine-5-carbonitrile;
(R)-3-[2-[3-(5-Amino-2,6-naphthyridin-3-yl)phenyl]ethynyl]-3-hydroxy-1-methyl-pyrrolidin-2-one;
(R)-3-[2-[3-(8-Amino-5-methyl-1,7-naphthyridin-2-yl)phenyl]ethynyl]-3-hydroxy-1-methyl-pyrrolidin-2-one;
(R)-3-((3-(8-Amino-5-phenylpyrido[3,4-d]pyrimidin-2-yl)phenyl)ethynyl)-3-hydroxy-1-methylpyrrolidin-2-one;
(R)-3-[2-[3-[8-Amino-5-(1-methylpyrazol-4-yl)pyrido[3,4-d]pyrimidin-2-yl]phenyl]ethynyl]-3-hydroxy-1-methyl-pyrrolidin-2-one;
(R)-3-[2-[3-[8-Amino-5-[1-(2-hydroxy-2-methyl-propyl)pyrazol-4-yl]pyrido[3,4-d]pyrimidin-2-yl]phenyl]ethynyl]-3-hydroxy-1-methyl-pyrrolidin-2-one;
(R)-3-[2-[3-[8-Amino-5-(1H-pyrazol-4-yl)pyrido[3,4-d]pyrimidin-2-yl]phenyl]ethynyl]-3-hydroxy-1-methyl-pyrrolidin-2-one;
(R)-3-[2-[3-[8-Amino-5-(3,5-dimethyl-1H-pyrazol-4-yl)pyrido[3,4-d]pyrimidin-2-yl]phenyl]ethynyl]-3-hydroxy-1-methyl-pyrrolidin-2-one;
(R)-4-Amino-6-(3-((3-hydroxy-1-methyl-2-oxopyrrolidin-3-yl)ethynyl)phenyl)quinazoline-8-carbonitrile;
(R)-3-[2-[3-[8-Amino-5-(5-methyl-1H-pyrazol-4-yl)pyrido[3,4-d]pyrimidin-2-yl]phenyl]ethynyl]-3-hydroxy-1-methyl-pyrrolidin-2-one;
(R)-Phenyl 8-amino-2-[3-[2-(3-hydroxy-1-methyl-2-oxo-pyrrolidin-3-yl)ethynyl]phenyl]pyrido[3,4-d]pyrimidine-5-carboxylate;
(R)-3-((3-(8-Amino-5-ethylpyrido[3,4-d]pyrimidin-2-yl)phenyl)ethynyl)-3-hydroxy-1-methylpyrrolidin-2-one;
(R)-3-((3-(8-Amino-5-isobutylpyrido[3,4-d]pyrimidin-2-yl)phenyl)ethynyl)-3-hydroxy-1-methylpyrrolidin-2-one;
(R)-2-[2-[3-(4-Aminopyrido[3,2-d]pyrimidin-6-yl)phenyl]ethynyl]-2-hydroxy-5,5-dimethyl-cyclopentanone;
(S)-2-[2-[3-(4-Aminopyrido[3,2-d]pyrimidin-6-yl)phenyl]ethynyl]-2-hydroxy-5,5-dimethyl-cyclopentanone;
(R)-3-[2-[3-[8-Amino-5-(pyrrolidin-1-ylmethyl)pyrido[3,4-d]pyrimidin-2-yl]phenyl]ethynyl]-3-hydroxy-1-methyl-pyrrolidin-2-one;
(R)-3-[2-[3-[8-Amino-5-[1-(2-aminoethyl)pyrazol-4-yl]pyrido[3,4-d]pyrimidin-2-yl]phenyl]ethynyl]-3-hydroxy-1-methyl-pyrrolidin-2-one;
(R)-3-[2-[3-[8-Amino-5-(dimethylaminomethyl)pyrido[3,4-d]pyrimidin-2-yl]phenyl]ethynyl]-3-hydroxy-1-methyl-pyrrolidin-2-one;
(R)-3-[2-[3-(4-Amino-8-methyl-pyrido[3,4-d]pyrimidin-6-yl)phenyl]ethynyl]-3-hydroxy-1-methyl-pyrrolidin-2-one;
(R)-4-(3-(8-Aminopyrimido[5,4-d]pyrimidin-2-yl)phenyl)-2-(thiazol-2-yl)but-3-yn-2-ol;
(R)-3-((3-(8-Amino-4,5-dimethylpyrido[3,4-d]pyrimidin-2-yl)phenyl)ethynyl)-3-hydroxy-1-methylpyrrolidin-2-one;
(R)-3-((3-(4-Aminopyrido[3,2-d]pyrimidin-6-yl)-4-methoxyphenyl)ethynyl)-3-hydroxy-1-methylpyrrolidin-2-one;
(R)-4-[4-[8-Amino-2-[3-[2-(3-hydroxy-1-methyl-2-oxo-pyrrolidin-3-yl)ethynyl]phenyl]pyrido[3,4-d]pyrimidin-5-yl]pyrazol-1-yl]butanenitrile;
(R)-3-((3-(4-Aminothieno[2,3-d]pyrimidin-6-yl)phenyl)ethynyl)-3-hydroxy-1-methylpyrrolidin-2-one;
(R)-3-((3-(7-Aminooxazolo[5,4-d]pyrimidin-2-yl)phenyl)ethynyl)-3-hydroxy-1-methylpyrrolidin-2-one;
(R)-3-((3-(6-Amino-9-methyl-9H-purin-8-yl)phenyl)ethynyl)-3-hydroxy-1-methylpyrrolidin-2-one;
(R)-7-((3-(8-Aminopyrimido[5,4-d]pyrimidin-2-yl)phenyl)ethynyl)-6,7-dihydro-5H-cyclopenta[b]pyridin-7-ol;
(R)-3-[2-[3-[8-Amino-5-(1-piperidylmethyl)pyrido[3,4-d]pyrimidin-2-yl]phenyl]ethynyl]-3-hydroxy-1-methyl-pyrrolidin-2-one;
(R)-7-[2-[3-(4-Aminopyrimido[5,4-d]pyrimidin-6-yl)phenyl]ethynyl]-5,6-dihydropyrrolo[1,2-a]imidazol-7-ol;

(R)-3-[2-[3-[8-Amino-5-[6-(trifluoromethyl)-3-pyridyl]pyrido[3,4-d]pyrimidin-2-yl]phenyl]ethynyl]-3-hydroxy-1-methyl-pyrrolidin-2-one;
(R)-3-[2-[3-(4-Amino-2-methyl-pteridin-6-yl)phenyl]ethynyl]-3-hydroxy-1-methyl-pyrrolidin-2-one;
(R)-3-((3-(4-Aminopyrido[3,2-d]pyrimidin-6-yl-2-d)-4-methylphenyl)ethynyl)-3-hydroxy-1-methylpyrrolidin-2-one;
(R)-3-((3-(4-Amino-2-methylpyrido[3,2-d]pyrimidin-6-yl)-4-methylphenyl)ethynyl)-3-hydroxy-1-methylpyrrolidin-2-one;
(R)-3-((3-(8-Amino-5-neopentylpyrido[3,4-d]pyrimidin-2-yl)phenyl)ethynyl)-3-hydroxy-1-methylpyrrolidin-2-one;
(R)-3-((5-(7-Aminothiazolo[5,4-d]pyrimidin-2-yl)-2-methylphenyl)ethynyl)-3-hydroxy-1-methylpyrrolidin-2-one;
(R)-3-((3-(7-Aminothiazolo[5,4-d]pyrimidin-2-yl)-5-methylphenyl)ethynyl)-3-hydroxy-1-methylpyrrolidin-2-one;
(R)-3-((3-(7-Aminothiazolo[5,4-d]pyrimidin-2-yl)-2-methylphenyl)ethynyl)-3-hydroxy-1-methylpyrrolidin-2-one;
(S)-7-((3-(8-Aminopyrimido[5,4-d]pyrimidin-2-yl)phenyl)ethynyl)-6,7-dihydro-5H-cyclopenta[b]pyridin-7-ol;
(R)-3-((3-(8-Amino-4,6-dimethylpyrimido[5,4-d]pyrimidin-2-yl)phenyl)ethynyl)-3-hydroxy-1-methylpyrrolidin-2-one;
(S)-4-(3-(4-Amino-2-methylpyrido[3,2-d]pyrimidin-6-yl)phenyl)-2-(2-methylthiazol-5-yl)but-3-yn-2-ol;
(R)-4-(3-(4-Amino-2-methylpyrido[3,2-d]pyrimidin-6-yl)phenyl)-2-(2-methylthiazol-5-yl)but-3-yn-2-ol;
(R)-3-((3-(4-Amino-7,8-dihydropyrido[4,3-d]pyrimidin-6(5H)-yl)phenyl)ethynyl)-3-hydroxy-1-methylpyrrolidin-2-one;
(R)-3-((3-(4-Aminopyrido[3,2-d]pyrimidin-6-yl-2-d)-4-methoxyphenyl)ethynyl)-3-hydroxy-1-methylpyrrolidin-2-one;
(R)-3-((3-(4-Amino-2-methylpyrido[3,2-d]pyrimidin-6-yl)-4-methoxyphenyl)ethynyl)-3-hydroxy-1-methylpyrrolidin-2-one;
(S)-4-(3-(4-Amino-2-methylpyrido[3,2-d]pyrimidin-6-yl)phenyl)-2-(4-methylthiazol-5-yl)but-3-yn-2-ol;
(R)-4-(3-(4-Amino-2-methylpyrido[3,2-d]pyrimidin-6-yl)phenyl)-2-(4-methylthiazol-5-yl)but-3-yn-2-ol;
(R)-4-(3-(4-Amino-2-methylpyrido[3,2-d]pyrimidin-6-yl)phenyl)-2-(thiazol-2-yl)but-3-yn-2-ol;
racemic-8-((3-(4-Amino-2-methylpyrido[3,2-d]pyrimidin-6-yl)phenyl)ethynyl)-5,6,7,8-tetrahydroquinolin-8-ol;
(S)-4-(3-(4-Amino-2-methylpyrido[3,2-d]pyrimidin-6-yl)phenyl)-2-(5-methylthiazol-2-yl)but-3-yn-2-ol;
(R)-4-(3-(4-Amino-2-methylpyrido[3,2-d]pyrimidin-6-yl)phenyl)-2-(5-methylthiazol-2-yl)but-3-yn-2-ol;
(R)-3-((3-(8-Amino-4-methylpyrimido[5,4-d]pyrimidin-2-yl-6-d)phenyl)ethynyl)-3-hydroxy-1-methylpyrrolidin-2-one;
(R)-tert-Butyl 3-amino-5-[3-[2-(3-hydroxy-1-methyl-2-oxo-pyrrolidin-3-yl)ethynyl]phenyl]indazole-1-carboxylate;
(R)-3-((3-(4-Amino-2-(fluoromethyl)pyrido[3,2-d]pyrimidin-6-yl)phenyl)ethynyl)-3-hydroxy-1-methylpyrrolidin-2-one;
(R)-3-[2-[3-[8-Amino-5-(pyrrolidin-1-ylmethyl)-1,7-naphthyridin-2-yl]phenyl]ethynyl]-3-hydroxy-1-methyl-pyrrolidin-2-one;
(R)-3-[2-[3-[8-Amino-5-(dimethylaminomethyl)-1,7-naphthyridin-2-yl]phenyl]ethynyl]-3-hydroxy-1-methyl-pyrrolidin-2-one;
(R)-3-((3-(4-Amino-2-(hydroxymethyl)pyrido[3,2-d]pyrimidin-6-yl)phenyl)ethynyl)-3-hydroxy-1-methylpyrrolidin-2-one;
(R)-3-[2-[3-(3-Amino-1H-indazol-5-yl)phenyl]ethynyl]-3-hydroxy-1-methyl-pyrrolidin-2-one;
(R)-3-((3-(4-Amino-2-cyclopropylpyrido[3,2-d]pyrimidin-6-yl)phenyl)ethynyl)-3-hydroxy-1-methylpyrrolidin-2-one;
(R)-3-((3-(4-Amino-2-(trifluoromethyl)pyrido[3,2-d]pyrimidin-6-yl)phenyl)ethynyl)-3-hydroxy-1-methylpyrrolidin-2-one;
(R)-3-((3-(8-Aminopyrimido[5,4-d]pyrimidin-2-yl)-4-methoxyphenyl)ethynyl)-3-hydroxy-1-methylpyrrolidin-2-one;
(R)-3-((3-(4-Amino-2,7-dimethylpyrido[3,2-d]pyrimidin-6-yl)phenyl)ethynyl)-3-hydroxy-1-methylpyrrolidin-2-one;
(R)-3-((3-(4-Amino-2H-pyrazolo[3,4-d]pyrimidin-2-yl)phenyl)ethynyl)-3-hydroxy-1-methylpyrrolidin-2-one;
(R)-4-(3-(4-Amino-2-methylpyrido[3,2-d]pyrimidin-6-yl)phenyl)-2-(4-methylthiazol-2-yl)but-3-yn-2-ol;
(S)-4-(3-(4-Amino-2-methylpyrido[3,2-d]pyrimidin-6-yl)phenyl)-2-(4-methylthiazol-2-yl)but-3-yn-2-ol;
(R)-3-[2-[3-(7-Amino-5-methyl-thiazolo[5,4-d]pyrimidin-2-yl)-4-methyl-phenyl]ethynyl]-3-hydroxy-1-methyl-pyrrolidin-2-one;
(R)-7-[2-[3-(7-Aminothiazolo[5,4-d]pyrimidin-2-yl)-4-methyl-phenyl]ethynyl]-5,6-dihydropyrrolo[1,2-a]imidazol-7-ol;
(R)-7-[2-[3-(7-Aminothiazolo[5,4-d]pyrimidin-2-yl)-4-methyl-phenyl]ethynyl]-5,6-dihydrocyclopenta[b]pyridin-7-ol;
1-[2-[3-(7-Aminothiazolo[5,4-d]pyrimidin-2-yl)-4-methyl-phenyl]ethynyl]cyclopentanol;
(S)-3-((3-(4-Amino-2-methylpyrido[3,2-d]pyrimidin-6-yl)phenyl)ethynyl)-3-hydroxy-1-methylpiperidin-2-one;
(R)-3-((3-(4-Amino-2-methylpyrido[3,2-d]pyrimidin-6-yl)phenyl)ethynyl)-3-hydroxy-1-methylpiperidin-2-one;
(R)-3-((3-(8-Aminopyrimido[5,4-d]pyrimidin-2-yl)-4-methylphenyl)ethynyl)-3-hydroxy-1-methylpyrrolidin-2-one;
(R)-3-((3-(4-Amino-7-methylpyrido[3,2-d]pyrimidin-6-yl)phenyl)ethynyl)-3-hydroxy-1-methylpyrrolidin-2-one;
(R)-4-[3-(4-Amino-2-methyl-pyrido[3,2-d]pyrimidin-6-yl)phenyl]-2-(2-pyridyl)but-3-yn-2-ol;
(S)-4-[3-(4-Amino-2-methyl-pyrido[3,2-d]pyrimidin-6-yl)phenyl]-2-(2-pyridyl)but-3-yn-2-ol;
(R)-4-(3-(4-Amino-2-methylpyrido[3,2-d]pyrimidin-6-yl)phenyl)-2-(4-(trifluoromethyl)thiazol-2-yl)but-3-yn-2-ol;
(S)-4-(3-(4-Amino-2-methylpyrido[3,2-d]pyrimidin-6-yl)phenyl)-2-(4-(trifluoromethyl)thiazol-2-yl)but-3-yn-2-ol;
(R)-3-((3-(7-Aminothiazolo[5,4-d]pyrimidin-2-yl)-4-methoxyphenyl)ethynyl)-3-hydroxy-1-methylpyrrolidin-2-one;
1-Allyl-3-((3-(4-Amino-2-methylpyrido[3,2-d]pyrimidin-6-yl)phenyl)ethynyl)-3-hydroxypyrrolidin-2-one;
racemic-1-Allyl-3-((3-(4-aminopyrido[3,2-d]pyrimidin-6-yl-2-d)phenyl)ethynyl)-3-hydroxypyrrolidin-2-one;
(R)-4-[3-(4-Amino-2-methyl-pyrido[3,2-d]pyrimidin-6-yl)phenyl]-2-pyrimidin-2-yl-but-3-yn-2-ol;
(S)-4-[3-(4-Amino-2-methyl-pyrido[3,2-d]pyrimidin-6-yl)phenyl]-2-pyrimidin-2-yl-but-3-yn-2-ol;
(S)-3-((3-(4-Aminopyrido[3,2-d]pyrimidin-6-yl-2-d)phenyl)ethynyl)-3-hydroxy-1-methylpiperidin-2-one;
(R)-4-[3-(4-Amino-2-methyl-pyrido[3,2-d]pyrimidin-6-yl)phenyl]-2-pyrazin-2-yl-but-3-yn-2-ol;
(S)-4-[3-(4-Amino-2-methyl-pyrido[3,2-d]pyrimidin-6-yl)phenyl]-2-pyrazin-2-yl-but-3-yn-2-ol;
racemic-4-(3-(4-Amino-2-methylpyrido[3,2-d]pyrimidin-6-yl)phenyl)-2-(1H-imidazol-4-yl)but-3-yn-2-ol;

(R)-3-((3-(2,4-Diaminopyrido[3,2-d]pyrimidin-6-yl)phenyl)ethynyl)-3-hydroxy-1-methylpyrrolidin-2-one;
(R)-3-((3-(4-Aminopyrido[3,2-d]pyrimidin-6-yl)phenyl)ethynyl)-3-(difluoromethyl)-1-methylpyrrolidin-2-one;
(S)-3-((3-(4-Aminopyrido[3,2-d]pyrimidin-6-yl)phenyl)ethynyl)-3-(difluoromethyl)-1-methylpyrrolidin-2-one;
(R)-3-((3-(4-Amino-2-(methoxymethyl)pyrido[3,2-d]pyrimidin-6-yl)phenyl)ethynyl)-3-hydroxy-1-methylpyrrolidin-2-one;
(R)-3-((3-(4-Aminopyrido[3,2-d]pyrimidin-6-yl)phenyl)ethynyl)-3-methoxy-1-methylpyrrolidin-2-one;
(R)-3-((3-(4-Amino-2-(fluoromethyl)pyrido[3,2-d]pyrimidin-6-yl)phenyl)ethynyl)-3-hydroxy-1-(methyl-d$_3$)pyrrolidin-2-one;
(S)-4-[3-(4-Amino-2-methyl-pyrido[3,2-d]pyrimidin-6-yl)phenyl]-2-thiazol-4-yl-but-3-yn-2-ol;
(R)-3-((3-(4-Amino-2-ethylpyrido[3,2-d]pyrimidin-6-yl)phenyl)ethynyl)-3-hydroxy-1-methylpyrrolidin-2-one;
(R)-3-((3-(4-Amino-2-hydroxypyrido[3,2-d]pyrimidin-6-yl)phenyl)ethynyl)-3-hydroxy-1-methylpyrrolidin-2-one;
(R)-4-[3-(4-Amino-2-methyl-pyrido[3,2-d]pyrimidin-6-yl)phenyl]-2-thiazol-4-yl-but-3-yn-2-ol;
(R)-4-(3-(4-Amino-2-methylpyrido[3,2-d]pyrimidin-6-yl)phenyl)-2-(5-methyl-1,3,4-oxadiazol-2-yl)but-3-yn-2-ol;
(R)-3-((3-(7-Aminothiazolo[4,5-d]pyrimidin-2-yl)phenyl)ethynyl)-3-hydroxy-1-methylpyrrolidin-2-one;
(R)-3-((3-(4-Amino-2-methyl-7,8-dihydropyrido[4,3-d]pyrimidin-6(5H)-yl)phenyl)ethynyl)-3-hydroxy-1-methylpyrrolidin-2-one;
(R)-3-[2-[3-(7-Aminothiazolo[5,4-d]pyrimidin-2-yl)-4-methyl-phenyl]ethynyl]-3-hydroxy-1-(trideuteriomethyl)pyrrolidin-2-one;
(R)-4-[3-(7-Aminothiazolo[5,4-d]pyrimidin-2-yl)-4-methyl-phenyl]-2-(5-methylisoxazol-3-yl)but-3-yn-2-ol;
(R)-6-[3-[2-(3-Hydroxy-1-methyl-2-oxo-pyrrolidin-3-yl)ethynyl]phenyl]-7H-imidazo[1,5-a]pyrazin-8-one;
(R)-3-((3-(8-Amino-1,5-naphthyridin-2-yl)phenyl)ethynyl)-3-hydroxy-1-methylpyrrolidin-2-one;
(R)-3-((3-(4-Amino-7,8-dihydropyrido[4,3-d]pyrimidin-6(5H)-yl)-4-methylphenyl)ethynyl)-3-hydroxy-1-methylpyrrolidin-2-one;
(R)-6-(3-((3-Hydroxy-1-methyl-2-oxopyrrolidin-3-yl)ethynyl)phenyl)pyrido[3,2-d]pyrimidin-4(3H)-one;
(R)-3-Hydroxy-1-methyl-3-((3-(4-(pyrrolidin-1-yl)pyrido[3,2-d]pyrimidin-6-yl)phenyl)ethynyl)pyrrolidin-2-one;
((R)-3-Hydroxy-1-methyl-3-((3-(pyrido[3,2-d]pyrimidin-6-yl)phenyl)ethynyl)pyrrolidin-2-one;
(R)-3-((3-(4-Amino-5,7,8,9-tetrahydro-6H-pyrimido[5,4-c]azepin-6-yl)phenyl)ethynyl)-3-hydroxy-1-methylpyrrolidin-2-one;
(R)-3-Hydroxy-1-methyl-3-((3-(4-(piperidin-1-yl)pyrido[3,2-d]pyrimidin-6-yl)phenyl)ethynyl)pyrrolidin-2-one;
(R)-3-((3-(4-(3,3-Dimethylazetidin-1-yl)pyrido[3,2-d]pyrimidin-6-yl)phenyl)ethynyl)-3-hydroxy-1-methylpyrrolidin-2-one;
(R)-3-((3-(4-(Ethylamino)pyrido[3,2-d]pyrimidin-6-yl)phenyl)ethynyl)-3-hydroxy-1-methylpyrrolidin-2-one;
(R)-3-Hydroxy-3-((3-(4-(3-hydroxyazetidin-1-yl)pyrido[3,2-d]pyrimidin-6-yl)phenyl)ethynyl)-1-methylpyrrolidin-2-one;
(R)-3-Hydroxy-3-methyl-3-((3-(4-(oxetan-3-ylamino)pyrido[3,2-d]pyrimidin-6-yl)phenyl)ethynyl)pyrrolidin-2-one;
(R)-3-Hydroxy-3-((3-(4-(3-methoxyazetidin-1-yl)pyrido[3,2-d]pyrimidin-6-yl)phenyl)ethynyl)-1-methylpyrrolidin-2-one;
(S)-3-((3-(4-(Azetidin-1-yl)pyrido[3,2-d]pyrimidin-6-yl)phenyl)ethynyl)-3-hydroxy-1-methylpyrrolidin-2-one;
(R)-3-((3-(4-(3,3-Difluoroazetidin-1-yl)pyrido[3,2-d]pyrimidin-6-yl)phenyl)ethynyl)-3-hydroxy-1-methylpyrrolidin-2-one;
(R)-3-((3-(8-(Azetidin-1-yl)-1,7-naphthyridin-2-yl)phenyl)ethynyl)-3-hydroxy-1-methylpyrrolidin-2-one;
(R)-3-((3-(1-(Azetidin-1-yl)isoquinolin-7-yl)phenyl)ethynyl)-3-hydroxy-1-methylpyrrolidin-2-one;
(R)-3-((3-(4-(Azetidin-1-yl)quinolin-6-yl)phenyl)ethynyl)-3-hydroxy-1-methylpyrrolidin-2-one;
(R)-3-((3-(4-(Cyclobutylamino)pyrido[3,2-d]pyrimidin-6-yl)phenyl)ethynyl)-3-hydroxy-1-methylpyrrolidin-2-one;
(R)-3-((3-(4-Amino-2-methylpyrido[3,2-d]pyrimidin-6-yl)-4-(trifluoromethoxy)phenyl)ethynyl)-3-hydroxy-1-methylpyrrolidin-2-one;
(R)—N-(6-(3-((3-Hydroxy-1-methyl-2-oxopyrrolidin-3-yl)ethynyl)phenyl)pyrido[3,2-d]pyrimidin-4-yl)acetamide;
(R)-3-((3-(4-(3-Fluoroazetidin-1-yl)pyrido[3,2-d]pyrimidin-6-yl)phenyl)ethynyl)-3-hydroxy-1-methylpyrrolidin-2-one;
(R)-2-((6-(3-((3-Hydroxy-1-methyl-2-oxopyrrolidin-3-yl)ethynyl)phenyl)pyrido[3,2-d]pyrimidin-4-yl)amino)acetonitrile;
(R)-3-((3-(4-((2,2-Difluoroethyl)amino)pyrido[3,2-d]pyrimidin-6-yl)phenyl)ethynyl)-3-hydroxy-1-methylpyrrolidin-2-one;
(R)-1-(6-(3-((3-Hydroxy-1-methyl-2-oxopyrrolidin-3-yl)ethynyl)phenyl)pyrido[3,2-d]pyrimidin-4-yl)azetidine-3-carbonitrile;
(R)-3-((3-(4-(Azetidin-1-yl)quinazolin-6-yl)phenyl)ethynyl)-3-hydroxy-1-methylpyrrolidin-2-one;
(R)-3-((3-(4-(3-Chloroazetidin-1-yl)pyrido[3,2-d]pyrimidin-6-yl)phenyl)ethynyl)-3-hydroxy-1-methylpyrrolidin-2-one;
(R)-3-Hydroxy-1-methyl-3-((3-(4-(3-(methylsulfonyl)azetidin-1-yl)pyrido[3,2-d]pyrimidin-6-yl)phenyl)ethynyl)pyrrolidin-2-one;
(R)-1-(6-(3-((3-Hydroxy-1-methyl-2-oxopyrrolidin-3-yl)ethynyl)phenyl)pyrido[3,2-d]pyrimidin-4-yl)-N-methyl-azetidine-3-carboxamide;
(R)-3-((3-(8-(Azetidin-1-yl)pyrido[3,4-d]pyrimidin-2-yl)phenyl)ethynyl)-3-hydroxy-1-methylpyrrolidin-2-one;
(S)-3-((3-(8-(Azetidin-1-yl)pyrido[3,4-d]pyrimidin-2-yl)phenyl)ethynyl)-3-hydroxy-1-methylpyrrolidin-2-one;
(R)-3-((3-(5-Bromo-8-methyl-1,7-naphthyridin-2-yl)phenyl)ethynyl)-3-hydroxy-1-methylpyrrolidin-2-one;
(R)-3-((3-(4,8-Dimethylpyrido[3,2-d]pyrimidin-6-yl)phenyl)ethynyl)-3-hydroxy-1-methylpyrrolidin-2-one;
(R)-2-(3-((3-Hydroxy-1-methyl-2-oxopyrrolidin-3-yl)ethynyl)phenyl)-8-methyl-1,7-naphthyridine-5-carbonitrile;
(R)-3-((3-(5,8-Dimethyl-1,7-naphthyridin-2-yl)phenyl)ethynyl)-3-hydroxy-1-methylpyrrolidin-2-one;
(R)-3-((3-(4-Amino-8-bromopyrido[3,2-d]pyrimidin-6-yl)phenyl)ethynyl)-3-hydroxy-1-methylpyrrolidin-2-one;
(S)-3-((3-(4-Amino-8-bromopyrido[3,2-d]pyrimidin-6-yl)phenyl)ethynyl)-3-hydroxy-1-methylpyrrolidin-2-one;
(R)-3-((3-(4-Amino-8-(tetrahydro-2H-pyran-4-yl)pyrido[3,2-d]pyrimidin-6-yl)phenyl)ethynyl)-3-hydroxy-1-methylpyrrolidin-2-one;
(S)-3-((3-(4-Amino-8-(tetrahydro-2H-pyran-4-yl)pyrido[3,2-d]pyrimidin-6-yl)phenyl)ethynyl)-3-hydroxy-1-methylpyrrolidin-2-one;
(R)-3-Hydroxy-1-methyl-3-((3-(4-phenylpyrido[3,2-d]pyrimidin-6-yl)phenyl)ethynyl)pyrrolidin-2-one;

(R)—N-(6-(3-((3-Hydroxy-1-methyl-2-oxopyrrolidin-3-yl)ethynyl)phenyl)-2-methylpyrido[3,2-d]pyrimidin-4-yl)acetamide;

(R)—N-(6-(3-((3-Hydroxy-1-methyl-2-oxopyrrolidin-3-yl)ethynyl)phenyl)pyrido[3,2-d]pyrimidin-4-yl-2-d)acetamide;

(S)-3-((3-(4-Aminopyrido[3,2-d]pyrimidin-6-yl)-4-methylphenyl)ethynyl)-3-hydroxy-1-methylpyrrolidin-2-one;

(3R,5R)-3-((3-(4-Aminopyrido[3,2-d]pyrimidin-6-yl-2-d)phenyl)ethynyl)-3-hydroxy-1,5-dimethylpyrrolidin-2-one;

(3R,5S)-3-((3-(4-Aminopyrido[3,2-d]pyrimidin-6-yl-2-d)phenyl)ethynyl)-3-hydroxy-1,5-dimethylpyrrolidin-2-one;

(3S,5S)-3-((3-(4-Aminopyrido[3,2-d]pyrimidin-6-yl-2-d)phenyl)ethynyl)-3-hydroxy-1,5-dimethylpyrrolidin-2-one;

(3S,5R)-3-((3-(4-Aminopyrido[3,2-d]pyrimidin-6-yl-2-d)phenyl)ethynyl)-3-hydroxy-1,5-dimethylpyrrolidin-2-one;

(3R,5R)-3-((3-(4-Amino-2-methylpyrido[3,2-d]pyrimidin-6-yl)phenyl)ethynyl)-3-hydroxy-1,5-dimethylpyrrolidin-2-one;

(3S,5S)-3-((3-(4-Amino-2-methylpyrido[3,2-d]pyrimidin-6-yl)phenyl)ethynyl)-3-hydroxy-1,5-dimethylpyrrolidin-2-one;

(3S,5R)-3-((3-(4-Amino-2-methylpyrido[3,2-d]pyrimidin-6-yl)phenyl)ethynyl)-3-hydroxy-1,5-dimethylpyrrolidin-2-one;

(3R,5S)-3-((3-(4-Amino-2-methylpyrido[3,2-d]pyrimidin-6-yl)phenyl)ethynyl)-3-hydroxy-1,5-dimethylpyrrolidin-2-one;

(R)—N-(6-(3-((3-Hydroxy-1-methyl-2-oxopyrrolidin-3-yl)ethynyl)phenyl)pyrido[3,2-d]pyrimidin-4-yl-2-d)methanesulfonamide;

(R)-3-((3-(4-Cyclopropylpyrido[3,2-d]pyrimidin-6-yl)phenyl)ethynyl)-3-hydroxy-1-methylpyrrolidin-2-one;

(R)-3-((3-(4-Aminopyrido[3,2-d]pyrimidin-6-yl)-4-(trifluoromethoxy)phenyl)ethynyl)-3-hydroxy-1-methylpyrrolidin-2-one;

(R)-3-Hydroxy-3-((3-(4-isopropylpyrido[3,2-d]pyrimidin-6-yl)phenyl)ethynyl)-1-methylpyrrolidin-2-one;

(1R,4R,5S)-4-((3-(4-Amino-2-methylpyrido[3,2-d]pyrimidin-6-yl)phenyl)ethynyl)-4-hydroxy-2-methyl-2-azabicyclo[3.1.0]hexan-3-one;

(1 S,4S,5R)-4-((3-(4-Amino-2-methylpyrido[3,2-d]pyrimidin-6-yl)phenyl)ethynyl)-4-hydroxy-2-methyl-2-azabicyclo[3.1.0]hexan-3-one;

(1 S,4S,5R)-4-((3-(4-Aminopyrido[3,2-d]pyrimidin-6-yl-2-d)phenyl)ethynyl)-4-hydroxy-2-methyl-2-azabicyclo[3.1.0]hexan-3-one;

(1R,4R,5S)-4-((3-(4-Aminopyrido[3,2-d]pyrimidin-6-yl-2-d)phenyl)ethynyl)-4-hydroxy-2-methyl-2-azabicyclo[3.1.0]hexan-3-one;

(R)-3-((3-(4-Amino-8-cyclopentylpyrido[3,2-d]pyrimidin-6-yl-2-d)phenyl)ethynyl)-3-hydroxy-1-methylpyrrolidin-2-one;

(R)-3-Hydroxy-1-methyl-3-((3-(4-(trifluoromethyl)pyrido[3,2-d]pyrimidin-6-yl)phenyl)ethynyl)pyrrolidin-2-one;

(R)-6-(3-((3-Hydroxy-1-methyl-2-oxopyrrolidin-3-yl)ethynyl)phenyl)pyrido[3,2-d]pyrimidine-4-carbonitrile;

(R)-3-Hydroxy-1-methyl-3-((3-(8-methyl-1,7-naphthyridin-2-yl)phenyl)ethynyl)pyrrolidin-2-one;

(1R,4R,5S)-4-((3-(4-amino-8-methylpyrido[3,2-d]pyrimidin-6-yl)phenyl)ethynyl)-4-hydroxy-2-methyl-2-azabicyclo[3.1.0]hexan-3-one;

(R)-3-((3-(4-Amino-8-(aminomethyl)pyrido[3,2-d]pyrimidin-6-yl-2-d)phenyl)ethynyl)-3-hydroxy-1-methylpyrrolidin-2-one;

(R)-3-((3-(4-Amino-8-isopropylpyrido[3,2-d]pyrimidin-6-yl-2-d)phenyl)ethynyl)-3-hydroxy-1-methylpyrrolidin-2-one;

(R)-3-((3-(4-Amino-8-(trifluoromethyl)pyrido[3,2-d]pyrimidin-6-yl)phenyl)ethynyl)-3-hydroxy-1-methylpyrrolidin-2-one;

(R)-3-((3-(4-Amino-2,8-dimethylpyrido[3,2-d]pyrimidin-6-yl)phenyl)ethynyl)-3-hydroxy-1-methylpyrrolidin-2-one;

(R)-3-((3-(4-Amino-8-(methyl-d$_3$)pyrido[3,2-d]pyrimidin-6-yl)phenyl)ethynyl)-3-hydroxy-1-methylpyrrolidin-2-one;

(R)-3-((3-(4-Amino-8-(piperidin-4-yl)pyrido[3,2-d]pyrimidin-6-yl-2-d)phenyl)ethynyl)-3-hydroxy-1-methylpyrrolidin-2-one;

(R)-3-((3-(4-Amino-2-fluoropyrido[3,2-d]pyrimidin-6-yl)phenyl)ethynyl)-3-hydroxy-1-methylpyrrolidin-2-one;

(R)-3-((3-(4-Amino-8-(difluoromethyl)pyrido[3,2-d]pyrimidin-6-yl)phenyl)ethynyl)-3-hydroxy-1-methylpyrrolidin-2-one;

(S)-3-((3-(4-Amino-8-(difluoromethyl)pyrido[3,2-d]pyrimidin-6-yl)phenyl)ethynyl)-3-hydroxy-1-methylpyrrolidin-2-one;

(3R,4S*)-3-((3-(4-Amino-2-methylpyrido[3,2-d]pyrimidin-6-yl)phenyl)ethynyl)-3-hydroxy-1,4-dimethylpyrrolidin-2-one;

(3R,4R*)-3-((3-(4-Amino-2-methylpyrido[3,2-d]pyrimidin-6-yl)phenyl)ethynyl)-3-hydroxy-1,4-dimethylpyrrolidin-2-one;

(3S,4S*)-3-((3-(4-Amino-2-methylpyrido[3,2-d]pyrimidin-6-yl)phenyl)ethynyl)-3-hydroxy-1,4-dimethylpyrrolidin-2-one;

(3S,4R*)-3-((3-(4-Amino-2-methylpyrido[3,2-d]pyrimidin-6-yl)phenyl)ethynyl)-3-hydroxy-1,4-dimethylpyrrolidin-2-one;

(R)-3-[2-[3-[4-Amino-8-(dimethylamino)pyrido[3,2-d]pyrimidin-6-yl]phenyl]ethynyl]-3-hydroxy-1-methyl-pyrrolidin-2-one;

(R)-3-[2-[3-[4-Amino-8-(methylamino)pyrido[3,2-d]pyrimidin-6-yl]phenyl]ethynyl]-3-hydroxy-1-methyl-pyrrolidin-2-one;

(R)-3-[2-[3-[4-Amino-8-(isopropylamino)pyrido[3,2-d]pyrimidin-6-yl]phenyl]ethynyl]-3-hydroxy-1-methyl-pyrrolidin-2-one;

(R)-3-[2-[3-[4-Amino-8-(cyclopropylamino)pyrido[3,2-d]pyrimidin-6-yl]phenyl]ethynyl]-3-hydroxy-1-methyl-pyrrolidin-2-one;

(R)-3-[2-[3-[4-Amino-8-(difluoromethoxy)pyrido[3,2-d]pyrimidin-6-yl]phenyl]ethynyl]-3-hydroxy-1-methyl-pyrrolidin-2-one;

(R)-3-[2-[3-[4-Amino-8-(3,3-difluoroazetidin-1-yl)pyrido[3,2-d]pyrimidin-6-yl]phenyl]ethynyl]-3-hydroxy-1-methyl-pyrrolidin-2-one;

(R)-3-[2-[3-(8-Amino-4-methyl-pyrimido[5,4-d]pyrimidin-2-yl)-4-methyl-phenyl]ethynyl]-3-hydroxy-1-methyl-pyrrolidin-2-one;

(R)-3-((3-(4-Amino-8-cyclopropylpyrido[3,2-d]pyrimidin-6-yl)phenyl)ethynyl)-3-hydroxy-1-methylpyrrolidin-2-one;

(R)-3-[2-[3-[4-Amino-8-pyrazol-1-yl-pyrido[3,2-d]pyrimidin-6-yl]phenyl]ethynyl]-3-hydroxy-1-methyl-pyrrolidin-2-one;

(R)-3-[2-[3-[4-Amino-8-(cyclopropoxy)pyrido[3,2-d]pyrimidin-6-yl]phenyl]ethynyl]-3-hydroxy-1-methyl-pyrrolidin-2-one;

(R)-3-[2-[3-[4-Amino-8-[1-(difluoromethyl)pyrazol-4-yl]oxy-pyrido[3,2-d]pyrimidin-6-yl]phenyl]ethynyl]-3-hydroxy-1-methyl-pyrrolidin-2-one;
(R)-3-[2-[3-[4-Amino-8-(3,3,3-trifluoropropoxy)pyrido[3,2-d]pyrimidin-6-yl]phenyl]ethynyl]-3-hydroxy-1-methyl-pyrrolidin-2-one;
(R)-3-[2-[3-[4-Amino-8-(2,2-difluoro-5-azaspiro[2.3]hexan-5-yl)pyrido[3,2-d]pyrimidin-6-yl]phenyl]ethynyl]-3-hydroxy-1-methyl-pyrrolidin-2-one;
(R)-3-((3-(4-Amino-8-ethylpyrido[3,2-d]pyrimidin-6-yl-2-d)phenyl)ethynyl)-3-hydroxy-1-methylpyrrolidin-2-one;
(R)-3-((3-(4-Amino-8-cyclobutylpyrido[3,2-d]pyrimidin-6-yl)phenyl)ethynyl)-3-hydroxy-1-methylpyrrolidin-2-one;
(R)-3-((3-(4-Amino-8-phenylpyrido[3,2-d]pyrimidin-6-yl)phenyl)ethynyl)-3-hydroxy-1-methylpyrrolidin-2-one;
(R)-3-((3-(4-Amino-8-(thiophen-2-yl)pyrido[3,2-d]pyrimidin-6-yl)phenyl)ethynyl)-3-hydroxy-1-methylpyrrolidin-2-one;
(R)-3-((3-(4-Amino-8-(furan-2-yl)pyrido[3,2-d]pyrimidin-6-yl)phenyl)ethynyl)-3-hydroxy-1-methylpyrrolidin-2-one;
(3R)-3-((3-(4-Amino-8-(azetidin-2-yl)pyrido[3,2-d]pyrimidin-6-yl-2-d)phenyl)ethynyl)-3-hydroxy-1-methylpyrrolidin-2-one;
(R)-3-((3-(4-Amino-8-vinylpyrido[3,2-d]pyrimidin-6-yl)phenyl)ethynyl)-3-hydroxy-1-methylpyrrolidin-2-one;
(R)-3-[2-[3-[4-Amino-8-[3-(trifluoromethyl)azetidin-1-yl]pyrido[3,2-d]pyrimidin-6-yl]phenyl]ethynyl]-3-hydroxy-1-methyl-pyrrolidin-2-one;
(R)-3-[2-[3-[4-Amino-8-(azetidin-1-yl)pyrido[3,2-d]pyrimidin-6-yl]phenyl]ethynyl]-3-hydroxy-1-methyl-pyrrolidin-2-one;
(R)-3-((3-(4-Amino-8-((2,2,2-trifluoroethyl)amino)pyrido[3,2-d]pyrimidin-6-yl)phenyl)ethynyl)-3-hydroxy-1-methylpyrrolidin-2-one;
(1R,4R,5S)-4-((3-(7-Aminothiazolo[5,4-d]pyrimidin-2-yl)-4-methylphenyl)ethynyl)-4-hydroxy-2-methyl-2-azabicyclo[3.1.0]hexan-3-one;
(3R,5R)-3-((3-(7-Aminothiazolo[5,4-d]pyrimidin-2-yl)-4-methylphenyl)ethynyl)-3-hydroxy-1,5-dimethylpyrrolidin-2-one; and
pharmaceutically acceptable salts thereof.

Illustrative embodiments of compounds of Formula (I) are compounds
(R)-3-[2-[3-(8-Aminopyrido[3,4-d]pyrimidin-2-yl)phenyl]ethynyl]-3-hydroxy-1-methyl-pyrrolidin-2-one;
(S)-3-[2-[3-(8-Aminopyrido[3,4-d]pyrimidin-2-yl)phenyl]ethynyl]-3-hydroxy-1-methyl-pyrrolidin-2-one;
(R)-3-[2-[3-(4-Aminopyrido[3,2-d]pyrimidin-6-yl)-4-methyl-phenyl]ethynyl]-3-hydroxy-1-methyl-pyrrolidin-2-one;
(R)-3-((3-(8-Amino-4-methylpyrimido[5,4-d]pyrimidin-2-yl)phenyl)ethynyl)-3-hydroxy-1-methylpyrrolidin-2-one;
(S)-3-((3-(8-Amino-4-methylpyrimido[5,4-d]pyrimidin-2-yl)phenyl)ethynyl)-3-hydroxy-1-methylpyrrolidin-2-one;
(R)-3-((3-(4-Amino-2-methylpyrido[3,2-d]pyrimidin-6-yl)phenyl)ethynyl)-3-hydroxy-1-methylpyrrolidin-2-one;
(S)-3-((3-(4-Amino-2-methylpyrido[3,2-d]pyrimidin-6-yl)phenyl)ethynyl)-3-hydroxy-1-methylpyrrolidin-2-one;
(R)-3-((3-(4-Aminopyrido[3,2-d]pyrimidin-6-yl-2-d)phenyl)ethynyl)-3-hydroxy-1-methylpyrrolidin-2-one;
(S)-3-((3-(4-Aminopyrido[3,2-d]pyrimidin-6-yl-2-d)phenyl)ethynyl)-3-hydroxy-1-methylpyrrolidin-2-one;
(R)-3-((3-(7-Aminothiazolo[5,4-d]pyrimidin-2-yl)-4-methylphenyl)ethynyl)-3-hydroxy-1-methylpyrrolidin-2-one;
(S)-3-((3-(7-Aminothiazolo[5,4-d]pyrimidin-2-yl)-4-methylphenyl)ethynyl)-3-hydroxy-1-methylpyrrolidin-2-one;
(R)-3-((3-(4-Aminopyrido[3,2-d]pyrimidin-6-yl)phenyl)ethynyl)-3-hydroxy-1-methylpyrrolidin-2-one;
(R)-3-[2-[3-(4-Aminopyrimido[5,4-d]pyrimidin-6-yl)phenyl]ethynyl]-3-hydroxy-1-methyl-pyrrolidin-2-one;
(R)-3-((3-(4-Amino-6-methylpyrimido[5,4-d]pyrimidin-2-yl)phenyl)ethynyl)-3-hydroxy-1-methylpyrrolidin-2-one;
(R)-3-[2-[3-(4-Aminopteridin-6-yl)phenyl]ethynyl]-3-hydroxy-1-methyl-pyrrolidin-2-one;
(R)-3-[2-[3-(4-Aminoquinazolin-6-yl)phenyl]ethynyl]-3-hydroxy-1-methyl-pyrrolidin-2-one;
(R)-7-[2-[3-(8-Aminopyrido[3,4-d]pyrimidin-2-yl)phenyl]ethynyl]-5,6-dihydropyrrolo[1,2-a]imidazol-7-ol;
(R)-4-[3-(8-Aminopyrido[3,4-d]pyrimidin-2-yl)phenyl]-2-(5-methyl-1,3,4-oxadiazol-2-yl)but-3-yn-2-ol;
(R)-3-[2-[3-(8-Amino-1,7-naphthyridin-2-yl)phenyl]ethynyl]-3-hydroxy-1-methyl-pyrrolidin-2-one;
(R)-3-((3-(8-Amino-3,4-dihydro-2,7-naphthyridin-2(1H)-yl)phenyl)ethynyl)-3-hydroxy-1-methylpyrrolidin-2-one;
(R)-3-[2-[3-(3-Amino-1-methyl-pyrazolo[4,3-b]pyridin-5-yl)phenyl]ethynyl]-3-hydroxy-1-methyl-pyrrolidin-2-one;
(R)-3-[2-[3-(3-Amino-1H-pyrazolo[4,3-b]pyridin-5-yl)phenyl]ethynyl]-3-hydroxy-1-methyl-pyrrolidin-2-one;
(R)-3-Hydroxy-1-methyl-3-((3-(4-methylpyrido[3,2-d]pyrimidin-6-yl)phenyl)ethynyl)pyrrolidin-2-one;
(R)-3-((3-(4-Ethoxypyrido[3,2-d]pyrimidin-6-yl)phenyl)ethynyl)-3-hydroxy-1-methylpyrrolidin-2-one;
(R)-3-((3-(4-(Dimethylamino)pyrido[3,2-d]pyrimidin-6-yl)phenyl)ethynyl)-3-hydroxy-1-methylpyrrolidin-2-one;
(R)-3-((3-(4-(Azetidin-1-yl)pyrido[3,2-d]pyrimidin-6-yl)phenyl)ethynyl)-3-hydroxy-1-methylpyrrolidin-2-one;
(R)-3-Hydroxy-1-methyl-3-((3-(4-(methylamino)pyrido[3,2-d]pyrimidin-6-yl)phenyl)ethynyl)pyrrolidin-2-one;
(R)-3-((3-(4-Amino-8-methylpyrido[3,2-d]pyrimidin-6-yl)phenyl)ethynyl)-3-hydroxy-1-methylpyrrolidin-2-one;
(R)-3-((3-(4-aminopyrido[3,2-d]pyrimidin-6-yl-2-d)-4-(trifluoromethoxy)phenyl)ethynyl)-3-hydroxy-1-methylpyrrolidin-2-one;
(R)-2-[3-[2-(3-Hydroxy-1-methyl-2-oxo-pyrrolidin-3-yl)ethynyl]phenyl]-7H-pyrido[3,4-d]pyrimidin-8-one;
(S)-2-[3-[2-(3-Hydroxy-1-methyl-2-oxo-pyrrolidin-3-yl)ethynyl]phenyl]-7H-pyrido[3,4-d]pyrimidin-8-one;
(R)-4-[3-(8-Aminopyrido[3,4-d]pyrimidin-2-yl)phenyl]-2-thiazol-2-yl-but-3-yn-2-ol;
1-[2-[3-(8-Aminopyrido[3,4-d]pyrimidin-2-yl)phenyl]ethynyl]cyclopentanol;
(R)-4-[3-(8-Aminopyrido[3,4-d]pyrimidin-2-yl)phenyl]-2-(5-methylisoxazol-3-yl)but-3-yn-2-ol;
4-[3-(8-Aminopyrido[3,4-d]pyrimidin-2-yl)phenyl]-2-methyl-but-3-yn-2-ol;
(R)-3-[2-[3-(1-Amino-7-isoquinolyl)phenyl]ethynyl]-3-hydroxy-1-methyl-pyrrolidin-2-one;
(R)-3-((3-(8-Amino-4-methylpyrido[3,4-d]pyrimidin-2-yl)phenyl)ethynyl)-3-hydroxy-1-methylpyrrolidin-2-one;
(R)-3-((3-(8-Amino-4-(trifluoromethyl)pyrido[3,4-d]pyrimidin-2-yl)phenyl)ethynyl)-3-hydroxy-1-methylpyrrolidin-2-one;
(R)-3-((3-(8-Amino-5-methylpyrido[3,4-d]pyrimidin-2-yl)phenyl)ethynyl)-3-hydroxy-1-methylpyrrolidin-2-one;
(R)-3-((5-(8-Aminopyrido[3,4-d]pyrimidin-2-yl)-2-methylphenyl)ethynyl)-3-hydroxy-1-methylpyrrolidin-2-one;
(R)-3-((3-(8-Aminopyrido[3,4-d]pyrimidin-2-yl)-2-methylphenyl)ethynyl)-3-hydroxy-1-methylpyrrolidin-2-one;
(R)-3-((3-(8-Aminopyrido[3,4-d]pyrimidin-2-yl)-5-methylphenyl)ethynyl)-3-hydroxy-1-methylpyrrolidin-2-one;
(R)-3-((3-(8-Aminopyrido[3,4-d]pyrimidin-2-yl)-4-methylphenyl)ethynyl)-3-hydroxy-1-methylpyrrolidin-2-one;

(R)-3-((3-(8-Amino-6-methylpyrido[3,4-d]pyrimidin-2-yl)phenyl)ethynyl)-3-hydroxy-1-methylpyrrolidin-2-one;
(R)-7-[2-[3-(8-aminopyrido[3,4-d]pyrimidin-2-yl)phenyl]ethynyl]-5,6-dihydrocyclopenta[b]pyridin-7-ol;
(S)-7-[2-[3-(8-Aminopyrido[3,4-d]pyrimidin-2-yl)phenyl]ethynyl]-5,6-dihydrocyclopenta[b]pyridin-7-ol;
(R)-2-[3-[2-(7-Hydroxy-5,6-dihydrocyclopenta[b]pyridin-7-yl)ethynyl]phenyl]-7H-pyrido[3,4-d]pyrimidin-8-one;
(R)-4-(3-(8-Amino-4-methylpyrido[3,4-d]pyrimidin-2-yl)phenyl)-2-(thiazol-2-yl)but-3-yn-2-ol;
(R)-4-(3-(8-Amino-4-(trifluoromethyl)pyrido[3,4-d]pyrimidin-2-yl)phenyl)-2-(thiazol-2-yl)but-3-yn-2-ol;
(R)-4-(3-(8-Amino-5-methylpyrido[3,4-d]pyrimidin-2-yl)phenyl)-2-(thiazol-2-yl)but-3-yn-2-ol;
(R)-4-(3-(8-Amino-6-methylpyrido[3,4-d]pyrimidin-2-yl)phenyl)-2-(thiazol-2-yl)but-3-yn-2-ol;
(R)-7-[2-[3-(8-Aminopyrido[3,4-d]pyrimidin-2-yl)-5-methyl-phenyl]ethynyl]-5,6-dihydrocyclopenta[b]pyridin-7-ol;
(R)-3-((3-(8-Aminopyrido[3,4-d]pyrimidin-2-yl)-4-methoxyphenyl)ethynyl)-3-hydroxy-1-methylpyrrolidin-2-one;
(R)-3-((3-(8-Aminopyrido[3,4-d]pyrimidin-2-yl)-4-isobutylphenyl)ethynyl)-3-hydroxy-1-methylpyrrolidin-2-one;
(R)-8-Amino-2-(3-((3-hydroxy-1-methyl-2-oxopyrrolidin-3-yl)ethynyl)phenyl)pyrido[3,4-d]pyrimidin-4(3H)-one;
(R)-3-((3-(8-Aminopyrido[3,4-d]pyrimidin-2-yl)-4-(trifluoromethoxy)phenyl)ethynyl)-3-hydroxy-1-methylpyrrolidin-2-one;
(R)-3-((3-(8-Amino-4-morpholinopyrido[3,4-d]pyrimidin-2-yl)phenyl)ethynyl)-3-hydroxy-1-methylpyrrolidin-2-one;
(R)-3-((3-(8-Amino-4-(dimethylamino)pyrido[3,4-d]pyrimidin-2-yl)phenyl)ethynyl)-3-hydroxy-1-methylpyrrolidin-2-one;
(R)-3-[2-[3-(4-Amino-1H-imidazo[4,5-c]pyridin-2-yl)phenyl]ethynyl]-3-hydroxy-1-methyl-pyrrolidin-2-one;
(R)-7-((3-(8-Amino-4-methylpyrido[3,4-d]pyrimidin-2-yl)phenyl)ethynyl)-6,7-dihydro-5H-cyclopenta[b]pyridin-7-ol;
(R)-7-((3-(8-Amino-4-(trifluoromethyl)pyrido[3,4-d]pyrimidin-2-yl)phenyl)ethynyl)-6,7-dihydro-5H-cyclopenta[b]pyridin-7-ol;
(R)-7-((3-(8-Amino-5-methylpyrido[3,4-d]pyrimidin-2-yl)phenyl)ethynyl)-6,7-dihydro-5H-cyclopenta[b]pyridin-7-ol;
(R)-7-((3-(8-Amino-6-methylpyrido[3,4-d]pyrimidin-2-yl)phenyl)ethynyl)-6,7-dihydro-5H-cyclopenta[b]pyridin-7-ol;
(S)-7-[2-[3-(8-Aminopyrido[3,4-d]pyrimidin-2-yl)phenyl]ethynyl]-5,6-dihydropyrrolo[1,2-a]imidazol-7-ol;
(R)-3-[2-[3-(8-Amino-5-methyl-pyrido[3,4-d]pyrimidin-2-yl)-4-methyl-phenyl]ethynyl]-3-hydroxy-1-methyl-pyrrolidin-2-one;
(R)-3-[2-[3-(8-Aminopyrido[3,4-d]pyrimidin-2-yl)phenyl]ethynyl]-3-hydroxy-1-(trideuteriomethyl)pyrrolidin-2-one;
(S)-3-[2-[3-(8-Aminopyrido[3,4-d]pyrimidin-2-yl)phenyl]ethynyl]-3-hydroxy-1-(trideuteriomethyl)pyrrolidin-2-one;
(R)-4-[3-(1-Amino-7-isoquinolyl)-4-methyl-phenyl]-2-thiazol-2-yl-but-3-yn-2-ol;
(R)-4-(3-(8-Aminopyrido[3,4-d]pyrimidin-2-yl)-4-methylphenyl)-2-(thiazol-2-yl)but-3-yn-2-ol;
(R)-3-[2-[3-(1-Amino-7-isoquinolyl)-4-methyl-phenyl]ethynyl]-3-hydroxy-1-(trideuteriomethyl)pyrrolidin-2-one;
(S)-3-[2-[3-(1-Amino-7-isoquinolyl)-4-methyl-phenyl]ethynyl]-3-hydroxy-1-(trideuteriomethyl)pyrrolidin-2-one;
(R)-3-[2-[3-(8-Aminopyrido[3,4-d]pyrimidin-2-yl)phenyl]ethynyl]-3-hydroxy-1-(2,2,2-trifluoroethyl)pyrrolidin-2-one;
(S)-3-[2-[3-(8-Aminopyrido[3,4-d]pyrimidin-2-yl)phenyl]ethynyl]-3-hydroxy-1-(2,2,2-trifluoroethyl)pyrrolidin-2-one;
(R)-4-(3-(8-Aminopyrido[3,4-d]pyrimidin-2-yl)-4-methylphenyl)-2-(5-methyl-1,3,4-oxadiazol-2-yl)but-3-yn-2-ol;
(R)-7-((3-(8-Aminopyrido[3,4-d]pyrimidin-2-yl)-4-methylphenyl)ethynyl)-6,7-dihydro-5H-cyclopenta[b]pyridin-7-ol;
(R)-3-[2-[3-(8-Amino-5-methyl-pyrido[3,4-d]pyrimidin-2-yl)-5-methyl-phenyl]ethynyl]-3-hydroxy-1-methyl-pyrrolidin-2-one;
(R)-3-[2-[3-(1-Amino-7-isoquinolyl)-4-methyl-phenyl]ethynyl]-3-hydroxy-1-(2,2,2-trifluoroethyl)pyrrolidin-2-one;
(R)-4-[3-(1-Amino-7-isoquinolyl)-4-methyl-phenyl]-2-(5-methyl-1,3,4-oxadiazol-2-yl)but-3-yn-2-ol;
(R)-4-[3-(1-Amino-7-isoquinolyl)-4-methyl-phenyl]-2-(5-methylisoxazol-3-yl)but-3-yn-2-ol;
(R)-7-[2-[3-(1-Amino-7-isoquinolyl)-4-methyl-phenyl]ethynyl]-5,6-dihydrocyclopenta[b]pyridin-7-ol;
(R)-7-[2-[3-(1-Amino-7-isoquinolyl)-4-methyl-phenyl]ethynyl]-5,6-dihydropyrrolo[1,2-a]imidazol-7-ol;
(R)-4-(3-(8-Aminopyrido[3,4-d]pyrimidin-2-yl)-4-methylphenyl)-2-(5-methylisoxazol-3-yl)but-3-yn-2-ol;
(R)-3-((3-(8-Amino-4-methylpyrido[3,4-d]pyrimidin-2-yl)phenyl)ethynyl)-3-hydroxy-1-(methyl-d$_3$)pyrrolidin-2-one;
(R)-7-((3-(8-Amino-4-methylpyrido[3,4-d]pyrimidin-2-yl)phenyl)ethynyl)-6,7-dihydro-5H-pyrrolo[1,2-a]imidazol-7-ol;
(R)-3-((3-(8-Amino-4-(methylamino)pyrido[3,4-d]pyrimidin-2-yl)phenyl)ethynyl)-3-hydroxy-1-methylpyrrolidin-2-one;
(R)-7-[2-[3-(8-Amino-5-methyl-pyrido[3,4-d]pyrimidin-2-yl)phenyl]ethynyl]-5,6-dihydropyrrolo[1,2-a]imidazol-7-ol;
(R)-3-[2-[3-(8-Amino-5-methyl-pyrido[3,4-d]pyrimidin-2-yl)phenyl]ethynyl]-3-hydroxy-1-(trideuteriomethyl)pyrrolidin-2-one;
(R)-4-[3-(8-Amino-1,7-naphthyridin-2-yl)phenyl]-2-(5-methyl-1,3,4-oxadiazol-2-yl)but-3-yn-2-ol;
(R)-4-[3-(8-Amino-1,7-naphthyridin-2-yl)phenyl]-2-(5-methylisoxazol-3-yl)but-3-yn-2-ol;
(R)-4-[3-(8-Amino-1,7-naphthyridin-2-yl)phenyl]-2-thiazol-2-yl-but-3-yn-2-ol;
(R)-7-[2-[3-(8-Amino-1,7-naphthyridin-2-yl)phenyl]ethynyl]-5,6-dihydropyrrolo[1,2-a]imidazol-7-ol;
(R)-3-[2-[3-(8-Amino-4-methyl-pyrido[3,4-d]pyrimidin-2-yl)phenyl]ethynyl]-3-hydroxy-1-(2,2,2-trifluoroethyl)pyrrolidin-2-one;
(R)-4-(3-(4-Aminopyrido[3,2-d]pyrimidin-6-yl)phenyl)-2-(thiazol-2-yl)but-3-yn-2-ol;
(R)-3-((3-(8-Amino-5-bromopyrido[3,4-d]pyrimidin-2-yl)phenyl)ethynyl)-3-hydroxy-1-methylpyrrolidin-2-one;
(R)-4-(3-(4-Aminopyrido[3,2-d]pyrimidin-6-yl)phenyl)-2-(5-methylisoxazol-3-yl)but-3-yn-2-ol;

(R)-3-[2-[3-(4-Aminophthalazin-6-yl)phenyl]ethynyl]-3-hydroxy-1-methyl-pyrrolidin-2-one;
(R)-4-(3-(4-Aminopyrido[3,2-d]pyrimidin-6-yl)phenyl)-2-(5-methyl-1,3,4-oxadiazol-2-yl)but-3-yn-2-ol;
(R)-3-((3-(8-Amino-4-isopropylpyrido[3,4-d]pyrimidin-2-yl)phenyl)ethynyl)-3-hydroxy-1-methylpyrrolidin-2-one;
(R)-3-[2-[3-[8-Amino-5-(trifluoromethyl)pyrido[3,4-d]pyrimidin-2-yl]phenyl]ethynyl]-3-hydroxy-1-methyl-pyrrolidin-2-one;
(R)-8-Amino-2-(3-((3-hydroxy-1-methyl-2-oxopyrrolidin-3-yl)ethynyl)phenyl)pyrido[3,4-d]pyrimidine-5-carbonitrile;
(R)-3-((3-(7-Aminothiazolo[5,4-d]pyrimidin-2-yl)phenyl)ethynyl)-3-hydroxy-1-methylpyrrolidin-2-one;
(R)-3-((3-(8-Amino-5-iodopyrido[3,4-d]pyrimidin-2-yl)phenyl)ethynyl)-3-hydroxy-1-methylpyrrolidin-2-one;
(R)-3-((3-(8-Amino-5-chloropyrido[3,4-d]pyrimidin-2-yl)phenyl)ethynyl)-3-hydroxy-1-methylpyrrolidin-2-one;
(R)-4-[3-(4-Aminoquinazolin-6-yl)phenyl]-2-(5-methyl-isoxazol-3-yl)but-3-yn-2-ol;
(R)-4-[3-(4-Aminoquinazolin-6-yl)phenyl]-2-thiazol-2-yl-but-3-yn-2-ol;
(R)-4-[3-(4-Aminoquinazolin-6-yl)phenyl]-2-(5-methyl-1,3,4-oxadiazol-2-yl)but-3-yn-2-ol;
2-(3-((1H-Pyrazol-5-yl)ethynyl)phenyl)-4-methylpyrido[3,4-d]pyrimidin-8-amine;
(R)-4-(3-(4-Aminopyrido[2,3-d]pyrimidin-6-yl)phenyl)-2-(thiazol-2-yl)but-3-yn-2-ol;
(R)-3-((3-(4-Aminopyrido[2,3-d]pyrimidin-6-yl)phenyl)ethynyl)-3-hydroxy-1-methylpyrrolidin-2-one;
(R)-3-((3-(4-Amino-8-methylquinazolin-6-yl)phenyl)ethynyl)-3-hydroxy-1-methylpyrrolidin-2-one;
(R)-3-[2-[3-(4-Aminopyrido[3,4-d]pyrimidin-6-yl)phenyl]ethynyl]-3-hydroxy-1-methyl-pyrrolidin-2-one;
(R)-3-[2-[3-(8-Amino-5-bromo-1,7-naphthyridin-2-yl)phenyl]ethynyl]-3-hydroxy-1-methyl-pyrrolidin-2-one;
(R)-3-[2-[3-(4-Amino-8-fluoro-quinazolin-6-yl)phenyl]ethynyl]-3-hydroxy-1-methyl-pyrrolidin-2-one;
(R)-3-((3-(4-Amino-8-methoxyquinazolin-6-yl)phenyl)ethynyl)-3-hydroxy-1-methylpyrrolidin-2-one;
(R)-3-((3-(4-Amino-8-(trifluoromethyl)quinazolin-6-yl)phenyl)ethynyl)-3-hydroxy-1-methylpyrrolidin-2-one;
(R)-3-((3-(4-Aminothiazolo[4,5-c]pyridin-2-yl)phenyl)ethynyl)-3-hydroxy-1-methylpyrrolidin-2-one;
(R)-3-((3-(4-Amino-8-chloroquinazolin-6-yl)phenyl)ethynyl)-3-hydroxy-1-methylpyrrolidin-2-one;
(R)-8-Amino-2-[3-[2-(3-hydroxy-1-methyl-2-oxo-pyrrolidin-3-yl)ethynyl]phenyl]-1,7-naphthyridine-5-carbonitrile;
(R)-3-[2-[3-(5-Amino-2,6-naphthyridin-3-yl)phenyl]ethynyl]-3-hydroxy-1-methyl-pyrrolidin-2-one;
(R)-3-[2-[3-(8-Amino-5-methyl-1,7-naphthyridin-2-yl)phenyl]ethynyl]-3-hydroxy-1-methyl-pyrrolidin-2-one;
(R)-3-((3-(8-Amino-5-phenylpyrido[3,4-d]pyrimidin-2-yl)phenyl)ethynyl)-3-hydroxy-1-methylpyrrolidin-2-one;
(R)-3-[2-[3-[8-Amino-5-(1-methylpyrazol-4-yl)pyrido[3,4-d]pyrimidin-2-yl]phenyl]ethynyl]-3-hydroxy-1-methyl-pyrrolidin-2-one;
(R)-3-[2-[3-[8-Amino-5-[1-(2-hydroxy-2-methyl-propyl)pyrazol-4-yl]pyrido[3,4-d]pyrimidin-2-yl]phenyl]ethynyl]-3-hydroxy-1-methyl-pyrrolidin-2-one;
(R)-3-[2-[3-[8-Amino-5-(1H-pyrazol-4-yl)pyrido[3,4-d]pyrimidin-2-yl]phenyl]ethynyl]-3-hydroxy-1-methyl-pyrrolidin-2-one;
(R)-3-[2-[3-[8-Amino-5-(3,5-dimethyl-1H-pyrazol-4-yl)pyrido[3,4-d]pyrimidin-2-yl]phenyl]ethynyl]-3-hydroxy-1-methyl-pyrrolidin-2-one;
(R)-4-Amino-6-(3-((3-hydroxy-1-methyl-2-oxopyrrolidin-3-yl)ethynyl)phenyl)quinazoline-8-carbonitrile;
(R)-3-[2-[3-[8-Amino-5-(5-methyl-1H-pyrazol-4-yl)pyrido[3,4-d]pyrimidin-2-yl]phenyl]ethynyl]-3-hydroxy-1-methyl-pyrrolidin-2-one;
(R)-Phenyl 8-amino-2-[3-[2-(3-hydroxy-1-methyl-2-oxo-pyrrolidin-3-yl)ethynyl]phenyl]pyrido[3,4-d]pyrimidine-5-carboxylate;
(R)-3-((3-(8-Amino-5-ethylpyrido[3,4-d]pyrimidin-2-yl)phenyl)ethynyl)-3-hydroxy-1-methylpyrrolidin-2-one;
(R)-3-((3-(8-Amino-5-isobutylpyrido[3,4-d]pyrimidin-2-yl)phenyl)ethynyl)-3-hydroxy-1-methylpyrrolidin-2-one;
(R)-2-[2-[3-(4-Aminopyrido[3,2-d]pyrimidin-6-yl)phenyl]ethynyl]-2-hydroxy-5,5-dimethyl-cyclopentanone;
(S)-2-[2-[3-(4-Aminopyrido[3,2-d]pyrimidin-6-yl)phenyl]ethynyl]-2-hydroxy-5,5-dimethyl-cyclopentanone;
(R)-3-[2-[3-[8-Amino-5-(pyrrolidin-1-ylmethyl)pyrido[3,4-d]pyrimidin-2-yl]phenyl]ethynyl]-3-hydroxy-1-methyl-pyrrolidin-2-one;
(R)-3-[2-[3-[8-Amino-5-[1-(2-aminoethyl)pyrazol-4-yl]pyrido[3,4-d]pyrimidin-2-yl]phenyl]ethynyl]-3-hydroxy-1-methyl-pyrrolidin-2-one;
(R)-3-[2-[3-[8-Amino-5-(dimethylaminomethyl)pyrido[3,4-d]pyrimidin-2-yl]phenyl]ethynyl]-3-hydroxy-1-methyl-pyrrolidin-2-one;
(R)-3-[2-[3-(4-Amino-8-methyl-pyrido[3,4-d]pyrimidin-6-yl)phenyl]ethynyl]-3-hydroxy-1-methyl-pyrrolidin-2-one;
(R)-4-(3-(8-Aminopyrimido[5,4-d]pyrimidin-2-yl)phenyl)-2-(thiazol-2-yl)but-3-yn-2-ol;
(R)-3-((3-(8-Amino-4,5-dimethylpyrido[3,4-d]pyrimidin-2-yl)phenyl)ethynyl)-3-hydroxy-1-methylpyrrolidin-2-one;
(R)-3-((3-(4-Aminopyrido[3,2-d]pyrimidin-6-yl)-4-methoxyphenyl)ethynyl)-3-hydroxy-1-methylpyrrolidin-2-one;
(R)-4-[4-[8-Amino-2-[3-[2-(3-hydroxy-1-methyl-2-oxo-pyrrolidin-3-yl)ethynyl]phenyl]pyrido[3,4-d]pyrimidin-5-yl]pyrazol-1-yl]butanenitrile;
(R)-3-((3-(4-Aminothieno[2,3-d]pyrimidin-6-yl)phenyl)ethynyl)-3-hydroxy-1-methylpyrrolidin-2-one;
(R)-3-((3-(7-Aminooxazolo[5,4-d]pyrimidin-2-yl)phenyl)ethynyl)-3-hydroxy-1-methylpyrrolidin-2-one;
(R)-3-((3-(6-Amino-9-methyl-9H-purin-8-yl)phenyl)ethynyl)-3-hydroxy-1-methylpyrrolidin-2-one;
(R)-7-((3-(8-Aminopyrimido[5,4-d]pyrimidin-2-yl)phenyl)ethynyl)-6,7-dihydro-5H-cyclopenta[b]pyridin-7-ol;
(R)-3-[2-[3-[8-Amino-5-(1-piperidylmethyl)pyrido[3,4-d]pyrimidin-2-yl]phenyl]ethynyl]-3-hydroxy-1-methyl-pyrrolidin-2-one;
(R)-7-[2-[3-(4-Aminopyrimido[5,4-d]pyrimidin-6-yl)phenyl]ethynyl]-5,6-dihydropyrrolo[1,2-a]imidazol-7-ol;
(R)-3-[2-[3-[8-Amino-5-[6-(trifluoromethyl)-3-pyridyl]pyrido[3,4-d]pyrimidin-2-yl]phenyl]ethynyl]-3-hydroxy-1-methyl-pyrrolidin-2-one;
(R)-3-[2-[3-(4-Amino-2-methyl-pteridin-6-yl)phenyl]ethynyl]-3-hydroxy-1-methyl-pyrrolidin-2-one;
(R)-3-((3-(4-Aminopyrido[3,2-d]pyrimidin-6-yl-2-d)-4-methylphenyl)ethynyl)-3-hydroxy-1-methylpyrrolidin-2-one;
(R)-3-((3-(4-Amino-2-methylpyrido[3,2-d]pyrimidin-6-yl)-4-methylphenyl)ethynyl)-3-hydroxy-1-methylpyrrolidin-2-one;
(R)-3-((3-(8-Amino-5-neopentylpyrido[3,4-d]pyrimidin-2-yl)phenyl)ethynyl)-3-hydroxy-1-methylpyrrolidin-2-one;
(R)-3-((5-(7-Aminothiazolo[5,4-d]pyrimidin-2-yl)-2-methylphenyl)ethynyl)-3-hydroxy-1-methylpyrrolidin-2-one;

(R)-3-((3-(7-Aminothiazolo[5,4-d]pyrimidin-2-yl)-5-methylphenyl)ethynyl)-3-hydroxy-1-methylpyrrolidin-2-one;
(R)-3-((3-(7-Aminothiazolo[5,4-d]pyrimidin-2-yl)-2-methylphenyl)ethynyl)-3-hydroxy-1-methylpyrrolidin-2-one;
(S)-7-((3-(8-Aminopyrimido[5,4-d]pyrimidin-2-yl)phenyl)ethynyl)-6,7-dihydro-5H-cyclopenta[b]pyridin-7-ol;
(R)-3-((3-(8-Amino-4,6-dimethylpyrimido[5,4-d]pyrimidin-2-yl)phenyl)ethynyl)-3-hydroxy-1-methylpyrrolidin-2-one;
(S)-4-(3-(4-Amino-2-methylpyrido[3,2-d]pyrimidin-6-yl)phenyl)-2-(2-methylthiazol-5-yl)but-3-yn-2-ol;
(R)-4-(3-(4-Amino-2-methylpyrido[3,2-d]pyrimidin-6-yl)phenyl)-2-(2-methylthiazol-5-yl)but-3-yn-2-ol;
(R)-3-((3-(4-Amino-7,8-dihydropyrido[4,3-d]pyrimidin-6(5H)-yl)phenyl)ethynyl)-3-hydroxy-1-methylpyrrolidin-2-one;
(R)-3-((3-(4-Aminopyrido[3,2-d]pyrimidin-6-yl-2-d)-4-methoxyphenyl)ethynyl)-3-hydroxy-1-methylpyrrolidin-2-one;
(R)-3-((3-(4-Amino-2-methylpyrido[3,2-d]pyrimidin-6-yl)-4-methoxyphenyl)ethynyl)-3-hydroxy-1-methylpyrrolidin-2-one;
(S)-4-(3-(4-Amino-2-methylpyrido[3,2-d]pyrimidin-6-yl)phenyl)-2-(4-methylthiazol-5-yl)but-3-yn-2-ol;
(R)-4-(3-(4-Amino-2-methylpyrido[3,2-d]pyrimidin-6-yl)phenyl)-2-(4-methylthiazol-5-yl)but-3-yn-2-ol;
(R)-4-(3-(4-Amino-2-methylpyrido[3,2-d]pyrimidin-6-yl)phenyl)-2-(thiazol-2-yl)but-3-yn-2-ol;
racemic-8-((3-(4-Amino-2-methylpyrido[3,2-d]pyrimidin-6-yl)phenyl)ethynyl)-5,6,7,8-tetrahydroquinolin-8-ol;
(S)-4-(3-(4-Amino-2-methylpyrido[3,2-d]pyrimidin-6-yl)phenyl)-2-(5-methylthiazol-2-yl)but-3-yn-2-ol;
(R)-4-(3-(4-Amino-2-methylpyrido[3,2-d]pyrimidin-6-yl)phenyl)-2-(5-methylthiazol-2-yl)but-3-yn-2-ol;
(R)-3-((3-(8-Amino-4-methylpyrimido[5,4-d]pyrimidin-2-yl-6-d)phenyl)ethynyl)-3-hydroxy-1-methylpyrrolidin-2-one;
(R)-tert-Butyl 3-amino-5-[3-[2-(3-hydroxy-1-methyl-2-oxo-pyrrolidin-3-yl)ethynyl]phenyl]indazole-1-carboxylate;
(R)-3-((3-(4-Amino-2-(fluoromethyl)pyrido[3,2-d]pyrimidin-6-yl)phenyl)ethynyl)-3-hydroxy-1-methylpyrrolidin-2-one;
(R)-3-[2-[3-[8-Amino-5-(pyrrolidin-1-ylmethyl)-1,7-naphthyridin-2-yl]phenyl]ethynyl]-3-hydroxy-1-methyl-pyrrolidin-2-one;
(R)-3-[2-[3-[8-Amino-5-(dimethylaminomethyl)-1,7-naphthyridin-2-yl]phenyl]ethynyl]-3-hydroxy-1-methyl-pyrrolidin-2-one;
(R)-3-((3-(4-Amino-2-(hydroxymethyl)pyrido[3,2-d]pyrimidin-6-yl)phenyl)ethynyl)-3-hydroxy-1-methylpyrrolidin-2-one;
(R)-3-[2-[3-(3-Amino-1H-indazol-5-yl)phenyl]ethynyl]-3-hydroxy-1-methyl-pyrrolidin-2-one;
(R)-3-((3-(4-Amino-2-cyclopropylpyrido[3,2-d]pyrimidin-6-yl)phenyl)ethynyl)-3-hydroxy-1-methylpyrrolidin-2-one;
(R)-3-((3-(4-Amino-2-(trifluoromethyl)pyrido[3,2-d]pyrimidin-6-yl)phenyl)ethynyl)-3-hydroxy-1-methylpyrrolidin-2-one;
(R)-3-((3-(8-Aminopyrimido[5,4-d]pyrimidin-2-yl)-4-methoxyphenyl)ethynyl)-3-hydroxy-1-methylpyrrolidin-2-one;
(R)-3-((3-(4-Amino-2,7-dimethylpyrido[3,2-d]pyrimidin-6-yl)phenyl)ethynyl)-3-hydroxy-1-methylpyrrolidin-2-one;
(R)-3-((3-(4-Amino-2H-pyrazolo[3,4-d]pyrimidin-2-yl)phenyl)ethynyl)-3-hydroxy-1-methylpyrrolidin-2-one;
(R)-4-(3-(4-Amino-2-methylpyrido[3,2-d]pyrimidin-6-yl)phenyl)-2-(4-methylthiazol-2-yl)but-3-yn-2-ol;
(S)-4-(3-(4-Amino-2-methylpyrido[3,2-d]pyrimidin-6-yl)phenyl)-2-(4-methylthiazol-2-yl)but-3-yn-2-ol;
(R)-3-[2-[3-(7-Amino-5-methyl-thiazolo[5,4-d]pyrimidin-2-yl)-4-methyl-phenyl]ethynyl]-3-hydroxy-1-methyl-pyrrolidin-2-one;
(R)-7-[2-[3-(7-Aminothiazolo[5,4-d]pyrimidin-2-yl)-4-methyl-phenyl]ethynyl]-5,6-dihydropyrrolo[1,2-a]imidazol-7-ol;
(R)-7-[2-[3-(7-Aminothiazolo[5,4-d]pyrimidin-2-yl)-4-methyl-phenyl]ethynyl]-5,6-dihydrocyclopenta[b]pyridin-7-ol;
1-[2-[3-(7-Aminothiazolo[5,4-d]pyrimidin-2-yl)-4-methyl-phenyl]ethynyl]cyclopentanol;
(S)-3-((3-(4-Amino-2-methylpyrido[3,2-d]pyrimidin-6-yl)phenyl)ethynyl)-3-hydroxy-1-methylpiperidin-2-one;
(R)-3-((3-(4-Amino-2-methylpyrido[3,2-d]pyrimidin-6-yl)phenyl)ethynyl)-3-hydroxy-1-methylpiperidin-2-one;
(R)-3-((3-(8-Aminopyrimido[5,4-d]pyrimidin-2-yl)-4-methylphenyl)ethynyl)-3-hydroxy-1-methylpyrrolidin-2-one;
(R)-3-((3-(4-Amino-7-methylpyrido[3,2-d]pyrimidin-6-yl)phenyl)ethynyl)-3-hydroxy-1-methylpyrrolidin-2-one;
(R)-4-[3-(4-Amino-2-methyl-pyrido[3,2-d]pyrimidin-6-yl)phenyl]-2-(2-pyridyl)but-3-yn-2-ol;
(S)-4-[3-(4-Amino-2-methyl-pyrido[3,2-d]pyrimidin-6-yl)phenyl]-2-(2-pyridyl)but-3-yn-2-ol;
(R)-4-(3-(4-Amino-2-methylpyrido[3,2-d]pyrimidin-6-yl)phenyl)-2-(4-(trifluoromethyl)thiazol-2-yl)but-3-yn-2-ol;
(S)-4-(3-(4-Amino-2-methylpyrido[3,2-d]pyrimidin-6-yl)phenyl)-2-(4-(trifluoromethyl)thiazol-2-yl)but-3-yn-2-ol;
(R)-3-((3-(7-Aminothiazolo[5,4-d]pyrimidin-2-yl)-4-methoxyphenyl)ethynyl)-3-hydroxy-1-methylpyrrolidin-2-one;
1-Allyl-3-((3-(4-Amino-2-methylpyrido[3,2-d]pyrimidin-6-yl)phenyl)ethynyl)-3-hydroxypyrrolidin-2-one;
racemic-1-Allyl-3-((3-(4-aminopyrido[3,2-d]pyrimidin-6-yl-2-d)phenyl)ethynyl)-3-hydroxypyrrolidin-2-one;
(R)-4-[3-(4-Amino-2-methyl-pyrido[3,2-d]pyrimidin-6-yl)phenyl]-2-pyrimidin-2-yl-but-3-yn-2-ol;
(S)-4-[3-(4-Amino-2-methyl-pyrido[3,2-d]pyrimidin-6-yl)phenyl]-2-pyrimidin-2-yl-but-3-yn-2-ol;
(S)-3-((3-(4-Aminopyrido[3,2-d]pyrimidin-6-yl-2-d)phenyl)ethynyl)-3-hydroxy-1-methylpiperidin-2-one;
(R)-4-[3-(4-Amino-2-methyl-pyrido[3,2-d]pyrimidin-6-yl)phenyl]-2-pyrazin-2-yl-but-3-yn-2-ol;
(S)-4-[3-(4-Amino-2-methyl-pyrido[3,2-d]pyrimidin-6-yl)phenyl]-2-pyrazin-2-yl-but-3-yn-2-ol;
racemic-4-(3-(4-Amino-2-methylpyrido[3,2-d]pyrimidin-6-yl)phenyl)-2-(1H-imidazol-4-yl)but-3-yn-2-ol;
(R)-3-((3-(2,4-Diaminopyrido[3,2-d]pyrimidin-6-yl)phenyl)ethynyl)-3-hydroxy-1-methylpyrrolidin-2-one;
(R)-3-((3-(4-Aminopyrido[3,2-d]pyrimidin-6-yl)phenyl)ethynyl)-3-(difluoromethyl)-1-methylpyrrolidin-2-one;
(S)-3-((3-(4-Aminopyrido[3,2-d]pyrimidin-6-yl)phenyl)ethynyl)-3-(difluoromethyl)-1-methylpyrrolidin-2-one;
(R)-3-((3-(4-Amino-2-(methoxymethyl)pyrido[3,2-d]pyrimidin-6-yl)phenyl)ethynyl)-3-hydroxy-1-methylpyrrolidin-2-one;
(R)-3-((3-(4-Aminopyrido[3,2-d]pyrimidin-6-yl)phenyl)ethynyl)-3-methoxy-1-methylpyrrolidin-2-one;
(R)-3-((3-(4-Amino-2-(fluoromethyl)pyrido[3,2-d]pyrimidin-6-yl)phenyl)ethynyl)-3-hydroxy-1-(methyl-$d_3$)pyrrolidin-2-one;
(S)-4-[3-(4-Amino-2-methyl-pyrido[3,2-d]pyrimidin-6-yl)phenyl]-2-thiazol-4-yl-but-3-yn-2-ol;

(R)-3-((3-(4-Amino-2-ethylpyrido[3,2-d]pyrimidin-6-yl)phenyl)ethynyl)-3-hydroxy-1-methylpyrrolidin-2-one;
(R)-3-((3-(4-Amino-2-hydroxypyrido[3,2-d]pyrimidin-6-yl)phenyl)ethynyl)-3-hydroxy-1-methylpyrrolidin-2-one;
(R)-4-[3-(4-Amino-2-methyl-pyrido[3,2-d]pyrimidin-6-yl)phenyl]-2-thiazol-4-yl-but-3-yn-2-ol;
(R)-4-(3-(4-Amino-2-methylpyrido[3,2-d]pyrimidin-6-yl)phenyl)-2-(5-methyl-1,3,4-oxadiazol-2-yl)but-3-yn-2-ol;
(R)-3-((3-(7-Aminothiazolo[4,5-d]pyrimidin-2-yl)phenyl)ethynyl)-3-hydroxy-1-methylpyrrolidin-2-one;
(R)-3-((3-(4-Amino-2-methyl-7,8-dihydropyrido[4,3-d]pyrimidin-6(5H)-yl)phenyl)ethynyl)-3-hydroxy-1-methylpyrrolidin-2-one;
(R)-3-[2-[3-(7-Aminothiazolo[5,4-d]pyrimidin-2-yl)-4-methyl-phenyl]ethynyl]-3-hydroxy-1-(trideuteriomethyl)pyrrolidin-2-one;
(R)-4-[3-(7-Aminothiazolo[5,4-d]pyrimidin-2-yl)-4-methyl-phenyl]-2-(5-methylisoxazol-3-yl)but-3-yn-2-ol;
(R)-6-[3-[2-(3-Hydroxy-1-methyl-2-oxo-pyrrolidin-3-yl)ethynyl]phenyl]-7H-imidazo[1,5-a]pyrazin-8-one;
(R)-3-((3-(8-Amino-1,5-naphthyridin-2-yl)phenyl)ethynyl)-3-hydroxy-1-methylpyrrolidin-2-one;
(R)-3-((3-(4-Amino-7,8-dihydropyrido[4,3-d]pyrimidin-6(5H)-yl)-4-methylphenyl)ethynyl)-3-hydroxy-1-methylpyrrolidin-2-one;
(R)-6-(3-(((3-Hydroxy-1-methyl-2-oxopyrrolidin-3-yl)ethynyl)phenyl)pyrido[3,2-d]pyrimidin-4(3H)-one;
(R)-3-Hydroxy-1-methyl-3-((3-(4-(pyrrolidin-1-yl)pyrido[3,2-d]pyrimidin-6-yl)phenyl)ethynyl)pyrrolidin-2-one;
((R)-3-Hydroxy-1-methyl-3-((3-(pyrido[3,2-d]pyrimidin-6-yl)phenyl)ethynyl)pyrrolidin-2-one;
(R)-3-((3-(4-Amino-5,7,8,9-tetrahydro-6H-pyrimido[5,4-c]azepin-6-yl)phenyl)ethynyl)-3-hydroxy-1-methylpyrrolidin-2-one;
(R)-3-Hydroxy-1-methyl-3-((3-(4-(piperidin-1-yl)pyrido[3,2-d]pyrimidin-6-yl)phenyl)ethynyl)pyrrolidin-2-one;
(R)-3-((3-(4-(3,3-Dimethylazetidin-1-yl)pyrido[3,2-d]pyrimidin-6-yl)phenyl)ethynyl)-3-hydroxy-1-methylpyrrolidin-2-one;
(R)-3-((3-(4-(Ethylamino)pyrido[3,2-d]pyrimidin-6-yl)phenyl)ethynyl)-3-hydroxy-1-methylpyrrolidin-2-one;
(R)-3-Hydroxy-3-((3-(4-(3-hydroxyazetidin-1-yl)pyrido[3,2-d]pyrimidin-6-yl)phenyl)ethynyl)-1-methylpyrrolidin-2-one;
(R)-3-Hydroxy-1-methyl-3-((3-(4-(oxetan-3-ylamino)pyrido[3,2-d]pyrimidin-6-yl)phenyl)ethynyl)pyrrolidin-2-one;
(R)-3-Hydroxy-3-((3-(4-(3-methoxyazetidin-1-yl)pyrido[3,2-d]pyrimidin-6-yl)phenyl)ethynyl)-1-methylpyrrolidin-2-one;
(S)-3-((3-(4-(Azetidin-1-yl)pyrido[3,2-d]pyrimidin-6-yl)phenyl)ethynyl)-3-hydroxy-1-methylpyrrolidin-2-one;
(R)-3-((3-(4-(3,3-Difluoroazetidin-1-yl)pyrido[3,2-d]pyrimidin-6-yl)phenyl)ethynyl)-3-hydroxy-1-methylpyrrolidin-2-one;
(R)-3-((3-(8-(Azetidin-1-yl)-1,7-naphthyridin-2-yl)phenyl)ethynyl)-3-hydroxy-1-methylpyrrolidin-2-one;
(R)-3-((3-(1-(Azetidin-1-yl)isoquinolin-7-yl)phenyl)ethynyl)-3-hydroxy-1-methylpyrrolidin-2-one;
(R)-3-((3-(4-(Azetidin-1-yl)quinolin-6-yl)phenyl)ethynyl)-3-hydroxy-1-methylpyrrolidin-2-one;
(R)-3-((3-(4-(Cyclobutylamino)pyrido[3,2-d]pyrimidin-6-yl)phenyl)ethynyl)-3-hydroxy-1-methylpyrrolidin-2-one;
(R)-3-((3-(4-Amino-2-methylpyrido[3,2-d]pyrimidin-6-yl)-4-(trifluoromethoxy)phenyl)ethynyl)-3-hydroxy-1-methylpyrrolidin-2-one;
(R)—N-(6-(3-((3-Hydroxy-1-methyl-2-oxopyrrolidin-3-yl)ethynyl)phenyl)pyrido[3,2-d]pyrimidin-4-yl)acetamide;
(R)-3-((3-(4-(3-Fluoroazetidin-1-yl)pyrido[3,2-d]pyrimidin-6-yl)phenyl)ethynyl)-3-hydroxy-1-methylpyrrolidin-2-one;
(R)-2-((6-(3-((3-Hydroxy-1-methyl-2-oxopyrrolidin-3-yl)ethynyl)phenyl)pyrido[3,2-d]pyrimidin-4-yl)amino)acetonitrile;
(R)-3-((3-(4-((2,2-Difluoroethyl)amino)pyrido[3,2-d]pyrimidin-6-yl)phenyl)ethynyl)-3-hydroxy-1-methylpyrrolidin-2-one;
(R)-1-(6-(3-((3-Hydroxy-1-methyl-2-oxopyrrolidin-3-yl)ethynyl)phenyl)pyrido[3,2-d]pyrimidin-4-yl)azetidine-3-carbonitrile;
(R)-3-((3-(4-(Azetidin-1-yl)quinazolin-6-yl)phenyl)ethynyl)-3-hydroxy-1-methylpyrrolidin-2-one;
(R)-3-((3-(4-(3-Chloroazetidin-1-yl)pyrido[3,2-d]pyrimidin-6-yl)phenyl)ethynyl)-3-hydroxy-1-methylpyrrolidin-2-one;
(R)-3-Hydroxy-1-methyl-3-((3-(4-(3-(methylsulfonyl)azetidin-1-yl)pyrido[3,2-d]pyrimidin-6-yl)phenyl)ethynyl)pyrrolidin-2-one;
(R)-1-(6-(3-((3-Hydroxy-1-methyl-2-oxopyrrolidin-3-yl)ethynyl)phenyl)pyrido[3,2-d]pyrimidin-4-yl)-N-methylazetidine-3-carboxamide;
(R)-3-((3-(8-(Azetidin-1-yl)pyrido[3,4-d]pyrimidin-2-yl)phenyl)ethynyl)-3-hydroxy-1-methylpyrrolidin-2-one;
(S)-3-((3-(8-(Azetidin-1-yl)pyrido[3,4-d]pyrimidin-2-yl)phenyl)ethynyl)-3-hydroxy-1-methylpyrrolidin-2-one;
(R)-3-((3-(5-Bromo-8-methyl-1,7-naphthyridin-2-yl)phenyl)ethynyl)-3-hydroxy-1-methylpyrrolidin-2-one;
(R)-3-((3-(4,8-Dimethylpyrido[3,2-d]pyrimidin-6-yl)phenyl)ethynyl)-3-hydroxy-1-methylpyrrolidin-2-one;
(R)-2-(3-((3-Hydroxy-1-methyl-2-oxopyrrolidin-3-yl)ethynyl)phenyl)-8-methyl-1,7-naphthyridine-5-carbonitrile;
(R)-3-((3-(5,8-Dimethyl-1,7-naphthyridin-2-yl)phenyl)ethynyl)-3-hydroxy-1-methylpyrrolidin-2-one;
(R)-3-((3-(4-Amino-8-bromopyrido[3,2-d]pyrimidin-6-yl)phenyl)ethynyl)-3-hydroxy-1-methylpyrrolidin-2-one;
(S)-3-((3-(4-Amino-8-bromopyrido[3,2-d]pyrimidin-6-yl)phenyl)ethynyl)-3-hydroxy-1-methylpyrrolidin-2-one;
(R)-3-((3-(4-Amino-8-(tetrahydro-2H-pyran-4-yl)pyrido[3,2-d]pyrimidin-6-yl)phenyl)ethynyl)-3-hydroxy-1-methylpyrrolidin-2-one;
(S)-3-((3-(4-Amino-8-(tetrahydro-2H-pyran-4-yl)pyrido[3,2-d]pyrimidin-6-yl)phenyl)ethynyl)-3-hydroxy-1-methylpyrrolidin-2-one;
(R)-3-Hydroxy-1-methyl-3-((3-(4-phenylpyrido[3,2-d]pyrimidin-6-yl)phenyl)ethynyl)pyrrolidin-2-one;
(R)—N-(6-(3-((3-Hydroxy-1-methyl-2-oxopyrrolidin-3-yl)ethynyl)phenyl)-2-methylpyrido[3,2-d]pyrimidin-4-yl)acetamide;
(R)—N-(6-(3-((3-Hydroxy-1-methyl-2-oxopyrrolidin-3-yl)ethynyl)phenyl)pyrido[3,2-d]pyrimidin-4-yl-2-d)acetamide;
(S)-3-((3-(4-Aminopyrido[3,2-d]pyrimidin-6-yl)-4-methylphenyl)ethynyl)-3-hydroxy-1-methylpyrrolidin-2-one;
(3R,5R)-3-((3-(4-Aminopyrido[3,2-d]pyrimidin-6-yl-2-d)phenyl)ethynyl)-3-hydroxy-1,5-dimethylpyrrolidin-2-one;
(3R,5S)-3-((3-(4-Aminopyrido[3,2-d]pyrimidin-6-yl-2-d)phenyl)ethynyl)-3-hydroxy-1,5-dimethylpyrrolidin-2-one;
(3S,5S)-3-((3-(4-Aminopyrido[3,2-d]pyrimidin-6-yl-2-d)phenyl)ethynyl)-3-hydroxy-1,5-dimethylpyrrolidin-2-one;

(3S,5R)-3-((3-(4-Aminopyrido[3,2-d]pyrimidin-6-yl-2-d)phenyl)ethynyl)-3-hydroxy-1,5-dimethylpyrrolidin-2-one;
(3R,5R)-3-((3-(4-Amino-2-methylpyrido[3,2-d]pyrimidin-6-yl)phenyl)ethynyl)-3-hydroxy-1,5-dimethylpyrrolidin-2-one;
(3S,5S)-3-((3-(4-Amino-2-methylpyrido[3,2-d]pyrimidin-6-yl)phenyl)ethynyl)-3-hydroxy-1,5-dimethylpyrrolidin-2-one;
(3S,5R)-3-((3-(4-Amino-2-methylpyrido[3,2-d]pyrimidin-6-yl)phenyl)ethynyl)-3-hydroxy-1,5-dimethylpyrrolidin-2-one;
(3R,5S)-3-((3-(4-Amino-2-methylpyrido[3,2-d]pyrimidin-6-yl)phenyl)ethynyl)-3-hydroxy-1,5-dimethylpyrrolidin-2-one;
(R)—N-(6-(3-((3-Hydroxy-1-methyl-2-oxopyrrolidin-3-yl)ethynyl)phenyl)pyrido[3,2-d]pyrimidin-4-yl-2-d)methanesulfonamide;
(R)-3-((3-(4-Cyclopropylpyrido[3,2-d]pyrimidin-6-yl)phenyl)ethynyl)-3-hydroxy-1-methylpyrrolidin-2-one;
(R)-3-((3-(4-Aminopyrido[3,2-d]pyrimidin-6-yl)-4-(trifluoromethoxy)phenyl)ethynyl)-3-hydroxy-1-methylpyrrolidin-2-one;
(R)-3-Hydroxy-3-((3-(4-isopropylpyrido[3,2-d]pyrimidin-6-yl)phenyl)ethynyl)-1-methylpyrrolidin-2-one;
(1R,4R,5S)-4-((3-(4-Amino-2-methylpyrido[3,2-d]pyrimidin-6-yl)phenyl)ethynyl)-4-hydroxy-2-methyl-2-azabicyclo[3.1.0]hexan-3-one;
(1 S,4S,5R)-4-((3-(4-Amino-2-methylpyrido[3,2-d]pyrimidin-6-yl)phenyl)ethynyl)-4-hydroxy-2-methyl-2-azabicyclo[3.1.0]hexan-3-one;
(1 S,4S,5R)-4-((3-(4-Aminopyrido[3,2-d]pyrimidin-6-yl-2-d)phenyl)ethynyl)-4-hydroxy-2-methyl-2-azabicyclo[3.1.0]hexan-3-one;
(1R,4R,5S)-4-((3-(4-Aminopyrido[3,2-d]pyrimidin-6-yl-2-d)phenyl)ethynyl)-4-hydroxy-2-methyl-2-azabicyclo[3.1.0]hexan-3-one;
(R)-3-((3-(4-Amino-8-cyclopentylpyrido[3,2-d]pyrimidin-6-yl-2-d)phenyl)ethynyl)-3-hydroxy-1-methylpyrrolidin-2-one;
(R)-3-Hydroxy-1-methyl-3-((3-(4-(trifluoromethyl)pyrido[3,2-d]pyrimidin-6-yl)phenyl)ethynyl)pyrrolidin-2-one;
(R)-6-(3-((3-Hydroxy-1-methyl-2-oxopyrrolidin-3-yl)ethynyl)phenyl)pyrido[3,2-d]pyrimidine-4-carbonitrile;
(R)-3-Hydroxy-1-methyl-3-((3-(8-methyl-1,7-naphthyridin-2-yl)phenyl)ethynyl)pyrrolidin-2-one;
(1R,4R,5S)-4-((3-(4-amino-8-methylpyrido[3,2-d]pyrimidin-6-yl)phenyl)ethynyl)-4-hydroxy-2-methyl-2-azabicyclo[3.1.0]hexan-3-one;
(R)-3-((3-(4-Amino-8-(aminomethyl)pyrido[3,2-d]pyrimidin-6-yl-2-d)phenyl)ethynyl)-3-hydroxy-1-methylpyrrolidin-2-one;
(R)-3-((3-(4-Amino-8-isopropylpyrido[3,2-d]pyrimidin-6-yl-2-d)phenyl)ethynyl)-3-hydroxy-1-methylpyrrolidin-2-one;
(R)-3-((3-(4-Amino-8-(trifluoromethyl)pyrido[3,2-d]pyrimidin-6-yl)phenyl)ethynyl)-3-hydroxy-1-methylpyrrolidin-2-one;
(R)-3-((3-(4-Amino-2,8-dimethylpyrido[3,2-d]pyrimidin-6-yl)phenyl)ethynyl)-3-hydroxy-1-methylpyrrolidin-2-one;
(R)-3-((3-(4-Amino-8-(methyl-d$_3$)pyrido[3,2-d]pyrimidin-6-yl)phenyl)ethynyl)-3-hydroxy-1-methylpyrrolidin-2-one;
(R)-3-((3-(4-Amino-8-(piperidin-4-yl)pyrido[3,2-d]pyrimidin-6-yl-2-d)phenyl)ethynyl)-3-hydroxy-1-methylpyrrolidin-2-one;
(R)-3-((3-(4-Amino-2-fluoropyrido[3,2-d]pyrimidin-6-yl)phenyl)ethynyl)-3-hydroxy-1-methylpyrrolidin-2-one;
(R)-3-((3-(4-Amino-8-(difluoromethyl)pyrido[3,2-d]pyrimidin-6-yl)phenyl)ethynyl)-3-hydroxy-1-methylpyrrolidin-2-one;
(S)-3-((3-(4-Amino-8-(difluoromethyl)pyrido[3,2-d]pyrimidin-6-yl)phenyl)ethynyl)-3-hydroxy-1-methylpyrrolidin-2-one;
(3R,4S*)-3-((3-(4-Amino-2-methylpyrido[3,2-d]pyrimidin-6-yl)phenyl)ethynyl)-3-hydroxy-1,4-dimethylpyrrolidin-2-one;
(3R,4R*)-3-((3-(4-Amino-2-methylpyrido[3,2-d]pyrimidin-6-yl)phenyl)ethynyl)-3-hydroxy-1,4-dimethylpyrrolidin-2-one;
(3S,4S*)-3-((3-(4-Amino-2-methylpyrido[3,2-d]pyrimidin-6-yl)phenyl)ethynyl)-3-hydroxy-1,4-dimethylpyrrolidin-2-one;
(3S,4R*)-3-((3-(4-Amino-2-methylpyrido[3,2-d]pyrimidin-6-yl)phenyl)ethynyl)-3-hydroxy-1,4-dimethylpyrrolidin-2-one;
(R)-3-[2-[3-[4-Amino-8-(dimethylamino)pyrido[3,2-d]pyrimidin-6-yl]phenyl]ethynyl]-3-hydroxy-1-methyl-pyrrolidin-2-one;
(R)-3-[2-[3-[4-Amino-8-(methylamino)pyrido[3,2-d]pyrimidin-6-yl]phenyl]ethynyl]-3-hydroxy-1-methyl-pyrrolidin-2-one;
(R)-3-[2-[3-[4-Amino-8-(isopropylamino)pyrido[3,2-d]pyrimidin-6-yl]phenyl]ethynyl]-3-hydroxy-1-methyl-pyrrolidin-2-one;
(R)-3-[2-[3-[4-Amino-8-(cyclopropylamino)pyrido[3,2-d]pyrimidin-6-yl]phenyl]ethynyl]-3-hydroxy-1-methyl-pyrrolidin-2-one;
(R)-3-[2-[3-[4-Amino-8-(difluoromethoxy)pyrido[3,2-d]pyrimidin-6-yl]phenyl]ethynyl]-3-hydroxy-1-methyl-pyrrolidin-2-one;
(R)-3-[2-[3-[4-Amino-8-(3,3-difluoroazetidin-1-yl)pyrido[3,2-d]pyrimidin-6-yl]phenyl]ethynyl]-3-hydroxy-1-methyl-pyrrolidin-2-one;
(R)-3-[2-[3-(8-Amino-4-methyl-pyrimido[5,4-d]pyrimidin-2-yl)-4-methyl-phenyl]ethynyl]-3-hydroxy-1-methyl-pyrrolidin-2-one;
(R)-3-((3-(4-Amino-8-cyclopropylpyrido[3,2-d]pyrimidin-6-yl)phenyl)ethynyl)-3-hydroxy-1-methylpyrrolidin-2-one;
(R)-3-[2-[3-(4-Amino-8-pyrazol-1-yl-pyrido[3,2-d]pyrimidin-6-yl)phenyl]ethynyl]-3-hydroxy-1-methyl-pyrrolidin-2-one;
(R)-3-[2-[3-[4-Amino-8-(cyclopropoxy)pyrido[3,2-d]pyrimidin-6-yl]phenyl]ethynyl]-3-hydroxy-1-methyl-pyrrolidin-2-one;
(R)-3-[2-[3-[4-Amino-8-[1-(difluoromethyl)pyrazol-4-yl]oxy-pyrido[3,2-d]pyrimidin-6-yl]phenyl]ethynyl]-3-hydroxy-1-methyl-pyrrolidin-2-one;
(R)-3-[2-[3-[4-Amino-8-(3,3,3-trifluoropropoxy)pyrido[3,2-d]pyrimidin-6-yl]phenyl]ethynyl]-3-hydroxy-1-methyl-pyrrolidin-2-one;
(R)-3-[2-[3-[4-Amino-8-(2,2-difluoro-5-azaspiro[2.3]hexan-5-yl)pyrido[3,2-d]pyrimidin-6-yl]phenyl]ethynyl]-3-hydroxy-1-methyl-pyrrolidin-2-one;
(R)-3-((3-(4-Amino-8-ethylpyrido[3,2-d]pyrimidin-6-yl-2-d)phenyl)ethynyl)-3-hydroxy-1-methylpyrrolidin-2-one;
(R)-3-((3-(4-Amino-8-cyclobutylpyrido[3,2-d]pyrimidin-6-yl)phenyl)ethynyl)-3-hydroxy-1-methylpyrrolidin-2-one;
(R)-3-((3-(4-Amino-8-phenylpyrido[3,2-d]pyrimidin-6-yl)phenyl)ethynyl)-3-hydroxy-1-methylpyrrolidin-2-one;

(R)-3-((3-(4-Amino-8-(thiophen-2-yl)pyrido[3,2-d]pyrimidin-6-yl)phenyl)ethynyl)-3-hydroxy-1-methylpyrrolidin-2-one;
(R)-3-((3-(4-Amino-8-(furan-2-yl)pyrido[3,2-d]pyrimidin-6-yl)phenyl)ethynyl)-3-hydroxy-1-methylpyrrolidin-2-one;
(3R)-3-((3-(4-Amino-8-(azetidin-2-yl)pyrido[3,2-d]pyrimidin-6-yl-2-d)phenyl)ethynyl)-3-hydroxy-1-methylpyrrolidin-2-one;
(R)-3-((3-(4-Amino-8-vinylpyrido[3,2-d]pyrimidin-6-yl)phenyl)ethynyl)-3-hydroxy-1-methylpyrrolidin-2-one;
(R)-3-[2-[3-[4-Amino-8-[3-(trifluoromethyl)azetidin-1-yl]pyrido[3,2-d]pyrimidin-6-yl]phenyl]ethynyl]-3-hydroxy-1-methyl-pyrrolidin-2-one;
(R)-3-[2-[3-[4-Amino-8-(azetidin-1-yl)pyrido[3,2-d]pyrimidin-6-yl]phenyl]ethynyl]-3-hydroxy-1-methyl-pyrrolidin-2-one; and
pharmaceutically acceptable salts thereof.

Illustrative embodiments of compounds of Formula (I) are compounds
(R)-3-[2-[3-(8-Aminopyrido[3,4-d]pyrimidin-2-yl)phenyl]ethynyl]-3-hydroxy-1-methyl-pyrrolidin-2-one;
(S)-3-[2-[3-(8-Aminopyrido[3,4-d]pyrimidin-2-yl)phenyl]ethynyl]-3-hydroxy-1-methyl-pyrrolidin-2-one;
(R)-3-[2-[3-(4-Aminopyrido[3,2-d]pyrimidin-6-yl)-4-methyl-phenyl]ethynyl]-3-hydroxy-1-methyl-pyrrolidin-2-one;
(R)-3-((3-(8-Amino-4-methylpyrimido[5,4-d]pyrimidin-2-yl)phenyl)ethynyl)-3-hydroxy-1-methylpyrrolidin-2-one;
(S)-3-((3-(8-Amino-4-methylpyrimido[5,4-d]pyrimidin-2-yl)phenyl)ethynyl)-3-hydroxy-1-methylpyrrolidin-2-one;
(R)-3-((3-(4-Amino-2-methylpyrido[3,2-d]pyrimidin-6-yl)phenyl)ethynyl)-3-hydroxy-1-methylpyrrolidin-2-one;
(S)-3-((3-(4-Amino-2-methylpyrido[3,2-d]pyrimidin-6-yl)phenyl)ethynyl)-3-hydroxy-1-methylpyrrolidin-2-one;
(R)-3-((3-(4-Aminopyrido[3,2-d]pyrimidin-6-yl-2-d)phenyl)ethynyl)-3-hydroxy-1-methylpyrrolidin-2-one;
(S)-3-((3-(4-Aminopyrido[3,2-d]pyrimidin-6-yl-2-d)phenyl)ethynyl)-3-hydroxy-1-methylpyrrolidin-2-one;
(R)-3-((3-(7-Aminothiazolo[5,4-d]pyrimidin-2-yl)-4-methylphenyl)ethynyl)-3-hydroxy-1-methylpyrrolidin-2-one;
(S)-3-((3-(7-Aminothiazolo[5,4-d]pyrimidin-2-yl)-4-methylphenyl)ethynyl)-3-hydroxy-1-methylpyrrolidin-2-one;
(R)-3-((3-(4-Aminopyrido[3,2-d]pyrimidin-6-yl)phenyl)ethynyl)-3-hydroxy-1-methylpyrrolidin-2-one;
(R)-3-[2-[3-(4-Aminopyrimido[5,4-d]pyrimidin-6-yl)phenyl]ethynyl]-3-hydroxy-1-methyl-pyrrolidin-2-one;
(R)-3-((3-(8-Amino-6-methylpyrimido[5,4-d]pyrimidin-2-yl)phenyl)ethynyl)-3-hydroxy-1-methylpyrrolidin-2-one;
(R)-3-[2-[3-(4-Aminopteridin-6-yl)phenyl]ethynyl]-3-hydroxy-1-methyl-pyrrolidin-2-one;
(R)-3-[2-[3-(4-Aminoquinazolin-6-yl)phenyl]ethynyl]-3-hydroxy-1-methyl-pyrrolidin-2-one;
(R)-7-[2-[3-(8-Aminopyrido[3,4-d]pyrimidin-2-yl)phenyl]ethynyl]-5,6-dihydropyrrolo[1,2-a]imidazol-7-ol;
(R)-4-[3-(8-Aminopyrido[3,4-d]pyrimidin-2-yl)phenyl]-2-(5-methyl-1,3,4-oxadiazol-2-yl)but-3-yn-2-ol;
(R)-3-[2-[3-(8-Amino-1,7-naphthyridin-2-yl)phenyl]ethynyl]-3-hydroxy-1-methyl-pyrrolidin-2-one;
(R)-3-((3-(8-Amino-3,4-dihydro-2,7-naphthyridin-2(1H)-yl)phenyl)ethynyl)-3-hydroxy-1-methylpyrrolidin-2-one;
(R)-3-[2-[3-(3-Amino-1-methyl-pyrazolo[4,3-b]pyridin-5-yl)phenyl]ethynyl]-3-hydroxy-1-methyl-pyrrolidin-2-one;
(R)-3-[2-[3-(3-Amino-1H-pyrazolo[4,3-b]pyridin-5-yl)phenyl]ethynyl]-3-hydroxy-1-methyl-pyrrolidin-2-one;
(R)-3-Hydroxy-1-methyl-3-((3-(4-methylpyrido[3,2-d]pyrimidin-6-yl)phenyl)ethynyl)pyrrolidin-2-one;
(R)-3-((3-(4-Ethoxypyrido[3,2-d]pyrimidin-6-yl)phenyl)ethynyl)-3-hydroxy-1-methylpyrrolidin-2-one;
(R)-3-((3-(4-(Dimethylamino)pyrido[3,2-d]pyrimidin-6-yl)phenyl)ethynyl)-3-hydroxy-1-methylpyrrolidin-2-one;
(R)-3-((3-(4-(Azetidin-1-yl)pyrido[3,2-d]pyrimidin-6-yl)phenyl)ethynyl)-3-hydroxy-1-methylpyrrolidin-2-one;
(R)-3-Hydroxy-1-methyl-3-((3-(4-(methylamino)pyrido[3,2-d]pyrimidin-6-yl)phenyl)ethynyl)pyrrolidin-2-one;
(R)-3-((3-(4-Amino-8-methylpyrido[3,2-d]pyrimidin-6-yl)phenyl)ethynyl)-3-hydroxy-1-methylpyrrolidin-2-one;
(R)-3-((3-(4-Aminopyrido[3,2-d]pyrimidin-6-yl-2-d)-4-(trifluoromethoxy)phenyl)ethynyl)-3-hydroxy-1-methylpyrrolidin-2-one; and
pharmaceutically acceptable salts thereof.

Additional illustrative embodiments of compounds of Formula (I) are compounds
(R)-3-[2-[3-(8-Aminopyrido[3,4-d]pyrimidin-2-yl)phenyl]ethynyl]-3-hydroxy-1-methyl-pyrrolidin-2-one;
(R)-7-[2-[3-(8-Aminopyrido[3,4-d]pyrimidin-2-yl)phenyl]ethynyl]-5,6-dihydropyrrolo[1,2-a]imidazol-7-ol;
(R)-3-((3-(4-Amino-2-methylpyrido[3,2-d]pyrimidin-6-yl)phenyl)ethynyl)-3-hydroxy-1-methylpyrrolidin-2-one;
(S)-3-((3-(8-Amino-4-methylpyrimido[5,4-d]pyrimidin-2-yl)phenyl)ethynyl)-3-hydroxy-1-methylpyrrolidin-2-one;
(R)-3-((3-(4-Aminopyrido[3,2-d]pyrimidin-6-yl-2-d)phenyl)ethynyl)-3-hydroxy-1-methylpyrrolidin-2-one;
(R)-3-((3-(4-(Dimethylamino)pyrido[3,2-d]pyrimidin-6-yl)phenyl)ethynyl)-3-hydroxy-1-methylpyrrolidin-2-one;
(R)-3-((3-(7-Aminothiazolo[5,4-d]pyrimidin-2-yl)-4-methylphenyl)ethynyl)-3-hydroxy-1-methylpyrrolidin-2-one;
(R)-3-((3-(4-Amino-8-methylpyrido[3,2-d]pyrimidin-6-yl)phenyl)ethynyl)-3-hydroxy-1-methylpyrrolidin-2-one;
(R)-3-((3-(8-Amino-3,4-dihydro-2,7-naphthyridin-2(1H)-yl)phenyl)ethynyl)-3-hydroxy-1-methylpyrrolidin-2-one;
(R)-3-Hydroxy-1-methyl-3-((3-(4-methylpyrido[3,2-d]pyrimidin-6-yl)phenyl)ethynyl)pyrrolidin-2-one;
(R)-3-((3-(4-Aminopyrido[3,2-d]pyrimidin-6-yl-2-d)-4-(trifluoromethoxy)phenyl)ethynyl)-3-hydroxy-1-methylpyrrolidin-2-one; and
pharmaceutically acceptable salts thereof.

Additional illustrative embodiments of compounds of Formula (I) are compounds
(R)-3-[2-[3-(8-Aminopyrido[3,4-d]pyrimidin-2-yl)phenyl]ethynyl]-3-hydroxy-1-methyl-pyrrolidin-2-one;
(R)-3-((3-(4-Amino-2-methylpyrido[3,2-d]pyrimidin-6-yl)phenyl)ethynyl)-3-hydroxy-1-methylpyrrolidin-2-one;
(S)-3-((3-(8-Amino-4-methylpyrimido[5,4-d]pyrimidin-2-yl)phenyl)ethynyl)-3-hydroxy-1-methylpyrrolidin-2-one;
(R)-3-((3-(4-(Dimethylamino)pyrido[3,2-d]pyrimidin-6-yl)phenyl)ethynyl)-3-hydroxy-1-methylpyrrolidin-2-one;
(R)-3-((3-(7-Aminothiazolo[5,4-d]pyrimidin-2-yl)-4-methylphenyl)ethynyl)-3-hydroxy-1-methylpyrrolidin-2-one;
(R)-3-Hydroxy-1-methyl-3-((3-(4-methylpyrido[3,2-d]pyrimidin-6-yl)phenyl)ethynyl)pyrrolidin-2-one; and
pharmaceutically acceptable salts thereof.

Additional illustrative embodiments of compounds of Formula (I) are compounds
(R)-3-[2-[3-(8-Aminopyrido[3,4-d]pyrimidin-2-yl)phenyl]ethynyl]-3-hydroxy-1-methyl-pyrrolidin-2-one;
(R)-3-((3-(4-Amino-2-methylpyrido[3,2-d]pyrimidin-6-yl)phenyl)ethynyl)-3-hydroxy-1-methylpyrrolidin-2-one;
(S)-3-((3-(8-Amino-4-methylpyrimido[5,4-d]pyrimidin-2-yl)phenyl)ethynyl)-3-hydroxy-1-methylpyrrolidin-2-one;
(R)-3-((3-(4-Aminopyrido[3,2-d]pyrimidin-6-yl-2-d)phenyl)ethynyl)-3-hydroxy-1-methylpyrrolidin-2-one;

(R)-3-((3-(4-(Dimethylamino)pyrido[3,2-d]pyrimidin-6-yl)phenyl)ethynyl)-3-hydroxy-1-methylpyrrolidin-2-one;

(R)-3-((3-(7-Aminothiazolo[5,4-d]pyrimidin-2-yl)-4-methylphenyl)ethynyl)-3-hydroxy-1-methylpyrrolidin-2-one; and pharmaceutically acceptable salts thereof.

Additional illustrative embodiments of compounds of Formula (I) are compounds (R)-3-[2-[3-(8-Aminopyrido[3,4-d]pyrimidin-2-yl)phenyl]ethynyl]-3-hydroxy-1-methyl-pyrrolidin-2-one;

(R)-7-[2-[3-(8-Aminopyrido[3,4-d]pyrimidin-2-yl)phenyl]ethynyl]-5,6-dihydropyrrolo[1,2-a]imidazol-7-ol;

(R)-3-((3-(4-Amino-2-methylpyrido[3,2-d]pyrimidin-6-yl)phenyl)ethynyl)-3-hydroxy-1-methylpyrrolidin-2-one;

(S)-3-((3-(8-Amino-4-methylpyrimido[5,4-d]pyrimidin-2-yl)phenyl)ethynyl)-3-hydroxy-1-methylpyrrolidin-2-one;

(R)-3-((3-(4-Aminopyrido[3,2-d]pyrimidin-6-yl-2-d)phenyl)ethynyl)-3-hydroxy-1-methylpyrrolidin-2-one; and pharmaceutically acceptable salts thereof.

Additional illustrative embodiments of compounds of Formula (I) are compounds (R)-3-[2-[3-(8-Aminopyrido[3,4-d]pyrimidin-2-yl)phenyl]ethynyl]-3-hydroxy-1-methyl-pyrrolidin-2-one; and pharmaceutically acceptable salts thereof.

Additional illustrative embodiments of compounds of Formula (I) are compounds (R)-7-[2-[3-(8-Aminopyrido[3,4-d]pyrimidin-2-yl)phenyl]ethynyl]-5,6-dihydropyrrolo[1,2-a]imidazol-7-ol; and pharmaceutically acceptable salts thereof.

Additional illustrative embodiments of compounds of Formula (I) are compounds (R)-3-((3-(4-Amino-2-methylpyrido[3,2-d]pyrimidin-6-yl)phenyl)ethynyl)-3-hydroxy-1-methylpyrrolidin-2-one; and pharmaceutically acceptable salts thereof.

Additional illustrative embodiments of compounds of Formula (I) are compounds (S)-3-((3-(8-Amino-4-methylpyrimido[5,4-d]pyrimidin-2-yl)phenyl)ethynyl)-3-hydroxy-1-methylpyrrolidin-2-one; and pharmaceutically acceptable salts thereof.

Additional illustrative embodiments of compounds of Formula (I) are compounds (R)-3-((3-(4-Aminopyrido[3,2-d]pyrimidin-6-yl-2-d)phenyl)ethynyl)-3-hydroxy-1-methylpyrrolidin-2-one; and pharmaceutically acceptable salts thereof.

Additional illustrative embodiments of compounds of Formula (I) are compounds (R)-3-((3-(4-(Dimethylamino)pyrido[3,2-d]pyrimidin-6-yl)phenyl)ethynyl)-3-hydroxy-1-methylpyrrolidin-2-one; and pharmaceutically acceptable salts thereof.

Additional illustrative embodiments of compounds of Formula (I) are compounds (R)-3-((3-(7-Aminothiazolo[5,4-d]pyrimidin-2-yl)-4-methylphenyl)ethynyl)-3-hydroxy-1-methylpyrrolidin-2-one; and pharmaceutically acceptable salts thereof.

Additional illustrative embodiments of compounds of Formula (I) are compounds (R)-3-((3-(4-Amino-8-methylpyrido[3,2-d]pyrimidin-6-yl)phenyl)ethynyl)-3-hydroxy-1-methylpyrrolidin-2-one; and pharmaceutically acceptable salts thereof.

Additional illustrative embodiments of compounds of Formula (I) are compounds (R)-3-((3-(8-Amino-3,4-dihydro-2,7-naphthyridin-2(1H)-yl)phenyl)ethynyl)-3-hydroxy-1-methylpyrrolidin-2-one; and pharmaceutically acceptable salts thereof.

Additional illustrative embodiments of compounds of Formula (I) are compounds (R)-3-Hydroxy-1-methyl-3-((3-(4-methylpyrido[3,2-d]pyrimidin-6-yl)phenyl)ethynyl)pyrrolidin-2-one; and pharmaceutically acceptable salts thereof.

Additional illustrative embodiments of compounds of Formula (I) are compounds (R)-3-((3-(4-Aminopyrido[3,2-d]pyrimidin-6-yl-2-d)-4-(trifluoromethoxy)phenyl)ethynyl)-3-hydroxy-1-methylpyrrolidin-2-one; and pharmaceutically acceptable salts thereof.

Additional illustrative embodiments of compounds of Formula (I) are compounds (3R,5R)-3-((3-(4-Aminopyrido[3,2-d]pyrimidin-6-yl-2-d)phenyl)ethynyl)-3-hydroxy-1,5-dimethylpyrrolidin-2-one;

(S)-3-((3-(4-Amino-2-methylpyrido[3,2-d]pyrimidin-6-yl)phenyl)ethynyl)-3-25 hydroxy-1-methylpyrrolidin-2-one;

(R)-3-[2-[3-(4-Aminopyrimido[5,4-d]pyrimidin-6-yl)phenyl]ethynyl]-3-hydroxy-1-methyl-pyrrolidin-2-one;

(R)-3-((3-(8-Amino-5-ethylpyrido[3,4-d]pyrimidin-2-yl)phenyl)ethynyl)-3-hydroxy-1-methylpyrrolidin-2-one;

(R)-3-((3-(4-Aminopyrido[3,2-d]pyrimidin-6-yl-2-d)phenyl)ethynyl)-3-hydroxy-1-methylpyrrolidin-2-one;

(R)-3-[2-[3-(8-Aminopyrido[3,4-d]pyrimidin-2-yl)phenyl]ethynyl]-3-hydroxy-1-methyl-pyrrolidin-2-one;

(R)-3-[2-[3-[4-Amino-8-(methylamino)pyrido[3,2-d]pyrimidin-6-yl]phenyl]ethynyl]-3-hydroxy-1-methyl-pyrrolidin-2-one;

(R)-3-((3-(8-Amino-5-ethylpyrido[3,4-d]pyrimidin-2-yl)phenyl)ethynyl)-3-hydroxy-1-methylpyrrolidin-2-one;

(R)-3-((3-(4-Amino-8-ethylpyrido[3,2-d]pyrimidin-6-yl-2-d)phenyl)ethynyl)-3-hydroxy-1-methylpyrrolidin-2-one;

(R)-3-((3-(4-Amino-2-methylpyrido[3,2-d]pyrimidin-6-yl)phenyl)ethynyl)-3-hydroxy-1-methylpyrrolidin-2-one;

(S)-3-((3-(8-Amino-4-methylpyrimido[5,4-d]pyrimidin-2-yl)phenyl)ethynyl)-3-hydroxy-1-methylpyrrolidin-2-one;

(S)-3-((3-(4-Aminopyrido[3,2-d]pyrimidin-6-yl-2-d)phenyl)ethynyl)-3-hydroxy-1-methylpyrrolidin-2-one;

(R)-3-((3-(8-Amino-5-chloropyrido[3,4-d]pyrimidin-2-yl)phenyl)ethynyl)-3-hydroxy-1-methylpyrrolidin-2-one;

(R)-3-((3-(4-Amino-8-cyclopentylpyrido[3,2-d]pyrimidin-6-yl-2-d)phenyl)ethynyl)-3-hydroxy-1-methylpyrrolidin-2-one;

(R)-3-((3-(4-Amino-8-methylpyrido[3,2-d]pyrimidin-6-yl)phenyl)ethynyl)-3-hydroxy-1-methylpyrrolidin-2-one;

(R)-3-[2-[3-(4-Aminoquinazolin-6-yl)phenyl]ethynyl]-3-hydroxy-1-methyl-pyrrolidin-2-one;

(R)-3-((3-(4-Amino-8-cyclopropylpyrido[3,2-d]pyrimidin-6-yl)phenyl)ethynyl)-3-hydroxy-1-methylpyrrolidin-2-one;

(R)-3-((3-(7-Aminothiazolo[5,4-d]pyrimidin-2-yl)-4-methylphenyl)ethynyl)-3-hydroxy-1-methylpyrrolidin-2-one;

(R)-3-((3-(4-Amino-7,8-dihydropyrido[4,3-d]pyrimidin-6(5H)-yl)-4-methylphenyl)ethynyl)-3-hydroxy-1-methylpyrrolidin-2-one;

(R)-3-((3-(4-Amino-8-(methyl-$d_3$)pyrido[3,2-d]pyrimidin-6-yl)phenyl)ethynyl)-3-hydroxy-1-methylpyrrolidin-2-one; and pharmaceutically acceptable salts thereof.

Additional illustrative embodiments of compounds of Formula (I) are compounds (R)-3-((3-(4-Aminopyrido[3,2-d]pyrimidin-6-yl-2-d)phenyl)ethynyl)-3-hydroxy-1-methylpyrrolidin-2-one;

(R)-3-[2-[3-[4-Amino-8-(methylamino)pyrido[3,2-d]pyrimidin-6-yl]phenyl]ethynyl]-3-hydroxy-1-methyl-pyrrolidin-2-one;
(R)-3-((3-(4-Amino-2-methylpyrido[3,2-d]pyrimidin-6-yl)phenyl)ethynyl)-3-hydroxy-1-methylpyrrolidin-2-one;
(S)-3-((3-(8-Amino-4-methylpyrimido[5,4-d]pyrimidin-2-yl)phenyl)ethynyl)-3-hydroxy-1-methylpyrrolidin-2-one;
(S)-3-((3-(4-Aminopyrido[3,2-d]pyrimidin-6-yl-2-d)phenyl)ethynyl)-3-hydroxy-1-methylpyrrolidin-2-one;
(R)-3-((3-(8-Amino-5-chloropyrido[3,4-d]pyrimidin-2-yl)phenyl)ethynyl)-3-hydroxy-1-methylpyrrolidin-2-one;
(R)-3-[2-[3-(8-Aminopyrido[3,4-d]pyrimidin-2-yl)phenyl]ethynyl]-3-hydroxy-1-methyl-pyrrolidin-2-one;
(R)-3-((3-(4-Amino-8-(methyl-d$_3$)pyrido[3,2-d]pyrimidin-6-yl)phenyl)ethynyl)-3-hydroxy-1-methylpyrrolidin-2-one; and
pharmaceutically acceptable salts thereof.

Additional illustrative embodiments of compounds of Formula (I) are compounds
(R)-3-[2-[3-[4-Amino-8-(methylamino)pyrido[3,2-d]pyrimidin-6-yl]phenyl]ethynyl]-3-hydroxy-1-methyl-pyrrolidin-2-one;
(R)-3-((3-(4-Amino-2-methylpyrido[3,2-d]pyrimidin-6-yl)phenyl)ethynyl)-3-hydroxy-1-methylpyrrolidin-2-one;
(S)-3-((3-(8-Amino-4-methylpyrimido[5,4-d]pyrimidin-2-yl)phenyl)ethynyl)-3-hydroxy-1-methylpyrrolidin-2-one;
(S)-3-((3-(4-Aminopyrido[3,2-d]pyrimidin-6-yl-2-d)phenyl)ethynyl)-3-hydroxy-1-methylpyrrolidin-2-one;
(R)-3-((3-(8-Amino-5-chloropyrido[3,4-d]pyrimidin-2-yl)phenyl)ethynyl)-3-hydroxy-1-methylpyrrolidin-2-one;
and pharmaceutically acceptable salts thereof.

Additional illustrative embodiments of compounds of Formula (I) are compounds
(R)-3-[2-[3-[4-Amino-8-(methylamino)pyrido[3,2-d]pyrimidin-6-yl]phenyl]ethynyl]-3-hydroxy-1-methyl-pyrrolidin-2-one; and
pharmaceutically acceptable salts thereof.

Additional illustrative embodiments of compounds of Formula (I) are compounds
(R)-3-((3-(4-Amino-2-methylpyrido[3,2-d]pyrimidin-6-yl)phenyl)ethynyl)-3-hydroxy-1-methylpyrrolidin-2-one; and
pharmaceutically acceptable salts thereof.

Additional illustrative embodiments of compounds of Formula (I) are compounds
(S)-3-((3-(4-Aminopyrido[3,2-d]pyrimidin-6-yl-2-d)phenyl)ethynyl)-3-hydroxy-1-methylpyrrolidin-2-one; and
pharmaceutically acceptable salts thereof.

Additional illustrative embodiments of compounds of Formula (I) are compounds
(R)-3-((3-(8-Amino-5-chloropyrido[3,4-d]pyrimidin-2-yl)phenyl)ethynyl)-3-hydroxy-1-methylpyrrolidin-2-one; and
pharmaceutically acceptable salts thereof.

Additional illustrative embodiments of compounds of Formula (I) are compounds
(R)-3-((3-(4-Amino-8-(methyl-d$_3$)pyrido[3,2-d]pyrimidin-6-yl)phenyl)ethynyl)-3-hydroxy-1-methylpyrrolidin-2-one; and
pharmaceutically acceptable salts thereof.

Additional illustrative embodiments of the invention are methods of treating a subject suffering from or diagnosed with a disease, disorder, or medical condition mediated by NIK activity, comprising administering to a subject in need of such treatment an effective amount of at least one of the compounds given above.

Additional illustrative embodiments of the invention are methods of treating a subject suffering from or diagnosed with a disease, disorder, or medical condition mediated by NIK activity, comprising administering to a subject in need of such treatment an effective amount of at least one of the compounds given above wherein the disease, disorder or medical condition is at least one of cancer, inflammatory disorders, autoimmune disorders, immunodermatologic disorders, and metabolic disorders.

Additional illustrative embodiments of the invention are methods of treating a subject suffering from or diagnosed with a disease, disorder, or medical condition mediated by NIK activity, comprising administering to a subject in need of such treatment an effective amount of at least one of the compounds given above wherein the disease, disorder or medical condition is at least one of SLE, RA, GvHD, transplant rejection, Sjogren's Syndrome, pemphigus vulgaris, palmoplantar pustulosis, hidradenitis suppurativa, obesity and diabetes.

Additional embodiments of the invention are pharmaceutical compositions each comprising an effective amount of at least one of the compounds given above or a pharmaceutically acceptable salt thereof.

The compounds of the invention, including their pharmaceutically acceptable salts, whether alone or in combination, (collectively, "active agent" or "active agents") are useful as NIK inhibitors in the methods of the invention. Such methods for modulating NIK activity comprise exposing NIK to an effective amount of at least one active agent of the invention.

In some embodiments, the NIK inhibitor is used in a subject diagnosed with or suffering from a disease, disorder, or medical condition mediated through NIK activity, such as those described herein. Symptoms or disease states are intended to be included within the scope of "diseases, disorders or medical conditions."

Accordingly, the invention relates to methods of using the active agents described herein to treat subjects diagnosed with or suffering from a disease, disorder, or medical condition mediated through NIK. The term "treat" or "treating" as used herein is intended to refer to administration of an active agent or composition of the invention to a subject for the purpose of affecting a therapeutic or prophylactic benefit through modulation of NIK. Treating includes reversing, ameliorating, alleviating, inhibiting the progress of, lessening the severity of, reducing, or preventing a disease, disorder, or condition, or one or more symptoms of such disease, disorder or condition mediated through modulation of NIK activity. The term "subject" refers to a mammalian patient in need of such treatment, such as a human. The term "inhibitors" or "inhibitor" refers to compounds that decrease, prevent, inactivate, desensitize or down-regulate NIK expression or activity.

When referring to inhibiting the target, an "effective amount" means an amount sufficient to inhibitorily affect the activity of NIK.

In treatment methods according to the invention, an effective amount of at least one active agent according to the invention is administered to a subject suffering from or diagnosed as having such a disease, disorder, or medical condition. An "effective amount" means then an amount or dose sufficient to generally bring about the desired therapeutic or prophylactic benefit in patients in need of such treatment for the designated disease, disorder, or medical condition. For a 70-kg human, an illustrative range for a dosage amount is from about 1 to 1000 mg/day in single or multiple dosage units.

Once improvement of the patient's disease, disorder, or condition has occurred, the dose may be adjusted for preventive or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

A pharmaceutical composition of the invention comprises an effective amount of at least one active agent in accordance with the invention.

Pharmaceutically acceptable excipients commonly used in pharmaceutical compositions are substances that are non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of such excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using pharmaceutically acceptable excipients and compounding techniques known or that become available to those of ordinary skill in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. The compositions may be formulated for any one of a plurality of administration routes, such as intravenous infusion, subcutaneous injection, topical administration, or oral administration.

For oral administration, the active agents of the invention can be provided in the form of tablets, capsules, or beads, or as a solution, emulsion, or suspension. To prepare the oral compositions, the active agents may be formulated to yield a dosage of, e.g., for a 70-kg human, from about 1 to 1000 mg/day in single or multiple dosage units as an illustrative range.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Illustrative examples of liquid oral excipients include ethanol, glycerol, water, and the like. Starch, polyvinyl-pyrrolidone (PVP), sodium starch glycolate, microcrystalline cellulose, and alginic acid are examples of disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating. Additional coating that may be used include coatings that are designed to release the compound or active agent as a function of time, pH or bacterial content.

Capsules for oral administration include hard and soft gelatin or (hydroxypropyl)methyl cellulose capsules. To prepare hard gelatin capsules, active ingredient(s) may be mixed with a solid, semi-solid, or liquid diluent. Soft gelatin capsules may be prepared by mixing the active ingredient with an oil such as peanut oil or olive oil, liquid paraffin, a mixture of mono and di-glycerides of short chain fatty acids, polyethylene glycol 400, or propylene glycol. Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository, enema or foam. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier. In another mode of administering the agents of the invention may utilize a patch formulation to effect transdermal delivery.

Active agents may alternatively be administered in methods of this invention by inhalation, via the nasal or oral routes, e.g., in a spray formulation also containing a suitable carrier.

Embodiments of this invention provide NIK inhibitors envisaged for use for the prevention and/or control of excessive inflammatory response.

Illustrative compounds useful in methods of this invention are described below by reference to the illustrative synthetic schemes ("Schemes") and specific examples for their preparation.

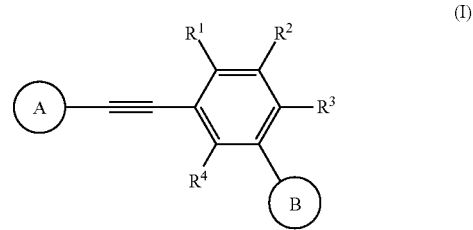

(I)

By way of illustration, but not as a limitation compounds of Formula (I) are prepared according to the following general preparation procedures given by Schemes 1-2. One of ordinary skill in the art will recognize that, to obtain the various compounds herein, starting materials may be suitably selected so that the ultimately desired substituents will be carried through the reaction scheme with or without protection as appropriate to yield the desired product. Alternatively, in the place of the ultimately desired substituent, a suitable group that may be carried through the reaction scheme and replaced as appropriate with the desired substituent. Unless otherwise specified, the variables in Schemes 1-2 are as defined above in reference to Formula (I).

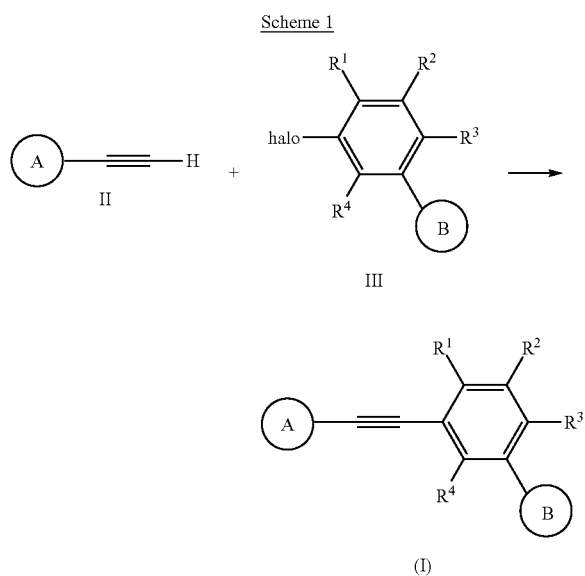

Scheme 1

As shown in Scheme 1, the cross-coupling reaction of compound II with compound III provides compounds of Formula (I). Addition of compound II to compound III with a suitable palladium catalyst such as $Pd(PPh_3)_2Cl_2$ or $(PdCl_2[P(cy)_3]_2)$, a base such as diisopropylethyl amine, TEA or mixtures thereof, a copper catalyst such as CuI, in a solvent such as THF, 1,4-dioxane, acetonitrile, DMF or mixtures thereof. at a temperature of about 40° C.-100° C., employing microwave or conventional heating, for a time period of about 2-4 hours provides compounds of Formula (I)

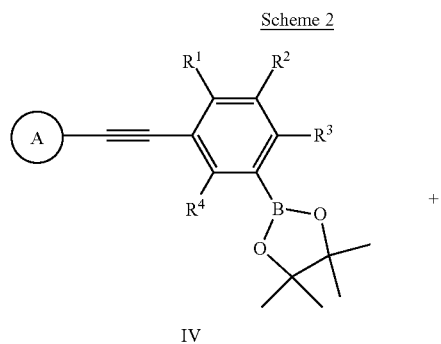

Scheme 2

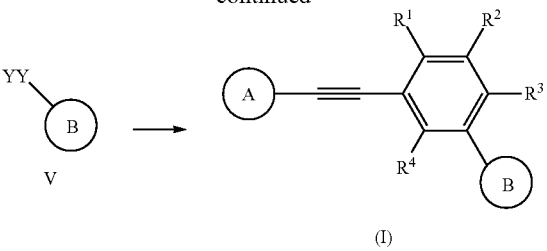

Compounds of Formula (I) are also prepared through an alternative cross-coupling reaction using compounds IV and V. Substituent YY in compound V is chloro, bromo, iodo or —$SCH_3$. In these reactions, compounds IV and V are combined with a suitable palladium catalyst such as palladium(II)bis(triphenylphosphine) dichloride ($Pd(PPh_3)_2Cl_2$), XPhos-Pd-G2 precatalyst (chloro(2-dicyclohexylphosphino-2',4',6'-triisopropyl-1,1'-biphenyl)[2-(2'-amino-1,1'-biphenyl)]palladium(II)), [1,1'-bis(diphenylphosphino)ferrocene]dichloropalladium(II) ($PdCl_2(dppf)$), $PdP(Ph_3)_4$, $PdCl_2(dtbpf)_2$ or mesylate[(di(1-adamantyl)-n-butylphosphine)-2-(2'-amino-1,1'-biphenyl)]palladium(II), [(di(1-adamantyl)-butylphosphine)-2-(2'-amino-1,1'-biphenyl)]palladium(II) methanesulfonate, a base such as $Cs_2CO_3$, $K_3PO_4$, $NaHCO_3$, $Na_2CO_3$, $K_2CO_3$ or mixtures thereof, in a solvent such as $H_2O$, 1,4-dioxane, ethanol, toluene, 1,2-dimethoxyethane or mixtures thereof, at a temperature ranging from about 40° C. to 100° C. for a time period of about 2-16 hours, employing microwave or conventional heating.

Where a protecting group is present on a compound of formula (IV) or (V), a final deprotection step is added, employing conditions known to one skilled in the art, to provide a compound of Formula (I). For example, if a dimethoxybenzyl group is used to protect an anilino group, it can be removed using a reagent such as DDQ or ceric ammonium nitrate in a solvent such as DCM, water or mixtures thereof. If the protecting group is a phenylsulfonamide, then a base such as LiOH, NaOH, KOH can be used in a suitable solvent, such as, THF, 1,4-dioxane, in combination with water and/or MeOH.

The following specific examples are provided to further illustrate embodiments within the scope of the invention.

In obtaining the compounds described in the examples below and the corresponding analytical data, the following experimental and analytical protocols were followed unless otherwise indicated.

Unless otherwise specified, reaction solutions were stirred at room temperature under a $N_{2(g)}$ or $Ar_{(g)}$ atmosphere. When solutions were "concentrated to dryness", they were concentrated using a rotary evaporator under reduced pressure, when solutions were dried, they are typically dried over a drying agent such as $MgSO_4$ or $Na_2SO_4$. Normal phase flash column chromatography (FCC) was performed on silica gel with prepackaged silica gel columns, such as RediSep®, using ethyl acetate (EtOAc)/hexanes, $CH_2Cl_2$/MeOH, or $CH_2Cl_2$/10% 2N $NH_3$ in MeOH, as eluent, unless otherwise indicated.

Thin-layer chromatography was performed using silica gel plates, such as Merck silica gel 60 $F_{254}$ 2.5 cm×7.5 cm 250 μm or 5.0 cm×10.0 cm 250 μm pre-coated silica gel plates. Preparative thin-layer chromatography was performed using silica gel plates such as EM Science silica gel 60 $F_{254}$ 20 cm×20 cm 0.5 mm pre-coated plates with a 20 cm×4 cm concentrating zone. Microwave reactions were carried out in a microwave reactor, such as a CEM Discover®, a Biotage Initiator™ or Optimizer™ microwave, at specified temperatures. Mass spectra were obtained on a mass spectrometer, such as Agilent series 1100 MSD using electrospray ionization (ESI) in positive mode unless otherwise indicated. Calculated mass corresponds to the exact mass. NMR spectra were obtained on an NMR spectrometer, such as a Bruker model DPX400 (400 MHz), DPX500 (500 MHz), DRX600 (600 MHz) spectrometer. The format of the $^1$H NMR data below is as follows: Chemical shift in ppm down field of the tetramethylsilane reference (multiplicity, coupling constant J in Hz, integration).

When trifluoroacetic acid salts were obtained, they were obtained by purification of the reaction product by preparative reverse phase HPLC, whereby the final products were isolated as either mono-, di- or tri trifluoroacetic acid salts.

Trifluoroacetic acid salts or hydrochloride salts of compounds of Formula (I) are converted to their respective free bases by partitioning any of such salts between a saturated aqueous sodium bicarbonate phase and a suitable organic solvent such as, ethyl acetate or dichloromethane. After the partitioning, the organic layer is then separated, and the aqueous layer is extracted twice with the suitable organic solvent. To finally get the free base, the combined organic extracts are washed with brine and concentrated to dryness Some of the examples provided below refer to a free base while ending the corresponding description with the preparation of the corresponding salt, such as the trifluoroacetic acid salt or the hydrochloride salt. It is understood that the free base in such examples is obtained in a way known to those of ordinary skill in the art, such as by following the partitioning and drying process described above.

Whenever a yield is given as a percentage, such yield refers to a mass of the entity for which the yield is given with respect to the maximum amount of the same entity that could be obtained under the particular stoichiometric conditions. Reagent concentrations that are given as percentages refer to mass ratios, unless indicated differently. Whether expressly indicated or not, yields given in the following examples are computed with respect to the dried form of the compound for which any such yield is given.

Chemical names were generated using ChemDraw Ultra 17.1 (CambridgeSoft Corp., Cambridge, Mass.) or OEMetaChem V1.4.0.4 (Open Eye).

Abbreviations and acronyms used herein include the following as shown below:

TABLE 1

| Abbreviations and acronyms defined | |
| --- | --- |
| Ac | acyl or acetyl |
| ACN or MeCN | acetonitrile |
| AcOH or HOAc | acetic acid |
| i-BCF | isobutyl chloroformate |
| BINAP | (2,2'-bis(diphenylphosphino)-1,1'-binaphthyl) |
| br | broad |
| Bu | butyl |
| (Boc)$_2$O | di-tert-butyl dicarbonate |
| n-BuOH | n-butanol |
| t-BuOK | potassium tert-butoxide |
| t-BuONO | tert-butyl nitrite |
| CD$_3$MgI | methyl-d$_3$-magnesium iodide |
| CH(OEt)$_3$ | triethyl orthoformate |
| (CF$_3$COO)$_2$IPh | [bis(trifluoroacetoxy)iodo]benzene |
| Cu(OAc)$_2$ | copper(II) acetate |
| d | doublet |
| DABCO | 1,4-diazabicyclo[2.2.2]octane |
| DCE | dichloroethane |
| DCM | dichloromethane |
| DDQ | 2,3-dichloro-5,6-dicyano-1,4-benzoquinone |

TABLE 1-continued

| Abbreviations and acronyms defined | |
| --- | --- |
| DEA | diethylamine |
| DIBAL-H | diisobutylaluminium hydride |
| DIEA or DIPEA | N,N-diisopropylethylamine |
| DMAP | 4-dimethylaminopyridine |
| DME | dimethoxyethane |
| DMF | N,N-dimethylformamide |
| DMF-DMA | N,N-dimethylformamide dimethyl acetal |
| DMSO | dimethyl sulfoxide |
| ESI | electrospray ionization |
| Et | ethyl |
| Et$_2$NH | diethylamine |
| Et$_2$O | diethyl ether |
| EtOAc | ethyl acetate |
| EtOH | ethanol |
| EtONa | sodium ethoxide |
| FCC | flash column chromatography |
| h | hour(s) |
| HEX | hexane |
| HPLC | high pressure liquid chromatography |
| Hz | Hertz |
| ICl | iodine monochloride |
| IPA | isopropanol |
| KOAc | potassium acetate |
| LDA | lithium diisopropylamide |
| LiHMDS | lithium bis(trimethylsilyl)amide |
| mmol | millimoles |
| m/z | mass-to-charge ratio |
| M+ | parent molecular ion |
| Me | methyl |
| MeI | methyl iodide |
| Me$_2$SO$_4$ | dimethyl sulfate |
| min | minute(s) |
| MS | mass spectrometry |
| MTBE | tert-butyl methyl ether |
| NMP | N-methyl-2-pyrrolidone |
| NMR | nuclear magnetic resonance |
| nt | not tested |
| PdCl$_2$(Cy*Phine)$_2$ | dichlorobis(tricyclohexylphosphine)palladium(II) |
| Pd(dppf)Cl$_2$ or PdCl$_2$(dppf) | [1,1'-bis(diphenylphosphino)ferrocene]dichloropalladium(II) |
| Pd(dtbpf)Cl$_2$ | [1,1-bis(di-tert-butylphosphino)ferrocene]dichloropalladium(II) |
| Pd(PPh$_3$)$_4$ | tetrakis(triphenylphosphine)palladium(0) |
| Pd(PPh$_3$)$_2$Cl$_2$ | bis(triphenylphosphine)palladium(II) dichloride |
| Pd(OAc)$_2$ | palladium(ll)acetate |
| PhI(OAc)$_2$ | (diacetoxyiodo)benzene |
| PhSiH$_3$ | phenylsilane |
| i-PrMgCl | isopropylmagnesium chloride |
| Pt/C | platinum on carbon |
| PTFE | polytetrafluoroethylene |
| rt | room temperature |
| SFC | supercritical fluid chromatography |
| TBAI | tetrabutylammonium iodide |
| TEA or Et$_3$N | triethylamine |
| TEMPO | (2,2,6,6-tetramethylpiperidin-1-yl)oxyl |
| TFA | trifluoroacetic acid |
| Tf$_2$O | trifluoromethanesulfonic anhydride |
| THF | tetrahydrofuran |
| TLC | thin layer chromatography |
| TMEDA | N,N,N,N-tetramethylethylenediamine |
| TMSBr | bromotrimethylsilane |
| TsOH•H$_2$O | p-toluenesulfonic acid monohydrate |
| v/v | volume-to-volume ratio |

Intermediate 1: 2-(3-Iodophenyl)pyrido[3,4-d]pyrimidin-8-amine

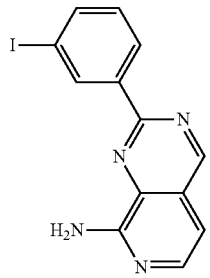 [SMILES: Nc1nccc2cnc(-c3cccc(I)c3)nc12]

Step A: 3-Amino-2-chloroisonicotinic acid. A 5 L round-bottomed flask equipped with an overhead stirrer was charged with methyl 3-amino-2-chloroisonicotinate (240 g, 1.29 mmol), MeOH (1.44 L), and water (0.48 L). To the resulting solution was added NaOH (139 g, 3.47 mmol) in water (1.20 L) and the mixture was stirred at 25-30° C. After 2 h, the mixture was diluted with water (0.72 L) and neutralized with concentrated HCl (290 mL, 12 M). The resulting mixture was stirred for 30 minutes. The solid was isolated by filtration, washed with water (240 mL×2) and dried under vacuum at 50-55° C. to afford 3-amino-2-chloroisonicotinic acid (224 g, 100%) as an off white solid. MS (ESI): mass calcd. for $C_7H_7ClN_2O_2$, 186.0; m/z. found, 187.0 $[M+H]^+$. $^1H$ NMR (400 MHz, DMSO-$d_6$) δ 13.66 (br s, 1H), 7.62 (d, J=4.0 Hz, 1H), 7.59 (d, J=4.0 Hz, 1H), 6.84 (br s, 2H).

Step B: 3-Amino-2-chloroisonicotinamide. A 3 L round-bottomed flask equipped with an overhead stirrer was charged with 3-amino-2-chloroisonicotinic acid (210 g, 1.22 mol), acetonitrile (2.10 L), and carbonyldiimidazole (236 g, 1.46 mol). The resultant mixture was stirred at 20-30° C. for 1 hour before pouring into a chilled 20 wt % aqueous ammonia solution (2.56 L). The resulting mixture was stirred for 30 minutes, the solid were isolated by filtration, washed with water (0.42 L×2) and dried under vacuum at 50-55° C. to afford 3-amino-2-chloroisonicotinamide (142 g, 68.1%) as a white solid. MS (ESI): mass calcd. for $C_6H_6ClN_3O$, 171.0; m/z. found, 172.0 $[M+H]^+$. $^1H$ NMR (400 MHz, DMSO-$d_6$) δ 8.18 (br s, 1H), 7.67 (br s, 1H), 7.61 (d, J=4.0 Hz, 1H), 7.50 (d, J=4.0 Hz, 1H), 6.76 (br s, 2H).

Step C: 4-(Aminomethyl)-2-chloropyridin-3-amine hydrochloride salt. A 2 L round-bottomed flask equipped with an overhead stirrer was charged with 3-amino-2-chloroisonicotinamide (24.3 g, 142 mmol) and THF (100 mL). The flask was purged with nitrogen and heated to 40-45° C. A solution of $BH_3$ in THF (1.00 L, 1 M) was added dropwise over 1 h, while maintaining an internal temperature of 40-45° C. The resultant mixture was continued stirring for 1 h, followed by quenching with MeOH (95.3 g, 2.98 mol). The reaction was then allowed to cool and 30 wt % HCl solution in EtOH (31.3 g, 284 mmol) was added followed by stirring for 1 hour. The suspension was filtered and resulting solid was washed with THF (48 mL×2) followed by drying under vacuum at 50-55° C. to afford 4-(aminomethyl)-2-chloropyridin-3-amine hydrochloride salt (26.5 g, 81%) as a yellow solid, which was used directly in the next synthetic step.

Step D: 8-Chloro-2-(3-iodophenyl)pyrido[3,4-d]pyrimidine. A 250 mL round-bottomed flask was charged with 3-iodobenzaldehyde (18.1 g, 115 mmol), PhI(OAc)$_2$ (62.9 g, 195 mmol), DCM (150 mL), and 4-(aminomethyl)-2-chloropyridin-3-amine hydrochloride salt (15.0 g, 65 mmol) at 25° C. After 2 h the resulting mixture was concentrated to dryness and the residue was purified FCC to afford 8-chloro-2-(3-iodophenyl)pyrido[3,4-d]pyrimidine (9.0 g, 38%). MS (ESI): mass calcd. for $C_{13}H_7ClIN_3$, 366.9; m/z. found, 367.9 $[M+H]^+$.

Step E: 2-(3-Iodophenyl)pyrido[3,4-d]pyrimidin-8-amine. A 2 L high pressure reactor was charged with 8-chloro-2-(3-iodophenyl)pyrido[3,4-d]pyrimidine (43.0 g, 0.12 mol) and a solution of $NH_3$ (645 mL, 2 M in IPA). The reactor was sealed and heated to 125-130° C. for 16 h. The resultant mixture was cooled, concentrated to 100 mL, diluted with water (430 mL), and stirred at 20-25° C. for 2 h. The product was isolated by filtration and dried to afford 2-(3-iodophenyl)pyrido[3,4-d]pyrimidin-8-amine (35 g, 84%) as a pale solid. MS (ESI): mass calcd. for $C_{13}H_9IN_4$, 348.0; m/z. found, 349.0 $[M+H]^+$.

Intermediate 2: (R)-3-Ethynyl-3-hydroxy-1-methylpyrrolidin-2-one

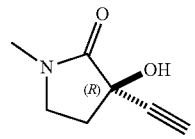

Step A: tert-Butyl 3-(methylamino)propanoate. A 2 L round-bottomed flask equipped with an overhead stirrer was charged with methylamine (500 mL, 3.48 mol, 30 wt % in EtOH) and EtOH (500 mL) followed by dropwise addition of tert-butyl acrylate (100 g, 0.78 mol) over 3 h at 20-25° C. The resultant mixture was stirred at rt for 3 h and then concentrated to dryness to give tert-butyl 3-(methylamino)propanoate (124 g) as a colorless oil. MS (ESI): mass calcd. for $C_8H_{17}NO_2$, 159.1; m/z. found, 160.2 $[M+H]^+$. $^1H$ NMR (400 MHz, CDCl$_3$) δ 2.79 (t, J=6.5 Hz, 2H), 2.43 (s, 3H), 2.41 (t, J=6.5 Hz, 2H), 1.44 (s, 9H).

Step B: tert-Butyl 4-hydroxy-1-methyl-5-oxo-2,5-dihydro-1H-pyrrole-3-carboxylate. A 50 L glass-lined reactor equipped with an overhead stirrer was charged with tert-butyl 3-(methylamino)propanoate (900 g, 5.65 mol), diethyl oxalate (827 g, 5.65 mol) and THF (18 L). The resultant mixture was warmed to 50-55° C. followed by addition of t-BuOK (633 g, 5.65 mol) batch-wise. After stirring for 1 h, the mixture was cooled to 20° C., concentrated to dryness, and water (5.00 L) was added which resulted in the formation of a suspension. The pH was adjusted to 1-2 with aqueous HCl and the resultant mixture was stirred at 20-25° C. for 1 h followed by filtration and drying to give tert-butyl 4-hydroxy-1-methyl-5-oxo-2,5-dihydro-1H-pyrrole-3-carboxylate (940 g, 78%) as an off-white solid. $^1H$ NMR (300 MHz, CDCl$_3$) δ 8.99 (s, 1H), 3.94 (s, 2H), 3.10 (s, 3H), 1.56 (s, 9H).

Step C: 4-Hydroxy-1-methyl-5-oxo-2,5-dihydro-1H-pyrrole-3-carboxylic acid. A 5 L round-bottomed flask equipped with an overhead stirrer was charged with tert-butyl 4-hydroxy-1-methyl-5-oxo-2,5-dihydro-1H-pyrrole-3-carboxylate (500 g, 2.34 mol) and TFA (2.00 L). The resultant mixture was stirred at 20-25° C. for 3 h and then concentrated to dryness. To the residue was added acetonitrile (1.50 L) with stirring at 20-25° C. for 1 h. The product was isolated by filtration and dried to give 4-hydroxy-1-methyl- 5-oxo-2,5-dihydro-1H-pyrrole-3-carboxylic acid (357 g, 97%) as an off-white solid. $^1$H NMR (300 MHz, CD$_3$OD) δ 4.04-3.98 (m, 2H), 3.08 (s, 3H).

Step D: 1-Methylpyrrolidine-2,3-dione. A 20 L round-bottomed flask equipped with an overhead stirrer was charged with 4-hydroxy-1-methyl-5-oxo-2,5-dihydro-1H-pyrrole-3-carboxylic acid (1000 g, 6.360 mol) and THF (15 L). The resultant mixture was heated to 65° C. After 4 h, the mixture was concentrated to dryness to give 1-methylpyrrolidine-2,3-dione (712 g, 99%) as a yellow solid. $^1$H NMR (400 MHz, CDCl$_3$) δ 3.70 (t, J=5.7 Hz, 2H), 3.13 (s, 3H), 2.72 (t, J=5.7 Hz, 2H).

Step E: (rac)-3-Ethynyl-3-hydroxy-1-methylpyrrolidin-2-one. A 10 L round-bottomed flask equipped with an overhead stirrer was charged with ethynylmagnesiumbromide (3.50 L, 0.5 M in THF). The flask was purged with nitrogen and cooled to −10° C. before adding 1-methylpyrrolidine-2,3-dione (120 g, 1.06 mol) over the course of 20 min. The resultant mixture was warmed to 20-25° C. and stirred for 16 h. The resulting mixture was quenched with aq. NH$_4$Cl (120 g in 360 mL H$_2$O) followed by dilution with DCM (3.50 L). After being slurried for 1 h, the suspension was filtered, and the filtrate was dried over anhydrous Na$_2$SO$_4$ (500 g) and treated with activated charcoal (24 g). The activated charcoal was removed by filtration and the filtrate was concentrated under vacuum to dryness. The residue was slurried in MTBE (360 mL) at 20-25° C. for 1 h. The product was isolated by filtration followed by drying to give (rac)-3-ethynyl-3-hydroxy-1-methylpyrrolidin-2-one (81 g, 55%) as a yellow solid. MS (ESI): mass calcd. for C$_7$H$_9$NO$_2$, 139.1; m/z. found, 140.1 [M+H]$^+$. $^1$H NMR (300 MHz, CD$_3$OD) δ 3.40 (dd, J=7.7, 5.3 Hz, 2H), 3.03 (s, 1H), 2.88 (s, 3H), 2.52-2.41 (m, 1H), 2.21 (dt, J=12.7, 7.7 Hz, 1H).

Step F: (R)-3-Ethynyl-3-hydroxy-1-methylpyrrolidin-2-one and (S)-3-Ethynyl-3-hydroxy-1-methylpyrrolidin-2-one. The enantiomers of (rac)-3-ethynyl-3-hydroxy-1-methylpyrrolidin-2-one were separated by chiral preparative SFC (CHIRALPAK AS-H 5 μm, 5×25 cm, mobile phase (80% CO$_2$, 20% IPA (0.1% DEA). Detection, UV at λ=220-254 nM) to yield (R)-3-ethynyl-3-hydroxy-1-methylpyrrolidin-2-one (40%) and (S)-3-ethynyl-3-hydroxy-1-methylpyrrolidin-2-one (Intermediate 3, 40%). Data for (R)-3-ethynyl-3-hydroxy-1-methylpyrrolidin-2-one: MS (ESI): mass calcd. for C$_7$H$_9$NO$_2$, 139.1; m/z. found, 140.1 [M+H]$^+$. $^1$H NMR (300 MHz, CD$_3$OD) δ 3.40 (dd, J=7.7, 5.3 Hz, 2H), 3.03 (s, 1H), 2.88 (s, 3H), 2.52-2.41 (m, 1H), 2.21 (dt, J=12.7, 7.7 Hz, 1H). [α]$^{20}_D$=−100.1 (c=1.01 in MeOH).

Intermediate 3:
(S)-3-Ethynyl-3-hydroxy-1-methylpyrrolidin-2-one

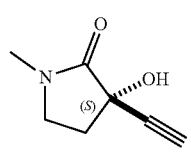

The chiral separation described in Intermediate 2, Step F provided (S)-3-ethynyl-3-hydroxy-1-methylpyrrolidin-2-one (40%). MS (ESI): mass calcd. for C$_7$H$_9$NO$_2$, 139.1; m/z. found, 140.1 [M+H]$^+$. $^1$H NMR (300 MHz, CD$_3$OD) δ 3.40 (dd, J=7.7, 5.3 Hz, 2H), 3.03 (s, 1H), 2.88 (s, 3H), 2.52-2.41 (m, 1H), 2.21 (dt, J=12.7, 7.7 Hz, 1H). [α]$^{20}_D$=+90.5 (c=1.19 in MeOH).

Intermediate 4: (R)-3-Hydroxy-1-methyl-3-((3-(4,4,5,5-tetramethyl-1,3,2-dioxaborolan-2-yl)phenyl)ethynyl)pyrrolidin-2-one

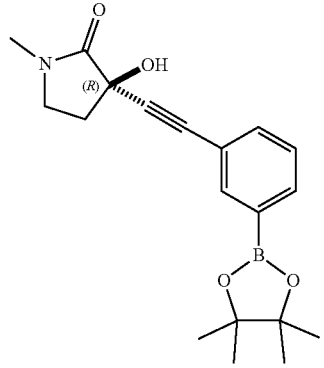

2-(3-Bromophenyl)-4,4,5,5-tetramethyl-1,3,2-dioxaborolane (9.22 g, 32.6 mmol), (R)-3-ethynyl-3-hydroxy-1-methylpyrrolidin-2-one (5.00 g, 35.9 mmol), and diethylamine (33.7 mL, 326 mmol) were suspended in degassed DMF (217 mL). Nitrogen gas was then bubbled through the reaction for 5 min. Copper(I) Iodide (1.24 g, 6.52 mmol), bis(triphenylphosphine)palladium(II) dichloride (2.29 g, 3.26 mmol) and triphenylphosphine (1.71 g, 6.52 mmol) were added to the mixture. The reaction was sealed and was then heated to 100° C. for 30 min. The resulting mixture was then passed through a plug of diatomaceous earth, such as Celite®, washed with DMF, and concentrated under reduced pressure. The resulting residue was purified by FCC (0% hexanes over 3 min, 25%-100% EtOAc/hexanes over 25 min, 100% EtOAc over 3 min) to give (R)-3-hydroxy-1-methyl-3-((3-(4,4,5,5-tetramethyl-1,3,2-dioxaborolan-2-yl)phenyl)ethynyl)pyrrolidin-2-one (7.50 g, 67.5%) as an off-white solid. MS (ESI): mass calcd. For C$_{19}$H$_{24}$BNO$_4$, 341.18; m/z. found, 342.1 [M+H]$^+$. $^1$H NMR (400 MHz, DMSO-d$_6$) δ 7.70-7.68 (m, 1H), 7.66 (dt, J=7.4, 1.3 Hz, 1H), 7.54 (dt, J=7.8, 1.5 Hz, 1H), 7.41 (td, J=7.6, 0.7 Hz, 1H), 6.44 (s, 1H), 3.37-3.32 (m, 2H), 2.80 (s, 3H), 2.46-2.37 (m, 1H), 2.20-2.02 (m, 1H), 1.30 (s, 12H).

Intermediate 5: (S)-3-Hydroxy-1-methyl-3-((3-(4,4,5,5-tetramethyl-1,3,2-dioxaborolan-2-yl)phenyl)ethynyl)pyrrolidin-2-one

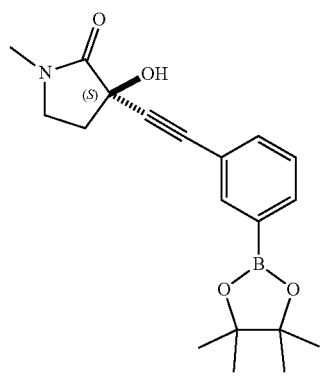

The title compound was prepared with analogous conditions described in Intermediate 4 using 2-(3-bromophenyl)-4,4,5,5-tetramethyl-1,3,2-dioxaborolane and (S)-3-ethynyl-3-hydroxy-1-methylpyrrolidin-2-one to afford (S)-3-hydroxy-1-methyl-3-((3-(4,4,5,5-tetramethyl-1,3,2-dioxaborolan-2-yl)phenyl)ethynyl)pyrrolidin-2-one (880 mg, 85%) as solid. MS (ESI): mass calcd. For $C_{19}H_{24}BNO_4$, 341.18; m/z. found, 342.1 $[M+H]^+$. $^1H$ NMR (400 MHz, DMSO-$d_6$) δ 7.70-7.68 (m, 1H), 7.66 (dt, J=7.4, 1.3 Hz, 1H), 7.54 (dt, J=7.8, 1.5 Hz, 1H), 7.41 (td, J=7.6, 0.7 Hz, 1H), 6.44 (s, 1H), 3.37-3.32 (m, 2H), 2.80 (s, 3H), 2.46-2.37 (m, 1H), 2.20-2.02 (m, 1H), 1.30 (s, 12H).

Intermediate 6: (R)-3-Hydroxy-1-methyl-3-((4-methyl-3-(4,4,5,5-tetramethyl-1,3,2-dioxaborolan-2-yl)phenyl)ethynyl)pyrrolidin-2-one

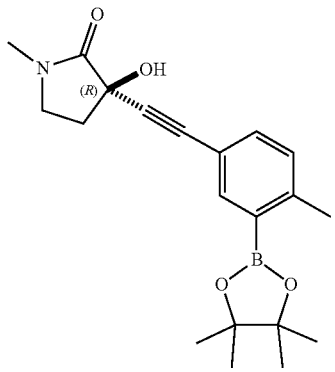

A nitrogen degassed solution of DMF (150 mL) was added to 2-(5-bromo-2-methylphenyl)-4,4,5,5-tetramethyl-1,3,2-dioxaborolane (6.67 g, 22.4 mmol), (R)-3-ethynyl-3-hydroxy-1-methylpyrrolidin-2-one (3.45 g, 24.8 mmol), and diethylamine (23.2 mL, 224 mmol) in a round-bottomed flask. Nitrogen was then bubbled through the mixture for 5 min, followed by addition of copper(I)iodide (0.86 g, 4.49 mmol), bis(triphenylphosphine)palladium(II) dichloride (1.58 g, 2.25 mmol) and triphenylphosphine (1.18 g, 4.49 mmol). The reaction vessel was sealed and was then heated to 100° C. for 30 min. The mixture was cooled to rt, passed through a plug of diatomaceous earth, such as Celite®, washed with DMF, and concentrated to dryness. The resulting residue was purified by FCC (0% hexanes over 3 min, 25%-100% ethyl acetate/hexanes over 25 min, 100% ethyl acetate over 3 min) to afford (R)-3-hydroxy-1-methyl-3-((4-methyl-3-(4,4,5,5-tetramethyl-1,3,2-dioxaborolan-2-yl)phenyl)ethynyl)pyrrolidin-2-one (5.86 g, 73.5%) as an off-white solid. MS (ESI): mass calcd. for $C_{20}H_{26}BNO_4$, 355.2; m/z. found, 356.1 $[M+H]^+$. $^1H$ NMR (500 MHz, CDCl$_3$) δ 7.84 (d, J=1.9 Hz, 1H), 7.37 (dd, J=7.9, 2.0 Hz, 1H), 7.08 (d, J=7.9 Hz, 1H), 3.51-3.47 (m, 1H), 3.38-3.34 (m, 1H), 2.94 (d, J=1.8 Hz, 3H), 2.65-2.61 (m, 1H), 2.51 (s, 3H), 2.38-2.35 (m, 1H), 1.33 (s, 12H).

Intermediate 7: 6-Chloro-2-methylpyrido[3,2-d]pyrimidin-4-amine

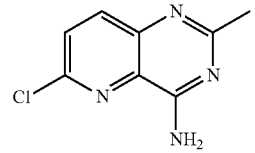

A vial containing 3-amino-6-chloropicolinonitrile (100 mg, 0.65 mmol) was charged with ethanimidamide hydrochloride salt (57.0 mg, 0.98 mmol), potassium phosphate tribasic (553 mg, 2.6 mmol), and THF (3 mL). The vial was sealed and heated to 80° C. for 16 h. The resulting mixture was cooled to rt and concentrated to dryness. To the residue was added water (3 mL) at 70° C. After stirring for 30 min, the resulting mixture was cooled to rt and stirred for another 30 min. The resulting solid was isolated by filtration and washed sequentially with water (3 mL) and Et$_2$O (10 mL) to afford 6-chloro-2-methylpyrido[3,2-d]pyrimidin-4-amine (70 mg, 55%) as a pale yellow solid. MS (ESI): mass calcd. for $C_8H_7ClN_4$, 194.04; m/z. found, 195.04 $[M+H]^+$. $^1H$ NMR (400 MHz, CDCl$_3$) δ 8.00 (d, J=8.7 Hz, 1H), 7.62 (d, J=8.7 Hz, 1H), 6.76 (s, 2H), 2.63 (s, 3H).

Intermediate 8: 6-Chloropyrido[3,2-d]pyrimidin-2-d-4-amine

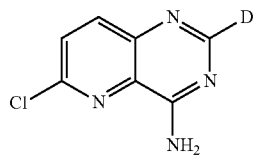 [SMILES: [2H]c1nc(N)c2nc(Cl)ccc2n1]

A 1 L round-bottomed flask was charged with a stir bar, 3-amino-6-chloropicolinonitrile (22.0 g, 0.14 mol), formamide-$d_3$ (20.6 g, 0.43 mol), K$_3$PO$_4$ (122 g, 0.57 mol), and cyclopentyl methyl ether (440 mL). The resultant mixture was stirred at 65° C. for 16 h before cooling to rt. Then the reaction mixture was filtered and the cake was slurried in water (100 mL) at 20° C. for 3 h. The solid was isolated by filtration and dried to give 6-chloropyrido[3,2-d]pyrimidin-2-d-4-amine (23.9 g, 94%) as a yellow solid. MS (ESI): mass calcd. for $C_7H_4DClN_4$, 181.0; m/z. found, 182.0 $[M+H]^+$. $^1H$ NMR (400 MHz, DMSO-$d_6$) δ 8.15 (d, J=8.8 Hz, 1H), 8.05 (br s, 1H), 7.95 (br s, 1H), 7.88 (d, J=8.8 Hz, 1H).

Intermediate 9: 2-(5-Iodo-2-methylphenyl)thiazolo[5,4-d]pyrimidin-7-amine

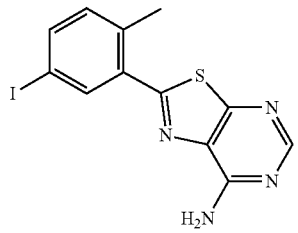

Step A: N-(4-Amino-6-oxo-1,6-dihydropyrimidin-5-yl)-5-iodo-2-methylbenzamide. A 2 L round-bottomed flask equipped with an overhead stirrer was charged with 5,6-diaminopyrimidin-4(3H)-one (47.3 g, 375 mmol), 5-iodo-2-methylbenzoic acid (108 g, 412 mmol), DMF (710 mL), and DIEA (153 g, 1.18 mol), successively. The flask was purged with nitrogen and cooled to 0-10° C. before adding 1-[bis(dimethylamino)methylene]-1H-1,2,3-triazolo[4,5-b]pyridinium 3-oxide hexafluorophosphate (148 g, 390 mmol). The resultant mixture was stirred for 1 h at 0-10° C. before warming to rt with stirring for 18 h. The mixture was diluted with acetonitrile (709 mL) with continued stirring for 30 min. The resulting solid was filtered and washed with acetonitrile (190 mL×3). The filter cake was collected and dried under vacuum at 50-55° C. to give N-(4-amino-6-oxo-1,6-dihydropyrimidin-5-yl)-5-iodo-2-methylbenzamide (108 g, 78.0%) as a light brown solid. $^1$H NMR (400 MHz, DMSO-$d_6$) δ 11.68 (s, 1H), 8.89 (s, 1H), 8.01 (s, 1H), 7.78 (s, 1H), 7.66 (d, J=8.0 Hz, 1H), 7.05 (d, J=8.0 Hz, 1H), 6.39 (s, 2H), 2.35 (s, 3H).

Step B: 2-(5-Iodo-2-methylphenyl)thiazolo[5,4-d]pyrimidin-7-amine. A 2 L round-bottomed flask equipped with an overhead stirrer was charged with N-(4-amino-6-oxo-1,6-dihydropyrimidin-5-yl)-5-iodo-2-methylbenzamide (110 g, 297 mmol), pyridine (1.10 L), and $P_2S_5$ (165 g, 742 mmol). The resultant mixture was heated at 100° C. for 1 h before cooling to rt. The mixture was concentrated to dryness, diluted with acetonitrile (550 mL), and neutralized with 1 N HCl (1.20 L). The resulting mixture was stirred for 1 h, the suspension was filtered, washed with MeOH (110 mL×3) and dried under vacuum at 50-55° C. The resulting solid was further purified by adding MeOH (1150 mL) at 60° C. and stirring for 1 h. The solid was collected by filtration and dried under vacuum at 50-55° C. to afford 2-(5-iodo-2-methylphenyl)thiazolo[5,4-d]pyrimidin-7-amine (88.4 g, 80.8%) as a light yellow solid. $^1$H NMR (300 MHz, DMSO-$d_6$) δ 8.33 (s, 1H), 8.15 (d, J=1.9 Hz, 1H), 7.81 (d, J=2.0 Hz, 2H), 7.78 (d, J=1.9 Hz, 1H), 7.23 (d, J=8.1 Hz, 1H), 2.57 (s, 3H).

Intermediate 10: (R)-7-Ethynyl-6,7-dihydro-5H-pyrrolo[1,2-a]imidazol-7-ol

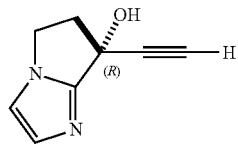

Step A: 6,7-Dihydro-5H-pyrrolo[1,2-a]imidazol-7-ol. A 5 L 3-necked round-bottomed flask purged and maintained with nitrogen was charged with 1H-imidazole (200 g, 2.93 mol), prop-2-enal (247 g, 4.41 mol), AcOH (12.3 g, 205 mmol), and dioxane (2.00 L). The resulting solution was stirred for 4 h at 100° C. The resulting mixture was cooled to rt and concentrated to dryness. The residue was purified by FCC (DCM/MeOH (30:1)) to afford 6,7-dihydro-5H-pyrrolo[1,2-a]imidazol-7-ol (125 g, 34.3%) as a white solid. MS (ESI): mass calcd. for $C_6H_8N_2O$, 124.0; m/z. found, 125.0 [M+H]$^+$.

Step B: 5,6-Dihydro-7H-pyrrolo[1,2-a]imidazol-7-one. A 5 L 3-necked round-bottomed flask purged and maintained with nitrogen was charged with 6,7-dihydro-5H-pyrrolo[1,2-a]imidazol-7-ol (125 g, 1.00 mol), DCM (2.5 L), and $MnO_2$ (615 g, 7.10 mol). The resulting solution was stirred at 25° C. After 72 h, the solids were removed by filtration. The resulting mixture was concentrated and the residue was purified by FCC (DCM/MeOH (30:1)) to afford 5,6-dihydro-7H-pyrrolo[1,2-a]imidazol-7-one (67 g, 54.5%) as a yellow solid. MS (ESI): mass calcd. for $C_6H_6N_2O$, 122.0; m/z. found, 123.0 [M+H]$^+$.

Step C: (R)-7-Ethynyl-6,7-dihydro-5H-pyrrolo[1,2-a]imidazol-7-ol and (S)-7-Ethynyl-6,7-dihydro-5H-pyrrolo[1,2-a]imidazol-7-ol. To a stirred mixture of 5, 6-7H-pyrrolo[1,2-a]imidazol-7-one (67.0 g, 549 mmol) in DCM (1.5 L) was added bromo(ethynyl)magnesium (213 g, 1.65 mmol) dropwise at 0° C. under a nitrogen atmosphere. The resulting solution was stirred for 1 h at 25° C. The reaction was then quenched with saturated aqueous NH$_4$Cl (500 mL). The resulting mixture was concentrated and was extracted with ethyl acetate (1 L×2). The combined organic extracts were washed with water (500 mL) and brine (500 mL). The organic layer was dried over anhydrous sodium sulfate, filtered, and concentrated to dryness. The resulting residue was purified by FCC (DCM:MeOH (20:1)) to afford 7-ethynyl-6,7-dihydro-5H-pyrrolo[1,2-a]imidazol-7-ol (23.9 g, 29.4%) as a white solid. The enantiomers of racemic-7-ethynyl-6,7-dihydro-5H-pyrrolo[1,2-a]imidazol-7-ol were separated by chiral preparative SFC (CHIRALPAK AD-33.0×100 mm, 3 μm; mobile phase, EtOH (0.1% DEA); 10% to 50% in 4.0 min, hold 2.0 min at 50%; 2 mL/min. Column Temperature: 35° C. UV at λ=220-254 nM) to afford (R)-7-ethynyl-6,7-dihydro-5H-pyrrolo[1,2-a]imidazol-7-ol (6.2 g) as a white solid and (S)-7-ethynyl-6,7-dihydro-5H-pyrrolo[1,2-a]imidazol-7-ol (Intermediate 11, 5.6 g) as a white solid. Data for (R)-7-ethynyl-6,7-dihydro-5H-pyrrolo[1,2-a]imidazol-7-ol: MS (ESI): mass calcd. for $C_8H_8N_2O$, 148.0; m/z. found, 149.0 [M+H]$^+$. $^1$H NMR (400 MHz, CD$_3$OD) δ 7.12-7.00 (m, 2H), 4.19-4.02 (m, 2H), 3.14 (s, 1H), 3.06-3.01 (m, 1H), 2.83-2.78 (m, 1H). [α]$^{20}_D$=−60.7 (c=0.29 in MeOH).

Intermediate 11: (S)-7-Ethynyl-6,7-dihydro-5H-pyrrolo[1,2-a]imidazol-7-ol

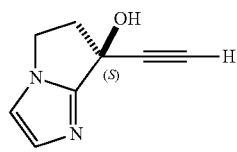

The chiral separation described in Intermediate 10, Step C provided (S)-7-ethynyl-6,7-dihydro-5H-pyrrolo[1,2-a]imidazol-7-ol (5.6 g) as a white solid. MS (ESI): mass calcd. for $C_8H_8N_2O$, 148.0; m/z. found, 149.0 [M+H]$^+$. $^1$H NMR (400 MHz, CD$_3$OD) δ 7.12-7.00 (m, 2H), 4.19-4.02 (m, 2H), 3.14 (s, 1H), 3.06-3.01 (m, 1H), 2.83-2.78 (m, 1H). [α]$^{20}_D$=+59.6 (c=0.27 in MeOH)

Intermediate 12:
2-(3-Iodophenyl)-1,7-naphthyridin-8-amine

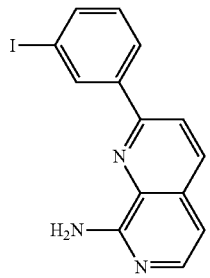 [SMILES: Nc1nccc2ccc(-c3cccc(I)c3)nc12]

Step A: 6-Chloro-3-methylpicolinamide. To a mixture of 6-chloro-3-methylpicolinic acid (450 g, 2.62 mol) in DCM (3.00 L) was added (COCl)$_2$ (466 mL, 5.32 mol) dropwise followed by DMF (38.3 mL, 498 mmol) slowly over 30 min at 0° C. After 2 h, the resulting mixture was warmed to rt and concentrated to dryness. The residue was diluted with DCM (500 mL) and was added dropwise to NH$_3$—H$_2$O (3.70 L, 24.0 mol, 25.0% v/v solution of NH$_3$) at 0° C. After 3 h, the resulting mixture was filtered and the filtrate was concentrated to dryness to afford 6-chloro-3-methylpicolinamide (390 g, 78.5%) as a yellow solid. $^1$H NMR (400 MHz, DMSO-d$_6$) δ 7.89 (br s, 1H), 7.79 (d, J=8.2 Hz, 1H), 7.59 (br s, 1H), 7.53 (d, J=8.2 Hz, 1H), 2.45 (s, 3H).

Step B: (E)-6-Chloro-N-((dimethylamino)methylene)-3-methylpicolinamide. To a mixture 6-chloro-3-methylpicolinamide (195 g, 1.14 mol) in THF (1.20 L) was added DMF-DMA (699 mL, 5.26 mol) in one portion at rt. The resulting mixture was heated to 90° C. After 16 h, the mixture was cooled to rt and concentrated to dryness to afford (E)-6-chloro-N-((dimethylamino)methylene)-3-methylpicolinamide as a black brown oil (540 g) which was used directly in next step.

Step C: 2-Chloro-1,7-naphthyridin-8(7H)-one. To a mixture of (E)-6-chloro-N-((dimethylamino)methylene)-3-methylpicolinamide (180 g, 798 mmol) in THF (900 mL) was added t-BuOK (798 mL, 1.00 M in THF) in one portion at rt. The brown mixture was heated to 90° C. After 3 h, the mixture was cooled to rt and concentrated to dryness. To the resulting residue was added ice (200 g), the pH was adjusted to 4 using 1 M HCl, and MeCN (400 mL) was added. The resulting mixture was heated at 80° C. for 4 h. The mixture was then cooled to 25° C. slowly and stirred for another 8 h. The resulting solid was collected by filtration and dried under vacuum to afford 2-chloro-1,7-naphthyridin-8(7H)-one (276 g, 63.9% yield) as a yellow solid. MS (ESI): mass calcd. for C$_8$H$_5$ClN$_2$O, 180.0; m/z. found, 181.2 [M+H]$^+$. $^1$H NMR (300 MHz, DMSO-d$_6$) δ 8.21 (d, J=8.44 Hz, 1H), 7.77 (d, J=8.44 Hz, 1H), 7.32 (d, J=6.97 Hz, 1H), 6.60 (d, J=6.97 Hz, 1H).

Step D: 2-(3-Aminophenyl)-1,7-naphthyridin-8(7H)-one. To a mixture of 2-chloro-1,7-naphthyridin-8(7H)-one (113 g, 626 mmol) in toluene (678 mL), MeOH (339 mL), and H$_2$O (113 mL) under nitrogen were added (3-aminophenyl) boronic acid (103 g, 751 mmol), Na$_2$CO$_3$ (133 g, 1.25 mol), Pd(PPh$_3$)$_4$ (14.5 g, 12.5 mmol). The resulting mixture was heated to 90° C. for 12 h. The resulting mixture was cooled to rt, the organic solvent was concentrated, and the remaining mixture was poured into water (2.5 L). The resulting suspension was filtered and the collected yellow solid was washed with water (500 mL×4). The yellow solid was triturated with EtOAc (1.5 L) and dried to afford 2-(3-aminophenyl)-1,7-naphthyridin-8(7H)-one (304 g, 83.8%) as a yellow solid. MS (ESI): mass calcd. for C$_{14}$H$_{11}$N$_3$O, 237.1; m/z. found, 238.2 [M+H]$^+$. $^1$H NMR (300 MHz, DMSO-d$_6$) δ 11.51 (br s, 1H), 8.05-8.17 (m, 2H), 7.48 (t, J=1.83 Hz, 1H), 7.23-7.32 (m, 2H), 7.16 (t, J=7.76 Hz, 1H), 6.67 (dd, J=1.47, 7.95 Hz, 1H), 6.55 (d, J=7.09 Hz, 1H), 5.25 (s, 2H).

Step E: 2-(3-Iodophenyl)-1,7-naphthyridin-8(7H)-one. To a mixture of 2-(3-aminophenyl)-1,7-naphthyridin-8(7H)-one (80.0 g, 337 mmol) and CuI (77.1 g, 405 mmol), CH$_2$I$_2$ (136 mL, 1.69 mol) in THF (800 mL) was added t-BuONO (120 mL, 1.01 mol) at 25° C. The resulting mixture was then heated to 70° C. After 1 h, the mixture was cooled to rt, filtered, and the filtrate concentrated to dryness to afford 2-(3-iodophenyl)-1,7-naphthyridin-8(7H)-one (200 g) as a yellow solid which was used directly in the next step. MS (ESI): mass calcd. for C$_{14}$H$_9$IN$_2$O, 347.9; m/z. found, 349.0 [M+H]$^+$.

Step F: 8-Chloro-2-(3-iodophenyl)-1,7-naphthyridine. 2-(3-Iodophenyl)-1,7-naphthyridin-8(7H)-one (330 g, 948 mmol) was added portion wise to POCl$_3$ (1.98 L, 21.3 mol) in a 5 L round-bottomed flask. The resulting mixture was heated to 120° C. After 12 h, the POCl$_3$ was removed from the vessel by distillation at 120° C. and the remaining residue was quenched with water (3 L). The mixture was adjusted to pH=9 with solid NaHCO$_3$ and the resulting mixture was partitioned between ethyl acetate (2 L) and water (1 L). The organic layer was separated, washed with ammonium hydroxide (800 mL×3) and brine (600 mL), dried over Na$_2$SO$_4$, filtered, and concentrated to afford 8-chloro-2-(3-iodophenyl)-1,7-naphthyridine (80.0 g) as brown solid which was used directly in next step. MS (ESI): mass calcd. for C$_{14}$H$_8$ClIN$_2$, 365.9; m/z. found, 366.6 [M+H]$^+$.

Step G: 2-(3-Iodophenyl)-N-(4-methoxybenzyl)-1,7-naphthyridin-8-amine. 8-Chloro-2-(3-iodophenyl)-1,7-naphthyridine (75.0 g, 205 mmol) was added to (4-methoxyphenyl)methanamine (265 mL, 2.05 mol) and resulting mixture was heated to 120° C. for 3 h. The mixture was cooled to rt and the pH was adjusted pH=1 using 1 M HCl. Ethyl acetate (300 mL) was added and the resulting mixture was filtered. The collected solid was washed by water and dried under vacuum to afford 2-(3-iodophenyl)-N-(4-methoxybenzyl)-1,7-naphthyridin-8-amine as yellow solid (61.0 g, 89.0%) which was used directly in next step. MS (ESI): mass calcd. for C$_{22}$H$_{18}$IN$_3$O, 467.1; m/z. found, 468.1 [M+H]$^+$. $^1$H NMR (400 MHz, DMSO-d$_6$) δ 10.27 (br s, 1H), 8.79 (s, 1H), 8.60-8.65 (m, 1H), 8.56-8.47 (m, 2H), 7.92 (d, J=7.82 Hz, 1H), 7.71 (d, J=6.97 Hz, 1H), 7.42-7.47 (m, 2H), 7.41-7.34 (m, 1H), 7.27 (d, J=6.97 Hz, 1H), 6.95-6.90 (m, 2H), 4.98 (br d, J=6.4 Hz, 2H), 3.72 (s, 3H).

Step H: 2-(3-Iodophenyl)-1,7-naphthyridin-8-amine. A solution of 2-(3-iodophenyl)-N-(4-methoxybenzyl)-1,7-naphthyridin-8-amine (60.0 g, 128 mmol) in TFA (150 mL) was stirred at 60° C. After 0.75 h, the mixture was concentrated to dryness. The resulting residue was partitioned between ethyl acetate (500 mL) saturated aqueous NaHCO$_3$ solution (200 mL). The organic layer was separated and washed with saturated aqueous NaHCO$_3$ (200 mL×2) and brine (100 mL). The organic layer was dried with anhydrous Na$_2$SO$_4$, filtered, and concentrated to dryness. The resulting residue was purified sequentially by FCC (petroleum ether: ethyl acetate=100:1 to 1:1) followed by preparative HPLC (Phenomenex Luna C18 10 μm, 250×50 mm; mobile phase: 20% ACN:water (0.1% TFA) increasing gradient to 50% ACN over 28 min. Detection, UV at λ=220-254 nM) to afford 2-(3-iodophenyl)-1,7-naphthyridin-8-amine (24.8 g, 52.1%) as a yellow solid. MS (ESI): mass calcd. for $C_{14}H_{10}N_3$, 346.9; m/z found, 348.1 [M+H]$^+$. $^1$H NMR (400 MHz, CDCl$_3$) δ 8.48 (s, 1H), 8.06 (d, J=8.4 Hz, 2H), 7.99-7.91 (m, 2H), 7.81 (d, J=7.8 Hz, 1H), 7.28-7.24 (m, 1H), 6.94 (d, J=5.9 Hz, 1H), 6.31 (br s, 2H).

Intermediate 13: (S)-2-(5-Methyl-1,3,4-oxadiazol-2-yl)but-3-yn-2-ol

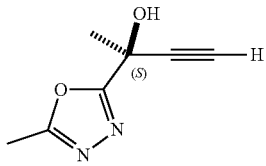

Step A: 1-(5-Methyl-1,3,4-oxadiazol-2-yl)ethan-1-one. A 2 L 3-necked round-bottomed flask was charged with a solution of N-methoxy-N,5-dimethyl-1,3,4-oxadiazole-2-carboxamide (56.0 g, 327 mmol) in THF (500 mL). The resulting solution was cooled to 0° C. and methylmagnesium bromide (320 mL, 2 M in THF) was added dropwise with stirring. After 1 h at 0° C., saturated aqueous NH$_4$Cl (300 mL) was added. The resulting mixture was extracted with ethyl acetate (200 mL×3) and the combined organic extracts were washed with brine (200 mL). The organic extract was dried over anhydrous Na$_2$SO$_4$, filtered, and concentrated to dryness. The residue was purified by FCC (ethyl acetate: petroleum ether (0:1-1:2)) to afford 1-(5-methyl-1,3,4-oxadiazol-2-yl)ethan-1-one (21 g, 51%) as a yellow solid. MS (ESI): mass calcd. for $C_5H_6N_2O_2$, 126.0; m/z. found, 127.0 [M+H]$^+$.

Step B: (S)-2-(5-Methyl-1,3,4-oxadiazol-2-yl)but-3-yn-2-ol and (R)-2-(5-Methyl-1,3,4-oxadiazol-2-yl)but-3-yn-2-ol. A 1 L 3-necked round-bottomed flask purged and maintained with nitrogen was charged with bromo(ethynyl)magnesium (500 mL, 2 M in THF). The solution was cooled to 0° C. followed by dropwise addition of a solution of 1-(5-methyl-1,3,4-oxadiazol-2-yl)ethan-1-one (21.0 g, 167 mmol) in THF (200 mL). The resulting solution was stirred for 2 h at rt. The reaction mixture was cooled to 0° C. and saturated aqueous NH$_4$Cl (300 mL) was added followed by H$_2$O (200 mL). The mixture was extracted with ethyl acetate (200 mL×3) and the combined organic extracts were washed with brine (200 mL). The organic extract was dried over anhydrous Na$_2$SO$_4$, filtered, and concentrated to dryness. The residue was purified by FCC (ethyl acetate/petroleum ether (0:1-1:2)) to afford (rac)-2-(5-methyl-1,3,4-oxadiazol-2-yl)but-3-yn-2-ol (15.2 g, 60%) as a yellow solid. The (R) and (S) enantiomers of (rac)-2-(5-methyl-1,3,4-oxadiazol-2-yl)but-3-yn-2-ol (15.2 g) were separated by chiral preparative SFC (Phenomenex Lux 5u Cellulose-4 5 μm, 5×25 cm; mobile phase, CO$_2$ (80%), IPA (0.1% DEA) (20%). Detector, UV 220 nm) to afford (S)-2-(5-methyl-1,3,4-oxadiazol-2-yl)but-3-yn-2-ol (5.3 g, 35%, >97% ee) as a yellow solid and ((R)-2-(5-methyl-1,3,4-oxadiazol-2-yl)but-3-yn-2-ol which was obtained as a yellow solid (Intermediate 14, 5.2 g, 34%, >97% ee). Data for (S)-2-(5-methyl-1,3,4-oxadiazol-2-yl)but-3-yn-2-ol: MS (ESI): mass calcd. for $C_7H_8N_2O_2$, 152.0; m/z. found, 153.0 [M+H]$^+$. $^1$H NMR (400 MHz, CDCl$_3$) δ 2.99 (s, 1H), 2.70 (s, 1H), 2.58 (s, 3H), 1.97 (s, 3H). [α]$^{20}_D$=+23.7 (c=1.06 in MeOH).

Intermediate 14: (R)-2-(5-Methyl-1,3,4-oxadiazol-2-yl)but-3-yn-2-ol

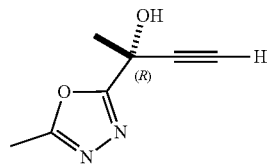

The chiral separation described in Intermediate 13, Step B provided ((R)-2-(5-methyl-1,3,4-oxadiazol-2-yl)but-3-yn-2-ol which was obtained as a yellow solid (5.2 g, 34%, >97% ee). MS (ESI): mass calcd. for $C_7H_8N_2O_2$, 152.0; m/z. found, 153.0 [M+H]$^+$. 1H NMR (400 MHz, CDCl$_3$) δ 2.99 (s, 1H), 2.70 (s, 1H), 2.58 (s, 3H), 1.97 (s, 3H). [α]$^{20}_D$=−20.5 (c=0.96 in MeOH).

Intermediate 15: 7-(3-Iodophenyl)-5,6,7,8-tetrahydro-2,7-naphthyridin-1-amine

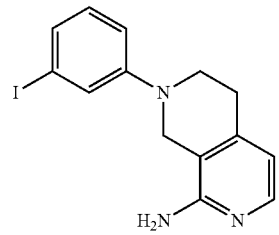 [SMILES: Nc1nccc2c1CN(c1cccc(I)c1)CC2]

5,6,7,8-Tetrahydro-2,7-naphthyridin-1-amine (500 mg, 3.35 mmol) was added to a stirred suspension of 3-iodophenylboronic acid (1.08 g, 4.36 mmol), Cu(OAc)$_2$ (122 mg, 0.672 mmol), powdered 4 Å molecular sieves (2.50 g), and DCM (25 mL). The resulting mixture was then stirred at 35° C. for 24 h under 02 (15 psi). The mixture was cooled to rt, filtered through a pad of diatomaceous earth, such as Celite©, and the pad was washed with DCM (15 mL). The filtrate was concentrated to dryness and the residue was purified by FCC (petroleum ether:ethyl acetate=1:0 to 0:1) to afford 7-(3-iodophenyl)-5,6,7,8-tetrahydro-2,7-naphthyridin-1-amine (260 mg, 21%) as a yellow oil. LCMS (ESI): mass calcd. for $C_{14}H_{14}IN_3$ 351.0 m/z. found 351.8 [M+H]$^+$.

Intermediate 16: 5-(3-Iodophenyl)-1H-pyrazolo[4,3-b]pyridin-3-amine

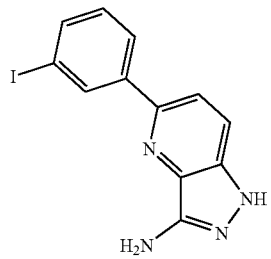 [SMILES: Nc1n[nH]c2ccc(-c3cccc(I)c3)nc12]

Step A: 5-Chloro-3-nitro-1H-pyrazolo[4,3-b]pyridine. To a solution of 5-chloro-1H-pyrazolo[4,3-b]pyridine (47.8 g, 311 mmol) in H$_2$SO$_4$ (700 mL) was added nitric acid (327 g, 3.58 mol, 69.0% purity) at 0° C. The mixture was stirred at 25° C. for 2 h followed by the addition of H$_2$O (100 mL). The resulting mixture was filtered and the collected solid was washed with H$_2$O (20 mL×3). The resulting solid was triturated with ethyl acetate:DCM=1:1 at 25° C. for 1 h to afford 5-chloro-3-nitro-1H-pyrazolo[4,3-b]pyridine (47.0 g, 74.2%) as a white solid. MS (ESI): mass calcd. for C$_6$H$_3$ClN$_4$O$_2$, 197.9; m/z. found, 199.0 [M+H]$^+$.

Step B: 3-Nitro-5-(3-(trimethylsilyl)phenyl)-1H-pyrazolo[4,3-b]pyridine. To a solution of 5-chloro-3-nitro-1H-pyrazolo[4,3-b]pyridine (9.00 g, 45.3 mmol), trimethyl-[3-(4,4,5,5-tetramethyl-1,3,2-dioxaborolan-2-yl)phenyl]silane (31.3 g, 90.6 mmol), K$_2$CO$_3$ (21.9 g, 158 mmol), 1,2-dimethoxyethane (160 mL), ethanol (160 mL) and H$_2$O (120 mL) was added Pd(PPh$_3$)$_2$Cl$_2$ (3.18 g, 4.53 mmol). The mixture was stirred at 90° C. for 24 h. To the resulting yellow mixture was added ethyl acetate (200 mL) and the mixture was filtered. The filtrate was washed with H$_2$O (200 mL) and brine (100 mL). The organic layer was dried over anhydrous Na$_2$SO$_4$, filtered, and concentrated to dryness. The residue was triturated with MTBE at 25° C. for 30 min and the resulting solid was collected by filtration to afford 3-nitro-5-(3-(trimethylsilyl)phenyl)-1H-pyrazolo[4,3-b]pyridine (12.0 g, 68.3%) as a yellow solid. $^1$H NMR (400 MHz, DMSO-d$_6$) δ 8.28 (s, 1H), 8.19-8.17 (m, 2H), 7.87 (d, J=8.8 Hz, 1H), 7.59-7.49 (m, 2H), 0.32 (s, 9H).

Step C: 5-(3-Iodophenyl)-3-nitro-1H-pyrazolo[4,3-b]pyridine. A solution of 3-nitro-5-(3-(trimethylsilyl)phenyl)-1H-pyrazolo[4,3-b]pyridine (17.0 g, 54.4 mmol) in TFA (85.0 mL) was charged with N-iodosuccinimide (13.3 g, 59.1 mmol) and chlorotrimethylsilane (690 µL, 5.44 mmol). The resulting mixture was stirred at 25° C. and after 1 h, to the resulting mixture was added saturated aqueous Na$_2$SO$_3$ (20 mL) and ethyl acetate (20 mL). The organic layer was washed with brine (20 mL), dried over anhydrous Na$_2$SO$_4$, filtered, and concentrated to dryness. The residue was triturated with MTBE at 25° C. for 30 min and the resulting solid was collected by filtration to afford 5-(3-iodophenyl)-3-nitro-1H-pyrazolo[4,3-b]pyridine (12.0 g, 55.9%) as a yellow solid. MS (ESI): mass calcd. for C$_{12}$H$_7$IN$_4$O$_2$, 365.9; m/z. found, 367.0 [M+H]$^+$.

Step D: 5-(3-Iodophenyl)-1H-pyrazolo[4,3-b]pyridin-3-amine. To a solution of 5-(3-iodophenyl)-3-nitro-1H-pyrazolo[4,3-b]pyridine (9.50 g, 25.9 mmol) in EtOH (190 mL) was added tin(II) chloride dihydrate (23.4 g, 103 mmol). The mixture was stirred at 80° C. for 1 h. To the resulting yellow mixture was added EtOH (100 mL) and the mixture was filtered. The organic layer was concentrated to dryness and saturated aqueous NaHCO$_3$ (100 mL) was added to the residue. The resulting mixture was extracted with ethyl acetate (200 mL×3). The combined organic extracts were dried over Na$_2$SO$_4$, filtered, and concentrated to dryness. The residue was triturated with DCM (20 mL) at 25° C. for 30 min and the resulting solid was collected by filtration to afford 5-(3-iodophenyl)-1-methyl-1H-pyrazolo[4,3-b]pyridin-3-amine (2.60 g, 29.8%) as a yellow solid. MS (ESI): mass calcd. for C$_{12}$H$_9$$_1$N$_4$, 335.9; m/z. found, 337.1 [M+H]$^+$. $^1$H NMR (400 MHz, DMSO-d$_6$) δ 11.74 (s, 1H), 8.55 (s, 1H), 8.11 (d, J=7.8 Hz, 1H), 7.87-7.84 (m, 1H), 7.77 (m, 2H), 7.28 (t, J=7.8 Hz, 1H), 5.48 (br s, 2H).

Intermediate 17: 5-(3-Iodophenyl)-1-methyl-1H-pyrazolo[4,3-b]pyridin-3-amine

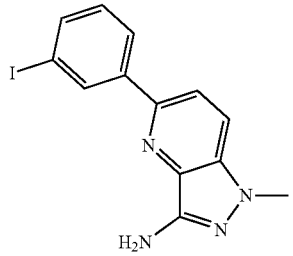 [SMILES: Cn1nc(N)c2nc(-c3cccc(I)c3)ccc21]

Step A: 5-Chloro-1-methyl-3-nitro-1H-pyrazolo[4,3-b]pyridine. A solution of 5-chloro-3-nitro-1H-pyrazolo[4,3-b]pyridine (400 mg, 2.01 mmol) in DMF (4 mL) was charged with iodomethane (286 mg, 2.01 mmol) and K$_2$CO$_3$ (278 mg, 2.01 mmol). The mixture was heated to 50° C. After 3 h, the resulting mixture was poured into ice water (20 mL), filtered, and the solid was collected. The solid was suspended in DCM (10 mL) and ethyl acetate (5 mL) and stirred for 2 h at rt. The solid was isolated by filtration and dried under reduced pressure to afford 5-chloro-1-methyl-3-nitro-1H-pyrazolo[4,3-b]pyridine (268 mg, 63%) as yellow solid. MS (ESI): mass calcd. for C$_7$HClN$_4$O$_2$, 212.0; m/z. found, 213.0 [M+H]$^+$.

Step B: 1-Methyl-3-nitro-5-(3-(trimethylsilyl)phenyl)-1H-pyrazolo[4,3-b]pyridine. To a mixture of 5-chloro-1-methyl-3-nitro-1H-pyrazolo[4,3-b]pyridine (20.0 g, 94.0 mmol), trimethyl(3-(4,4,5,5-tetramethyl-1,3,2-dioxaborolan-2-yl)phenyl)silane (20.0 g, 103 mmol), K$_2$CO$_3$ (26.0 g, 188 mmol) in H$_2$O (70 mL), EtOH (70 mL) and DME (70 mL) under nitrogen was added [1,1'-bis(diphenylphosphino)ferrocene]dichloropalladium(II) (3.44 g, 4.70 mmol). The mixture was sparged with nitrogen and then heated to 90° C. After 16 h, the black mixture was filtered and water (500 mL) was added. The aqueous phase was extracted with ethyl acetate/IPA (2.5 L/0.25 L) and the organic phase was washed with brine (300 mL). The organic extract was dried over anhydrous Na$_2$SO$_4$, filtered, and concentrated to dryness. The residue was triturated with MTBE (100 mL) at 25° C. for 16 h and the resulting solid was collected by filtration to afford 1-methyl-3-nitro-5-(3-(trimethylsilyl)phenyl)-1H-pyrazolo[4,3-b]pyridine (3.80 g, 12.4% yield) was obtained as a brown solid. MS (ESI): mass calcd. For C$_{16}$H$_{18}$N$_4$O$_2$Si, 326.1; m/z. found, 327.1 [M+H]$^+$.

Step C: 5-(3-Iodophenyl)-1-methyl-3-nitro-1H-pyrazolo[4,3-b]pyridine. A solution of 1-methyl-3-nitro-5-(3-(trimethylsilyl)phenyl)-1H-pyrazolo[4,3-b]pyridine (4.70 g, 14.4 mmol) in TFA (50 mL) was charged with N-iodosuccinimide (3.24 g, 14.4 mmol) and chlorotrimethylsilane (182 µL, 1.44 mmol). The mixture was stirred under nitrogen at 25° C. for 30 min. The resulting black mixture was concentrated to dryness. The resulting residue was diluted with DCE (10 ml) and concentrated to dryness three times. The product was triturated with MTBE at 25° C. for 1 h and the solid was collected by filtration to afford 5-(3-iodophenyl)-1-methyl-3-nitro-1H-pyrazolo[4,3-b]pyridine (4.2 g, 77%) as a black solid. For C$_{13}$H$_9$$_1$N$_4$O$_2$, 379.9; m/z. found, 381.1 [M+H]$^+$.

Step D: 5-(3-Iodophenyl)-1-methyl-1H-pyrazolo[4,3-b]pyridin-3-amine. To a solution of 5-(3-iodophenyl)-1-methyl-3-nitro-1H-pyrazolo[4,3-b]pyridine (6.30 g, 16.5 mmol) in EtOH (60 mL) was added tin(II) chloride dihydrate (14.9 g, 66.2 mmol). The mixture was stirred at 80° C.

for 4 h. To the resulting black mixture was added saturated aqueous NaHCO$_3$ (200 mL). This mixture was extracted with ethyl acetate (200 mL×3). The combined organic extracts were dried over Na$_2$SO$_4$, filtered, and concentrated to dryness. The residue was purified by FCC to afford 5-(3-iodophenyl)-1-methyl-1H-pyrazolo[4,3-b]pyridin-3-amine which was triturated with MTBE (30 mL) to afford 5-(3-iodophenyl)-1-methyl-1H-pyrazolo[4,3-b]pyridin-3-amine (2.58 g, 45%) as a yellow solid. MS (ESI): mass calcd. for C$_{13}$H$_{11}$IN$_4$, 350.0; m/z. found, 350.8 [M+H]$^+$. $^1$H NMR (400 MHz, DMSO-d$_6$) δ 8.51-8.61 (m, 1H), 8.13 (d, J=8.0 Hz, 1H), 7.93 (s, 2H), 7.74 (d, J=7.8 Hz, 1H), 7.28 (t, J=7.9 Hz, 1H), 5.58 (s, 2H), 3.79 (s, 3H).

Intermediate 18: 6-Chloro-4-methylpyrido[3,2-d]pyrimidine

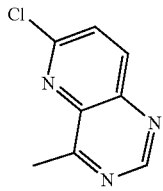

A microwave vial was charged with 4,6-dichloropyrido[3,2-d]pyrimidine (350 mg, 1.75 mmol) and THF (12 mL). The mixture was sparged with argon for 5 min and then treated with Pd(PPh$_3$)$_4$ (202 mg, 0.18 mmol). The resulting mixture was sparged with argon for another 5 min followed by addition of Al(CH$_3$)$_3$ (0.42 mL, 2 M in THF) at 0° C. The mixture was subjected to microwave irradiation at 70° C. in for 1 h. After the reaction mixture was allowed to cool to rt, it was poured into saturated aqueous NH$_4$Cl (20 mL) and extracted with ethyl acetate (30 mL×3). The combined organic extracts were concentrated to dryness and purified by FCC (petroleum ether:ethyl acetate=1:0 to 1:1) to afford 6-chloro-4-methylpyrido[3,2-d]pyrimidine (120 mg, 38%) as a yellow solid. MS (ESI): mass calcd. for C$_8$H$_6$ClN$_3$ 179.03 m/z found 179.9 [M+H]$^+$. $^1$H NMR (400 MHz, DMSO-d$_6$) δ 9.25 (s, 1H), 8.48 (d, J=9.0 Hz, 1H), 8.08 (d, J=8.8 Hz, 1H), 2.93 (s, 3H).

Intermediate 19: 6-Chloro-4-ethoxypyrido[3,2-d]pyrimidine

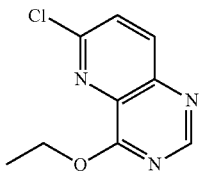

4,6-Dichloropyrido[3,2-d]pyrimidine (300 mg, 1.50 mmol) was added to a suspension of NaHCO$_3$ (372 mg, 4.43 mmol) and EtOH (20 mL). The resulting mixture was heated to 85° C. under nitrogen atmosphere for 12 h before cooling to rt. The mixture was concentrated to dryness and H$_2$O (5 mL) was added with stirring at rt. After 2 h, the resulting suspension was isolated by filtration and the filter cake was washed with water (1 mL×3) before drying under reduced pressure to afford 6-chloro-4-ethoxypyrido[3,2-d]pyrimidine (300 mg, 92%) as a white solid. MS (ESI): mass calcd. for C$_9$H$_8$ClN$_3$O, 209.04; m/z. found 210.1 [M+H]$^+$. $^1$H NMR (400 MHz, DMSO-d$_6$) δ 8.89 (s, 1H), 8.39 (d, J=8.8 Hz, 1H), 8.03 (d, J=8.8 Hz, 1H), 4.64 (q, J=7.0 Hz, 2H), 1.47 (t, J=7.0 Hz, 3H).

Intermediate 20: 6-Chloro-N,N-dimethylpyrido[3,2-d]pyrimidin-4-amine

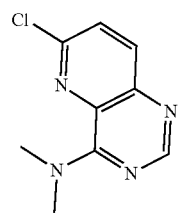

A 20 mL vial containing 4,6-dichloropyrido[3,2-d]pyrimidine (300 mg, 1.50 mmol) was charged with DMF (8 mL) and DIEA (0.52 mL, 3.02 mmol) at rt. To the resulting solution was added N,N-dimethylamine 40% in water (0.19 mL, 1.5 mmol) dropwise over 2 min. After 45 min, the resulting mixture was concentrated and the residue was purified by FCC (100% DCM increasing to 5% MeOH-DCM) to afford 6-chloro-N,N-dimethylpyrido[3,2-d]pyrimidin-4-amine (145 mg, 46%) as a yellow solid. MS (ESI): mass calcd. For C$_9$H$_9$ClN$_4$, 208.65; m/z. found, 209.05 [M+H]$^+$. $^1$H NMR (400 MHz, CDCl$_3$) δ 8.57 (s, 1H), 8.01 (d, J=8.8 Hz, 1H), 7.55 (d, J=8.8 Hz, 1H), 3.63 (s, 6H).

Intermediate 21: 4-(Azetidin-1-yl)-6-chloropyrido[3,2-d]pyrimidine

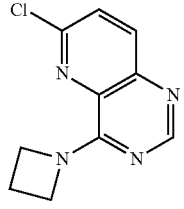

Azetidine (71.3 mg, 1.25 mmol) was added to a mixture of 4,6-dichloropyrido[3,2-d]pyrimidine (250 mg, 1.25 mmol), DIPEA (0.87 mL, 5.00 mmol), and DMF (2.5 mL). The resulting mixture was stirred at rt. After 1.5 h, the resulting mixture was filtered and the filter cake was dried under reduced pressure to afford 4-(azetidin-1-yl)-6-chloropyrido[3,2-d]pyrimidine (200 mg, 73%). as a white solid. MS (ESI): mass calcd. For C$_{10}$H$_9$ClN$_4$, 220.05; m/z. found, 221.05 [M+H]$^+$. $^1$H NMR (400 MHz, CD$_3$OD) δ 8.34 (s, 1H), 7.97 (d, J=8.8 Hz, 1H), 7.69 (d, J=8.8 Hz, 1H), 4.88 (t, J=7.7 Hz, 2H), 4.36 (t, J=7.7 Hz, 2H), 2.82-2.21 (m, 2H).

Intermediate 22: 6-Chloro-N-methylpyrido[3,2-d]pyrimidin-4-amine

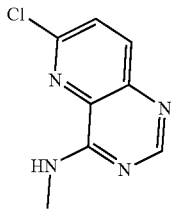

A 20 mL round-bottomed flask was charged with 6-chloropyrido[3,2-d]pyrimidin-4-amine (200 mg, 1.11 mmol), and DMF (4 mL) followed by portionwise addition of NaH (36.0 mg, 60% purity), 0.90 mmol) at 0° C. To the resulting mixture was added iodomethane (2.20 g, 16.0 mmol) dropwise at 0° C. The resultant mixture was stirred for 5 h with gradual warming to rt before quenching with aqueous HCl (1 mL, 1M). The resulting solution was directly purified by preparative HPLC (Xtimate C18×10 μm, 250 mm×50 mm, (eluent: 18% to 48% (v/v) $CH_3CN$ and $H_2O$ with 0.04% $NH_3 \cdot H_2O$ and 10 mM $NH_4HCO_3$). Detection, UV at λ=220-254 nM) to afford 6-chloro-N-methylpyrido[3,2-d]pyrimidin-4-amine (100 mg, 47%) as a white solid. MS (ESI): mass calcd. For $C_8H_7ClN_4$ 194.04 m/z found 195.1 [M+H]$^+$. $^1$H NMR (400 MHz, DMSO-$d_6$) δ 8.50-8.43 (m, 2H), 8.11 (d, J=8.8 Hz, 1H), 7.83 (d, J=8.8 Hz, 1H), 2.97 (d, J=4.9 Hz, 3H).

Intermediate 23: 6-(3-Bromophenyl)-N-(2,4-dimethoxybenzyl)pyrimido[5,4-d]pyrimidin-4-amine

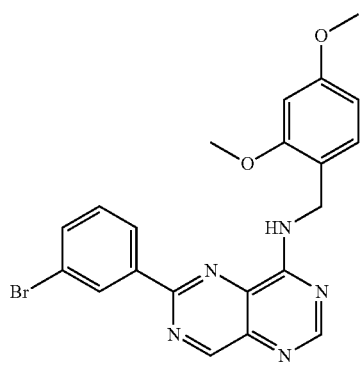 [SMILES: COc1ccc(CNc2ncnc3cnc(-c4cccc(Br)c4)nc23)c(OC)c1]

Step A: 8-Chloro-2-(methylthio)pyrimido[5,4-d]pyrimidine. To a 250 mL round-bottomed flask containing 6-(methylthio)pyrimido[5,4-d]pyrimidin-4-ol (3.80 g, 19.6 mmol) and toluene (100 mL) was added phosphorus oxychloride (11.0 mL, 120 mmol). The resulting mixture was stirred while heating at 115° C. for 15 h before cooling to rt. The resulting mixture was slowly poured into $H_2O$ (100 mL) and the pH of the mixture was adjusted to pH=7-8 with solid $K_2CO_3$. The resulting mixture was extracted with ethyl acetate (50 mL×3). The combined organic extracts were washed with saturated aqueous $NaHCO_3$ (35 mL), brine (35 mL), dried over anhydrous $MgSO_4$, filtered, and concentrated to dryness. The resulting residue was triturated with MTBE:ethyl acetate (1:1, 50 mL) and the resulting solid was isolated by filtration to afford 8-chloro-2-(methylthio)pyrimido[5,4-d]pyrimidine (2.5 g, 60%) as a grey solid. $^1$H NMR (400 MHz, DMSO-$d_6$) δ 9.11 (s, 1H), 8.14 (s, 1H), 2.56 (s, 3H).

Step B: N-(2,4-Dimethoxybenzyl)-6-(methylthio)pyrimido[5,4-d]pyrimidin-4-amine. A 250 mL round-bottomed flask was charged with 8-chloro-2-(methylthio)pyrimido[5,4-d]pyrimidine, (3.1 g, 15 mmol), 1-butanol (150 mL), (2,4-dimethoxyphenyl)methanamine (2.7 mg, 16 mmol), and DIPEA (7.3 mL, 44 mmol). The resulting mixture was stirred while heating at 120° C. for 2.5 h before cooling to rt, concentrating to dryness, and diluting with ethyl acetate (250 mL). The organic layer was washed with brine (100 mL×2), dried over anhydrous $Na_2SO_4$, filtered, and concentrated to dryness to afford N-(2,4-dimethoxybenzyl)-6-(methylthio)pyrimido[5,4-d]pyrimidin-4-amine (5.16 g) as a brown solid, which was used in the next step without further purification. $^1$H NMR (400 MHz, DMSO-$d_6$) δ 9.18 (s, 1H), 8.75 (t, J=8.0 Hz, 1H), 8.47 (s, 1H), 7.05 (d, J=8.8 Hz, 1H), 6.58 (d, J=2.0 Hz, 1H), 6.43 (dd, J=2.4, 8.4 Hz, 1H), 4.70-4.64 (m, 2H), 3.84 (s, 3H), 3.72 (s, 3H), 2.68 (s, 3H).

Step C: 6-(3-Bromophenyl)-N-(2,4-dimethoxybenzyl)pyrimido[5,4-d]pyrimidin-4-amine. A 100 mL three neck round-bottomed flask was charged with N-(2,4-dimethoxybenzyl)-6-(methylthio)pyrimido[5,4-d]pyrimidin-4-amine, (500 mg, 1.46 mmol), (3-bromophenyl)boronic acid (585 mg, 2.91 mmol), and 1,4-dioxane (10 mL). The resulting mixture was sparged with argon for 5 min and then treated with [1,1'-bis(diphenylphosphino)ferrocene]dichloropalladium(II) (53 mg, 0.07 mmol) and copper(I) 2-hydroxy-3-methylbenzoate (625 mg, 2.91 mmol). The mixture was then sparged with argon for another 5 min and then heated to 100° C. for 3 h. The resulting mixture was cooled to rt, filtered through a pad of diatomaceous earth, such as Celite©, and the pad was washed with MeOH (30 mL). The resulting filtrate was concentrated to dryness and purified by FCC (petroleum ether:ethyl acetate=1:0 to 1:1) to afford 6-(3-bromophenyl)-N-(2,4-dimethoxybenzyl)pyrimido[5,4-d]pyrimidin-4-amine (370 mg, 56%) as a yellow solid. MS (ESI): mass calcd. for $C_{21}H_{18}BrN_5O_2$ 451.1 m/z found 451.9 [M+H]$^+$.

Intermediate 24: 6-Chloro-8-methylpyrimido[5,4-d]pyrimidin-4-amine

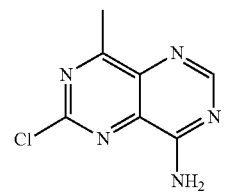

Step A: 5-Amino-2-chloro-6-methylpyrimidine-4-carbonitrile. To a solution of methyl 5-amino-2-chloro-6-methylpyrimidine-4-carboxylate (3.0 g, 17 mmol) and $CH_3CN$ (30 mL) were added tetrabutylammonium cyanide (5.0 g, 19 mmol) and 1,4-diazabicyclo[2.2.2]octane (2.8 g, 25 mmol). The resultant mixture was stirred at 50° C. for 16 h before cooling to rt, pouring it into water (30 mL), and extracting with ethyl acetate (50 mL×3). The combined organic extracts were dried over anhydrous $Na_2SO_4$, filtered, and concentrated to dryness. The resulting residue was purified by FCC (petroleum ether:ethyl acetate=1:0 to 1:1) to afford 5-amino-2-chloro-6-methylpyrimidine-4-carbonitrile (1.1 g, 38%) as a yellow solid. MS (ESI): mass calcd. For $C_6H_5ClN_4$ 168.02 m/z found 168.8 $[M+H]^+$. $^1$H NMR (400 MHz, $CDCl_3$) δ 4.58 (br s, 2H), 2.51 (s, 3H).

Step B: 6-Chloro-8-methylpyrimido[5,4-d]pyrimidin-4-amine. To a solution of 5-amino-2-chloro-6-methylpyrimidine-4-carbonitrile, (150 mg, 0.89 mmol), formamidine acetate (185 mg, 1.78 mmol), and 1,4-dioxane (3 mL) was added DIPEA (0.7 mL, 4 mmol). The resultant mixture was stirred at 110° C. for 16 h before cooling to rt and concentrating to dryness. The resulting residue was purified by FCC (petroleum ether:ethyl acetate=1:0 to 1:1) to afford 6-chloro-8-methylpyrimido[5,4-d]pyrimidin-4-amine (106 mg, 61%) as a brown solid. MS (ESI): mass calcd. for $C_7H_6ClN_5$ 195.03 m/z found 196.1 $[M+H]^+$.

Intermediate 25: 6-Chloro-N-(2,4-dimethoxybenzyl)-2-methylpyrimido[5,4-d]pyrimidin-4-amine

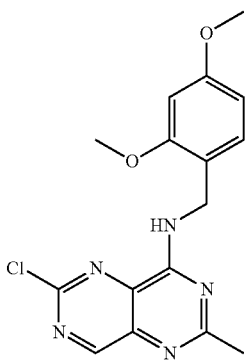 [SMILES: COc1ccc(CNc2nc(C)nc3cnc(Cl)nc23)c(OC)c1]

Step A: 6-Chloro-2-methylpyrimido[5,4-d]pyrimidin-4(3H)-one. A 250 mL three-necked round-bottomed flask was charged with ethyl 5-amino-2-chloropyrimidine-4-carboxylate (2.0 g, 9.9 mmol) and $CH_3CN$ (70 mL). To the resulting mixture was bubbled HCl gas (>1.3 M) at rt for 0.5 h. The resultant mixture was stirred at 80° C. for 2 h before cooling to rt. The resulting solid was isolated by filtration and the filter cake was washed with acetonitrile (20 mL×2) before drying under reduced pressure to afford 6-chloro-2-methylpyrimido[5,4-d]pyrimidin-4(3H)-one (2.0 g). MS (ESI): mass calcd. for $C_7H_5ClN_4O$, 196.02; m/z. found 196.8 $[M+H]^+$. $^1$H NMR (400 MHz, DMSO-$d_6$) δ 9.22 (s, 1H), 2.40 (s, 3H).

Step B: 6-Chloro-N-(2,4-dimethoxybenzyl)-2-methylpyrimido[5,4-d]pyrimidin-4-amine. Oxalyl chloride (968 mg, 7.63 mmol) was added to a solution of 6-chloro-2-methylpyrimido[5,4-d]pyrimidin-4(3H)-one, (500 mg, 2.54 mmol), DMF (18.0 mg, 0.25 mmol), and DCM (5 mL). The mixture was stirred at rt for 16 h before concentrating to dryness. The resulting residue was dissolved in THF (5 mL), n-BuOH (1 mL), DIPEA (3.30 g, 26.0 mmol) and (2,4-dimethoxyphenyl)methanamine (425 mg, 2.54 mmol) was added at rt. After 16 h, the mixture was poured into water (50 mL) and extracted with ethyl acetate (50 mL×3). The combined organic extracts were washed with brine (50 mL), dried over anhydrous $Na_2SO_4$, filtered, and concentrated to dryness. The resulting residue was purified by FCC (petroleum ether:ethyl acetate=10:1 to 1:1) to afford 6-chloro-N-(2,4-dimethoxybenzyl)-2-methylpyrimido[5,4-d]pyrimidin-4-amine (350 mg, 40%) as a pale yellow solid. MS (ESI): mass calcd. for $C_{16}H_{16}ClN_5O_2$ 345.10 m/z found 346.1 $[M+H]^+$.

Intermediate 26: 6-(3-Iodophenyl)-8-methylpyrido[3,2-d]pyrimidin-4-amine

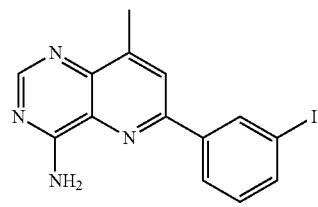 [SMILES: Cc1cc(-c2cccc(I)c2)nc2c(N)ncnc12]

Step A: Methyl 3-amino-4-bromo-6-chloropicolinate. A solution of methyl 3-amino-6-chloropicolinate (1.59 g, 8.51 mmol) in DMF (20 mL) was treated with N-bromosuccinimide (1.62 g, 8.99 mmol) and then heated to 80° C. After 1.5 h, additional N-bromosuccinimide (0.19 g, 1.09 mmol) was added and stirred for 2 h. The resulting mixture was then concentrated to dryness. To the residue was added ethyl acetate (150 mL) and saturated aqueous $NaHCO_3$ (150 mL). The organic layer was separated and washed with brine (150 mL×2). The organic extract was dried over anhydrous ($MgSO_4$), filtered, and concentrated to dryness to afford methyl 3-amino-4-bromo-6-chloropicolinate (2.2 g, 96%). MS (ESI): mass calcd. for $C_7H_6BrClN_2O_2$, 263.9; m/z found, 264.9 $[M+H]^+$. $^1$H NMR (400 MHz, $CDCl_3$) δ 7.59 (s, 1H), 6.40 (br s, 2H), 3.98 (s, 3H).

Step B: Methyl 3-amino-6-chloro-4-methylpicolinate. A round-bottomed flask was charged with methyl 3-amino-4-bromo-6-chloropicolinate (1.08 g, 4.08 mmol) and [1,1'-bis(diphenylphosphino)ferrocene] dichloropalladium(II)-complex with dichloromethane (0.34 g, 0.41 mmol). The vessel was sealed with a septum, evacuated, and then purged with nitrogen three times. The flask was charged with degassed 1,4-dioxane (25 mL) followed by degassed $K_2CO_3$ (12 mL, 2M in $H_2O$) and trimethylboroxine (0.61 mL, 4.32 mmol). The resulting mixture was heated to 80° C. After 1 h, the mixture was cooled to rt, diluted with ethyl acetate (150 mL), and washed with brine (150 mL×2). The organic extract was dried over anhydrous $MgSO_4$, filtered, and concentrated to dryness. The residue was purified by FCC to yield methyl 3-amino-6-chloro-4-methylpicolinate (422 mg, 52%). MS (ESI): mass calcd. for $C_8H_9ClN_2O_2$, 200.0; m/z. found, 201.0 $[M+H]^+$. $^1$H NMR (400 MHz, $CDCl_3$) δ 7.16 (s, 1H), 5.91 (br s, 2H), 3.96 (s, 3H), 2.22 (s, 3H).

Step C: Methyl 3-amino-4-methyl-6-(3-(trimethylsilyl)phenyl)picolinate. A flask was charged with methyl 3-amino-6-chloro-4-methylpicolinate (0.41 g, 2.06 mmol), (3-(trimethylsilyl)phenyl)boronic acid (0.52 g, 2.67 mmol), and chloro(2-dicyclohexylphosphino-2',4',6'-triisopropyl-1,1'-biphenyl)[2-(2'-amino-1,1'-biphenyl)]palladium(II) (0.16 g, 0.20 mmol). The vessel was sealed with a septum, evacuated, and then purged with nitrogen three times. The flask was charged with degassed 1,4-dioxane (10 mL) followed by degassed K$_2$CO$_3$ (5 mL, 2M in H$_2$O) and then heated to 80° C. After 1 h, the mixture was cooled to rt, diluted with ethyl acetate (150 mL), and washed with brine (150 mL×2). The organic extract was dried over anhydrous (MgSO$_4$), filtered, concentrated to dryness. The residue was purified by FCC to yield methyl 3-amino-4-methyl-6-(3-(trimethylsilyl)phenyl)picolinate (600 mg, 93%). MS (ESI): mass calcd. for C$_{17}$H$_{22}$N$_2$O$_2$Si, 314.2; m/z. found, 315.1 [M+H]$^+$. $^1$H NMR (400 MHz, CDCl$_3$) δ 8.00 (s, 1H), 7.91-7.86 (m, 1H), 7.60 (s, 1H), 7.52-7.48 (m, 1H), 7.42 (t, J=7.5 Hz, 1H), 5.88 (s, 2H), 3.99 (s, 3H), 2.30 (s, 3H), 0.31 (s, 9H).

Step D: Methyl 3-amino-6-(3-iodophenyl)-4-methylpicolinate. To a solution of methyl 3-amino-4-methyl-6-(3-(trimethylsilyl)phenyl)picolinate (0.5 g, 1.6 mmol) in DCM (13 mL) at 0° C. was added iodine monochloride (8.0 mL, 1M in DCM). The resulting mixture was warmed to rt. After 2 h, the mixture was concentrated and purified directly via FCC to afford methyl 3-amino-6-(3-iodophenyl)-4-methylpicolinate (135 mg, 23%). MS (ESI): mass calcd. for C$_{14}$H$_{131}$N$_2$O$_2$, 368.00; m/z. found, 369.0 [M+H]$^+$. $^1$H NMR (400 MHz, CDCl$_3$) δ 8.27 (s, 1H), 7.95-7.80 (m, 1H), 7.66 (d, J=7.3 Hz, 1H), 7.56 (s, 1H), 7.22-7.08 (m, 1H), 5.93 (br s, 2H), 4.00 (s, 3H), 2.28 (s, 3H).

Step E: 6-(3-Iodophenyl)-8-methylpyrido[3,2-d]pyrimidin-4(3H)-one. A mixture of methyl 3-amino-6-(3-iodophenyl)-4-methylpicolinate (0.14 g, 0.37 mmol) in THF (2 mL) was treated with formamide (4 mL) and then subjected to microwave irradiation at 175° C. for 30 min and then 200° C. for an additional 30 min. The resulting mixture was diluted with H$_2$O (10 mL), the resulting solid was collected by filtration, and dried under vacuum to afford 6-(3-iodophenyl)-8-methylpyrido[3,2-d]pyrimidin-4(3H)-one (75 mg, 56%). MS (ESI): mass calcd. for C$_{14}$H$_{10}$IN$_3$O, 362.99; m/z. found, 364.0 [M+H]$^+$.

Step F: 4-Chloro-6-(3-iodophenyl)-8-methylpyrido[3,2-d]pyrimidine. A suspension of 6-(3-iodophenyl)-8-methylpyrido[3,2-d]pyrimidin-4(3H)-one (0.14 g, 0.39 mmol) in phosphorus oxychloride (3 mL) was treated with DIPEA (0.15 mL) and then subjected to microwave irradiation at 100° C. for 30 min. The resulting mixture was then concentrated to dryness. The residue was dissolved in DCM (10 mL) and DIPEA (0.5 mL). The resulting mixture was concentrated dryness, triturated with MeCN (15 mL), and the resulting solid was collected by filtration to afford chloro-6-(3-iodophenyl)-8-methylpyrido[3,2-d]pyrimidine (126 mg, 83%). MS (ESI): mass calcd. for C$_{14}$H$_9$ClIN$_3$, 380.95; m/z. found, 382.0 [M+H]$^+$.

Step G: 6-(3-Iodophenyl)-8-methylpyrido[3,2-d]pyrimidin-4-amine. A solution of 4-chloro-6-(3-iodophenyl)-8-methylpyrido[3,2-d]pyrimidine (0.13 g, 0.33 mmol) and NH$_3$ (3 mL, 2M in MeOH) was subjected to microwave irradiation at 100° C. for 30 min. The resulting mixture was concentrated to dryness and purified via FCC to afford 6-(3-iodophenyl)-8-methylpyrido[3,2-d]pyrimidin-4-amine (53 mg, 44%). MS (ESI): mass calcd. for C$_{14}$H$_9$ClIN$_3$, 362.00; m/z. found, 363.0 [M+H]$^+$.

Intermediate 27: (R)-3-Hydroxy-1-methyl-3-((3-(4, 4,5,5-tetramethyl-1,3,2-dioxaborolan-2-yl)-4-(trifluoromethoxy)phenyl)ethynyl)pyrrolidin-2-one

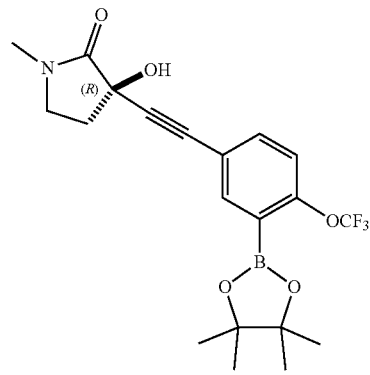

Step A: 2-(5-Bromo-2-(trifluoromethoxy)phenyl)-4,4,5,5-tetramethyl-1,3,2-dioxaborolane. A mixture of (5-bromo-2-(trifluoromethoxy)phenyl)boronic acid (29.5 g, 104 mmol) and 2,3-dimethylbutane-2,3-diol (12.4 g, 105 mmol) in THF (260 mL) was purged with N$_2$, and then stirred at 25° C. for 36 h under nitrogen. The reaction mixture was concentrated to dryness to provide the title compound, 2-(5-Bromo-2-(trifluoromethoxy)phenyl)-4,4,5,5-tetramethyl-1,3,2-dioxaborolane, (38.0 g, 95.0%) as a white solid. MS (ESI): mass calcd. For C$_{13}$H$_{15}$BBrF$_3$O$_3$, 366.02; m/z. found, 342.1 [M+H]$^+$.

Step B: (R)-3-Hydroxy-1-methyl-3-((3-(4,4,5,5-tetramethyl-1,3,2-dioxaborolan-2-yl)-4-(trifluoromethoxy)phenyl) ethynyl)pyrrolidin-2-one. A 1 L round-bottomed flask was charged with Pd(PPh$_3$)$_4$ (7.9 g, 6.8 mmol), 2-[5-bromo-2-(trifluoromethoxy)phenyl]-4,4,5,5-tetramethyl-1,3,2-dioxaborolane (25 g, 68 mmol), (R)-3-ethynyl-3-hydroxy-1-methylpyrrolidin-2-one (14.2 g, 102.2 mmol), CuI (2.6 g, 14 mmol), tributylphosphonium; tetrafluoroborate (1.9 g, 6.8 mmol), piperidine (20 mL, 204 mmol), and DMF (300 mL). The reaction mixture was degassed with N$_2$ and stirred at 60° C. for 16 h under nitrogen. The reaction mixture was diluted with water (1500 mL) and extracted with EtOAc (2×200 mL) and DCM (5×100 mL). The combined organic layers were washed with brine (100 mL), dried over Na$_2$SO$_4$, filtered, and concentrated to dryness. The crude residue was purified by FCC (0-40% ethylacetate/petroleum ether) followed by preparative HPLC (Welch Xtimate C18 10 μm, 250×50 mm; mobile phase: [water (0.1% TFA)-ACN]; B %: 30%-66%, 20 min. Detection, UV at λ=220-254 nM) to provide (R)-3-hydroxy-1-methyl-3-[2-[3-(4,4,5,5-tetramethyl-1,3,2-dioxaborolan-2-yl)-4-(trifluoromethoxy)phenyl]ethynyl]pyrrolidin-2-one (4.3 g, 14%) as a brown solid. MS (ESI): mass calcd. for C$_{20}$H$_{23}$BF$_3$NO$_5$, 425.16; m/z found, 426.0 [M+H]$^+$. $^1$H NMR (400 MHz, CDCl$_3$) δ 7.80 (d, J=2.2 Hz, 1H), 7.45 (dd, J=8.5, 2.3 Hz, 1H), 7.10 (d, J=7.8 Hz, 1H), 3.47-3.36 (m, 1H), 3.35-3.23 (m, 1H), 2.89 (s, 3H), 2.64-2.46 (m, 1H), 2.37-2.20 (m, 1H), 1.27 (s, 12H).

Intermediate 28: 2-(3-Bromophenyl)pyrido[3,4-d]pyrimidin-8-amine

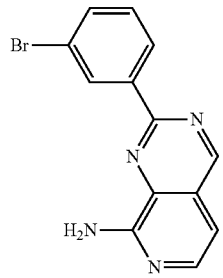 [SMILES: Nc1nccc2cnc(-c3cccc(Br)c3)nc12]

Step A: tert-Butyl (2-chloropyridin-3-yl)carbamate. A 2 L 3-necked round-bottom flask, purged and maintained with an inert atmosphere of nitrogen. was charged with a solution of 2-chloropyridin-3-amine (60 g, 467 mmol) in THF (700 mL). This was followed by the addition of sodium bis(trimethylsilyl)amide (516 mL, 1027 mmol, 0.5 M in THF) dropwise with stirring at −10° C. The mixture was stirred for 30 min at −10° C. To this was added a solution of Boc₂O (112 g, 516 mmol) in THF (100 mL) dropwise with stirring at −10° C. The resulting solution was stirred for 1 h at −10° C. and subsequently partitioned with hydrogen chloride solution (500 mL, 2N). The resulting mixture was extracted with ethyl acetate (200 mL×3). The combined organic layers were washed with brine (200 mL×3) and the resulting organic layer was dried over anhydrous sodium sulfate, filtered, and concentrated to dryness. The residue was purified by FCC to yield tert-butyl N-(2-chloropyridin-3-yl)carbamate (89 g, 83%) as an off-white solid.

Step B: tert-Butyl (2-chloro-4-formylpyridin-3-yl)carbamate. A 3 L 4-necked round-bottomed flask, purged and maintained with an inert atmosphere of nitrogen, was charged with a solution of tert-butyl N-(2-chloropyridin-3-yl)carbamate (105 g, 459 mmol) in THF (1600 mL), and tetramethylethylenediamine (118 g, 1.01 mol). The resulting solution was cooled with stirring to −78° C. and n-BuLi (405 mL, 2.5 M) was added dropwise. The solution was warmed to −40° C. and stirred for 1 h. The resulting solution was cooled to −78° C. and N,N-dimethylformamide (84 g, 1.2 mol) was added dropwise and stirred for 1 h. The resulting solution was partitioned with a saturated ammonium chloride solution (500 mL) and extracted with ethyl acetate (200 mL×3). The combined organic layers were washed with brine (200 mL×3), dried over anhydrous sodium sulfate, filtered, and concentrated to dryness. The residue was purified by FCC to yield tert-butyl N-(2-chloro-4-formylpyridin-3-yl)carbamate (75 g, 64%) as a light yellow solid.

Step C: 3-Amino-2-chloroisonicotinaldehyde. A 3 L 4-necked round-bottomed flask, purged and maintained with an inert atmosphere of nitrogen, was charged with a solution of tert-butyl N-(2-chloro-4-formylpyridin-3-yl)carbamate (75 g, 292 mmol) in DCM (1500 mL). The resulting solution was cooled to 0° C. and trifluoroacetic acid (300 mL) was added dropwise with stirring. The resulting solution was warmed to rt, stirred for 12 h, and then partitioned with a saturated solution of sodium carbonate (800 mL). The mixture was extracted with DCM (200 mL×2) and the combined organic layers were dried over anhydrous sodium sulfate, filtered, and concentrated to dryness. The residue was suspended in n-hexane (200 mL) and stirred for 20 min. The resulting solids were collected by filtration to afford 3-amino-2-chloropyridine-4-carbaldehyde (30 g, 66%) as a yellow solid. MS (ESI): mass calcd. for $C_6H_5ClN_2O$, 156.01; m/z. found, 157 [M+H]⁺. ¹H NMR (300 MHz, CDCl₃) δ 9.99 (s, 1H), 7.89 (d, J=4.8 Hz, 1H), 7.38 (d, J=5.1 HZ, 1H), 6.56 (br s, 2H).

Step D: 2-(3-Bromophenyl)-8-chloropyrido[3,4-d]pyrimidine. A 250-mL 3-necked round-bottomed flask, purged and maintained with an inert atmosphere of nitrogen, was charged with a solution of 3-amino-2-chloropyridine-4-carbaldehyde (28 g, 179 mmol) in water (56 mL), (3-bromophenyl)methanamine (83 g, 446 mmol), tert-butyl hydrogen peroxide (32 g, 359 mmol), pyridine (1.5 g, 19 mmol), and 12 (4.6 g, 18 mmol). The resulting solution heated to 90° C. After 12 h, the resulting mixture was cooled to rt and ethyl acetate (500 mL) was added. The resulting mixture was washed with brine (100 mL×3) and the organic layer was dried over anhydrous sodium sulfate, filtered, and concentrated to dryness. The residue was purified by FCC to yield 2-(3-bromophenyl)-8-chloropyrido[3,4-d]pyrimidine (18 g, 31%) as a light yellow solid.

Step E: 2-(3-Bromophenyl)pyrido[3,4-d]pyrimidin-8-amine. A 250 mL sealed tube was charged with 2-(3-bromophenyl)-8-chloropyrido[3,4-d]pyrimidine (18 g, 56 mmol) and a solution of NH₃ in IPA (180 mL, 2M). The resulting solution was heated to 145° C. After 12 h, the resulting mixture was cooled to rt and concentrated to dryness. The resulting residue was diluted with DCM (1000 mL), washed with brine (100 mL×3), and the organic layer was dried over anhydrous sodium sulfate, filtered, and concentrated to dryness. The resulting solid was recrystallized from ethyl acetate and the solid was collected by filtration to afford 2-(3-bromophenyl)pyrido[3,4-d]pyrimidin-8-amine (10.1 g, 60%) as a light brown solid. MS (ESI): mass calcd. For $C_{13}H_9BrN_4$, 300.0; m/z. found, 301.1 [M+H]⁺. ¹H NMR (300 MHz, DMSO-d₆) δ 9.61 (s, 1H), 8.94 (s, 1H), 8.69 (d, J=8.1 Hz, 1H), 8.35 (brs, 2H), 7.95 (d, J=6.1 Hz, 1H), 7.78 (d, J=7.8 Hz, 1H), 7.54 (t, J=7.9 Hz, 1H), 7.13 (d, J=6.0 Hz, 1H).

Intermediate 29: 2-(3-Bromophenyl)pyrido[3,4-d]pyrimidin-8(7H)-one

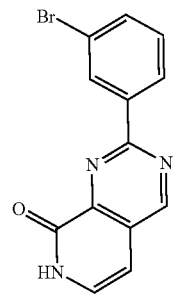 [SMILES: O=c1[nH]ccc2cnc(-c3cccc(Br)c3)nc12]

A flask was charged with 2-(3-bromophenyl)-8-chloropyrido[3,4-d]pyrimidine [Intermediate 28: Step D, 2.0 g, 6.2 mmol], hydrogen chloride (10 mL, 6N) and THF (10 mL). The resulting solution was stirred for 2 h at 80° C. The resulting mixture was cooled to rt and the pH was adjusted to 8 with saturated aqueous sodium bicarbonate. The resulting mixture was extracted with ethyl acetate (50 mL×3) and the combined organic layers concentrated to dryness to provide 2-(3-bromophenyl)pyrido[3,4-d]pyrimidin-8(7H)- one (1.6 g, 85%) as a light yellow solid. MS (ESI): mass calcd. for $C_{13}H_8BrN_3O$, 301.0; m/z. found, 302.0 $[M+H]^+$.

Intermediate 30: (R)-2-Thiazol-2-ylbut-3-yn-2-ol

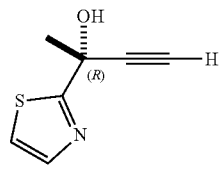

A 5 L 4-necked round-bottomed flask was charged with a solution of ethynylmagnesium bromide (1889 mL, 0.5 M in THF) under an inert atmosphere of nitrogen. To this solution was added 1-(1,3-thiazol-2-yl)ethan-1-one (60 g, 472 mmol) dropwise with stirring at rt. After 2 h, the resulting solution was partitioned with saturated aqueous ammonium chloride (900 mL) and water (600 mL). The resulting mixture was extracted with ethyl acetate (600 mL×3) and the combined organic layers were washed with brine (600 mL×2), dried over anhydrous sodium sulfate, filtered, and concentrated to dryness. The crude residue (65 g, 90%) of (R) and (S) enantiomers was further purified by chiral preparative SFC (CHIRALPAK IG 4.6×50 mm, 3 um; mobile phase, $CO_2$ (80%), MeOH (0.1% DEA); Detector, λ=254 nm) to afford (R)-2-(1,3-thiazol-2-yl)but-3-yn-2-ol (21 g, 32%, >97% ee) as a yellow solid and (S)-2-(1,3-thiazol-2-yl)but-3-yn-2-ol (Intermediate 31, 21 g, 32%) as a yellow solid. Data for (R)-2-(1,3-thiazol-2-yl)but-3-yn-2-ol: MS (ESI): mass calcd. for $C_7H_7NOS$, 153.0; m/z. found, 153.9 $[M+H]^+$. 1H NMR (400 MHz, CDCl$_3$) δ 7.78 (d, J=3.3 Hz, 1H), 7.36 (d, J=3.3 Hz, 1H), 3.66 (s, 1H), 2.72 (s, 1H), 1.98 (s, 3H). $[α]^{20}_D$=−34.6.5 (c=0.54 in MeOH).

Intermediate 31: (S)-2-Thiazol-2-ylbut-3-yn-2-ol

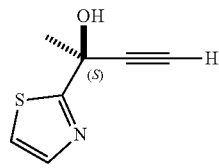

The chiral separation described in Intermediate 30 provided (S)-2-(1,3-thiazol-2-yl)but-3-yn-2-ol (21 g, 32%, >97% ee) as a yellow solid. MS (ESI): mass calcd. for $C_7H_7NOS$, 153.0; m/z. found, 153.9 $[M+H]^+$. $^1$H NMR (400 MHz, CDCl$_3$) δ 7.78 (d, J=3.3 Hz, 1H), 7.36 (d, J=3.3 Hz, 1H), 3.66 (s, 1H), 2.72 (s, 1H), 1.98 (s, 3H). $[α]^{20}_D$=+35.3 (c=0.51 in MeOH).

Intermediate 32: (R)-2-(5-Methylisoxazol-3-yl)but-3-yn-2-ol

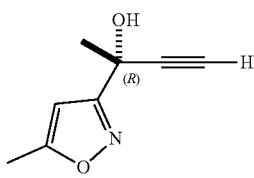

Into a 1 L round-bottomed flask, purged and maintained with an inert atmosphere of nitrogen, was placed ethynylmagnesium bromide (480 mL, 0.5 M in THF). The vessel was cooled to 0° C. and a solution of 1-(5-methyl-1,2-oxazol-3-yl)ethan-1-one (20 g, 160 mmol) in THF (200 mL) was added dropwise with stirring. The resulting solution was allowed to warm and stirred for 2 h at 25° C. The resulting solution was cooled to 0° C. and saturated aqueous ammonium chloride (300 mL) was added, followed by water (200 mL). The resulting mixture was extracted with ethyl acetate (200 mL×2) and the combined organic layers were washed with brine (200 mL). The organic layer was dried over anhydrous sodium sulfate, filtered, and concentrated to dryness. The resulting residue was purified by FCC (gradient 0:1 to 1:10 ethyl acetate:petroleum ether to afford racemic 2-(5-methyl-1,2-oxazol-3-yl)but-3-yn-2-ol (19.7 g, 82%) as a yellow oil. From the resulting material, 18 g was further purified by preparative chiral SFC (Phenomenex Lux 5u Cellulose-4, 5×25 cm, 5 µm; mobile phase, $CO_2$ (70%), IPA:HEX=1:1 (30%); Detection at λ=220 nm) to afford (R)-2-(5-methyl-1,2-oxazol-3-yl)but-3-yn-2-ol (5.1 g, 28%, >97% ee) as a yellow solid and (S)-2-(5-methyl-1,2-oxazol-3-yl)but-3-yn-2-ol (Intermediate 33, 5.1 g, 28%, >97 ee) as a yellow solid. Data for (R)-2-(5-methyl-1,2-oxazol-3-yl)but-3-yn-2-ol: MS (ESI): mass calcd. for $C_8H_9NO_2$, 151.1; m/z. found, 152.0 $[M+H]^+$. $^1$H NMR (400 MHz, DMSO-d$_6$) δ 6.36 (s, 1H), 6.25 (d, J=0.6 Hz, 1H), 3.51 (s, 1H), 2.38 (s, 3H), 1.67 (s, 3H). $[α]^{20}_D$=−11.3 (c=0.51 in MeOH).

Intermediate 33: (S)-2-(5-Methylisoxazol-3-yl)but-3-yn-2-ol

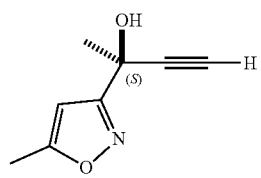

The chiral separation described in Intermediate 32 provided (S)-2-(5-methyl-1,2-oxazol-3-yl)but-3-yn-2-ol (5.1 g, 28%, >97% ee) as a yellow solid. MS (ESI): mass calcd. for $C_8H_9NO_2$, 151.1; m/z. found, 152.0 $[M+H]^+$. $^1$H NMR (400 MHz, DMSO-d$_6$) δ 6.36 (s, 1H), 6.25 (d, J=0.6 Hz, 1H), 3.51 (s, 1H), 2.38 (s, 3H), 1.67 (s, 3H). $[α]^{20}_D$=+8.27 (c=0.54 in MeOH).

Intermediate 34: 2-(3-Iodophenyl)-4-methylpyrido[3,4-d]pyrimidin-8-amine

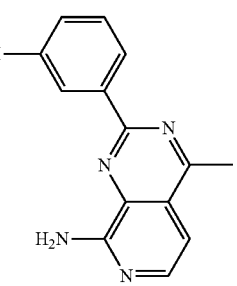

Step A: tert-Butyl (2-chloro-4-(1-hydroxyethyl)pyridin-3-yl)carbamate. To a 500 mL 4-neck round-bottomed flask, purged and maintained with an inert atmosphere of nitrogen, was placed a solution of tert-butyl N-(2-chloropyridin-3-yl) carbamate (20 g, 87 mmol) in THF (200 mL), TMEDA (22 g, 191 mmol). The resulting solution was cooled to at −78° C. followed by dropwise addition of n-BuLi (76.8 mL, 192 mmol). The resulting solution was warmed to −30° C. and stirred for 30 min and then cooled to −78° C. followed by addition of acetaldehyde in THF (43.6 mL, 5M). The resulting solution was stirred for 30 min at −78° C. The resulting solution was warmed to 0° C., followed by addition of saturated aqueous ammonium chloride (300 mL). The resulting solution was extracted with ethyl acetate (500 mL×2), the combined organic layers were washed with brine (500 mL), dried over anhydrous sodium sulfate, filtered, and concentrated dryness. The residue purified by FCC (1:3, ethyl acetate/petroleum ether) to afford tert-butyl N-[2-chloro-4-(1-hydroxyethyl)pyridin-3-yl]carbamate (21 g, 88%) as a white solid.

Step B: tert-Butyl (4-acetyl-2-chloropyridin-3-yl)carbamate. To a 500 mL 3-neck round-bottomed flask, purged and maintained with an inert atmosphere of nitrogen, was added tert-butyl N-[2-chloro-4-(1-hydroxyethyl)pyridin-3-yl]carbamate (21 g, 77 mmol), DMSO (210 mL), and 2-iodobenzoic acid (43.2 g, 154 mmol). The resulting solution was stirred for 3 h at rt and then partitioned with water (500 mL). The resulting mixture was extracted with ethyl acetate (500 mL×2). The combined organic layers were washed with brine (500 mL), dried over anhydrous sodium sulfate, filtered, and concentrated to dryness. This resulted in tert-butyl N-(4-acetyl-2-chloropyridin-3-yl)carbamate (18 g, 86%) as a yellow solid that was used directly in the next step.

Step C: 1-(3-Amino-2-chloropyridin-4-yl)ethan-1-one. To a 500-mL 3-neck round-bottomed flask, purged and maintained with an inter atmosphere of nitrogen, was added a solution of tert-butyl N-(4-acetyl-2-chloropyridin-3-yl) carbamate (18 g, 66 mmol) in DCM (180 mL), and trifluoroacetic acid (90 mL) at rt. After 12 h, the resulting mixture was concentrated to dryness and the pH of the residue was adjusted to 7 with saturated aqueous sodium bicarbonate. The resulting mixture was extracted with ethyl acetate (500 mL×2). The combined organic layers were washed with brine (300 mL), dried over anhydrous sodium sulfate, filtered, and concentrated to dryness. This resulted in 1-(3-amino-2-chloropyridin-4-yl)ethan-1-one (8.5 g, 75%) as a yellow solid that was used directly in the next step.

Step D: N-(4-Acetyl-2-chloropyridin-3-yl)-3-iodobenzamide. To a 250 mL 3-neck round-bottomed flask, purged and maintained with an inert atmosphere of nitrogen, was added a solution of 1-(3-amino-2-chloropyridin-4-yl)ethan-1-one (6 g, 35 mmol) in 1,4-dioxane (240 mL), 3-iodobenzoyl chloride (19 g, 70 mmol), and DIEA (9.1 g, 70 mmol). The resulting solution was heated at 110° C. After 12 h, the resulting solution was cooled and water (300 mL) was added. The resulting mixture was extracted with ethyl acetate (300 mL×2). The combined organic layers were washed with brine (300 mL), dried over anhydrous sodium sulfate, filtered, and concentrated to dryness. The residue was purified by FCC (1:5, ethyl acetate/petroleum ether) to afford N-(4-acetyl-2-chloropyridin-3-yl)-3-iodobenzamide (9.3 g, 66%) as a yellow solid.

Step E: 8-Chloro-2-(3-iodophenyl)-4-methylpyrido[3,4-d]pyrimidine. To a 40 mL 3-neck round-bottomed flask, was placed N-(4-acetyl-2-chloropyridin-3-yl)-3-iodobenzamide (1.9 g, 4.7 mmol) and NH$_3$ in IPA (25 mL, 2M). The resulting solution was heated at 90° C. After 2 h, the resulting mixture was cooled, filtered, and the solid that was collected was washed with IPA (50 mL) to afford 8-chloro-2-(3-iodophenyl)-4-methylpyrido[3,4-d]pyrimidine (6.2 g, 70%) as a yellow solid.

Step F: 2-(3-Iodophenyl)-4-methylpyrido[3,4-d]pyrimidin-8-amine. Into a 300 mL pressure tank reactor, was placed 8-chloro-2-(3-iodophenyl)-4-methylpyrido[3,4-d]pyrimidine (6.2 g, 16 mmol), NH$_3$ in IPA (120 mL, 2 M), and condensed ammonia (60 mL). The resulting solution was stirred at 145° C. in autoclave. After 12 h, the vessel was cooled to rt and the solids were collected by filtration. The resulting solids were washed with MeOH (100 mL) and dried to afford 2-(3-iodophenyl)-4-methylpyrido[3,4-d]pyrimidin-8-amine (3.7 g, 63%) as a red solid. MS (ESI): mass calcd. for C$_{14}$H$_{11}$IN$_4$, 362.0; m/z. found, 363.0 [M+H]$^+$. $^1$H NMR (300 MHz, DMSO-d$_6$) δ 9.03 (s, 1H), 8.70 (d, J=8.1 Hz, 1H), 7.99 (d, J=5.7 Hz, 1H), 7.90 (d, J=7.8 Hz, 1H), 7.44 (s, 2H), 7.35 (t, J=7.8 Hz, 1H), 7.07 (d, J=5.7 Hz, 1H), 2.87 (s, 3H).

Intermediate 35: 2-(3-Bromophenyl)-4-(trifluoromethyl)pyrido[3,4-d]pyrimidin-8-amine

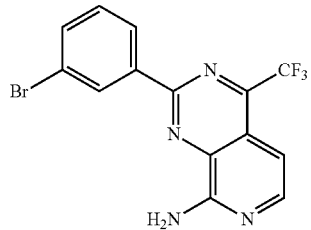 [SMILES: Nc1nccc2c(C(F)(F)F)nc(-c3cccc(Br)c3)nc12]

Step A: tert-Butyl (2-chloropyridin-3-yl)carbamate. Into a 2 L 3-neck round-bottomed flask, purged and maintained with an inert atmosphere of nitrogen, was placed a solution of 2-chloropyridin-3-amine (50 g, 389 mmol) in THF (500 mL). The resulting solution was cooled −10° C. followed by the addition of sodium bis(trimethylsilyl)amide (430 mL, 856 mmol) for 30 min. After which time (Boc)$_2$O (94 g, 429 mmol) in THF (200 mL) was added dropwise and the resulting solution was stirred at −10° C. After 2 h, the pH of the resulting solution was adjusted to 7 with hydrogen chloride (2 N) and extracted with ethyl acetate (1000 mL×2). The combined organic layers were washed with brine (1000 mL), dried over anhydrous sodium sulfate, filtered, and concentrated to dryness. The resulting residue was purified by FCC (1:10, ethyl acetate/petroleum ether) to afford tert-butyl N-(2-chloropyridin-3-yl)carbamate (70 g, 79%) as a white solid.

Step B: tert-Butyl N-[2-chloro-4-(2,2,2-trifluoro-1,1-dihydroxyethyl)pyridin-3-yl]carbamate. To a 500 mL 3-necked round-bottomed flask, purged and maintained with an inert atmosphere of nitrogen, was added tert-butyl N-(2-chloropyridin-3-yl)carbamate (20 g, 87 mmol), TMEDA (22 g, 192 mmol), and THF (200 mL). This was followed by the addition of n-BuLi (76.8 mL, 1.5 M) dropwise with stirring at −78° C. The mixture was stirred for 30 min at −78° C. and then stirred for 30 min at −40° C. To the resulting mixture was added 2,2,2-trifluoro-N-methoxy-N-methylacetamide (34 g, 218 mmol) dropwise with stirring at −78° C. The resulting mixture was stirred for 30 min at −40° C. and then partitioned with saturated aqueous ammonium chloride (100 mL). The resulting mixture was extracted with ethyl acetate (200 mL×2). The combined organic layers were washed with brine (100 mL), dried over anhydrous sodium sulfate, filtered, and concentrated to dryness. The residue was purified by FCC (1:10, ethyl acetate/petroleum ether) to afford tert-butyl N-[2-chloro-4-(2,2,2-trifluoro-1,1-dihydroxyethyl)pyridin-3-yl]carbamate (26 g, 87%) as a white solid.

Step C: 1-(3-Amino-2-chloropyridin-4-yl)-2,2,2-trifluoroethane-1,1-diol as a trifluoroacetic acid salt. Into a 1 L 3-necked round-bottomed flask, purged and maintained with an inert atmosphere of nitrogen, was placed tert-butyl N-[2-chloro-4-(2,2,2-trifluoro-1,1-dihydroxyethyl)pyridin-3-yl]carbamate (26 g, 76 mmol), trifluoroacetic acid (130 mL), and DCM (260 mL) at rt. After 4 h, the resulting mixture was concentrated to dryness to afford 1-(3-amino-2-chloropyridin-4-yl)-2,2,2-trifluoroethane-1,1-diol, trifluoroacetic acid salt (28 g, crude) as a yellow solid.

Step D: 2-(3-Bromophenyl)-8-chloro-4-(trifluoromethyl)-1H,2H-pyrido[3,4-d]pyrimidine. Into a 500 mL pressure tank reactor was placed 1-(3-amino-2-chloropyridin-4-yl)-2,2,2-trifluoroethane-1,1-diol as a trifluoroacetic acid salt (10 g, 28 mmol), 3-bromobenzaldehyde (38 g, 206 mmol), a 30% aqueous ammonia (12 g), and ACN (200 mL). The resulting solution was stirred for 16 h at 52° C. followed by increasing the temperature to 90° C. for an additional 16 h. The resulting mixture was concentrated to dryness and purified by FCC (1:5, ethyl acetate/petroleum ether) to afford 2-(3-bromophenyl)-8-chloro-4-(trifluoromethyl)-1H, 2H-pyrido[3,4-d]pyrimidine (13 g, crude) as a yellow solid.

Step E: 2-(3-Bromophenyl)-8-chloro-4-(trifluoromethyl) pyrido[3,4-d]pyrimidine. Into a 250-mL 3-necked round-bottom flask, purged and maintained with an inert atmosphere of nitrogen, was placed 2-(3-bromophenyl)-8-chloro-4-(trifluoromethyl)-1H,2H-pyrido[3,4-d]pyrimidine (12 g, 31 mmol), CH$_3$CN (120 mL), and 2,3-dichloro-5,6-dicyanobenzoquinone (6.96 g). The resulting solution was stirred for 2 h at 25° C. The pH of the solution was adjusted to 8 with saturated aqueous sodium bicarbonate. The resulting mixture was extracted with DCM (100 mL×3). The combined organic layers were washed with brine (100 mL), dried over anhydrous sodium sulfate, filtered, and concentrated to dryness. The residue was purified by FCC (1:10, ethyl acetate/petroleum ether) to afford 2-(3-bromophenyl)-8-chloro-4-(trifluoromethyl)pyrido[3,4-d]pyrimidine (5.5 g, 46%) as a yellow solid.

Step F: 2-(3-Bromophenyl)-4-(trifluoromethyl)pyrido[3, 4-d]pyrimidin-8-amine. Into a 250 mL pressure tank reactor, was placed 2-(3-bromophenyl)-8-chloro-4-(trifluoromethyl) pyrido[3,4-d]pyrimidine (4.5 g, 12 mmol) and NH$_3$ in IPA (90 mL, 2M). The resulting solution was stirred for 16 h at 145° C. The reaction mixture was cooled, the solids were collected by filtration. To the solid was added MeOH (30 mL) and the mixture was stirred for 1 h. The solids were collected by filtration to afford 2-(3-bromophenyl)-4-(trifluoromethyl)pyrido[3,4-d]pyrimidin-8-amine (3.9 g, 91%) as a yellow solid. MS (ESI): mass calcd. for C$_{14}$H$_8$BrF$_3$N$_4$, 367.9; m/z. found, 369.0 [M+H]$^+$. $^1$H NMR (300 MHz, DMSO-d$_6$) δ 8.92 (s, 1H), 8.66 (d, J=8.1 Hz, 1H), 8.12 (d, J=6.0 Hz, 1H), 7.91 (br s, 2H), 7.79 (d, J=7.2 Hz, 1H), 7.56 (t, J=7.8 Hz, 1H), 7.00-6.97 (m, 1H). $^{19}$F NMR (282 MHz, DMSO-d$_6$, ppm): δ −65.26.

Intermediate 36: 2-(3-Bromophenyl)-5-methylpyrido[3,4-d]pyrimidin-8-amine

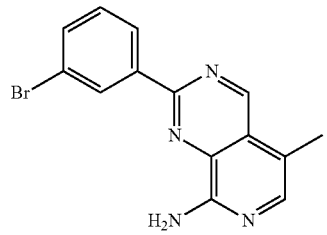 [SMILES: Cc1cnc(N)c2nc(-c3cccc(Br)c3)ncc12]

Step A: tert-Butyl N-(2-chloro-5-methylpyridin-3-yl)carbamate. Into a 1 L 3-necked round-bottomed flask, purged and maintained with an inert atmosphere of nitrogen, was placed a solution of 2-chloro-5-methylpyridin-3-amine (19 g, 133 mmol) in THF (190 mL). The resulting solution was cooled −10° C. followed by the addition of sodium bis (trimethylsilyl)amide (147 mL, 2M) for 30 min. After which time (Boc)$_2$O (32 g, 147 mmol) in THF (320 mL) was added dropwise and the resulting solution was stirred at −10° C. After 2 h, the pH of the resulting solution was adjusted to 7 with hydrogen chloride (2 N) and extracted with ethyl acetate (500 mL×2). The combined organic layers were washed with brine (500 mL), dried over anhydrous sodium sulfate, filtered, and concentrated to dryness. The resulting residue was purified by FCC (1:11, ethyl acetate/petroleum ether) to afford tert-butyl N-(2-chloro-5-methylpyridin-3-yl) carbamate (32 g, 99%) as a light yellow solid.

Step B: tert-Butyl N-(2-chloro-4-formyl-5-methylpyridin-3-yl)carbamate. Into a 500 mL 3-necked round-bottomed flask, purged and maintained with an inert atmosphere of nitrogen, was placed a solution of tert-butyl N-(2-chloro-5-methylpyridin-3-yl)carbamate (20 g, 82 mmol) in THF (200 mL) and TMEDA (21 g, 181 mmol). The vessel was cooled to −78° C. and n-BuLi (72 mL, 2.5 M) was added dropwise. The resulting solution was stirred for 30 min at −35° C. The resulting solution was cooled to −78° C. and N,N-dimethylformamide (15 g, 205 mmol) was added dropwise with stirring. After 30 min, saturated aqueous ammonium chloride (200 mL) was added and the resulting mixture was extracted with ethyl acetate (500 mL×2). The combined organic layers were washed with brine (500 mL), dried over anhydrous sodium sulfate, filtered, and concentrated to dryness. The residue was purified by FCC (1:5, ethyl acetate/petroleum ether) to afford tert-butyl N-(2-chloro-4-formyl-5-methylpyridin-3-yl)carbamate (11.9 g, 53%) as a yellow solid.

Step C: 3-Amino-2-chloro-5-methylpyridine-4-carbaldehyde. Into a 500 mL 3-necked round-bottomed flask, purged and maintained with an inter atmosphere of nitrogen, was placed a solution of tert-butyl N-(2-chloro-4-formyl-5-methylpyridin-3-yl)carbamate (12 g, 44 mmol) in DCM (120 mL), and trifluoroacetic acid (60 mL) at rt. After 12 h, the resulting mixture was concentrated to dryness and the residue was diluted with saturated aqueous sodium bicarbonate until the pH=7. The resulting mixture was extracted with ethyl acetate (500 mL×2). The combined organic layers were washed with brine (500 mL), dried over anhydrous sodium sulfate, filtered, and concentrated to dryness to afford 3-amino-2-chloro-5-methylpyridine-4-carbaldehyde (7 g, 93%) as a yellow solid.

Step D: 2-(3-Bromophenyl)-8-chloro-5-methylpyrido[3,4-d]pyrimidine. Into a 50-mL sealed tube, was placed 3-amino-2-chloro-5-methylpyridine-4-carbaldehyde (1.0 g, 5.8 mmol), 3-bromobenzene-1-carboximidamide hydrochloride (1.7 g, 7.1 mmol), tert-butanol (20 mL), TEA (0.6 g), and pyridine (1.2 g). The resulting solution was stirred for 14 h at 90° C. The procedure was repeated 5 times and the combined reaction mixtures were cooled to rt and diluted with water (500 mL). The resulting mixture was extracted with ethyl acetate (500 mL×3). The combined organic layers were washed with hydrogen chloride (500 mL, 1 N) and brine (500 mL), dried over anhydrous sodium sulfate, filtered and concentrated to dryness. The residue was purified by FCC (3:10, ethyl acetate/petroleum ether to afford 2-(3-bromophenyl)-8-chloro-5-methylpyrido[3,4-d]pyrimidine (4.2 g, 35%) as a yellow solid.

Step E: 2-(3-Bromophenyl)-5-methylpyrido[3,4-d]pyrimidin-8-amine. Into a 250 mL pressure tank reactor, was placed 2-(3-bromophenyl)-8-chloro-5-methylpyrido[3,4-d]pyrimidine (4.2 g, 13 mmol) and $NH_3$ in IPA (84 mL, 2M). The resulting solution was stirred for 16 h at 145° C. in an oil bath. The reaction mixture was cooled, concentrated to dryness, and the solids were collected by filtration. The solids were added to a 250 mL pressure tank reactor and $NH_3$ in MeOH (84 mL, 7N) and resulting mixture was stirred for 16 h at 145° C. in an oil bath. The reaction mixture was cooled, the solids were collected by filtration. The solids were added to $Et_2O$ (30 mL), the mixture was allowed to stir for 1 h, and the solids were collected by filtration to afford 2-(3-bromophenyl)-5-methylpyrido[3,4-d]pyrimidin-8-amine (2.5 g, 63%) as a yellow solid. MS (ESI): mass calcd. for $C_{14}H_{11}BrN_4$, 314.0; m/z. found, 315.0 $[M+H]^+$. $^1H$ NMR (300 MHz, DMSO-$d_6$) δ 9.62 (s, 1H), 8.90 (s, 1H), 8.68 (d, J=7.8 Hz, 1H), 7.83 (s, 1H), 7.75 (d, J=8.7 Hz, 1H), 7.53 (t, J=7.8 Hz, 1H), 7.29 (s, 2H), 2.46 (s, 3H).

Intermediate 37: 2-(3-Iodophenyl)-6-methylpyrido [3,4-d]pyrimidin-8-amine

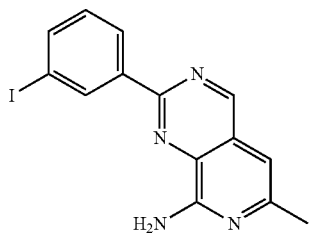 [SMILES: Cc1cc2cnc(-c3cccc(I)c3)nc2c(N)n1]

Step A: tert-Butyl N-(2-chloropyridin-3-yl)carbamate. Into a 2 L 3-necked round-bottomed flask, purged and maintained with an inert atmosphere of nitrogen, was placed a solution of 2-chloropyridin-3-amine (50 g, 389 mmol) in THF (500 mL). The resulting solution was cooled −10° C. followed by the addition of sodium bis(trimethylsilyl)amide (430 mL, 2M) for 30 min. After which time $(Boc)_2O$ (94 g, 428 mmol) in THF (200 mL) was added dropwise and the resulting solution was stirred at −10° C. After 2 h, the pH of the resulting solution was adjusted to 7 with hydrogen chloride (2 N) and extracted with ethyl acetate (1000 mL×2). The combined organic layers were washed with brine (1000 mL), dried over anhydrous sodium sulfate, filtered, and concentrated to dryness. The resulting residue was purified by FCC (1:11, ethyl acetate/petroleum ether) to afford tert-butyl N-(2-chloropyridin-3-yl)carbamate (80 g, 90%) as a white solid.

Step B: tert-Butyl N-(2-chloro-4-formylpyridin-3-yl)carbamate. Into a 500 mL 3-necked round-bottomed flask, purged and maintained with an inert atmosphere of nitrogen, was placed a solution of tert-butyl N-(2-chloropyridin-3-yl)carbamate (20 g, 87 mmol) in THF (200 mL), and TMEDA (22.3 g, 191 mmol). The vessel was cooled to −78° C. and n-BuLi (78 mL, 2.5 M) was added dropwise. The resulting solution was stirred for 30 min at −35° C. The resulting solution was cooled to −78° C. and N,N-dimethylformamide (16 g, 218 mmol) was added dropwise with stirring. After 30 min, saturated aqueous ammonium chloride (500 mL) was added and the resulting mixture was extracted with ethyl acetate (500 mL×2). The combined organic layers were washed with brine (500 mL), dried over anhydrous sodium sulfate, filtered, and concentrated to dryness. The residue was purified by FCC (1:5, ethyl acetate/petroleum ether) to afford tert-butyl N-(2-chloro-4-formylpyridin-3-yl)carbamate (28 g, 82%) as a white solid.

Step C: 3-Amino-2-chloropyridine-4-carbaldehyde. Into a 1000-mL 3-necked round-bottom flask, was placed a solution of tert-butyl N-(2-chloro-4-formylpyridin-3-yl)carbamate (55 g, 214 mmol) in DCM (550 mL), and trifluoroacetic acid (270 mL). After 12 h, the resulting mixture was concentrated to dryness and the residue was diluted with saturated aqueous sodium bicarbonate until the pH=7. The resulting mixture was extracted with ethyl acetate (500 mL×2). The combined organic layers were washed with brine (500 mL), dried over anhydrous sodium sulfate, filtered, and concentrated to dryness. The residue was purified by FCC (1:3, ethyl acetate/petroleum ether) to afford 3-amino-2-chloropyridine-4-carbaldehyde (19 g, 57%) as a yellow solid.

Step D: 3-Amino-6-bromo-2-chloropyridine-4-carbaldehyde. Into a 500 mL 3-necked round-bottomed flask, purged and maintained with an inert atmosphere of nitrogen, was placed a solution of 3-amino-2-chloropyridine-4-carbaldehyde (19 g, 121 mmol) in N,N-dimethylformamide (190 mL), and boranylidene(sulfanyl)amine (24 g, 404 mmol) at rt. After 1 h, the resulting mixture was partitioned with ice water (1000 mL) and the solids were collected by filtration to afford 3-amino-6-bromo-2-chloropyridine-4-carbaldehyde (25 g, 87%) as a yellow solid.

Step E: 3-Amino-2-chloro-6-methylpyridine-4-carbaldehyde. Into a 500 mL 3-necked round-bottomed flask, purged and maintained with an inert atmosphere of nitrogen, was placed a solution of 3-amino-6-bromo-2-chloropyridine-4-carbaldehyde (25 g, 106 mmol) in 1,4-dioxane (250 mL), water (50 mL), methylboronic acid (19 g, 319 mmol), potassium carbonate (71 g, 509 mmol), and $Pd(dppf)Cl_2$ (3.9 g, 5.3 mmol). The resulting solution was stirred at 90° C. After 12 h, the reaction mixture was cooled to rt and water (300 mL) was added. The resulting mixture was extracted with ethyl acetate (300 mL×2). The combined organic layers were washed with brine (200 mL), dried over anhydrous sodium sulfate, filtered, and concentrated to dryness. The residue was purified by FCC (1:5, ethyl acetate/petroleum ether) to afford 2-chloro-6-methylpyridine-4-carbaldehyde (6.6 g, 36%) as a yellow solid.

Step F: 8-Chloro-2-(3-iodophenyl)-6-methylpyrido[3,4-d]pyrimidine. A 40 mL sealed tube was charged with a solution of 3-amino-2-chloro-6-methylpyridine-4-carbaldehyde (1.3 g, 7.6 mmol) in tert-butanol (26 mL), 3-iodobenzene-1-carboximidamide (2.3 g, 9.2 mmol), TEA (0.8 g, 7.6 mmol), and pyridine (1.5 g, 19 mmol). The resulting solution was stirred at 90° C. After 12 h, the resulting mixture was cooled to rt and water (40 mL) was added. The resulting mixture was extracted with ethyl acetate (60 mL×3). The combined organic layers were washed with hydrogen chloride (50 mL, 2 N) and brine (50 mL). The resulting organic layer was dried over anhydrous sodium sulfate, filtered, and concentrated to dryness. The residue was purified by FCC (1:10, ethyl acetate/petroleum ether) to afford 8-chloro-2-(3-iodophenyl)-6-methylpyrido[3,4-d]pyrimidine (1.2 g, 33%) of as a yellow solid.

Step G: 2-(3-Iodophenyl)-6-methylpyrido[3,4-d]pyrimidin-8-amine. Into a 300 mL vial, purged and maintained with an inert atmosphere of nitrogen, was placed 8-chloro-2-(3-iodophenyl)-6-methylpyrido[3,4-d]pyrimidine (4.8 g, 13 mmol), $NH_3$ in IPA (90 mL, 2M), and $NH_4OH$ (45 mL, 28% $NH_3$ in water). The resulting solution was stirred at 145° C. After 12 h, the mixture was cooled, the solids were collected by filtration, and the solid (3.5 g) was further purified by preparative HPLC to afford 2-(3-iodophenyl)-6-methylpyrido[3,4-d]pyrimidin-8-amine (2 g, 45%) as a yellow solid. MS (ESI): mass calcd. for $C_{14}H_{11}IN_4$, 362.2; m/z. found, 363.0 [M+H]$^+$. $^1$H NMR (300 MHz, DMSO-$d_6$) δ 9.42 (s, 1H), 9.03 (s, 1H), 8.67 (d, J=8.1 Hz, 1H), 7.89 (d, J=7.8 Hz, 1H), 7.55 (br s, 2H), 7.35 (t, J=5.7 Hz, 1H), 6.86 (s, 1H), 2.42 (s, 3H).

Intermediate 38: (R)-7-Ethynyl-6,7-dihydro-5H-cyclopenta[b]pyridin-7-ol

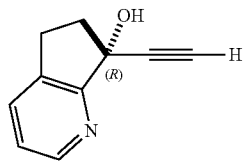

Step A: 6,7-Dihydro-5H-cyclopenta[b]pyridine 1-oxide. To a stirred solution of (1Z)—N-(cyclopent-1-en-1-yl)ethan-1-imine (250 g, 2.29 mol) in DCM (5000 mL) were added meta-chloroperoxybenzoic acid (454 g, 2.10 mol, 80% purity) in portions at 0° C. under nitrogen atmosphere. The resulting mixture was stirred for 2 h at rt under nitrogen atmosphere. The resulting mixture was concentrated to dryness and the resulting residue purified by FCC (20:1, $CH_2Cl_2$/MeOH) to afford 6,7-dihydro-5H-cyclopenta[b]pyridine 1-oxide (220 g, 71.08%) as a white solid. MS (ESI): mass calcd. for $C_8H_9NO$, 135.0; m/z. found, 136.2 [M+H]$^+$.

Step B: 6,7-Dihydro-5H-cyclopenta[b]pyridin-7-yl acetate. A solution of 6,7-dihydro-5H-cyclopenta[b]pyridine 1-oxide (220 g, 1.63 mol) in $Ac_2O$ (2 L) was stirred for 2 h at 100° C. under nitrogen atmosphere. The resulting mixture was concentrated to dryness and purified by FCC (3:1, petroleum ether/ethyl acetate to afford 6,7-dihydro-5H-cyclopenta[b]pyridin-7-yl acetate (215 g, 74.5%) as an orange oil.

Step C: 6,7-Dihydro-5H-cyclopenta[b]pyridin-7-ol. To a stirred solution of 6,7-dihydro-5H-cyclopenta[b]pyridin-7-yl acetate (215 g, 1.21 mol) in EtOH (500 mL) was added the solution of KOH (68.1 g, 1.21 mol) in EtOH (1.2 L) dropwise at 0° C. under a nitrogen atmosphere. The resulting mixture was stirred for 1 h at rt under nitrogen atmosphere. The resulting mixture was concentrated to one-third the volume and extracted with DCM (1 L× 3). The combined organic layers were washed with brine (1 L), dried over anhydrous $Na_2SO_4$, filtered, and concentrated to dryness. The resulting residue was purified by FCC (20:1, $CH_2Cl_2$/MeOH) to afford 5H,6H,7H-cyclopenta[b]pyridin-7-ol (140 g, 85.3%) as a light brown solid.

Step D: 5,6-Dihydro-7H-cyclopenta[b]pyridin-7-one. To a stirred solution of 6,7-dihydro-5H-cyclopenta[b]pyridin-7-ol (140 g, 1.04 mol) in DCM (1.5 L) was added dioxomanganese (632 g, 7.27 mol) in portions at 0° C. under nitrogen atmosphere. The resulting mixture was stirred at rt under nitrogen atmosphere. After 12 h, the solid was collected by filtration and washed with DCM (500 mL×3). The filtrate was concentrated to dryness and the resulting residue was purified by FCC (5:1, petroleum ether/ethyl to afford 5,6-dihydro-7H-cyclopenta[b]pyridin-7-one (80 g, 58%) as a dark green solid. MS (ESI): mass calcd. for $C_8H_7NO$, 133.0; m/z. found, 134.2 [M+H]$^+$.

Step E: (R)-7-Ethynyl-6,7-dihydro-5H-cyclopenta[b]pyridin-7-ol. To a stirred solution of bromo(ethynyl)magnesium (1.4 L, 0.7 mol) was added a solution of 5,6-dihydro-7H-cyclopenta[b]pyridin-7-one (80 g, 0.7 mol) in THF (800 mL) dropwise at 0° C. under a nitrogen atmosphere. The resulting mixture was stirred for 2 h at rt under nitrogen atmosphere. After which time the resulting mixture was cooled to 0° C. and saturated aqueous ammonium chloride (1 L) was added. The resulting mixture was extracted with ethyl acetate (1 L×3). The combined organic layers were washed with brine (1 L), dried over anhydrous $Na_2SO_4$, filtered, and concentrated to dryness. The resulting residue was purified by FCC (20:1, $CH_2Cl_2$/MeOH) to afford racemic 7-ethynyl-6,7-dihydro-5H-cyclopenta[b]pyridin-7-ol (56 g, 62%) as an off-white solid. The (R) and (S) enantiomers of racemic 7-ethynyl-6,7-dihydro-5H-cyclopenta[b]pyridin-7-ol (28 g) were separated by chiral preparative SFC (Chiral-IC 4.6×100 mm, 5 μm; co-solvent: MeOH (0.1% DEA); Gradient (B %): 10% to 50% in 4.0 min, hold 2.0 min at 50%; Flow rate: 4 ml/min; Temperature: 35° C.; Detector, UV 220 nm) to afford (R)-7-ethynyl-6,7-dihydro-5H-cyclopenta[b]pyridin-7-ol (13.1 g, 47%, 97% ee) as an off-white solid and (S)-7-Ethynyl-6,7-dihydro-5H-cyclopenta[b]pyridin-7-ol (Intermediate 39, 13.1 g, 47%, 97% ee) as an off-white solid. Data for (R)-7-ethynyl-6,7-dihydro-5H-cyclopenta[b]pyridin-7-ol: MS (ESI): mass calcd. for $C_{10}H_9NO$, 159.0; m/z. found, 160.0 [M+H]$^+$. $^1$H NMR (400 MHz, CDCl$_3$) δ 8.61-8.41 (m, 1H), 7.68-7.52 (m, 1H), 7.24-7.15 (m, 1H), 4.36 (s, 1H), 3.14-2.91 (m, 2H), 2.78-2.68 (m, 1H), 2.66 (s, 1H), 2.58-2.36 (m, 1H). $[\alpha]^{20}_D$=−81.9 (c=0.34 in MeOH).

Intermediate 39: (S)-7-Ethynyl-6,7-dihydro-5H-cyclopenta[b]pyridin-7-ol

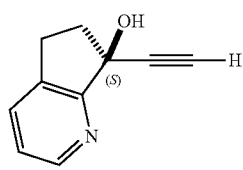

The chiral separation described in Intermediate 38 provided (S)-7-Ethynyl-6,7-dihydro-5H-cyclopenta[b]pyridin-7-ol (13.1 g, 47%, 97% ee) as an off-white solid. MS (ESI): mass calcd. for $C_{10}H_9NO$, 159.0; m/z. found, 160.0 [M+H]$^+$. $^1$H NMR (400 MHz, CDCl$_3$) δ 8.61-8.41 (m, 1H), 7.68-7.52 (m, 1H), 7.24-7.15 (m, 1H), 4.36 (s, 1H), 3.14-2.91 (m, 2H), 2.78-2.68 (m, 1H), 2.66 (s, 1H), 2.58-2.36 (m, 1H). [α]²⁰_D=+81.1 (c=0.33 in MeOH).

Intermediate 40: 2-(3-Iodophenyl)pyrido[3,4-d]pyrimidin-8(7H)-one

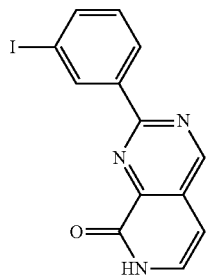 [SMILES: O=c1[nH]ccc2cnc(-c3cccc(I)c3)nc12]

Step A: 2-(3-Iodophenyl)-8-methoxypyrido[3,4-d]pyrimidine. To a solution of (3-iodophenyl)methanamine (7.7 g, 33 mmol), 4-hydroxy-TEMPO (450 mg, 2.61 mmol), and o-xylene (30 mL) at rt was added 3-amino-2-methoxyisonicotinaldehyde (2.0 g, 13 mmol). The resulting mixture was stirred at 120° C. for 16 h under O2 (15 psi) and then cooled to rt. The suspension was filtered, and the filter cake was washed with ethyl acetate (20 mL×3) and then dried under reduced pressure to provide the title compound (1 g, 22%). The resulting title compound was recrystallized from ethyl acetate (5 mL) to provide 2-(3-iodophenyl)-8-methoxypyrido[3,4-d]pyrimidine (770 mg, 17%) as a yellow solid. MS (ESI): mass calcd. for $C_{14}H_{10}IN_3O$, 363.0; m/z. found, 363.9 [M+H]⁺.

Step B: 2-(3-Iodophenyl)pyrido[3,4-d]pyrimidin-8(7H)-one. Into a 100 mL round-bottomed flask was placed pyridine hydrochloride (13.0 g, 112 mmol) and 2-(3-iodophenyl)-8-methoxypyrido[3,4-d]pyrimidine (1.77 g, 4.87 mmol). The resulting mixture was stirred under N₂ at 170° C. for 3 h and then cooled to rt. The mixture was purified by FCC (20:1 to 0:1 gradient, petroleum ether/ethyl acetate) to provide 2-(3-iodophenyl)pyrido[3,4-d]pyrimidin-8(7H)-one (1.2 g, 70%) as a yellow solid. MS (ESI): mass calcd. for $C_{13}H_8IN_3O$, 349.0; m/z. found, 349.9 [M+H]⁺.

Intermediate 41: 2-Methylsulfanylpyrido[3,4-d]pyrimidin-8-amine

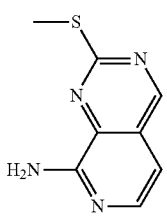

Step A: Methyl 5-[(E)-2-ethoxyethenyl]-2-(methylsulfanyl)pyrimidine-4-carboxylate. Into a 3 L 4-necked round-bottomed flask, purged and maintained with an inert atmosphere of nitrogen, was placed methyl 5-bromo-2-(methylsulfanyl)pyrimidine-4-carboxylate (130 g, 494 mmol), 1,4-dioxane (1.5 L), 2-[(E)-2-ethoxyethenyl]-4,4,5,5-tetramethyl-1,3,2-dioxaborolane (198 g, 999 mmol), Pd(dppf)Cl₂ (10.9 g, 14.9 mmol), water (300 mL), and K₃PO₄ (233 g, 1.10 mol). The resulting solution was stirred at 80° C. After 16 h, the resulting mixture was poured into water (1.7 L) and extracted with ethyl acetate (2 L×3). The combined organic layers were concentrated and the residue was purified by FCC (5:95, ethyl acetate/petroleum ether) to afford methyl 5-[(E)-2-ethoxyethenyl]-2-(methylsulfanyl)pyrimidine-4-carboxylate (87, 69%) as a yellow solid. MS (ESI): mass calcd. for $C_{11}H_{14}N_2O_3S$, 254.3; m/z. found, 255.0 [M+H]⁺.

Step B: 5-[(E)-2-Ethoxyethenyl]-2-(methylsulfanyl)pyrimidine-4-carboxamide. Into a 1 L sealed tube, was placed methyl 5-[(E)-2-ethoxyethenyl]-2-(methylsulfanyl)pyrimidine-4-carboxylate (50 g, 197 mmol) and NH₃ in MeOH (500 mL, 7N). The resulting solution was stirred at 55° C. After 2 h, the resulting mixture was concentrated to dryness to afford 5-[(E)-2-ethoxyethenyl]-2-(methylsulfanyl)pyrimidine-4-carboxamide (47 g, solid) which was used in the next step without further purification. MS (ESI): mass calcd. for $C_{10}H_{13}N_3O_2S$, 239.3; m/z. found, 240.0 [M+H]⁺.

Step C: 2-(Methylsulfanyl)-7H,8H-pyrido[3,4-d]pyrimidin-8-one. Into a 2 L round-bottomed flask, was placed 5-[(E)-2-ethoxyethenyl]-2-(methylsulfanyl)pyrimidine-4-carboxamide (46 g, 192), toluene (920 mL), and p-toluenesulfonic acid monohydrate (3.3 g, 19 mmol). The resulting solution was stirred at 90° C. After 2 h, the resulting mixture was cooled to 0° C. with an ice/salt bath. The resulting solution was diluted with 2 L of petroleum ether, the resulting solids were collected by filtration, and washed with petroleum ether (100 mL×3). The resulting organic filtrate was concentrated to dryness to afford 2-(methylsulfanyl)-7H,8H-pyrido[3,4-d]pyrimidin-8-one (31.4, 85%) as a yellow solid. MS (ESI): mass calcd. for $C_8H_7N_3OS$, 193.2; m/z. found, 194.0 [M+H]⁺.

Step D: 8-Chloro-2-(methylsulfanyl)pyrido[3,4-d]pyrimidine. Into a 1 L round-bottomed flask, was placed 2-(methylsulfanyl)-7H,8H-pyrido[3,4-d]pyrimidin-8-one (31.4 g, 163 mmol), ACN (500 mL), and POCl₃ (73.7 g, 481 mmol). The resulting solution was heated at 70° C. After 2 h, the resulting mixture was concentrated to dryness. To the resulting residue was added water (1 L) portion wise. The pH of the solution was adjusted to 8 with saturated aqueous sodium carbonate. The solids were collected by filtration and the filtrate was concentrated to dryness to afford 8-chloro-2-(methylsulfanyl)pyrido[3,4-d]pyrimidine (32.1 g, 93%) as a brown solid. MS (ESI): mass calcd. for $C_8H_6ClN_3S$, 211.0; m/z. found, 212.0 [M+H]⁺.

Step E: 2-(Methylsulfanyl)pyrido[3,4-d]pyrimidin-8-amine. Into a 1 L sealed tube, was placed 8-chloro-2-(methylsulfanyl)pyrido[3,4-d]pyrimidine (32.1 g, 152 mmol) and NH₃ in IPA (320 mL, 2M). The resulting solution was heated at 145° C. After 16 h, the resulting mixture was concentrated to dryness and purified by FCC (3:1, DCM/ethyl acetate) to afford 2-(methylsulfanyl)pyrido[3,4-d]pyrimidin-8-amine (11.3 g, 39%) as a yellow solid. MS (ESI): mass calcd. for $C_8H_8N_4S$, 192.1; m/z. found, 193.0 [M+H]⁺. ¹H NMR (300 MHz, DMSO-d₆) δ 9.3-9.2 (m, 1H), 7.97-7.87 (m, 1H), 7.06 (s, 2H), 7.0-6.9 (m, 1H), 2.7-2.6 (m, 3H).

Intermediate 42: 2-(5-Bromo-2-isobutylphenyl)pyrido[3,4-d]pyrimidin-8-amine

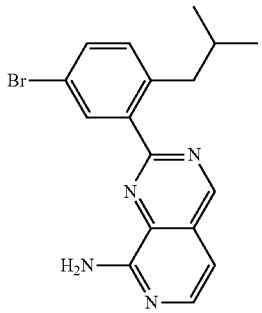 [SMILES: CC(C)Cc1ccc(Br)cc1-c1ncc2ccnc(N)c2n1]

Step A: 5-Bromo-2-isobutylbenzonitrile. In a round-bottomed flask were added 5-bromo-2-iodobenzonitrile (1.9 g, 6.2 mmol), tri(furan-2-yl)phosphane (0.14 g, 0.61 mmol), and bis(dibenzylideneacetone)palladium(0). The vessel was sealed with a septum, and the atmosphere was evacuated and then purged with $N_2$ (3×). The vessel was charged with dry THF (20 mL) and allowed to stir at rt until the initial homogeneous red solution turned homogeneous yellow (about 15 minutes). The resulting mixture was then treated with isobutyl zinc bromide (13 mL, 6.5 mmol, 0.5 M in THF) and stirred for 30 min at rt. The mixture was diluted with $CH_2Cl_2$ (20 mL), filtered through a pad of diatomaceous earth, and concentrated to dryness. The residue was purified by FCC to afford 2-(5-bromo-2-isobutylphenyl)pyrido[3,4-d]pyrimidin-8-amine (1.2 g, 79%). MS (ESI): mass calcd. for $C_{11}H_{12}BrN$, 237.02; m/z. found, 238.1 [M+H]$^+$. $^1$H NMR (400 MHz, CDCl$_3$) δ 7.74-7.72 (m, 1H), 7.64-7.60 (m, 1H), 7.16 (d, J=8.3 Hz, 1H), 2.67 (d, J=7.3 Hz, 2H), 2.03-1.89 (m, 1H), 0.95 (d, J=6.6 Hz, 6H).

Step B: (5-Bromo-2-isobutylphenyl)methanamine. In a 100 mL round-bottomed flask, a homogeneous solution of 5-bromo-2-isobutylbenzonitrile (1.4 g, 5.9 mmol) in dry THF (20 mL) was cooled to 0° C. under an atmosphere of $N_2$ and then slowly treated with $BH_3$-THF complex (13 mL, 13 mmol, 1 M in THF). Upon complete addition of $BH_3$-THF, the resulting solution was warmed to rt. A water-cooled reflux condenser was attached and the solution heated at 75° C. for 90 min. The resulting mixture was then cooled to rt and acidified to about pH 2 with HCl (about 3 mL, 1M). After 10 minutes, the pH of the mixture was adjusted to >pH 10 with 1 M NaOH. The mixture was then diluted with ethyl acetate (100 mL) and washed with brine (100 mL×2). The combined organic layer was dried ($MgSO_4$), filtered, and concentrated to near dryness. The residue was purified via FCC to yield (5-bromo-2-isobutylphenyl)methanamine (1.2 g, 73%) contaminated with about 12% n-BuOH (w/w) which was used without further purification. MS (ESI): mass calcd. for $C_{11}H_{16}BrN$, 241.05; m/z. found, 242.1 [M+H]$^+$. $^1$H NMR (400 MHz, CDCl$_3$) δ 7.52-7.49 (m, 1H), 7.31-7.27 (m, 1H), 6.99 (d, J=8.1 Hz, 1H), 3.85 (s, 2H), 2.46 (d, J=7.3 Hz, 2H), 1.86-1.74 (m, 1H), 0.91 (d, J=6.6 Hz, 6H).

Step C: 2-(5-Bromo-2-isobutylphenyl)-8-chloropyrido[3,4-d]pyrimidine. 2-(5-Bromo-2-isobutylphenyl)-8-chloropyrido[3,4-d]pyrimidine was prepared using conditions analogous to those described in Step A of Example 53, utilizing 3-amino-2-chloroisonicotinaldehyde and (5-bromo-2-isobutylphenyl)methanamine (462 mg, 29%). MS (ESI): mass calcd. for $C_{17}H_{15}BrClN_3$, 375.01; m/z. found, 376.1 [M+H]$^+$. $^1$H NMR (400 MHz, CDCl$_3$) δ 9.61 (s, 1H), 8.56 (d, J=5.4 Hz, 1H), 8.27 (d, J=2.2 Hz, 1H), 7.75 (d, J=5.4 Hz, 1H), 7.57-7.51 (m, 1H), 7.21 (d, J=8.2 Hz, 1H), 3.13 (d, J=7.2 Hz, 2H), 1.79-1.67 (m, 1H), 0.82 (d, J=6.6 Hz, 6H).

Step D: 2-(5-Bromo-2-isobutylphenyl)-N-(2,4-dimethoxybenzyl)pyrido[3,4-d]pyrimidin-8-amine. To a microwave vial was added a solution of 2-(5-bromo-2-isobutylphenyl)-8-chloropyrido[3,4-d]pyrimidine (0.45 g, 1.20 mmol) in dry THF (3 mL), DIPEA (0.6 mL, 3.4 mmol) and (2,4-dimethoxyphenyl)methanamine (0.5 mL, 3.3 mmol). The vial was then crimp-sealed and heated in a microwave reactor at 150° C. for 1 h. The resulting heterogeneous mixture was then diluted with ACN (10 mL), briefly sonicated, filtered, and concentrated to dryness. The residue was purified via FCC to afford 2-(5-bromo-2-isobutylphenyl)-N-(2,4-dimethoxybenzyl)pyrido[3,4-d]pyrimidin-8-amine (0.6 g, 90%). MS (ESI): mass calcd. for $C_{26}H_{27}BrN_4O_2$, 506.13; m/z. found, 507.3 [M+H]$^+$. $^1$H NMR (400 MHz, CDCl$_3$) δ 9.29 (s, 1H), 8.16 (d, J=5.8 Hz, 1H), 8.02 (d, J=2.2 Hz, 1H), 7.51-7.46 (m, 1H), 7.31 (d, J=8.2 Hz, 1H), 7.24 (t, J=5.9 Hz, 1H), 7.15 (d, J=8.2 Hz, 1H), 6.86 (d, J=5.8 Hz, 1H), 6.50 (d, J=2.3 Hz, 1H), 6.46-6.41 (m 1H), 4.77 (d, J=5.9 Hz, 2H), 3.88 (s, 3H), 3.80 (s, 3H), 2.90 (d, J=7.1 Hz, 2H), 1.66-1.54 (m, 1H), 0.73 (d, J=6.6 Hz, 6H).

Step E: 2-(5-Bromo-2-isobutylphenyl)pyrido[3,4-d]pyrimidin-8-amine. A homogeneous solution of 2-(5-bromo-2-isobutylphenyl)-N-(2,4-dimethoxybenzyl)pyrido[3,4-d]pyrimidin-8-amine (0.57 g, 1.09 mmol) in THF (5 mL) at room temperature was treated with TFA (7 mL) and then heated at 80° C. for 15 min. The resulting mixture was then cooled to rt and concentrated to dryness. The residue was dissolved in $CH_2Cl_2$ (10 mL), followed by DIPEA (1 mL). The mixture was then concentrated to dryness and purified via FCC to afford 2-(5-bromo-2-isobutylphenyl)pyrido[3,4-d]pyrimidin-8-amine (0.14 g, 37%). MS (ESI): mass calcd. for $C_{17}H_{17}BrN_4$, 356.06; m/z. found, 357.1 [M+H]$^+$. $^1$H NMR (400 MHz, CDCl$_3$) δ 9.37 (s, 1H), 8.12 (d, J=5.7 Hz, 1H), 8.04 (d, J=2.2 Hz, 1H), 7.54-7.49 (m, 1H), 7.18 (d, J=8.2 Hz, 1H), 7.03 (d, J=5.7 Hz, 1H), 6.02 (s, 2H), 2.92 (d, J=7.1 Hz, 2H), 1.70-1.59 (m, 1H), 0.78 (d, J=6.6 Hz, 6H).

Intermediate 43: 8-Amino-2-(3-iodophenyl)pyrido[3,4-d]pyrimidin-4(3H)-one

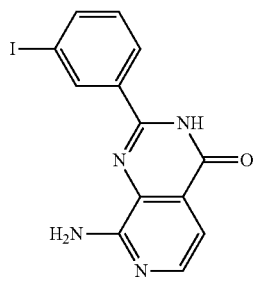 [SMILES: Nc1nccc2c(=O)[nH]c(-c3cccc(I)c3)nc12]

Step A: 3-Amino-2-chloroisonicotinic acid. A 500 mL round-bottomed flask was charged with 3-aminoisonicotinic acid (5.0 g, 36 mmol) and concentrated HCl (110 mL, 37%). The mixture was cooled to 0° C. and treated dropwise with 50% $H_2O_2$ (2.2 mL, 38 mmol). The resulting mixture was stirred for 1 h at 0° C., followed by 1 h at rt. The resulting solid was isolated by filtration, rinsed with cold ACN (25 mL) and dried under high-vacuum to afford 3-amino-2-chloroisonicotinic acid (2.8 g, 45%) which was used without further purification. MS (ESI): mass calcd. for $C_6H_5ClN_2O_2$, 172.0; m/z. found, 173.1 $[M+H]^+$. $^1H$ NMR (400 MHz, DMSO-$d_6$) δ 13.69 (br s, 1H), 7.68-7.56 (m, 2H), 6.85 (br s, 2H).

Step B: 8-Chloro-2-(3-iodophenyl)pyrido[3,4-d]pyrimidin-4(3H)-one. A sealable 100 mL round-bottomed flask was charged with a solution of 3-amino-2-chloroisonicotinic acid (2.8 g, 16 mmol) and DIPEA (8.5 mL, 18 mmol) in DMF (40 mL). The mixture was cooled to 0° C. and treated with a solution of 3-iodobenzoyl chloride (4.8 g, 18 mmol) in THF (2 mL). The resulting mixture was then warmed to rt and treated with additional 3-iodobenzoyl chloride (0.47 g). After 30 min, 1-[bis(dimethylamino)methylene]-1H-1,2,3-triazolo[4,5-b]pyridinium 3-oxide hexafluorophosphate (6.1 g, 16 mmol) was added in one portion, followed by heating at 60° C. After 1 h, resulting mixture was then cooled to rt and treated with NH$_4$OH (6 mL, 43 mmol, 28%). The vessel was then sealed and heated at 100° C. for 3 h. The resulting mixture was then cooled to rt and concentrated to dryness. The residue was triturated with HCl (100 mL, 1M), isolated via filtration, and dried under high-vacuum to yield 8-chloro-2-(3-iodophenyl)pyrido[3,4-d]pyrimidin-4(3H)-one (3.5 g, 56%) which was used without further purification. MS (ESI): mass calcd. for $C_{13}H_7ClIN_3O$, 382.93; m/z. found, 384.0 $[M+H]^+$. $^1H$ NMR (400 MHz, DMSO-$d_6$) δ 13.12 (s, 1H), 8.56 (s, 1H), 8.43 (d, J=5.1 Hz, 1H), 8.23 (d, J=7.9 Hz, 1H), 8.03-7.97 (m, 2H), 7.40 (t, J=7.9 Hz, 1H).

Step C: 8-((2,4-Dimethoxybenzyl)amino)-2-(3-iodophenyl)pyrido[3,4-d]pyrimidin-4(3H)-one. 8-((2,4-Dimethoxybenzyl)amino)-2-(3-iodophenyl)pyrido[3,4-d]pyrimidin-4(3H)-one was prepared using conditions analogous to those described in Step D of Intermediate 42, utilizing 8-chloro-2-(3-iodophenyl)pyrido[3,4-d]pyrimidin-4(3H)-one. MS (ESI): mass calcd. for $C_{22}H_{19}IN_4O_3$, 514.05; m/z. found, 515.1 $[M+H]^+$. $^1H$ NMR (400 MHz, DMSO-$d_6$) δ 12.79 (s, 1H), 8.69 (s, 1H), 8.34 (d, J=8.0 Hz, 1H), 7.95 (d, J=5.5 Hz, 2H), 7.73 (t, J=6.2 Hz, 1H), 7.35 (t, J=7.9 Hz, 1H), 7.06 (d, J=8.3 Hz, 1H), 6.98 (d, J=5.4 Hz, 1H), 6.58 (d, J=2.3 Hz, 1H), 6.46-6.39 (m, 1H), 4.62 (d, J=6.2 Hz, 2H), 3.87 (s, 3H), 3.72 (s, 3H).

Step D: 8-Amino-2-(3-iodophenyl)pyrido[3,4-d]pyrimidin-4(3H)-one. 8-Amino-2-(3-iodophenyl)pyrido[3,4-d]pyrimidin-4(3H)-one was prepared using conditions analogous to those described in Step E of Intermediate 42, utilizing 8-((2,4-dimethoxybenzyl)amino)-2-(3-iodophenyl)pyrido[3,4-d]pyrimidin-4(3H)-one. MS (ESI): mass calcd. for $C_{13}H_9IN_4O$, 363.98; m/z. found, 365.1 $[M+H]^+$. $^1H$ NMR (400 MHz, DMSO-$d_6$) δ 12.72 (s, 1H), 8.73 (s, 1H), 8.36 (d, J=7.9 Hz, 1H), 7.93 (d, J=5.9 Hz, 2H), 7.33 (t, J=7.9 Hz, 1H), 7.04-6.94 (m, 3H).

Intermediate 44: 4,8-Dichloro-2-(3-iodophenyl)pyrido[3,4-d]pyrimidine

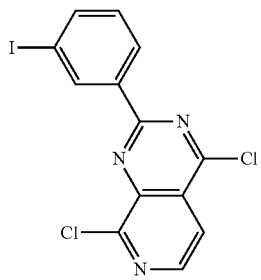 [SMILES: Clc1nc(-c2cccc(I)c2)nc2c(Cl)nccc12]

Step A: 2-(3-Iodophenyl)-8-methoxypyrido[3,4-d]pyrimidin-4(3H)-one. A 500 mL round-bottomed flask was charged with 3-amino-2-methoxyisonicotinic acid (20.0 g, 119 mmol), DIEA (73 mL, 416 mmol), and DMF (250 mL) followed by a solution of 3-iodobenzoyl chloride (34.8 g, 131 mmol, 1.10 eq) in THF (100 mL). The yellow mixture was stirred at 25° C. for 5 min. After 30 min, 1-[bis(dimethylamino)methylene]-1H-1,2,3-triazolo[4,5-b]pyridinium 3-oxide hexafluorophosphate (48 g, 125 mmol) was added. After 30 min, NH$_4$OH (98 mL, 714 mmol, 28.0% purity) was added and the thick mixture was stirred for 30 min. After which time, the yellow mixture was heated at 120° C. After 12 h, the resulting mixture was cooled and concentrated to dryness. The residue was suspended in HCl (1000 mL, 1 N), sonicated for 5 min, and the solid was collected by filtration. The resulting solid was triturated with THF (200 mL) to afford 2-(3-iodophenyl)-8-methoxypyrido[3,4-d]pyrimidin-4(3H)-one (30 g) as a yellow solid.

Step B: 4,8-Dichloro-2-(3-iodophenyl)pyrido[3,4-d]pyrimidine. A 1 L round-bottomed flask was charged with 2-(3-iodophenyl)-8-methoxypyrido[3,4-d]pyrimidin-4(3H)-one (38 g, 100 mmol) and POCl$_3$ (197 mL, 2.12 mmol). The yellow mixture was heated at 80° C. under N$_2$ atmosphere for 12 h. The resulting mixture was left standing at rt for 2 days and then the mixture was concentrated to dryness. The residue was purified by FCC (100% DCM) to afford 4,8-dichloro-2-(3-iodophenyl)pyrido[3,4-d]pyrimidine (26 g, 63%) as a yellow solid.

Intermediate 45: (R)-3-Ethynyl-3-hydroxy-1-(methyl-d$_3$)pyrrolidin-2-one

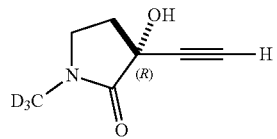

Step A: 4-((tert-Butoxycarbonyl)amino)-2-hydroxybutanoic acid. Into a 5 L 3-necked round-bottomed flask, purged and maintained with an inert atmosphere of nitrogen, was placed a solution of 4-amino-2-hydroxybutanoic acid (200 g, 1.67 mol) in water (1 L). This was followed by the addition of K$_2$CO$_3$ (695 g, 4.99 mol) in several batches at 0° C. To this mixture was added a solution of di-tert-butyl dicarbonate (436 g, 2 mol) in dioxane (1 L) dropwise with stirring at 0° C. The resulting solution was stirred for 24 h at 20-25° C. The resulting mixture was washed with petroleum ether (1 L×2). The combined water phase was cooled to 0° C. with a water/ice bath and adjusted to pH=4-5 with HCl (6N). The resulting solution was extracted with ethyl acetate (1 L×4). The combined organic layers combined were dried over anhydrous sodium sulfate, filtered, and concentrated to dryness to afford 4-((tert-butoxycarbonyl)amino)-2-hydroxybutanoic acid (260 g, 71%) as a yellow oil.

Step B: Methyl 4-((tert-butoxycarbonyl)amino)-2-hydroxybutanoate. Into a 5 L 3-necked round-bottomed flask, purged and maintained with an inert atmosphere of nitrogen, was placed a solution of 4-[[(tert-butoxy)carbonyl]amino]-2-hydroxybutanoic acid (260 g, 1.19 mol) in N,N-dimethylformamide (2.5 L) and Cs$_2$CO$_3$ (503 g, 1.54 mol). After 10 min, iodomethane (202 g, 1.42 mol) was added dropwise to the mixture with stirring at rt. After 4.5 h, the mixture was poured into water/ice (2 L) and extracted with ethyl acetate (2 L×2). The combined organic extracts were washed with brine (1 L×2), dried over anhydrous sodium sulfate, filtered, and concentrated to dryness. This afforded methyl 4-((tert-butoxycarbonyl)amino)-2-hydroxybutanoate (180 g, 65%) as a yellow oil.

Step C: Methyl 4-((tert-butoxycarbonyl)amino)-2-((tert-butyldimethylsilyl)oxy)butanoate. Into a 5 L 3-necked round-bottomed flask, purged and maintained with an inert atmosphere of nitrogen, was placed a solution of methyl 4-[[(tert-butoxy)carbonyl]amino]-2-hydroxybutanoate (180 g, 0.77 mol) in dichloromethane (1.8 L) and imidazole (108 g, 1.54 mol). This was followed by the addition of tert-butyl (chloro)dimethylsilane (231 g, 1.53 mol) in several batches at 0° C. The resulting solution was warmed to rt and stirred for 16 h. After which time, the mixture was poured into water/ice (1 L) and extracted with dichloromethane (1.5 L×3). The combined organic extracts were washed with brine (1 L), dried over anhydrous sodium sulfate, filtered, and concentrated to dryness. The resulting residue was purified by FCC (1:10, ethyl acetate/petroleum ether) to afford methyl 4-((tert-butoxycarbonyl)amino)-2-((tert-butyldimethylsilyl)oxy)butanoate (200 g, 75%) as a light yellow oil.

Step D: Methyl 4-((tert-butoxycarbonyl)(methyl-$d_3$)amino)-2-((tert-butyldimethylsilyl)oxy)butanoate. Into a 1 L 3-necked round-bottomed flask, purged and maintained with an inert atmosphere of nitrogen, was placed methyl 4-[[(tert-butoxy)carbonyl]amino]-2-[(tert-butyldimethylsilyl)oxy]butanoate (50.0 g, 144 mmol), N,N-dimethylformamide (500 mL), and CD3I (62.6 g, 432 mmol). The resulting solution was cooled to 0° C. and sodium hydride (8.60 g, 358 mmol, 60%) was added in several batches at 0° C. After 2 h at 0° C., the mixture was poured into saturated aqueous of NH$_4$Cl (250 mL). The resulting mixture was extracted with ethyl acetate (500 mL×2). The combined organic extracts were washed with brine (500 mL), dried over anhydrous sodium sulfate, filtered, and concentrated to dryness. The above procedure (Step D) was repeated 3× and afforded methyl 4-((tert-butoxycarbonyl)(methyl-$d_3$)amino)-2-((tert-butyldimethylsilyl)oxy)butanoate (200 g, 95%) as a light yellow oil.

Step E: Methyl 4-((tert-butoxycarbonyl)(methyl-$d_3$)amino)-2-hydroxybutanoate. Into a 3 L 3-necked round-bottomed flask, purged and maintained with an inert atmosphere of nitrogen, was placed methyl 4-((tert-butoxycarbonyl)(methyl-$d_3$)amino)-2-((tert-butyldimethylsilyl)oxy)butanoate (200 g, 549 mmol), methanol (2 L), and amine hydrofluoride (204 g, 5.51 mol). The resulting solution was heated at 50° C. After 12 h, the resulting solution was cooled to rt, concentrated to dryness, and diluted with water (1 L). The resulting mixture was extracted with ethyl acetate (1 L×3). The combined organic extracts were washed with brine (1 L), dried over anhydrous sodium sulfate, and concentrated to dryness. This afforded methyl 4-((tert-butoxycarbonyl)(methyl-$d_3$)amino)-2-hydroxybutanoate (137 g) as a light yellow oil which was used directly in the next step without further purification.

Step F: Methyl 4-((tert-butoxycarbonyl)(methyl-$d_3$)amino)-2-oxobutanoate. A 3 L 3-necked round-bottomed flask, purged and maintained with an inert atmosphere of nitrogen, was charged with methyl 4-((tert-butoxycarbonyl)(methyl-$d_3$)amino)-2-hydroxybutanoate (137 g, 547 mmol), dichloromethane (1.4 L), and 1,1,1-tris(acetyloxy)-1,1-dihydro-1,2-benziodoxol-3-(1H)-one, (Dess-Martin periodinane, 348 g, 821 mmol) at 5° C. The resulting mixture was stirred for 3 h at rt. After which time the mixture was poured into aqueous sodium bicarbonate (2 L). The resulting solids were filtered off and filtrate was extracted with dichloromethane (1.5 L×3). The combined organic extracts were washed with brine (1 L), dried over anhydrous sodium sulfate, filtered, and concentrated to dryness. The resulting residue was purified by FCC (1:3, ethyl acetate/petroleum ether) to afford methyl 4-((tert-butoxycarbonyl)(methyl-$d_3$)amino)-2-oxobutanoate (81 g, 60%) as a yellow oil. $^1$H NMR (300 MHz, CDCl$_3$) δ 3.90 (s, 3H), 3.56 (t, J=6.6 Hz, 2H), 3.08 (t, J=6.6 Hz, 2H), 1.48 (s, 9H).

Step G: Methyl 2-(2-((tert-butoxycarbonyl)(methyl-$d_3$)amino)ethyl)-2-hydroxybut-3-ynoate. Into a 1 L 3-necked round-bottomed flask, purged and maintained with an inert atmosphere of nitrogen, was placed a solution of methyl 4-((tert-butoxycarbonyl)(methyl-$d_3$)amino)-2-oxobutanoate (20 g, 81 mmol) in THF (0.2 L). The solution was cooled to −78° C., followed by dropwise addition of bromo(ethynyl)magnesium (274 mL, 138 mmol). The resulting solution was stirred for at −40° C. After 2 h, saturated aqueous NH$_4$Cl (100 mL) was added dropwise at −70° C. The resulting mixture was warmed slowly rt and extracted with ethyl acetate (800 mL×3). The combined organic extracts were washed with brine (800 mL), dried over anhydrous sodium sulfate, filtered, and concentrated to dryness. The above procedure (Step G) was repeated 3× and the combined residues afforded methyl 2-(2-((tert-butoxycarbonyl)(methyl-$d_3$)amino)ethyl)-2-hydroxybut-3-ynoate (82 g) as a yellow oil.

Step H: Methyl 2-hydroxy-2-(2-((methyl-$d_3$)amino)ethyl)but-3-ynoate as a trifluoroacetate salt. Into a 1 L 3-necked round-bottomed flask purged and maintained with an inert atmosphere of nitrogen, was placed a solution of methyl 2-(2-((tert-butoxycarbonyl)(methyl-$d_3$)amino)ethyl)-2-hydroxybut-3-ynoate (70.0 g, 255 mmol), dichloromethane (420 mL), and trifluoroacetic acid (140 mL). The resulting solution was stirred for 1 h at rt. The resulting mixture was concentrated to dryness and used directly in the next step without further purification.

Step I: (R)-3-Ethynyl-3-hydroxy-1-(methyl-$d_3$)pyrrolidin-2-one. Into a 1 L 3-necked round-bottomed flask purged and maintained with an inert atmosphere of nitrogen, was placed a solution of methyl 2-hydroxy-2-(2-((methyl-$d_3$)amino)ethyl)but-3-ynoate as a trifluoroacetate salt (70.0 g, 243 mmol), methanol (700 mL), and potassium carbonate (133 g, 964 mmol). The resulting solution was stirred for 3 h at rt. The resulting solids were filtered off and the filtrate was concentrated to dryness. The resulting residue was purified by FCC (1:5, ethyl acetate/petroleum ether) and then recrystallized from diethyl ether (100 mL) to afford racemic 3-ethynyl-3-hydroxy-1-(methyl-$d_3$)pyrrolidin-2-one (16 g, 46%) as a yellow solid. This material was further purified by preparative chiral SFC (Chiralpak AS-H, 5×25 cm, 5 µm; mobile phase, CO$_2$ (80%) and IPA (0.1% DEA) (20%); Detector, UV at λ=220 nm) to afford (R)-3-ethynyl-3-hydroxy-1-(methyl-$d_3$)pyrrolidin-2-one (5.4 g, 34%, >97% ee) as a brown solid and (S)-3-ethynyl-3-hydroxy-1-(methyl-$d_3$)pyrrolidin-2-one [Intermediate 46, 5.2 g, 33%, >97% ee] as a brown solid. Data for (R)-3-ethynyl-3-hydroxy-1-(methyl-$d_3$)pyrrolidin-2-one: MS (ESI): mass calcd. for C$_7$H$_6$D$_3$NO$_2$, 142.08; m/z. found, 143.2 [M+H]$^+$. $^1$H NMR (400 MHz, CD$_3$OD) δ 3.41-3.38 (t, J=5.2 Hz, 2H), 3.03 (s, 1H), 2.48-2.43 (m, 1H), 2.24-2.17 (m, 1H).

Intermediate 46: (S)-3-Ethynyl-3-hydroxy-1-(methyl-d₃)pyrrolidin-2-one

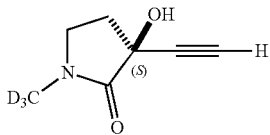

The chiral separation described in Intermediate 45, Step I provided (S)-3-ethynyl-3-hydroxy-1-(methyl-d₃)pyrrolidin-2-one (5.2 g, 33%, >97% ee) as a brown solid. MS (ESI): mass calcd. for C₇H₆D₃NO₂, 142.08; m/z. found, 143.2 [M+H]⁺. ¹H NMR (400 MHz, CD₃OD) δ 3.41-3.38 (t, J=5.2 Hz, 2H), 3.03 (s, 1H), 2.48-2.43 (m, 1H), 2.24-2.17 (m, 1H).

Intermediate 47:
7-(5-Iodo-2-methylphenyl)isoquinolin-1-amine

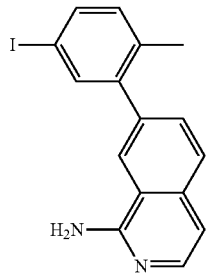 [SMILES: Cc1ccc(I)cc1-c1ccc2ccnc(N)c2c1]

Step A: bis-tert-Butyl (7-bromoisoquinolin-1-yl)carbamate. In a 1 L round-bottomed flask, DMAP (0.13 g, 1.05 mmol) was added to a suspension of 7-bromoisoquinolin-1-amine (4.7 g, 21 mmol) and di-tert-butyl decarbonate (9.2 g, 42 mmol) in DCM (210 mL). The resulting mixture was stirred at rt for 16 h, the resulting solid was collected filtration, and triturated with ethyl acetate to afford bis-tert-butyl (7-bromoisoquinolin-1-yl)carbamate (6.1 g, 68%) as a colorless solid. MS (ESI): mass calcd. for C₁₉H₂₃BrN₂O₄, 422.08; m/z. found, 421.3, 423.1 [M+H]⁺. ¹H NMR (400 MHz, Chloroform-d) δ 8.47 (d, J=5.7 Hz, 1H), 8.15 (s, 1H), 7.84-7.73 (m, 2H), 7.65 (dd, J=5.7, 1.0 Hz, 1H), 1.36 (s, 18H).

Step B: bis-tert-Butyl (7-(5-amino-2-methylphenyl)isoquinolin-1-yl)carbamate. To a 20 mL vial were added bis-tert-butyl (7-bromoisoquinolin-1-yl)carbamate (1.0 g, 2.4 mmol), 4-methyl-3-(4,4,5,5-tetramethyl-1,3,2-dioxaborolan-2-yl)aniline (0.82 g, 3.54 mmol) and 1,4-dioxane (16 mL). The solution was purged with N₂ for 10 min, cesium carbonate (2.3 g, 7.09 mmol) and (2-dicyclohexylphosphino-2',6'-diisopropoxy-1,1'-biphenyl)[2-(2'-amino-1,1'-biphenyl)]palladium(II) methanesulfonate (0.2 g, 0.14 mmol) were added and the vial was sealed and stirred at rt. After 12 h, (2-dicyclohexylphosphino-2',6'-diisopropoxy-1,1'-biphenyl)[2-(2'-amino-1,1'-biphenyl)]palladium(II) methanesulfonate (0.1 g, 0.07 mmol) was added and the mixture was heated at 50° C. for 3 h, cooled to the rt, and partitioned between ethyl acetate (20 mL) and water (40 mL). The organic layer was separated, concentrated to dryness, and purified by FCC (0 to 60% gradient using ethyl acetate and hexanes) to afford bis-tert-butyl (7-(5-amino-2-methylphenyl)isoquinolin-1-yl)carbamate (0.8 g, 75%) as a red oil. MS (ESI): mass calcd. for C₂₆H₃₁N₃O₄, 449.55; m/z. found, 450.1 [M+H]⁺. ¹H NMR (500 MHz, DMSO-d₆) δ 8.42 (d, J=5.7 Hz, 1H), 8.11 (d, J=8.4 Hz, 1H), 7.94 (d, J=5.6 Hz, 1H), 7.78 (dd, J=8.4, 1.7 Hz, 1H), 7.63-7.54 (m, 1H), 6.99 (d, J=8.2 Hz, 1H), 6.56 (dd, J=8.1, 2.4 Hz, 1H), 6.48 (d, J=2.3 Hz, 1H), 5.02 (s, 2H), 2.03 (s, 3H), 1.28 (s, 18H).

Step C: bis-tert-Butyl (7-(5-iodo-2-methylphenyl)isoquinolin-1-yl)carbamate. In a 50 mL round-bottomed flask, 4-methylbenzenesulfonic acid (1.3 g, 7.7 mmol) was added to a solution of bis-tert-butyl (7-(5-amino-2-methylphenyl)isoquinolin-1-yl)carbamate (1.2 g, 2.6 mmol) in ACN (7 mL) at 0° C. and the mixture was stirred for 30 min maintaining the reaction temperature. A solution of sodium nitrite (0.4 g, 5.2 mmol) in water (3.5 mL) was added, followed by a solution of potassium iodide (0.9 g, 5.2 mmol) in water (3.5 mL). The mixture was slowly allowed to warm to rt over 2 h, then partitioned between DCM (30 mL) and saturated aqueous sodium bicarbonate (10 mL). The organic layer was separated, concentrated to dryness, and the resulting residue was purified by FCC (0 to 60% gradient of ethyl acetate and hexanes) to afford bis-tert-butyl (7-(5-iodo-2-methylphenyl)isoquinolin-1-yl)carbamate (0.7 g, 49%) as an orange solid. MS (ESI): mass calcd. for C₂₆H₂₉IN₂O₄, 560.43; m/z. found, 561.2 [M+H]⁺. ¹H NMR (400 MHz, DMSO-d₆) δ 8.46 (d, J=5.7 Hz, 1H), 8.16 (d, J=8.4 Hz, 1H), 7.97 (d, J=5.7 Hz, 1H), 7.86 (dd, J=8.4, 1.7 Hz, 1H), 7.71 (dd, J=8.0, 1.9 Hz, 1H), 7.68 (s, 1H), 7.57 (d, J=1.9 Hz, 1H), 7.19 (d, J=8.1 Hz, 1H), 2.19 (s, 3H), 1.32 (s, 18H).

Step D: 7-(5-Iodo-2-methylphenyl)isoquinolin-1-amine. In a 100 mL round-bottomed flask, TFA (0.5 mL, 6.27 mmol) was added to a solution of bis-tert-butyl (7-(5-iodo-2-methylphenyl)isoquinolin-1-yl)carbamate (0.70 g, 1.25 mmol) in DCM (20 mL). The mixture was stirred at rt for 16 h, partitioned between DCM (20 mL) and water (10 mL), and the pH was adjusted to 12 with saturated aqueous sodium bicarbonate. The organic extract was separated, concentrated to dryness, and the resulting residue purified by FCC (0 to 5% gradient of MeOH and DCM) to afford 7-(5-iodo-2-methylphenyl)isoquinolin-1-amine (0.4 g, 89%) as a red oil. MS (ESI): mass calcd. for C₁₆H₁₃IN₂, 360.20; m/z. found, 361.0 [M+H]⁺.

Intermediate 48. 2-(5-Bromo-2-methylphenyl)pyrido[3,4-d]pyrimidin-8-amine

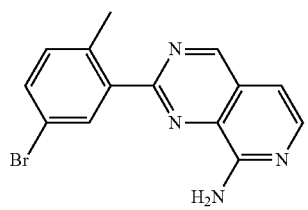 [SMILES: Cc1ccc(Br)cc1-c1ncc2ccnc(N)c2n1]

To a vial was added the following solid reagents: Intermediate 41 [2-(methylthio)pyrido[3,4-d]pyrimidin-8-amine, 200 mg, 1.04 mmol], (5-bromo-2-methylphenyl)boronic acid (334 mg, 1.55 mmol), PdCl₂(dppf) (30 mg, 0.041 mmol) and copper(I) 3-methylsalicylate (334 mg, 1.55 mmol). Then 1,4-dioxane was added (18 mL, which was degassed with argon for 20 min prior to use). The vial was sealed and then evacuated/purged with nitrogen 3 times. The mixture was then placed in a pre-heated aluminum mantle at 100° C. After 2.75 h, the contents were filtered through a pad of diatomaceous earth which was rinsed with NH₃ in MeOH (2M) and ethyl acetate (2:1) to give a brownish oil which was purified by FCC (100% DCM increasing to 5% 2M NH₃-MeOH-DCM) to give 2-(5-bromo-2-methylphenyl) pyrido[3,4-d]pyrimidin-8-amine (40 mg, 12%) as a yellow solid. MS (ESI): mass calcd. For C₁₄H₁₁BrN₄, 314.02; m/z found, 315.0 [M+H]⁺. ¹H NMR (400 MHz, Chloroform-d) δ 9.36 (s, 1H), 8.17 (d, J=2.2 Hz, 1H), 7.50 (dd, J=8.2, 2.2 Hz, 1H), 7.22 (d, J=8.2 Hz, 2H), 7.09 (br s, 1H), 6.10 (br s, 1H), 2.61 (s, 3H).

Intermediate 49: (R)-3-ethynyl-3-hydroxy-1-(2,2,2-trifluoroethyl)pyrrolidin-2-one

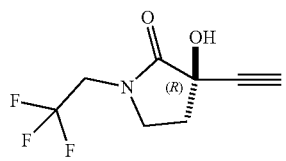

Step A: tert-Butyl 3-((2,2,2-trifluoroethyl)amino)propanoate. Into a 2 L round-bottomed flask, was placed tert-butyl 3-aminopropanoate hydrochloride (100 g, 550 mmol), THF (500 mL), DMF (500 mL), DIEA (273 mL, 2.11 mol), and 2,2,2-trifluoroethyl trifluoromethanesulfonate (192 g, 826 mmol). The resulting solution was stirred rt for 12 h. The resulting solution was diluted with ethyl acetate (2 L), washed with saturated aqueous NaHCO₃ (1 L) and brine (1 L×2). The organic layer was dried over anhydrous sodium sulfate, filtered, and concentrated to dryness. The residue was purified by FCC (1:3, ethyl acetate/ petroleum ether) to afford tert-butyl 3-[(2,2,2-trifluoroethyl) amino]propanoate (90 g, 72%) as a colorless oil. MS (ESI): mass calcd. for C₉H₁₆F₃NO₂, 227.1; m/z. found, 228.2 [M+H]⁺.

Step B: tert-Butyl 3-(2-ethoxy-2-oxo-N-(2,2,2-trifluoroethyl)acetamido)propanoate. Into a 2 L round-bottomed flask, was placed tert-butyl 3-[(2,2,2-trifluoroethyl)amino] propanoate (90 g, 397 mmol), DCM (1000 mL), and TEA (165 mL, 1.20 mol). This was followed by the addition of ethyl oxalochloridate (65 g, 475 mmol) dropwise with stirring at 5° C. The resulting solution was stirred for 1 h at rt. The resulting mixture was partitioned into water (1 L), the organic layer was separated, and washed with brine (1 L). The resulting organic layer was dried over anhydrous sodium sulfate, filtered, and concentrated to dryness. The residue was purified by FCC (1:3, ethyl acetate/petroleum ether) to afford tert-butyl 3-[2-ethoxy-2-oxo-N-(2,2,2-trifluoroethyl)acetamido]propanoate (110 g, 85%) of as yellow oil.

Step C: tert-Butyl 4,5-dioxo-1-(2,2,2-trifluoroethyl)pyrrolidine-3-carboxylate. Into a 2 L 3-necked round-bottomed flask was placed tert-butyl 3-[2-ethoxy-2-oxo-N-(2,2,2-trifluoroethyl)acetamido]propanoate (110 g, 336 mmol) and THF (1.2 L). To the solution was added t-BuOK (38.5 g, 343 mmol) in portions. The resulting solution was stirred for 2 h at 70° C. and then partitioned with water (500 mL). The pH of the solution was adjusted to 4 with HCl (6 N). The resulting solution was extracted with ethyl acetate (1 L) and the organic layer was washed with brine (1 L). The resulting organic layer was dried over anhydrous sodium sulfate, filtered, and concentrated to dryness. The residue afforded tert-butyl 4,5-dioxo-1-(2,2,2-trifluoroethyl)pyrrolidine-3-carboxylate (70 g, 74%) as a yellow semi-solid that was used directly in the next step.

Step D: 4,5-Dioxo-1-(2,2,2-trifluoroethyl)pyrrolidine-3-carboxylic acid. Into a 2 L round-bottomed flask was placed tert-butyl 4,5-dioxo-1-(2,2,2-trifluoroethyl)pyrrolidine-3-carboxylate (200 g, 711 mmol) and 2,2,2-trifluoroacetaldehyde (800 mL). The resulting solution was stirred for 1 h at rt and then the resulting mixture was concentrated to dryness. The resulting residue was precipitated by the addition of ACN (800 mL) and stirred for 1 h. The solids were collected by filtration and washed with ACN (200 mL) to afford 4,5-dioxo-1-(2,2,2-trifluoroethyl)pyrrolidine-3-carboxylic acid (110 g, 69%) as a white solid. MS (ESI): mass calcd. for C₇H₆F₃NO₄, 225.0; m/z. found, 226.0 [M+H]⁺. ¹H NMR (400 MHz, CD₃OD) δ 4.31-3.97 (m, 5H).

Step E: 1-(2,2,2-Trifluoroethyl)pyrrolidine-2,3-dione. Into a 2 L round-bottomed flask was placed 4,5-dioxo-1-(2, 2,2-trifluoroethyl)pyrrolidine-3-carboxylic acid (90 g, 399 mmol) and THF (1.2 L). The resulting solution was stirred for 10 h at 70° C. The resulting mixture was cooled to rt and concentrated to dryness to afford 1-(2,2,2-trifluoroethyl) pyrrolidine-2,3-dione (70 g, 96.68%) as a white solid.

Step F: (R)-3-Ethynyl-3-hydroxy-1-(2,2,2-trifluoroethyl) pyrrolidin-2-one. Into a 5 L round-bottomed flask, purged and maintained with an inert atmosphere of nitrogen, was placed 1-(2,2,2-trifluoroethyl)pyrrolidine-2,3-dione (70 g, 387 mmol) and THF (1.6 L). This was followed by the addition of bromo(ethynyl)magnesium (1.6 L, 775 mmol) dropwise with stirring at 0° C. The resulting solution was stirred for 48 h at rt. The reaction was partitioned with saturated aqueous ammonium chloride (3 L) and extracted with ethyl acetate (2 L×2). The combined organic layers were dried over anhydrous sodium sulfate, filtered, and concentrated to dryness. The residue was purified by FCC (1:1, ethyl acetate/petroleum) ether to afford racemic 3-ethynyl-3-hydroxy-1-(2,2,2-trifluoroethyl)pyrrolidin-2-one (13 g, 16%) as a light yellow solid. The (R) and (S) enantiomers were separated by chiral preparative SFC (Column, CHIRALPAK AD-H SFC, 5×25 cm, 5um; mobile phase, CO₂ (87%) and IPA:HEX=1:1 (13%)) to afford (R)-3-ethynyl-3-hydroxy-1-(2,2,2-trifluoroethyl)pyrrolidin-2-one (6.1 g, 36%, >97% ee) as a yellow solid and (S)-3-ethynyl-3-hydroxy-1-(2,2,2-trifluoroethyl)pyrrolidin-2-one (Intermediate 50, 6 g, 35%, >97% ee) as a yellow solid. Data for (R)-3-ethynyl-3-hydroxy-1-(2,2,2-trifluoroethyl)pyrrolidin-2-one: MS (ESI): mass calcd. for C₈H₈F₃NO₂, 207.0; m/z. found, 208.0 [M+H]⁺. ¹H NMR (400 MHz, CD₃OD) δ 4.13 (dq, J=15.2, 9.4 Hz, 1H), 3.98 (dq, J=15.2, 9.2 Hz, 1H), 3.57 (dd, J=7.8, 5.1 Hz, 2H), 3.09 (s, 1H), 2.51 (dt, J=12.7, 5.1 Hz, 1H), 2.27 (dt, J=12.7, 7.8 Hz, 1H). ¹⁹F-NMR (400 MHz, CD₃OD) δ 71.48 (s). [α]²⁰_D=−79.3 (c=0.32 in MeOH).

Intermediate 50: (S)-3-Ethynyl-3-hydroxy-1-(2,2,2-trifluoroethyl)pyrrolidin-2-one

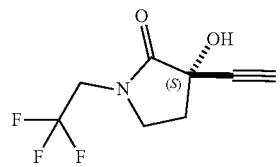

The chiral separation described in Intermediate 49 provided (S)-3-ethynyl-3-hydroxy-1-(2,2,2-trifluoroethyl)pyrrolidin-2-one (6 g, 35%, >97% ee) as a yellow solid. MS (ESI): mass calcd. for C₈H₈F₃NO₂, 207.0; m/z. found, 208.0

[M+H]⁺. ¹H NMR (400 MHz, CD₃OD) δ 4.13 (dq, J=15.2, 9.4 Hz, 1H), 3.98 (dq, J=15.2, 9.2 Hz, 1H), 3.57 (dd, J=7.8, 5.1 Hz, 2H), 3.09 (s, 1H), 2.51 (dt, J=12.7, 5.1 Hz, 1H), 2.27 (dt, J=12.7, 7.8 Hz, 1H). ¹⁹F-NMR (400 MHz, CD₃OD) δ 71.48 (s). [α]$^{20}_D$=+58.5 (c=0.30 in MeOH).

Intermediate 51: 2-(3-Iodophenyl)-4-isopropylpyrido[3,4-d]pyrimidin-8-amine

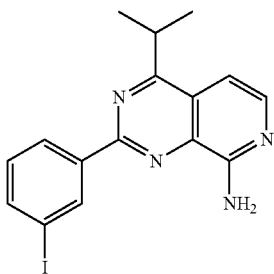 [SMILES: CC(C)c1nc(-c2cccc(I)c2)nc2c(N)nccc12]

Step A: tert-Butyl (2-chloro-4-(1-hydroxy-2-methylpropyl)pyridin-3-yl)carbamate. A homogeneous solution of tert-butyl (2-chloropyridin-3-yl)carbamate (2.0 g, 8.8 mmol) and TMEDA (4.0 mL, 27 mmol) in dry THF (50 mL) was cooled to −45° C. under an atmosphere of N₂ and treated dropwise with n-BuLi (10.5 mL, 26.2 mmol, 2.5 M in hexanes). After 30 min, iso-butyraldehyde (3.0 mL, 33 mmol) was added dropwise. After 10 min, saturated aqueous NH₄Cl (50 mL) was added and the resulting mixture was warmed to rt. The mixture was diluted with ethyl acetate (200 mL), the organic layer was separated and washed with brine (250 mL×2). The organic layer was dried (MgSO₄), filtered, and concentrated to dryness. The residue was purified via FCC to yield tert-butyl (2-chloro-4-(1-hydroxy-2-methylpropyl)pyridin-3-yl)carbamate (2.4 g, 91%). MS (ESI): mass calcd. for C₁₄H₂₁ClN₂O₃, 300.12; m/z. found, 301.2 [M+H]⁺. ¹H NMR (400 MHz, CDCl₃) δ 8.26 (d, J=5.1 Hz, 1H), 7.37 (d, J=4.2 Hz, 1H), 6.39 (s, 1H), 4.43 (s, 1H), 3.52 (s, 1H), 2.08-1.96 (m, 1H), 1.51 (s, 9H), 1.13-0.97 (m, 3H), 0.79-0.63 (m, 3H).

Step B: tert-Butyl (2-chloro-4-isobutyrylpyridin-3-yl)carbamate. A homogeneous solution of tert-butyl (2-chloro-4-(1-hydroxy-2-methylpropyl)pyridin-3-yl)carbamate (2.4 g, 7.9 mmol) in CH₂Cl₂ was cooled to 0° C. and treated with 1,1,1-tris(acetyloxy)-1,1-dihydro-1,2-benziodoxol-3-(1H)-one (Dess-Martin periodinane, 3.8 g, 8.8 mmol) in one portion. The resulting mixture was immediately removed from the cooling bath and allowed to warm to rt. After 1 h at rt, additional 1,1,1-tris(acetyloxy)-1,1-dihydro-1,2-benziodoxol-3-(1H)-one (Dess-Martin periodinane, 0.3 g, 0.7 mmol) was added at rt. After 1 h, the mixture was diluted with CH₂Cl₂ (200 mL) and washed with saturated aqueous NaHCO₃ (250 mL) followed by brine (200 mL×2). The organic layer was dried (MgSO₄), filtered, and concentrated to dryness. The residue was purified by FCC to afford tert-butyl (2-chloro-4-isobutyrylpyridin-3-yl)carbamate (2.2 g, 91%). MS (ESI): mass calcd. for C₁₄H₁₉ClN₂O₃, 298.11; m/z. found, 299.1 [M+H]⁺. ¹H NMR (400 MHz, CDCl₃) δ 8.25 (d, J=4.9 Hz, 1H), 7.31 (d, J=4.9 Hz, 1H), 6.96 (br s, 1H), 3.19 (hept, J=6.9 Hz, 1H), 1.49 (s, 9H), 1.16 (d, J=6.9 Hz, 6H).

Step C: 1-(3-Amino-2-chloropyridin-4-yl)-2-methylpropan-1-one. A homogeneous solution of tert-butyl (2-chloro-4-isobutyrylpyridin-3-yl)carbamate (2.2 g, 7.2 mmol) in CH₂Cl₂ (60 mL) was treated with TFA (6.0 mL, 78 mmol) at rt. After 40 min, the mixture was concentrated to near dryness and the residue was purified via FCC to yield 1-(3-amino-2-chloropyridin-4-yl)-2-methylpropan-1-one (1.4 g, 99%). MS (ESI): mass calcd. for C₉H₁₁ClN₂O, 198.06; m/z. found, 199.1 [M+H]⁺. ¹H NMR (400 MHz, CDCl₃) δ 7.74 (d, J=5.2 Hz, 1H), 7.50 (d, J=5.3 Hz, 1H), 6.74 (s, 2H), 3.55 (hept, J=6.8 Hz, 1H), 1.22 (d, J=6.8 Hz, 6H).

Step D: 8-Chloro-2-(3-iodophenyl)-4-isopropylpyrido[3,4-d]pyrimidine. A homogeneous solution of 1-(3-amino-2-chloropyridin-4-yl)-2-methylpropan-1-one (1.1 g, 5.3 mmol) and (3-iodophenyl)methanamine (1.3 g, 5.6 mmol) in o-xylenes (2 mL) was heated for 30 min at 100° C. The mixture was cooled to rt, treated with 4-hydroxy-2,2,6,6-tetramethylpiperidin-1-oxyl (1.1 g, 6.4 mmol), and then heated at 140° C. After 2 h, the mixture was cooled to rt, treated with additional 4-hydroxy-2,2,6,6-tetramethylpiperidin-1-oxyl (0.4 g, 2.5 mmol) and heated at 140° C. After 30 min the mixture was cooled to rt, diluted with CH₂Cl₂ (10 mL), and filtered through a pad of diatomaceous earth. The filtrate was concentrated and purified by FCC to yield 8-chloro-2-(3-iodophenyl)-4-isopropylpyrido[3,4-d]pyrimidine (0.3 g, 12%). MS (ESI): mass calcd. for C₁₆H₁₃ClIN₃, 408.98; m/z. found, 410.1 [M+H]⁺.

Step E: N-(2,4-Dimethoxybenzyl)-2-(3-iodophenyl)-4-isopropylpyrido[3,4-d]pyrimidin-8-amine. N-(2,4-Dimethoxybenzyl)-2-(3-iodophenyl)-4-isopropylpyrido[3,4-d]pyrimidin-8-amine was prepared using conditions analogous to those described in Step D of Intermediate 42, utilizing 8-chloro-2-(3-iodophenyl)-4-isopropylpyrido[3,4-d]pyrimidine. MS (ESI): mass calcd. for C₂₅H₂₅IN₄O₂, 540.10; m/z. found, 541.2 [M+H]⁺. ¹H NMR (400 MHz, CDCl₃) δ 8.92-8.89 (m, 1H), 8.59-8.54 (m, 1H), 8.08 (d, J=6.0 Hz, 1H), 7.85-7.77 (m, 1H), 7.53 (t, J=5.9 Hz, 1H), 7.31 (d, J=8.3 Hz, 1H), 7.24 (t, J=7.9 Hz, 1H), 6.94 (d, J=6.1 Hz, 1H), 6.53 (d, J=2.3 Hz, 1H), 6.47-6.42 (m, 1H), 4.81 (d, J=6.1 Hz, 2H), 3.98 (s, 3H), 3.80 (s, 3H), 3.77-3.69 (m, 1H), 1.44 (d, J=6.8 Hz, 6H).

Step F: 2-(3-Iodophenyl)-4-isopropylpyrido[3,4-d]pyrimidin-8-amine. 2-(3-Iodophenyl)-4-isopropylpyrido[3,4-d]pyrimidin-8-amine was prepared using conditions analogous to those described in Step E of Intermediate 42, utilizing N-(2,4-dimethoxybenzyl)-2-(3-iodophenyl)-4-isopropylpyrido[3,4-d]pyrimidin-8-amine. MS (ESI): mass calcd. for C₁₆H₁₅IN₄, 390.03; m/z. found, 391.0 [M+H]⁺. ¹H NMR (400 MHz, CDCl₃) δ 8.94 (t, J=1.6 Hz, 1H), 8.62-8.57 (m, 1H), 8.04 (d, J=6.0 Hz, 1H), 7.86-7.79 (m, 1H), 7.29-7.23 (m, 1H), 7.12 (d, J=6.0 Hz, 1H), 6.11 (d, J=64.0 Hz, 2H), 3.81-3.73 (m, 1H), 1.47 (d, J=6.8 Hz, 6H).

Intermediate 52: 2-(3-Iodophenyl)thiazolo[5,4-d]pyrimidin-7-amine

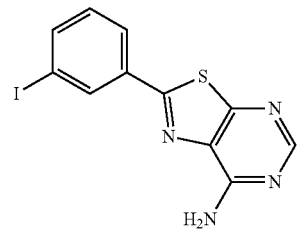 [SMILES: Nc1ncnc2sc(-c3cccc(I)c3)nc12]

Step A: N-(4-Amino-6-oxo-1,6-dihydropyrimidin-5-yl)-3-iodobenzamide. A 50 mL round-bottomed flask was charged with 5,6-diaminopyrimidin-4(3H)-one (0.26 g, 2.02 mmol), and 1,4-dioxane (10 mL), followed by treatment with DIPEA (1 mL, 5.80 mmol) and 3-iodobenzoyl chloride (0.3 mL, 2.139 mmol, 1.9 g/mL). After 1 h at rt, the resulting mixture was diluted with MeCN (15 mL) and briefly sonicated. The resulting solid was isolated by filtration and dried under high-vacuum to yield N-(4-amino-6-oxo-1,6-dihydropyrimidin-5-yl)-3-iodobenzamide (537 mg, 75%) as a yellow solid which was used without further purification. MS (ESI): mass calcd. for $C_{11}H_{91}N_4O_2$, 355.98; m/z found, 357.0 $[M+H]^+$. $^1H$ NMR (400 MHz, DMSO-$d_6$) δ 11.73 (s, 1H), 9.15 (s, 1H), 8.33 (s, 1H), 7.93 (d, J=10.7 Hz, 2H), 7.79 (s, 1H), 7.29 (s, 1H), 6.42 (s, 2H).

Step B: 2-(3-Iodophenyl)thiazolo[5,4-d]pyrimidin-7-amine. A 50 mL round-bottomed flask was charged with N-(4-amino-6-oxo-1,6-dihydropyrimidin-5-yl)-3-iodobenzamide (0.42 g, 1.19 mmol) and pyridine (5 mL). The resulting solution was cooled to 0° C. and treated with phosphorus pentasulfide (0.35 g, 1.55 mmol). The resulting mixture was warmed to rt and then heated at 100° C. for 1 h. The mixture was then cooled to rt and treated with additional phosphorus pentasulfide (0.19 g, 0.84 mmol). After an additional 30 min of heating at 100° C., the mixture was cooled to rt, diluted with $H_2O$ (25 mL), and adjusted to about pH 5 with 1M HCl. The resulting solid was collected by filtration and dried to afford 2-(3-iodophenyl)thiazolo[5,4-d]pyrimidin-7-amine (0.32 g, 76%) as a yellow solid. MS (ESI): mass calcd. for $C_{11}H_7IN_4S$, 353.94; m/z. found, 354.9 $[M+H]^+$. $^1H$ NMR (400 MHz, DMSO-$d_6$) δ 8.51-8.47 (m, 1H), 8.32 (s, 1H), 8.03 (d, J=8.2 Hz, 1H), 7.94 (d, J=8.3 Hz, 1H), 7.84 (br s, 2H), 7.38 (t, J=7.9 Hz, 1H).

Intermediate 53: (R)-2-(5-Methylisoxazol-3-yl)-4-(3-(4,4,5,5-tetramethyl-1,3,2-dioxaborolan-2-yl)phenyl)but-3-yn-2-ol

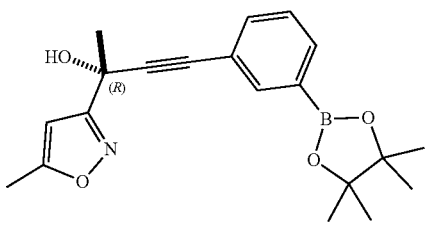

The title compound was prepared using conditions analogous to those described for the preparation of Intermediate 4 except utilizing 2-(3-iodophenyl)-4,4,5,5-tetramethyl-1,3,2-dioxaborolane and Intermediate 32 [(R)-2-(5-methylisoxazol-3-yl)but-3-yn-2-ol] to afford a quantitative yield of an orange solid. MS (ESI): mass calcd. for $C_{20}H_{24}BNO_4$, 353.18; m/z. found, 354.1 $[M+H]^+$. $^1H$ NMR (400 MHz, CDCl$_3$) δ 7.90 (br s, 1H), 7.74-7.76 (m, 1H), 7.50-7.55 (m, 1H), 7.36-7.27 (m, 1H), 6.14 (br s, 1H), 2.96 (br s, 1H), 2.43 (s, 3H), 1.94 (s, 3H), 1.34 (s, 12H).

Intermediate 54: (R)-4-(3-(4,4,5,5-Tetramethyl-1,3,2-dioxaborolan-2-yl)phenyl)-2-(thiazol-2-yl)but-3-yn-2-ol

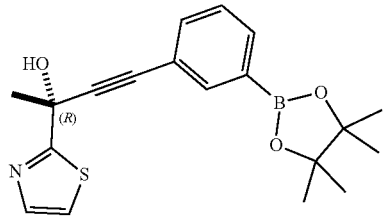

The title compound was prepared using conditions analogous to those described for the preparation of Intermediate 4 utilizing 2-(3-iodophenyl)-4,4,5,5-tetramethyl-1,3,2-dioxaborolane and Intermediate 30 [(R)-2-(thiazol-2-yl)but-3-yn-2-ol] to afford to afford (295 mg, 54%) as an amber solid. MS (ESI): mass calcd. for $C_{19}H_{22}BNO_3S$, 355.14; m/z. found, 356.10 $[M+H]^+$. $^1H$ NMR (400 MHz, CDCl$_3$) δ 7.92 (t, J=1.6 Hz, 1H), 7.81-7.72 (m, 2H), 7.54 (dt, J=7.7, 1.5 Hz, 1H), 7.36-7.28 (m, 2H), 2.03 (s, 3H), 1.34 (s, 12H).

Intermediate 55: (R)-2-(5-methyl-1,3,4-oxadiazol-2-yl)-4-(3-(4,4,5,5-tetramethyl-1,3,2-dioxaborolan-2-yl)phenyl)but-3-yn-2-ol

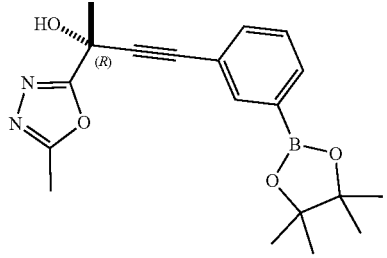

The title compound was prepared using conditions analogous to those described for the preparation of Intermediate 4 utilizing 2-(3-iodophenyl)-4,4,5,5-tetramethyl-1,3,2-dioxaborolane and Intermediate 14 [(R)-2-(5-methyl-1,3,4-oxadiazol-2-yl)but-3-yn-2-ol]. MS (ESI): mass calcd. for $C_{19}H_{23}BN_2O_4$, 354.18; m/z. found, 355.1 $[M+H]^+$. $^1H$ NMR (400 MHz, CDCl$_3$) δ 7.90 (br s, 1H), 7.74-7.76 (m, 1H), 7.50-7.55 (m, 1H), 7.32 (t, J=7.6 Hz, 1H), 6.14 (br s, 1H), 2.58 (s, 3H), 2.04 (s, 3H), 1.34 (s, 12H).

Intermediate 56: 6-Bromopyrido[2,3-d]pyrimidin-4-amine

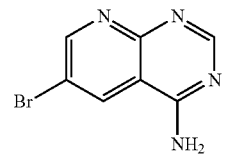

Two side-by-side reactions were conducted in a 20 mL sealable vials each containing 6-bromo-4-chloropyrido[2,3- d]pyrimidine (505 mg, 2.07 mmol) and ammonia (6 mL, 7 N in MeOH). The vials were sealed and placed in a pre-heated aluminum mantle at 100° C. After 20 min, the resulting mixtures were cooled, combined, and diluted with ethyl acetate (30 mL). The resulting white solids were collected by filtration, washed with Et₂O (30 mL) and dried to afford 6-bromopyrido[2,3-d]pyrimidin-4-amine (844 mg, 91%) as a white solid. MS (ESI): mass calcd. for $C_7H_5BrN_4$ 225.05 m/z found 226.95 [M+H]⁺. ¹H NMR (400 MHz, DMSO-$d_6$) δ 9.10-8.97 (m, 2H), 8.56 (s, 1H), 8.23 (br s, 2H).

Intermediate 57:
6-Bromo-8-methylquinazolin-4-amine

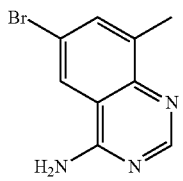

Step A: 6-Bromo-8-iodoquinazolin-4(3H)-one. A suspension of methyl 2-amino-5-bromo-3-iodobenzoate (2.04 g, 5.73 mmol) and ammonium formate (0.70 g, 11.1 mmol) in formamide (7 mL) was heated in a microwave reactor for 30 min at 200° C. The mixture was then diluted with H₂O (100 mL) and briefly sonicated. The resulting solid was isolated by filtration, washed with H₂O (25 mL×2), and dried to afford 6-bromo-8-iodoquinazolin-4(3H)-one (1.61 g, 80%). MS (ESI): mass calcd. for $C_8H_4BrIN_2O$, 349.86; m/z. found, 351.0 [M+H]⁺. ¹H NMR (400 MHz, DMSO-$d_6$) δ 12.64 (br s, 1H), 8.51 (d, J=2.2 Hz, 1H), 8.25 (s, 1H), 8.19 (d, J=2.2 Hz, 1H).

Step B: 6-Bromo-4-chloro-8-iodoquinazoline. A suspension of 6-bromo-8-iodoquinazolin-4(3H)-one (1.14 g, 3.23 mmol) in phosphoryl chloride (10 mL) was cooled to 0° C. and treated with DIPEA (0.7 mL, 4.06 mmol). The mixture was warmed to rt and then heated in a microwave reactor for 1 h at 120° C. After which time, the mixture was concentrated to dryness and the residue was purified FCC to afford 6-bromo-4-chloro-8-iodoquinazoline (0.93 g, 78%) as a white solid. MS (ESI): mass calcd. for $C_8H_3BrClIN_2$, 367.82; m/z. found, 368.9 [M+H]⁺. ¹H NMR (400 MHz, DMSO-$d_6$) δ 9.22 (s, 1H), 8.85 (d, J=2.0 Hz, 1H), 8.45 (d, J=2.0 Hz, 1H).

Step C: 6-Bromo-N-(2,4-dimethoxybenzyl)-8-iodoquinazolin-4-amine. 6-Bromo-N-(2,4-dimethoxybenzyl)-8-iodoquinazolin-4-amine was prepared using conditions analogous to those described in Step D of Intermediate 42 utilizing 6-bromo-4-chloro-8-iodoquinazoline. MS (ESI): mass calcd. for $C_{17}H_{15}BrIN_3O_2$, 498.94; m/z. found, 500.0 [M+H]⁺. ¹H NMR (400 MHz, DMSO-$d_6$) δ 8.80 (t, J=5.3 Hz, 1H), 8.70 (d, J=1.9 Hz, 1H), 8.58-8.44 (m, 2H), 7.11 (d, J=8.3 Hz, 1H), 6.58 (d, J=2.3 Hz, 1H), 6.48-6.42 (m, 1H), 4.64 (d, J=5.3 Hz, 2H), 3.82 (s, 3H), 3.74 (s, 3H).

Step D: 6-Bromo-N-(2,4-dimethoxybenzyl)-8-methylquinazolin-4-amine. In a 20 mL scintillation vial were added 6-bromo-N-(2,4-dimethoxybenzyl)-8-iodoquinazolin-4-amine (0.16 g, 0.32 mmol), Cs₂CO₃, and Pd(dppf)Cl₂ (0.03 g, 0.05 mmol). The vial was sealed with a septum, the atmosphere was evacuated, purged with N₂ (3×) and the vial was charged with dry 1,4-dioxane (3 mL) followed by trimethylboroxine (0.05 mL, 0.35 mmol). The vial was then placed in a heating block that had been pre-heated at 100° C. and allowed to stir. After 1 h, additional trimethylboroxine (0.04 g) was added and the resulting mixture stirred for an additional 30 min. The resulting mixture was then cooled to rt, diluted with CH₂Cl₂ (10 mL), and filtered through diatomaceous earth. The filtrate was concentrated to dryness and purified via FCC to yield 6-bromo-N-(2,4-dimethoxybenzyl)-8-methylquinazolin-4-amine (97 mg, 78%). MS (ESI): mass calcd. for $C_{18}H_{18}BrN_3O_2$, 387.06; m/z. found, 388.1 [M+H]⁺. ¹H NMR (400 MHz, DMSO-$d_6$) δ 8.59 (t, J=5.4 Hz, 1H), 8.55-8.43 (m, 2H), 7.80 (s, 1H), 7.09 (d, J=8.3 Hz, 1H), 6.58 (d, J=2.3 Hz, 1H), 6.47-6.42 (m, 1H), 4.62 (d, J=5.4 Hz, 2H), 3.82 (s, 3H), 3.73 (s, 3H), 2.55 (s, 3H).

Step E: 6-Bromo-8-methylquinazolin-4-amine. 6-Bromo-8-methylquinazolin-4-amine was prepared using conditions analogous to those described in Step E of Intermediate 42 utilizing 6-bromo-N-(2,4-dimethoxybenzyl)-8-methylquinazolin-4-amine. MS (ESI): mass calcd. for $C_9H_8BrN_3$, 236.99; m/z. found, 238.0 [M+H]⁺. ¹H NMR (400 MHz, DMSO-$d_6$) δ 8.44 (s, 1H), 8.34 (s, 1H), 7.96-7.70 (m, 3H), 2.54 (s, 3H).

Intermediate 58:
6-Chloropyrido[3,4-d]pyrimidin-4-amine

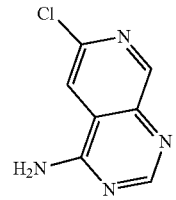 [SMILES: Nc1ncnc2cnc(Cl)cc12]

To a sealed vial containing 4,6-dichloropyrido[3,4-d]pyrimidine (200 mg, 1.00 mmol) and DCE (2.5 mL), was added NH₃ (1.0 mL, 7M in MeOH). The vial was heated at 60° C. for 2 h. After which time additional NH₃ (1.0 mL, 7M in MeOH) was added and the mixture was heated at 66° C. After 1 h, the mixture was cooled to rt and the resulting solid was collected by filtration to afford 6-chloropyrido[3,4-d]pyrimidin-4-amine (176 mg, 97%) as a beige solid. MS (ESI): mass calcd. For $C_7H_5ClN_4$, 180.02; m/z found, 181.1 [M+H]⁺. ¹H NMR (400 MHz, DMSO-$d_6$) δ 8.93 (s, 1H), 8.53 (s, 1H), 8.37-8.31 (m, 1H), 8.26 (s, 2H).

Intermediate 59:
6-Bromo-8-methoxyquinazolin-4-amine

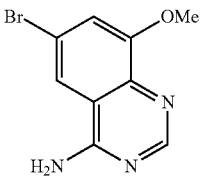 [SMILES: COc1cc(Br)cc2c(N)ncnc12]

Step A: Methyl 2-amino-5-bromo-3-methoxybenzoate. To a 100 mL round-bottomed flask were added methyl 2-amino-3-methoxybenzoate (2.6 g, 11 mmol) and TFA (20 mL). N-bromosuccinimide (2.2 g, 12 mmol) was then added in one portion at rt. After 30 min, the resulting mixture was concentrated to dryness, the residue was dissolved in DCM (100 mL) and washed with saturated aqueous NaHCO$_3$ (100 mL×2). The organic layer was dried (MgSO$_4$), filtered, and concentrated to dryness. The resulting residue was purified by FCC to yield methyl 2-amino-5-bromo-3-methoxybenzoate (2.1 g, 61%). MS (ESI): mass calcd. for C$_9$H$_{10}$BrNO$_3$, 258.98; m/z found, 260.0 [M+H]$^+$. $^1$H NMR (400 MHz, DMSO-d$_6$) δ 7.43 (d, J=2.2 Hz, 1H), 7.10 (d, J=2.2 Hz, 1H), 6.49 (br s, 2H), 3.85 (s, 3H), 3.80 (s, 3H).

Step B: 6-Bromo-8-methoxyquinazolin-4(3H)-one. 6-Bromo-8-methoxyquinazolin-4(3H)-one was prepared using conditions analogous to those described in Step A of Intermediate 57, utilizing methyl 2-amino-5-bromo-3-methoxybenzoate. MS (ESI): mass calcd. for C$_9$H$_7$BrN$_2$O$_2$, 253.97; m/z. found, 255.0 [M+H]$^+$.

Step C: 6-bromo-4-chloro-8-methoxyquinazoline. A sealable vial was charged with 6-bromo-8-methoxyquinazolin-4(3H)-one (0.49 g, 1.61 mmol) and phosphoryl chloride (5 mL). The resulting mixture was heated in a microwave reactor at 120° C. After 1 h, the resulting mixture was cooled to rt and purified by FCC to afford 6-bromo-4-chloro-8-methoxyquinazoline (75 mg, 17%) as a white solid. MS (ESI): mass calcd. for C$_9$H$_6$BrClN$_2$O, 271.94; m/z. found, 273.0 [M+H]$^+$. $^1$H NMR (400 MHz, CDCl$_3$) δ 9.07 (s, 1H), 8.01 (d, J=1.9 Hz, 1H), 7.37 (d, J=1.8 Hz, 1H), 4.11 (s, 3H).

Step D: 6-Bromo-8-methoxyquinazolin-4-amine. 6-Bromo-8-methoxyquinazolin-4-amine was prepared using conditions analogous to those described in Step B of Example 40 utilizing 6-bromo-4-chloro-8-methoxyquinazoline at 80° C. MS (ESI): mass calcd. for C$_9$H$_8$BrN$_3$O, 252.99; m/z. found, 254.0 [M+H]$^+$.

Intermediate 60: 2-(3-Iodophenyl)thiazolo[4,5-c]pyridin-4-amine

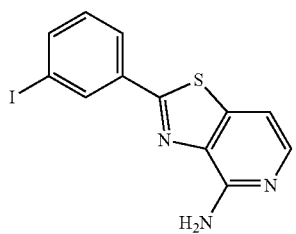

Step A: N-(4-Chloropyridin-3-yl)-3-iodobenzamide. A suspension of 4-chloropyridin-3-amine (0.25 g, 1.94 mmol) in THF (4 mL) was treated with DIPEA (1 mL, 5.80 mmol) followed by 3-iodobenzoyl chloride (0.30 mL, 2.18 mmol). After 30 min MeOH (5 mL) was added and the resulting mixture was concentrated to dryness. The residue was triturated with MeCN (10 mL) and briefly sonicated. The resulting solid was isolated by filtration and dried to afford N-(4-chloropyridin-3-yl)-3-iodobenzamide (0.36 g, 52%) as a white solid. MS (ESI): mass calcd. for C$_{12}$H$_8$ClIN$_2$O, 357.94; m/z. found, 359.0 [M+H]$^+$. $^1$H NMR (400 MHz, DMSO-d$_6$) δ 10.48 (s, 1H), 8.68 (s, 1H), 8.46 (d, J=5.3 Hz, 1H), 8.35 (s, 1H), 8.01 (d, J=7.8 Hz, 2H), 7.70 (d, J=5.3 Hz, 1H), 7.38 (t, J=7.8 Hz, 1H).

Step B: 2-(3-Iodophenyl)thiazolo[4,5-c]pyridine. A suspension of N-(4-chloropyridin-3-yl)-3-iodobenzamide (0.25 g, 0.68 mmol) in o-xylenes (5 mL) was treated with 2,4-bis(4-methoxyphenyl)-2,4-dithioxo-1,3,2,4-dithiadiphosphetane (0.21 g, 0.49 mmol) and then the reaction mixture was heated at 110° C. After 13 h, the resulting mixture was cooled to rt and concentrated to dryness. The resulting residue was purified by FCC to yield 2-(3-iodophenyl)thiazolo[4,5-c]pyridine (173 mg, 75%). MS (ESI): mass calcd. for C$_{12}$H$_7$IN$_2$S, 337.94; m/z. found, 339.0 [M+H]$^+$. $^1$H NMR (400 MHz, DMSO-d$_6$) δ 9.35 (s, 1H), 8.56 (d, J=5.4 Hz, 1H), 8.46 (t, J=1.6 Hz, 1H), 8.32-8.23 (m, 1H), 8.14 (d, J=7.8 Hz, 1H), 8.00 (d, J=8.3 Hz, 1H), 7.41 (t, J=7.8 Hz, 1H).

Step C: 2-(3-Iodophenyl)thiazolo[4,5-c]pyridine 5-oxide. A homogeneous solution of 2-(3-iodophenyl)thiazolo[4,5-c]pyridine (0.16 g, 0.47 mmol) in CHCl$_3$ (5 mL) was treated with meta-chloroperoxybenzoic acid (0.13 g, 0.54 mmol) in one portion at rt. After 1 h, additional meta-chloroperoxybenzoic acid (0.10 g, 0.41 mmol) was added and the mixture allowed to stir. After 1 h, the mixture was diluted with CH$_2$Cl$_2$ (30 mL) and washed with saturated aqueous NaHCO$_3$ (25 mL) followed by brine (25 mL×2). The organic layer was dried (MgSO$_4$), filtered, and concentrated to dryness. The residue was suspended in MeCN (10 mL) and briefly sonicated. The resulting solid was isolated by filtration and dried to afford 2-(3-iodophenyl)thiazolo[4,5-c]pyridine 5-oxide (0.15 g, 70%) which was used without further purification. MS (ESI): mass calcd. for C$_{12}$H$_7$IN$_2$OS, 353.93; m/z. found, 355.0 [M+H]$^+$. $^1$H NMR (400 MHz, DMSO-d$_6$) δ 9.09 (s, 1H), 8.43 (s, 1H), 8.33-8.28 (m, 1H), 8.24 (d, J=7.0 Hz, 1H), 8.11 (d, J=7.8 Hz, 1H), 8.01 (d, J=7.8 Hz, 1H), 7.41 (t, J=7.8 Hz, 1H).

Step D: 4-Chloro-2-(3-iodophenyl)thiazolo[4,5-c]pyridine. A suspension of 2-(3-iodophenyl)thiazolo[4,5-c]pyridine 5-oxide (0.13 g, 0.29 mmol) in phosphoryl chloride (3 mL) was stirred at rt. After 30 min, the resulting mixture was concentrated to dryness and purified by FCC to yield 4-chloro-2-(3-iodophenyl)thiazolo[4,5-c]pyridine (71 mg, 65%) as a white solid. MS (ESI): mass calcd. for C$_{12}$H$_6$ClIN$_2$S, 371.90; m/z. found, 372.9 [M+H]$^+$. $^1$H NMR (400 MHz, CDCl$_3$) δ 8.49 (t, J=1.7 Hz, 1H), 8.33 (d, J=5.4 Hz, 1H), 8.10-8.05 (m, 1H), 7.92-7.86 (m, 1H), 7.81 (d, J=5.4 Hz, 1H), 7.30-7.24 (m, 1H).

Step E: N-(2,4-Dimethoxybenzyl)-2-(3-iodophenyl)thiazolo[4,5-c]pyridin-4-amine. N-(2,4-Dimethoxybenzyl)-2-(3-iodophenyl)thiazolo[4,5-c]pyridin-4-amine was prepared using conditions analogous to those described in Step D of Intermediate 42 utilizing 4-chloro-2-(3-iodophenyl)thiazolo[4,5-c]pyridine. MS (ESI): mass calcd. for C$_{21}$H$_{18}$IN$_3$O$_2$S, 503.02; m/z. found, 504.1 [M+H]$^+$. $^1$H NMR (400 MHz, CDCl$_3$) δ 8.39 (t, J=1.6 Hz, 1H), 8.03 (d, J=5.7 Hz, 1H), 7.95-7.90 (m, 1H), 7.80-7.75 (m, 1H), 7.33 (d, J=8.3 Hz, 1H), 7.19 (t, J=7.9 Hz, 1H), 7.03 (d, J=5.7 Hz, 1H), 6.50 (d, J=2.3 Hz, 1H), 6.48-6.43 (m, 1H), 6.25 (t, J=5.4 Hz, 1H), 4.77 (d, J=5.7 Hz, 2H), 3.88 (s, 3H), 3.81 (s, 3H).

Step F: 2-(3-Iodophenyl)thiazolo[4,5-c]pyridin-4-amine. 2-(3-Iodophenyl)thiazolo[4,5-c]pyridin-4-amine was prepared using conditions analogous to those described in Step E of Intermediate 42 utilizing N-(2,4-dimethoxybenzyl)-2-(3-iodophenyl)thiazolo[4,5-c]pyridin-4-amine. MS (ESI): mass calcd. for C$_{12}$H$_8$IN$_3$S, 352.95; m/z. found, 354.0 [M+H]$^+$.

Intermediate 61:
7-(3-Iodophenyl)-2,6-naphthyridin-1(2H)-one

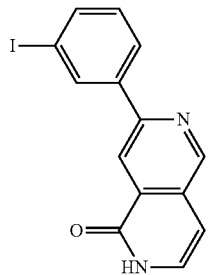 [SMILES: O=c1[nH]ccc2cnc(-c3cccc(I)c3)cc12]

Step A: 2-(Benzyloxy)-5-bromopyridine. To a 20 L 4-necked round-bottomed flask were added 5-bromopyridin-2-ol (500 g, 2.87 mol), (bromomethyl)benzene (500 g, 2.92 mol, 1.02 equiv), THF (7.5 L) and Ag$_2$CO$_3$ (475 g, 1.72 mol) under a nitrogen atmosphere. The resulting mixture was stirred for overnight at 65° C. The mixture was allowed to cool to rt, filtered, and filtrate was concentrated to dryness. The resulting residue was triturated with petroleum ether (1 L). The resulting solid was collected by filtration and dried to afford 2-(benzyloxy)-5-bromopyridine (456 g, 60.1%) as a brown solid. MS (ESI): mass calcd. for C$_{12}$H$_{10}$BrNO, 262.9; m/z. found, 263.9 [M+H]$^+$.

Step B: 2-(Benzyloxy)-5-bromoisonicotinaldehyde. To a 10 L 4-necked round-bottomed flask were added 2-(benzyloxy)-5-bromopyridine (456 g, 1.73 mol) and THF (4.5 L) under a nitrogen atmosphere. To resulting mixture was added LDA (1.04 L, 2 M in THF/hexane) dropwise at −78° C. The resulting mixture was stirred for additional 1 h at −78° C. and N,N-dimethylformamide (139 g, 1.89 mol) was added dropwise at −78° C. The resulting mixture was stirred for additional 0.5 h at −78° C. The reaction mixture was warmed to 0° C. and saturated aqueous NaHCO$_3$ (3 L) was added. The aqueous layer was extracted with ethyl acetate (2.5 L×2). The combined organic layer was washed with brine (1 L), dried with Na$_2$SO$_4$, filtered, and concentrated to dryness to afford 2-(benzyloxy)-5-bromoisonicotinaldehyde (408 g, 81%) as a brown solid. MS (ESI): mass calcd. for C$_{13}$H$_{10}$BrNO$_2$, 290.9; m/z. found, 291.9 [M+H]$^+$.

Step C: 2-(Benzyloxy)-5-bromoisonicotinic acid. To a 3 L 4-necked round-bottomed flask were added 2-(benzyloxy)-5-bromopyridine-4-carbaldehyde (408 g, 1.39 mol) and formic acid (1.6 L) at 0° C. To the resulting mixture was added hydrogen peroxide (473 g, 4.17 mol, 30%) dropwise. The resulting mixture was stirred for an additional 3 h at rt. The resulting mixture was diluted with water (3 L) and the resulting solids were collected by filtration to afford 2-(benzyloxy)-5-bromoisonicotinic acid (275 g, 64%) as an off-white solid. MS (ESI): mass calcd. for C$_{13}$H$_{10}$BrNO$_3$, 306.9; m/z found, 307.9 [M+H]$^+$.

Step D: 2-(Benzyloxy)-5-bromoisonicotinamide. Into a 5 L 4-necked round-bottomed flask were added 2-(benzyloxy)-5-bromopyridine-4-carboxylic acid (275 g, 892 mmol) and THF (2.75 L) at 0° C. under a nitrogen atmosphere. To the above mixture was added TEA (135 g, 1.38 mol), followed by addition of i-BCF (158 g, 1.16 mol) dropwise over 15 min at 0-10° C. The resulting mixture was stirred for additional 0.5 h at 0° C. To the above mixture was added ammonium hydroxide (275 mL, 3.85 mol, 30%) in one portion. The resulting mixture was stirred for additional 15 min at rt and then concentrated to dryness. The resulting solid was collected by filtration, washed with water (1 L) and dried to afford 2-(benzyloxy)-5-bromoisonicotinamide (190 g, 69%) as an off-white solid. MS (ESI): mass calcd. for C$_{13}$H$_{11}$BrN$_2$O$_2$, 306.0; m/z. found, 306.9 [M+H]$^+$.

Step E: (E)-2-(Benzyloxy)-5-(2-ethoxyvinyl)isonicotinamide. Into a 3 L 4-necked round-bottomed flask were added 2-(benzyloxy)-5-bromopyridine-4-carboxamide (190 g, 619 mmol), 2-[(E)-2-ethoxyethenyl]-4,4,5,5-tetramethyl-1,3,2-dioxaborolane (245 g, 1.24 mol), Na$_2$CO$_3$ (131 g, 1.24 mol), EtOH (630 mL), toluene (630 mL), and H$_2$O (630 mL), under nitrogen atmosphere. To the resulting mixture was added Pd(PPh$_3$)$_4$ (50.04 g, 43.3 mmol) and the reaction mixture was heated at 70° C. After 12 h, the resulting mixture was cooled to rt and concentrated to dryness. The residue was diluted with ethyl acetate (3 L) and the organic layer was washed with water (2 L×2). The organic layer was dried with Na$_2$SO$_4$, filtered, and concentrated to dryness. The residue was purified by FCC (1:0 to 1:1, petroleum ether/ethyl acetate) to afford (E)-2-(benzyloxy)-5-(2-ethoxyvinyl)isonicotinamide (112 g, 61%) as an off-white solid. MS (ESI): mass calcd. for C$_{17}$H$_{18}$N$_2$O$_3$, 298.1; m/z. found, 299.1 [M+H]$^+$.

Step F: 7-(Benzyloxy)-2,6-naphthyridin-1(2H)-one. To a 5 L 4-necked round-bottomed flask were added (E)-2-(benzyloxy)-5-(2-ethoxyvinyl)isonicotinamide (112 g, 375 mmol) and toluene (2.8 L) under nitrogen atmosphere. To the resulting mixture was added TsOH·H$_2$O (7.14 g, 37.5 mmol) and the reaction mixture was heated to 90° C. After 4 h, the mixture was concentrated and purified by trituration with 5:1 petroleum ether/ethyl acetate (300 mL) to afford 7-(benzyloxy)-2,6-naphthyridin-1(2H)-one (84 g, 89%) as an off-white solid. MS (ESI): mass calcd. for C$_{15}$H$_{12}$N$_2$O$_2$, 252.1; m/z. found, 253.2 [M+H]$^+$.

Step G: 7-(Benzyloxy)-1-methoxy-2,6-naphthyridine. To a 5 L 4-necked round-bottomed flask were added 7-(benzyloxy)-1,2-dihydro-2,6-naphthyridin-1-one (84 g, 332 mmol), CHCl$_3$ (2.5 L), MeI (189 g, 1.31 mol) and Ag$_2$CO$_3$ (101 g, 366 mmol) under nitrogen atmosphere. The resulting mixture was heated at 40° C. under darkness. After 4 h, resulting mixture was cooled and filtered through a pad of diatomaceous earth. The filtrate was concentrated and the residue was purified by FCC (1:0 to 3:1, petroleum ether/ethyl acetate) to afford 7-(benzyloxy)-1-methoxy-2,6-naphthyridine (25 g, 28%) as an off-white solid. MS (ESI): mass calcd. for C$_{16}$H$_{14}$N$_2$O$_2$, 266.1; m/z. found, 267.2 [M+H]$^+$.

Step H: 5-Methoxy-2,6-naphthyridin-3-ol. To a 1 L 3-necked round-bottom flask were added 7-(benzyloxy)-1-methoxy-2,6-naphthyridine (25 g, 93.88 mmol) and trifluoroacetic acid (600 mL) under nitrogen atmosphere. The resulting mixture was stirred overnight at room temperature. The mixture cooled to 0-5° C. The pH of the mixture was adjusted to pH 8 with saturated NaHCO$_3$ (aq.). The precipitated solids were collected by filtration, dried under infrared light. This resulted in 5-methoxy-2,6-naphthyridin-3-ol (12.3 g, 74.37%) as an off-white solid. MS (ESI): mass calcd. for C$_9$H$_8$N$_2$O$_2$, 176.1; m/z. found, 177.2 [M+H]$^+$.

Step I: 5-Methoxy-2,6-naphthyridin-3-yl trifluoromethanesulfonate. To a 1 L 3-necked round-bottomed flask were added 5-methoxy-2,6-naphthyridin-3-ol (12.3 g, 69.8 mmol), DCM (500 mL) and TEA (14.0 g, 139 mmol) at 0° C. under nitrogen atmosphere. To the resulting mixture was added Tf$_2$O (24 g, 84 mmol, 1.2) dropwise at 0° C. After 2 h, the resulting mixture was warmed to rt and washed with water (200 mL). The organic layer was dried with Na$_2$SO$_4$, filtered, and concentrated to dryness to afford 5-methoxy-2,6-naphthyridin-3-yl trifluoromethanesulfonate (15.5 g, crude) as a brown oil which was used directly in the next step. MS (ESI): mass calcd. for $C_{10}H_7F_3N_2O_4S$, 308.0; m/z found, 309.1 $[M+H]^+$.

Step J: 3-(5-Methoxy-2,6-naphthyridin-3-yl)aniline. Into a 500 mL 3-necked round-bottomed flask were added 5-methoxy-2,6-naphthyridin-3-yl trifluoromethanesulfonate (16 g, 50 mmol), (3-aminophenyl)boronic acid (10 g, 75 mmol), $K_2CO_3$ (21 g, 151 mmol), dioxane (225 mL), $H_2O$ (75 mL) and $Pd(PPh_3)_4$ (2.9 g, 2.5 mmol) under nitrogen atmosphere. The resulting mixture was heated at 80° C. After 12 h, resulting mixture was cooled to rt and concentrated to dryness. The resulting residue was diluted with water (300 mL) and extracted with ethyl acetate (100 mL×3). The combined organic layers were washed with water (100 mL), dried over anhydrous $Na_2SO_4$, filtered, and concentrated to dryness. The residue was purified by FCC (1:1, petroleum ether/ethyl acetate) to afford 3-(5-methoxy-2,6-naphthyridin-3-yl)aniline (12.3 g, 97.3%) as an off-white solid. MS (ESI): mass calcd. for $C_{15}H_{13}N_3O$, 251.1; m/z. found, 252.1 $[M+H]^+$.

Step K: 7-(3-Iodophenyl)-1-methoxy-2,6-naphthyridine. To a 250 mL round-bottomed flask were added 3-(5-methoxy-2,6-naphthyridin-3-yl)aniline (12 g, 49 mmol) and TFA (100 mL). The resulting solution was concentrated to dryness. To the residue was added MeCN (180 mL) followed by $HBF_4 \cdot Et_2O$ (9.5 g, 59 mmol) and then tert-butyl nitrite (6.1 g, 59 mmol) at 5° C. under nitrogen atmosphere. The resulting mixture was stirred for additional 30 min at rt. After which time, the resulting mixture was diluted with diethyl ether (450 mL) and the precipitated solids were collected by filtration. The resulting solid was added into a 250 mL 3-necked round-bottomed flask followed by TBAI (19 g, 53 mmol) and $CH_3CN$ (100 mL) at rt. The resulting mixture was stirred for additional 0.5 h at rt, before concentrating to dryness. The resulting residue was diluted with water (200 mL) and extracted with ethyl acetate (200 mL). The organic layers were dried over anhydrous $Na_2SO_4$, filtered, and concentrated to dryness. The residue was purified by FCC (90:5:5, petroleum ether/ethyl acetate/DCM) to afford 7-(3-iodophenyl)-1-methoxy-2,6-naphthyridine (13 g, 73%) as an off-white solid. MS (ESI): mass calcd. for $C_{15}H_{11}IN_2O$, 361.9; m/z. found, 363.1 $[M+H]^+$.

Step L: 7-(3-iodophenyl)-2,6-naphthyridin-1(2H)-one. To a 1 L 3-necked round-bottomed flask, purged and maintained with an inert atmosphere of nitrogen, was added 7-(3-iodophenyl)-1-methoxy-2,6-naphthyridine (13 g, 36 mmol), 1,4-dioxane (200 mL), and HCl/dioxane (200 mL, 6.58 mol). The resulting solution was heated at 40° C. After 12 h, the resulting mixture was concentrated. The resulting residue was diluted with water (200 mL) and the pH of the solution was adjusted to 8 with saturated aqueous $NaHCO_3$. The resulting solids were collected by filtration and recrystallized from DMF (120 mL) and water (50 mL) to afford 7-(3-iodophenyl)-2,6-naphthyridin-1(2H)-one (5.8 g, 45%) as a yellow solid. MS (ESI): mass calcd. for $C_{14}H_9IN_2O$, 347.9; m/z. found, 349.0 $[M+H]^+$. $^1H$ NMR (300 MHz, DMSO-$d_6$) δ 11.71 (s, 1H), 9.17 (s, 1H), 8.53 (t, J=1.8 Hz, 1H), 8.47 (s, 1H), 8.18 (dt, J=8.0, 1.3 Hz, 1H), 7.81 (dt, J=7.9, 1.2 Hz, 1H), 7.40-7.28 (m, 2H), 6.73 (d, J=7.0 Hz, 1H).

Intermediate 62:
7-(3-Iodophenyl)-2,6-naphthyridin-1-amine

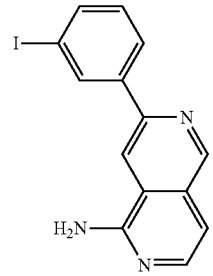 [SMILES: Nc1nccc2cnc(-c3cccc(I)c3)cc12]

Step A: 1-Chloro-7-(3-iodophenyl)-2,6-naphthyridine. To a microwave vial were added $POCl_3$ (3.0 mL, 32 mmol) and Intermediate 61 [7-(3-iodophenyl)-2,6-naphthyridin-1(2H)-one (1.0 g, 2.9 mmol)]. The flask was sealed and irradiated in a microwave reactor at 100° C. for 30 min two times. The reaction mixture was diluted with DCM (30 mL) and transferred to a round bottomed flask, cooled in an ice bath, and slowly quenched with ice. The pH was adjusted to pH 8 with saturated aqueous sodium bicarbonate. The organic layer was separated and concentrated to afford 1-chloro-7-(3-iodophenyl)-2,6-naphthyridine (1.14 g) that was used without purification. MS (ESI): mass calcd. for $C_{14}H_8ClN_2$, 366.59; m/z. found, 366.9 $[M+H]^+$. $^1H$ NMR (500 MHz, DMSO-$d_6$) δ 9.62 (d, J=1.0 Hz, 1H), 8.65-8.61 (m, 1H), 8.53 (d, J=5.5 Hz, 1H), 8.51-8.46 (m, 1H), 8.31-8.23 (m, 1H), 8.13 (dd, J=5.6, 0.9 Hz, 1H), 7.91-7.82 (m, 1H), 7.37 (t, J=7.8 Hz, 1H).

Step B: N-(2,4-Dimethoxybenzyl)-7-(3-iodophenyl)-2,6-naphthyridin-1-amine: N-(2,4-Dimethoxybenzyl)-7-(3-iodophenyl)-2,6-naphthyridin-1-amine was prepared using conditions analogous to those described in Step D of Intermediate 42 utilizing 1-chloro-7-(3-iodophenyl)-2,6-naphthyridine to afford it (1.3 g, 89%) as a colorless solid. MS (ESI): mass calcd. for $C_{23}H_{20}IN_3O_2$, 497.34; m/z. found, 498.0 $[M+H]^+$. $^1H$ NMR (500 MHz, DMSO-$d_6$) δ 9.21 (d, J=0.8 Hz, 1H), 8.82 (t, J=1.0 Hz, 1H), 8.62 (t, J=1.8 Hz, 1H), 8.33-8.25 (m, 1H), 8.17 (t, J=5.7 Hz, 1H), 8.00 (d, J=5.7 Hz, 1H), 7.84-7.73 (m, 1H), 7.34 (t, J=7.9 Hz, 1H), 7.15 (d, J=8.4 Hz, 1H), 7.05 (dd, J=5.8, 0.8 Hz, 1H), 6.59 (d, J=2.4 Hz, 1H), 6.45 (dd, J=8.4, 2.4 Hz, 1H), 4.68 (d, J=5.5 Hz, 2H), 3.84 (s, 3H), 3.73 (s, 3H).

Step C: 7-(3-Iodophenyl)-2,6-naphthyridin-1-amine. 7-(3-Iodophenyl)-2,6-naphthyridin-1-amine was prepared using conditions analogous to those described in Step E of Intermediate 42 utilizing N-(2,4-dimethoxybenzyl)-7-(3-iodophenyl)-2,6-naphthyridin-1-amine to afford 7-(3-iodophenyl)-2,6-naphthyridin-1-amine (1.2 g, crude) that was 90% pure by $^1H$ NMR and used without further purification. MS (ESI): mass calcd. for $C_{14}H_{10}IN_3$, 347.16; m/z. found, 348.0 $[M+H]^+$. $^1H$ NMR (500 MHz, DMSO-$d_6$) δ 9.23 (d, J=0.8 Hz, 1H), 8.73 (s, 1H), 8.62 (t, J=1.7 Hz, 1H), 8.28 (d, J=7.9 Hz, 1H), 7.96 (d, J=5.8 Hz, 1H), 7.80 (d, J=7.8 Hz, 1H), 7.48 (s, 2H), 7.35 (t, J=7.8 Hz, 1H), 7.09 (d, J=5.8 Hz, 1H).

Intermediate 63: 4-Amino-6-bromoquinazoline-8-carbonitrile

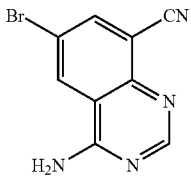

Step A: 6-Bromo-8-iodoquinazolin-4-amine. 6-Bromo-8-iodoquinazolin-4-amine was prepared using conditions analogous to those described in Step B of Example 40 utilizing 6-bromo-4-chloro-8-iodoquinazoline. MS (ESI): mass calcd. for $C_8H_5BrIN_3$, 348.87; m/z. found, 350.0 $[M+H]^+$.

Step B: 4-Amino-6-bromoquinazoline-8-carbonitrile. To a vial were added 6-bromo-8-iodoquinazolin-4-amine (0.24 g, 0.69 mmol), zinc cyanide (0.04 g, 0.36 mmol), and tetrakis(triphenylphosphine)palladium(0) (0.09 g, 0.08 mmol). The vial was sealed with a septum, the atmosphere was evacuated, and then purged with $N_2$ (3×). The vial was then charged with dry DMF (5 mL), placed in a heating block that had been pre-heated at 100° C., and allowed to stir for 3 min. Afterwards, the resulting mixture was cooled to rt and concentrated to dryness. The resulting residue was triturated with MeCN (10 mL), the solid was isolated by filtration to afford 4-amino-6-bromoquinazoline-8-carbonitrile (133 mg, 67%, contaminated with 4-aminoquinazoline-6,8-dicarbonitrile about 13% w/w) as a white solid. MS (ESI): mass calcd. for $C_9H_5BrN_4$, 247.97; m/z. found, 248.9 $[M+H]^+$.

Intermediate 64: (R)-2-Ethynyl-2-hydroxy-5,5-dimethylcyclopentan-1-one

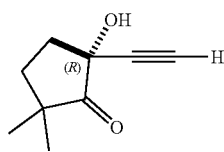

Step A: 2-Methyl-5-oxocyclopent-1-en-1-yl acetate. To a 2 L round-bottomed flask, were placed 2-hydroxy-3-methylcyclopent-2-en-1-one (500 g, 4.45 mol), and acetic anhydride (1.5 L). The resulting solution was heated at 100° C. for 1 h. The resulting mixture was cooled to rt, concentrated to dryness, and the residue was recrystallized from 5:1 petroleum ether/ethyl acetate to afford 2-methyl-5-oxocyclopent-1-en-1-yl acetate (400 g, 58%) as a yellow solid.

Step B: 7-Methyl-1,4-dioxaspiro[4.4]non-6-en-6-yl acetate. Into a 5 L 3-necked round-bottomed flask were placed 2-methyl-5-oxocyclopent-1-en-1-yl acetate (400 g, 2.59 mol), (diethoxymethoxy)ethane (769 g, 5.19 mol), 4-methylbenzene-1-sulfonic acid (223 g, 130 mmol), ethane-1,2-diol (805 g, 1.29 mol), and toluene (2 L). The resulting solution was heated at 110° C. After 4 h, the resulting solution was partitioned with saturated aqueous $NaHCO_3$ (1 L). The resulting mixture was extracted with ethyl acetate (1 L×3). The combined organic layers were washed with brine (1 L) and concentrated to dryness. The residue was purified by FCC (1:1, ethyl acetate/petroleum ether to afford 7-methyl-1,4-dioxaspiro[4.4]non-6-en-6-yl acetate (160 g, 31%) as a yellow solid.

Step C: 7-Methyl-1,4-dioxaspiro[4.4]nonan-6-one. Into a 2 L round-bottomed flask, were placed 7-methyl-1,4-dioxaspiro[4.4]non-6-en-6-yl acetate (160 g, 807 mmol), NaOH (32 g, 800 mmol), and MeOH (1 L). The resulting solution was stirred for 1 h at rt. After which time the solution was partitioned with water (2 L) and extracted with ethyl acetate (1 L×3). The combined organic layers were washed with brine (1 L) and concentrated to dryness. The residue was purified by FCC (1:1, ethyl acetate/petroleum ether to afford 7-methyl-1,4-dioxaspiro[4.4]nonan-6-one. This reaction sequence was repeated twice to provide the title compound (160 g, 63%) as a yellow oil.

Step D: 7,7-Dimethyl-1,4-dioxaspiro[4.4]nonan-6-one. Into a 2 L 3-necked round-bottomed flask, were placed THF (1 L) followed by the addition of NaH (49 g, 1.22 mol, 60%), and 18-crown-6 (27 g, 102 mmol) at 0° C. To the mixture was added 7-methyl-1,4-dioxaspiro[4.4]nonan-6-one (160 g, 1.02 mol) dropwise with stirring. The mixture was stirred for 1 h at rt. To the resulting mixture was added MeI (174 g, 1.22 mol) followed by heating at 65° C. After 2 h, the mixture was cooled to rt and partitioned with saturated aqueous $NH_4Cl$ (1 L). The resulting mixture was extracted with ethyl acetate (500 mL×3). The combined organic layers were concentrated to dryness and purified by FCC (1:5, ethyl acetate/petroleum ether) to afford 7,7-dimethyl-1,4-dioxaspiro[4.4]nonan-6-one (110 g, 63%) as an off-white solid.

Step E: 2-Hydroxy-5,5-dimethylcyclopent-2-en-1-one. Into a 1 L round-bottomed flask were placed 7,7-dimethyl-1,4-dioxaspiro[4.4]nonan-6-one (110 g, 646 mmol) and $H_2SO_4$ (500 mL, 10%). The resulting solution was heated at 80° C. After 1 h, the resulting mixture was cooled with a water/ice bath and diluted with saturated aqueous $NaHCO_3$ (1 L). The resulting mixture was extracted with DCM (500 mL×3), the combined organic layers were washed with brine (500 mL) and concentrated to dryness. The residue was purified by FCC (1:1, ethyl acetate/petroleum ether) to afford 2-hydroxy-5,5-dimethylcyclopent-2-en-1-one 70 g, 86%) as light yellow oil.

Step F: 4,4-Dimethyl-5-oxocyclopent-1-en-1-yl trifluoromethanesulfonate. Into a 2-L round-bottomed flask were placed 2-hydroxy-5,5-dimethylcyclopent-2-en-1-one (70 g, 554 mmol), $Et_3N$ (281 g, 2.77 mol), and DCM (1 L). This was followed by the addition of trifluoromethanesulfonyloxy trifluoromethanesulfonoperoxoate (349 g, 1.11 mol) dropwise with stirring at 0° C. After 2.5 h, water (500 mL) was added, the organic layer was separated, and concentrated to dryness. The residue was purified by FCC (1:10, ethyl acetate/petroleum ether) to afford 4,4-dimethyl-5-oxocyclopent-1-en-1-yl trifluoromethanesulfonate (70 g, 49%) as a yellow oil.

Step G: 5,5-Dimethyl-2-[2-(trimethylsilyl)ethynyl]cyclopent-2-en-1-one. To a 1 L 3-necked round-bottomed flask, purged and maintained with an inert atmosphere of nitrogen, were placed 4,4-dimethyl-5-oxocyclopent-1-en-1-yl trifluoromethanesulfonate (70 g, 271 mmol), dichloropalladium; bis(triphenylphosphane) (9.5 g, 14 mmol), ethynyltrimethylsilane (4.0 g, 407 mmol), $Et_3N$ (5.5 g, 542 mmol), CuI (2.6 g, 14 mmol), and ACN (500 mL). The resulting solution was heated at 60° C. After 2 h, the solids were filtered off and filtrate was concentrated to dryness. The resulting residue was diluted with ethyl acetate (500 mL), washed with water (100 mL×3), and organic layer was concentrated to dryness. The residue was purified by FCC (1:10, ethyl acetate/ petroleum ether) to afford 5,5-dimethyl-2-[2-(trimethylsilyl)ethynyl]cyclopent-2-en-1-one (40 g, 71%) as a yellow solid.

Step H: 2-Hydroxy-5,5-dimethyl-2-[2-(trimethylsilyl)ethynyl]cyclopentan-1-one. Into a 1 L 3-necked round-bottomed flask, were placed 5,5-dimethyl-2-[2-(trimethylsilyl)ethynyl]cyclopent-2-en-1-one (40 g, 194 mmol), IPA (400 mL), and bis(2,4-pentanedionato)cobalt (Co(acac)$_2$, 20 g, 77 mmol). To the resulting mixture was introduced O$_2$ for 1 h. This was followed by the addition of PhSiH$_3$ (42 g, 388 mmol). The resulting solution was stirred at rt. After 16 h, the mixture was partitioned with water (1 L) and the resulting mixture was extracted with ethyl acetate (500 mL×3). The combined organic layers were concentrated to dryness and the residue was purified by FCC (1:10, ethyl acetate/petroleum ether) to afford 2-hydroxy-5,5-dimethyl-2-[2-(trimethylsilyl)ethynyl]cyclopentan-1-one (12 g, 28%) as a light yellow oil Step I: (R)-2-Ethynyl-2-hydroxy-5,5-dimethylcyclopentan-1-one. To a 500 mL round-bottomed flask were placed 2-hydroxy-5,5-dimethyl-2-[2-(trimethylsilyl)ethynyl]cyclopentan-1-one (12 g, 53 mmol), methanol (100 mL), and K$_2$CO$_3$ (7.4 g, 53 mmol). The resulting solution was stirred at rt. After 1 h, the resulting solution was partitioned with water (200 mL). The resulting mixture was extracted with ethyl acetate (200 mL×2) and combined organic layers were concentrated to dryness. The residue was purified by FCC (1:5, ethyl acetate/petroleum ether) to afford racemic 2-ethynyl-2-hydroxy-5,5-dimethylcyclopentan-1-one (3.8 g, 47%) as a yellow solid. The enantiomers were separated by purification by chiral preparative SFC (WHELK-01 (RR) 4.6×10 mm, 3.5 µM; mobile phase, hexane:EtOH=95:5; Detector λ=210 nm) to afford (1.1 g, 29%; >97% ee) of (R)-2-ethynyl-2-hydroxy-5,5-dimethylcyclopentan-1-one as an off-white solid and (S)-2-ethynyl-2-hydroxy-5,5-dimethylcyclopentan-1-one (Intermediate 65, 0.9 g, 24%; >97% ee) as an off-white solid. Data for (R)-2-ethynyl-2-hydroxy-5,5-dimethylcyclopentan-1-one: $^1$H NMR (400 MHz, CDCl$_3$) δ 2.61 (s, 1H), 2.44-2.39 (m, 1H), 2.05-1.85 (m, 3H), 1.27 (s, 3H), 1.15 (s, 3H). [α]$^{20}_D$=−113.5 (c=0.2 in MeOH).

Intermediate 65: (S)-2-Ethynyl-2-hydroxy-5,5-dimethylcyclopentan-1-one

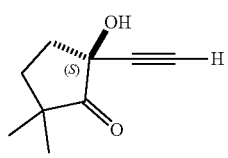

The title compound was prepared using the chiral separation conditions in Step I of Intermediate 64 to afford (S)-2-ethynyl-2-hydroxy-5,5-dimethylcyclopentan-1-one (0.9 g, 24%; >97% ee) as an off-white solid. $^1$H NMR (400 MHz, CDCl$_3$) δ 2.61 (s, 1H), 2.44-2.39 (m, 1H), 2.05-1.85 (m, 3H), 1.27 (s, 3H), 1.15 (s, 3H). [α]$^{20}_D$=+111.7 (c=0.2 in MeOH).

Intermediate 66: (R)-2-Hydroxy-5,5-dimethyl-2-((3-(4,4,5,5-tetramethyl-1,3,2-dioxaborolan-2-yl)phenyl)ethynyl)cyclopentan-1-one

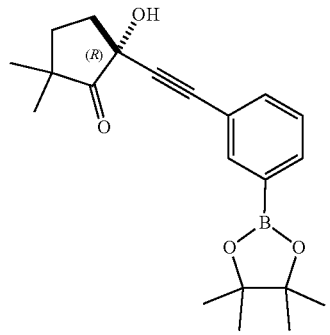

The title compound was prepared using conditions analogous to those described for the preparation of Intermediate 4 utilizing 2-(3-iodophenyl)-4,4,5,5-tetramethyl-1,3,2-dioxaborolane and Intermediate 64 ((R)-2-ethynyl-2-hydroxy-5,5-dimethylcyclopentan-1-one) to afford (R)-2-hydroxy-5,5-dimethyl-2-((3-(4,4,5,5-tetramethyl-1,3,2-dioxaborolan-2-yl)phenyl)ethynyl)cyclopentan-1-one (155 mg, 72%) as a colorless solid. MS (ESI): mass calcd. For C$_{21}$H$_{27}$BO$_4$, 354.25; m/z. found, 372.1 [M+18]$^+$. $^1$H NMR (500 MHz, DMSO-d$_6$) δ 7.69-7.61 (m, 2H), 7.53 (dt, J=7.8, 1.5 Hz, 1H), 7.41 (t, J=7.7 Hz, 1H), 6.44 (s, 1H), 2.32-2.20 (m, 1H), 2.11-1.99 (m, 1H), 1.90-1.75 (m, 2H), 1.30 (s, 12H), 1.11 (s, 3H), 1.07 (s, 3H).

Intermediate 67: (S)-2-Hydroxy-5,5-dimethyl-2-((3-(4,4,5,5-tetramethyl-1,3,2-dioxaborolan-2-yl)phenyl)ethynyl)cyclopentan-1-one

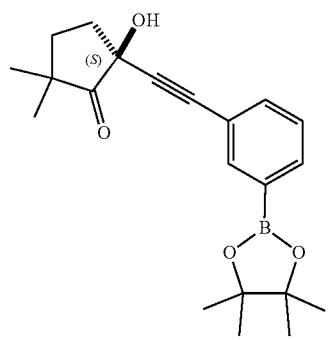

The title compound was prepared using conditions analogous to those described for the preparation of Intermediate 4 utilizing 2-(3-iodophenyl)-4,4,5,5-tetramethyl-1,3,2-dioxaborolane and Intermediate 65 ((S)-2-ethynyl-2-hydroxy-5,5-dimethylcyclopentan-1-one) to afford (S)-2-hydroxy-5,5-dimethyl-2-((3-(4,4,5,5-tetramethyl-1,3,2-dioxaborolan-2-yl)phenyl)ethynyl)cyclopentan-1-one as a colorless solid. MS (ESI): mass calcd. For C$_{21}$H$_{27}$BO$_4$, 354.25; m/z. found, 372.1 [M+18]$^+$. $^1$H NMR (500 MHz, DMSO-d$_6$) δ 7.72-7.61 (m, 2H), 7.54 (dt, J=7.7, 1.5 Hz, 1H), 7.41 (t, J=7.7 Hz, 1H), 6.44 (s, 1H), 2.32-2.19 (m, 1H), 2.11-1.96 (m, 1H), 1.92-1.75 (m, 2H), 1.30 (s, 12H), 1.12 (s, 3H), 1.07 (s, 3H).

Intermediate 68: 6-(3-Iodophenyl)-8-methylpyrido[3,4-d]pyrimidin-4-amine

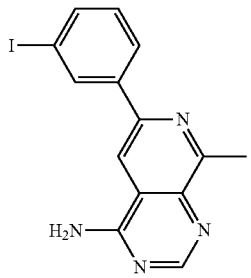 [SMILES: Cc1nc(-c2cccc(I)c2)cc2c(N)ncnc12]

Step A: Ethyl 6-(3-iodophenyl)-2-methyl-3-nitroisonicotinate. To a sealable vial were added ethyl 4-(3-iodophenyl)-2,4-dioxobutanoate (1.00 g, 3.00 mmol), 1-nitroprop-1-en-2-amine (308 mg, 3.0 mmol), and acetic acid (3 mL). The mixture was stirred at 35° C. for 16 hr. After that time the mixture was partitioned with water (20 mL) and ethyl acetate (20 mL). The organic layer was separated, washed with water (20 mL×2), saturated aqueous NaHCO$_3$ (25 mL), and then brine (25 mL). The organic layer was dried over sodium sulfate, filtered, and concentrated to dryness. The residue was purified by FCC (0 to 50%, ethyl acetate/heptane) to afford ethyl 6-(3-iodophenyl)-2-methyl-3-nitroisonicotinate as a white solid (756 mg). MS (ESI): mass calcd. for $C_{15}H_{13}IN_2O_4$, 412.00; m/z. found, 413.1 [M+H]$^+$. $^1$H NMR (400 MHz, CDCl$_3$) δ 8.41 (t, J=1.7 Hz, 1H), 8.04-7.92 (m, 2H), 7.86-7.76 (m, 1H), 7.24 (t, J=7.9 Hz, 1H), 4.42 (q, J=7.1 Hz, 2H), 2.69 (s, 3H), 1.39 (t, J=7.1 Hz, 3H).

Step B: Ethyl 3-amino-6-(3-iodophenyl)-2-methylisonicotinate. To a sealable vial were added ethyl 6-(3-iodophenyl)-2-methyl-3-nitroisonicotinate (365 mg, 0.09), sodium hydrosulfite (544 mg, 2.6 mmol), and ethanol (10 mL), water (2 mL). The mixture was heated at 80° C. After 16 h, additional sodium hydrosulfite (308 mg, 1.7 mmol) was added and heating was continued for 4 h at 80° C. At that time, the mixture was cooled to rt and concentrated to dryness. The residue was partitioned between water (50 mL) and DCM (50 mL). The organic layer was separated and the aqueous layer was extracted with DCM (3×50 mL). The combined organic layers were dried over sodium sulfate, filtered, and concentrated to dryness to provide ethyl 3-amino-6-(3-iodophenyl)-2-methylisonicotinate (330 mg) as a white solid which was used in the next step without further purification. MS (ESI): mass calcd. for $C_{15}H_{151}N_2O_2$, 382.02; m/z. found, 383.1 [M+H]$^+$.

Step C: 6-(3-Iodophenyl)-8-methylpyrido[3,4-d]pyrimidin-4(3H)-one. To a sealable microwave vial were added ethyl 3-amino-6-(3-iodophenyl)-2-methylisonicotinate (330 mg, 0.86 mmol) and formamide (4 mL, 100 mmol). The vial was capped and heated in a microwave reactor at 200° C. for 60 min. After cooling, the mixture was diluted with MeCN (5 mL), the resulting solid was collected by filtration, and washed with MeCN (5 mL). The solid was dried on high vacuum to afford 6-(3-iodophenyl)-8-methylpyrido[3,4-d]pyrimidin-4(3H)-one (243 mg) as a light brown solid. MS (ESI): mass calcd. for $C_{14}H_{10}IN_3O$, 363.00; m/z. found, 364.0 [M+H]$^+$.

Step D: 6-(3-Iodophenyl)-8-methylpyrido[3,4-d]pyrimidin-4-amine. To a sealable vial were added 6-(3-iodophenyl)-8-methylpyrido[3,4-d]pyrimidin-4(3H)-one (127 mg, 0.35 mmol), POCl$_3$ (1.00 mL, 11.0 mmol), and N,N-dimethylaniline (89.0 μL, 0.70 mmol). The vial was capped and heated at 100° C. After 1 h, the mixture was cooled to rt, diluted with DCM (5 mL), and cooled to 0° C. This solution was then added dropwise to NH$_4$OH (28% aq.). Additional MeCN (5 mL) was added, to form an emulsion, and the mixture was stirred at rt. After 16 h, the mixture was partitioned with ethyl acetate (25 mL) and brine (50 mL). The organic layer was separated, and aqueous layer was extracted with ethyl acetate (25 mL×3). The combined organic layers were dried over sodium sulfate, filtered, and concentrated to dryness. The resulting residue was triturated with DCM (about 15 mL) to afford 6-(3-iodophenyl)-8-methylpyrido[3,4-d]pyrimidin-4-amine (92 mg) as a white solid that was used without further purification. MS (ESI): mass calcd. for $C_{14}H_{11}IN_4$, 362.00; m/z. found, 363.0 [M+H]$^+$. $^1$H NMR (400 MHz, CD$_3$OD) δ 8.54 (d, J=1.8 Hz, 1H), 8.48 (s, 1H), 8.39 (s, 1H), 8.14 (d, J=7.9 Hz, 1H), 7.78 (d, J=7.8 Hz, 1H), 7.27 (t, J=7.9 Hz, 1H), 2.93 (s, 3H).

Intermediate 69: (R)-4-(3-(8-((2,4-Dimethoxybenzyl)amino)pyrimido[5,4-d]pyrimidin-2-yl)phenyl)-2-(thiazol-2-yl)but-3-yn-2-ol

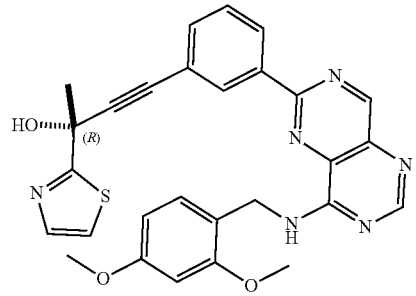

To a microwave vial were added Intermediate 23 [(6-(3-bromophenyl)-N-(2,4-dimethoxybenzyl)pyrimido[5,4-d]pyrimidin-4-amine, 200 mg, 0.442 mmol)], Intermediate 30 [((R)-2-(thiazol-2-yl)but-3-yn-2-ol, 81 mg, 0.53 mmol)], TEA (2 mL), and DMF (2 mL). The mixture was sparged with Ar for 5 min and then treated with dichlorobis(tricyclohexylphophine)palladium(II) (57 mg, 0.044 mmol) and CuI (17 mg, 0.089 mmol). The mixture was sparged with Ar for another 5 min and was then subjected to microwave irradiation for 1 h at 100° C. The reaction mixture was then allowed to cool to rt. The suspension was filtered through a pad of diatomaceous earth, such as Celite® and the pad was washed with ethyl acetate (10 mL). The filtrate was concentrated to dryness and the residue was purified by FCC (1:0 to 1:5 gradient, petroleum ether/ethyl acetate) to afford (R)-4-(3-(8-((2,4-dimethoxybenzyl)amino)pyrimido[5,4-d]pyrimidin-2-yl)phenyl)-2-(thiazol-2-yl)but-3-yn-2-ol (200 mg, 83%) as a yellow solid. MS (ESI): mass calcd. for $C_{28}H_{24}N_6O_3S$, 524.2; m/z. found 525.1 [M+H]$^+$.

Intermediate 70: 4,5-Dimethyl-2-(methylthio)pyrido[3,4-d]pyrimidin-8-amine

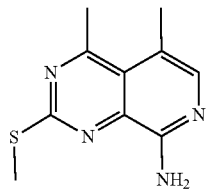

Step A: 6-Methyl-2-thioxo-2,3-dihydropyrimidin-4(1H)-one. Into a 20 L 4-necked round-bottomed flask, purged and maintained with an inert atmosphere of nitrogen, was placed ethyl 3-oxobutanoate (1500 g, 11.53 mol), ethanol (7500 mL) and EtONa (801 g). This was followed by the addition of thiourea (894 g, 11.74 mol) in portions at 60° C. The resulting mixture was heated for 3 h at 85° C. The reaction mixture was then cooled to 25° C. and the solids were collected by filtration. The resulting solid was dissolved in 5 L of $H_2O$. The pH of the solution was adjusted to 2 with hydrogen chloride. The solids were collected by filtration and dried to afford 6-methyl-2-thioxo-2,3-dihydropyrimidin-4(1H)-one (1200 g, 73%) as a white solid. $^1$H NMR (300 MHz, DMSO-$d_6$) δ 12.2-12.3 (m, 2H), 5.68 (s, 1H), 2.07 (s, 3H).

Step B: 6-Methyl-2-(methylthio)pyrimidin-4(1H)-one. Into a 20 L 4-necked round-bottomed flask purged and maintained with an inert atmosphere of nitrogen, was placed 6-methyl-2-sulfanylidene-1,2,3,4-tetrahydropyrimidin-4-one (1200 g, 8.44 mol), water (7200 mL), sodium hydroxide (744 g, 18.60 mol), and $Me_2SO_4$ (1065 g, 8.45 mol). The resulting mixture was heated for 3 h at 110° C. The reaction mixture was cooled to 25° C. and the pH of the solution was adjusted to 2 with hydrogen chloride (6 N). The resulting solids were collected by filtration and dried to afford 6-methyl-2-(methylthio)pyrimidin-4(1H)-one (1000 g, 76%) as a white solid. $^1$H NMR (300 MHz, DMSO-$d_6$) δ 12.8 (br s, 1H), 5.97 (br s, 1H), 2.47-2.65 (m, 3H), 2.27 (s, 3H).

Step C: 5-Bromo-6-methyl-2-(methylthio)pyrimidin-4(1H)-one. Into a 20 L 4-necked round-bottomed flask purged and maintained with an inert atmosphere of nitrogen, was placed 6-methyl-2-(methylsulfanyl)-1,4-dihydropyrimidin-4-one (700 g, 4.48 mol), AcOH (14 L), and $Br_2$ (780 g, 4.88 mol). The resulting solution was stirred for 3 h at 25° C. The solids were collected by filtration and dried to afford 5-bromo-6-methyl-2-(methylthio)pyrimidin-4(1H)-one (700 g, 66%) as a yellow solid. MS (ESI): mass calcd. for $C_6H_7BrN_2OS$ 235.10 m/z found 236.1 [M+H]$^+$.

Step D: 5-Bromo-4-chloro-6-methyl-2-(methylthio)pyrimidine. Into a 5 L 4-necked round-bottomed flask, purged and maintained with an inert atmosphere of nitrogen, was placed 5-bromo-6-methyl-2-(methylsulfanyl)-1,4-dihydropyrimidin-4-one heated for 2 h at 90° C. The reaction mixture was cooled to 25° C. and concentrated to dryness. The resulting residue was diluted with $H_2O$ (2 L) and ethyl acetate (5 L). The organic layer was separated and the aqueous layer was extracted with ethyl acetate (2 L×3). The combined organic layers were washed with brine (2 L), dried over anhydrous sodium sulfate, filtered, and concentrated to dryness. The residue was purified by FCC (1:19, ethyl acetate/petroleum ether) to afford 5-bromo-4-chloro-6-methyl-2-(methylsulfanyl)pyrimidine (700 g, 93%) as a white solid. MS (ESI): mass calcd. for $C_6H_6BrClN_2S$, 251.91; m/z. found 253.1 [M+H]$^+$.

Step E: Methyl 5-bromo-6-methyl-2-(methylthio)pyrimidine-4-carboxylate. Into a 5 L pressure tank reactor, was placed 5-bromo-4-chloro-6-methyl-2-(methylsulfanyl)pyrimidine (300 g, 1.18 mol), methanol (3000 mL), TEA (490 mL), Pd(dppf)Cl$_2$ (17.4 g, 23.78 mmol), and CO (15 atm). The resulting solution was heated for 14 h at 80° C. The mixture was cooled to 25° C. and concentrated to dryness. The resulting residue was diluted with $H_2O$ (2 L) and extracted with ethyl acetate (2 L×3). The combined organic layers were washed with brine (2 L), dried over anhydrous sodium sulfate, filtered, and concentrated to dryness. The residue was purified by FCC (1:10, ethyl acetate/petroleum ether) to afford methyl 5-bromo-6-methyl-2-(methylsulfanyl)pyrimidine-4-carboxylate (150 g, 46%) as a white solid. MS (ESI): mass calcd. for $C_8H_9BrN_2O_2S$, 275.9; m/z. found 277.0 [M+H]$^+$.

Step F: N-Allyl-5-bromo-6-methyl-2-(methylthio)pyrimidine-4-carboxamide. Into a 2 L pressure tank reactor, was placed methyl 5-bromo-6-methyl-2-(methylsulfanyl)pyrimidine-4-carboxylate (120 g, 432 mmol), methanol (1200 mL) and prop-2-en-1-amine (180 mL). The resulting solution was heated for 5 h at 90° C. The reaction mixture was cooled to 25° C. and concentrated to dryness. The resulting residue was diluted with diethyl ether (500 mL) and stirred for 10 min. The solids were collected by filtration and dried to afford N-allyl-5-bromo-6-methyl-2-(methylthio)pyrimidine-4-carboxamide (110 g, 84%) as a yellow solid. MS (ESI): mass calcd. for $C_{10}H_{12}BrN_3OS$ 300.99 m/z found 302.0 [M+H]$^+$.

Step G: 4,5-Dimethyl-2-(methylthio)pyrido[3,4-d]pyrimidin-8(7H)-one. Into a 3 L 4-necked round-bottomed flask, purged and maintained with an inert atmosphere of nitrogen, was placed 5-bromo-6-methyl-2-(methylsulfanyl)-N-(prop-2-en-1-yl)pyrimidine-4-carboxamide (110 g, 364 mmol), N,N-dimethylformamide (1100 mL), DIPEA (243 mL) and trans-di(μ-acetato)bis[o-(di-o-tolyl-phosphino)benzyl]dipalladium(II) (6.85 g, 7.30 mmol). The resulting solution was heated for 14 h at 145° C. The mixture was cooled to 25° C. and concentrated to dryness. The resulting residue was diluted with DCM (2 L) and $H_2O$ (1 L). The resulting solids were filtered off and the filtrate was extracted with DCM (1 L×3). The combined organic layers were washed with brine (1 L), dried over anhydrous sodium sulfate, filtered, and concentrated to dryness. The residue was purified by FCC (19:1, ethyl acetate/petroleum ether) to afford 4,5-dimethyl-2-(methylthio)pyrido[3,4-d]pyrimidin-8(7H)-one (50 g, 62%) as a yellow solid. MS (ESI): mass calcd. for $C_{10}H_{11}N_3OS$ 221.06 m/z found 222.1 [M+H]$^+$.

Step H: 8-Bromo-4,5-dimethyl-2-(methylthio)pyrido[3,4-d]pyrimidine. Into a 1 L 3-necked round-bottomed flask, purged and maintained with an inert atmosphere of nitrogen, was placed 4,5-dimethyl-2-(methylsulfanyl)-7H,8H-pyrido[3,4-d]pyrimidin-8-one (50 g, 226 mmol), CH$_3$CN (500 mL) and POBr$_3$ (260 g). The resulting solution was heated for 3 h at 70° C. The reaction mixture was cooled to 25° C. and poured over water/ice (1 L). The resulting mixture was diluted with ethyl acetate (2 L), the solids were filtered off, and the filtrate was extracted with ethyl acetate (1 L×3). The combined organic layers were washed with brine (1 L), dried over anhydrous sodium sulfate, filtered, and concentrated to dryness. The residue was purified by FCC (1:5, ethyl acetate/petroleum ether) to afford 8-bromo-4,5-dimethyl-2-(methylsulfanyl)pyrido[3,4-d]pyrimidine (20 g, 31%) as a yellow solid. MS (ESI): mass calcd. for $C_{10}H_{10}BrN_3S$, 284.18; m/z. found 285.0 [M+H]$^+$.

Step I: 4,5-Dimethyl-2-(methylthio)pyrido[3,4-d]pyrimidin-8-amine. Into a 2 L pressure tank reactor, was placed 8-bromo-4,5-dimethyl-2-(methylsulfanyl)pyrido[3,4-d]pyrimidine (20 g, 70 mmol), NMP (400 mL), NH₃ in H₂O (400 mL, 25%), and oxodicopper (10.1 g, 70 mmol). The resulting solution was heated for 14 h at 120° C. The mixture was cooled to rt, the solids were filtered off, and filtrate was extracted with ethyl acetate (2 L×3). The combined organic layers were washed with water (1 L) and brine (1 L). The organic layer was dried over anhydrous sodium sulfate, filtered, and concentrated to dryness. The residue was purified by FCC (19:1, ethyl acetate/petroleum ether) to afford 4,5-dimethyl-2-(methylsulfanyl)pyrido[3,4-d]pyrimidin-8-amine (10 g, 67%) as a yellow solid. MS (ESI): mass calcd. for $C_{10}H_{12}N_4S$, 220.1; m/z. found 221.1 [M+H]⁺.

Intermediate 71: 2-(3-Bromophenyl)-4,5-dimethylpyrido[3,4-d]pyrimidin-8-amine

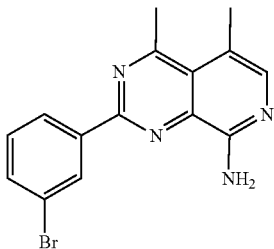 [SMILES: Cc1cnc(N)c2nc(-c3cccc(Br)c3)nc(C)c12]

To a 100 mL three-necked round-bottomed flask was added Intermediate 70 [4,5-dimethyl-2-(methylthio)pyrido[3,4-d]pyrimidin-8-amine (300 mg, 1.36 mmol)], (3-bromophenyl)boronic acid (547 mg, 2.72 mmol), and 1,4-dioxane (10 mL). The mixture was sparged with Ar for 5 min and then treated with [1,1'-bis(diphenylphosphino)ferrocene]dichloropalladium(II) (50 mg, 0.068 mmol) and copper(I) 2-hydroxy-3-methylbenzoate (585 mg, 2.73 mmol). The mixture was sparged with Ar for another 5 min and then stirred while heating at 100° C. for 2 h before cooling to rt. The suspension was filtered through a pad of diatomaceous earth, such as Celite® and the pad washed with methanol. The filtrate was concentrated to dryness and the residue was purified by FCC (eluent: petroleum ether:ethyl acetate (containing 10% methanol)=1:0 to 0:1) to afford 2-(3-bromophenyl)-4,5-dimethylpyrido[3,4-d]pyrimidin-8-amine (230 mg, 45%) as a brown solid. MS (ESI): mass calcd. for $C_{15}H_{13}BrN_4$ 328.0 m/z found 328.8 [M+H]⁺.

Intermediate 72: (R)-3-Hydroxy-3-((4-methoxy-3-(4,4,5,5-tetramethyl-1,3,2-dioxaborolan-2-yl)phenyl)ethynyl)-1-methylpyrrolidin-2-one

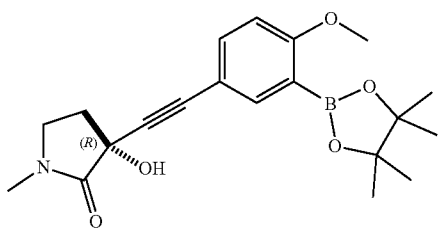

To a 20 mL microwave tube was added 2-(5-bromo-2-methoxyphenyl)-4,4,5,5-tetramethyl-1,3,2-dioxaborolane (300 mg, 0.958 mmol), Intermediate 2 [((R)-3-ethynyl-3-hydroxy-1-methylpyrrolidin-2-one, 147 mg, 1.06 mmol)], Et₂NH (0.99 mL, 9.57 mmol), and DMF (6 mL). The mixture was sparged with N₂ for 5 min and then treated with copper(I) iodide (91 mg, 0.48 mmol), Pd(PPh₃)₂Cl₂ (135 mg, 0.192 mmol), and PPh₃ (50 mg, 0.19 mmol). The mixture was sparged with N₂ for another 5 min and then subjected to microwave irradiation at 90° C. in for 30 min. After the reaction mixture was allowed to cool to rt, the suspension was filtered through a pad of diatomaceous earth, such as Celite® and the pad washed with ethyl acetate (60 mL). The filtrate was concentrated to dryness and the residue was purified by FCC (10:1 to 1:1 gradient, petroleum ether/ethyl acetate) to afford (R)-3-hydroxy-3-((4-methoxy-3-(4,4,5,5-tetramethyl-1,3,2-dioxaborolan-2-yl)phenyl)ethynyl)-1-methylpyrrolidin-2-one (80 mg, 14%) as a yellow oil. MS (ESI): mass calcd. for $C_{20}H_{26}BNO_5$ 371.2 m/z. found 372.2 [M+H]⁺.

Intermediate 73: 6-Bromopyrido[3,2-d]pyrimidin-4-amine

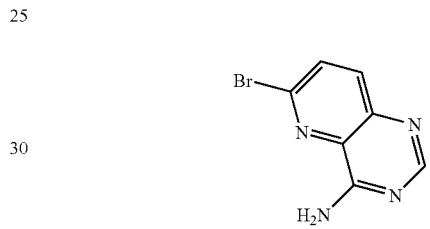

Trimethylsilyl bromide (0.59 mL, 4.47 mmol) was added to a solution of 6-chloropyrido[3,2-d]pyrimidin-4-amine (100 mg, 0.554 mmol) and CH₃CN (20 mL). The resulting mixture was heated at 85° C. for 16 h before cooling to rt and concentrated to dryness. The residue was triturated with petroleum ether:ethyl acetate (1:1, 5 mL) and the suspension isolated via filtration. The filter cake was washed with petroleum ether:ethyl acetate (1:1, 2 mL) before drying under reduced pressure to afford 6-bromopyrido[3,2-d]pyrimidin-4-amine (110 mg, 88%) as a brown solid. MS (ESI): mass calcd. for $C_7H_5BrN_4$ 224.0 m/z. found 227.0 [M+H]⁺.

Intermediate 74: 2-(3-Iodophenyl)oxazolo[5,4-d]pyrimidin-7-amine

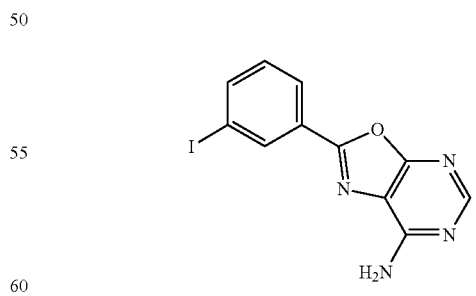

Step A: N-(4,6-Dichloropyrimidin-5-yl)-3-iodobenzamide. A homogeneous solution of 4,6-dichloropyrimidin-5-amine (0.50 g, 2.97 mmol) in NMP (8 mL) was treated with a solution of 3-iodobenzoyl chloride (0.87 g, 3.27 mmol) in NMP (2 mL) at rt. The resulting solution was heated at 90° C. After 12 h, the resulting mixture was cooled to rt and partitioned with saturated aqueous NaHCO₃ (50 mL). The mixture was diluted with H₂O (200 mL) and the resulting solid was isolated via filtration, rinsed with additional H₂O (25 mL), and dried to afford 2-(3-iodophenyl) oxazolo[5,4-d]pyrimidin-7-amine (995 mg, 85%) as a white solid. MS (ESI): mass calcd. for $C_{11}H_6Cl_2IN_3O$, 392.89; m/z. found, 393.9 [M+H]⁺. ¹H NMR (400 MHz, DMSO-d₆) δ 10.93 (s, 1H), 8.95 (s, 1H), 8.36 (t, J=1.6 Hz, 1H), 8.08-7.98 (m, 2H), 7.40 (t, J=7.8 Hz, 1H).

Step B: 7-Chloro-2-(3-iodophenyl)oxazolo[5,4-d]pyrimidine. A suspension of N-(4,6-dichloropyrimidin-5-yl)-3-iodobenzamide (0.81 g, 2.06 mmol) in dry MeCN (12 mL) was treated with DIPEA (0.8 mL, 4.64 mmol) and then heated in a microwave reactor for 30 min at 150° C. The mixture was then diluted with additional MeCN (15 mL) and cooled to 0° C. The resulting solid was isolated via filtration, rinsed with additional cold MeCN (10 mL), and dried to afford 7-chloro-2-(3-iodophenyl)oxazolo[5,4-d]pyrimidine (606 mg, 82%) as a white solid. MS (ESI): mass calcd. for $C_{11}H_5ClIN_3O$, 356.92; m/z found, 358.0 [M+H]⁺. ¹H NMR (400 MHz, DMSO-d₆) δ 8.95 (s, 1H), 8.52 (s, 1H), 8.28 (d, J=7.8 Hz, 1H), 8.11 (d, J=7.8 Hz, 1H), 7.47 (t, J=7.9 Hz, 1H).

Step C: 2-(3-Iodophenyl)oxazolo[5,4-d]pyrimidin-7-amine. A suspension of 7-chloro-2-(3-iodophenyl)oxazolo [5,4-d]pyrimidine (0.27 g, 0.76 mmol) in THF (3 mL) was treated with NH₃ (4 mL, 2N in MeOH) at rt and then heated in a microwave reactor for 30 min at 100° C. Afterwards, the mixture was concentrated to dryness. The resulting residue was suspended in H₂O (15 mL), adjusted to about pH 9 with saturated aqueous NaHCO₃, and briefly sonicated. The resulting solid was isolated via filtration, rinsed with additional H₂O (5 mL), and dried to afford 2-(3-iodophenyl) oxazolo[5,4-d]pyrimidin-7-amine (199 mg, 77%) as a white solid. MS (ESI): mass calcd. for $C_{11}H_7IN_4O$, 337.97; m/z. found, 339.0 [M+H]⁺.

Intermediate 75: (R)-7-((3-(8-((2,4-Dimethoxybenzyl)amino)pyrimido[5,4-d]pyrimidin-2-yl)phenyl) ethynyl)-6,7-dihydro-5H-cyclopenta[b]pyridin-7-ol

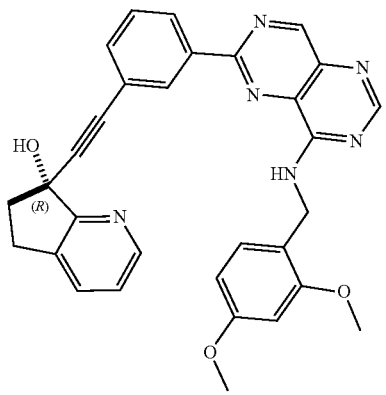

The title compound was prepared with analogous conditions described in Intermediate 69 utilizing Intermediate 38 (R)-7-ethynyl-6,7-dihydro-5H-cyclopenta[b]pyridin-7-ol to afford (R)-7-((3-(8-((2,4-dimethoxybenzyl)amino)pyrimido [5,4-d]pyrimidin-2-yl)phenyl)ethynyl)-6,7-dihydro-5H-cyclopenta[b]pyridin-7-ol (150 mg, 43%) as a yellow solid. MS (ESI): mass calcd. for $C_{31}H_{26}N_6O_3$ 530.2 m/z found 531.2 [M+H]⁺.

Intermediate 76: (R)-7-((3-(8-((2,4-Dimethoxybenzyl)amino)pyrimido[5,4-d]pyrimidin-2-yl)phenyl) ethynyl)-6,7-dihydro-5H-pyrrolo[1,2-a]imidazol-7-ol

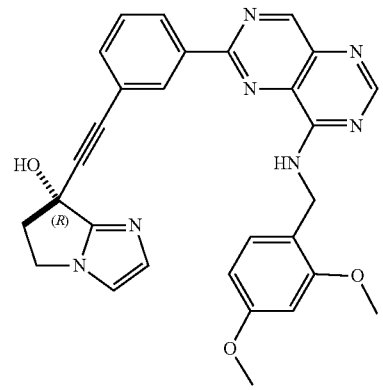

The title compound was prepared with analogous conditions described in Intermediate 69 utilizing Intermediate 10 [(R)-7-ethynyl-6,7-dihydro-5H-pyrrolo[1,2-a]imidazol-7-ol] to afford (R)-7-((3-(8-((2,4-dimethoxybenzyl)amino)pyrimido[5,4-d]pyrimidin-2-yl)phenyl)ethynyl)-6,7-dihydro-5H-pyrrolo[1,2-a]imidazol-7-ol (70 mg, 46%) as a brown solid. MS (ESI): mass calcd. for $C_{29}H_{25}N_7O_3$ 519.2 m/z found 520.3 [M+H]⁺.

Intermediate 77: 6-(3-Iodophenyl)-2-methylpteridine-4-amine

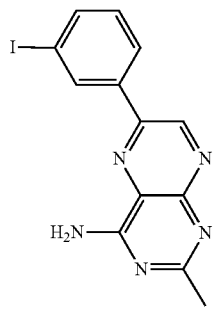 [SMILES: Cc1nc(N)c2nc(-c3cccc(I)c3)cnc2n1]

Step A: 3-Amino-6-(3-(trimethylsilyl)phenyl)pyrazine-2-carbonitrile. To a sealable vial were added 3-amino-6-bromopyrazine-2-carbonitrile (400 mg, 2.0 mmol), 3-trimethylsilylphenylboronic acid (488 mg, 2.5 mmol), dioxane (12 mL), and NaHCO₃ (4.00 mL, 8.0 mmol, 2M). The mixture was sparged with argon for 10 min then PdCl₂(dppf) (147 mg, 0.2 mmol) was added, the vial was sealed and then heated at 90° C. for 3 h. The mixture was cooled to rt, diluted with ethyl acetate (25 mL) and water (25 mL). The organic layer was separated and the aqueous layer was extracted with ethyl acetate (25 mL×3). The combined organic layers were then dried over sodium sulfate, filtered, and concentrated to dryness. The resulting residue was purified by FCC (10 to 100% gradient using ethyl acetate in heptane) to afford 3-amino-6-(3-(trimethylsilyl)phenyl)pyrazine-2-carbonitrile as a pale yellow solid (588 mg). MS (ESI): mass calcd. for $C_{14}H_{16}N_4Si$, 268.11; m/z. found, 269.1 [M+H]⁺.

Step B: 2-Methyl-6-(3-(trimethylsilyl)phenyl)pteridin-4-amine. To a round-bottomed flask were added 3-amino-6-(3-(trimethylsilyl)phenyl)pyrazine-2-carbonitrile (588 mg, 2.2 mmol), acetamidine hydrochloride (872 mg, 8.8 mmol), DIEA (1.9 mL, 11 mmol), and EtOH (37 mL). The mixture was heated to reflux under nitrogen for 7 h. At that time, the mixture was cooled to rt, at which time a solid precipitate formed which was collected by vacuum filtration, and washed with EtOH (10 mL), to provide 2-methyl-6-(3-(trimethylsilyl)phenyl)pteridin-4-amine as an off-white solid (138 mg). MS (ESI): mass calcd. for $C_{16}H_{19}N_5Si$, 309.14; m/z. found, 310.2 $[M+H]^+$.

Step C: 6-(3-Iodophenyl)-2-methylpteridine-4-amine. To a sealable vial were added 2-methyl-6-(3-(trimethylsilyl)phenyl)pteridin-4-amine (138 mg, 0.45 mmol) and DCM (13 mL). The mixture was cooled to 0° C., then a 1M solution of ICl in DCM (2.3 mL, 2.3 mmol) was added in a dropwise manner. After the addition was complete, the reaction was warmed to rt. After 2 h, MeCN (1 mL) was added followed by an additional quantity of 1 M ICl in DCM (1.3 mL, 1.3 mmol). After 1 h, the mixture was diluted with saturated aqueous $Na_2S_2O_3$ (25 mL), and saturated aqueous $NaHCO_3$ (25 mL). The resulting biphasic mixture was extracted with DCM (25 mL×3). The combined organic layers were concentrated to dryness to afford 6-(3-iodophenyl)-2-methylpteridine-4-amine (158 mg, crude) as a red solid which was used without further purification. MS (ESI): mass calcd. for $C_{13}H_{10}IN_5$, 363.00; m/z. found, 364.0 $[M+H]^+$. $^1H$ NMR (400 MHz, $CD_3OD$) δ 9.54 (s, 1H), 8.73 (t, J=1.8 Hz, 1H), 8.30 (dt, J=8.0, 1.3 Hz, 1H), 7.89 (dt, J=7.8, 1.3 Hz, 1H), 7.34 (t, J=7.9 Hz, 1H), 2.59 (s, 3H).

Intermediate 78: 6-Chloro-2,8-dimethylpyrimido[5,4-d]pyrimidin-4-amine

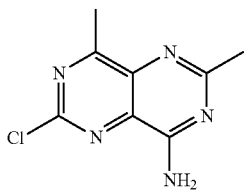

A 50 mL round-bottomed flask was charged with DIPEA (0.9 mL, 5.3 mmol), 5-amino-2-chloro-6-methylpyrimidine-4-carbonitrile, (200 mg, 1.2 mmol), acetimidamide hydrochloride (224 mg, 2.4 mmol), and 1,4-dioxane (5 mL). The mixture was heated at 110° C. for 16 h before cooling to rt. The resulting mixture was poured into water (10 mL) and extracted with ethyl acetate (10 mL×3). The combined organic extracts were washed with brine (10 mL), dried over anhydrous $Na_2SO_4$, filtered, and concentrated to dryness. The resulting residue was purified by FCC (eluent: petroleum ether:ethyl acetate=10:1 to 1:1) to afford 6-chloro-2,8-dimethylpyrimido[5,4-d]pyrimidin-4-amine (200 mg, 66%) as a yellow solid. MS (ESI): mass calcd. for $C_8H_8ClN_5$ 209.1 m/z found 209.9 $[M+H]^+$.

Intermediate 79: (S)-2-(2-Methylthiazol-5-yl)but-3-yn-2-ol

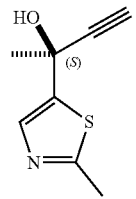

Step A: N-Methoxy-N,2-dimethylthiazole-5-carboxamide. To a solution of 2-methylthiazole-4-carboxylic acid (46.0 g, 321 mmol) in THF (350 mL) and DCM (100 mL) was added carbonyldiimidazole (67.7 g, 418 mmol). The white suspension was stirred at 20° C. for 2 h followed by addition of N-methoxymethanamine hydrochloride salt (40.7 g, 418 mmol). The white suspension was stirred at 20° C. After 12 h, the mixture was filtered, the filtrate was concentrated, the residue was diluted with ethyl acetate (600 mL), washed with water (100 mL) and brine (100 mL), dried over $Na_2SO_4$. The organic layer was concentrated, and the residue was purified by FCC (30 to 50% ethyl acetate/petroleum ether) to afford N-methoxy-N,2-dimethylthiazole-5-carboxamide (51.0 g, 80.9% yield, 95.0% purity) as a brown oil. MS (ESI): mass calcd. for $C_7H_{10}N_2O_2S$, 186.05; m/z. found, 186.8 $[M+H]^+$.

Step B: 1-(2-Methylthiazol-5-yl)ethan-1-one. To a solution of N-methoxy-N,2-dimethylthiazole-4-carboxamide (38.0 g, 204 mmol) in THF (400 mL) was added MeMgBr (102 mL, 3M in THF) at 0° C. The brown suspension was stirred at 0-20° C. for 3 h. The reaction mixture was poured into ice-cold saturated aqueous $NH_4Cl$ (500 mL), and then extracted with ethyl acetate (800 mL). The layers were washed with brine (100 mL), dried over anhydrous $Na_2SO_4$, filtered and concentrated under reduced pressure. The residue was purified by FCC (25-45% gradient, ethyl acetate/petroleum ether) to afford 1-(2-methylthiazol-5-yl)ethan-1-one (25.8 g, 84.1% yield) as a yellow solid. MS (ESI): mass calcd. for $C_6H_7NOS$, 141.02; m/z. found, 141.8 $[M+H]^+$.

Step C: 2-(2-Methylthiazol-5-yl)-4-(trimethylsilyl)but-3-yn-2-ol. To a solution of ethynyl(trimethyl)silane (35.5 g, 361 mmol, 50.0 mL) in THF (250 mL) was added n-BuLi (108 mL, 2.5 M in hexanes) at −65° C. The yellow solution was stirred at −65° C. for 1 h. To the solution was added 1-(2-methylthiazol-4-yl)ethan-1-one (25.5 g, 181 mmol) in THF (50 mL). The yellow solution was stirred at −65° C. for 1.5 hrs. The resulting solution was poured into saturated aqueous $NH_4Cl$ (200 mL) and then extracted with ethyl acetate (200 mL×2). The combined organic layers were washed with brine (100 mL), dried over $Na_2SO_4$, filtered, and concentrated to dryness. To the residue in MeOH (300 mL) was added $K_2CO_3$ (49.9 g, 361 mmol) and the mixture was stirred at 25° C. After 12 h, the mixture was filtered and concentrated. The residue was extracted with ethyl acetate (800 mL), washed with water (100 mL) and brine (100 mL), dried over anhydrous $Na_2SO_4$, filtered, and concentrated to dryness. The resulting residue was purified by FCC (25-45% ethyl acetate/petroleum ether) to afford 2-(2-methylthiazol-5-yl)but-3-yn-2-ol (19.0 g, 59.7% yield) as a yellow solid. $^1H$ NMR (400 MHz, $CDCl_3$) δ 7.60 (s, 1H), 3.70 (s, 1H), 2.69 (s, 1H), 2.66 (s, 3H), 1.87 (s, 3H).

Step D. (S)-2-(2-methylthiazol-5-yl)but-3-yn-2-ol. Racemic 2-(2-methylthiazol-5-yl)but-3-yn-2-ol (19.0 g, 113.6 mmol) was purified by preparative SFC (DAICEL CHIRAL-PAK IC (250×50 mm, 10 μm); mobile phase: [0.1% NH₃H₂O EtOH]; B %: 25%) to provide (S)-2-(2-methylthi-azol-5-yl)but-3-yn-2-ol (8.0 g, 41.6% yield, 97.6% ee). [α]²⁰_D=4.10 (c=0.1 in MeOH) and (R)-2-(2-methylthiazol-5-yl)but-3-yn-2-ol (Intermediate 81, 7.5 g, 39% yield, 99.9% ee). [α]²⁰_D=−4.40 (c=0.1 in MeOH).

Intermediate 80: (S)-2-(2-Methylthiazol-5-yl)-4-(3-(4,4,5,5-tetramethyl-1,3,2-dioxaborolan-2-yl)phenyl)but-3-yn-2-ol

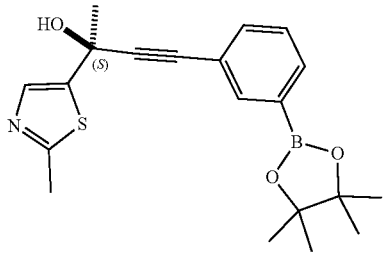

(S)-2-(2-Methylthiazol-5-yl)-4-(3-(4,4,5,5-tetramethyl-1,3,2-dioxaborolan-2-yl)phenyl)but-3-yn-2-ol was prepared with analogous conditions described in Intermediate 4 utilizing Intermediate 79 [(S)-2-(2-methylthiazol-5-yl)but-3-yn-2-ol]. MS (ESI): mass calcd. for C₂₀H₂₄BNO₃S, 369.2; m/z. found, 370.2 [M+H]⁺. ¹H NMR (400 MHz, CDCl₃) δ 7.91 (t, J=1.4 Hz, 1H), 7.77 (dt, J=7.4, 1.3 Hz, 1H), 7.71 (s, 1H), 7.53 (dt, J=7.7, 1.6 Hz, 1H), 7.33 (t, J=7.6 Hz, 1H), 2.69 (s, 3H), 1.95 (s, 3H), 1.35 (s, 12H).

Intermediate 81: (R)-2-(2-methylthiazol-5-yl)but-3-yn-2-ol

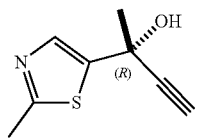

(R)-2-(2-methylthiazol-5-yl)but-3-yn-2-ol was prepared with analogous conditions described in the chiral separation described in Step D for Intermediate 79 to afford (R)-2-(2-methylthiazol-5-yl)but-3-yn-2-ol (7.5 g, 39% yield, 99.9% ee). [α]²⁰_D=−4.40 (c=0.1 in MeOH).

Intermediate 82: (R)-2-(2-Methylthiazol-5-yl)-4-(3-(4,4,5,5-tetramethyl-1,3,2-dioxaborolan-2-yl)phenyl)but-3-yn-2-ol

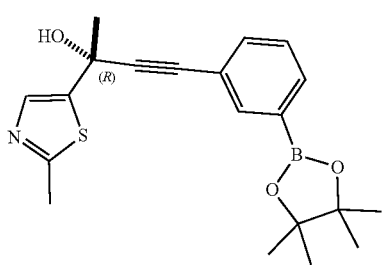

(R)-2-(2-Methylthiazol-5-yl)-4-(3-(4,4,5,5-tetramethyl-1,3,2-dioxaborolan-2-yl)phenyl)but-3-yn-2-ol was prepared with analogous conditions described in Intermediate 4 utilizing Intermediate 81 (R)-2-(2-methylthiazol-5-yl)but-3-yn-2-ol. MS (ESI): mass calcd. for C₂₀H₂₄BNO₃S, 369.2; m/z. found, 370.2 [M+H]⁺. ¹H NMR (400 MHz, CDCl₃) δ 7.91 (t, J=1.4 Hz, 1H), 7.77 (dt, J=7.4, 1.3 Hz, 1H), 7.71 (s, 1H), 7.53 (dt, J=7.7, 1.6 Hz, 1H), 7.33 (t, J=7.6 Hz, 1H), 2.69 (s, 3H), 1.95 (s, 3H), 1.35 (s, 12H).

Intermediate 83: 6-(3-Iodophenyl)-5,6,7,8-tetrahydropyrido[4,3-d]pyrimidin-4-amine

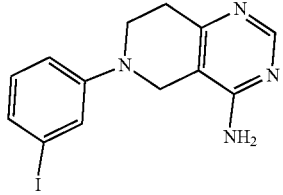 [SMILES: Nc1ncnc2c1CN(c1cccc(I)c1)CC2]

Step A: Dimethyl 3,3'-((3-iodophenyl)azanediyl)dipropionate. A solution of 3-iodoaniline (10.0 g, 45.6 mmol), methyl acrylate (17.8 g, 207 mmol), and 1,1,1,3,3,3-hexafluoro-2-propanol (45 mL) was heated at 58° C. After 48 h, the resulting mixture was cooled to rt and concentrated to dryness. The resulting residue was purified by FCC (10:1 to 4:1 gradient, petroleum ether/ethyl acetate) to afford dimethyl 3,3'-((3-iodophenyl)azanediyl)dipropionate (8.8 g, 49%), as a yellow oil. MS (ESI): mass calcd. for C₁₄H₁₈INO₄ 391.0 m/z found 392.0 [M+H]⁺.

Step B: Methyl 1-(3-iodophenyl)-4-oxopiperidine-3-carboxylate. TiCl₄ (22.5 mL, 1 M in CH₂Cl₂) was added to a −40° C. (dry ice/ethanol) solution of dimethyl 3,3'-((3-iodophenyl)azanediyl)dipropanoate, (8.8 g, 22 mmol) and CH₂Cl₂ (30 mL). Then, the mixture was stirred at −40° C. for 3 h before treating with Et₃N (6.3 mL, 45 mmol) dropwise. The resultant mixture was stirred for 16 h with gradual warming to rt. After which time, brine (10 mL) was added to the mixture followed by adjusting the pH to 8 by an addition of Et₃N. The resulting suspension was filtered through a pad of diatomaceous earth, such as Celite® and the pad washed with ethyl acetate (30 mL). The filtrate was diluted with water (100 mL) and the resultant mixture was extracted with ethyl acetate (20 mL×3). The combined organic extracts were dried over anhydrous Na₂SO₄, filtered, and concentrated to dryness. The resulting residue was purified by FCC (10:1 to 5:1 gradient, petroleum ether/ethyl acetate) to afford methyl 1-(3-iodophenyl)-4-oxopiperidine-3-carboxylate (4.6 g, 57%) as a yellow oil. MS (ESI): mass calcd. for C₁₃H₁₄INO₃ 359.0 m/z found 360.0 [M+H]⁺.

Step C: 6-(3-Iodophenyl)-5,6,7,8-tetrahydropyrido[4,3-d]pyrimidin-4-ol. Methyl 1-(3-iodophenyl)-4-oxopiperidine-3-carboxylate, (4.6 g, 13 mmol) was added to a solution of formamidine acetate (2.0 g, 19 mmol), sodium methoxide (3.7 g, 68 mmol), and methanol (50 mL). The mixture was heated at 90° C. for 3 h before cooling to rt, diluting with ethyl acetate (50 mL), and adjusting the pH to 7 with acetic acid. Then, the mixture was poured into water (100 mL). The layers were separated and the aqueous layer was extracted with ethyl acetate (20 mL×3). The combined organic extracts were washed with brine (10 mL), dried over anhydrous Na₂SO₄, filtered, and concentrated to dryness to afford 6-(3-iodophenyl)-5,6,7,8-tetrahydropyrido[4,3-d]pyrimidin- 4-ol (2.8 g, 61%), as a pale yellow solid. MS (ESI): mass calcd. for $C_{13}H_{12}IN_3O$, 353.0; m/z. found 354.0 [M+H]$^+$.

Step D: 4-Chloro-6-(3-iodophenyl)-5,6,7,8-tetrahydropyrido[4,3-d]pyrimidine. POCl$_3$ (651 mg, 4.25 mmol) was added to a solution of 6-(3-iodophenyl)-5,6,7,8-tetrahydropyrido[4,3-d]pyrimidin-4-ol, (1.00 g, 2.83 mmol), Et$_3$N (573 mg, 5.66 mmol), and toluene (10 mL). The mixture was heated at 90° C. After 16 h, the mixture was cooled to rt and concentrated to dryness. The resulting residue was purified by FCC (10:1 to 1:1 gradient, petroleum ether:ethyl acetate) to afford 4-chloro-6-(3-iodophenyl)-5,6,7,8-tetrahydropyrido[4,3-d]pyrimidine (650 mg, 62%) as a pale yellow solid. MS (ESI): mass calcd. for $C_{13}H_{11}ClIN_3$ 371.0 m/z found 372.0 [M+H]$^+$.

Step E: 6-(3-Iodophenyl)-5,6,7,8-tetrahydropyrido[4,3-d]pyrimidin-4-amine. A mixture of 4-chloro-6-(3-iodophenyl)-5,6,7,8-tetrahydropyrido[4,3-d]pyrimidine, (200 mg, 0.54 mmol), CuSO$_4$·5H$_2$O (67.0 mg, 0.27 mmol), NH$_3$·H$_2$O (10 mL, 28%), and 1,4-dioxane (20 mL) in sealed tube was stirred at 100° C. After 16 h, the mixture was cooled to rt and concentrated to dryness. The resulting residue was re-dissolved in methanol (10 mL) and filtered. The filtrate was concentrated to afford 6-(3-iodophenyl)-5,6,7,8-tetrahydropyrido[4,3-d]pyrimidin-4-amine (150 mg), which was used without further purification. MS (ESI): mass calcd. for $C_{13}H_{13}IN_4$ 352.0 m/z found 353.0 [M+H]$^+$.

Intermediate 84: (S)-2-(4-Methylthiazol-5-yl)but-3-yn-2-ol

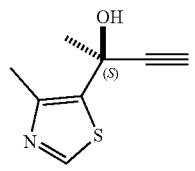

(S)-2-(4-Methylthiazol-5-yl)but-3-yn-2-ol was prepared with analogous conditions described in Step A of Intermediate 79 utilizing 4-methylthiazole-5-carboxylic acid. Racemic 2-(4-methylthiazol-5-yl)but-3-yn-2-ol (16.0 g, 95.7 mmol) was purified by preparative SFC (DAICEL CHIRALPAK IC (250×50 mm, 10 µm); mobile phase: [0.1% NH$_3$H$_2$O IPA]; B %: 20%) to afford (S)-2-(4-methylthiazol-5-yl)but-3-yn-2-ol (7.5 g, 46% yield, 99.9% ee). $[\alpha]^{20}_D$=7.60 (c=0.1 in MeOH) and (R)-2-(4-methylthiazol-5-yl)but-3-yn-2-ol (Intermediate 85, 7.5 g, 46% yield, 98.6% ee purity) as a yellow solid Intermediate 85: (R)-2-(4-Methylthiazol-5-yl)but-3-yn-2-ol

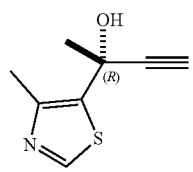

(R)-2-(4-Methylthiazol-5-yl)but-3-yn-2-ol was prepared with analogous conditions described in Step A of Intermediate 79 utilizing 4-methylthiazole-5-carboxylic acid and chiral separation described in Intermediate 84 to afford (7.5 g, 46% yield, 98.6% ee purity) as a yellow solid. $[\alpha]^{20}_D$=−7.70 (c=0.1 in MeOH).

Intermediate 86: (S)-2-(4-methylthiazol-5-yl)-4-(3-(4,4,5,5-tetramethyl-1,3,2-dioxaborolan-2-yl)phenyl)but-3-yn-2-ol

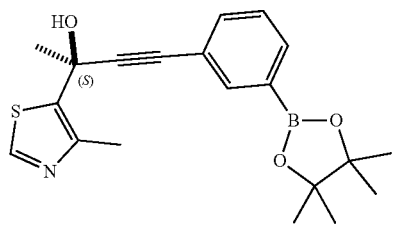

(S)-2-(4-methylthiazol-5-yl)-4-(3-(4,4,5,5-tetramethyl-1,3,2-dioxaborolan-2-yl)phenyl)but-3-yn-2-ol was prepared with analogous conditions described in Intermediate 4 utilizing Intermediate 84 (S)-2-(4-Methylthiazol-5-yl)but-3-yn-2-ol. MS (ESI): mass calcd. for $C_{20}H_{24}BNO_3S$, 369.2; m/z. found, 370.1 [M+H]$^+$. $^1$H NMR (400 MHz, CDCl$_3$) δ 8.55 (s, 1H), 7.87 (br s, 1H), 7.76 (d, J=7.4 Hz, 1H), 7.50 (d, J=7.8 Hz, 1H), 7.38-7.28 (m, 1H), 2.64 (s, 3H), 1.93 (s, 3H), 1.34 (s, 12H).

Intermediate 87: (R)-2-(4-methylthiazol-5-yl)-4-(3-(4,4,5,5-tetramethyl-1,3,2-dioxaborolan-2-yl)phenyl)but-3-yn-2-ol

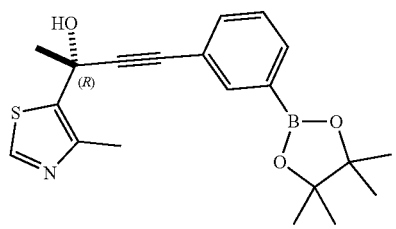

(R)-2-(4-methylthiazol-5-yl)-4-(3-(4,4,5,5-tetramethyl-1,3,2-dioxaborolan-2-yl)phenyl)but-3-yn-2-ol was prepared with analogous conditions described in Intermediate 4 utilizing Intermediate 85 (R)-2-(4-Methylthiazol-5-yl)but-3-yn-2-ol. MS (ESI): mass calcd. for $C_{20}H_{24}BNO_3S$, 369.2; m/z. found, 370.2 [M+H]$^+$. $^1$H NMR (400 MHz, CDCl$_3$) δ 8.55 (s, 1H), 7.87 (br s, 1H), 7.76 (d, J=7.4 Hz, 1H), 7.50 (d, J=7.8 Hz, 1H), 7.38-7.28 (m, 1H), 2.64 (s, 3H), 1.93 (s, 3H), 1.34 (s, 12H).

Intermediate 88: racemic-8-Ethynyl-5,6,7,8-tetrahydroquinolin-8-ol

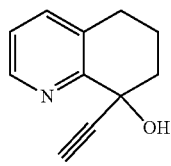

To a 250 mL round-bottomed flask containing ethynyl-magnesium bromide (16 mL, 0.5 M in THF) and THF (25 mL) at 0° C. was added 6,7-dihydroquinolin-8(5H)-one (1.0 g, 6.79 mmol) in THF (25 mL) dropwise. After 45 min, the mixture was warmed to rt and additional ethynylmagnesium bromide (3.0 mL, 0.5 M in THF) was added. The mixture was then heated at 40° C. After 2 h, the mixture partitioned with saturated aqueous NH$_4$Cl (50 mL). The resulting mixture was extracted with ethyl acetate (50 mL×3) and the combined organics were washed with brine (50 mL), dried over MgSO$_4$, filtered, and concentrated to dryness. The resulting residue was purified by FCC (0 to 100% hexanes/ethyl acetate) to afford racemic-8-ethynyl-5,6,7,8-tetrahydroquinolin-8-ol (1.03 g, 87%) as an off-white solid. MS (ESI): mass calcd. for C$_{11}$H$_{11}$NO, 173.1; m/z found, 174.1 [M+H]$^+$. $^1$H NMR (500 MHz, CDCl$_3$) δ 8.46 (d, J=4.7 Hz, 1H), 7.45 (d, J=7.7, Hz, 1H), 7.18 (dd, J=7.8, 4.7 Hz, 1H), 4.61 (s, 1H), 2.93-2.79 (m, 2H), 2.57 (s, 1H), 2.53-2.42 (m, 1H), 2.22-2.08 (m, 1H), 2.08-1.96 (m, 2H).

Intermediate 89: racemic-8-((3-(4,4,5,5-Tetramethyl-1,3,2-dioxaborolan-2-yl)phenyl)ethynyl)-5,6,7,8-tetrahydroquinolin-8-ol

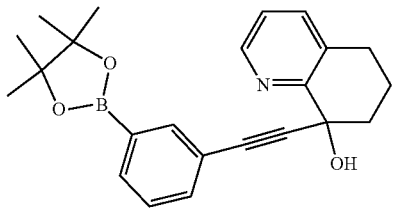 [SMILES: CC1(C)OB(c2cccc(C#CC3(O)CCCc4cccnc43)c2)OC1(C)C]

racemic-8-((3-(4,4,5,5-Tetramethyl-1,3,2-dioxaborolan-2-yl)phenyl)ethynyl)-5,6,7,8-tetrahydroquinolin-8-ol was prepared with analogous conditions described in Intermediate 4 utilizing Intermediate 88 racemic-8-ethynyl-5,6,7,8-tetrahydroquinolin-8-ol to afford racemic-8-((3-(4,4,5,5-tetramethyl-1,3,2-dioxaborolan-2-yl)phenyl)ethynyl)-5,6,7,8-tetrahydroquinolin-8-ol (530 mg, 61%) as a brown oil. MS (ESI): mass calcd. for C$_{23}$H$_{26}$BNO$_3$, 375.2; m/z. found, 376.2 [M+H]$^+$. $^1$H NMR (400 MHz, CDCl$_3$) δ 8.46 (d, J=4.7, 1H), 7.87-7.62 (m, 2H), 7.42-752 (m, 2H), 7.36-7.21 (m, 2H), 7.15-7.20 (m, 1H), 2.82-7.93 (m, 2H), 2.64-2.37 (m, 1H), 2.30-1.89 (m, 4H), 1.65 (br s, 1H), 1.33 (br s, 12H).

Intermediate 90. (R)-2-(5-methylthiazol-2-yl)but-3-yn-2-ol

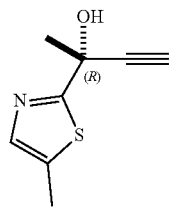

The title compound was prepared with analogous conditions described in Step B of Intermediate 79 utilizing 1-(5-methylthiazol-2-yl)ethan-1-one. Racemic 2-(4-methylthiazol-5-yl)but-3-yn-2-ol (16.0 g) was purified by preparative SFC (DAICEL CHIRALPAK AD (250×50 mm, 10 μm); mobile phase: [0.1% NH$_3$—H$_2$O EtOH]; B %: 25%). The first eluting enantiomer (R)-2-(5-methylthiazol-2-yl)but-3-yn-2-ol (6.5 g, 27% yield, 98.3% ee) was a yellow solid. [α]$^{20}_D$=−173.4 (c=0.1 in MeOH).

Intermediate 91: (S)-2-(5-methylthiazol-2-yl)but-3-yn-2-ol

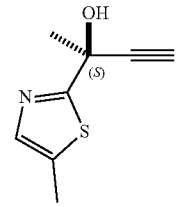

The title compound was prepared with analogous conditions described in Step B of Intermediate 79 utilizing 1-(5-methylthiazol-2-yl)ethan-1-one and chiral separation described in Intermediate 90 to afford (S)-2-(5-methylthiazol-2-yl)but-3-yn-2-ol (6.5 g, 38.7 mmol, 27.3% yield, 99.7% purity) (6.8 g, 28.% yield, 99.6% ee) as a yellow solid. [α]$^{20}_D$=+177.0 (c=0.1 in MeOH).

Intermediate 92: (R)-2-(5-methylthiazol-2-yl)-4-(3-(4,4,5,5-tetramethyl-1,3,2-dioxaborolan-2-yl)phenyl)but-3-yn-2-ol

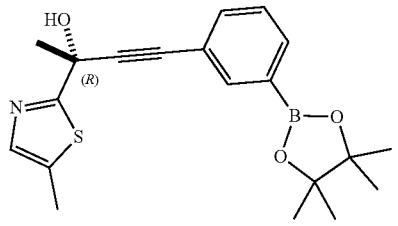

(R)-2-(5-methylthiazol-2-yl)-4-(3-(4,4,5,5-tetramethyl-1,3,2-dioxaborolan-2-yl)phenyl)but-3-yn-2-ol was prepared with analogous conditions described in Intermediate 4 utilizing Intermediate 90 (R)-2-(5-methylthiazol-2-yl)but-3-yn-2-ol. MS (ESI): mass calcd. for C$_{20}$H$_{24}$BNO$_3$S, 369.2; m/z. found, 370.2 [M+H]$^+$. $^1$H NMR (400 MHz, CDCl$_3$) δ 7.91 (br s, 1H), 7.75 (d, J=7.5 Hz, 1H), 7.53 (d, J=7.8, 1H), 7.38 (br s, 2H), 7.31 (t, J=7.6 Hz, 1H), 2.46 (s, 3H), 1.99 (s, 3H), 1.34 (s, 12H).

Intermediate 93: (S)-2-(5-methylthiazol-2-yl)-4-(3-(4,4,5,5-tetramethyl-1,3,2-dioxaborolan-2-yl)phenyl)but-3-yn-2-ol

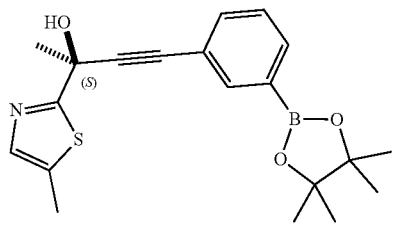

(S)-2-(5-methylthiazol-2-yl)-4-(3-(4,4,5,5-tetramethyl-1,3,2-dioxaborolan-2-yl)phenyl)but-3-yn-2-ol was prepared with analogous conditions described in Intermediate 4 utilizing Intermediate 91 (S)-2-(5-methylthiazol-2-yl)but-3-yn-2-ol. MS (ESI): mass calcd. for $C_{20}H_{24}BNO_3S$, 369.2; m/z. found, 370.2 [M+H]$^+$. $^1$H NMR (400 MHz, CDCl$_3$) δ 7.91 (br s, 1H), 7.75 (d, J=7.5 Hz, 1H), 7.53 (d, J=7.8, 1H), 7.38 (br s, 2H), 7.31 (t, J=7.6 Hz, 1H), 2.46 (s, 3H), 1.99 (s, 3H), 1.34 (s, 12H).

Intermediate 94: 6-Chloro-8-methylpyrimido[5,4-d]pyrimidin-2-d-4-amine

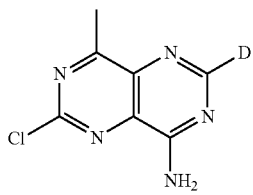

The title compound was prepared with analogous conditions described in Step B of Intermediate 24 utilizing formamide-1-d to afford 6-chloro-8-methylpyrimido[5,4-d]pyrimidin-2-d-4-amine (25 mg, 10%) as a yellow solid. MS (ESI): mass calcd. for $C_7H_5ClDN_5$ 196.0 m/z found 197.1 [M+H]$^+$. $^1$H NMR (400 MHz, CDCl$_3$) δ 6.88 (br s., 1H), 6.04 (br s., 1H), 2.97 (s, 3H).

Intermediate 95: 5-(3-Iodophenyl)-1H-indazol-3-amine

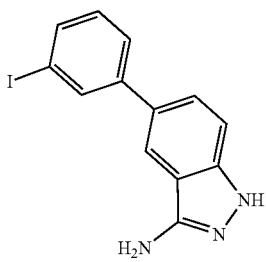 [SMILES: Nc1n[nH]c2ccc(-c3cccc(I)c3)cc12]

Step A: 5-Bromo-1H-indazol-3-amine. To a round-bottomed flask were added 5-bromo-2-fluorobenzonitrile (21.2 g, 106 mmol), hydrazine monohydrate (15.7 mL, 318 mmol) and EtOH (211 mL) and the mixture was heated at 80° C. After 16 h, the resulting mixture was cooled to rt and the solid was collected by filtration. The precipitate was washed with DCM (20 mL) to afford 5-bromo-1H-indazol-3-amine (17.8 g, 79%) as a white solid. MS (ESI): mass calcd. for $C_7H_6BrN_3$, 212.05; m/z. found, 213.9 [M+H]$^+$. $^1$H NMR (400 MHz, DMSO-d$_6$) δ 7.94 (d, J=1.7 Hz, 1H), 7.31 (dd, J=8.8, 1.9 Hz, 1H), 7.22 (d, J=8.8 Hz, 1H), 5.44 (s, H), 3.87 (br s, 1H).

Step B: tert-Butyl 3-amino-5-bromo-1H-indazole-1-carboxylate. A 1 L round-bottomed flask was charged with DMAP (1.0 g, 8.4 mmol), 5-bromo-1H-indazol-3-amine (18 g, 84 mmol), di-tert-butyl decarbonate (19 g, 84 mmol), and DCM (400 mL). The mixture was stirred at rt. After 16 h, the volume was reduced 80% in vacuo and the resulting precipitate was collected by filtration to afford tert-butyl 3-amino-5-bromo-1H-indazole-1-carboxylate (15.0 g, 57%) as a colorless solid. MS (ESI): mass calcd. for $C_{12}H_{14}BrN_3O_2$, 312.17; m/z. found, 257.9, 259.9 [M−tBu]$^+$. $^1$H NMR (400 MHz, DMSO-d$_6$) δ 8.12 (d, J=1.9 Hz, 1H), 7.89 (d, J=8.9 Hz, 1H), 7.65 (dd, J=8.8, 2.0 Hz, 1H), 6.41 (s, 2H), 1.58 (s, 9H).

Step C: tert-Butyl 3-amino-5-(3-(trimethylsilyl)phenyl)-1H-indazole-1-carboxylate. To a vial were added 6-bromoquinazolin-4-amine (150 mg, 0.67 mmol), tert-butyl 3-amino-5-bromo-1H-indazole-1-carboxylate (0.50 g, 1.60 mmol), (3-(trimethylsilyl)phenyl)boronic acid (0.40 g, 1.08 mmol), Na$_2$CO$_3$ (3.2 mL, 6.40 mmol, 2M), THF (16 mL, purged with N$_2$ for 10 min), and 1,1'-bis[di t-butylphosphino)ferrocene]palladium (21 mg, 0.03 mmol). The vial was sealed and heated at 60° C. After 4 h, the mixture was cooled to rt and additional (3-(trimethylsilyl)phenyl)boronic acid (0.40 g, 1.08 mmol) was added. The vial was sealed and heated at 100° C. After 16 h, the mixture was cooled to rt and partitioned between ethyl acetate (20 mL) and water (10 mL). The organic layer was separated and concentrated to dryness. The resulting residue was purified by FCC (0-60% gradient, ethyl acetate+10% MeOH and hexanes) to afford tert-butyl 3-amino-5-(3-(trimethylsilyl)phenyl)-1H-indazole-1-carboxylate (0.46 g, 76%) as a brown solid. MS (ESI): mass calcd. for $C_{21}H_{27}N_3O_2Si$, 381.55; m/z. found, 326.0 [M−tBu]$^+$. $^1$H NMR (400 MHz, DMSO-d$_6$) δ 8.21-8.16 (m, 1H), 8.05-7.94 (m, 1H), 7.85 (dd, J=8.7, 1.8 Hz, 1H), 7.82-7.79 (m, 1H), 7.71-7.66 (m, 1H), 7.58-7.44 (m, 2H), 6.41 (s, 2H), 1.61 (s, 9H), 0.32 (s, 9H).

Step D: tert-Butyl 3-amino-5-(3-iodophenyl)-1H-indazole-1-carboxylate. A solution of ICl in DCM (6.0 mL, 6.07 mmol, 1 M) was slowly added to a solution of tert-butyl 3-amino-5-(3-(trimethylsilyl)phenyl)-1H-indazole-1-carboxylate (0.46 g, 1.21 mmol) in DCM (12 mL) at 0° C. After 2 h, the resulting mixture was diluted with DCM (20 mL) and saturated aqueous sodium thiosulfate (25 mL). The organic was separated and concentrated to dryness. The resulting residue was purified by FCC (0-70% gradient, ethyl acetate/hexanes) to afford tert-butyl 3-amino-5-(3-iodophenyl)-1H-indazole-1-carboxylate (0.34 g, 65%) as a brown solid. MS (ESI): mass calcd. for $C_{18}H_{18}N_3O_2$, 435.26; m/z. found, 380.0 [M−tBu]$^+$. $^1$H NMR (500 MHz, DMSO-d$_6$) δ 8.25-8.18 (m, 1H), 8.08-8.05 (m, 1H), 8.00 (d, J=8.6 Hz, 1H), 7.85 (dd, J=8.7, 1.8 Hz, 1H), 7.78-7.70 (m, 2H), 7.34-7.22 (m, 1H), 6.40 (s, 2H), 1.60 (s, 9H).

Step E: 5-(3-Iodophenyl)-1H-indazol-3-amine. A 50 mL round-bottomed flask was charged with TFA (0.6 mL, 7.8 mmol), tert-butyl 3-amino-5-(3-iodophenyl)-1H-indazole-1-carboxylate (0.34 g, 0.78 mmol) and DCM (2 mL) at rt. After 4 h, additional TFA (0.6 mL, 7.8 mmol) was added and stirring was continued. After 16 h, additional TFA (2 mL, 1.5 g/mL, 26.13 mmol) was added and stirring was continued. After 4 h, the mixture was diluted with DCM (20 mL) and the pH was adjusted to 8 with saturated aqueous sodium bicarbonate. The organic was separated and concentrated to dryness. The resulting residue was purified by FCC (0-10% gradient, MeOH+2M NH$_3$ in MeOH and DCM) to afford 5-(3-iodophenyl)-1H-indazol-3-amine (0.20 g, 77%) as a colorless solid. MS (ESI): mass calcd. for $C_{13}H_{10}N_3I$, 335.15; m/z. found, 336.1. [M+H]$^+$.

Intermediate 96: 6-Chloro-2-(fluoromethyl)pyrido[3,2-d]pyrimidin-4-amine

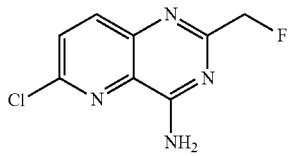 [SMILES: Nc1nc(CF)nc2ccc(Cl)nc12]

A vial was charged with 3-amino-6-chloropicolinonitrile (500 mg, 3.26 mmol), 2-fluoroacetimidamide (400 mg, 5.25 mmol), potassium phosphate (2.80 g, 13.2 mmol) and THF (12 mL). The vial was sealed and heated at 80° C. in an aluminum heating mantle. After 22 h, the mixture was cooled to rt, water (15 mL) was added, and the contents was heated at 70° C. for 30 min. The resulting mixture was cooled to rt and stirred for an additional 70 min. The solid contents were collected by filtration, rinsed with water (15 mL) and Et$_2$O (10 mL) and dried under vacuum to afford 6-chloro-2-(fluoromethyl)pyrido[3,2-d]pyrimidin-4-amine (540 mg, 78%) as a dark grey solid. MS (ESI): mass calcd. for $C_8H_6ClFN_4$, 212.0; m/z. found, 213.1 [M+H]$^+$. $^1$H NMR (400 MHz, CD$_3$OD) δ 8.09 (d, J=8.8 Hz, 1H), 7.80 (d, J=8.8 Hz, 1H), 5.40 (s, 1H), 5.28 (s, 1H).

Intermediate 97. (4-Amino-6-chloropyrido[3,2-d]pyrimidin-2-yl)methanol

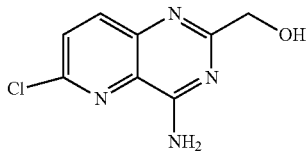 [SMILES: Nc1nc(CO)nc2ccc(Cl)nc12]

(4-Amino-6-chloropyrido[3,2-d]pyrimidin-2-yl)methanol was prepared with analogous conditions described in Intermediate 96 utilizing 2-fluoroacetimidamide. MS (ESI): mass calcd. for $C_8H_7ClN_4O$, 210.0; m/z. found, 211.1 [M+H]$^+$. 1H NMR (400 MHz, CD$_3$OD) δ 8.07 (d, J=8.8 Hz, 1H), 7.77 (d, J=8.8 Hz, 1H), 4.59 (s, 2H).

Intermediate 98. 6-Chloro-2-cyclopropylpyrido[3,2-d]pyrimidin-4-amine

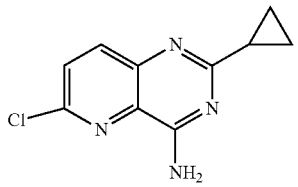 [SMILES: Nc1nc(C2CC2)nc2ccc(Cl)nc12]

6-Chloro-2-cyclopropylpyrido[3,2-d]pyrimidin-4-amine was prepared with analogous conditions described in Intermediate 96 utilizing cyclopropanecarboximidamide hydrochloride. MS (ESI): mass calcd. for $C_{10}H_9ClN_4$, 220.1; m/z. found, 221.1 [M+H]$^+$. $^1$H NMR (400 MHz, CD$_3$OD) δ 7.94 (d, J=8.8 Hz, 1H), 7.71 (d, J=8.8 Hz, 1H), 2.06 (tt, J=8.1, 4.7 Hz, 1H), 1.21-1.08 (m, 2H), 1.06-0.92 (m, 2H).

Intermediate 99. 6-Chloro-2-(trifluoromethyl)pyrido[3,2-d]pyrimidin-4-amine

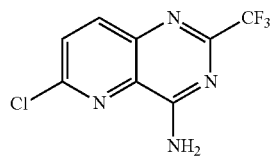 [SMILES: Nc1nc(C(F)(F)F)nc2ccc(Cl)nc12]

6-Chloro-2-(trifluoromethyl)pyrido[3,2-d]pyrimidin-4-amine was prepared with analogous conditions described in Intermediate 96 utilizing 2,2,2-trifluoroacetimidamide. MS (ESI): mass calcd. for $C_8H_4ClF_3N_4$, 248.0; m/z. found, 249.0 [M+H]$^+$. $^1$H NMR (400 MHz, CD$_3$OD) δ 8.19 (d, J=8.8 Hz, 1H), 7.87 (d, J=8.8 Hz, 1H).

Intermediate 100: 6-(5-Bromo-2-methoxyphenyl)-N-(2,4-dimethoxybenzyl)pyrimido[5,4-d]pyrimidin-4-amine

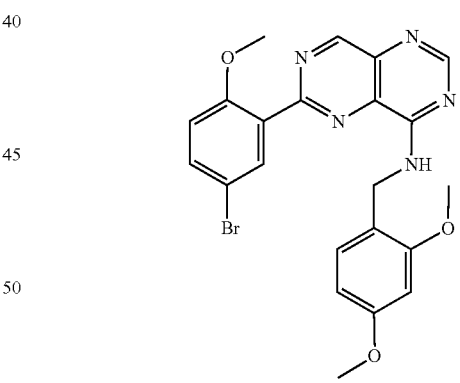

The title compound was prepared with analogous conditions described in Step C of Intermediate 23 utilizing (5-bromo-2-methoxyphenyl)boronic acid to afford 6-(5-bromo-2-methoxyphenyl)-N-(2,4-dimethoxybenzyl)pyrimido[5,4-d]pyrimidin-4-amine (400 mg, 38%) as a brown solid. MS (ESI): mass calcd. for $C_{22}H_{20}BrN_5O_3$ 481.1 m/z found 484.1 [M+H]$^+$.

Intermediate 101: (R)-3-((3-(8-((2,4-Dimethoxybenzyl)amino)pyrimido[5,4-d]pyrimidin-2-yl)-4-methoxyphenyl)ethynyl)-3-hydroxy-1-methylpyrrolidin-2-one

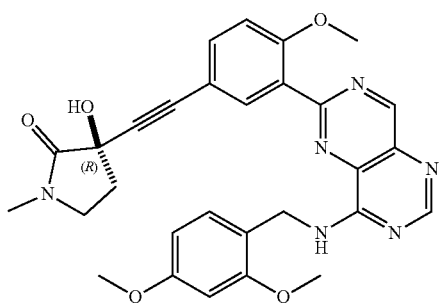

The title compound was prepared with analogous conditions described in Intermediate 69 utilizing Intermediate 100 6-(5-bromo-2-methoxyphenyl)-N-(2,4-dimethoxybenzyl)pyrimido[5,4-d]pyrimidin-4-amine and Intermediate 2 (R)-3-ethynyl-3-hydroxy-1-methylpyrrolidin-2-one to afford (R)-3-((3-(8-((2,4-dimethoxybenzyl)amino)pyrimido[5,4-d]pyrimidin-2-yl)-4-methoxyphenyl)ethynyl)-3-hydroxy-1-methylpyrrolidin-2-one (210 mg, 54%) as a brown solid. MS (ESI): mass calcd. for $C_{29}H_{28}N_6O_5$ 540.2 m/z found 541.2 $[M+H]^+$.

Intermediate 102: 2-(3-Bromophenyl)-2H-pyrazolo[4,3-d]pyrimidin-7-amine

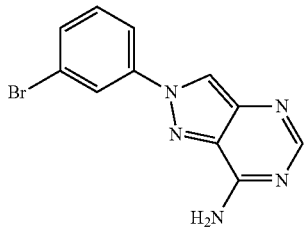 [SMILES: Nc1ncnc2cn(-c3cccc(Br)c3)nc12]

Step A: 4-Amino-1-(3-bromophenyl)-1H-pyrazole-3-carbonitrile. $Cu(OAc)_2$ (0.67 g, 3.70 mmol) was added to a mixture of 4-amino-1H-pyrazole-3-carbonitrile (0.80 g, 7.40 mmol), (3-bromophenyl)boronic acid (2.23 g, 11.1 mmol), pyridine (1.91 mL, 23.7 mmol), 4 Å molecular sieves (3 g), and DMF (30 mL). The resultant mixture was heated at 95° C. for 18 h under air before cooling to rt. The suspension was filtered through a pad of diatomaceous earth, such as Celite® and the pad washed with ethyl acetate (150 mL). The filtrate was concentrated to dryness. The resulting residue was purified by FCC (1:0 to 1:1 gradient, petroleum ether/ethyl acetate) to afford 4-amino-1-(3-bromophenyl)-1H-pyrazole-3-carbonitrile (640 mg, 33%) as a white solid. MS (ESI): mass calcd. for $C_{10}H_7BrN_4$ 262.0 m/z found 262.9 $[M+H]^+$.

Step B: 2-(3-Bromophenyl)-2H-pyrazolo[4,3-d]pyrimidin-7-amine. DIPEA (1.20 mL, 6.87 mmol) was added to a solution of 4-amino-1-(3-bromophenyl)-1H-pyrazole-3-carbonitrile (400 mg, 1.52 mmol), formimidamide acetate (317 mg, 3.05 mmol), and 1,4-dioxane (5 mL). The mixture was stirred at 100° C. for 16 h before cooling to rt. The resulting solid was collected by filtration and the filter cake was washed with water (50 mL×3) and toluene (8 mL) before drying under reduced pressure to afford 2-(3-bromophenyl)-2H-pyrazolo[4,3-d]pyrimidin-7-amine (287 mg, 55%) as a brown solid. MS (ESI): mass calcd. for $C_{11}H_8BrN_5$ 289.0 m/z found 290.0 $[M+H]^+$.

Intermediate 103: (S)-2-(4-Methylthiazol-2-yl)but-3-yn-2-ol

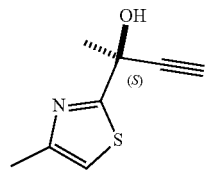

The title compound was prepared with analogous conditions described in Step B of Intermediate 79 utilizing 1-(4-methylthiazol-2-yl)ethan-1-one. Racemic 2-(4-methylthiazol-2-yl)but-3-yn-2-ol (16.0 g) was purified by preparative SFC (DAICEL CHIRALPAK AD, 250×50 mm, 10 μm) to afford (S)-2-(4-methylthiazol-2-yl)but-3-yn-2-ol (6.5 g, 27% yield, 99.5% ee) as light yellow solid. $[\alpha]^{20}_D$=+10.3 (c=0.1 in MeOH) and (R)-2-(4-methylthiazol-2-yl)but-3-yn-2-ol (Intermediate 104, 5.5 g, 23% yield, 99.9% ee) as a light yellow solid.

Intermediate 104: (R)-2-(4-Methylthiazol-2-yl)but-3-yn-2-ol

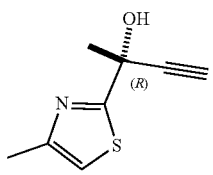

The title compound was prepared with analogous conditions described in Step B of Intermediate 79 utilizing 1-(4-methylthiazol-2-yl)ethan-1-one and chiral separation described in Intermediate 103 to afford (R)-2-(4-methylthiazol-2-yl)but-3-yn-2-ol (5.5 g, 23% yield, 99.9% ee) as a light yellow solid. $[\alpha]^{20}_D$=−10.2 (c=0.1 in MeOH)

Intermediate 105: 2-(5-Iodo-2-methylphenyl)-5-methylthiazolo[5,4-d]pyrimidin-7-amine

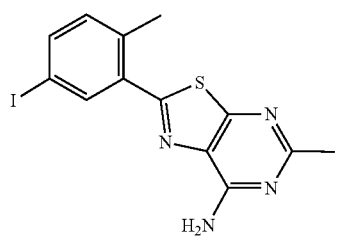 [SMILES: Cc1nc(N)c2nc(-c3cc(I)ccc3C)sc2n1]

Step A: 5,6-Diamino-2-methylpyrimidin-4(3H)-one. To a 100 mL round-bottomed flask equipped with an reflux condenser under a $N_2$ atmosphere, was added 28% sodium methoxide solution in MeOH (16.0 mL, 70.5 mmol), dropwise, to a solution of ethyl 2-acetamido-2-cyanoacetate (6.00 g, 35.6 mmol) and acetamidine hydrochloride (3.50 g, 35.2 mmol) in MeOH (16 mL). The mixture was heated to reflux. After 1 h, the resulting mixture was cooled to 0° C. and the precipitate was collected by filtration. The resulting crystals were suspended in water (14 mL) and concentrated HCl (13.2 mL) was added dropwise by addition funnel. After the addition was complete, the mixture was heated at 85° C. for 3 h, cooled to rt, and aqueous NaOH was added (22 mL, 176.30, 8M) was added. The mixture was heated at 85° C. for 1 h and the resulting precipitate was collected by filtration to afford 5,6-diamino-2-methylpyrimidin-4(3H)-one (1.6 g, 32%) as a pink solid. MS (ESI): mass calcd. for $C_5H_8N_4O$, 140.15; m/z. found, 141.1 $[M+H]^+$. $^1H$ NMR (400 MHz, DMSO-$d_6$) δ 1H NMR (500 MHz, $CDCl_3$) δ 5.56 (s, 2H), 3.53 (s, 2H), 2.13 (s, 3H).

Step B: N-(4-Amino-2-methyl-6-oxo-1,6-dihydropyrimidin-5-yl)-5-iodo-2-methylbenzamide. Oxalyl chloride (0.20 mL, 2.35 mmol) was added dropwise to a solution of 5-iodo-2-methylbenzoyl chloride (0.56 g, 2.14 mmol) in DCM (21 mL), followed by DMF (2 drops from a glass pipette). The reaction was stirred at rt and concentrated to dryness. The crude residue was taken up in dioxane (3 mL) and added dropwise to a suspension of 5,6-diamino-2-methylpyrimidin-4(3H)-one (0.30 g, 2.14 mmol) and DIPEA (0.74 mL, 4.28 mmol). The mixture was stirred for 10 min at rt, DMSO (10 mL) was then added and the reaction was stirred for 1 h. The resulting solid was collected by filtration to afford N-(4-amino-2-methyl-6-oxo-1,6-dihydropyrimidin-5-yl)-5-iodo-2-methylbenzamide (0.55 g, 67%) as a colorless solid. $^1H$ NMR (400 MHz, DMSO-$d_6$) δ 11.58 (s, 1H), 8.80 (s, 1H), 7.99 (d, J=1.9 Hz, 1H), 7.66 (dd, J=8.0, 2.0 Hz, 1H), 7.04 (d, J=8.1 Hz, 1H), 6.26 (s, 2H), 2.35 (s, 3H), 2.17 (s, 3H).

Step C: 2-(5-Iodo-2-methylphenyl)-5-methylthiazolo[5,4-d]pyrimidin-7-amine. Phosphorus pentasulfide (0.80 g, 3.58 mmol) to a suspension of N-(4-amino-2-methyl-6-oxo-1,6-dihydropyrimidin-5-yl)-5-iodo-2-methylbenzamide (0.55 g, 1.43 mmol) in pyridine (7.2 mL, 1.43 mmol) at 0° C. in a vial. The vial was sealed and heated to 100° C. for 3 h, cooled to rt, water (3 mL) was added and the solid was isolated by filtration.

The solid was returned to a vial, suspended in pyridine (7.2 mL, 1.43 mmol) and phosphorus pentasulfide (0.36 g, 1.61 mmol) was added at 0° C. The vial was sealed and heated to 150° C. for 3 h, then cooled to rt, quenched with 1M HCl (10 mL), and the solid was isolated by filtration to afford 2-(5-iodo-2-methylphenyl)-5-methylthiazolo[5,4-d]pyrimidin-7-amine (0.21 g, 38%) as a colorless solid. MS (ESI): mass calcd. for $C_{13}H_{11}IN_4S$, 382.23; m/z. found, 383.0 $[M+H]^+$. $^1H$ NMR (400 MHz, DMSO-$d_6$) δ 8.12 (d, J=1.9 Hz, 1H), 7.78 (dd, J=8.1, 1.9 Hz, 1H), 7.67 (s, 2H), 7.22 (d, J=8.1 Hz, 1H), 2.56 (s, 3H), 2.45 (s, 3H).

Intermediate 106:
(R)-3-Ethynyl-3-hydroxy-1-methylpiperidin-2-one

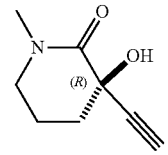

Step A: 3-(Benzyloxy)pyridin-2-ol. To a solution of pyridine-2,3-diol (130 g, 1.17 mol) in EtOH (1.5 L) was added KOH (65.6 g, 1.17 mol) and benzylbromide (210.1 g, 1.23 mol) at 10° C. The resulting mixture was heated at 40° C. and stirred. After 2 h, the mixture was concentrated to dryness. The residue was diluted with water (1.0 L) and extracted with $CH_2Cl_2$ (500 mL×3). The combined organic layers were washed with brine (400 mL×2), dried over $Na_2SO_4$, filtered, and concentrated to dryness. The residue was purified by stirring in EtOH (500 mL) for 30 min, the resulting solid was filtered, and filter cake was dried to give 3-(benzyloxy)pyridin-2-ol (150 g, 58.0%) as a brown solid. $^1H$ NMR (400 MHz, $CDCl_3$) δ 13.35 (br s, 1H), 7.45-7.50 (m, 5H), 7.06-7.27 (m, 1H), 6.75-6.77 (m, 1H), 6.12-6.16 (m, 1H), 5.17 (s, 2H).

Step B: 3-(Benzyloxy)-1-methylpyridin-2(1H)-one. To a solution of 3-(benzyloxy)pyridin-2-ol (150 g, 745 mmol) in DMSO (1.5 L) was added KOH (62.7 g, 1.12 mol) at 15° C. After 30 min, $CH_3I$ (162.0 g, 1.14 mol) was added drop wise while maintaining the reaction temperature at 15° C. After 2 h, the mixture was diluted with water (2.0 L) at 15° C. and extracted with $CH_2Cl_2$ (500 mL×3). The combined organic layers were washed with water (500 mL×2) and brine (500 mL×2), dried over $Na_2SO_4$, filtered, and concentrated to dryness. The resulting residue was stirred with MTBE (500 mL) for 40 min, the resulting solid was collected by filtration, and the filter cake was dried to give 3-(benzyloxy)-1-methylpyridin-2(1H)-one (130 g, 78.0% yield) as a gray solid. $^1H$ NMR (400 MHz, $CDCl_3$) δ 7.27-7.44 (m, 5H), 6.90-6.91 (m, 1H), 6.63-6.50 (m, 1H), 5.97-6.02 (m, 1H), 5.14 (s, 2H), 3.58 (s, 3H).

Step C: 3-Hydroxy-1-methylpyridin-2(1H)-one. To a solution of 3-(benzyloxy)-1-methylpyridin-2(1H)-one (130 g, 604 mmol) in MeOH (1.0 L) was added Pd/C (10 g, 60.4 mmol) under $N_2$. The suspension was degassed under vacuum and purged with $H_2$ several times. The mixture was stirred under $H_2$ (15 psi) at 20° C. for 16 h. After which time the reaction mixture was filtered, washed with MeOH 300 mL, and concentrated to dryness to give 3-hydroxy-1-methylpyridin-2(1H)-one (74.0 g, 93.0%) as a pink solid. $^1H$ NMR (400 MHz, $CDCl_3$) δ 6.74-6.83 (m, 2H), 6.08-6.15 (m, 1H), 3.64 (s, 3H).

Step D: 3-Hydroxy-1-methylpiperidin-2-one. To a solution of 3-hydroxy-1-methylpyridin-2(1H)-one (74.0 g, 591.4 mmol) in MeOH (1.0 L) was added Rh/C (8.01 g, 7.92 mmol) at 20° C. under $N_2$. The suspension was degassed under vacuum and purged with $H_2$ several times. The mixture was stirred under $H_2$ (45 psi) at 50° C. for 16 h. The reaction mixture was then filtered, and the filtrate was concentrated to dryness to afford 3-hydroxy-1-methylpiperidin-2-one (70.0 g, 87.1% yield) as a black brown oil.

Step E: 1-Methylpiperidine-2,3-dione. To a solution of 3-hydroxy-1-methylpiperidin-2-one (50.0 g, 387.1 mmol) in DCM (500 mL) was added 1,1,1-tris(acetyloxy)-1,1-dihydro-1,2-benziodoxol-3-(1H)-one (Dess-Martin periodinane, 197.0 g, 464.5 mmol) and the mixture was stirred at 25° C. for 16 h under N$_2$. The reaction mixture was filtered and concentrated to dryness. The residue was purified by FCC (10-40% gradient, ethyl acetate/DCM) to afford 1-methylpiperidine-2,3-dione (18.5 g) as a light red solid.

Step F: 3-Hydroxy-1-methyl-3-((trimethylsilyl)ethynyl)piperidin-2-one. To a solution of ethynyl(trimethyl)silane (11.6 g, 118 mmol) in THF (100 mL) was added n-BuLi (35.4 mL, 2.5 M in hexanes) below −60° C. and the mixture was stirred at −70° C. for 0.5 h under N$_2$. To the mixture was added 1-methylpiperidine-2,3-dione (7.50 g, 58.9 mmol) in THF (150 mL) and the reaction mixture was stirred at −70° C. for 1 h under N$_2$. To the resulting mixture was added AcOH (5.7 g). The mixture was filtered and the filtrate was concentrated to dryness to afford 3-hydroxy-1-methyl-3-((trimethylsilyl)ethynyl)piperidin-2-one (26.5 g) obtained as a red liquid, which was used directly in the next step without purification.

Step G: (R)-3-Ethynyl-3-hydroxy-1-methylpiperidin-2-one. To a solution of 3-hydroxy-1-methyl-3-((trimethylsilyl)ethynyl)piperidin-2-one (26.0 g, 115.4 mmol) in MeOH (600 mL) was added K$_2$CO$_3$ (36.67 g, 265.4 mmol) and the mixture was stirred at 25° C. for 16 h. The reaction mixture was filtered and concentrated under reduced pressure. The residue was purified by FCC (15% ethyl acetate/DCM) to afford racemic-1-methylpiperidine-2,3-dione (10 g) which was further purified by chiral preparative SFC (DAICEL CHIRALPAK AD (250×50 mm, 10 μm); mobile phase: [0.1% NH$_3$H$_2$O EtOH]; B %: 30%) to afford (R)-3-ethynyl-3-hydroxy-1-methylpiperidin-2-one (4.41 g, 24.1% yield, >97% ee) as light yellow solid and (S)-3-ethynyl-3-hydroxy-1-methylpiperidin-2-one (4.67 g, 26.4% yield, >97% ee). Data for (R)-3-ethynyl-3-hydroxy-1-methylpiperidin-2-one: MS (ESI): mass calcd. for C$_8$H$_{11}$NO$_2$, 153.08; m/z found, 153.80 [M+H]$^+$. $^1$H NMR (400 MHz, CDCl$_3$) δ 4.29 (s, 1H), 3.32-3.36 (m, 2H), 2.94 (s, 3H), 2.48 (s, 1H), 2.24-2.33 (m, 2H), 1.89-1.96 (m, 2H).

Intermediate 107:
(S)-3-Ethynyl-3-hydroxy-1-methylpiperidin-2-one

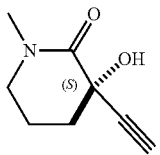

The title compound was prepared with analogous conditions described in Intermediate 106 and utilizing the chiral separation described to afford (S)-3-ethynyl-3-hydroxy-1-methylpiperidin-2-one (4.67 g, 26.4% yield, >97% ee) was obtained as light yellow solid. MS (ESI): mass calcd. for C$_8$H$_{11}$NO$_2$, 153.08; m/z. found, 153.80 [M+H]$^+$. $^1$H NMR (400 MHz, CDCl$_3$) δ 4.29 (s, 1H), 3.32-3.36 (m, 2H), 2.94 (s, 3H), 2.48 (s, 1H), 2.24-2.33 (m, 2H), 1.89-1.96 (m, 2H).

Intermediate 108: 6-(5-Bromo-2-methylphenyl)-N-(2,4-dimethoxybenzyl)pyrimido[5,4-d]pyrimidin-4-amine

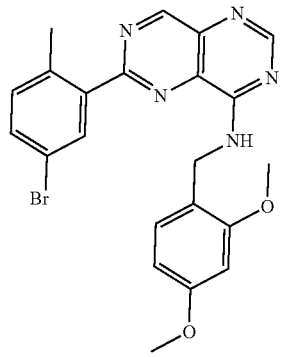 [SMILES: COc1ccc(CNc2ncnc3cnc(-c4cc(Br)ccc4C)nc23)c(OC)c1]

The title compound was prepared with analogous conditions described in Step C of Intermediate 23 utilizing (5-bromo-2-methylphenyl)boronic acid to afford 6-(5-bromo-2-methylphenyl)-N-(2,4-dimethoxybenzyl)pyrimido[5,4-d]pyrimidin-4-amine (180 mg, 30%) as a yellow solid. MS (ESI): mass calcd. for C$_{22}$H$_{20}$BrN$_5$O$_2$ 465.05 m/z found 467.8 [M+H]$^+$.

Intermediate 109: (R)-3-((3-(8-((2,4-Dimethoxybenzyl)amino)pyrimido[5,4-d]pyrimidin-2-yl)-4-methylphenyl)ethynyl)-3-hydroxy-1-methylpyrrolidin-2-one

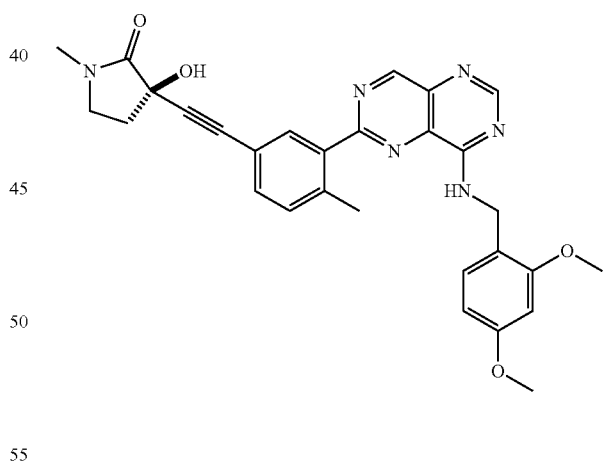

The title compound was prepared with analogous conditions described in Intermediate 69 utilizing Intermediate 108 6-(5-bromo-2-methylphenyl)-N-(2,4-dimethoxybenzyl)pyrimido[5,4-d]pyrimidin-4-amine and Intermediate 2 (R)-3-ethynyl-3-hydroxy-1-methylpyrrolidin-2-one to afford (R)-3-((3-(8-((2,4-dimethoxybenzyl)amino)pyrimido[5,4-d]pyrimidin-2-yl)-4-methylphenyl)ethynyl)-3-hydroxy-1-methylpyrrolidin-2-one (140 mg, 89%) as a brown solid. MS (ESI): mass calcd. for C$_{29}$H$_{28}$N$_6$O$_4$ 524.2 m/z found 525.2 [M+H]$^+$.

Intermediate 110: 6-(3-Iodophenyl)-2-methylpyrido[3,2-d]pyrimidin-4-amine

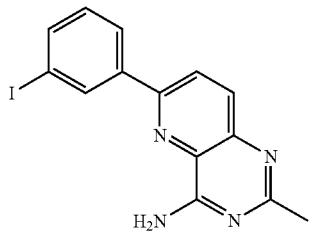 [SMILES: Cc1nc(N)c2nc(-c3cccc(I)c3)ccc2n1]

Step A: 2-Methyl-6-(3-(trimethylsilyl)phenyl)pyrido[3,2-d]pyrimidin-4-amine. To a 10 L round-bottomed flask equipped with overhead stirrer were added acetonitrile (3000 mL), 6-chloro-2-methylpyrido[3,2-d]pyrimidin-4-amine (150 g, 0.77 mol), 4-(trimethylsilyl) phenylboronic acid (165 g, 0.85 mol), aqueous $Cs_2CO_3$ (1 M, 750 mL) and $Pd(dppf)Cl_2$ (28.2 g, 38.5 mmol) under nitrogen successively. The resultant mixture was heated to 75° C. and maintained at this temperature for 2 h. After completion of the reaction, $H_2O$ (2250 mL) was added and the mixture was further heated at 65° C. for 1 h. The resultant mixture was then allowed to cool to rt gradually. The product was isolated by filtration followed by washing with acetonitrile/water (1/3, 1800 mL) and drying under vacuum at 45° C. to give 2-methyl-6-(3-(trimethylsilyl)phenyl)pyrido[3,2-d]pyrimidin-4-amine (261 g, 88%) as an gray solid. MS (ESI): mass calcd. for $C_{17}H_{20}N_4Si$, 308.15; m/z. found, 309.15 $[M+H]^+$. $^1H$ NMR (400 MHz, DMSO-$d_6$) δ 8.44-8.34 (m, 3H), 8.05 (m, 1H), 7.90 (s, 2H), 7.62 (m, 1H), 7.52 (m, 1H), 2.47 (s, 3H), 0.34 (s, 9H).

Step B: 6-(3-Iodophenyl)-2-methylpyrido[3,2-d]pyrimidin-4-amine. To a 10 L round-bottomed flask equipped with overhead stirrer were added $CH_2Cl_2$ (6 L) and 2-methyl-6-(3-(trimethylsilyl)phenyl)pyrido[3,2-d]pyrimidin-4-amine (300 g, 0.97 mol). A solution of ICl (395 g, 2.92 mol) in DCM (1500 mL) was then added dropwise at 15° C. and the reaction mixture was stirred at this temperature for 1 h. The precipitate was isolated by filtration and dried under vacuum at 50° C. This crude material was combined with product from a second 100 g batch, and the resultant solid was dissolved in DMSO (3750 mL). Then an aqueous solution of $K_2HPO_4$ (8 wt %) was added dropwise to the above solution and stirred at 20° C. for 2 h. The precipitate was isolated by filtration followed by slurrying in water (8 L) at 20° C. for 4 h then drying to give a light brown solid. This solid was combined with a 360 g batch, and the resultant solid was further slurried in acetonitrile (12 L) at 60° C. for 4 h followed by cooling to 20° C. The product was isolated by filtration and dried to give 6-(3-iodophenyl)-2-methylpyrido[3,2-d]pyrimidin-4-amine (905 g, 83%) as an gray solid. MS (ESI): mass calcd. for $C_{14}H_{11}IN_4$, 362.0; m/z. found, 363.0 $[M+H]^+$.

Intermediate 111: (R)-2-(Pyridin-2-yl)but-3-yn-2-ol

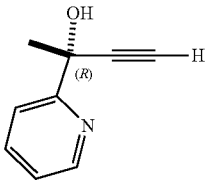

A 1 L round-bottomed flask was charged with THF (200 mL), ethynyltrimethylsilane (32.4 g, 330 mmol, 45.7 mL) under $N_2$ at −70° C. Then n-BuLi (99.0 mL, 2.5 M in hexanes) was added dropwise and the mixture was stirred at −70° C. for 0.5 hrs. Then 1-(pyridin-2-yl)ethan-1-one (20.0 g, 165 mmol, 18.5 mL) in THF (100 mL) was added drop-wise and the mixture was stirred at −70° C. for 1 h. To the mixture was added saturated aqueous $NH_4Cl$ (200 mL). The reaction mixture was then warmed to rt and extracted with ethyl acetate (30 mL×3). The combined organic layers were washed with brine (40 mL), dried over $Na_2SO_4$, filtered, and concentrated to dryness. The residue was diluted with MeOH (400 mL) and $K_2CO_3$ (45.6 g, 330 mmol) was added. The resulting mixture was stirred at 15° C. for 16 h. The reaction mixture was filtered and concentrated to dryness and then diluted with ethyl acetate (450 mL). The organic layer was washed with water (150 mL) and brine (150 mL). The resulting organic layer was dried over anhydrous $Na_2SO_4$, filtered, and concentrated to dryness. The residue was purified by FCC (10.0-20.0% gradient, ethyl acetate/petroleum ether) to afford racemic-2-(pyridin-2-yl)but-3-yn-2-ol (15.5 g). The racemic material was further separated by chiral preparative SFC (DAICEL CHIRALCEL OJ (250×50 mm, 10 um); mobile phase: [0.1% $NH_3H_2O$ EtOH]; B %: 15%) to afford (R)-2-(pyridin-2-yl)but-3-yn-2-ol (4.70 g, 19.2% yield, >97% ee) as a yellow solid and (S)-2-(pyridin-2-yl)but-3-yn-2-ol (Intermediate 112, 4.50 g, 18.5% yield, >97% ee) as a yellow solid. Data for (R)-2-(pyridin-2-yl)but-3-yn-2-ol: MS (ESI): mass calcd. for $C_9H_9NO$, 147.0; m/z. found, 148.1 $[M+H]^+$. $^1H$ NMR (400 MHz, $CDCl_3$) δ 8.54 (d, J=4.77 Hz, 1H), 7.78 (td, J=7.72, 1.63 Hz, 1H), 7.63 (d, J=8.03 Hz, 1H), 7.27-7.32 (m, 1H), 5.50 (br s, 1H), 2.55 (s, 1H), 1.80 (s, 3H).

Intermediate 112: (S)-2-(Pyridin-2-yl)but-3-yn-2-ol

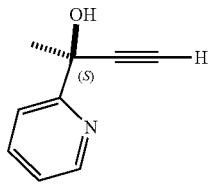

The title compound was prepared with analogous conditions described in Intermediate 111 and utilizing the chiral separation described to afford (S)-2-(pyridin-2-yl)but-3-yn-2-ol (4.50 g, 18.5% yield, >97% ee) as a yellow solid. MS (ESI): mass calcd. for $C_9H_9NO$, 147.0; m/z. found, 148.1 $[M+H]^+$. $^1H$ NMR (400 MHz, $CDCl_3$) δ 8.54 (d, J=4.77 Hz, 1H), 7.78 (td, J=7.72, 1.63 Hz, 1H), 7.63 (d, J=8.03 Hz, 1H), 7.27-7.32 (m, 1H), 5.50 (br s, 1H), 2.55 (s, 1H), 1.80 (s, 3H).

Intermediate 113: (R)-2-(4-(Trifluoromethyl)thiazol-2-yl)but-3-yn-2-ol

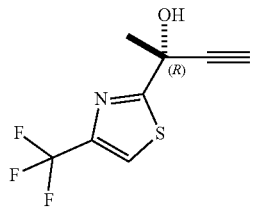

Step A: Ethyl 4-(trifluoromethyl)thiazole-2-carboxylate. To a solution of ethyl 2-amino-2-thioxo-acetate (139 g, 1.05 mol) in EtOH (1.1 L) was added 3-bromo-1,1,1-trifluoropropan-2-one (200 g, 1.05 mol, 108.7 mL). The yellow suspension was stirred at 90° C. for 16 h. 1,8-diazabicyclo[5.4.0]undec-7-ene (159 g, 1.05 mol, 158 mL) was added to this suspension at 15° C. The resulting brown solution was stirred at 15° C. for 40 h. The reaction mixture was concentrated to dryness, the residue was diluted with DCM (1 L), washed with water (200 mL×2), and brine (100 mL). The organic layer was separated and dried over anhydrous $Na_2SO_4$, filtered, and concentrated to dryness. The resulting residue was purified by FCC (2-3%, ethyl acetate/petroleum ether) to afford ethyl 4-(trifluoromethyl)thiazole-2-carboxylate (90.0, 35.1%) as a yellow oil. MS (ESI): mass calcd. for $C_7H_6F_3NO_2S$, 225.01; m/z. found, 225.9 $[M+H]^+$.

Step B: 4-(Trifluoromethyl)thiazole-2-carboxylic acid. To a solution of ethyl 4-(trifluoromethyl)thiazole-2-carboxylate (70.0 g, 311 mmol) in THF (500 mL) and MeOH (500 mL) was added $LiOH-H_2O$ (363 mL, 3 M). The yellow suspension was stirred at 15° C. for 12 h. The mixture was concentrated to dryness. The mixture was dissolved in water (300 mL), acidified to approximately pH=2 with concentrated HCl, and the resulting yellow solid was collected by filtration. The solid was dissolved in ethyl acetate (800 mL), washed with water (100 mL), and brine (100 mL). The organic layer was separated dried over $Na_2SO_4$, filtered, and concentrated to dryness. The resulting residue was triturated with petroleum ether (500 mL), the solid was collected by filtration, and used without further purification to afford 4-(trifluoromethyl)thiazole-2-carboxylic acid (50.0 g, 77.5%) as a yellow solid.

Step C: N-methoxy-N-methyl-4-(trifluoromethyl)thiazole-2-carboxamide. To a solution of 4-(trifluoromethyl)thiazole-2-carboxylic acid (40.0 g, 203 mmol) in THF (400 mL) was added carbonyldiimidazole (42.8 g, 264 mmol). The brown solution was heated at 40° C. for 2 h. N-methoxymethanamine hydrochloride salt (25.7 g, 263.8 mmol) was added to this solution. The resulting yellow suspension was stirred at 15° C. for 12 h. The reaction mixture was filtered and the filtrate was concentrated. The residue was extracted with ethyl acetate (600 mL×2), washed with water (100 mL) and brine (100 mL). The organic layer was dried over $Na_2SO_4$, filtered, and concentrated to dryness. The residue was purified by FCC (8-15% gradient, ethyl acetate/petroleum ether) to afford N-methoxy-N-methyl-4-(trifluoromethyl)thiazole-2-carboxamide (67.5 g, 66.4%) as a yellow solid.

Step D: 1-(4-(Trifluoromethyl)thiazol-2-yl)ethan-1-one. To a solution of N-methoxy-N-methyl-4-(trifluoromethyl)thiazole-2-carboxamide (67.5 g, 281 mmol) in THF (700 mL) was added MeMgCl (141 mL, 3 M in THF) dropwise at 0° C. The resulting yellow solution was stirred at 0-15° C. for 5 h. The mixture was poured into saturated aqueous $NH_4Cl$ (300 mL) and extracted with ethyl acetate (500 mL). The organic layers were washed with brine (100 mL), dried over $Na_2SO_4$, filtered, and concentrated to dryness. The residue was purified by FCC (4-5% gradient, ethyl acetate/petroleum ether) to afford 1-(4-(trifluoromethyl)thiazol-2-yl)ethan-1-one (45.0 g, 77.9%) as a yellow oil.

Step E: 2-(4-(Trifluoromethyl)thiazol-2-yl)-4-(trimethylsilyl)but-3-yn-2-ol. To a solution of ethynyl(trimethyl)silane (44.0 g, 448 mmol, 62.1 mL) in THF (350 mL) was added n-BuLi (143.5 mL, 2.5 M in hexanes) dropwise at −65° C. The yellow solution was stirred at −65° C. for 1.5 h. A solution of 1-(4-(trifluoromethyl)thiazol-2-yl)ethan-1-one (35.0 g, 179 mmol) in THF (50 mL) was added and the resulting yellow solution was stirred at −65° C. for 1.5 h. The reaction mixture was poured into saturated aqueous $NH_4Cl$ (500 mL) and extracted with ethyl acetate (800 mL). The organics were washed with brine (100 mL), dried over $Na_2SO_4$, filtered, and concentrated to dryness to afford 2-(4-(trifluoromethyl)thiazol-2-yl)-4-(trimethylsilyl)but-3-yn-2-ol which was used directly in the next step without further purification.

Step F: 2-(4-(Trifluoromethyl)thiazol-2-yl)but-3-yn-2-ol. 2-(4-(Trifluoromethyl)thiazol-2-yl)-4-(trimethylsilyl)but-3-yn-2-ol was dissolved in MeOH (600 mL) and $K_2CO_3$ (49.6 g, 359 mmol) was added to the resulting solution. The yellow suspension was stirred at 15° C. for 3 h. The mixture was concentrated, extracted with ethyl acetate (600 mL×2), washed with water (200 mL) and brine (100 mL). The organic extracts were dried over $Na_2SO_4$, filtered, and concentrated to dryness. The residue was purified by FCC (4-5%, ethyl acetate/petroleum ether) to afford racemic 2-(4-(trifluoromethyl)thiazol-2-yl)but-3-yn-2-ol (34.0 g) as a yellow solid. The material was purified by chiral preparative SFC (DAICEL CHIRALCEL OD (250×50 mm, 10 μm); mobile phase: [Neu-IPA]; B %: 15%) to afford (R)-2-(4-(trifluoromethyl)thiazol-2-yl)but-3-yn-2-ol (10.0 g, 25.1%, 99.3% ee) as a yellow solid, $[\alpha]^{20}_D$=−64.4 (c=0.1 in MeOH) and (S)-2-(4-(trifluoromethyl)thiazol-2-yl)but-3-yn-2-ol (Intermediate 114, 14.0 g, 35.1%, 93.2% ee) as a yellow solid.

Intermediate 114: (S)-2-(4-(Trifluoromethyl)thiazol-2-yl)but-3-yn-2-ol

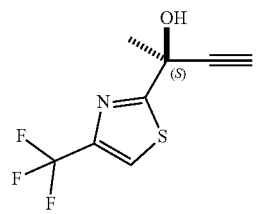

The title compound was prepared with analogous conditions described in Intermediate 113 and utilizing the chiral separation described to afford (S)-2-(4-(trifluoromethyl)thiazol-2-yl)but-3-yn-2-ol (14.0 g, 35.1%, 93.2% ee) as a yellow solid. $[\alpha]^{20}_D$=+58.3 (c=0.1 in MeOH).

Intermediate 115: 2-(5-Iodo-2-methoxyphenyl)thiazolo[5,4-d]pyrimidin-7-amine

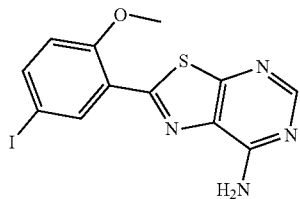 [SMILES: COc1ccc(I)cc1-c1nc2c(N)ncnc2s1]

Step A: 5-Iodo-2-methoxybenzoyl chloride. Oxalyl chloride (1.83 mL, 21.6 mmol) was added to a solution of 5-iodo-2-methoxybenzoic acid (2.0 g, 7.2 mmol), dichloromethane (20 mL), and DMF (0.2 mL) that had been cooled to 0° C. (ice/water). The mixture was stirred at rt. After 2 h, the resultant mixture was concentrated to dryness to afford 5-Iodo-2-methoxybenzoyl chloride (2.1 g) as a clear oil, which was used in the next step without further purification. MS (ESI): mass calcd. for $C_9H_9IO_3$ (methyl ester) 292.0 m/z. found 293.0 $[M+H]^+$.

Step B: N-(4-Amino-6-hydroxypyrimidin-5-yl)-5-iodo-2-methoxybenzamide. 5-iodo-2-methoxybenzoyl chloride (2.1 g, crude) was added to a solution of 5,6-diaminopyrimidin-4-ol (851 mg, 6.75 mmol), DIPEA (3.5 mL, 20 mmol), and 1,4-dioxane (30 mL). The resultant mixture was stirred at rt. After 2 h, the reaction mixture was diluted in $CH_3CN$ (30 mL) and the suspension was isolated via filtration. The filter cake was washed with $CH_3CN$ (30 mL) and dried to afford N-(4-amino-6-hydroxypyrimidin-5-yl)-5-iodo-2-methoxybenzamide (1.5 g, 55%) as a yellow solid. MS (ESI): mass calcd. for $C_{12}H_{11}IN_4O_3$ 385.99 m/z. found 387.0 $[M+H]^+$.

Step C: 2-(5-Iodo-2-methoxyphenyl)thiazolo[5,4-d]pyrimidin-7-amine. N-(4-Amino-6-hydroxypyrimidin-5-yl)-5-iodo-2-methoxybenzamide (500 mg, 1.30 mmol), $P_2S_5$ (863 mg, 3.88 mmol), and pyridine (20 mL) were added to a 100 mL round-bottomed flask. The mixture was heated at 110° C. for 1 h before cooling to rt and adjusting the pH to 7-8 with 1 N HCl. The suspension was isolated via filtration and the filter cake was washed with MeOH (10 mL) before drying under reduced pressure to afford 2-(5-Iodo-2-methoxyphenyl)thiazolo[5,4-d]pyrimidin-7-amine (500 mg, crude) as a brown solid. The crude material was further purified by reverse phase preparative HPLC (Xtimate C18 250×50 mm×10 μm, (eluent: 55% to 85% (v/v) $CH_3CN$ and $H_2O$ with 0.04% $NH_3H_2O$ and 10 mM $NH_4HCO_3$) to afford 2-(5-Iodo-2-methoxyphenyl)thiazolo[5,4-d]pyrimidin-7-amine (300 mg) as a white solid. MS (ESI): mass calcd. for $C_{12}H_9IN_4OS$ 384.0 m/z, found 385.0 $[M+H]^+$.

Intermediate 116: racemic-1-Allyl-3-ethynyl-3-hydroxypyrrolidin-2-one

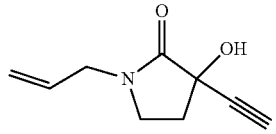

Step A: Ethyl 3-(allylamino)propanoate. Ethyl acrylate (150 g, 1.50 mol, 163 mL) and prop-2-en-1-amine (85.5 g, 1.50 mol, 112 mL) in EtOH (900 mL) at were combined at 0° C. The mixture was stirred at 25° C. for 24 h. The resulting material was concentrated to dryness to afford ethyl 3-(allylamino)propanoate (240 g) as a light oil.

Step B: Ethyl 1-allyl-4,5-dioxopyrrolidine-3-carboxylate. Sodium (42.1 g, 1.83 mol) was added to MeOH (993 mL) portion-wised at 25° C., then the mixture was concentrated. To the residue was added diisopropylether (900 mL) and ethyl 3-(allylamino)propanoate (240 g, 1.53 mol) slowly. Then, to this mixture was added a solution of diethyl oxalate (223 g, 1.53 mol, 208 mL) in diisopropylether (100 mL) drop-wised at 25° C. with stirring. After 12 h, the mixture was concentrated to dryness. To the residue was added ethyl acetate (2000 mL) and $H_2O$ (1000 mL). The water layer was extracted with ethyl acetate (500 mL×3). The combined organics were concentrated to dryness to afford ethyl 1-allyl-4,5-dioxopyrrolidine-3-carboxylate (300 g) as a yellow oil.

Step C: 1-Allylpyrrolidine-2,3-dione. Ethyl 1-allyl-4,5-dioxopyrrolidine-3-carboxylate (150 g, 710 mmol) was combined with HCl (1.65 L, 10% purity) at 25° C. The mixture was stirred at 100° C. After 4 h, the mixture was cooled to 25° C. and extracted with DCM (1500 mL×3). The combined organic layers were concentrated to dryness. The residue was purified by FCC (20:1 to 1:1 gradient, petroleum ether/ethyl acetate) to afford 1-allylpyrrolidine-2,3-dione (50.0 g, 25.3%) as an orange oil.

Step D: 1-Allyl-3-ethynyl-3-hydroxypyrrolidin-2-one. To a mixture of ethynyl(trimethyl)silane (35.3 g, 359 mmol, 49.8 mL) in THF (300 mL) was added n-BuLi (108 mL, 2.5 M in hexanes) at −70° C. under $N_2$. The mixture was stirred at −70° C. for 30 min, then the mixture was added to a solution of 1-allylpyrrolidine-2,3-dione (25.0 g, 179 mmol) in THF (500 mL) at −70° C. After the addition, the reaction was stirred for 1 h. The reaction mixture was poured into AcOH (10.0 ml) and the mixture was concentrated to dryness. The residue was diluted in MeOH (1000 mL) and $K_2CO_3$ (100 g) was added. The reaction mixture was stirred at 25° C. After 12 h, the mixture was concentrated to dryness and the residue was purified by FCC (1:0 gradient, DCM/MeOH) to afford racemic-1-allyl-3-ethynyl-3-hydroxypyrrolidin-2-one (5.60 g, 18.7%) as an orange oil. MS (ESI): mass calcd. for $C_9H_{11}NO_2$, 165.08; m/z. found, 166.2 $[M+H]^+$. $^1H$ NMR (400 MHz, $CDCl_3$) δ 5.69-5.76 (m, 1H), 5.19-5.23 (m, 2H), 4.21 (br s, 1H), 3.91-3.93 (m, 2H), 3.31-3.38 (m, 2H), 2.31-2.56 (m, 2H), 2.23-2.29 (m, 1H).

Intermediate 117: 6-(3-Iodophenyl)pyrido[3,2-d]pyrimidin-2-d-4-amine

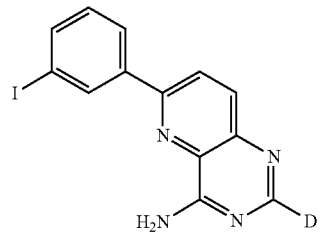 [SMILES: [2H]c1nc(N)c2nc(-c3cccc(I)c3)ccc2n1]

The title compound was prepared with analogous conditions described in Intermediate 110 utilizing 6-chloropyrido[3,2-d]pyrimidin-2-d-4-amine in Step A to afford 6-(3-iodophenyl)pyrido[3,2-d]pyrimidin-2-d-4-amine (135 g, 88%) as a light brown solid. MS (ESI): mass calcd. for C₁₃H₈DIN₄, 348.99; m/z. found, 350.0 [M+H]+. ¹H-NMR (400 MHz, DMSO-d₆) δ 8.84 (m, 1H), 8.47 (m, 1H), 8.40 (m, 2H), 8.12 (m, 2H), 7.86 (m, 1H), 7.34 (m, 1H).

Intermediate 118: (R)-2-(Pyrimidin-2-yl)but-3-yn-2-ol

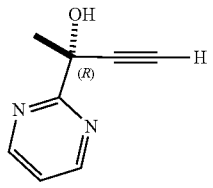

The title compound was prepared with analogous conditions described in Intermediate 111 utilizing 1-(pyrimidin-2-yl)ethan-1-one and chiral preparative SFC (DAICEL CHIRALPAK IC (250×50 mm, 10 μm); mobile phase: [0.1% NH₃H₂O, EtOH]; B %: 15%) to afford (R)-2-(pyrimidin-2-yl)but-3-yn-2-ol (4.29 g, 85.4%, >97% ee) as a brown oil and (S)-2-(pyrimidin-2-yl)but-3-yn-2-ol (Intermediate 119, 4.40 g, 86.1%, >97% ee). Data for (R)-2-(Pyrimidin-2-yl)but-3-yn-2-ol: MS (ESI): mass calcd. for C₈H₈N₂O, 148.0; m/z. found, 148.8 [M+H]⁺. ¹H NMR (400 MHz, CDCl₃) δ 8.81 (d, J=5.02 Hz, 2H), 7.31 (t, J=4.89 Hz, 1H), 2.55 (s, 1H), 1.92 (s, 3H).

Intermediate 119: (S)-2-(Pyrimidin-2-yl)but-3-yn-2-ol

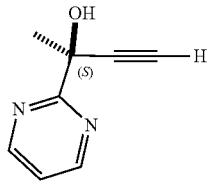

The title compound was prepared with analogous conditions described in Intermediate 111 utilizing 1-(pyrimidin-2-yl)ethan-1-one and chiral preparative SFC (DAICEL CHIRALPAK IC (250×50 mm, 10 μm); mobile phase: [0.1% NH₃H₂O, EtOH]; B %: 15%) to afford (S)-2-(pyrimidin-2-yl)but-3-yn-2-ol (4.40 g, 86.1%, >97% ee) as a brown oil. MS (ESI): mass calcd. for C₈H₈N₂O, 148.0; m/z. found, 148.8 [M+H]⁺. ¹H NMR (400 MHz, CDCl₃) δ 8.81 (d, J=5.02 Hz, 2H), 7.31 (t, J=4.89 Hz, 1H), 2.55 (s, 1H), 1.92 (s, 3H).

Intermediate 120: (R)-2-(Pyrazin-2-yl)but-3-yn-2-ol

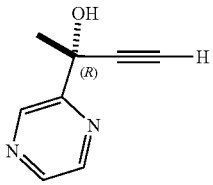

The title compound was prepared with analogous conditions described in Intermediate 111 utilizing 1-(pyrazin-2-yl)ethan-1-one and chiral preparative SFC (DAICEL CHIRALPAK AD (250×50 mm, 10 μm); mobile phase: [0.1% NH₃H₂O-MeOH]; B %: 10%-10%) to afford (R)-2-(pyrazin-2-yl)but-3-yn-2-ol (5.71 g, 23.5%, >97% ee) as a brown oil and (S)-2-(pyrazin-2-yl)but-3-yn-2-ol (6.11 g, 25.1%, >97% ee). Data for (R)-2-(pyrazin-2-yl)but-3-yn-2-ol: MS (ESI): mass calcd. for C₈H₈N₂O, 148.0; m/z. found, 148.8 [M+H]⁺. ¹H NMR (400 MHz, CDCl₃) δ 8.99 (d, J=1.26 Hz, 1H), 8.58 (d, J=2.51 Hz, 1H), 8.51-8.55 (m, 1H), 2.65 (s, 1H), 1.86 (s, 3H).

Intermediate 121: (S)-2-(Pyrazin-2-yl)but-3-yn-2-ol

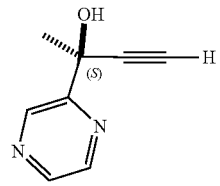

The title compound was prepared with analogous conditions described in Intermediate 111 utilizing 1-(pyrazin-2-yl)ethan-1-one and chiral preparative SFC (DAICEL CHIRALPAK AD (250×50 mm, 10 μm); mobile phase: [0.1% NH₃H₂O-MeOH]; B %: 10%-10%) to afford (S)-2-(pyrazin-2-yl)but-3-yn-2-ol (6.11 g, 25.1%, >97% ee) as a brown oil. MS (ESI): mass calcd. for C₈H₈N₂O, 148.0; m/z. found, 148.8 [M+H]⁺. ¹H NMR (400 MHz, CDCl₃) δ 8.99 (d, J=1.26 Hz, 1H), 8.58 (d, J=2.51 Hz, 1H), 8.51-8.55 (m, 1H), 2.65 (s, 1H), 1.86 (s, 3H).

Intermediate 122. 6-(3-Bromophenyl)pyrido[3,2-d]pyrimidine-2,4-diamine

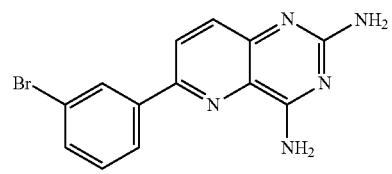 [SMILES: Nc1nc(N)c2nc(-c3cccc(Br)c3)ccc2n1]

Step A: 6-Chloropyrido[3,2-d]pyrimidine-2,4-diamine. NaOH (1.66 g, 7.82 mmol) was added to a solution of 3-amino-6-chloropicolinonitrile (300 mg, 1.95 mmol), guanidine hydrochloride (224 mg, 2.35 mmol), and CH₃CH₂OH (30 mL). The mixture was heated at 80° C. for 4 h before cooling to rt and pouring it into water (70 mL). The resulting solid was collected by filtration and triturated with ethyl acetate:methanol (10:1, 300 mL). The resulting solid was dried to afford 6-chloropyrido[3,2-d]pyrimidine-2,4-diamine (270 mg, crude) which was used in the next step without further purification. MS (ESI): mass calcd. for C₇HClN₅ 195.0 m/z found 196.1 [M+H]⁺.

Step B: 6-(3-Bromophenyl)pyrido[3,2-d]pyrimidine-2,4-diamine. 6-chloropyrido[3,2-d]pyrimidine-2,4-diamine (200 mg, 1.02 mmol), 2-(3-bromophenyl)-4,4,5,5-tetramethyl-1,3,2-dioxaborolane (286 mg, 1.01 mmol), Cs₂CO₃ (899 mg, 2.76 mmol), DMF (4 mL), and H₂O (2 mL) were added to a microwave tube. The mixture was sparged with Ar for 5 min and then treated with Pd(dppf)Cl$_2$ (67.3 mg, 0.09 mmol). The mixture was sparged with Ar for another 5 min and then subjected to microwave irradiation at 100° C. in for 1 h. After the reaction mixture was allowed to cool to rt, it was concentrated to dryness to afford 6-(3-bromophenyl) pyrido[3,2-d]pyrimidine-2,4-diamine (200 mg) which was used in the next step without further purification. MS (ESI): mass calcd. for C$_{13}$H$_{10}$BrN$_5$ 315.0 m/z found 316.0 [M+H]$^+$.

Intermediate 123: racemic-3-(Difluoromethyl)-1-methyl-3-((3-(4,4,5,5-tetramethyl-1,3,2-dioxaborolan-2-yl)phenyl)ethynyl)pyrrolidin-2-one

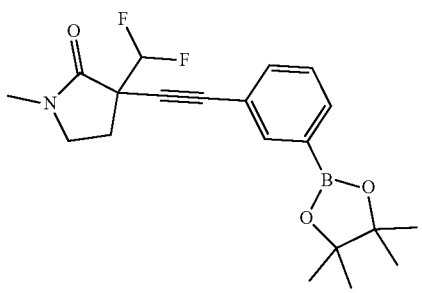

Step A: Methyl 1-methyl-2-oxopyrrolidine-3-carboxylate. LiHMDS (120 mL, 1 M in THF) was added to a −78° C. (dry ice/ethanol) solution of 1-methylpyrrolidin-2-one (10.0 g, 101 mmol) in THF (100 mL). The reaction mixture was stirred at −78° C. for 1 h. Then, a solution of methyl carbonochloridate (10.91 g, 116 mmol) and THF (50 mL) was added dropwise at −78° C. After 2 h, the mixture was poured into saturated aqueous NH$_4$Cl (200 mL) and extracted with ethyl acetate (200 mL×3). The combined organic extracts were washed with brine (300 mL), dried over anhydrous Na$_2$SO$_4$, filtered, and concentrated to dryness. The resulting residue as purified by FCC (1:0 to 1:3 gradient, petroleum ether:ethyl acetate) to afford methyl 1-methyl-2-oxopyrrolidine-3-carboxylate (4 g, 25%) as a colorless oil. $^1$H NMR (400 MHz, CDCl$_3$) δ 3.74 (s, 3H), 3.54-3.28 (m, 3H), 2.85 (s, 3H), 2.45-2.33 (m, 1H), 2.31-2.17 (m, 1H).

Step B: Methyl 3-(difluoromethyl)-1-methyl-2-oxopyrrolidine-3-carboxylate. LiHMDS (24 mL, 1 M in THF) was added to a −78° C. (dry ice/ethanol) solution of methyl 1-methyl-2-oxopyrrolidine-3-carboxylate (2.5 g, 16 mmol) and THF (50 mL). Then, the reaction mixture was stirred at −78° C. for 1 h before warming to rt. The reaction mixture was stirred under chlorodifluoromethane (15 psi) for 2 h at rt before pouring into saturated aqueous NH$_4$Cl (200 mL) and extracting with ethyl acetate (200×3 mL). The combined organic extracts were washed with brine (300 mL), dried over anhydrous Na$_2$SO$_4$, filtered, and concentrated to dryness. The resulting residue was purified by FCC (1:0 to 1:2 gradient, petroleum ether:ethyl acetate) to afford methyl 3-(difluoromethyl)-1-methyl-2-oxopyrrolidine-3-carboxylate (2.3 g, 67%) as a colorless oil. MS (ESI): mass calcd. for C$_8$H$_{11}$F$_2$NO$_3$ 207.1 m/z found 207.9 [M+H]$^+$. $^1$H NMR (400 MHz, CDCl$_3$) δ 6.65-6.22 (m, 1H), 3.79 (s, 3H), 3.56-3.45 (m, 1H), 3.42-3.33 (m, 1H), 2.87 (s, 3H), 2.60-2.51 (m, 1H), 2.49-2.40 (m, 1H).

Step C: 3-(Difluoromethyl)-1-methyl-2-oxopyrrolidine-3-carbaldehyde. DIBAL-H (10 mL, 1 M in toluene) was added to a −60° C. (dry ice/ethanol) solution of methyl 3-(difluoromethyl)-1-methyl-2-oxopyrrolidine-3-carboxylate (1.0 g, 4.8 mmol) and methylene chloride (30 mL). The reaction mixture was stirred for 1.5 h at −60° C. before quenching with 1 N HCl (50 mL) and warming to rt. The mixture was stirred for 30 min at rt and then extracted with methylene chloride (50 mL×3). The combined organic extracts were washed with brine (100 mL), dried over anhydrous Na$_2$SO$_4$, filtered and concentrated to dryness under reduced pressure to afford 3-(difluoromethyl)-1-methyl-2-oxopyrrolidine-3-carbaldehyde (900 mg) as a yellow oil. MS (ESI): mass calcd. for C$_7$H$_9$F$_2$NO$_2$ 177.2 m/z found 178.1 [M+H]$^+$.

Step D: 3-(Difluoromethyl)-3-ethynyl-1-methylpyrrolidin-2-one. K$_2$CO$_3$ (1.4 g, 10 mmol) was added to a mixture of 3-(difluoromethyl)-1-methyl-2-oxopyrrolidine-3-carbaldehyde (900 mg), dimethyl (1-diazo-2-oxopropyl)phosphonate (1.95 g, 10.2 mmol), and MeOH (20 mL). The mixture was stirred at rt for 16 h. The mixture was filtered through a pad of diatomaceous earth, such as Celite® and the pad washed with ethyl acetate (10 mL). The filtrate was concentrated to dryness. The resulting residue was purified by FCC (1:0 to 1:1 gradient, petroleum ether:ethyl acetate) to afford 3-(difluoromethyl)-3-ethynyl-1-methylpyrrolidin-2-one (500 mg) as a colorless oil. MS (ESI): mass calcd. for C$_8$H$_9$F$_2$NO 173.1 m/z found 174.1 [M+H]$^+$.

Step E: 3-(Difluoromethyl)-1-methyl-3-((3-(4,4,5,5-tetramethyl-1,3,2-dioxaborolan-2-yl)phenyl)ethynyl)pyrrolidin-2-one. 2-(3-Iodophenyl)-4,4,5,5-tetramethyl-1,3,2-dioxaborolane (280 mg, 0.85 mmol), 3-(difluoromethyl)-3-ethynyl-1-methylpyrrolidin-2-one (130 mg, 0.75 mmol), TEA (2.5 mL), and DMF (2.5 mL) were added to a microwave tube. The mixture was purged with Ar for 5 min and then treated with Pd(PPh$_3$)$_2$Cl$_2$ (53 mg, 0.076 mmol) and CuI (29 mg, 0.15 mmol). The mixture was purged with Ar for another 5 min and then stirred at 70° C. for 2 h before cooling to rt. The resulting mixture was poured into aqueous LiCl (4% in water, 20 mL) and extracted with ethyl acetate (20 mL×4). The combined organic extracts were washed with brine (50 mL), dried over anhydrous Na$_2$SO$_4$, filtered and concentrated to dryness to afford a mixture of 3-(difluoromethyl)-1-methyl-3-((3-(4,4,5,5-tetramethyl-1,3,2-dioxaborolan-2-yl)phenyl)ethynyl)pyrrolidin-2-one and (3-((3-(difluoromethyl)-1-methyl-2-oxopyrrolidin-3-yl) ethynyl)phenyl)boronic acid (360 mg) as a brown oil which was used without further purification. MS (ESI): mass calcd. for C$_{20}$H$_{24}$BF$_2$NO$_3$ 375.2 m/z found 376.2 [M+H]$^+$.

Intermediate 124. 6-Chloro-2-(methoxymethyl) pyrido[3,2-d]pyrimidin-4-amine

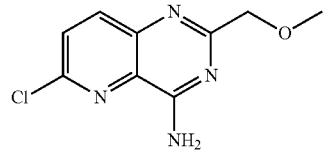

6-Chloro-2-(methoxymethyl)pyrido[3,2-d]pyrimidin-4-amine was prepared with analogous conditions described in Intermediate 96 utilizing 2-methoxyacetimidamide hydrochloride. MS (ESI): mass calcd. for C$_9$H$_9$ClN$_4$O, 224.1; m/z. found, 225.1 [M+H]$^+$. 1H NMR (400 MHz, CD$_3$OD) δ 8.07 (d, J=8.8 Hz, 1H), 7.78 (d, J=8.8 Hz, 1H), 4.49 (s, 2H), 3.49 (s, 3H).

Intermediate 125: (R)-3-((3-Bromophenyl)ethynyl)-3-methoxy-1-methylpyrrolidin-2-one

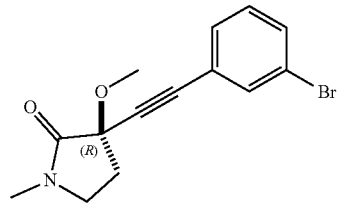

Sodium hydride in mineral oil (41 mg, 60% purity, 1.0 mmol) was added in portions to a solution of (R)-3-((3-bromophenyl)ethynyl)-3-hydroxy-1-methylpyrrolidin-2-one (200 mg, 0.68 mmol) and DMF (6 mL) that had been cooled to 0° C. (ice/water). Then, iodomethane (1.6 g, 11 mmol) was added dropwise to above mixture at 0° C. The resultant mixture was stirred for 2 h with gradual warming to rt. The mixture was diluted with water (20 mL) and extracted with ethyl acetate (15 mL×3). The combined organic extracts were washed with brine (15 mL), dried over anhydrous $Na_2SO_4$, filtered, and concentrated to dryness. The resulting residue was purified by FCC (10:1 to 1:4 gradient, petroleum ether/ethyl acetate) to afford (R)-3-((3-bromophenyl)ethynyl)-3-methoxy-1-methylpyrrolidin-2-one (200 mg, 95%) as a yellow oil. MS (ESI): mass calcd. for $C_{14}H_{14}BrNO_2$ 307.0 m/z found 310.0 [M+H]$^+$. $^1$H NMR (400 MHz, DMSO-$d_6$) δ 7.72-7.69 (m, 1H), 7.66-7.61 (m, 1H), 7.52-7.48 (m, 1H), 7.39-7.34 (m, 1H), 3.46 (s, 3H), 3.39-3.35 (m, 2H), 2.79 (s, 3H), 2.47-2.41 (m, 1H), 2.33-2.25 (m, 1H).

Intermediate 126: (R)-3-Methoxy-1-methyl-3-((3-(4,4,5,5-tetramethyl-1,3,2-dioxaborolan-2-yl)phenyl)ethynyl)pyrrolidin-2-one

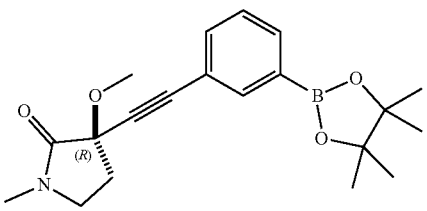

(R)-3-((3-Bromophenyl)ethynyl)-3-methoxy-1-methylpyrrolidin-2-one (150 mg, 0.487 mol), 4,4,4',4',5,5,5',5'-octamethyl-2,2'-bi(1,3,2-dioxaborolane) (136 mg, 0.536 mmol), KOAc (143 mg, 1.46 mmol) were dissolved in 1,4-dioxane (4 mL). The resultant mixture was sparged with Ar for 5 min and then treated with Pd(dppf)Cl$_2$ (36 mg, 0.049 mmol). The mixture was sparged with Ar for another 5 min and then stirred while heating at 100° C. for 1 h before cooling to rt. The suspension was filtered through a pad of diatomaceous earth, such as Celite® and the pad washed with ethyl acetate (15 mL) and concentrated to dryness. The resulting residue was purified by FCC (1:0 to 1:1 gradient, petroleum ether/ethyl acetate) to afford (R)-3-methoxy-1-methyl-3-((3-(4,4,5,5-tetramethyl-1,3,2-dioxaborolan-2-yl)phenyl)ethynyl)pyrrolidin-2-one (200 mg, 51%) as a yellow oil. MS (ESI): Mass calcd. for $C_{20}H_{26}BNO_4$ 355.2 m/z found 356.2 [M+H]$^+$.

Intermediate 127: (R)-3-hydroxy-1-(methyl-$d_3$)-3-((3-(4,4,5,5-tetramethyl-1,3,2-dioxaborolan-2-yl)phenyl)ethynyl)pyrrolidin-2-one

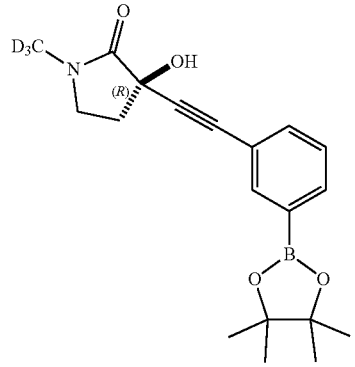

(R)-3-hydroxy-1-(methyl-$d_3$)-3-((3-(4,4,5,5-tetramethyl-1,3,2-dioxaborolan-2-yl)phenyl)ethynyl)pyrrolidin-2-one was prepared with analogous conditions described in Intermediate 4 utilizing Intermediate 45 [(R)-3-ethynyl-3-hydroxy-1-(methyl-$d_3$)pyrrolidin-2-one]. For $C_{19}H_{21}D_3BNO_4$, 344.2; m/z. found, 345.1 [M+H]$^+$.

Intermediate 128: (R)-2-(Thiazol-4-yl)but-3-yn-2-ol

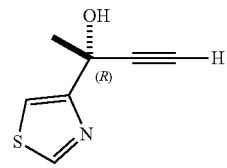

(R)-2-(Thiazol-4-yl)but-3-yn-2-ol was prepared with analogous conditions described in Intermediate 111 utilizing 1-(thiazol-4-yl)ethan-1-one and chiral preparative SFC (DAICEL CHIRALCEL OD (250×50 mm, 10 μm); mobile phase: [0.1% NH$_3$H$_2$O EtOH]; B %: 20%-20%) to afford (R)-2-(thiazol-4-yl)but-3-yn-2-ol (6.80 g, 29.2%, >97% ee) as a yellow solid and (S)-2-(thiazol-4-yl)but-3-yn-2-ol (Intermediate 129, 6.80 g, 29.5%, >97% ee) as a yellow solid. Data for (R)-2-(thiazol-4-yl)but-3-yn-2-ol: MS (ESI): mass calcd. for $C_7H_7NOS$, 153.0; m/z. found, 153.8 [M+H]$^+$. $^1$H NMR (400 MHz, CDCl$_3$) δ 8.81 (d, J=2.0 Hz, 1H), 7.44 (d, J=2.0 Hz, 1H), 3.72 (br s, 1H), 2.64 (s, 1H), 1.91 (s, 3H). [α]$^{20}_D$=−36.5 (c=0.01 in MeOH).

Intermediate 129: (S)-2-(Thiazol-4-yl)but-3-yn-2-ol

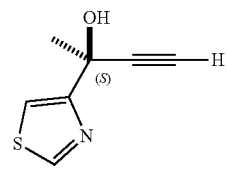

The title compound was prepared with analogous conditions described in Intermediate 128 utilizing the chiral preparative SFC method to afford (S)-2-(thiazol-4-yl)but-3-yn-2-ol (6.80 g, 29.5%, >97% ee) as a yellow solid. MS (ESI): mass calcd. for $C_7H_7NOS$, 153.0; m/z. found, 153.8 $[M+H]^+$. $^1H$ NMR (400 MHz, $CDCl_3$) δ 8.81 (d, J=2.0 Hz, 1H), 7.44 (d, J=2.0 Hz, 1H), 3.72 (br s, 1H), 2.64 (s, 1H), 1.91 (s, 3H). $[α]^{20}_D$=+38.4 (c=0.01 in MeOH).

Intermediate 130: 6-Chloro-2-ethylpyrido[3,2-d]pyrimidin-4-amine

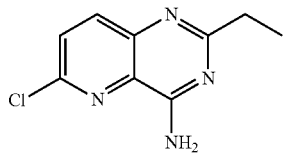

To a vial containing 3-amino-6-chloropyridine-2-carboxylic (500 mg, 3.26 mmol) was added propionamidine hydrochloride (553 mg, 5.10 mmol) and potassium phosphate (2.81 g, 13.2 mmol) followed by THF (15 mL). The vial was sealed, purged with nitrogen, and heated at 80° C. in an aluminum heating mantle. After 22 h, the mixture was concentrated to dryness. The resulting residue was diluted with water (about 60 mL) and heated at 70° C. for 60 min. The reaction mixture was gradually cooled to rt and stirred for an additional 90 min. The reaction mixture was filtered and the solid was rinsed with water (50 mL) and then with $Et_2O$ (50 mL) to afford 6-chloro-2-ethylpyrido[3,2-d]pyrimidin-4-amine (601 mg, 51%) as a grayish solid. MS (ESI): mass calcd. for $C_9H_9ClN_4$, 208.1; m/z. found, 209.0 $[M+H]^+$. $^1H$ NMR (400 MHz, $CD_3OD$) δ 8.01 (d, J=8.8 Hz, 1H), 7.76 (d, J=8.8 Hz, 1H), 2.78 (q, J=7.6 Hz, 2H), 1.34 (t, J=7.6 Hz, 3H).

Intermediate 131. 4-Amino-6-chloropyrido[3,2-d]pyrimidin-2-ol

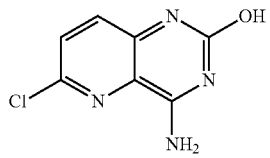 [SMILES: Nc1nc(O)nc2ccc(Cl)nc12]

Step A: 4-Amino-6-chloropyrido[3,2-d]pyrimidin-2-ol. 3-Amino-6-chloropicolinonitrile (500 mg, 3.26 mmol) and urea (980 mg, 16.3 mmol) were heated at 175° C. for 30 min under Ar atmosphere. The mixture was poured into $H_2O$ (20 mL) and stirred at rt for 4 h. The resulting solid was collected by filtration and the filter cake was washed with $H_2O$ (20 mL) before drying under reduced pressure. The resulting residue was poured into $CHCl_3$ (20 mL) and heated at 50° C. for 2 h. The suspension was isolated via filtration before cooling to rt and the filter cake was washed with $CHCl_3$ (15 mL). The solid was added to a solution of DMSO: DMF (1:1, 8 mL) and heated at 100° C. for 2 h. The resulting solid was isolated by filtration before cooling to rt and the filter cake was washed with DMF (5 mL). The filtrate was concentrated under reduced pressure to afford 4-amino-6-chloropyrido[3,2-d]pyrimidin-2-ol (180 mg, 28%) as a yellow solid. MS (ESI): mass calcd. for $C_7H_5ClN_4O$, 196.0; m/z. found 197.1 $[M+H]^+$. $^1H$ NMR (400 MHz, DMSO-$d_6$) δ 10.88 (br s, 1H), 8.02 (br s, 1H), 7.80 (br s, 1H), 7.69 (d, J=8.8 Hz, 1H), 7.56 (d, J=8.8 Hz, 1H).

Intermediate 132: 2-(3-Iodophenyl)thiazolo[4,5-d]pyrimidin-7-amine

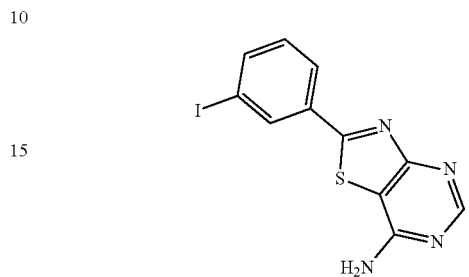

Step A: N-(6-Chloro-5-fluoropyrimidin-4-yl)-3-iodobenzamide. Sodium hydride in mineral oil (1.08 g, 27.0 mmol, 60% purity) was added to a solution of 6-chloro-5-fluoropyrimidin-4-amine (2.00 g, 13.6 mmol), and DMF (50 mL) that had been cooled to 0° C. (ice/water). The mixture was stirred for 30 min with gradual warming to rt and then treated with 3-iodobenzoyl chloride (3.97 g, 14.9 mmol). The reaction mixture was stirred at rt for 16 h before quenching with $H_2O$ (200 mL) and extracting with ethyl acetate (200 mL×3). The combined organic extracts were dried over anhydrous $Na_2SO_4$, filtered, and concentrated to dryness to afford N-(6-chloro-5-fluoropyrimidin-4-yl)-3-iodobenzamide (3.7 g) as a white solid. MS (ESI): mass calcd. for $C_{11}H_6ClFIN_3O$, 376.9; m/z. found 377.7 $[M+H]^+$.

Step B: 2-(3-Iodophenyl)thiazolo[4,5-d]pyrimidine-7-thiol. N-(6-Chloro-5-fluoropyrimidin-4-yl)-3-iodobenzamide (500 mg, 1.32 mmol), $P_2S_5$ (883 mg, 3.97 mmol), and pyridine (20 mL) were added to a 100 mL round-bottomed flask. The mixture was heated at 110° C. for 2 h before cooling to rt and adjusting the pH to pH=7-8 with 1 N HCl. The suspension was isolated via filtration and the filter cake was washed with MeOH (30 mL) before drying under reduced pressure to afford 2-(3-iodophenyl)thiazolo[4,5-d]pyrimidine-7-thiol (500 mg) as a brown solid. MS (ESI): mass calcd. for $C_{11}H_6IN_3S_2$ 370.9 m/z found 372.0 $[M+H]^+$.

Step C: 2-(3-Iodophenyl)-7-(methylthio)thiazolo[4,5-d]pyrimidine. MeI (4.0 g, 28 mmol) was added a mixture of 2-(3-iodophenyl)thiazolo[4,5-d]pyrimidine-7-thiol (1.10 g, 2.96 mmol), $Et_3N$ (1.45 ml, 10.4 mmol), and DMSO (50 ml). The mixture was stirred at rt for 16 h under $N_2$ before pouring it into water (100 mL) and extracting with ethyl acetate (100 mL×3). The combined organic extracts were washed with brine (100 mL×2), dried over anhydrous $Na_2SO_4$, filtered and concentrated to dryness to afford 2-(3-iodophenyl)-7-(methylthio)thiazolo[4,5-d]pyrimidine (820 mg). MS (ESI): mass calcd. for $C_{12}H_8IN_3S_2$ 384.9 m/z found 385.8 $[M+H]^+$.

Step D: 2-(3-Iodophenyl)-7-(methylsulfonyl)thiazolo[4,5-d]pyrimidine. m-chloroperbenzoic acid (470 mg, 2.18 mmol, 80% purity) was added to a mixture of 2-(3-iodophenyl)-7-(methylthio)thiazolo[4,5-d]pyrimidine (700 mg, 1.82 mmol) and dichloromethane (30 mL) at 0° C. The mixture was allowed to warm to rt. After 16 h, the resulting mixture was poured into $H_2O$ (300 mL). The resulting suspension was isolated via filtration. The filter cake was washed with $H_2O$ (50 mL). The filter cake was set aside. The aqueous layer of the filtrate was extracted with ethyl acetate (200 mL×3), the combined extracts were dried over anhydrous Na$_2$SO$_4$, filtered and concentrated under reduced pressure. The resulting residue was combined with the filter cake and dried under reduced pressure to afford 2-(3-iodophenyl)-7-(methylsulfonyl)thiazolo[4,5-d]pyrimidine (1 g) as a yellow solid. MS (ESI): mass calcd. for C$_{12}$H$_8$IN$_3$O$_2$S$_2$ 416.9 m/z found 417.9 [M+H]$^+$.

Step E: 2-(3-Iodophenyl)thiazolo[4,5-d]pyrimidin-7-amine. 2-(3-Iodophenyl)-7-(methylsulfonyl)thiazolo[4,5-d]pyrimidine (900 mg, 2.16 mmol), conc. NH$_3$·H$_2$O (25 mL, 28%), and 1,4-dioxane (50 mL) were added to a 250 mL round-bottomed flask. The resultant mixture was stirred at rt for 3 h before adjusting the pH to pH=7-8 with 1 N HCl. The mixture was concentrated to dryness. The resulting residue was successively purified by FCC (10:1 to 1:1 gradient, petroleum ether/ethyl acetate) and by preparative reverse phase HPLC (Xtimate C18 150×25 mm, 5 μm, (eluent: 23% to 53% (v/v) CH$_3$CN and H$_2$O with 0.2% HCOOH) to afford 2-(3-iodophenyl)thiazolo[4,5-d]pyrimidin-7-amine (240 mg, 30%) as a white solid. MS (ESI): mass calcd. for C$_{11}$H$_7$IN$_4$S, 353.9; m/z. found 355.0 [M+H]$^+$.

Intermediate 133: 6-(3-Iodophenyl)-2-methyl-5,6,7,8-tetrahydropyrido[4,3-d]pyrimidin-4-amine

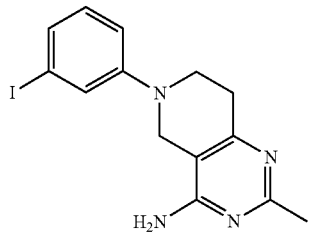 [SMILES: Cc1nc(N)c2c(n1)CCN(c1cccc(I)c1)C2]

The title compound was prepared with analogous conditions described in Intermediate 83 utilizing acetamidine hydrochloride in Step C to afford 6-(3-iodophenyl)-2-methyl-5,6,7,8-tetrahydropyrido[4,3-d]pyrimidin-4-amine (100 mg, 46%), as a yellow solid. MS (ESI): mass calcd. for C$_{14}$H$_{15}$IN$_4$ 366.0 m/z found 367.0 [M+H]$^+$.

Intermediate 134: 5-(3-Iodophenyl)-1-methyl-1H-pyrazolo[4,3-b]pyridin-3-amine

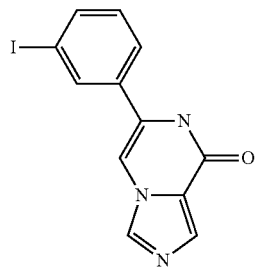

was diluted with water (1 L) and the resulting mixture was extracted with ethyl acetate (200 mL×3). The combined organic layers were washed with brine (200 mL×3), dried over anhydrous Na$_2$SO$_4$, filtered, and concentrated to dryness to afford methyl 1-trityl-1H-imidazole-4-carboxylate (71.0 g) as an off-white solid.

Step B: 1-(2-(3-Iodophenyl)-2-oxoethyl)-5-(methoxycarbonyl)-3-trityl-1H-imidazol-3-ium. A mixture of 2-bromo-1-(3-iodophenyl)ethan-1-one (28.4 g, 76.9 mmol), methyl 1-trityl-1H-imidazole-4-carboxylate (25.0 g, 76.9 mmol) in CH$_3$CN (500 mL) was heated at 80° C. for 3 h under N$_2$ atmosphere. The reaction mixture was concentrated to dryness to afford 1-(2-(3-iodophenyl)-2-oxoethyl)-5-(methoxycarbonyl)-3-trityl-1H-imidazol-3-ium (47.2 g) as a yellow solid. MS (ESI): mass calcd. for C$_{32}$H$_{26}$IN$_2$O$_3$+, 613.1 m/z found, 613.1 [M]$^+$.

Step C: Methyl 1-(2-(3-iodophenyl)-2-oxoethyl)-1H-imidazole-5-carboxylate. A mixture of 1-(2-(3-iodophenyl)-2-oxoethyl)-5-(methoxycarbonyl)-3-trityl-1H-imidazol-3-ium (47.2 g, 76.9 mmol) in AcOH (250 mL) and H$_2$O (50 mL) was heated at 80° C. for 3 h. The mixture was concentrated to an approximate volume of 200 mL, diluted with water (300 mL), and the resulting mixture was extracted with EtOAc (100 mL×5). The combined organic layers were washed with saturated aqueous NaHCO$_3$ (100 mL), brine (100 mL), dried over anhydrous Na$_2$SO$_4$, filtered, and concentrated to dryness. The residue was purified FCC (0-80% gradient, ethyl acetate/petroleum ether) to afford methyl 1-(2-(3-iodophenyl)-2-oxoethyl)-1H-imidazole-5-carboxylate (5.35 g) as a yellow solid.

Step D: 6-(3-Iodophenyl)imidazo[1,5-a]pyrazin-8(7H)-one. A mixture of methyl 1-(2-(3-iodophenyl)-2-oxoethyl)-1H-imidazole-5-carboxylate (6.85 g, 18.5 mmol) and NH$_4$OAc (14.3 g, 185 mmol) in dioxane (150 mL) was heated at 100° C. for 50 h under N$_2$ atmosphere. After cooling to rt, the mixture was diluted with water (100 mL) and ethyl acetate (100 mL) was added. The reaction mixture was stirred for 30 min and filtered. The cake was washed with ethyl acetate (50 mL×2) and dried to afford 6-(3-iodophenyl)imidazo[1,5-a]pyrazin-8(7H)-one (5.40 g, 85.3%) as a grey solid. MS (ESI): mass calcd. for C$_{12}$H$_{81}$N$_3$O, 336.9; m/z. found, 337.9 [M+H]$^+$. $^1$H NMR (400 MHz, DMSO-d$_6$) δ 11.04 (s, 1H), 8.30 (s, 1H), 8.06 (s, 1H), 7.87 (s, 1H), 7.83-7.80 (m, 2H), 7.70 (d, 1H), 7.31-7.27 (m, 1H).

Intermediate 135: tert-Butyl (6-(3-bromophenyl)-1,5-naphthyridin-4-yl)carbamate

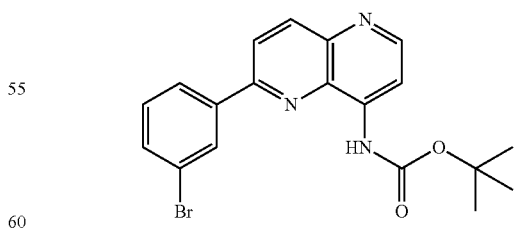

Step A: 6-Bromo-1,5-naphthyridin-4-ol. Trimethylsilyl bromide (3.0 mL, 23 mmol) was added drop-wise to a solution of 6-chloro-1,5-naphthyridin-4-ol (0.5 g, 2.8 mmol) and CH$_3$CN (40 mL). The resultant mixture was heated at 85° C. for 16 h before cooling to rt. The reaction mixture was concentrated to dryness. To the resulting residue was added Step A: Methyl 1-trityl-1H-imidazole-4-carboxylate. A mixture of methyl 1H-imidazole-5-carboxylate (25.0 g, 198 mmol), triphenylmethyl chloride (55.3 g, 198 mmol) and TEA (30.1 g, 297 mmol, 41.4 mL) in CH$_3$CN (900 mL) was stirred at 25° C. for 20 h under N$_2$ atmosphere. The mixture H₂O (40 mL) and the mixture stirred at rt for 1 h. The resulting solid was isolated via filtration and the filter cake was washed with H₂O (10 mL) before drying under reduced pressure to afford 6-bromo-1,5-naphthyridin-4-ol (1 g) as a brown solid, which used into next step without further purification. MS (ESI): mass calcd. for C₈H₅BrN₂O, 224.0; m/z. found 225.1 [M+H]⁺.

Step B: 6-(3-Bromophenyl)-1,5-naphthyridin-4-ol. Pd(dppf)Cl₂ (168 mg, 0.23 mmol) was added to a mixture of 6-bromo-1,5-naphthyridin-4-ol, (1.00 g, 4.44 mmol), 2-(3-bromophenyl)-4,4,5,5-tetramethyl-1,3,2-dioxaborolane (629 mg, 2.22 mmol), Cs₂CO₃ (2.17 g, 6.67 mmol), 1,4-dioxane (40 mL), and H₂O (10 mL) under N₂ atmosphere. The mixture was heated at 100° C. for 16 h before cooling to rt. The suspension was filtered through a pad of diatomaceous earth, such as Celite® and the pad washed with MeOH (40 mL). The filtrate was concentrated to dryness. The resulting residue was purified by FCC (1:0 to 0:1 gradient, petroleum ether/ethyl acetate, then 1:0 to 4:1 gradient, dichloromethane/methanol) to afford 6-(3-bromophenyl)-1,5-naphthyridin-4-ol (850 mg, crude) as a brown solid. MS (ESI): mass calcd. for C₁₄H₉BrN₂O, 300.0; m/z. found 303.0 [M+H]⁺.

Step C: 2-(3-Bromophenyl)-8-chloro-1,5-naphthyridine. A solution of 6-(3-bromophenyl)-1,5-naphthyridin-4-ol, (800 mg, crude) and POCl₃ (38.1 g, 249 mmol) was stirred at 110° C. for 16 h. After which time, the mixture was cooled to rt and concentrated to dryness. To the resulting residue was added to H₂O (40 mL) and the pH was adjusted to 7 with NaOH (2 M in water). The resulting mixture was extracted with ethyl acetate (50 mL×4). The combined organic extracts were concentrated to dryness. The residue was purified by FCC (1:0 to 1:4 gradient, petroleum ether/ethyl acetate) to afford 2-(3-bromophenyl)-8-chloro-1,5-naphthyridine (450 mg), as a brown solid. MS (ESI): mass calcd. for C₁₄H₈BrClN₂ 319.0 m/z found 320.7 [M+H]⁺.

Step D: 6-(3-Bromophenyl)-1,5-naphthyridin-4-amine. To MeOH (20 mL) was bubbled NH₃ gas (>1.3 M) at −78° C. (dry ice/EtOH) over 30 minutes. The resulting NH₃MeOH solution and 2-(3-bromophenyl)-8-chloro-1,5-naphthyridine, (400 mg, 1.25 mmol) were added to a 50 mL sealed tube. The mixture was stirred at 120° C. for 36 h before cooling to rt. The suspension was concentrated to dryness and the residue was purified by preparative reverse phase HPLC (Xtimate C18 250×50 mm×10 µm (eluent: 40% to 70% (v/v) CH₃CN and H₂O with 0.04% NH₃·H₂O and 10 mM NH₄HCO₃) to afford 6-(3-bromophenyl)-1,5-naphthyridin-4-amine (200 mg, 53%) as a white solid. MS (ESI): mass calcd. for C₁₄H₁₀BrN₃ 299.0 m/z found 301.0 [M+H]⁺.

Step E: tert-Butyl (6-(3-bromophenyl)-1,5-naphthyridin-4-yl)carbamate. Boc₂O (116 mg, 0.53 mmol) was added to a solution of 6-(3-bromophenyl)-1,5-naphthyridin-4-amine, (40 mg, 0.133 mmol), TEA (0.24 mL, 1.4 mmol), and dichloromethane (2 mL). The mixture was stirred at 50° C. for 3 h before cooling to rt. The mixture was concentrated to dryness to afford tert-butyl (6-(3-bromophenyl)-1,5-naphthyridin-4-yl)carbamate (53 mg) as a brown oil, which used into next step without further purification. MS (ESI): mass calcd. for C₁₉H₁₈BrN₃O₂ 399.1 m/z found 400.1 [M+H]⁺.

Intermediate 136: 6-(5-Iodo-2-methylphenyl)-5,6,7,8-tetrahydropyrido[4,3-d]pyrimidin-4-amine

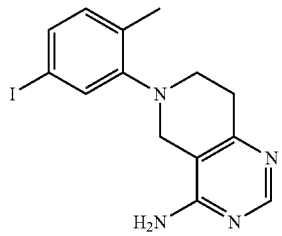 [SMILES: Cc1ccc(I)cc1N1CCc2ncnc(N)c2C1]

6-(5-Iodo-2-methylphenyl)-5,6,7,8-tetrahydropyrido[4,3-d]pyrimidin-4-amine was prepared with analogous conditions described in Intermediate 83 utilizing 5-iodo-2-methylaniline in Step A to afford (70 mg, 62%) as a yellow solid. MS (ESI): mass calcd. for C₁₄H₁₅IN₄ 366.0 m/z found 366.9 [M+H]⁺.

Intermediate 137: 6-Bromopyrido[3,2-d]pyrimidin-4(3H)-one

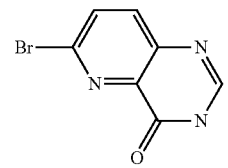 [SMILES: O=c1[nH]cnc2ccc(Br)nc12]

Step A: 6-Chloropyrido[3,2-d]pyrimidin-4(3H)-one. 3-Amino-6-chloropicolinamide (500 mg, 2.91 mmol) was added to diethoxymethyl acetate (4 mL). The mixture was heated at 100° C. for 16 h before cooled to rt. The suspension was concentrated to dryness. The resulting residue was triturated with CH₃Cl (3 mL) at 50° C. for 1 h. After cooling to rt, the suspension was isolated via filtration. The filter cake was washed with CH₃Cl (1 mL) before drying under reduced pressure to afford 6-chloropyrido[3,2-d]pyrimidin-4(3H)-one (800 mg) as a white solid, which used in next step without further purification. MS (ESI): mass calcd. for C₇H₄ClN₃O, 181.0; m/z. found 181.8 [M+H]⁺.

Step B: 6-Bromopyrido[3,2-d]pyrimidin-4(3H)-one. Trimethylsilyl bromide (2.9 mL, 22 mmol) was added drop-wise to a solution of 6-chloropyrido[3,2-d]pyrimidin-4(3H)-one, (500 mg, 2.75 mmol) and DMF (5 mL) at rt. The resultant mixture was heated at 85° C. for 16 h before cooling to rt and pouring it into H₂O (20 mL). The mixture was concentrated to dryness. The resulting residue was poured into DMF (20 mL) and stirred at rt for 1 hour. The suspension was isolated via filtration. The filter cake was washed with DMF (10 mL) before drying under reduced pressure. The resulting residue was purified by preparative reverse phase HPLC (Xtimate C18 250×25 mm, 5 µm (eluent: 5% to 35% (v/v) CH₃CN and H₂O with 0.2% HCOOH) to afford 6-bromopyrido[3,2-d]pyrimidin-4(3H)-one (100 mg) as a yellow solid. MS (ESI): mass calcd. for C₇H₄BrN₃O, 225.0; m/z. found 247.8 [M+Na]⁺.

Intermediate 138: 6-Chloro-4-(pyrrolidin-1-yl)pyrido[3,2-d]pyrimidine

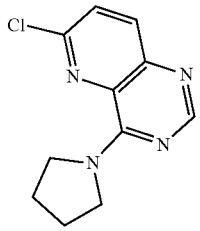 [SMILES: Clc1ccc2ncnc(N3CCCC3)c2n1]

The title compound was prepared with analogous conditions described in Intermediate 25 utilizing pyrrolidine to afford 6-chloro-4-(pyrrolidin-1-yl)pyrido[3,2-d]pyrimidine (165 mg) as a light orange solid. MS (ESI): mass calcd. for $C_{11}H_{11}ClN_4$, 234.1; m/z. found, 235.1 [M+H]$^+$. $^1$H NMR (400 MHz, CDCl$_3$) δ 8.56 (s, 1H), 7.99 (d, J=8.7 Hz, 1H), 7.54 (d, J=8.8 Hz, 1H), 4.36 (t, J=6.9 Hz, 2H), 3.83 (t, J=6.8 Hz, 2H), 2.05 (dq, J=41.8, 6.9 Hz, 4H).

Intermediate 139: 6-(3-Iodophenyl)-6,7,8,9-tetrahydro-5H-pyrimido[5,4-c]azepin-4-amine

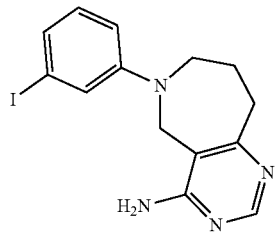 [SMILES: Nc1ncnc2c1CN(c1cccc(I)c1)CCC2]

Step A: tert-Butyl 4-hydroxy-5,7,8,9-tetrahydro-6H-pyrimido[5,4-c]azepine-6-carboxylate. 1-tert-Butyl 4-ethyl 5-oxoazepane-1,4-dicarboxylate (2.0 g, 7.0 mmol) was added to a solution of formimidamide acetate (1.1 g, 11 mmol), sodium methoxide (1.7 mg, 31 mmol), and methanol (15 mL). The mixture was heated at 90° C. for 6 h before cooling to rt, pouring it into water (20 mL), adjusting to pH=7 with 1 M HCl, and then extracting with ethyl acetate (30 mL×3). The combined organic extracts were dried over anhydrous Na$_2$SO$_4$, filtered, and concentrated to dryness. The resulting residue was purified by FCC (1:0 to 10:1 gradient, ethyl acetate/methanol) to afford tert-butyl 4-hydroxy-5,7,8,9-tetrahydro-6H-pyrimido[5,4-c]azepine-6-carboxylate (1.5 g, 81%) as a white solid. MS (ESI): mass calcd. for $C_{13}H_{19}N_3O_3$ 265.1 m/z found 266.2 [M+H]$^+$.

Step B: tert-Butyl 4-((2,4-dimethoxybenzyl)amino)-5,7,8,9-tetrahydro-6H-pyrimido[5,4-c]azepine-6-carboxylate. (Benzotriazol-1-yloxytris(dimethylamino)phosphonium hexafluorophosphate) (3.3 g, 7.5 mmol) was added to a solution of tert-butyl-4-hydroxy-8,9-dihydro-5H-pyrimido[5,4-c]azepine-6(7H)-carboxylate (1.5 g, 5.7 mmol), 1,8-diazabicyclo[5.4.0]undec-7-ene (1.7 mL, 7.5 mmol), and DMF (20 mL). After stirring for 5 min, (2,4-dimethoxyphenyl)methanamine (1.8 mL, 11 mmol) was added. The mixture was heated at 60° C. for 16 h before cooling to rt, pouring it into H$_2$O (300 mL), and extracting with ethyl acetate (100 mL×3). The combined organic extracts were dried over anhydrous Na$_2$SO$_4$, filtered, and concentrated to dryness. The resulting residue was purified by FCC (1:0 to 1:1 gradient, petroleum ether/ethyl acetate) followed by preparative reverse phase HPLC (Phenomenex luna C18 250×50 mm×10 um (eluent: 10% to 45% (v/v) CH$_3$CN and H$_2$O with 0.225% HCOOH) to afford tert-butyl 4-((2,4-dimethoxybenzyl)amino)-5,7,8,9-tetrahydro-6H-pyrimido[5,4-c]azepine-6-carboxylate (770 mg) as a white solid. MS (ESI): mass calcd. for $C_{22}H_{30}N_4O_4$ 414.2 m/z found 415.3 [M+H]$^+$.

Step C: N-(2,4-Dimethoxybenzyl)-6,7,8,9-tetrahydro-5H-pyrimido[5,4-c]azepin-4-amine. tert-Butyl 4-((2,4-dimethoxybenzyl)amino)-8,9-dihydro-5H-pyrimido[5,4-c]azepine-6(7H)-carboxylate (1.3 g, 3.1 mmol) was added to a solution of HCl (6 mL, 4N in 1,4-dioxane). The mixture was stirred for 12 h at rt. The suspension was concentrated to dryness. The resulting residue was purified by preparative reverse phase HPLC (Xtimate C18 150×40 mm×10 μm column (eluent: 2% to 32% (v/v) CH$_3$CN and H$_2$O with 0.225% HCOOH) to afford N-(2,4-dimethoxybenzyl)-6,7,8,9-tetrahydro-5H-pyrimido[5,4-c]azepin-4-amine (350 mg, 34%) as a colorless oil. MS (ESI): mass calcd. for $C_{17}H_{22}N_4O_2$ 314.2 m/z found 315.2 [M+H]$^+$.

Step D: N-(2,4-Dimethoxybenzyl)-6-(3-iodophenyl)-6,7,8,9-tetrahydro-5H-pyrimido[5,4-c]azepin-4-amine. Pyridine 1-oxide (261 mg, 2.74 mmol) was added to a pre-stirring suspension of N-(2,4-dimethoxybenzyl)-6,7,8,9-tetrahydro-5H-pyrimido[5,4-c]azepin-4-amine (330 mg, 0.92 mmol), (3-iodophenyl)boronic acid (681 mg, 2.75 mmol), Cu(OAc)$_2$ (249 mg, 1.37 mmol), pyridine (253 mg, 3.20 mmol), 4 Å molecular sieves (2 g), and DMF (10 mL). The resultant mixture was stirred at rt for 36 h under air. The suspension was filtered through a pad of diatomaceous earth, such as Celite©. The filtrate was diluted with H$_2$O (60 mL) and extracted with ethyl acetate (50 mL×3). The combined organic extracts were dried over anhydrous Na$_2$SO$_4$, filtered and concentrated to dryness. The resulting residue was purified by FCC (5:1 to 0:1 gradient, petroleum ether/ethyl acetate) to afford N-(2,4-dimethoxybenzyl)-6-(3-iodophenyl)-6,7,8,9-tetrahydro-5H-pyrimido[5,4-c]azepin-4-amine (160 mg, 34%) as a brown solid. MS (ESI): mass calcd. for $C_{23}H_{25}IN_4O_2$ 516.1 m/z. found 517.1 [M+1]$^+$.

Step E: 6-(3-Iodophenyl)-6,7,8,9-tetrahydro-5H-pyrimido[5,4-c]azepin-4-amine. TFA (6 mL) was added to N-(2,4-dimethoxybenzyl)-6-(3-iodophenyl)-6,7,8,9-tetrahydro-5H-pyrimido[5,4-c]azepin-4-amine (160 mg, 0.31 mmol). The resultant mixture was heated at 60° C. for 5 h before cooling to rt. The resultant mixture was concentrated to dryness. The resulting residue was purified by preparative reverse phase HPLC (Boston Green ODS C18 150×30 mm×5 μm column (eluent: 30% to 60% (v/v) CH$_3$CN and H$_2$O with 0.04% NH$_3$H$_2$O+10 mM NH$_4$HCO$_3$) to afford N-(2,4-dimethoxybenzyl)-6-(3-iodophenyl)-6,7,8,9-tetrahydro-5H-pyrimido[5,4-c]azepin-4-amine (60 mg, 53%) as a white solid. MS (ESI): mass calcd. for $C_{14}H_{15}IN_4$ 366.0 m/z. found 367.1 [M+1]$^+$.

Intermediate 140: 6-Chloro-4-(piperidin-1-yl)pyrido[3,2-d]pyrimidine

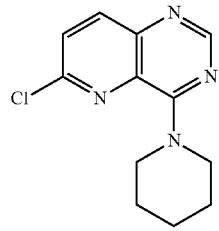 [SMILES: Clc1ccc2ncnc(N3CCCCC3)c2n1]

6-Chloro-4-(piperidin-1-yl)pyrido[3,2-d]pyrimidine was prepared with analogous conditions described in Intermediate 25 utilizing piperidine. MS (ESI): mass calcd. for $C_{12}H_{13}ClN_4$, 248.1; m/z. found, 249.1 [M+H]$^+$. $^1$H NMR (500 MHz, CDCl$_3$) δ 8.56 (s, 1H), 8.01 (d, J=8.8 Hz, 1H), 7.54 (d, J=8.7 Hz, 1H), 4.34 (s, 4H), 1.92-1.67 (m, 6H).

Intermediate 141: 6-Chloro-4-(3,3-dimethylazetidin-1-yl)pyrido[3,2-d]pyrimidine

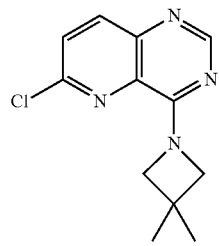 [SMILES: CC1(C)CN(c2ncnc3ccc(Cl)nc23)C1]

6-Chloro-4-(3,3-dimethylazetidin-1-yl)pyrido[3,2-d]pyrimidine was prepared with analogous conditions described in Intermediate 25 utilizing 3,3-dimethylazetidine hydrochloride. MS (ESI): mass calcd. for $C_{12}H_{13}ClN_4$, 248.1; m/z. found, 249.1 [M+H]$^+$. $^1$H NMR (500 MHz, CDCl$_3$) δ 8.53 (s, 1H), 7.97 (d, J=8.8 Hz, 1H), 7.53 (d, J=8.8 Hz, 1H), 4.58 (t, J=0.9 Hz, 2H), 4.03 (t, J=1.0 Hz, 2H), 1.40 (s, 6H).

Intermediate 142: 6-Chloro-N-ethylpyrido[3,2-d]pyrimidin-4-amine

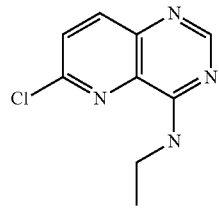

6-Chloro-N-ethylpyrido[3,2-d]pyrimidin-4-amine was prepared with analogous conditions described in Intermediate 25 utilizing ethylamine. MS (ESI): mass calcd. for $C_9H_9ClN_4$, 208.1; m/z. found, 209.0 [M+H]$^+$. $^1$H NMR (500 MHz, CDCl$_3$) δ 8.63 (s, 1H), 8.03 (d, J=8.7 Hz, 1H), 7.61 (d, J=8.7 Hz, 1H), 6.98 (s, 1H), 3.69 (qd, J=7.3, 5.8 Hz, 2H), 1.37 (t, J=7.3 Hz, 3H).

Intermediate 143: 1-(6-Chloropyrido[3,2-d]pyrimidin-4-yl)azetidin-3-ol

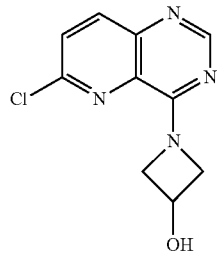 [SMILES: OC1CN(c2ncnc3ccc(Cl)nc23)C1]

1-(6-Chloropyrido[3,2-d]pyrimidin-4-yl)azetidin-3-ol was prepared with analogous conditions described in Intermediate 25 utilizing azetidin-3-ol hydrochloride. MS (ESI): mass calcd. for $C_{10}H_9ClN_4O$, 236.1; m/z. found, 237.1 [M+H]$^+$.

Intermediate 144: 6-Chloro-N-(oxetan-3-yl)pyrido[3,2-d]pyrimidin-4-amine

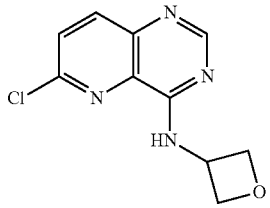

6-Chloro-N-(oxetan-3-yl)pyrido[3,2-d]pyrimidin-4-amine was prepared with analogous conditions described in Intermediate 25 utilizing oxetan-3-amine. MS (ESI): mass calcd. for $C_{10}H_9ClN_4O$, 236.1; m/z. found, 237.1 [M+H]$^+$. $^1$H NMR (500 MHz, CDCl$_3$) δ 8.62 (s, 1H), 8.08 (d, J=8.8 Hz, 1H), 7.66 (d, J=8.8 Hz, 1H), 7.37 (s, 1H), 5.38-5.45 (m, 1H), 5.17-5.01 (m, 2H), 4.74-4.76 (m, 2H).

Intermediate 145: 6-Chloro-4-(3-methoxyazetidin-1-yl)pyrido[3,2-d]pyrimidine

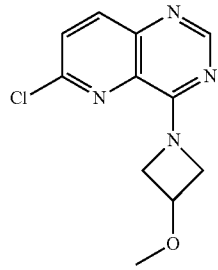 [SMILES: COC1CN(c2ncnc3ccc(Cl)nc23)C1]

6-Chloro-4-(3-methoxyazetidin-1-yl)pyrido[3,2-d]pyrimidine was prepared with analogous conditions described in Intermediate 25 utilizing 3-methoxyazetidine hydrochloride. MS (ESI): mass calcd. for $C_{11}H_{11}ClN_4O$, 250.1; m/z. found, 251.2 [M+H]$^+$. $^1$H NMR (500 MHz, CDCl$_3$) δ 8.55 (s, 1H), 7.99 (d, J=8.8 Hz, 1H), 7.55 (d, J=8.8 Hz, 1H), 5.06

(dd, J=12.0, 6.2 Hz, 1H), 4.73 (d, J=11.5 Hz, 1H), 4.52 (t, J=8.8 Hz, 1H), 4.40 (tt, J=6.3, 4.0 Hz, 1H), 4.24 (d, J=10.5 Hz, 1H), 3.39 (s, 3H).

Intermediate 146: 6-Chloro-4-(3,3-difluoroazetidin-1-yl)pyrido[3,2-d]pyrimidine

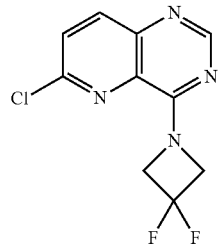 [SMILES: FC1(F)CN(c2ncnc3ccc(Cl)nc23)C1]

6-Chloro-4-(3,3-difluoroazetidin-1-yl)pyrido[3,2-d]pyrimidine was prepared with analogous conditions described in Intermediate 25 utilizing 3,3-difluoroazetidine hydrochloride. MS (ESI): mass calcd. for $C_{10}H_7ClF_2N_4$, 256.0; m/z. found, 257.1 [M+H]$^+$. $^1$H NMR (500 MHz, CDCl$_3$) δ 8.63 (s, 1H), 8.06 (d, J=8.8 Hz, 1H), 7.61 (d, J=8.8 Hz, 1H), 5.18 (s, 2H), 4.69 (s, 2H). $^{19}$F NMR (376 MHz, CDCl$_3$) δ −100.96 (m).

Intermediate 147: 2-(3-Bromophenyl)-8-chloro-1,7-naphthyridine

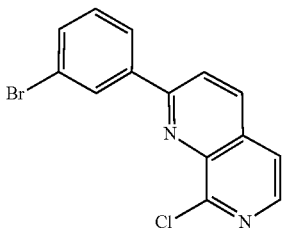 [SMILES: Clc1nccc2ccc(-c3cccc(Br)c3)nc12]

A solution of 2-(3-bromophenyl)-1,7-naphthyridin-8-ol (690 mg, 2.29 mmol) and POCl$_3$ (32.5 g, 212 mmol) was heated at 110° C. for 16 h before cooling to rt. The mixture was concentrated to dryness and the resulting residue was purified by FCC (1:0 to 1:4 gradient, petroleum ether/ethyl acetate) to afford 2-(3-bromophenyl)-8-chloro-1,7-naphthyridine (390 mg, 47%) as a yellow solid. MS (ESI): mass calcd. for $C_{14}H_8BrClN_2$ 318.0 m/z found 321.0 [M+H]$^+$.

Intermediate 148: 8-(Azetidin-1-yl)-2-(3-bromophenyl)-1,7-naphthyridine

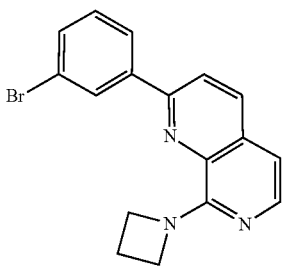 [SMILES: Brc1cccc(-c2ccc3ccnc(N4CCC4)c3n2)c1]

Azetidine (152 mg, 2.66 mmol) was added to a mixture of 2-(3-bromophenyl)-8-chloro-1,7-naphthyridine (340 mg, 1.06 mmol), DIPEA (0.74 mL, 4.2 mmol), and DMF (5 mL). The mixture was heated at 50° C. for 1.5 h. Azetidine (152 mg, 2.66 mmol) and DIPEA (0.35 mL, 2.0 mmol) were added to the mixture. The mixture was heated at 50° C. for 1.5 h before cooling to rt, pouring it into H$_2$O (20 mL), and extracting with ethyl acetate (30 mL×3). The combined organic extracts were washed with brine, dried over anhydrous Na$_2$SO$_4$, filtered, and concentrated to dryness. The resulting residue was purified by FCC (1:0 to 0:1 gradient, petroleum ether/ethyl acetate) and preparative reverse phase HPLC (Xtimate C18 250×50 mm×10 μm (eluent: 70% to 100% (v/v) CH$_3$CN and H$_2$O with 0.04% NH$_3$H$_2$O+10 mM NH$_4$HCO$_3$) to afford 8-(azetidin-1-yl)-2-(3-bromophenyl)-1,7-naphthyridine (130 mg, 28%) as a yellow solid. MS (ESI): mass calcd. for $C_{17}H_{14}BrN_3$ 339.04 m/z found 340.0 [M+H]$^+$.

Intermediate 149: 1-(Azetidin-1-yl)-7-bromoisoquinoline

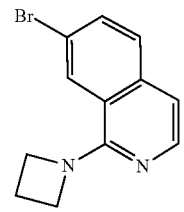 [SMILES: Brc1ccc2ccnc(N3CCC3)c2c1]

Azetidine (589 mg, 10.3 mmol) was added to a mixture of 7-bromo-1-chloroisoquinoline (500 mg, 2.06 mmol), DIPEA (2.2 mL, 12.6 mmol), and DMF (6 mL). The mixture was heated at 50° C. for 4 h before cooling to rt. Additional azetidine (589 mg, 10.3 mmol) was added to the mixture. The mixture was heated at 50° C. for 12 h before cooling to rt, pouring it into H$_2$O (20 mL), and extracting with ethyl acetate (30 mL×3). The combined organic extracts were washed with brine, dried over anhydrous Na$_2$SO$_4$, filtered, and concentrated to dryness. The resulting residue was purified by FCC (1:0 to 2:3 gradient, petroleum ether/ethyl acetate) to afford 1-(azetidin-1-yl)-7-bromoisoquinoline (450 mg, 79%) as a yellow solid. MS (ESI): mass calcd. for $C_{12}H_{11}BrN_2$ 262.0 m/z found 265.0 [M+H]$^+$. $^1$H NMR (400 MHz, DMSO-d$_6$) δ 7.99 (s, 1H), 7.95 (d, J=5.6 Hz, 1H), 7.72-7.70 (m, 2H), 7.01 (d, J=5.6 Hz, 1H), 4.30 (t, J=7.6 Hz, 4H), 2.38-2.26 (m, 2H).

Intermediate 150: 4-(Azetidin-1-yl)-6-bromoquinoline

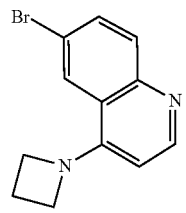

Azetidine (590 mg, 10.3 mmol) was added to a mixture of 6-bromo-4-chloroquinoline (500 mg, 2.06 mmol), DIPEA (2.2 mL, 13 mmol), and DMF (6 mL). The mixture was heated at 50° C. for 7 h before cooling to rt. Additional azetidine (590 mg, 10.3 mmol) and DIPEA (2.2 mL, 13 mmol), and DMF (4 mL) were added to the mixture. The mixture was heated at 50° C. for 12 h before cooling to rt, pouring it into H$_2$O (30 mL) and extracting with ethyl acetate (30 mL×3). The combined organic extracts were washed with brine, dried over anhydrous Na$_2$SO$_4$, filtered, and concentrated to dryness. The resulting residue was purified by FCC (1:0 to 2:3 gradient, petroleum ether/ethyl acetate) to afford 4-(azetidin-1-yl)-6-bromoquinoline (470 mg, 82%) as a white solid. MS (ESI): mass calcd. for C$_{12}$H$_{11}$BrN$_2$ 262.01 m/z found 265.0 [M+H]$^+$. $^1$H NMR (400 MHz, DMSO-d$_6$) δ 8.42 (d, J=5.3 Hz, 1H), 8.05 (d, J=1.8 Hz, 1H), 7.75 (s, 1H), 7.73 (d, J=2.0 Hz, 1H), 6.28 (d, J=5.3 Hz, 1H), 4.35 (t, J=7.5 Hz, 4H), 2.47-2.37 (m, 2H).

Intermediate 151: 6-Chloro-N-cyclobutylpyrido[3,2-d]pyrimidin-4-amine

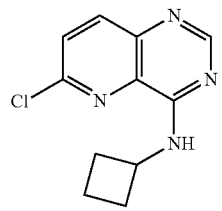 [SMILES: Clc1ccc2ncnc(NC3CCC3)c2n1]

6-Chloro-N-cyclobutylpyrido[3,2-d]pyrimidin-4-amine was prepared with analogous conditions described in Intermediate 25 utilizing cyclobutylamine. MS (ESI): mass calcd. for C$_{11}$H$_{11}$ClN$_4$, 234.1; m/z. found, 235.1 [M+H]$^+$. $^1$H NMR (500 MHz, CDCl$_3$) δ 8.61 (s, 1H), 8.02 (d, J=8.8 Hz, 1H), 7.61 (dd, J=8.7, 1.2 Hz, 1H), 7.11 (br s, 1H), 4.72-4.82 (m, 1H), 2.62-2.39 (m, 2H), 2.22-2.02 (m, 2H), 1.78-1.86 (m, 2H).

Intermediate 152: 6-Chloro-4-(3-fluoroazetidin-1-yl)pyrido[3,2-d]pyrimidine

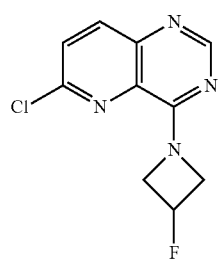 [SMILES: FC1CN(c2ncnc3ccc(Cl)nc23)C1]

6-Chloro-4-(3-fluoroazetidin-1-yl)pyrido[3,2-d]pyrimidine was prepared with analogous conditions described in Intermediate 25 utilizing 3-fluoroazetidine hydrochloride. MS (ESI): mass calcd. for C$_{10}$H$_8$ClFN$_4$, 238.0; m/z. found, 239.0 [M+H]$^+$. $^1$H NMR (500 MHz, CDCl$_3$) δ 8.57 (s, 1H), 8.01 (d, J=8.8 Hz, 1H), 7.57 (d, J=8.8 Hz, 1H), 5.54-5.58 (m, 1H), 5.42-5.48 (m, 1H), 5.18 (s, 1H), 4.97 (s, 1H), 4.65 (s, 1H), 4.56-4.33 (m, 1H). $^{19}$F NMR (376 MHz, CDCl$_3$) δ −180.33 (m).

Intermediate 153: 2-((6-Chloropyrido[3,2-d]pyrimidin-4-yl)amino)acetonitrile

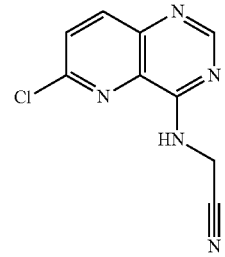 [SMILES: N#CCNc1ncnc2ccc(Cl)nc12]

2-((6-Chloropyrido[3,2-d]pyrimidin-4-yl)amino)acetonitrile was prepared with analogous conditions described in Intermediate 25 utilizing aminoacetonitrile hydrochloride. MS (ESI): mass calcd. for C$_9$H$_6$ClN$_5$, 219.0; m/z. found, 220.0 [M+H]$^+$. $^1$H NMR (500 MHz, CDCl$_3$) δ 8.78 (s, 1H), 8.15 (d, J=8.8 Hz, 1H), 7.70 (d, J=8.8 Hz, 1H), 7.17 (s, 1H), 4.61 (d, J=6.3 Hz, 2H).

Intermediate 154: 6-Chloro-N-(2,2-difluoroethyl)pyrido[3,2-d]pyrimidin-4-amine

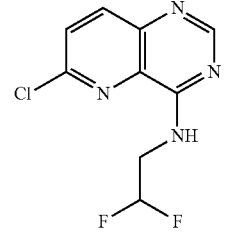 [SMILES: FC(F)CNc1ncnc2ccc(Cl)nc12]

6-Chloro-N-(2,2-difluoroethyl)pyrido[3,2-d]pyrimidin-4-amine was prepared with analogous conditions described in Intermediate 25 utilizing 2,2-difluoroethan-1-amine. MS (ESI): mass calcd. for C$_9$H$_7$ClF$_2$N$_4$, 244.0; m/z. found, 245.0 [M+H]$^+$. $^1$H NMR (400 MHz, CDCl$_3$) δ 8.67 (s, 1H), 8.09 (d, J=8.8 Hz, 1H), 7.66 (d, J=8.8 Hz, 1H), 7.16 (s, 1H), 6.07 (t, J=4.2 Hz, 1H), 4.18-4.00 (m, 2H).

Intermediate 155: 1-(6-Chloropyrido[3,2-d]pyrimidin-4-yl)azetidine-3-carbonitrile

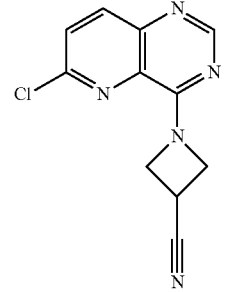 [SMILES: N#CC1CN(c2ncnc3ccc(Cl)nc23)C1]

1-(6-Chloropyrido[3,2-d]pyrimidin-4-yl)azetidine-3-carbonitrile was prepared with analogous conditions described in Intermediate 25 utilizing azetidine-3-carbonitrile hydrochloride. MS (ESI): mass calcd. for $C_{11}H_8ClN_5$, 245.1; m/z. found, 246.0 [M+H]$^+$. $^1$H NMR (500 MHz, CDCl$_3$) δ 8.61 (s, 1H), 8.15-7.94 (m, 1H), 7.73-7.45 (m, 1H), 5.08-5.30 (m, 2H), 4.55-4.75 (m, 2H), 3.68-3.75 (m, 1H).

Intermediate 156:
4-(Azetidin-1-yl)-6-bromoquinazoline

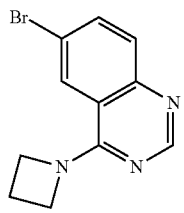 [SMILES: Brc1ccc2ncnc(N3CCC3)c2c1]

A sealable 50 mL vial was charged with azetidine (0.6 mL, 8.2 mmol), 6-bromo-4-chloroquinazoline (0.2 g, 0.8 mmol), DIPEA (1.7 mL, 9.8 mmol), and DMF (15 mL). The mixture was heated at 70° C. for 12 h before cooling to rt, pouring it into H$_2$O (30 mL), and extracting with ethyl acetate (30 mL×3). The combined organic extracts were washed with brine, dried over anhydrous Na$_2$SO$_4$, filtered, and concentrated to dryness. The resulting residue was FCC (1:0 to 0:1 gradient, petroleum ether/ethyl acetate) to afford 4-(azetidin-1-yl)-6-bromoquinazoline (140 mg, 64.5%) as a white solid. MS (ESI): mass calcd. for $C_{11}H_{10}BrN_3$ 263.0 m/z found 263.8 [M+H]$^+$.

Intermediate 157: 6-Chloro-4-(3-chloroazetidin-1-yl)pyrido[3,2-d]pyrimidine

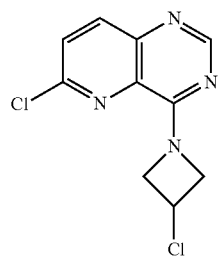

6-Chloro-4-(3-chloroazetidin-1-yl)pyrido[3,2-d]pyrimidine was prepared with analogous conditions described in Intermediate 25 utilizing 3-chloroazetidine hydrochloride. MS (ESI): mass calcd. for $C_{10}H_8Cl_2N_4$, 254.0; m/z. found, 255.0 [M+H]$^+$.

Intermediate 158: 6-Chloro-4-(3-(methylsulfonyl) azetidin-1-yl)pyrido[3,2-d]pyrimidine

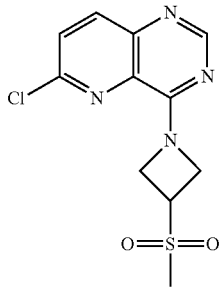 [SMILES: CS(=O)(=O)C1CN(c2ncnc3ccc(Cl)nc23)C1]

6-Chloro-4-(3-(methylsulfonyl)azetidin-1-yl)pyrido[3,2-d]pyrimidine was prepared with analogous conditions described in Intermediate 25 utilizing 3-(methylsulfonyl) azetidine. MS (ESI): mass calcd. for $C_{11}H_{11}ClN_4O_2S$, 298.0; m/z. found, 299.0 [M+H]$^+$. $^1$H NMR (400 MHz, CDCl$_3$) δ 8.61 (s, 1H), 8.04 (d, J=8.8 Hz, 1H), 7.60 (d, J=8.8 Hz, 1H), 5.21 (s, 2H), 4.60-4.78 (m, 2H), 4.18-4.26 (m, 1H), 2.99 (s, 3H).

Intermediate 159. 1-(6-Chloropyrido[3,2-d]pyrimidin-4-yl)-N-methylazetidine-3-carboxamide

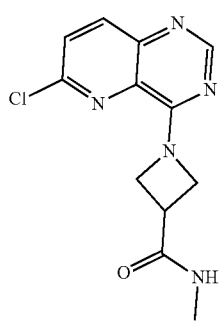 [SMILES: CNC(=O)C1CN(c2ncnc3ccc(Cl)nc23)C1]

1-(6-Chloropyrido[3,2-d]pyrimidin-4-yl)-N-methylazetidine-3-carboxamide was prepared with analogous conditions described in Intermediate 25 utilizing N-methylazetidine-3-carboxamide hydrogen chloride. MS (ESI): mass calcd. for $C_{12}H_{12}ClN_5O$, 277.1; m/z. found, 278.1 [M+H]$^+$ $_1$H NMR (400 MHz, CDCl$_3$) δ 8.54 (s, 1H), 7.97 (d, J=8.8 Hz, 1H), 7.54 (d, J=8.7 Hz, 1H), 5.73 (s, 1H), 5.03 (d, J=7.3 Hz, 2H), 4.65-4.38 (m, 2H), 3.47 (p, J=7.3 Hz, 1H), 2.90 (d, J=4.8 Hz, 3H).

Intermediate 160: 8-(Azetidin-1-yl)-2-(3-bromophenyl)pyrido[3,4-d]pyrimidine

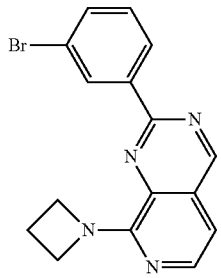 [SMILES: Brc1cccc(-c2ncc3ccnc(N4CCC4)c3n2)c1]

To a solution of 2-(3-bomophenyl)-8-chloropyrido[3,4-d]pyrimidine (Intermediate 28, Step D) (200 mg, 0.62 mmol) and DIEA (0.11 mL, 0.63 mmol) in DMA (2 mL) was added azetidine (0.21 mL, 3.12 mmol) and the mixture heated at 80° C. After 2 h, the mixture was diluted with water (10 mL) and extracted with ethyl acetate (30 mL). The organic was separated, concentrated to dryness, and the residue was purified by FCC (0-10% MeOH/DCM) to afford 8-(azetidin-1-yl)-2-(3-bromophenyl)pyrido[3,4-d]pyrimidine (168 mg, 79%) as an orange solid. MS (ESI): mass calcd. for $C_{16}H_{13}BrN_4$, 340.03; m/z. found, 341.1 $[M+H]^+$. $^1H$ NMR (500 MHz, DMSO-$d_6$) δ 9.52 (s, 1H), 8.54 (s, 1H), 8.42 (d, J=7.8 Hz, 1H), 8.11 (d, J=5.5 Hz, 1H), 7.75 (d, J=7.4 Hz, 1H), 7.58-7.47 (m, 1H), 7.05 (d, J=5.6 Hz, 1H), 4.55 (s, 6H).

Intermediate 161: 5-Bromo-2-(3-iodophenyl)-8-methyl-1,7-naphthyridine

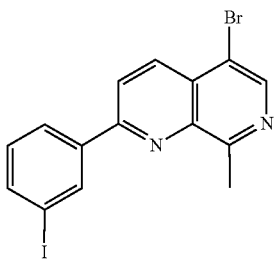 [SMILES: Cc1ncc(Br)c2ccc(-c3cccc(I)c3)nc12]

Step A: 5-Bromo-2-chloro-3-nitroisonicotinaldehyde. N,N-Dimethylformamide dimethyl acetal (8.88 mL, 66.8 mmol) was added to a solution of 5-bromo-2-chloro-4-methyl-3-nitropyridine (8.40 g, 33 mmol) and DMF (40 mL). The mixture was heated at 90° C. for 3 h before cooling to rt. The mixture was diluted with THF (100 mL), then a solution of NaIO$_4$ (21.4 g, 100 mmol) and water (100 mL) was added. The resultant mixture was stirred at rt for 16 h before pouring into H$_2$O (200 mL) and extracting with ethyl acetate (200 mL×3). The combined organic extracts were dried over anhydrous Na$_2$SO$_4$, filtered, and concentrated to dryness under reduced pressure to afford a residue, which was purified by FCC (1:0 to 3:1 gradient, petroleum ether/ethyl acetate) to afford 5-bromo-2-chloro-3-nitroisonicotinaldehyde (3.0 g, 34%) as a brown oil, which was used in the next step without further purification.

Step B: 3-Amino-5-bromo-2-chloroisonicotinaldehyde. Iron powder (1.9 g, 34 mmol) was added to a mixture of 5-bromo-2-chloro-3-nitroisonicotinaldehyde (3.0 g, 11 mmol), NH$_4$Cl (3.0 g, 57 mmol), EtOH (80 mL), and H$_2$O (10 mL). The resultant mixture was heated at 70° C. for 2 h before cooling to rt. The suspension was filtered through a pad of a pad of diatomaceous earth, such as Celite® and the pad washed with EtOH (50 mL). The filtrate was concentrated to dryness under reduced pressure to a residue, which was purified by FCC (20:1 to 5:1 gradient, petroleum ether/ethyl acetate) to afford 3-amino-5-bromo-2-chloroisonicotinaldehyde (260 mg, 10%) as a yellow solid. MS (ESI): mass calcd. for $C_6H_4BrClN_2O$, 233.9; m/z. found 235.0 $[M+H]^+$.

Step C: 5-Bromo-8-chloro-2-(3-iodophenyl)-1,7-naphthyridine. Potassium hydroxide (74.0 mg, 1.30 mmol) was added to the solution of 3-amino-5-bromo-2-chloroisonicotinaldehyde (260 mg, 1.10 mmol), 1-(3-iodophenyl)ethanone (272 mg, 1.11 mmol), and CH$_3$CN (5 mL). The resultant mixture was heated at 70° C. for 2 h before cooling to rt. The suspension was filtered through a pad of diatomaceous earth, such as Celite® and the pad washed with CH$_3$CN (20 mL). The filtrate was concentrated to dryness under reduced pressure to afford a residue, which was purified by FCC (1:0 to 3:1 gradient, petroleum ether/ethyl acetate) to afford 5-bromo-8-chloro-2-(3-iodophenyl)-1,7-naphthyridine (160 mg, 29%) as a yellow solid. MS (ESI): mass calcd. for $C_{14}H_7BrClIN_2$ 443.9 m/z. found 444.9 $[M+H]^+$.

Step D: 5-Bromo-2-(3-iodophenyl)-8-methyl-1,7-naphthyridine. Methylmagnesium bromide (0.30 mL, 3.0 M in THF) was added to a solution of tris(((Z)-4-oxopent-2-en-2-yl)oxy)iron (17.0 mg, 0.05 mmol), 5-bromo-8-chloro-2-(3-iodophenyl)-1,7-naphthyridine (220 mg, 0.49 mmol), and THF (5 mL) that had been cooled to 0° C. (ice/water). The resultant mixture was stirred for 1 h with gradual warming to rt before pouring into saturated aqueous NH$_4$Cl (30 mL) and extracting with ethyl acetate (30 mL×3). The combined organic extracts were dried over anhydrous Na$_2$SO$_4$, filtered, and concentrated to dryness under reduced pressure to afford a residue, which was purified by FCC (1:0 to 3:1 gradient, petroleum ether/ethyl acetate) to afford 5-bromo-2-(3-iodophenyl)-8-methyl-1,7-naphthyridine (120 mg, 54%) as a yellow solid. MS (ESI): mass calcd. for $C_{15}H_{10}BrIN_2$ 423.9 m/z. found 424.9 $[M+H]^+$.

Intermediate 162. 6-Chloro-4,8-dimethylpyrido[3,2-d]pyrimidine

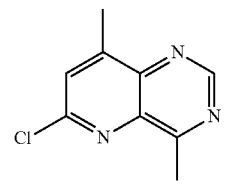

Step A: 1-(3-Amino-4-bromo-6-chloropyridin-2-yl)ethanone. Methylmagnesium bromide (13 mL, 38.7 mmol, 3.0 M in 2-methyltetrahydrofuran) was added to a solution of 3-amino-4-bromo-6-chloropicolinonitrile (3.0 g, 13 mmol) and THF (30 mL) that had been cooled to −10° C. (ice/salt). The resultant mixture was stirred at rt for 2 h. The reaction was then poured into saturated aqeuous NH$_4$Cl (50 mL), and extracted with ethyl acetate (30 mL×3). The combined organic extracts were washed with saturated NaHCO$_3$ (10 mL) and brine (10 mL), dried over anhydrous Na$_2$SO$_4$, filtered, and concentrated to dryness. The resulting residue was purified by FCC (1:0 to 10:1 gradient, petroleum ether/ethyl acetate) to afford 6-chloro-4,8-dimethylpyrido[3,2-d]pyrimidine (400 mg, 12%) as a yellow solid. MS (ESI): mass calcd. for $C_7H_6BrClN_2O$, 247.9; m/z. found 248.9 [M+H]$^+$.

Step B: 8-Bromo-6-chloro-4-methylpyrido[3,2-d]pyrimidine. A mixture of 1-(3-amino-4-bromo-6-chloropyridin-2-yl)ethanone (400 mg, 1.60 mmol), NH$_4$OAc (1.2 g, 16 mmol), and CH(OEt)$_3$ (2.67 mL, 16.0 mmol) was heated at 110° C. for 16 h. The mixture was then cooled to rt, poured into H$_2$O (10 mL), and extracted with ethyl acetate (10 mL×3). The combined organic extracts were washed with brine, dried over anhydrous Na$_2$SO$_4$, filtered, and concentrated to dryness. The resulting residue was purified by FCC (1:0 to 10:1 gradient, petroleum ether/ethyl acetate) to give the title compound (119 mg, 25%) as a yellow solid. MS (ESI): mass calcd. for $C_8H_5BrClN_3$ 256.9 m/z, found 258.0 [M+H]$^+$.

Step C: 6-Chloro-4,8-dimethylpyrido[3,2-d]pyrimidine. 8-Bromo-6-chloro-4-methylpyrido[3,2-d]pyrimidine (280 mg, 1.08 mmol), 2,4,6-trimethyl-1,3,5,2,4,6-trioxatriborinane (0.15 mL, 1.08 mmol), and K$_2$CO$_3$ (449 mg, 3.25 mmol) were added to a 5 mL microwave tube and the resulting mixture dissolved in 1,4-dioxane (2 mL) and H$_2$O (0.5 mL). The resultant mixture was sparged with Ar for 5 min and then treated with Pd(dppf)Cl$_2$·CH$_2$Cl$_2$ (88 mg, 0.11 mmol). The resultant mixture was sparged with Ar for another 5 min and then subjected to microwave irradiation at 70° C. in for 1 h. After the reaction mixture was allowed to cool to rt, it was concentrated to dryness. The resulting residue was purified by FCC (1:0 to 10:1 gradient, petroleum ether/ethyl acetate) to afford 6-chloro-4,8-dimethylpyrido[3,2-d]pyrimidine (87 mg, 40%) as a yellow solid. MS (ESI): mass calcd. for $C_9H_8ClN_3$ 193.0 m/z. found 194.1 [M+H]$^+$.

Intermediate 163: 6,8-dibromopyrido[3,2-d]pyrimidin-4-amine

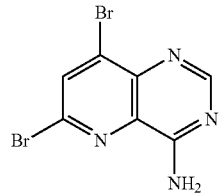 [SMILES: Nc1ncnc2c(Br)cc(Br)nc12]

A 100 mL three-necked round-bottomed flask was charged with 8-bromo-6-chloropyrido[3,2-d]pyrimidin-4-amine (1.0 g, 3.9 mmol) and HBr (50 mL, 40 wt. % in AcOH). The mixture was heated at 50° C. for 3 h before cooling to rt. After that, the mixture was concentrated to dryness under reduced pressure. The resulting residue was triturated with CH$_3$CN (10 mL) and filtered. The filter cake was washed with CH$_3$CN (10 mL) and dried to afford 6,8-dibromopyrido[3,2-d]pyrimidin-4-amine (800 mg) as a yellow solid, which was used without further purification. MS (ESI): mass calcd. for $C_7H_4Br_2N_4$ 301.9 m/z. found 302.9 [M+H]$^+$.

Intermediate 164: 1,3-Dioxoisoindolin-2-yl tetrahydro-2H-pyran-4-carboxylate

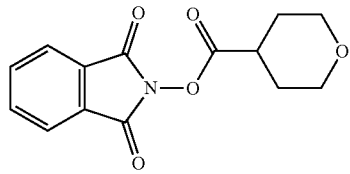 [SMILES: O=C(ON1C(=O)c2ccccc2C1=O)C1CCOCC1]

N-(3-Dimethylaminopropyl)-N'-ethylcarbodiimide hydrochloride (3.53 g, 18.4 mmol) was added to a solution of 2-hydroxyisoindoline-1,3-dione (2.00 g, 12.3 mmol), tetrahydro-2H-pyran-4-carboxylic acid (2.39 g, 18.4 mmol), and methylene chloride (25 mL) that had been cooled to 0° C. (ice/water). The resultant mixture was stirred at rt for 16 h. The mixture was then concentrated to dryness. The resulting residue was purified by FCC (1:0 to 0:1 gradient, petroleum ether/ethyl acetate) to afford 1,3-dioxoisoindolin-2-yl tetrahydro-2H-pyran-4-carboxylate (3.3 g, 98%) as a white solid. $^1$H NMR (400 MHz, CDCl$_3$) δ 7.95-7.88 (m, 2H), 7.85-7.78 (m, 2H), 4.09-4.01 (m, 2H), 3.61-3.51 (m, 2H), 3.08-2.98 (m, 1H), 2.12-1.95 (m, 4H).

Intermediate 165: 6-Chloro-8-(tetrahydro-2H-pyran-4-yl)pyrido[3,2-d]pyrimidin-4-amine

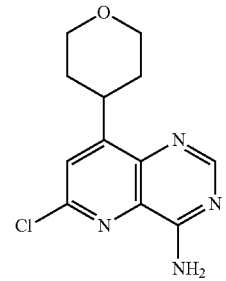 [SMILES: Nc1ncnc2c(C3CCOCC3)cc(Cl)nc12]

A 250 mL round-bottomed flask was charged with 6-chloropyrido[3,2-d]pyrimidin-4-amine (1.40 g, 7.75 mmol), 1,3-dioxoisoindolin-2-yl tetrahydro-2H-pyran-4-carboxylate (3.20 g, 11.6 mmol) and DMSO (80 mL). The mixture was sparged with Ar for 5 min and then treated with [4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate (435 mg, 0.39 mmol). The mixture was sparged with Ar for another 5 min and treated with TFA (2.30 mL, 31.0 mmol). The resultant mixture was stirred under irradiation with a blue LED at 25° C. for 16 h. The mixture was then poured into H$_2$O (400 mL) and stirred at rt for 1 hour. The suspension was filtered, and the filtrate cake was washed with H$_2$O (50 mL). The filtrate was neutralized with saturated aqueous NaHCO$_3$ to pH=7-8. The resulting precipitate was collected by filtration and purified by preparative reverse phase HPLC (Welch Xtimate C18 100×40 mm, 3 μm column, eluent: 8% to 30% (v/v) CH$_3$CN and H$_2$O with 0.075% TFA) to afford 6-chloro-8-(tetrahydro-2H-pyran-4-yl)pyrido[3,2-d]pyrimidin-4-amine (250 mg, 8%) as a white solid. $^1$H NMR (400 MHz, DMSO-d$_6$) δ 8.70-8.35 (m, 3H), 7.79 (s, 1H), 3.97-3.93 (m, 2H), 3.80-3.68 (m, 1H), 3.55-3.44 (m, 2H), 1.85-1.67 (m, 4H).

Intermediate 166.
6-Chloro-4-phenylpyrido[3,2-d]pyrimidine

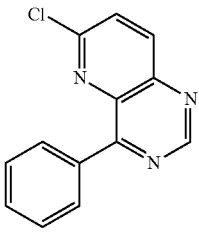 [SMILES: Clc1ccc2ncnc(-c3ccccc3)c2n1]

A 20 mL sealable microwave vial was charged with 4,6-dichloropyrido[3,2-d]pyrimidine (300 mg, 1.50 mmol), phenylboronic acid (146 mg, 1.20 mmol), $Cs_2CO_3$ (980 mg, 3.01 mmol), and 1,4-dioxane (16 mL). The mixture was sparged with Ar for 5 min and then treated with Pd(dppf)Cl$_2$ (110 mg, 0.15 mmol). The mixture was sparged with Ar for another 5 min and then subjected to microwave irradiation at 65° C. for 0.5 h. After the reaction mixture was allowed to cool to rt, the suspension was filtered through a pad of diatomaceous earth, such as Celite® and the pad washed with ethyl acetate (50 mL). The filtrate was concentrated to dryness. The resulting residue was purified by FCC (1:0 to 5:1 gradient, petroleum ether/ethyl acetate) followed by additional purification by preparative reverse phase HPLC (YMC-Triart Prep C18 250×50 mm, 10 μm, eluent: 60% to 90% (v/v) $CH_3CN$ and $H_2O$ with 0.04% $NH_3H_2O$+10 mM $NH_4HCO_3$) to afford 6-chloro-4-phenylpyrido[3,2-d]pyrimidine (80 mg, 22%) as a white solid. MS (ESI): mass calcd. for $C_{13}H_8ClN_3$ 241.0 m/z found 242.1 $[M+H]^+$. $^1H$ NMR (400 MHz, DMSO-d$_6$) δ 9.49 (s, 1H), 8.56 (d, J=8.8 Hz, 1H), 8.29-8.25 (m, 2H), 8.12 (d, J=8.8 Hz, 1H), 7.65-7.60 (m, 3H).

Intermediate 167: (3S,5S)-3-Ethynyl-3-hydroxy-1,5-dimethylpyrrolidin-2-one

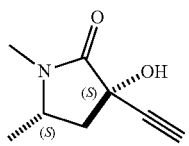

Step A: tert-Butyl 3-(methylamino)butanoate. To a 1 L four-necked round-bottomed flask equipped with an overhead stirrer was added methylamine (420 mL, 2.98 mol, 30 wt % in EtOH). Then tert-butyl but-2-enoate (212 g, 1.49 mol) was charged dropwise over 2 h at 20-25° C. The resulting mixture was warmed to 45-50° C. and stirred at this temperature for 3 h. The mixture was cooled to rt and concentrated to dryness to afford tert-butyl 3-(methylamino) butanoate (245 g) as a colorless oil. LC-MS (ESI): mass calcd. for $C_9H_{19}NO_2$, 173.1; m/z. found, 174.1 $[M+H]^+$. $^1H$ NMR (300 MHz, CDCl$_3$) δ 2.96 (q, J=6.4 Hz, 1H), 2.49-2.33 (m, 4H), 2.24 (dd, J=15.1, 6.1 Hz, 1H), 1.46 (s, 9H), 1.11 (d, J=6.4 Hz, 3H).

Step B: tert-Butyl 3-(2-ethoxy-N-methyl-2-oxoacetamido)butanoate. To a 5 L four-necked round-bottomed flask equipped with an overhead stirrer were added tert-butyl 3-(methylamino)butanoate (245 g, 1.41 mol), TEA (295 mL, 2.12 mol) and DCM (2450 mL). The resultant mixture was cooled to 0-10° C. followed by charging ethyl 2-chloro-2-oxoacetate (231 g, 1.69 mol) dropwise at this temperature. After stirring at 0-10° C. for 0.5 h, the reaction was poured into saturated aqueous $NaHCO_3$ (1600 mL). After phase separation, the aqueous phase was extracted with DCM (1000 mL), the combined organic phases were dried over $Na_2SO_4$, filtered, and concentrated to dryness to afford tert-butyl 3-(2-ethoxy-N-methyl-2-oxoacetamido)butanoate (373.5 g, 96%) as a brown oil. LC-MS (ESI): mass calcd. for $C_{13}H_{23}NO_5$, 273.2; m/z. found, 274.1 $[M+H]^+$.

Step C: tert-Butyl 4-hydroxy-1,2-dimethyl-5-oxo-2,5-dihydro-1H-pyrrole-3-carboxylate. To a 2 L four-necked round-bottom flask equipped with an overhead stirrer were added tert-butyl 3-(2-ethoxy-N-methyl-2-oxoacetamido)butanoate (50.0 g, 0.18 mol), and THF (1.0 L). The resultant mixture was cooled to 0-10° C. followed by charging NaOEt (18.7 g, 0.27 mol) portion-wise at 0-10° C. The resulting mixture was warmed to 15-25° C. and stirred at this temperature for 1 h. After which, the mixture was charged into aqueous citric acid (57.7 g, 0.27 mol, in 250 mL $H_2O$) dropwise at 15-25° C. After phase separation, the aqueous phase was extracted with MTBE (500 mL). The combined organic phases were washed with brine (500 mL), dried over $Na_2SO_4$, filtered, and concentrated to dryness. The resulting residue was slurried with n-heptane (200 mL) at 10-20° C. for 1 h. The resulting solid was isolated by filtration followed by drying to give tert-butyl 4-hydroxy-1,2-dimethyl-5-oxo-2,5-dihydro-1H-pyrrole-3-carboxylate (30.3 g, 72%) as a yellow solid. LC-MS (ESI): mass calcd. for $C_{11}H_{17}NO_4$, 227.1; m/z found, 228.1 $[M+H]^+$. $^1H$ NMR (300 MHz, CDCl$_3$) δ 9.18 (s, 1H), 4.05 (q, J=6.6 Hz, 1H), 3.02 (d, J=0.6 Hz, 3H), 1.57 (s, 9H), 1.41 (d, J=6.6 Hz, 3H).

Step D: 4-Hydroxy-1,2-dimethyl-5-oxo-2,5-dihydro-1H-pyrrole-3-carboxylic acid. To a 2 L four-necked round-bottomed flask equipped with overhead stirrer were added tert-butyl 4-hydroxy-1,2-dimethyl-5-oxo-2,5-dihydro-1H-pyrrole-3-carboxylate (180 g, 0.79 mol) and TFA (720 mL). The resultant mixture was stirred at 10-15° C. for 1 h. Then the mixture was concentrated under vacuum to dryness. The residue was slurried in acetonitrile (720 mL) at 10-15° C. for 1 h. The resulting solid was isolated by filtration and dried to give 4-hydroxy-1,2-dimethyl-5-oxo-2,5-dihydro-1H-pyrrole-3-carboxylic acid (120 g, 88%) as a white solid. LC-MS (ESI): mass calcd. for $C_7H_9NO_4$, 171.0; m/z. found, 172.1 $[M+H]^+$. $^1H$ NMR (400 MHz, CD$_3$OD) δ 4.17 (q, J=6.6 Hz, 1H), 3.03 (d, J=0.6 Hz, 3H), 1.44 (d, J=6.6 Hz, 3H)

Step E: 1,5-Dimethylpyrrolidine-2,3-dione. To a 2 L four-necked round-bottomed flask equipped with an overhead stirrer were added 4-hydroxy-1,2-dimethyl-5-oxo-2,5-dihydro-1H-pyrrole-3-carboxylic acid (60 g, 0.35 mol) and THF (900 mL). The resultant mixture was warmed to 60-70° C. and maintained at this temperature for 9 h. The resulting mixture was concentrated to dryness to afford 1,5-dimethylpyrrolidine-2,3-dione as a yellow oil (41.8 g, 94%). LC-MS (ESI): mass calcd. for $C_6H_9NO_2$, 127.1; m/z found, 128.1 $[M+H]^+$. $^1H$ NMR (400 MHz, CDCl$_3$) δ 3.98-3.86 (m, 1H), 3.13 (d, J=1.9 Hz, 3H), 2.94 (ddd, J=19.7, 7.3, 1.9 Hz, 1H), 2.34 (dt, J=19.9, 2.5 Hz, 1H), 1.44 (dd, J=6.5, 1.9 Hz, 3H).

Step F: 3-Ethynyl-3-hydroxy-1,5-dimethylpyrrolidin-2-one. To a 3-L four-necked round-bottomed flask equipped with an overhead stirrer was added ethynylmagnesiumbromide (1.29 L, 0.65 mol, 0.5 M in THF). The flask was purged with nitrogen and cooled to −10° C. before charging 1,5-dimethylpyrrolidine-2,3-dione (41 g, 0.32 mol) over the course of 20 min. The resultant mixture was warmed to 20-25° C. and maintained at this temperature for 16 h. Then the reaction was poured into aqueous NH₄Cl (120 g in 360 mL H₂O) followed by dilution with DCM (1000 mL). After stirring for 1 h, the suspension was filtered and combined with the filtrate generated from another 41 g batch of reaction. The combined filtrates were dried over Na₂SO₄, filtered, and concentrated to dryness. The residue was purified by silica gel column chromatography FCC (0:1:1 to 1:20:0 gradient, MeOH/DCM/PE) to afford a mixture of 3-ethynyl-3-hydroxy-1,5-dimethylpyrrolidin-2-one isomers as a yellow solid (21.8 g, 22%). The mixture was further purified by chiral SFC (Phenomenex Lux 5 µm, Cellulose-45×25 cm, mobile phase A: CO₂: 80%; mobile phase B: EtOH (2 mM NH₃-MeOH): 20%) to afford a mixture, (Mixture A), of (3R,5R)-3-ethynyl-3-hydroxy-1,5-dimethylpyrrolidin-2-one and (3S,5S)-3-ethynyl-3-hydroxy-1,5-dimethylpyrrolidin-2-one (18.6 g) and a mixture, (Mixture B), of (3R,5S)-3-ethynyl-3-hydroxy-1,5-dimethylpyrrolidin-2-one and (3S,5R)-3-ethynyl-3-hydroxy-1,5-dimethylpyrrolidin-2-one (2.3 g). Mixture A, (3R,5R)-3-ethynyl-3-hydroxy-1,5-dimethylpyrrolidin-2-one and (3S,5S)-3-ethynyl-3-hydroxy-1,5-dimethylpyrrolidin-2-one, was further purified by chiral SFC (Phenomenex Lux 5 µm, Cellulose-45×25 cm, mobile phase A: CO₂: 80%; mobile phase B: EtOH (2 mM NH₃-MeOH): 20%) to afford (3S,5S)-3-ethynyl-3-hydroxy-1,5-dimethylpyrrolidin-2-one (7.3 g, 39%. >97% ee) as a yellow solid and (3R,5R)-3-ethynyl-3-hydroxy-1,5-dimethylpyrrolidin-2-one (Intermediate 168, 7.2 g, 39%, >97% ee) as a yellow solid. Data for (3S,5S)-3-ethynyl-3-hydroxy-1,5-dimethylpyrrolidin-2-one: LC-MS (ESI): mass calcd. for $C_8H_{11}NO_2$, 153.1; m/z. found, 154.1 [M+H]⁺. ¹H NMR (400 MHz, CDCl₃) δ 3.64 (dp, J=8.2, 6.3 Hz, 1H), 2.89 (s, 3H), 2.71 (dd, J=12.7, 6.0 Hz, 1H), 2.55 (s, 1H), 1.86 (dd, J=12.7, 8.2 Hz, 1H), 1.31 (d, J=6.3 Hz, 3H). $[\alpha]_D^{25}$=83.5° (c=0.93 in MeOH).

Intermediate 168. (3R,5R)-3-Ethynyl-3-hydroxy-1,5-dimethylpyrrolidin-2-one

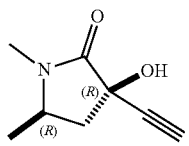

The title compound was prepared utilizing the chiral separation described in Step F of Intermediate 167 to afford (3R,5R)-3-ethynyl-3-hydroxy-1,5-dimethylpyrrolidin-2-one (7.2 g, 39%, >97% ee) as a yellow solid. LC-MS (ESI): mass calcd. for $C_8H_{11}NO_2$, 153.1; m/z. found, 154.1 [M+H]⁺. ¹H NMR (400 MHz, CDCl₃) δ 3.64 (dp, J=8.2, 6.3 Hz, 1H), 2.89 (s, 3H), 2.71 (dd, J=12.7, 6.0 Hz, 1H), 2.55 (s, 1H), 1.86 (dd, J=12.7, 8.2 Hz, 1H), 1.31 (d, J=6.3 Hz, 3H). $[\alpha]_D^{25}$=−79.4° (c=1.00 in MeOH).

Intermediate 169: (3R,5S)-3-Ethynyl-3-hydroxy-1,5-dimethylpyrrolidin-2-one

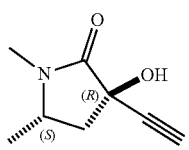

The title compound was prepared separating Mixture B from as described in Intermediate 167. Mixture B, (3R,5S)-3-ethynyl-3-hydroxy-1,5-dimethylpyrrolidin-2-one and (3S,5R)-3-ethynyl-3-hydroxy-1,5-dimethylpyrrolidin-2-one (2.3 g), was separated by chiral SFC (CHIRALPAKIG, 5 µm, 5×25 cm, mobile phase A: CO₂ 84%; mobile phase B: EtOH (2 mM NH₃-MeOH) 16%) to afford (3R,5S)-3-ethynyl-3-hydroxy-1,5-dimethylpyrrolidin-2-one (0.5 g, 2.7%, >97% ee) as a yellow solid and (3S,5R)-3-ethynyl-3-hydroxy-1,5-dimethylpyrrolidin-2-one. Data for (3R,5S)-3-ethynyl-3-hydroxy-1,5-dimethylpyrrolidin-2-one (Intermediate 170, 0.4 g, 2.2%, >97% ee) as a yellow solid: LC-MS (ESI): mass calcd. for $C_8H_{11}NO_2$, 153.1; m/z. found, 154.1 [M+H]⁺. ¹H NMR (400 MHz, CDCl₃) δ 3.65 (dqd, J=8.0, 6.5, 3.6 Hz, 1H), 2.90 (s, 3H), 2.63 (s, 1H), 2.52 (dd, J=13.3, 7.9 Hz, 1H), 2.24 (dd, J=13.3, 3.6 Hz, 1H), 1.36 (d, J=6.5 Hz, 3H).

Intermediate 170: (3S,5R)-3-Ethynyl-3-hydroxy-1,5-dimethylpyrrolidin-2-one

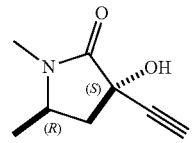

The title compound was prepared utilizing the chiral separation described in Intermediate 169 to afford (3S,5R)-3-Ethynyl-3-hydroxy-1,5-dimethylpyrrolidin-2-one (0.4 g, 2.2%, >97% ee) as a yellow solid. LC-MS (ESI): mass calcd. for $C_8H_{11}NO_2$, 153.1; m/z. found, 154.1 [M+H]⁺. ¹H NMR (400 MHz, CDCl₃) δ 3.65 (dqd, J=8.0, 6.5, 3.6 Hz, 1H), 2.90 (s, 3H), 2.63 (s, 1H), 2.52 (dd, J=13.3, 7.9 Hz, 1H), 2.24 (dd, J=13.3, 3.6 Hz, 1H), 1.36 (d, J=6.5 Hz, 3H).

Intermediate 171: N-(6-(3-Iodophenyl)pyrido[3,2-d]pyrimidin-4-yl-2-d)methanesulfonamide

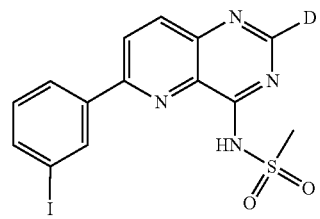 [SMILES: [2H]c1nc(NS(C)(=O)=O)c2nc(-c3cccc(I)c3)ccc2n1]

To a vial containing NaH (72.0 mg, 1.79 mmol, 60% in mineral oil) were added dry DMF (6 mL) and Intermediate 117 [6-(3-iodophenyl)pyrido[3,2-d]pyrimidin-2-d-4-amine (400 mg, 1.15 mmol)] in 7 mL DMF at rt. After 20 min, methane sulfonyl chloride (0.13 mL, 1.72 mmol) was introduced dropwise at rt. The resulting mixture was stirred for 28 h. After which time, the mixture was concentrated to dryness. The resulting residue was purified by FCC (100% DCM increasing to 5% MeOH-DCM) to afford N-(6-(3-iodophenyl)pyrido[3,2-d]pyrimidin-4-yl-2-d)methanesulfonamide (60 mg, 12%) as a yellow solid. MS (ESI): mass calcd. for $C_{14}H_{10}DIN_4O_2S$ 426.97 m/z found 428.9 [M+H]⁺. ¹H NMR (500 MHz, CD30D, contains 5 drops CDCl₃) δ 8.72 (s, 1H), 8.42 (d, J=8.9 Hz, 1H), 8.26 (dd, J=17.6, 8.3 Hz, 2H), 7.86 (d, J=7.8 Hz, 1H), 7.30 (t, J=7.8 Hz, 1H), 3.46 (s, 3H), 3.00 (s, 1H).

Intermediate 172: 6-Chloro-4-cyclopropylpyrido[3,2-d]pyrimidine

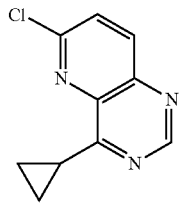 [SMILES: Clc1ccc2ncnc(C3CC3)c2n1]

Cyclopropylmagnesium bromide (2.00 mL, 1.00 mmol, 0.50 M solution in THF) was added dropwise to a mixture of 4,6-dichloropyrido[3,2-d]pyrimidine (200 mg, 1.00 mmol), tris(((Z)-4-oxopent-2-en-2-yl)oxy)iron (21.0 mg, 0.06 mmol), and THF (5 mL) that had been cooled to 0° C. (ice/water). The resultant mixture was stirred for 2 h with gradual warming to rt. The mixture was then poured into water (20 mL) and extracted with methylene chloride (20 mL×3). The combined organic extracts were washed with brine (10 mL), dried over anhydrous $Na_2SO_4$, filtered, and concentrated to dryness. The resulting residue was purified by preparative reverse phase HPLC (Boston Prime C18 150×30 mm, 5 μm (eluent: 50% to 80% (v/v) $CH_3CN$ and $H_2O$ with 0.04% $NH_3H_2O+10$ mM $NH_4HCO_3$) to afford 6-chloro-4-cyclopropylpyrido[3,2-d]pyrimidine (50 mg, 24%) as a white solid. MS (ESI): mass calcd. for $C_{10}H_8ClN_3$ 205.0 m/z found 206.1 [M+H]⁺. ¹H NMR (400 MHz, $CDCl_3$) δ 9.12 (s, 1H), 8.24 (d, J=8.6 Hz, 1H), 7.76 (d, J=8.8 Hz, 1H), 3.49 (dd, J=4.3, 8.5 Hz, 1H), 1.52-1.41 (m, 2H), 1.40-1.32 (m, 2H).

Intermediate 173: 6-Chloro-4-isopropylpyrido[3,2-d]pyrimidine

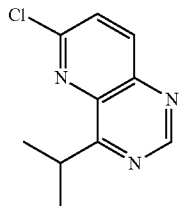

i-PrMgCl (0.6 mL, 1.2 mmol, 2.0 M in THF) was added to a solution of tris(((Z)-4-oxopent-2-en-2-yl)oxy)iron (21 mg, 0.059 mmol) and THF (3 mL) that had been cooled to −70° C. (dry ice/acetone). The resultant mixture was stirred at −70° C. for 0.5 hours, and then treated with a solution of 4,6-dichloropyrido[3,2-d]pyrimidine (0.2 g, 1.0 mmol) and THF (2 mL). The resultant mixture was stirred for 2 h with gradual warming to rt. The mixture was then poured into saturated aqueous $NH_4Cl$ (5 mL) and extracted with ethyl acetate (30 mL×3). The combined organic extracts were dried over anhydrous $Na_2SO_4$, filtered, and concentrated to dryness. The resulting residue was purified by FCC (20:1 to 5:1 gradient, petroleum ether/ethyl acetate) to afford the product 6-chloro-4-isopropylpyrido[3,2-d]pyrimidine (80 mg) as a yellow oil. MS (ESI): mass calcd. for $C_{10}H_{10}ClN_3$ 207.1 m/z found 208.1 [M+H]⁺.

Intermediate 174: (1S,4S,5R)-4-Ethynyl-4-hydroxy-2-methyl-2-azabicyclo[3.1.0]hexan-3-one

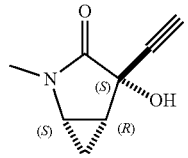

Step A: 2-Chloro-N-cyclopropyl-N-methylacetamide. To a 3 L four-necked round-bottomed flask equipped with an overhead stirrer were added MTBE (1000 mL), $H_2O$ (1000 mL) and N-methylcyclopropanamine hydrochloride (200 g, 1.86 mol). After cooing to 10-15° C., $K_2CO_3$ (642.3 g, 4.65 mol) was added portion wise under $N_2$ at the same temperature. The resulting mixture was warmed to 25° C. followed by charging chloroacetyl chloride (231 g, 2.01 mol) dropwise at the same temperature. The resulting mixture was stirred at 25° C. for 0.5 h. After phase separation, the aqueous phase was extracted with MTBE (2000 mL×2). The combined organic phases were concentrated to dryness. The residue was further purified by vacuum distillation to afford 2-chloro-N-cyclopropyl-N-methylacetamide (240 g, 82%) as a colorless oil. ¹H NMR (400 MHz, $CDCl_3$) δ 4.34 (s, 2H), 2.99 (s, 3H), 2.81-2.78 (m, 1H), 0.93-0.78 (m, 4H).

Step B: 2-Methyl-2-azabicyclo[3.1.0]hexan-3-one. To a 1 L four-necked round-bottomed flask equipped with a magnetic stir were added toluene (600 mL), $Pd_2(dba)_3$ (26.0 g, 0.03 mol), 2-dicyclohexylphosphino-2',4',6'-triisopropylbiphenyl (56.2 g, 0.05 mol) and $K_2CO_3$ (24.8 g, 0.41 mol) at 25° C. under $N_2$. After heating to 100° C., 2-chloro-N-cyclopropyl-N-methylacetamide (20.0 g, 0.14 mol) was added dropwise under $N_2$. The resulting mixture was stirred at 100° C. for 16 h. The mixture was cooled to 25° C., filtered through a pad of diatomaceous earth, and rinsed with toluene. The filtrate was collected and concentrated under vacuum to remove most of the solvent. The residue was further purified by vacuum distillation to afford 2-methyl-2-azabicyclo[3.1.0]hexan-3-one as yellow oil (11 g, 58% w/w assay by Q-NMR, purity: 59.1% by GC, yield: 26%, the major impurity was N-cyclopropyl-N-methylacetamide). ¹H NMR (400 MHz, $CDCl_3$) δ 2.99-2.96 (ddt, J=7.0, 4.9, 1.8 Hz, 1H), 2.86 (s, 3H), 2.74 (dd, J=17.9, 7.3 Hz, 1H), 2.33 (d, J=17.9 Hz, 1H), 1.45 (dtdd, J=8.3, 7.3, 4.7, 0.9 Hz, 1H), 0.82 (ddd, J=8.4, 5.9, 5.0 Hz, 1H), 0.27 (ddd, J=5.8, 4.8, 2.1 Hz, 1H).

Step C: 2-Methyl-4,4-bis(methylthio)-2-azabicyclo[3.1.0]hexan-3-one. To a 5 L four-necked round-bottomed flask equipped with an overhead stirrer were added THF (3000 mL) and 2-methyl-2-azabicyclo[3.1.0]hexan-3-one (60.0 g, 58% w/w, 0.54 mol). After cooing to −40 to −30° C., LDA (810 mL, 1.62 mol, 2.0 M in THF) was added dropwise under $N_2$ at the same temperature. The resulting mixture was stirred at −40 to −30° C. for 1 h followed by adding S-methyl methanesulfonothioate (204 g, 1.62 mol). After stirring at −40 to −30° C. for 1 hour, the reaction mixture was quenched by saturated aqueous $NH_4Cl$ at 0 to 20° C. After phases separation, the aqueous phase was extracted with EtOAc (400 mL×3). The combined organic phases were concentrated to dryness. The residue was purified by FCC (10:1 to 2:1 gradient, ethyl acetate/petroleum ether) to give two crops of 2-methyl-4,4-bis(methylthio)-2-azabicyclo[3.1.0]hexan-3-one as light brown oil (1st crop: 77.8 g, 52.5% w/w; 2nd crop: 17.5 g, 76.0% w/w, yield: 85%). LC-MS (ESI, m/z): mass calcd. for $C_8H_{13}N_3OS_2$, 203.0; m/z. found, 156.1 [M−MeS]+. $^1$H NMR (400 MHz, CDCl$_3$) δ 3.18 (ddd, J=7.2, 4.9, 2.5 Hz, 1H), 2.92 (s, 3H), 2.32 (s, 3H), 2.25 (s, 3H), 1.67 (ddd, J=8.5, 6.9, 4.7 Hz, 1H), 1.00 (ddd, J=8.5, 6.2, 4.9 Hz, 1H), 0.79 (ddd, J=6.1, 4.7, 2.5 Hz, 1H).

Step D: 2-Methyl-2-azabicyclo[3.1.0]hexane-3,4-dione. To a 2 L four-necked round-bottom flask equipped with an overhead stirrer were added acetonitrile (1360 mL), H$_2$O (136 mL) and 2-methyl-4,4-bis(methylthio)-2-azabicyclo[3.1.0]hexan-3-one (24.8 g, 54.7% w/w, 66.7 mmol). The resulting mixture was cooled to −5 to 0° C. followed by charging (CF$_3$COO)$_2$IPh (57.5 g, 2.0 eq.) portion wise at −5 to 0° C. After stirring at −5 to 0° C. for 2 h, the reaction mixture poured into saturated aqueous NaHCO$_3$ at 0 to 20° C. After removing most of acetonitrile by concentration under vacuum, the resulting solution was extracted with i-PrOH/CHCl$_3$=1:3 (100 mL×15). The combined organic phases were concentrated to dryness. The residue was slurried with ethyl acetate (150 mL) to give the title compound as off-white solid (8.0 g, 96%). LC-MS (ESI, m/z): mass calcd. for $C_6H_7NO_2$, 125.0; m/z. found, 126.1 [M+H]+. $^1$H NMR (400 MHz, CDCl$_3$) δ 3.70 (ddd, J=5.3, 4.5, 2.7 Hz, 1H), 3.12 (s, 3H), 2.33 (ddd, J=9.7, 5.3, 4.4 Hz, 1H), 1.61 (ddd, J=9.9, 5.8, 4.4 Hz, 1H), 1.53 (ddd, J=5.8, 4.4, 2.7 Hz, 1H).

Step E: 4-Ethynyl-4-hydroxy-2-methyl-2-azabicyclo[3.1.0]hexan-3-one. To a 3 L four-necked round-bottomed flask equipped with an overhead stirrer were added ethynylmagnesium bromide (1391 mL, 695.3 mmol, 0.5 M in THF). After cooing to −78° C., a solution of 2-methyl-2-azabicyclo[3.1.0]hexane-3,4-dione (29.00 g, 231.8 mmol) in THF (725 mL) was added dropwise under N$_2$ at −78° C. The resulting mixture was stirred at −78° C. for 1 h then gradually warmed to 0° C. followed by quenching with aqueous NH$_4$Cl at 0-20° C. After phases separation, the aqueous phase was extracted with i-PrOH/CHCl$_3$=1:3 (300 mL×3). The combined organic phases were concentrated to dryness. The residue was purified FCC (10:1 to 1:2 gradient, ethyl acetate/petroleum ether) to afford Mixture C, a mixture of (1R,4R,5S)-4-ethynyl-4-hydroxy-2-methyl-2-azabicyclo[3.1.0]hexan-3-one and (1 S,4S,5R)-4-ethynyl-4-hydroxy-2-methyl-2-azabicyclo[3.1.0]hexan-3-one (15.6 g) and Mixture D, a mixture of (1R,4S,5S)-4-ethynyl-4-hydroxy-2-methyl-2-azabicyclo[3.1.0]hexan-3-one and (1 S,4R,5R)-4-ethynyl-4-hydroxy-2-methyl-2-azabicyclo[3.1.0]hexan-3-one (3.4 g). Mixture C was further purified by chiral SFC (Chiralpak AD-H, 30×250 mm, 5 μm, mobile phase A: CO$_2$; mobile phase B: MeOH (2 mM NH$_3$ in MeOH)) to afford (1 S,4S,5R)-4-ethynyl-4-hydroxy-2-methyl-2-azabicyclo[3.1.0]hexan-3-one (7.3 g, 21%, >97% ee) as a white solid and (1 S,4S,5R)-4-ethynyl-4-hydroxy-2-methyl-2-azabicyclo[3.1.0]hexan-3-one (Intermediate 175, 7.3 g, 21%, >97% ee) as a white solid. Data for (1 S,4S,5R)-4-ethynyl-4-hydroxy-2-methyl-2-azabicyclo[3.1.0]hexan-3-one: LC-MS (ESI, m/z): mass calcd. for $C_8H_9NO_2$, 151.0; m/z. found, 152.1 [M+H]+. $^1$H NMR (400 MHz, CDCl$_3$) δ 3.37 (s, 1H), 3.16 (ddd, J=7.0, 4.8, 2.4 Hz, 1H), 2.95 (s, 3H), 2.67 (s, 1H), 2.07 (ddd, J=8.6, 6.8, 4.8 Hz, 1H), 0.95 (ddd, J=8.6, 6.5, 4.7 Hz, 1H), 0.78 (ddd, J=6.5, 4.8, 2.5 Hz, 1H). $[α]_D^{25}$=66.4° (c=1.02 in EtOH).

Intermediate 175: (1R,4R,5S)-4-Ethynyl-4-hydroxy-2-methyl-2-azabicyclo[3.1.0]hexan-3-one

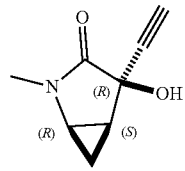

The title compound was prepared utilizing the chiral separation described in Intermediate 174 to afford (1R,4R,5S)-4-ethynyl-4-hydroxy-2-methyl-2-azabicyclo[3.1.0]hexan-3-one (7.3 g, 21%, >97% ee) as a white solid. LC-MS (ESI, m/z): mass calcd. for $C_8H_9NO_2$, 151.0; m/z. found, 152.1 [M+H]+. $^1$H NMR (400 MHz, CDCl$_3$) δ 3.37 (s, 1H), 3.16 (ddd, J=7.0, 4.8, 2.4 Hz, 1H), 2.95 (s, 3H), 2.67 (s, 1H), 2.07 (ddd, J=8.6, 6.8, 4.8 Hz, 1H), 0.95 (ddd, J=8.6, 6.5, 4.7 Hz, 1H), 0.78 (ddd, J=6.5, 4.8, 2.5 Hz, 1H). $[α]_D^{25}$=−65.6° (c=1.08 in EtOH).

Intermediate 176: (1R,4S,5S)-4-ethynyl-4-hydroxy-2-methyl-2-azabicyclo[3.1.0]hexan-3-one

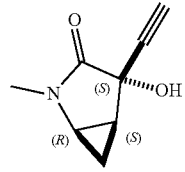

The title compound was prepared by separation of Mixture D which was isolated as described in Intermediate 174. Separation using chiral SFC (chiralpak AD-H, 30×250 mm, 5 μm, mobile phase A: CO$_2$; mobile phase B: MeOH (2 mM NH$_3$ in MeOH)) to affored (1R,4S,5S)-4-ethynyl-4-hydroxy-2-methyl-2-azabicyclo[3.1.0]hexan-3-one (1.4 g, 4%, >97% ee) as a white solid and (1 S,4R,5R)-4-Ethynyl-4-hydroxy-2-methyl-2-azabicyclo[3.1.0]hexan-3-one (Intermediate 177, 1.4 g, 4%, >97% ee) as a white solid. Data for (1R,4S,5S)-4-ethynyl-4-hydroxy-2-methyl-2-azabicyclo[3.1.0]hexan-3-one: LC-MS (ESI, m/z): mass calcd. for $C_8H_9NO_2$, 151.0; m/z. found, 152.1 [M+H]+. $^1$H NMR (400 MHz, CDCl$_3$)$^1$H NMR (400 MHz, CDCl$_3$) δ 4.69-3.57 (m, 1H), 3.11 (ddd, J=7.0, 4.9, 2.4 Hz, 1H), 2.95 (s, 3H), 2.56 (s, 1H), 1.97 (ddd, J=9.1, 6.7, 4.9 Hz, 1H), 1.09 (ddd, J=9.1, 6.6, 4.8 Hz, 1H), 0.67 (ddd, J=6.6, 4.9, 2.4 Hz, 1H).

Intermediate 177: (1 S,4R,5R)-4-Ethynyl-4-hydroxy-2-methyl-2-azabicyclo[3.1.0]hexan-3-one

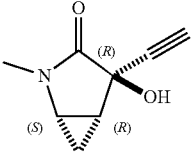

The title compound was prepared utilizing the chiral separation described in Intermediate 176 to afford (1 S,4R, 5R)-4-ethynyl-4-hydroxy-2-methyl-2-azabicyclo[3.1.0]hexan-3-one (1.4 g, 4%, >97% ee) as a white solid. LC-MS (ESI, m/z): mass calcd. for $C_8H_9NO_2$, 151.0; m/z. found, 152.1 [M+H]⁺. ¹H NMR (400 MHz, CDCl₃) ¹H NMR (400 MHz, CDCl₃) δ 4.69-3.57 (m, 1H), 3.11 (ddd, J=7.0, 4.9, 2.4 Hz, 1H), 2.95 (s, 3H), 2.56 (s, 1H), 1.97 (ddd, J=9.1, 6.7, 4.9 Hz, 1H), 1.09 (ddd, J=9.1, 6.6, 4.8 Hz, 1H), 0.67 (ddd, J=6.6, 4.9, 2.4 Hz, 1H).

Intermediate 178: 6-Chloro-4-(trifluoromethyl)pyrido[3,2-d]pyrimidine

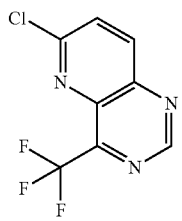 [SMILES: FC(F)(F)c1ncnc2ccc(Cl)nc12]

Step A: tert-Butyl (6-chloro-2-formylpyridin-3-yl)carbamate. Methyllithium (6.4 mL, 10 mmol, 1.6 M in hexane) was added dropwise to a solution of tert-butyl (2-bromo-6-chloropyridin-3-yl)carbamate (3.0 g, 9.8 mmol) and THF (25 mL) that had been cooled to −72° C. (dry ice/EtOH) under N₂. The resultant mixture was stirred at −72° C. (dry ice/EtOH) for 55 min before treating with n-BuLi (4.29 mL, 10.7 mmol, 2.5 M in hexane). The resultant mixture was stirring at −55° C. (dry ice/EtOH) for 1 hour, treated with DMF (1.21 mL, 15.6 mmol), and then stirred at −45° C. (dry ice/EtOH) for 0.5 hours. The mixture was then poured into H₂O (50 mL) and HOAc (8 mL) and extracted with ethyl acetate (200 mL×3). The combined organic extracts were dried over anhydrous Na₂SO₄, filtered, and concentrated to dryness. The resulting residue was purified by FCC (1:0 to 5:1, gradient, petroleum ether/ethyl acetate) to afford tert-butyl (6-chloro-2-formylpyridin-3-yl)carbamate (900 mg, 36%) as a yellow solid. ¹H NMR (400 MHz, CDCl₃) δ 10.19 (br. s, 1H), 9.99 (d, J=0.8 Hz, 1H), 8.89 (d, J=9.0 Hz, 1H), 7.48 (d, J=9.0 Hz, 1H), 1.54 (s, 9H).

Step B: tert-Butyl (6-chloro-2-(2,2,2-trifluoro-1-hydroxyethyl)pyridin-3-yl)carbamate. Tetrabutylammonium fluoride (6.62 mL, 6.62 mmol, 1.0 M in THF) was added dropwise to a solution of tert-butyl (6-chloro-2-formylpyridin-3-yl)carbamate (850 mg, 3.31 mmol), trimethyl(trifluoromethyl)silane (4.71 g, 33.1 mmol) and THF (20 mL) that had been cooled to 0° C. (ice/water). The resultant mixture was stirred at rt for 1 h. The mixture was then poured into water (30 mL) and extracted with ethyl acetate (80 mL×3). The combined organic extracts were washed with brine (10 mL×2), dried over anhydrous Na₂SO₄, filtered, and concentrated to dryness. The resulting residue was purified by FCC (0:1 to 5:1 gradient, petroleum ether/ethyl acetate) to afford tert-butyl (6-chloro-2-(2,2,2-trifluoro-1-hydroxyethyl)pyridin-3-yl)carbamate (870 mg, 79%) as a white solid.

Step C: tert-Butyl (6-chloro-2-(2,2,2-trifluoroacetyl)pyridin-3-yl)carbamate. 1,1,1-Tris(acetyloxy)-1,1-dihydro-1,2-benziodoxol-3-(1H)-one (Dess-Martin periodinane, 2.26 g, 5.33 mmol) was added to a solution of tert-butyl (6-chloro-2-(2,2,2-trifluoro-1-hydroxyethyl)pyridin-3-yl)carbamate (870 mg, 2.66 mmol) and methylene chloride (30 mL) that had been cooled to 0° C. (ice/water). The mixture was stirred for 2 h with gradual warming to rt. Methylene chloride (50 mL), saturated aqueous NaHCO₃ (5 mL) and saturated aqueous Na₂S₂O₃ (5 mL) were then added and the mixture stirred for 3 min. Two phases were separated. The organic phase was washed with brine, dried over anhydrous Na₂SO₄, filtered, and concentrated to dryness. The resulting residue was purified by FCC (1:0 to 5:1 gradient, petroleum ether/ethyl acetate) to afford tert-butyl (6-chloro-2-(2,2,2-trifluoroacetyl)pyridin-3-yl)carbamate (750 mg, 66%) as a colorless oil. ¹H NMR (400 MHz, CDCl₃) δ 10.02 (br. s, 1H), 8.98 (d, J=9.0 Hz, 1H), 7.55 (d, J=9.3 Hz, 1H), 1.61 (s, 9H).

Step D: 1-(3-Amino-6-chloropyridin-2-yl)-2,2,2-trifluoroethan-1-one. tert-Butyl (6-chloro-2-(2,2,2-trifluoroacetyl)pyridin-3-yl)carbamate (740 mg, 2.28 mmol), TFA (3 mL), and DCM (12 mL) were added to a 50 mL round-bottomed flask. The resultant mixture was stirred at rt for 1 h. The mixture was then concentrated under reduced pressure to dryness, re-dissolved in ethyl acetate (40 mL), washed with saturated aqueous NaHCO₃ (10 mL), dried over anhydrous Na₂SO₄, filtered, and concentrated to dryness. The resulting residue was purified by FCC (0:1 to 3:1 gradient, petroleum ether/ethyl acetate) to afford 1-(3-amino-6-chloropyridin-2-yl)-2,2,2-trifluoroethan-1-one (510 mg, 71%) as a yellow solid.

Step E: 6-Chloro-4-(trifluoromethyl)pyrido[3,2-d]pyrimidine. 1-(3-Amino-6-chloropyridin-2-yl)-2,2,2-trifluoroethanone (510 mg, 2.27 mmol) was added to a mixture of ammonium acetate (875 mg, 11.4 mmol) and triethoxymethane (5 mL), in a 5 mL microwave tube. The resultant mixture was subjected to microwave irradiation at 140° C. in for 1 h. After the reaction mixture was allowed to cool to rt, it was concentrated to dryness, suspended in water (30 mL), and extracted with ethyl acetate (60 mL×3). The combined organic extracts were washed with brine (10 mL), dried over anhydrous Na₂SO₄, filtered, and concentrated to dryness. The resulting residue was purified by FCC (1:0 to 5:1 gradient, petroleum ether/ethyl acetate) to afford 6-chloro-4-(trifluoromethyl)pyrido[3,2-d]pyrimidine (190 mg, 36%) as a brown solid. ¹H NMR (400 MHz, DMSO-d₆) δ 9.66 (s, 1H), 8.69 (d, J=8.8 Hz, 1H), 8.26 (d, J=8.8 Hz, 1H).

Intermediate 179: 6-(3-Iodophenyl)pyrido[3,2-d]pyrimidine-4-carbonitrile

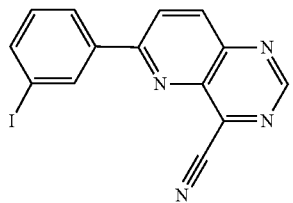 [SMILES: N#Cc1ncnc2ccc(-c3cccc(I)c3)nc12]

Step A: 6-(3-Aminophenyl)pyrido[3,2-d]pyrimidin-4-ol. 6-Chloropyrido[3,2-d]pyrimidin-4-ol (1.0 g, 6.0 mmol), 3-(4,4,5,5-tetramethyl-1,3,2-dioxaborolan-2-yl)aniline (1.2 g, 5.5 mmol) was added to a solution of K₂CO₃ (1.9 g, 14 mmol), 1,4-dioxane (60 mL), and H₂O (15 mL). The mixture was sparged with Ar for 5 min and then treated with Pd(PPh₃)₄ (0.6 g, 0.6 mmol). The mixture was sparged with Ar for another 5 min and then heated at 105° C. for 16 h. The mixture was then cooled to rt and concentrated to dryness. The resulting residue was purified by FCC (1:0 to 0:1 gradient, petroleum ether/ethyl acetate, then 1:0 to 5:1 gradient ethyl acetate:methanol) to afford 6-(3-aminophenyl)pyrido[3,2-d]pyrimidin-4-ol (670 mg, 51%) as a yellow solid. LC-MS (ESI): mass calcd. for $C_{13}H_{10}N_4O$, 238.1 m/z found 239.1 [M+H]$^+$.

Step B: 6-(3-Iodophenyl)pyrido[3,2-d]pyrimidin-4-ol. 6-(3-Aminophenyl)pyrido[3,2-d]pyrimidin-4-ol (670 mg, 2.81 mmol) and HCl (20 mL, 37 wt. %) were added to 250 mL round-bottomed flask. The resultant mixture was stirred at rt for 2 h. Then the mixture was cooled to 0° C. and treated with a solution of NaNO$_2$ (291 mg, 4.22 mmol) and H$_2$O (2 mL). The resultant mixture was stirred at 0° C. for 15 min before treating with a solution of potassium iodide (4.67 g, 28.1 mmol) and water (28 mL). The resultant mixture was stirred for 16 h with gradual warming to rt. The mixture was neutralized with NaOH (1 M in H$_2$O) and extracted with ethyl acetate (80 mL×3). The combined organic extracts were dried over anhydrous Na$_2$SO$_4$, filtered, and concentrated to dryness. The resulting residue was purified by FCC (20:1 to 0:1 gradient, petroleum ether/ethyl acetate) to afford 6-(3-iodophenyl)pyrido[3,2-d]pyrimidin-4-ol (500 mg, 51%) as a brown solid. MS (ESI): mass calcd. for $C_{13}H_8IN_3O$, 349.0; m/z found 350.0 [M+H]$^+$.

Step C: 4-Chloro-6-(3-iodophenyl)pyrido[3,2-d]pyrimidine. Oxalyl chloride (1.82 mL, 21.5 mmol) was added dropwise to a mixture of 6-(3-iodophenyl)pyrido[3,2-d]pyrimidin-4-ol (250 mg, 0.72 mmol), DMF (0.2 mL), and methylene chloride (6 mL). The resultant mixture was heated at 40° C. for 16 h. The mixture was then concentrated to dryness to afford 4-chloro-6-(3-iodophenyl)pyrido[3,2-d]pyrimidine (280 mg) as a brown solid which was used without further purification in the next step. LC-MS (ESI): mass calcd. for $C_{14}H_7IN_4$ 357.97 m/z found 359.0 [M+H]$^+$.

Step D: 6-(3-Iodophenyl)pyrido[3,2-d]pyrimidine-4-carbonitrile. Tetrabutylammonium cyanide (409 mg, 1.52 mmol) was added to a solution of 4-chloro-6-(3-iodophenyl)pyrido[3,2-d]pyrimidine (280 mg), DABCO (256 mg, 2.28 mmol), and CH$_3$CN (15 mL). The resultant mixture was stirred at rt for 2 h. The mixture was then quenched with H$_2$O (60 mL) and extracted with ethyl acetate (60 mL×3). The combined organic extracts were washed with brine, dried over anhydrous Na$_2$SO$_4$, filtered, and concentrated to dryness. The resulting residue was purified by FCC (20:1 to 0:1 gradient, petroleum ether/ethyl acetate) to afford 6-(3-iodophenyl)pyrido[3,2-d]pyrimidine-4-carbonitrile (80 mg, 28%) as a brown solid. MS (ESI): mass calcd. for $C_{14}H_7IN_4$ 358.0 m/z found 359.0 [M+H]$^+$.

Intermediate 180:
2-(3-Iodophenyl)-8-methyl-1,7-naphthyridine

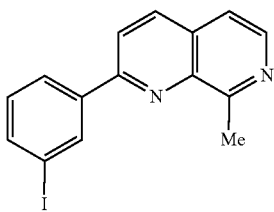 [SMILES: Cc1nccc2ccc(-c3cccc(I)c3)nc12]

Step A: (3-Amino-2-methylpyridin-4-yl)methanol. Aluminum(III) lithium hydride (0.82 g, 21.7 mmol) was added to a solution of methyl 3-amino-2-methylisonicotinate (3.00 g, 18.0 mmol) and THF (30 mL) that had been cooled to −20° C. (ethanol/dry ice). The resultant mixture was stirred at 0° C. (ice/water) for 1 h. The reaction was then quenched with ethyl acetate (20 ml) and filtered. The filter cake was washed with ethyl acetate (10 mL) and concentrated to dryness under reduced pressure to afford (3-amino-2-methylpyridin-4-yl)methanol (3.0 g) as a white solid. MS (ESI): mass calcd. for $C_7H_{10}N_2O$, 138.1; m/z. found 139.2 [M+H]$^+$.

Step B: 3-Amino-2-methylisonicotinaldehyde. 1,1,1-Tris(acetyloxy)-1,1-dihydro-1,2-benziodoxol-3-(1H)-one (Dess-Martin periodinane, 13.8 g, 32.6 mmol) was added to a solution of (3-amino-2-methylpyridin-4-yl)methanol (3.0 g, 21.7 mmol) and methylene chloride (50 mL) that had been cooled to 0° C. (ice/water). The resultant mixture was stirred at rt for 1 h. The reaction mixture was then filtered through a pad of diatomaceous earth such as, Celite®, and the pad washed with ethyl ethanol (100 mL). The filtrate was concentrated to dryness to afford 3-amino-2-methylisonicotinaldehyde (1.5 g, crude) as a yellow oil. MS (ESI): mass calcd. for $C_7H_8N_2O$, 136.1; m/z. found 137.1 [M+H]$^+$.

Step C: 2-(3-Iodophenyl)-8-methyl-1,7-naphthyridine. 1-(3-Iodophenyl)ethanone (2.71 g, 11.0 mmol) was added to a mixture of 3-amino-2-methylisonicotinaldehyde (1.5 g, 11.0 mmol, crude), potassium hydroxide (0.74 g, 13.2 mmol), and ethanol (20 mL). The resultant mixture was stirred at 70° C. for 16 h. The mixture was then concentrated to dryness. The resulting residue was purified by FCC (1:0 to 1:3 gradient, petroleum ether/ethyl ethanol) to afford 2-(3-iodophenyl)-8-methyl-1,7-naphthyridine (170 mg, 3.8%) as a yellow oil. MS (ESI): mass calcd. for $C_{15}H_{11}IN_2$ 346.0 m/z. found 347.0 [M+H]$^+$.

Intermediate 181. 6-chloro-8-methylpyrido[3,2-d]pyrimidin-4-amine

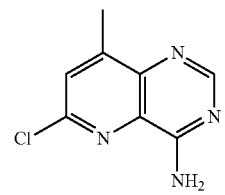

Step A: 3-Amino-4-bromo-6-chloropicolinonitrile. N-Bromosuccinimide (3.4 g, 19 mmol) was added to a solution of 3-amino-6-chloropicolinonitrile (2.7 g, 18 mmol) and DMF (50 mL). The resultant mixture was heated at 90° C. for 2 h. The mixture was then cooled to rt, treated with saturated aqueous Na$_2$SO$_3$ (100 mL) and stirred for 1 h. The resultant mixture was treated with saturated aqueous NaHCO$_3$ (100 mL) and extracted with ethyl acetate (40 mL×3). The combined organic extracts were washed with brine (10 mL), dried over anhydrous Na$_2$SO$_4$, filtered, and concentrated to dryness. The resulting residue was purified by FCC (1:0 to 1:1 gradient, petroleum ether/ethyl acetate) to afford the title compound (1.3 g, 30%) as a yellow solid. MS (ESI): mass calcd. for $C_6H_3BrClN_3$ 230.9 m/z. found 233.7 [M+H]$^+$.

Step B: 3-Amino-6-chloro-4-methylpicolinonitrile. 3-Amino-4-bromo-6-chloropicolinonitrile (1.2 g, 5.2 mmol), 2,4,6-trimethyl-1,3,5,2,4,6-trioxatriborinane (0.79 mL, 5.7 mmol), K$_2$CO$_3$ (13 mL, 26 mmol, 2.0 M in water), and 1,4-dioxane (30 mL) were added to a 100 mL round-bottomed flask. The mixture was sparged with Ar for 5 min and then treated with [1,1'-bis(diphenylphosphino)ferrocene]dichloropalladium(II), complex with dichloromethane (422 mg, 0.52 mmol). The mixture was sparged with Ar for another 5 min and the resultant mixture was heated at 80° C. for 2 h. The mixture was then cooled to rt, diluted with H$_2$O (100 mL), and extracted with ethyl acetate (60 mL×3). The combined organic extracts were washed with brine (10 mL), dried with anhydrous Na$_2$SO$_4$, filtered, and concentrated to dryness. The resulting residue was purified by FCC (5:1 to 1:1 gradient, petroleum ether/ethyl acetate) to afford 3-amino-6-chloro-4-methylpicolinonitrile (600 mg, 69%) as a yellow solid. MS (ESI): mass calcd. for C$_7$H$_6$ClN$_3$ 167.0 m/z. found 168.1 [M+H]$^+$.

Step C: 6-Chloro-8-methylpyrido[3,2-d]pyrimidin-4-amine. 3-Amino-6-chloro-4-methylpicolinonitrile (1.05 g, 6.27 mmol), formimidamide acetate (5.22 g, 50.1 mmol), K$_3$PO$_4$ (13.3 g, 62.7 mmol), and 1,4-dioxane (30 mL) were added to 100 mL round-bottomed flask. The reaction mixture was stirred at 90° C. for 2 h. The mixture was then cooled to rt, diluted with H$_2$O (100 mL), and extracted with ethyl acetate (60 mL×3). The combined organic extracts were washed with brine (10 mL), dried over anhydrous Na$_2$SO$_4$, filtered, and concentrated to dryness. The resulting residue was purified by FCC (1:0 to 1:1 gradient, petroleum ether/ethyl acetate) to afford 6-chloro-8-methylpyrido[3,2-d]pyrimidin-4-amine (1.0 g, 82%) as a yellow solid. MS (ESI): mass calcd. for C$_8$H$_7$ClN$_4$ 194.0 m/z. found 195.1 [M+H]$^+$.

Intermediate 182: (1R,4R,5S)-4-Hydroxy-2-methyl-4-((3-(4,4,5,5-tetramethyl-1,3,2-dioxaborolan-2-yl)phenyl)ethynyl)-2-azabicyclo[3.1.0]hexan-3-one

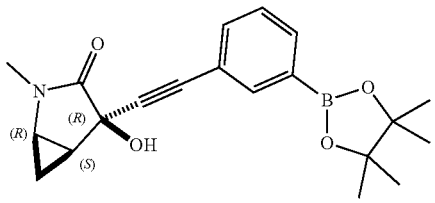

Step A: (1R,4R,5S)-4-((3-Bromophenyl)ethynyl)-4-hydroxy-2-methyl-2-azabicyclo[3.1.0]hexan-3-one. Intermediate 175 [(1R,4R,5S)-4-ethynyl-4-hydroxy-2-methyl-2-azabicyclo[3.1.0]hexan-3-one (500 mg, 3.31 mmol)], 1-bromo-3-iodobenzene (1.03 g, 3.64 mmol), triethylamine (2.20 mL, 16.6 mmol), and DMF (6 mL) were added to a 50 mL round-bottomed flask. The mixture was sparged with Ar for 5 min and then treated with Pd(PPh$_3$)$_2$Cl$_2$ (232 mg, 0.33 mmol) and CuI (126 mg, 0.66 mmol). The mixture was sparged with Ar for another 5 min and then heated at 40° C. for 16 h. The mixture was then concentrated to dryness. The resulting residue was purified by FCC (1:0 to 0:1 gradient, petroleum ether/ethyl acetate) to afford (1R,4R,5S)-4-((3-bromophenyl)ethynyl)-4-hydroxy-2-methyl-2-azabicyclo[3.1.0]hexan-3-one (800 mg, 79%) as a white solid. MS (ESI): mass calcd. for C$_{14}$H$_{12}$BrNO$_2$ 305.0 m/z. found 305.9 [M+H]$^+$.

Step B: (1R,4R,5S)-4-Hydroxy-2-methyl-4-((3-(4,4,5,5-tetramethyl-1,3,2-dioxaborolan-2-yl)phenyl)ethynyl)-2-azabicyclo[3.1.0]hexan-3-one. (1R,4R,5S)-4-((3-Bromophenyl)ethynyl)-4-hydroxy-2-methyl-2-azabicyclo[3.1.0]hexan-3-one (700 mg, 2.29 mmol), 4,4,4',4',5,5,5',5'-octamethyl-2,2'-bi(1,3,2-dioxaborolane) (1.16 g, 4.57 mmol), KOAc (673 mg, 6.86 mmol), and [1,1'-bis(diphenylphosphino)ferrocene]dichloropalladium(II) (167 mg, 0.23 mmol), and 1,4-dioxane (15 mL) were combined in a microwave tube. The resultant mixture was sparged with Ar for another 5 min and then subjected to microwave irradiation at 100° C. in for 1 h. After the reaction mixture was allowed to cool to rt, the suspension was filtered through a pad of diatomaceous earth, such as Celite® and the pad washed with ethyl acetate (50 mL×2). The filtrate was concentrated to dryness to afford (1R,4R,5S)-4-hydroxy-2-methyl-4-((3-(4,4,5,5-tetramethyl-1,3,2-dioxaborolan-2-yl)phenyl)ethynyl)-2-azabicyclo[3.1.0]hexan-3-one (2.5 g) as a black solid, which was used in the next step without further purification. MS (ESI): mass calcd. for C$_{20}$H$_{24}$BNO$_4$ 353.2 m/z. found 354.1 [M+H]$^+$.

Intermediate 183: 6-Chloro-8-(trifluoromethyl)pyrido[3,2-d]pyrimidin-4-amine

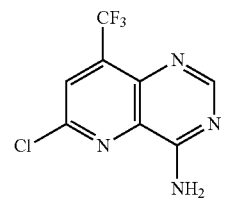 [SMILES: Nc1ncnc2c(C(F)(F)F)cc(Cl)nc12]

Step A: 3-Amino-6-chloro-4-(trifluoromethyl)picolinonitrile. A mixture of 3-amino-4-bromo-6-chloropicolinonitrile (1.00 g, 4.30 mmol), (1,10-phenanthroline)(trifluoromethyl)copper(I) (1.61 mg, 5.16 mmol), and DMF (30 mL) was sparged with Ar for 5 min, then the resultant mixture was heated at 100° C. for 16 h. The mixture was then cooled to rt, triturated with ethyl acetate (200 mL), filtered, and the filtrate concentrated to dryness. The resulting residue was purified by reverse phase preparative HPLC to afford 3-amino-6-chloro-4-(trifluoromethyl)picolinonitrile (200 mg, 20%) as a white solid. MS (ESI): mass calcd. for C$_7$H$_3$ClF$_3$N$_3$ 221.0 m/z. found 222.0 [M+H]$^+$.

Step B: 6-Chloro-8-(trifluoromethyl)pyrido[3,2-d]pyrimidin-4-amine. 3-Amino-6-chloro-4-(trifluoromethyl)picolinonitrile (200 mg, 0.90 mmol), formimidamide acetate (0.752 g, 7.22 mmol), K$_3$PO$_4$ (1.916 g, 9.027 mmol), and 1,4-dioxane (10 mL) were added to 100 mL round-bottomed flask. The mixture was heated at 90° C. for 3 h. The mixture was then cooled to rt, diluted with H$_2$O (50 mL), and extracted with ethyl acetate (50 mL×3). The combined organic extracts were dried over anhydrous Na$_2$SO$_4$, filtered, and concentrated to dryness. The resulting residue was purified by FCC (1:0 to 1:1 gradient, petroleum ether/ethyl acetate) to afford 6-chloro-8-(trifluoromethyl)pyrido[3,2-d]pyrimidin-4-amine (75 mg, 33%) as a yellow solid. MS (ESI): mass calcd. for C$_8$H$_4$ClF$_3$N$_4$ 248.0 m/z. found 249.1 [M+H]$^+$. $^1$H NMR (400 MHz, DMSO-d$_6$) δ 8.52 (s, 1H), 8.32 (br. s, 1H), 8.27 (s, 1H), 8.25 (br. s, 1H). $^{19}$F NMR (376 MHz, DMSO-d$_6$) δ −61.29 (s, 3F).

Intermediate 184: 6-Chloro-2,8-dimethylpyrido[3,2-d]pyrimidin-4-amine

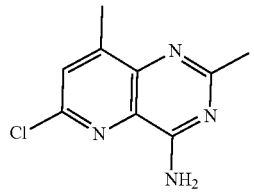

Step A: 3-Amino-6-chloro-4-methylpicolinonitrile. A solution of 3-amino-4-bromo-6-chloropicolinonitrile (600 mg, 2.58 mmol), 2,4,6-trimethyl-1,3,5,2,4,6-trioxatriborinane (0.44 mL, 3.1 mmol), $K_2CO_3$ (6.4 mL, 2.0 M in $H_2O$, 13 mmol), and 1,4-dioxane (5 mL) was sparged with Ar for 5 min. [1,1'-bis(diphenylphosphino)ferrocene]dichloropalladium(II), complex with dichloromethane (211 mg, 0.258 mmol) was added to the mixture. Then, the resultant mixture was sparged with Ar for another 5 min and the mixture was then subjected to microwave irradiation at 80° C. in for 1 h. The reaction mixture was allowed to cool to rt and concentrated to dryness. The resulting residue was purified by FCC (1:0 to 1:1 gradient, petroleum ether/ethyl acetate) to afford 3-amino-6-chloro-4-methylpicolinonitrile (226 mg, 46%) as a yellow solid. MS (ESI): mass calcd. for $C_7H_6ClN_3$ 167.0 m/z. found 167.9 $[M+H]^+$.

Step B: 6-Chloro-2,8-dimethylpyrido[3,2-d]pyrimidin-4-amine. 3-Amino-6-chloro-4-methylpicolinonitrile (310 mg, 1.85 mmol), acetimidamide hydrochloride (525 mg, 5.55 mmol), $K_3PO_4$ (2.35 g, 11.1 mmol), and THF (25 mL) were added to a 100 mL round-bottomed flask. The reaction mixture was heated at 80° C. for 12 h. The mixture was then cooled to rt and concentrated to dryness. The resulting residue was purified by FCC (1:0 to 0:1 gradient, petroleum ether/ethyl acetate) to afford 6-chloro-2,8-dimethylpyrido[3,2-d]pyrimidin-4-amine (191 mg, 45%) as a yellow solid. MS (ESI): mass calcd. for $C_9H_9ClN_4$ 208.1 m/z. found 209.1 $[M+H]^+$.

Intermediate 185: 6-Chloro-8-(methyl-d$_3$)pyrido[3,2-d]pyrimidin-4-amine

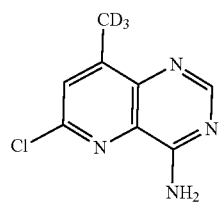 [SMILES: [2H]C([2H])([2H])c1cc(Cl)nc2c(N)ncnc12]

Step A: 8-Bromo-6-chloropyrido[3,2-d]pyrimidin-4-amine. $K_3PO_4$ (3.66 g, 17.2 mmol) was added to a solution of 3-amino-4-bromo-6-chloropicolinonitrile (1.0 g, 4.3 mmol), formamidine acetate (900 mg, 8.65 mmol), and 1,4-dioxane (12 mL). The resultant mixture was heated at 90° C. for 3 h. The mixture was then diluted with water (40 mL). The resultant suspension was filtered. The filter cake was triturated in ethyl acetate (20 mL) at 75° C. for 1 h. Then the suspension was filtered, the filter cake was washed with ethyl acetate (3 mL), and dried under reduced pressure to afford 8-bromo-6-chloropyrido[3,2-d]pyrimidin-4-amine (950 mg, 85%) as a yellow solid. $^1$H NMR (400 MHz, DMSO-d$_6$) δ 8.49 (s, 1H), 8.37 (s, 1H), 8.24 (br. s, 1H), 8.11 (br. s, 1H).

Step B: 6-Chloro-8-(methyl-d$_3$)pyrido[3,2-d]pyrimidin-4-amine. A solution of CD3MgI (6.4 mL, 6.4 mmol, 1.0 M in Et$_2$O) was added to a solution of tris(((Z)-4-oxopent-2-en-2-yl)oxy)iron (77 mg, 0.22 mmol), 8-bromo-6-chloropyrido[3,2-d]pyrimidin-4-amine (550 mg, 2.12 mmol), and THF (20 mL) that had been cooled to 0° C. (ice/water). The resultant mixture was stirred for 2.5 h with gradual warming to rt. The mixture was then washed with saturated aqueous NH$_4$Cl (20 mL) and extracted with ethyl acetate (20 mL×4). The combined organic extracts were dried over anhydrous Na$_2$SO$_4$, filtered, and concentrated to dryness. The resulting residue was purified by FCC (1:0 to 1:3 gradient, petroleum ether/ethyl acetate) to give 6-chloro-8-(methyl-d$_3$)pyrido[3,2-d]pyrimidin-4-amine (270 mg, 63%) as a yellow solid. MS (ESI): mass calcd. for $C_8H_4D_3ClN_4$ 197.1 m/z found 197.9 $[M+H]^+$. $^1$H NMR (400 MHz, DMSO-d$_6$) δ 8.45 (s, 1H), 7.97 (br. s, 1H), 7.84 (br. s, 1H), 7.78 (s, 1H).

Intermediate 186: 6-Chloro-2-fluoropyrido[3,2-d]pyrimidin-4-amine

Step A: 6-Chloropyrido[3,2-d]pyrimidine-2,4-diamine. Sodium methanolate (5.3 g, 98 mmol) and ethanol (300 mL) were added to a 500 mL round-bottomed flask. The resultant mixture was stirred at rt for 1 h. 3-Amino-6-chloropicolinonitrile (5.0 g, 33 mmol) and guanidine hydrochloride (6.2 g, 65 mmol) were added. The resultant mixture was heated at 80° C. for 4 h. The mixture was then concentrated under reduced pressure to afford a residue, which was dissolved in H$_2$O (100 mL), and extracted with ethyl acetate (60 mL×3). The combined organic extracts were washed with brine (20 mL), dried over anhydrous Na$_2$SO$_4$, filtered, and concentrated to dryness. The resulting residue was purified by FCC (1:0 to 92:8 gradient, ethyl acetate/MeOH) to afford 6-chloropyrido[3,2-d]pyrimidine-2,4-diamine (4.0 g, 53%) as a yellow solid. MS (ESI): mass calcd. for $C_7H_6ClN_5$ 195.0 m/z. found 196.1 $[M+H]^+$.

Step B: 6-Chloro-2-fluoropyrido[3,2-d]pyrimidin-4-amine. 6-Chloropyrido[3,2-d]pyrimidine-2,4-diamine (500 mg, 2.56 mmol) and HF. pyridine (7.0 mL, HF:pyridine=7:3 wt./wt.) were added to a 50 mL polytetrafluoroethylene bottle and the mixture was cooled to 0° C. (ice/water). Sodium nitrite (529 mg, 7.67 mmol) was added dropwise. The resultant mixture was stirred at rt for 1 h. The mixture was then neutralized with saturated aqueous NaHCO$_3$ to pH=7 and extracted with ethyl acetate (40 mL×3). The combined organic extracts were washed with brine (10 mL), dried over anhydrous Na$_2$SO$_4$, filtered, and concentrated to dryness. The resulting residue was purified by FCC (1:0 to 10:1 gradient, ethyl acetate/MeOH) to afford 6-chloro-2-fluoropyrido[3,2-d]pyrimidin-4-amine (50 mg, 8%) as a white solid. MS (ESI): mass calcd. for $C_7H_4ClFN_4$ 198.0 m/z. found 199.0 $[M+1]^+$. $^1$H NMR (400 MHz, DMSO-d$_6$)

δ 8.66 (br. s, 1H), 8.53 (br. s, 1H), 8.09-8.04 (m, J=8.8 Hz, 1H), 7.91-7.86 (m, J=8.8 Hz, 1H).

Intermediate 187: 6-Chloro-8-(difluoromethyl) pyrido[3,2-d]pyrimidin-4-amine

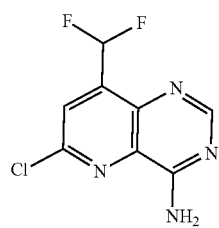 [SMILES: Nc1ncnc2c(C(F)F)cc(Cl)nc12]

Trifluoroacetic acid (123 μL, 1.66 mmol) was added to a mixture of 6-chloropyrido[3,2-d]pyrimidin-4-amine (300 mg, 1.66 mmol), zinc difluoromethanesulfinate (DFMS) (982 mg, 3.32 mmol), and dichloromethane (6 mL) at rt, then followed by slow addition of tert-butylhydroperoxide (70% solution in water, 683 μL, 4.99 mmol) with vigorous stirring. The mixture was stirred at rt for 16 h. The mixture was then concentrated to dryness. The resulting residue was purified by preparative reverse phase HPLC (Venusil ASB Phenyl 150×30 mm, 5 μm column (eluent: 30% to 60% (v/v) CH$_3$CN and H$_2$O with 0.05% HCl) to afford 6-chloro-8-(difluoromethyl)pyrido[3,2-d]pyrimidin-4-amine (50 mg, 13%) as a white solid. MS (ESI): mass calcd. for C$_8$H$_5$ClF$_2$N$_4$ 230.0 m/z. found 231.0 [M+H]$^+$. $^1$H NMR (400 MHz, CD$_3$OD) δ 8.62 (s, 1H), 8.30 (s, 1H), 7.60-7.30 (m, 1H). $^{19}$F NMR (376 MHz, CD$_3$OD) δ −119.83 (s, 2F).

Intermediate 188: (3R,4S*)-3-Ethynyl-3-hydroxy-1, 4-dimethylpyrrolidin-2-one

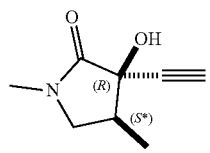

Step A: tert-Butyl 2-oxo-4-(triethylsilyl)but-3-ynoate. A suspension of CuI (0.35 g, 1.84 mmol) in THF (175 mL) and triethylamine (6.52 g, 64.4 mmol) was treated with ethynyltriethylsilane (5.20 g, 37.1 mmol) and tert-butyl 2-chloro-2-oxoacetate (10.0 g, 60.8 mmol). After stirring for 16 h at rt, water was added (50 mL), and the mixture was stirred for 20 min. The phases were then separated, and the aqueous layer was washed with ethyl acetate (50 mL). The organic layers were combined, concentrated to dryness. The resulting residue was purified by FCC (100% petroleum ether) to provide tert-Butyl 2-oxo-4-(triethylsilyl)but-3-ynoate (10.8 g) as an oil which was used directly in the next step. $^1$H NMR (300 MHz, CDCl$_3$) δ 1.57 (s, 9H), 1.04 (t, J=7.9 Hz, 9H), 0.8-0.62 (m, 6H).

Step B: tert-Butyl 2-hydroxy-2-(1-oxopropan-2-yl)-4-(triethylsilyl)but-3-ynoate. A mixture of tert-butyl 2-oxo-4-(triethylsilyl)but-3-ynoate (10 g, 37.3 mmol), THF (125 mL), and DL-proline (0.26 g, 2.26 mmol) was cooled to 0° C. and treated with propionaldehyde (8.6 g, 148 mmol). After 1 h, the mixture was warmed to 45° C. and aged for 16 h. The mixture was then cooled to rt and water (60 mL) was added. After stirring for 20 min, ethyl acetate (60 mL×3) was used to extract the mixture. The combined organic layers were concentrated to dryness and purified by reverse phase preparative HPLC (Ultimate XB-C18 10 μm, Mobile Phase A: H$_2$O+0.05% TFA; Mobile Phase B: ACN, Flow Rate: 500 mL/min, Detection UV at 210 nm & 254 nm) to afford tert-Butyl 2-hydroxy-2-(1-oxopropan-2-yl)-4-(triethylsilyl)but-3-ynoate as a mixture of diastereomers (56:44) (4.85 g, 40%) as an oil, which was not suitable for storage. $^1$H NMR (400 MHz, CDCl$_3$) δ 10.00 (s, 0.44H), 9.88 (s, 0.56H), 2.92-2.79 (m, 1H), 1.52 (s, 3.96H), 1.50 (s, 5.04H), 1.25 (d, J=7.0 Hz, 1.68H), 1.12 (d, J=7.0 Hz, 1.32H), 1.01 (m, 9H), 0. 64 (m, 6H).

Step C: 3-Hydroxy-1,4-dimethyl-3-((triethylsilyl)ethynyl)pyrrolidin-2-one. A mixture of tert-butyl 2-hydroxy-2-(1-oxopropan-2-yl)-4-(triethylsilyl)but-3-ynoate (9.0 g, 28 mmol), MeNH$_2$ (21 ml, 41 mmol, 2 N in MeOH) and 2-picoline-borane (2.9 g, 28 mmol) in methanol (45 mL) was stirred at rt for 16 h. The mixture was concentrated to dryness and purified by reverse phase preparative HPLC (Ultimate XB-C18 10 μm, Mobile Phase A: H$_2$O+0.05% TFA; Mobile Phase B: ACN, Flow Rate: 500 mL/min, Detection UV at 210 nm & 254 nm) to afford 3-hydroxy-1,4-dimethyl-3-((triethylsilyl)ethynyl)pyrrolidin-2-one as a mixture of diastereomers (1.4 g) as an oil, which was not suitable for storage. MS (ESI): mass calcd. for C$_{14}$H$_{25}$NO$_2$Si, 267.2; m/z found, 268.2 [M+H]$^+$.

Step D: 3-Ethynyl-3-hydroxy-1,4-dimethylpyrrolidin-2-one. A mixture of 3-hydroxy-1,4-dimethyl-3-((triethylsilyl)ethynyl)pyrrolidine-2-one (1.4 g, 5.2 mmol) and K$_2$CO$_3$ (1.5 g, 11 mmol) in methanol (30 mL) was stirred at rt for 16 h. The mixture was concentrated to dryness. The resulting residue was purified by FCC (0% to 50% gradient, ethyl acetate/petroleum ether) and preparative chiral SFC (Chiral Art Cellulose-SC 20 mm×250 mm, 5 μm, supercritical CO$_2$ with 30% IPA (2 mM ammonia in MeOH), detection UV at 220 nm) to provide (3R,4S*)-3-ethynyl-3-hydroxy-1,4-dimethylpyrrolidin-2-one (Intermediate 188), (3R,4R*)-3-Ethynyl-3-hydroxy-1,4-dimethylpyrrolidin-2-one (Intermediate 189), (3S,4S*)-3-ethynyl-3-hydroxy-1,4-dimethylpyrrolidin-2-one (Intermediate 190), and (3S,4R*)-3-Ethynyl-3-hydroxy-1,4-dimethylpyrrolidin-2-one (Intermediate 191). The stereochemical assignment at the 4-position (4R* or 4S*) was assigned in each isomer. (3R,4S*)-3-ethynyl-3-hydroxy-1,4-dimethylpyrrolidin-2-one (90 mg, 24%, >97% ee). MS (ESI): mass calcd. for C$_8$H$_{11}$NO$_2$, 153.1; m/z. found, 154.1 [M+H]$^+$. $^1$H NMR (300 MHz, CDCl$_3$) δ 3.42 (br s, 1H), 3.29 (dd, J=9.7, 7.6 Hz, 1H), 3.00 (t, J=9.6 Hz, 1H), 2.90 (s, 3H), 2.61 (s, 1H), 2.43 (m, 1H), 1.26 (d, J=6.8 Hz, 3H).

Intermediate 189: (3R,4R*)-3-Ethynyl-3-hydroxy-1, 4-dimethylpyrrolidin-2-one

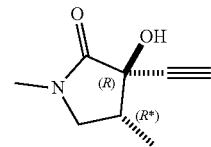

The title compound was prepared utilizing the chiral separation described in Intermediate 188 to afford (3R,4R*)-3-ethynyl-3-hydroxy-1,4-dimethylpyrrolidin-2-one (80 mg, 10%, >97% ee). MS (ESI): mass calcd. for $C_8H_{11}NO_2$, 153.1; m/z. found, 154.1 [M+H]$^+$. $^1$H NMR (300 MHz, CDCl$_3$) δ 3.51 (dd, J=9.7, 6.6 Hz, 1H), 3.15 (br s, 1H), 2.99 (dd, J=9.7, 4.9 Hz, 1H), 2.91 (s, 3H), 2.70-2.58 (m, 1H), 2.54 (s, 1H), 1.12 (d, J=7.0 Hz, 3H).

Intermediate 190: (3S,4S*)-3-Ethynyl-3-hydroxy-1,4-dimethylpyrrolidin-2-one

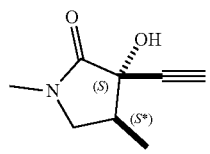

The title compound was prepared utilizing the chiral separation described in Intermediate 188 to afford (3S,4S*)-3-ethynyl-3-hydroxy-1,4-dimethylpyrrolidin-2-one (150 mg, 19%, >97% ee). MS (ESI): mass calcd. for $C_8H_{11}NO_2$, 153.1; m/z. found, 154.1 [M+H]$^+$. $^1$H NMR (300 MHz, CDCl$_3$) δ 3.51 (dd, J=9.7, 6.6 Hz, 1H), 3.15 (br s, 1H), 2.99 (dd, J=9.7, 4.9 Hz, 1H), 2.91 (s, 3H), 2.70-2.58 (m, 1H), 2.54 (s, 1H), 1.12 (d, J=7.0 Hz, 3H).

Intermediate 191: (3S,4R*)-3-Ethynyl-3-hydroxy-1,4-dimethylpyrrolidin-2-one

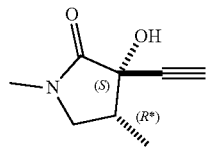

The title compound was prepared utilizing the chiral separation described in Intermediate 188 to afford (3S,4R*)-3-ethynyl-3-hydroxy-1,4-dimethylpyrrolidin-2-one (80 mg, 10%, >97% ee). MS (ESI): mass calcd. for $C_8H_{11}NO_2$, 153.1; m/z. found, 154.1 [M+H]$^+$. $^1$H NMR (300 MHz, CDCl$_3$) δ 3.42 (br s, 1H), 3.29 (dd, J=9.7, 7.6 Hz, 1H), 3.00 (t, J=9.6 Hz, 1H), 2.90 (s, 3H), 2.61 (s, 1H), 2.43 (m, 1H), 1.26 (d, J=6.8 Hz, 3H).

Intermediate 192: 3-Amino-4-bromo-6-chloropicolinonitrile

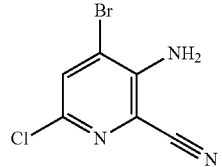 [SMILES: N#Cc1nc(Cl)cc(Br)c1N]

To a flask containing 3-amino-6-chloropyridine-2-carbonitrile (2.50 g, 16.3 mmol) was added DMF (125 ml). To this solution was added N-bromosuccinimide (3.76 g, 21.2 mmol). The resulting mixture was sealed and stirred for 90 min at 90° C. After which time, 75% of the DMF was evaporated and the remainder was stirred with aqueous sodium thiosulfate (25 mL) at rt for 25 min, then further diluted with water (50 mL) and saturated aqueous sodium bicarbonate (25 mL). The resulting mixture was then extracted with EtOAc (75 mL×5). The combined organic layers were dried over MgSO$_4$, filtered, and concentrated to dryness. The resulting residue was purified by FCC (100% DCM increasing to 50% ethyl acetate in DCM) to afford 3-amino-4-bromo-6-chloropicolinonitrile (2.8 g, 74%) as a yellow solid. MS (ESI): mass calcd. for $C_6H_3BrClN_3$, 230.9; m/z. found, 231.9 [M+H]$^+$. $^1$H NMR (400 MHz, CDCl$_3$) δ 7.60 (s, 1H), 4.93 (s, 2H).

Intermediate 193: 8-Bromo-6-chloropyrido[3,2-d]pyrimidin-4-amine

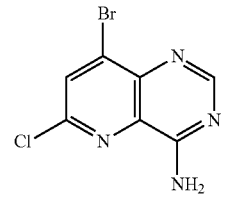 [SMILES: Nc1ncnc2c(Br)cc(Cl)nc12]

To K$_3$PO$_4$ (1.1 g, 5.2 mmol) was added to a solution of 3-amino-4-bromo-6-chloropicolinonitrile (0.3 g, 1.3 mmol) and formamidine acetate (0.3 mg, 2.6 mmol) in 1,4-dioxane (4 mL). The mixture was heated at 90° C. After 3 h, the mixture was concentrated to dryness and diluted with water (20 mL). The resulting suspension was filtered, the filter cake was isolated, and triturated in ethyl acetate (10 mL) at 75° C.

After 2 h, the suspension was filtered, and the filter cake was washed with ethyl acetate (3 mL). The resulting solid was purified by FCC (100% DCM increasing to 50% ethyl acetate in DCM) to afford 3-amino-4-bromo-6-chloropicolinonitrile (2.8 g, 74%) as a yellow solid. MS (ESI): mass calcd. for $C_7H_4BrClN_4$, 257.9; m/z. found, 258.9 [M+H]$^+$. $^1$H NMR (400 MHz, DMSO-d$_6$) δ 8.46 (s, 1H), 8.33 (s, 1H), 8.21 (br s, 1H), 8.08 (br s, 1H).

Intermediate 194: 6,8-Dichloropyrido[3,2-d]pyrimidin-4-amine

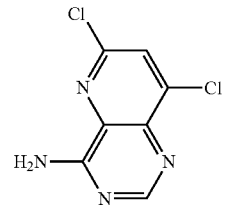 [SMILES: Nc1ncnc2c(Cl)cc(Cl)nc12]

A flask was charged with a solution of 3-amino-4,6-dichloropicolinonitrile (1.21 g, 6.34 mmol), K$_3$PO$_4$ (13.6 g, 64.0 mmol), and 1,4-dioxane (50 mL) followed by formimidamide acetate (3.87 g, 37.1 mmol). The resulting mixture was heated at 100° C. for 16 h. The resulting mixture was cooled to rt and concentrated to dryness. The residue was diluted with H$_2$O (50 mL) and stirred at rt for 16 h. The resulting mixture was filtered, the filtered cake was washed with water (200 mL), and the solid was collected. The resulting solid was added to DCM (50 mL) and the mixture was stirred at rt for 40 min. The resulting solids were collected by filtration and dried to afford 6,8-dichloropyrido[3,2-d]pyrimidin-4-amine (1.35 g, 97.5%) as a white solid. MS (ESI): mass calcd. for $C_7H_4Cl_2N_4$, 214.0; m/z. found, 215.0 [M+H]$^+$. $^1$H NMR (500 MHz, CDCl$_3$) δ 8.72 (s, 1H), 7.81 (s, 1H), 5.95-5.48 (m, 2H).

Intermediate 195: 3-Amino-6-Chloro-4-cyclopropylpicolinonitrile

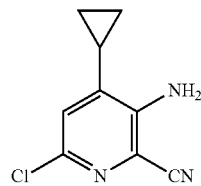 [SMILES: N#Cc1nc(Cl)cc(C2CC2)c1N]

In a 5 mL microwave vial under nitrogen, 3-amino-4-bromo-6-chloropicolinonitrile (0.15 g, 0.58 mmol) was dissolved in degassed toluene (2.90 mL) and H$_2$O (0.29 ml), and the mixture was then further sparged under nitrogen. To this solution was added potassium cyclopropyltrifluoroborate (0.13 g, 0.87 mmol), cesium carbonate (0.57 g, 1.74 mmol), and catacxium Pd G4 (CAS No. 2230788-67-5, 0.06 g, 0.09 mmol). The resulting mixture was sealed and stirred for 24 h at 95° C. under microwave irradiation. The resulting mixture was cooled to rt and was filtered over diatomaceous earth such as, Celite®, rinsed with acetone, and evaporated to dryness. The resulting residue was purified by preparative reverse phase HPLC (XBridge Prep C18 5 μm, 50×250 mm column using a 0 to 100% gradient of MeCN/20 mM NH$_4$OH in H$_2$O over 22 min. Detection, UV at λ=220-254 nM) to afford 3-amino-6-Chloro-4-cyclopropylpicolinonitrile (62 mg, 55%) as a colorless solid. MS (ESI): mass calcd. for CH$_8$ClN$_3$, 193.0; m/z. found, 194.1 [M+H]$^+$. $^1$H NMR (600 MHz, CD$_3$OD) δ 7.07 (d, J=0.9 Hz, 1H), 1.80 (ttd, J=8.4, 5.3, 0.9 Hz, 1H), 1.13-1.05 (m, 2H), 0.76-0.68 (m, 2H).

Intermediate 196: 6-Chloro-8-cyclopropylpyrido[3,2-d]pyrimidin-4-amine

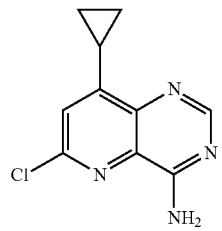 [SMILES: Nc1ncnc2c(C3CC3)cc(Cl)nc12]

In a vial under nitrogen, 3-amino-6-chloro-4-cyclopropylpicolinonitrile (0.05 g, 0.25 mmol) was dissolved in THF (2.53 ml). To this solution was added potassium phosphate tribasic (0.32 g, 1.52 mmol) and formimidamide acetate (0.08 g, 0.76 mmol). The resulting mixture was sealed and stirred for 3 h at 80° C. The resulting mixture was cooled to rt and evaporated to dryness. To the resulting residue, H$_2$O (5 mL) was added and the resulting mixture was stirred at 80° C. for 30 minutes, followed by removal from heat and a further 20 minutes of stirring at rt. The resulting solid was filtered and rinsed with H$_2$O (20 mL). The precipitate was dried under vacuum to afford 6-chloro-8-cyclopropylpyrido[3,2-d]pyrimidin-4-amine (42 mg, 75%) as a white solid. MS (ESI): mass calcd. for $C_{10}H_9ClN_4$, 220.1; m/z. found, 221.1 [M+H]$^+$. $^1$H NMR (500 MHz, CD$_3$OD) δ 8.44 (s, 1H), 7.22 (d, J=0.5 Hz, 1H), 2.91 (tt, J=8.7, 5.2 Hz, 1H), 1.36-1.23 (m, 2H), 1.04-0.97 (m, 2H).

Intermediate 197: 6-Chloro-8-(3,3,3-trifluoropropoxy)pyrido[3,2-d]pyrimidin-4-amine

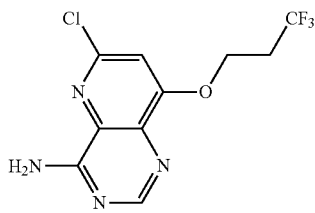 [SMILES: Nc1ncnc2c(OCCC(F)(F)F)cc(Cl)nc12]

A flask was charged with 6-chloro-8-(3,3,3-trifluoropropoxy)pyrido[3,2-d]pyrimidin-4-amine (29.5 mg, 0.15 mmol) from Step A of Example 303, 3-bromo-1,1,1-trifluoropropane (39.8 mg, 0.23 mmol), Cs$_2$CO$_3$ (147 mg, 0.45 mmol), and CH$_3$CN (1 mL). The mixture was heated at 120° C. After 2 h, the mixture was cooled to rt and concentrated to dryness. The resulting residue was purified by FCC (0 to 5% gradient, MeOH/DCM) to afford 6-chloro-8-(3,3,3-trifluoropropoxy)pyrido[3,2-d]pyrimidin-4-amine (16 mg, 36%) as a white solid. MS (ESI): mass calcd. for $C_{10}H_8CF_3N_3O$, 292.0; m/z. found, 293.1 [M+H]$^+$.

Intermediate 198. 6-Chloro-8-cyclobutylpyrido[3,2-d]pyrimidin-4-amine

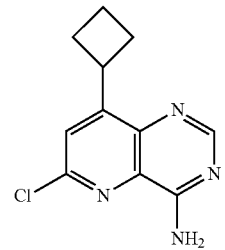 [SMILES: Nc1ncnc2c(C3CCC3)cc(Cl)nc12]

A flask was charged with 6-chloropyrido[3,2-d]pyrimidin-4-amine (1.40 g, 7.75 mmol), 1,3-dioxoisoindolin-2-yl cyclobutanecarboxylate (2.852 g, 11.63 mmol), and DMSO (25 mL). The mixture was sparged with Ar for 5 min and then treated with [4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate (435 mg, 0.39 mmol). The mixture was sparged with Ar for another 5 min, and treated with TFA (2.30 mL, 31.0 mmol). The resultant mixture was stirred via blue LED (405 nm) irradiation at 25° C. for 16 h. The mixture was then poured into H$_2$O (100 mL) and stirred at rt for 0.5 h. The suspension was filtered, and the filtrate cake washed with H$_2$O (50 mL). The filtrate was neutralized with saturated aqueous NaHCO$_3$ to pH=7-8. The resulting precipitate was collected by filtration and purified by preparative reverse phase HPLC (Welch Xtimate C18 100×40 mm, 3 μm column (eluent: 8% to 30%

(v/v) CH₃CN and H₂O with 0.075% TFA) to afford 6-chloro-8-cyclobutylpyrido[3,2-d]pyrimidin-4-amine (130 mg, 4.8%) as a white solid. ¹H NMR (400 MHz, DMSO-d₆) δ 8.92-8.57 (m, 2H), 8.51 (s, 1H), 7.83 (s, 1H), 4.23-4.04 (m, 1H), 2.41-2.32 (m, 2H), 2.28-2.12 (m, 2H), 2.11-1.95 (m, 1H), 1.88-1.71 (m, 1H).

Intermediate 199: 6-Chloro-8-phenylpyrido[3,2-d]pyrimidin-4-amine as a trifluoroacetic acid salt

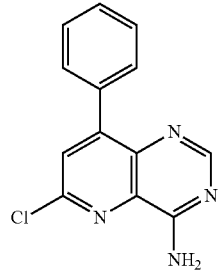 [SMILES: Nc1ncnc2c(-c3ccccc3)cc(Cl)nc12]

In a vial under nitrogen, 8-bromo-6-chloropyrido[3,2-d]pyrimidin-4-amine (0.04 g, 0.11 mmol) was dissolved in degassed THF (3.08 mL) and H₂O (0.15 mL). The resulting mixture was further sparged under nitrogen. To this solution was added cesium carbonate (0.150 g, 0.031 mmol), potassium phenyltirfluoroborate (0.04 g, 0.23 mmol), palladium (II) acetate (3.00 mg, 0.02 mmol), and triphenylphosphine (8.00 mg, 0.03 mmol). The resulting mixture was sealed and stirred for 40 h at 80° C. The resulting mixture was cooled to rt and was filtered over diatomaceous earth such as, Celite®, rinsed with acetone, and evaporated to dryness. The resulting residue was purified by preparative reverse phase HPLC (Welch Xtimate C18 10 μm, 250×50 mm; mobile phase: [water (0.1% TFA)-ACN]; B %: 10%-60%, 20 min, 100% 5 min. Detection, UV at λ=220-254 nM) to afford 6-chloro-8-phenylpyrido[3,2-d]pyrimidin-4-amine as a trifluoroacetic acid salt (50 mg, 82%) as a light orange solid. MS (ESI): mass calcd. for C₁₃H₉ClN₄, 256.1; m/z. found, 257.1 [M+H]⁺. ¹H NMR (500 MHz, CD₃OD) δ 8.52 (s, 1H), 8.00 (s, 1H), 7.67-7.61 (m, 5H).

Intermediate 200: 6-Chloro-8-(thiophen-2-yl)pyrido[3,2-d]pyrimidin-4-amine as a Trifluoroacetic Acid Salt

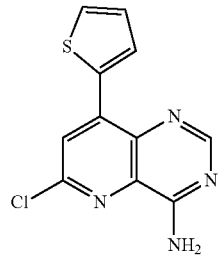 [SMILES: Nc1ncnc2c(-c3cccs3)cc(Cl)nc12]

6-Chloro-8-(thiophen-2-yl)pyrido[3,2-d]pyrimidin-4-amine was prepared with analogous conditions described in Intermediate 199 using thiophene-2-boronic acid and purified by preparative reverse phase HPLC (Welch Xtimate C18 250×50 mm, 10 μm; mobile phase: [water (0.1% TFA)-ACN]; B %: 10%-60%, 20 min, 100% 5 min. Detection, UV at λ=220-254 nM) to afford 6-chloro-8-(thiophen-2-yl)pyrido[3,2-d]pyrimidin-4-amine as a trifluoroacetic acid salt (30 mg, 69%) as a white solid. MS (ESI): mass calcd. for C₁₁H₇ClN₄S, 262.0; m/z. found, 263.0 [M+H]⁺. ¹H NMR (500 MHz, CD₃OD) δ 8.52 (s, 1H), 8.25-8.21 (m, 1H), 8.10-8.07 (m, 1H), 7.86-7.81 (m, 1H), 7.26 (ddd, J=4.8, 3.8, 0.8 Hz, 1H).

Intermediate 201: 6-Chloro-8-(furan-2-yl)pyrido[3,2-d]pyrimidin-4-amine as a Trifluoroacetic Acid Salt

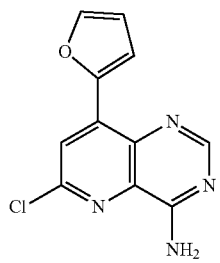 [SMILES: Nc1ncnc2c(-c3ccco3)cc(Cl)nc12]

6-Chloro-8-(furan-2-yl)pyrido[3,2-d]pyrimidin-4-amine was prepared with analogous conditions described in Intermediate 199 using furan-2-boronic acid and isolated using preparative HPLC (Welch Xtimate C18 250×50 mm, 10 μm; mobile phase: [water (0.1% TFA)-ACN]; B %: 10%-60%, 20 min, 100% 5 min. Detection, UV at λ=220-254 nM) to afford 6-chloro-8-(furan-2-yl)pyrido[3,2-d]pyrimidin-4-amine as a trifluoroacetic acid salt (18 mg, 43%) as white solid. MS (ESI): mass calcd. for C₁₁H₇ClN₄O, 246.0; m/z. found, 247.1 [M+H]⁺. ¹H NMR (500 MHz, CD₃OD) δ 8.55 (s, 1H), 8.22-8.18 (m, 1H), 7.94-7.91 (m, 1H), 7.90-7.87 (m, 1H), 6.76 (dt, J=3.6, 1.9 Hz, 1H).

Intermediate 202: tert-Butyl 2-(4-amino-6-(3-(((R)-3-hydroxy-1-methyl-2-oxopyrrolidin-3-yl)ethynyl)phenyl)pyrido[3,2-d]pyrimidin-8-yl-2-d)azetidine-1-carboxylate

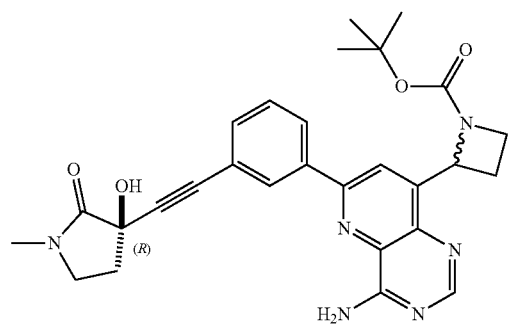

The title compound was prepared with analogous conditions described in Example 308 utilizing 1-(tert-butyl) 2-(1,3-dioxoisoindolin-2-yl) azetidine-1,2-dicarboxylate to afford tert-butyl 2-(4-amino-6-(3-(((R)-3-hydroxy-1-methyl-2-oxopyrrolidin-3-yl)ethynyl)phenyl)pyrido[3,2-d]pyrimidin-8-yl-2-d)azetidine-1-carboxylate as a mixture diastereomers (115 mg, 22%) as a white solid. MS (ESI):

mass calcd. for $C_{28}H_{30}N_6O_4$, 515.2; m/z. found, 516.2 [M+H]+. $^1$H NMR (500 MHz, CD$_3$OD) δ 8.46 (s, 1H), 8.44 (s, 1H), 8.30 (d, J=7.9 Hz, 1H), 7.62 (dt, J=7.7, 1.4 Hz, 1H), 7.56 (t, J=7.8 Hz, 1H), 5.91-5.83 (m, 1H), 4.18 (q, J=8.3 Hz, 1H), 4.14-4.06 (m, 1H), 3.50 (dd, J=7.4, 5.6 Hz, 2H), 2.95 (d, J=1.0 Hz, 3H), 2.93-2.90 (m, 1H), 2.61 (dt, J=13.1, 5.6 Hz, 1H), 2.35 (dt, J=13.0, 7.3 Hz, 1H), 2.25 (ddt, J=11.5, 9.3, 6.9 Hz, 1H), 1.50-1.36 (m, 9H).

Intermediate 203: 6-Chloro-8-vinylpyrido[3,2-d]pyrimidin-4-amine

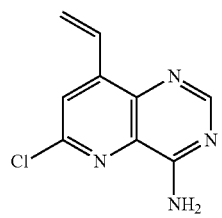

The title compound was prepared with analogous conditions described in Intermediate 199 using potassium vinyltrifluoroborate to afford 6-chloro-8-vinylpyrido[3,2-d]pyrimidin-4-amine (24 mg, 60%) as a white solid. MS (ESI): mass calcd. for $C_9H_7ClN_4$, 206.0; m/z. found, 207.1 [M+H]+. $^1$H NMR (500 MHz, CD$_3$OD) δ 8.43 (d, J=1.2 Hz, 1H), 7.96 (d, J=1.2 Hz, 1H), 7.60 (dd, J=17.8, 11.2 Hz, 1H), 6.31 (d, J=17.8 Hz, 1H), 5.76 (d, J=11.2 Hz, 1H).

Intermediate 204: 2-(3-Iodophenyl)-5-(trifluoromethyl)pyrido[3,4-d]pyrimidin-8-amine

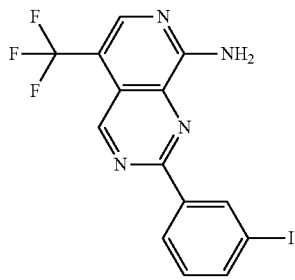 [SMILES: Nc1ncc(C(F)(F)F)c2cnc(-c3cccc(I)c3)nc12]

Step A: 2-Methoxy-3-nitro-5-(trifluoromethyl)pyridine. Sodium methoxide (2.24 g, 13.2 mmol, 32% in MeOH solution) was added to a solution of 2-chloro-3-nitro-5-(trifluoromethyl)pyridine (2.00 g, 8.23 mmol) and MeOH (20 mL) that had been cooled to 0° C. (ice/water). The resultant mixture was stirred at 0° C.-5° C. for 10 min before pouring into ice and extracting with ethyl acetate (35 mL×2). The combined organic extracts were washed with brine (15 mL), dried over anhydrous MgSO$_4$, filtered, and concentrated to dryness to afford 2-methoxy-3-nitro-5-(trifluoromethyl)pyridine (1.9 g, 97%) as a pale-yellow oil. $^1$H NMR (400 MHz, CDCl$_3$) δ 8.71-8.68 (m, 1H), 8.54-8.51 (m, 1H), 4.21 (s, 3H).

Step B: 2-Methoxy-5-(trifluoromethyl)pyridin-3-amine. A flask was charged with 2-methoxy-3-nitro-5-(trifluoromethyl)pyridine (3.8 g, 17 mmol), MeOH (30 mL), and wet Pd/C (400 mg, 0.19 mmol, 5 wt. %). The resultant mixture was stirred at rt under H$_2$ atmosphere (15 psi, balloon). After 1 h, the mixture was filtered through a pad of Celite® and the filtrate was concentrated to dryness to afford 2-methoxy-5-(trifluoromethyl)pyridin-3-amine (3.0 g, 91%) as a pale-yellow oil. $^1$H NMR (400 MHz, DMSO-d$_6$) δ 7.70 (s, 1H), 7.06 (d, J=2.0 Hz, 1H), 5.49 (s, 2H), 3.93 (s, 3H).

Step C: tert-Butyl (2-methoxy-5-(trifluoromethyl)pyridin-3-yl)carbamate. Sodium bis(trimethylsilyl)amide (32.0 mL, 1 M in THF, 32.0 mmol) was added drop-wise under a nitrogen atmosphere to a solution of 2-methoxy-5-(trifluoromethyl)pyridin-3-amine (3.00 g, 15.6 mmol) and anhydrous THF (40 mL) that had been cooled to 0° C. (ice/water). The resultant mixture was stirred for 20 min at rt before adding a drop-wise solution of (Boc)$_2$O (3.75 g, 17.2 mmol) and anhydrous THF (10 mL). The resultant mixture was stirred at rt for 3 h. After which time saturated aqueous NH$_4$Cl (100 mL) was added to the mixture and extracted with ethyl acetate (50 mL×3). The combined organic extracts were washed with saturated aqueous NH$_4$Cl (50 mL), brine (50 mL), dried over anhydrous MgSO$_4$, filtered, and concentrated to dryness. The resulting residue was purified by FCC (15:1, petroleum ether/ethyl acetate) to afford tert-butyl (2-methoxy-5-(trifluoromethyl)pyridin-3-yl)carbamate (3.9 g, 85%) as a yellow oil. $^1$H NMR (400 MHz, DMSO-d$_6$) δ 8.74 (s, 1H), 8.33 (br. s., 1H), 8.23 (s, 1H), 3.97 (s, 3H), 1.47 (s, 9H).

Step D: tert-Butyl (4-formyl-2-methoxy-5-(trifluoromethyl)pyridin-3-yl)carbamate. To a flask under an atmosphere of nitrogen containing tert-butyl (2-methoxy-5-(trifluoromethyl)pyridin-3-yl)carbamate (3.8 g, 13 mmol), TMEDA (4.3 mL, 29 mmol), and anhydrous THF (35 mL) was added n-BuLi (11 mL, 29 mmol, 2.5 M in THF) drop-wise. The resultant mixture was stirred at −10° C. for 2 h and then cooled to −78° C. before treating with a drop-wise solution of DMF (2.85 g, 39.0 mmol) and anhydrous THF (5 mL). The resultant mixture was stirred at −78° C. for 3 h and then stirred for 14 h with gradual warming to rt before pouring into saturated aqueous NH$_4$Cl (100 mL). The mixture was extracted with ethyl acetate (45 mL×2). The combined organic extracts were washed with saturated aqueous NH$_4$Cl (50 mL×2), brine (50 mL), dried over anhydrous MgSO$_4$, filtered, and concentrated to dryness. The resulting residue was purified by FCC (15:1 to 8:1 gradient, petroleum ether/ethyl acetate) to afford an impure product that was triturated with petroleum ether (5 mL) and MTBE (5 mL). The resulting solid was collected by filtration, the filter cake was washed with a solution of petroleum ether and MTBE (1:1, 5 mL) to afford tert-butyl (4-formyl-2-methoxy-5-(trifluoromethyl)pyridin-3-yl)carbamate (2.0 g, 48%) as a yellow solid. LC-MS (ESI): mass calcd. For $C_{13}H_{15}F_3N_2O_4$ 320.10 m/z. found 321.1 [M+H]+. $^1$H NMR (400 MHz, DMSO-d$_6$) δ 10.07-10.00 (m, 1H), 9.38 (s, 1H), 8.50 (s, 1H), 4.01 (s, 3H), 1.42 (s, 9H).

Step E: 3-Amino-2-methoxy-5-(trifluoromethyl)isonicotinaldehyde. A solution of TFA (2.00 mL, 27.4 mmol) and anhydrous DCM (5 mL) was added slowly to a solution of tert-butyl (4-formyl-2-methoxy-5-(trifluoromethyl)pyridin-3-yl)carbamate (1.00 g, 3.12 mmol) and anhydrous dichloromethane (15 mL) that had been cooled to 0° C. The resultant mixture was stirred at 0° C. for 30 min before neutralizing to pH=7 with saturated aqueous NaHCO$_3$ and extracting with DCM (35 mL×3). The combined organic extracts were washed with saturated aqueous NaHCO$_3$ (15 mL), brine (15 mL), dried over MgSO$_4$, filtered, and concentrated to dryness. The resulting residue was purified by FCC (15:1, petroleum ether/ethyl acetate) to afford 3-amino- 2-methoxy-5-(trifluoromethyl)isonicotinaldehyde (600 mg, 87%) as a pale yellow solid. LC-MS (ESI): mass calcd. For $C_8H_7F_3N_2O_2$ 220.05 m/z. found 220.7 [M+H]$^+$.

Step F: 2-(3-Iodophenyl)-8-methoxy-5-(trifluoromethyl) pyrido[3,4-d]pyrimidine. 3-Amino-2-methoxy-5-(trifluoromethyl)isonicotinaldehyde (600 mg, 2.72 mmol), 3-iodobenzylamine (1.91 g, 8.18 mmol), 4-hydroxy-2,2,6,6-tetramethylpiperidin-1-oxyl (117 mg, 0.68 mmol), and o-xylene (10 mL) were added to a flask. The resultant mixture was heated at 120° C. for 15 h under O2 atmosphere (15 psi) before cooling to rt. The resulting suspension was filtered through a pad of Celite® and the filtrate concentrated to dryness under reduced pressure. The resulting residue was purified by FCC (15:1, petroleum ether:ethyl acetate) to afford 2-(3-iodophenyl)-8-methoxy-5-(trifluoromethyl)pyrido[3,4-d]pyrimidine (720 mg, 61%) as a pale yellow solid. $^1$H NMR (400 MHz, DMSO-d$_6$) δ 9.78-9.72 (m, 1H), 8.84-8.79 (m, 1H), 8.66 (s, 1H), 8.52 (d, J=8.0 Hz, 1H), 7.98 (d, J=7.6 Hz, 1H), 7.46-7.40 (m, 1H), 4.23 (s, 3H).

Step G: 8-Chloro-2-(3-iodophenyl)-5-(trifluoromethyl)pyrido[3,4-d]pyrimidine. A flask was charged with 2-(3-iodophenyl)-8-methoxy-5-(trifluoromethyl)pyrido[3,4-d]pyrimidine (1.00 g, 2.32 mmol) and POCl$_3$ (15.0 mL, 163 mmol). The mixture was heated at 115° C. After 5 h, the mixture was cooled to rt and poured into H$_2$O (100 mL) and the pH was adjusted to 7-8 with solid K$_2$CO$_3$. The mixture was extracted with ethyl acetate (50 mL×3). The combined organic extracts were washed with saturated aqueous NaHCO$_3$ (30 mL), brine (30 mL), dried over MgSO$_4$, filtered, and concentrated to dryness. The resulting residue was purified by FCC (1:0 to 15:1 gradient, petroleum ether/ethyl acetate) to afford an impure 8-chloro-2-(3-iodophenyl)-5-(trifluoromethyl)pyrido[3,4-d]pyrimidine (520 mg) as a white solid which was used in the next step without further purification. LC-MS (ESI): mass calcd. for $C_{14}H_6ClF_3IN_3$ 434.92 m/z. found 436.0 [M+H]$^+$.

Step H: 2-(3-Iodophenyl)-5-(trifluoromethyl)pyrido[3,4-d]pyrimidin-8-amine. A flask was charged with 8-chloro-2-(3-iodophenyl)-5-(trifluoromethyl)pyrido[3,4-d]pyrimidine (420 mg, 0.423 mmol, 43.9% purity), NH$_3$·H$_2$O (10 mL, 25% purity), and 1,4-dioxane (10 mL). The mixture was heated at 120° C. After 10 h, the mixture was cooled to rt. This procedure was repeated and the combined mixtures were poured into H$_2$O (10 mL) and extracted with ethyl acetate (30 mL). The aqueous layer was extracted with ethyl acetate (15 mL×2). The combined organic extracts were washed with brine (10 mL), dried over MgSO$_4$, filtered, and concentrated to dryness. The residue was triturated with a solution of petroleum ether and ethyl acetate (3:1, 10 mL). The resulting solid was isolated by filtration, the filter cake was washed with a solution petroleum ether:ethyl acetate (3:1, 5 mL), and dried under reduced pressure to afford 2-(3-iodophenyl)-5-(trifluoromethyl)pyrido[3,4-d]pyrimidin-8-amine (240 mg, 99%) as a pale yellow solid. $^1$H NMR (400 MHz, DMSO-d$_6$) δ 9.57-9.47 (m, 1H), 9.13-9.04 (m, 1H), 8.72 (d, J=8.0 Hz, 1H), 8.53 (br. s., 1H), 8.34 (s, 1H), 8.29 (br. s., 1H), 7.94 (d, J=8.0 Hz, 1H), 7.42-7.33 (m, 1H).

Example 1: (R)-3-[2-[3-(8-Aminopyrido[3,4-d]pyrimidin-2-yl)phenyl]ethynyl]-3-hydroxy-1-methyl-pyrrolidin-2-one

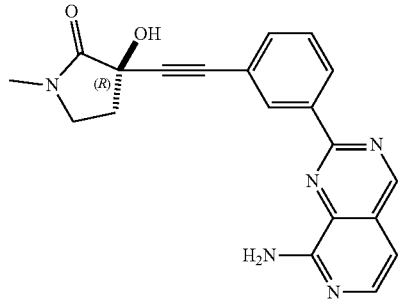

A 500 mL round-bottomed flask under nitrogen was charged with a stir bar, 2-(3-iodophenyl)pyrido[3,4-d]pyrimidin-8-amine (15 g, 43 mmol), Pd(PPh$_3$)$_2$Cl$_2$ (3.0 g, 4.3 mmol), CuI (0.9 g, 4.3 mmol), DIPEA (11 g, 85 mol), (R)-3-ethynyl-3-hydroxy-1-methylpyrrolidin-2-one (14 g, 99 mmol), and THF (300 mL). The resultant mixture was stirred at 60° C. for 2 h before cooling to 20° C. The product was isolated by filtration then purified by FCC to afford (R)-3-[2-[3-(8-aminopyrido[3,4-d]pyrimidin-2-yl)phenyl]ethynyl]-3-hydroxy-1-methyl-pyrrolidin-2-one (9.0 g, 58%) as light yellow solid. MS (ESI): mass calcd. for $C_{20}H_{17}N_5O_2$, 359.14; m/z. found, 360.1 [M+H]$^+$. $^1$H NMR (400 MHz, DMSO-d$_6$) δ 9.53 (s, 1H), 8.76-8.71 (m, 1H), 8.70-8.67 (m, 1H), 8.02 (d, J=5.6 Hz, 1H), 7.62-7.53 (m, 2H), 7.45 (s, 2H), 7.04 (d, J=5.6 Hz, 1H), 6.50 (s, 1H), 3.42-3.36 (m, 2H), 2.83 (s, 3H), 2.50-2.44 (m, 1H), 2.28-2.17 (m, 1H).

Example 2: (S)-3-[2-[3-(8-Aminopyrido[3,4-d]pyrimidin-2-yl)phenyl]ethynyl]-3-hydroxy-1-methyl-pyrrolidin-2-one

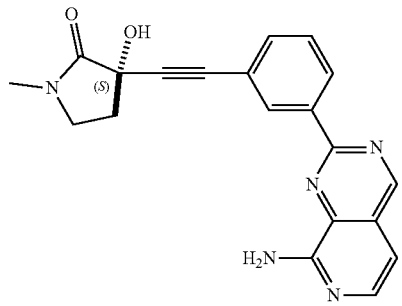

The title compound was prepared with analogous conditions described in Example 1 using 2-(3-iodophenyl)pyrido[3,4-d]pyrimidin-8-amine and (S)-3-ethynyl-3-hydroxy-1-methylpyrrolidin-2-one to afford (S)-3-[2-[3-(8-aminopyrido[3,4-d]pyrimidin-2-yl)phenyl]ethynyl]-3-hydroxy-1-methyl-pyrrolidin-2-one. MS (ESI): mass calcd. for $C_{20}H_{17}N_5O_2$, 359.14; m/z. found, 360.1 [M+H]$^+$. $^1$H NMR (400 MHz, DMSO-d$_6$) δ 9.53 (s, 1H), 8.76-8.71 (m, 1H), 8.70-8.67 (m, 1H), 8.02 (d, J=5.6 Hz, 1H), 7.62-7.53 (m, 2H), 7.45 (s, 2H), 7.04 (d, J=5.6 Hz, 1H), 6.50 (s, 1H), 3.42-3.36 (m, 2H), 2.83 (s, 3H), 2.50-2.44 (m, 1H), 2.28-2.17 (m, 1H).

Example 3: (R)-3-[2-[3-(4-Aminopyrido[3,2-d]pyrimidin-6-yl)-4-methyl-phenyl]ethynyl]-3-hydroxy-1-methyl-pyrrolidin-2-one

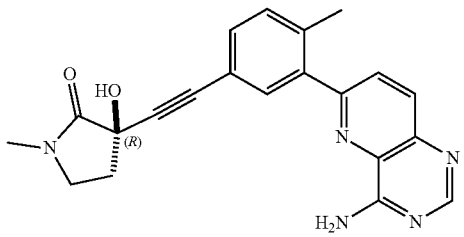

A 20 mL microwave vial was charged with 6-chloropyrido[3,2-d]pyrimidin-4-amine (75.0 mg, 0.42 mmol), (R)-3-hydroxy-1-methyl-3-((4-methyl-3-(4,4,5,5-tetramethyl-1,3,2-dioxaborolan-2-yl)phenyl)ethynyl)pyrrolidin-2-one (148 mg, 0.42 mmol), $K_3PO_4$ (264 mg, 1.24 mmol), 1,4-dioxane (5 mL), and $H_2O$ (1 mL). The resulting mixture was sparged with argon for 5 min and then treated with [1,1'-bis(di-tert-butylphosphino)ferrocene]dichloropalladium(II) ($PdCl_2$(dtbpf)) (27.0 mg, 0.04 mmol). The mixture was sparged with argon for another 5 min and the resultant mixture was subjected to microwave irradiation at 85° C. for 1 h before it was cooled to rt. The resulting mixture was poured into water (30 mL) and extracted with ethyl acetate (30 mL×3). The combined organic extracts were dried over anhydrous $Na_2SO_4$, filtered, and concentrated to dryness. The resulting residue was purified sequentially by FCC (DCM:MeOH gradient=50:1 to 10:1) and preparative SFC (DAICEL CHIRALCEL OD 10 μm, 250 mm×30 mm, eluent: 45% to 45% (v/v) supercritical $CO_2$ in EtOH and $H_2O$ with 0.1% $NH_3$. Detection, UV at λ=220-254 nM) to afford (R)-3-((3-(4-aminopyrido[3,2-d]pyrimidin-6-yl)-4-methylphenyl)ethynyl)-3-hydroxy-1-methylpyrrolidin-2-one (23.6 mg, 15%) as a pale yellow solid. MS (ESI): mass calcd. for $C_{21}H_{19}N_5O_2$, 373.15; m/z. found, 373.9 [M+H]$^+$. $^1$H NMR (400 MHz, $CDCl_3$) δ 8.66 (s, 1H), 8.48 (s, 1H), 8.07 (s, 1H), 8.03 (d, J=8.7 Hz, 1H), 7.31 (d, J=8.7 Hz, 1H), 7.29-7.26 (m, 1H), 7.16 (d, J=7.9 Hz, 1H), 7.00 (s, 1H), 6.51 (d, J=1.7 Hz, 1H), 3.55-3.45 (m, 2H), 2.98 (s, 3H), 2.69-2.58 (m, 1H), 2.51-2.39 (m, 1H), 2.31 (s, 3H).

Example 4: (R)-3-((3-(8-Amino-4-methylpyrimido[5,4-d]pyrimidin-2-yl)phenyl)ethynyl)-3-hydroxy-1-methylpyrrolidin-2-one

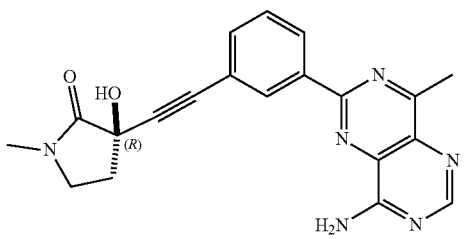

In a 20 mL microwave vial under nitrogen, 6-chloro-8-methylpyrimido[5,4-d]pyrimidin-4-amine (0.30 g, 1.53 mmol), (R)-3-hydroxy-1-methyl-3-((3-(4,4,5,5-tetramethyl-1,3,2-dioxaborolan-2-yl)phenyl)ethynyl)pyrrolidin-2-one (0.65 g, 1.92 mmol), mesylate[(di(1-adamantyl)-n-butylphosphine)-2-(2'-amino-1,1'-biphenyl)]palladium(II) (cataCXium® A Pd G3) (0.17 g, 0.23 mmol), and $NaHCO_3$ (0.52 g, 6.14 mmol) were suspended in degassed $H_2O$ (6.14 ml), degassed toluene (10.2 mL), and degassed EtOH (5.11 mL). The resulting mixture was stirred for 5 min at rt and then irradiated in a microwave reactor for 30 min at 120° C. The resulting mixture was cooled to rt and was partitioned between ethyl acetate (25 mL) and water (25 mL). The organic layer was separated, and the aqueous layer was extracted with ethyl acetate (2×20 mL). The combined organic extracts were washed with brine (25 mL), dried over $Na_2SO_4$, filtered, and concentrated to dryness. The resulting residue was sequentially purified by FCC (100% ethyl acetate, over 7 min; 0-20% MeOH/DCM over 10 min) and then preparative HPLC (Waters XBridge Prep C18 OBD 5 μm, 50×250 mm; Gradient, 90:10 to 0:100 water:$CH_3CN$ over 25 min; Flow rate, 113 mL/min; Detection, UV at λ=220-254 nM) to afford (R)-3-((3-(8-amino-4-methylpyrimido[5,4-d]pyrimidin-2-yl)phenyl)ethynyl)-3-hydroxy-1-methylpyrrolidin-2-one (266 mg, 46%) as a white solid. MS (ESI): mass calcd. for $C_{20}H_{18}N_6O_2$, 374.15; m/z. found, 375.1 [M+H]$^+$. $^1$H NMR (500 MHz, DMSO-$d_6$) δ 8.66-8.60 (m, 1H), 8.60 (s, 1H), 8.43 (s, 1H), 8.39 (s, 1H), 8.18 (s, 1H), 7.56-7.41 (m, 2H), 6.42 (s, 1H), 3.34-3.28 (m, 2H), 2.81 (s, 3H), 2.75 (s, 3H), 2.42-2.34 (m, 1H), 2.19-2.05 (m, 1H).

Example 5: (S)-3-((3-(8-Amino-4-methylpyrimido[5,4-d]pyrimidin-2-yl)phenyl)ethynyl)-3-hydroxy-1-methylpyrrolidin-2-one

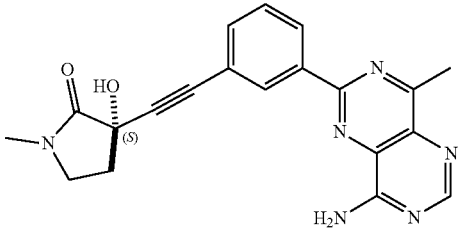

The title compound (24 mg, 9%) was prepared with analogous conditions described in Example 4 using 6-chloro-8-methylpyrimido[5,4-d]pyrimidin-4-amine and (S)-3-hydroxy-1-methyl-3-((3-(4,4,5,5-tetramethyl-1,3,2-dioxaborolan-2-yl)phenyl)ethynyl)pyrrolidin-2-one. MS (ESI): mass calcd. for $C_{20}H_{18}N_6O_2$, 374.15; m/z found, 375.1 [M+H]$^+$. $^1$H NMR (500 MHz, DMSO-$d_6$) δ 8.66-8.60 (m, 1H), 8.60 (s, 1H), 8.43 (s, 1H), 8.39 (s, 1H), 8.18 (s, 1H), 7.56-7.41 (m, 2H), 6.42 (s, 1H), 3.34-3.28 (m, 2H), 2.81 (s, 3H), 2.75 (s, 3H), 2.42-2.34 (m, 1H), 2.19-2.05 (m, 1H).

Example 6: (R)-3-((3-(4-Amino-2-methylpyrido[3,2-d]pyrimidin-6-yl)phenyl)ethynyl)-3-hydroxy-1-methylpyrrolidin-2-one

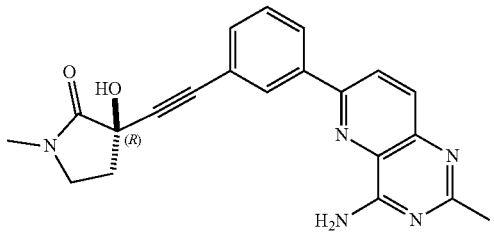

A 50 mL round-bottomed flask containing 6-chloro-2-methylpyrido[3,2-d]pyrimidin-4-amine (460 mg, 2.36 mmol), (R)-3-hydroxy-1-methyl-3-((3-(4,4,5,5-tetramethyl-1,3,2-dioxaborolan-2-yl)phenyl)ethynyl)pyrrolidin-2-one (920 mg, 2.70 mmol), and Pd(PPh$_3$)$_4$ (260 mg, 0.22 mmol) was charged with 1,4-dioxane (35 mL) and K$_2$CO$_3$ (5 mL, 2M in H$_2$O) which were degassed together with nitrogen for 20 min prior to use. The flask containing the resulting mixture was fitted with a reflux condenser and evacuated/purged with nitrogen 3 times before heating at 95° C. After 1.75 h, the contents were cooled to rt, filtered through a pad of diatomaceous earth, such as Celite®, and the pad was washed with THF (25 mL) and ethyl acetate (25 mL). The filtrate was concentrated onto diatomaceous earth, such as Celite©, (5 g) and purified by FCC (100% DCM increasing to 10% MeOH-DCM) to provide a yellow solid which was recrystallized from MeOH and dried to afford (R)-3-((3-(4-amino-2-methylpyrido[3,2-d]pyrimidin-6-yl)phenyl)ethynyl)-3-hydroxy-1-methylpyrrolidin-2-one (620 mg, 70%) as an off-white solid. MS (ESI): mass calcd. for C$_{21}$H$_{19}$N$_5$O$_2$, 373.15; m/z. found, 374.2 [M+H]$^+$. $^1$H NMR (400 MHz, CD$_3$OD) δ 8.37 (br s, 1H), 8.31 (d, J=8.9 Hz, 1H), 8.22-8.30 (m, 1H), 8.04 (d, J=8.8 Hz, 1H), 7.58-7.44 (m, 2H), 3.56-3.41 (m, 2H), 2.94 (s, 3H), 2.64-2.58 (m, 1H), 2.55 (s, 3H), 2.40-2.27 (m, 1H).

Example 7: (S)-3-((3-(4-Amino-2-methylpyrido[3,2-d]pyrimidin-6-yl)phenyl)ethynyl)-3-hydroxy-1-methylpyrrolidin-2-one

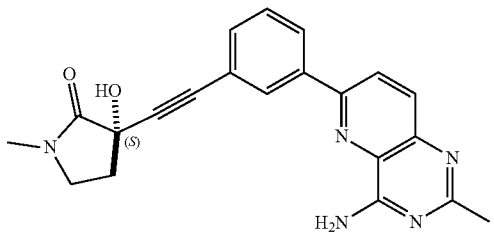

The title compound (88 mg, 85%) was prepared using analogous conditions described in Example 6 using (S)-3-hydroxy-1-methyl-3-((3-(4,4,5,5-tetramethyl-1,3,2-dioxaborolan-2-yl)phenyl)ethynyl)pyrrolidin-2-one. MS (ESI): mass calcd. for C$_{21}$H$_{19}$N$_5$O$_2$, 373.15; m/z. found, 374.2 [M+H]$^+$. $^1$H NMR (400 MHz, CD$_3$OD) δ 8.37 (br s, 1H), 8.31 (d, J=8.9 Hz, 1H), 8.22-8.30 (m, 1H), 8.04 (d, J=8.8 Hz, 1H), 7.58-7.44 (m, 2H), 3.56-3.41 (m, 2H), 2.94 (s, 3H), 2.64-2.58 (m, 1H), 2.55 (s, 3H), 2.40-2.27 (m, 1H).

Example 8: (R)-3-((3-(4-Aminopyrido[3,2-d]pyrimidin-6-yl-2-d)phenyl)ethynyl)-3-hydroxy-1-methylpyrrolidin-2-one

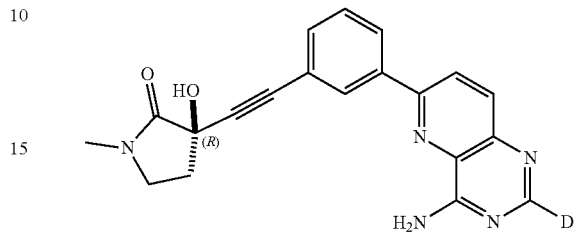

A 20 mL vial containing 6-chloropyrido[3,2-d]pyrimidin-2-d-4-amine (170 mg, 0.94 mmol), (R)-3-hydroxy-1-methyl-3-((3-(4,4,5,5-tetramethyl-1,3,2-dioxaborolan-2-yl)phenyl)ethynyl)pyrrolidin-2-one (372 mg, 1.09 mmol) and Pd(PPh$_3$)$_4$ (104 mg, 0.09 mmol) was charged with 1,4-dioxane (12 mL) and K$_2$CO$_3$ (2 mL, 2M in H$_2$O) which were degassed together with argon for 25 min prior to use. The vial was sealed, evacuated, and purged with nitrogen 3 times and heated at 90° C. for 2 h, the contents were cooled to rt, filtered through a pad of diatomaceous earth, such as Celite® pad, and rinsed further with ethyl acetate (25 mL) and THF (25 mL). The filtrate was concentrated onto diatomaceous earth, such as Celite® (5 g) and purified by FCC (100% DCM increasing to 7% MeOH-DCM) to initially afford (311 mg) as a yellow solid. The resulting material was dissolved in CH$_3$CN (10 mL), heated to reflux for 5 min, and cooled to rt. The resulting solid was collected by filtration, washed with Et$_2$O (20 mL), and dried to afford (R)-3-((3-(4-aminopyrido[3,2-d]pyrimidin-6-yl-2-d)phenyl)ethynyl)-3-hydroxy-1-methylpyrrolidin-2-one (170 mg, 50%) as a pale yellow solid. MS (ESI): mass calcd. for C$_{20}$H$_{16}$DN$_5$O$_2$, 360.14; m/z. found, 361.1 [M+H]$^+$. $^1$H NMR (400 MHz, CD$_3$OD) δ 8.38 (br s, 1H), 8.34 (d, J=8.9 Hz, 1H), 8.22-8.26 (m, 1H), 8.12 (d, J=8.8 Hz, 1H), 7.44-7.58 (m, 2H), 3.55-3.44 (m, 2H), 2.94 (s, 3H), 2.58-2.65 (m, 1H), 2.28-2.38 (m, 1H).

Example 9: (S)-3-((3-(4-Aminopyrido[3,2-d]pyrimidin-6-yl-2-d)phenyl)ethynyl)-3-hydroxy-1-methylpyrrolidin-2-one

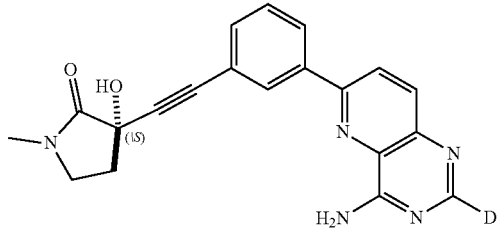

The title compound was prepared using analogous conditions described in Example 8 using (S)-3-hydroxy-1-methyl-3-((3-(4,4,5,5-tetramethyl-1,3,2-dioxaborolan-2-yl)phenyl)ethynyl)pyrrolidin-2-one using FCC to afford (S)-3-

((3-(4-aminopyrido[3,2-d]pyrimidin-6-yl-2-d)phenyl)ethynyl)-3-hydroxy-1-methylpyrrolidin-2-one (9 mg, 9%). MS (ESI): mass calcd. for $C_{20}H_{16}DN_5O_2$, 360.14; m/z. found, 361.1 [M+H]$^+$. $^1$H NMR (400 MHz, CD$_3$OD) δ 8.38 (br s, 1H), 8.34 (d, J=8.9 Hz, 1H), 8.22-8.26 (m, 1H), 8.12 (d, J=8.8 Hz, 1H), 7.44-7.58 (m, 2H), 3.55-3.44 (m, 2H), 2.94 (s, 3H), 2.58-2.65 (m, 1H), 2.28-2.38 (m, 1H).

Example 10: (R)-3-((3-(7-Aminothiazolo[5,4-d]pyrimidin-2-yl)-4-methylphenyl)ethynyl)-3-hydroxy-1-methylpyrrolidin-2-one

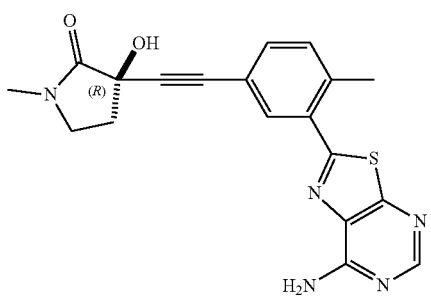

A 3 L round-bottomed flask equipped with an overhead stirrer under nitrogen was charged with 2-(5-iodo-2-methylphenyl)thiazolo[5,4-d]pyrimidin-7-amine (45.0 g, 122 mmol), (R)-3-ethynyl-3-hydroxy-1-methylpyrrolidin-2-one (20.4 g, 147 mmol), CuI (2.32 g, 12.2 mmol), Pd(PPh$_3$)$_2$Cl$_2$ (17.1 g, 24.4 mmol), DMF (450 mL) and DIEA (47.3 g, 366 mmol). The resultant mixture was heated to 90° C. for 2 h, then cooled to rt followed by dilution with CH$_3$CN (1800 mL). The suspension was filtered and washed with CH$_3$CN (90 mL). The filtrate was concentrated and purified by FCC (DCM:MeOH=50:1 to 20:1 with 1% TFA) to afford (R)-3-((3-(7-aminothiazolo[5,4-d]pyrimidin-2-yl)-4-methylphenyl)ethynyl)-3-hydroxy-1-methylpyrrolidin-2-one (7.5 g, 16.2%) as a light yellow solid. MS (ESI): mass calcd. for $C_{19}H_{17}N_5O_2S$, 379.1; m/z. found, 380.1 [M+H]$^+$. $^1$H NMR (400 MHz, CD$_3$OD) δ 8.31 (s, 1H), 7.91-7.83 (m, 1H), 7.50-7.45 (m, 1H), 7.38 (d, J=8.0 Hz, 1H), 3.51-3.44 (m, 2H), 2.93 (s, 3H), 2.66 (s, 3H), 2.62-2.54 (m, 1H), 2.36-2.26 (m, 1H).

Example 11: (S)-3-((3-(7-Aminothiazolo[5,4-d]pyrimidin-2-yl)-4-methylphenyl)ethynyl)-3-hydroxy-1-methylpyrrolidin-2-one

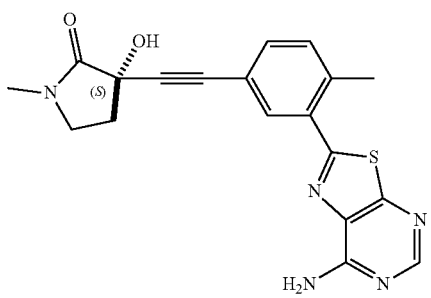

The title compound (50 mg, 53%) was prepared using analogous conditions described in Example 10 using 2-(5-iodo-2-methylphenyl)thiazolo[5,4-d]pyrimidin-7-amine and (S)-3-ethynyl-3-hydroxy-1-methylpyrrolidin-2-one. MS (ESI): mass calcd. for $C_{19}H_{17}N_5O_2S$, 379.11; m/z. found, 380.1 [M+H]$^+$. $^1$H NMR (400 MHz, CD$_3$OD) δ 8.31 (s, 1H), 7.91-7.83 (m, 1H), 7.50-7.45 (m, 1H), 7.38 (d, J=8.0 Hz, 1H), 3.51-3.44 (m, 2H), 2.93 (s, 3H), 2.66 (s, 3H), 2.62-2.54 (m, 1H), 2.36-2.26 (m, 1H).

Example 12: (R)-3-((3-(4-Aminopyrido[3,2-d]pyrimidin-6-yl)phenyl)ethynyl)-3-hydroxy-1-methylpyrrolidin-2-one

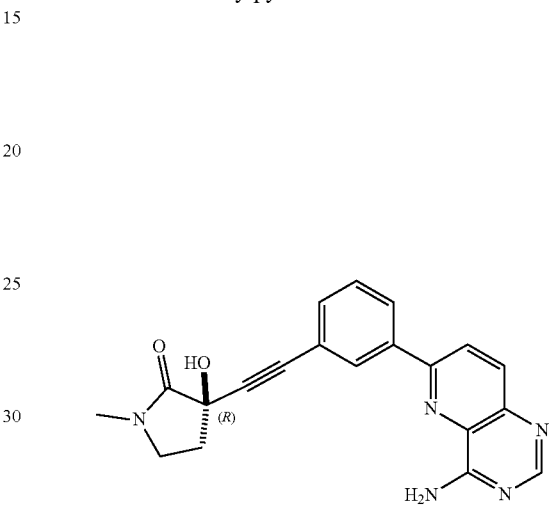

A 20 mL vial containing 6-chloropyrido[3,2-b]pyrimidin-4-amine (150 mg, 0.83 mmol), (R)-3-hydroxy-1-methyl-3-((3-(4,4,5,5-tetramethyl-1,3,2-dioxaborolan-2-yl)phenyl)ethynyl)pyrrolidin-2-one (330 mg, 0.97 mmol), and Pd(PPh$_3$)$_4$ (95.0 mg, 0.82 mmol) was charged with 1,4-dioxane (10 mL) and K$_2$CO$_3$ (1.4 mL, 2M in H$_2$O). The 1,4-dioxane and aqueous K$_2$CO$_3$ mixture was degassed together with argon for 25 min prior to use. The vial was sealed, evacuated, and purged with nitrogen 3 times before heating to 80° C. After 2 h, the contents were filtered through a pad of diatomaceous earth, such as Celite© which was washed with THF (25 mL) and ethyl acetate (25 mL). The filtrate was concentrated to dryness, the resulting residue was dissolved in DCM-THF (1:1), loaded onto diatomaceous earth, such as Celite© (4 g), and purified by FCC (100% DCM increasing to 10% MeOH-DCM) to afford (R)-3-((3-(4-aminopyrido[3,2-d]pyrimidin-6-yl)phenyl)ethynyl)-3-hydroxy-1-methylpyrrolidin-2-one (247 mg, 82%) as an off-white solid. MS (ESI): mass calcd. for $C_{20}H_{17}N_5O_2$, 359.14; m/z. found, 360.15 [M+H]$^+$. $^1$H NMR (400 MHz, CD$_3$OD) δ 8.40 (s, 1H), 8.38 (br s, 1H), 8.34 (d, J=8.9 Hz, 1H), 8.22-8.26 (m, 1H), 8.12 (d, J=8.8 Hz, 1H), 7.58-7.44 (m, 2H), 3.55-3.44 (m, 2H), 2.94 (s, 3H), 2.58-2.65 (m, 1H), 2.28-2.38 (m, 1H).

Example 13: (R)-3-[2-[3-(4-Aminopyrimido[5,4-d]pyrimidin-6-yl)phenyl]ethynyl]-3-hydroxy-1-methyl-pyrrolidin-2-one

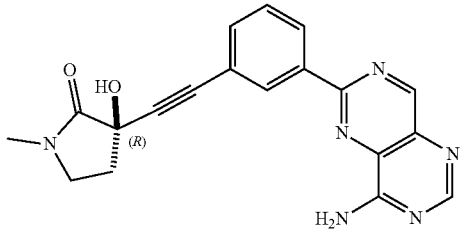

Step A: (R)-3-((3-(8-((2,4-Dimethoxybenzyl)amino)pyrimido[5,4-d]pyrimidin-2-yl)phenyl)ethynyl)-3-hydroxy-1-methylpyrrolidin-2-one. A 10 mL microwave vial was charged with 6-(3-bromophenyl)-N-(2,4-dimethoxybenzyl)pyrimido[5,4-d]pyrimidin-4-amine, (300 mg, 0.66 mmol), (R)-3-ethynyl-3-hydroxy-1-methylpyrrolidin-2-one (102 mg, 0.77 mmol), TEA (2 mL), and DMF (2 mL). The resulting mixture was sparged with argon for 5 min and then treated with dichlorobis(tricyclohexylphosphine)palladium (II) (85.0 mg, 0.07 mmol) (PdCl$_2$[P(cy)$_3$]$_2$) and CuI (25 mg, 0.13 mmol). The resulting mixture was sparged with argon for 5 min and then subjected to microwave irradiation at 100° C. for 1 h. The resulting mixture was cooled to rt and additional (R)-3-ethynyl-3-hydroxy-1-methylpyrrolidin-2-one (51.0 mg, 0.37 mmol), dichlorobis(tricyclohexylphosphine)palladium(II) (42.0 mg, 0.03 mmol), and CuI (12 mg, 0.06 mmol) were added. The resulting mixture was sparged with argon for 5 min and then subjected to microwave irradiation at 100° C. for 1 h. The resulting mixture was cooled to rt, filtered through a pad of diatomaceous earth, such as Celite©, and the pad was washed with ethyl acetate (10 mL). The filtrate was diluted with water (10 mL) and extracted with ethyl acetate (10 mL×3). The combined organic extracts were dried over anhydrous Na$_2$SO$_4$, filtered, and concentrated to dryness. The resulting residue was purified by FCC (petroleum ether:ethyl acetate=1:0 to 0:1) to afford (R)-3-((3-(8-(2,4-dimethoxybenzyl)amino)pyrimido[5,4-d]pyrimidin-2-yl)phenyl)ethynyl)-3-hydroxy-1-methylpyrrolidin-2-one (130 mg, 34%) as a yellow solid. MS (ESI): mass calcd. for C$_{28}$H$_{26}$N$_6$O$_4$ 510.20 m/z found 511.2 [M+H]$^+$.

Step B: (R)-3-[2-[3-(4-Aminopyrimido[5,4-d]pyrimidin-6-yl)phenyl]ethynyl]-3-hydroxy-1-methyl-pyrrolidin-2-one. A 10 mL round-bottomed flask was charged with cerium ammonium nitrate (344 mg, 0.63 mmol), (R)-3-((3-(8-((2,4-dimethoxybenzyl)amino)pyrimido[5,4-d]pyrimidin-2-yl)phenyl)ethynyl)-3-hydroxy-1-methylpyrrolidin-2-one (80.0 mg, 0.16 mmol), CH$_3$CN (1 mL), and H$_2$O (1 mL). The resulting mixture was stirred at rt for 10 min before diluting with saturated aqueous NaHCO$_3$ (1 mL) and extracting with ethyl acetate:methanol (10:1, 10 mL×5). The combined organic extracts were dried over anhydrous Na$_2$SO$_4$, filtered, and concentrated to dryness. The resulting residue was purified by preparative HPLC (Xtimate C18 5 μm, 150 mm×25 mm, eluent: 13% to 43% (v/v) CH$_3$CN and H$_2$O with 0.225% HCOOH. Detection, UV at λ=220-254 nM) to afford (R)-3-[2-[3-(4-aminopyrimido[5,4-d]pyrimidin-6-yl)phenyl]ethynyl]-3-hydroxy-1-methyl-pyrrolidin-2-one as a gray solid (16.6 mg, 25%). MS (ESI): mass calcd. for C$_{19}$H$_{16}$N$_6$O$_2$, 360.1; m/z found, 361.1 [M+H]$^+$. $^1$H NMR (400 MHz, DMSO-d$_6$): δ 9.40 (s, 1H), 8.68-8.63 (m, 2H), 8.53 (s, 1H), 8.26-8.09 (m, 2H), 7.61-7.54 (m, 2H), 6.16 (br. s, 1H), 3.42-3.36 (m, 2H), 2.83 (s, 3H), 2.62-2.52 (m, 1H), 2.29-2.21 (m, 1H).

Example 14: (R)-3-((3-(8-Amino-6-methylpyrimido[5,4-d]pyrimidin-2-yl)phenyl)ethynyl)-3-hydroxy-1-methylpyrrolidin-2-one

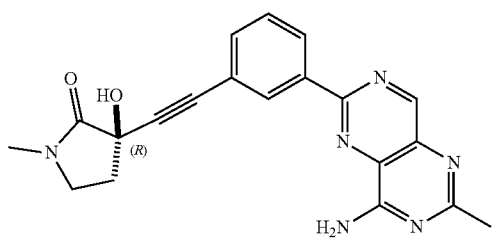

Step A: (R)-3-((3-(8-((2,4-Dimethoxybenzyl)amino)-6-methylpyrimido[5,4-d]pyrimidin-2-yl)phenyl)ethynyl)-3-hydroxy-1-methylpyrrolidin-2-one. A 20 mL microwave vial was charged with 6-chloro-N-(2,4-dimethoxybenzyl)-2-methylpyrimido[5,4-d]pyrimidin-4-amine, (Intermediate 25, 200 mg, 0.578 mmol), (R)-3-hydroxy-1-methyl-3-((3-(4,4,5,5-tetramethyl-1,3,2-dioxaborolan-2-yl)phenyl)ethynyl)pyrrolidin-2-one (217 mg, 0.64 mmol), K$_3$PO$_4$ (368 mg, 1.73 mmol), 1,4-dioxane (5 mL), and H$_2$O (1 mL). The resulting mixture was sparged with nitrogen for 5 min and then treated with [1,1'-bis(di-tert-butylphosphino)ferrocene]dichloropalladium(II) (41.0 mg, 0.06 mmol). The mixture was sparged with nitrogen for another 5 min and the resultant mixture was then subjected to microwave irradiation at 90° C. for 1 h. The resulting mixture was cooled to rt, concentrated to dryness, and purified by FCC (petroleum ether:ethyl acetate=1:0 to 0:1) to afford (R)-3-((3-(8-((2,4-dimethoxybenzyl)amino)-6-methylpyrimido[5,4-d]pyrimidin-2-yl)phenyl)ethynyl)-3-hydroxy-1-methylpyrrolidin-2-one (120 mg) as a brown solid, which was used in the next step without further purification. MS (ESI): mass calcd. for C$_{29}$H$_{28}$N$_6$O$_4$ 524.22 m/z found 525.2 [M+H]$^+$.

Step B: (R)-3-((3-(8-Amino-6-methylpyrimido[5,4-d]pyrimidin-2-yl)phenyl)ethynyl)-3-hydroxy-1-methylpyrrolidin-2-one. A 50 mL round-bottomed flask was charged with (R)-3-((3-(8-((2,4-dimethoxybenzyl)amino)-6-methylpyrimido[5,4-d]pyrimidin-2-yl)phenyl)ethynyl)-3-hydroxy-1-methylpyrrolidin-2-one (110 mg, 0.21 mmol), DCM (10 mL), H$_2$O (2 mL), and 2,3-dichloro-5,6-dicyano-1,4-benzoquinone (DDQ) (57 mg, 0.25 mmol). The resultant mixture was stirred at rt for 1 h before pouring it into saturated aqueous NaHCO$_3$ (50 mL) and extracting with DCM (50 mL×3). The combined organic extracts were washed with H$_2$O (30 mL×3), dried over anhydrous Na$_2$SO$_4$, filtered, and concentrated to dryness. The resulting residue was purified by sequential FCC (petroleum ether:ethyl acetate=1:0 to 0:1, then, DCM:MeOH=1:0 to 10:1) and further purified by preparative HPLC (Boston Prime C18, 150 mm×30 mm×5 μm column (eluent: 20% to 50% (v/v) CH$_3$CN and H$_2$O with 0.04% NH$_{3+10}$ mM NH$_4$HCO$_3$). Detection, UV at λ=220-254 nM) to afford (R)-3-((3-(8-amino-6-methylpyrimido[5,4-d]pyrimidin-2-yl)phenyl)ethynyl)-3-hydroxy-1-methylpyrrolidin-2-one (31.5 mg, 40%) as a white solid. MS (ESI): mass calcd. for C$_{20}$H$_{18}$N$_6$O$_2$ 374.15 m/z found 375.2 [M+H]$^+$. $^1$H NMR (400 MHz, DMSO-d$_6$) δ 9.32 (s, 1H), 8.69-8.63 (m, 2H), 8.46 (br s, 1H), 8.25 (br s, 1H), 7.61-7.54 (m, 2H), 6.51 (s, 1H), 3.39-3.37 (m, 2H), 2.81 (s, 3H), 2.49 (s, 3H), 2.48-2.45 (m, 1H), 2.25-2.16 (m, 1H).

Example 15: (R)-3-[2-[3-(4-Aminopteridin-6-yl) phenyl]ethynyl]-3-hydroxy-1-methyl-pyrrolidin-2-one

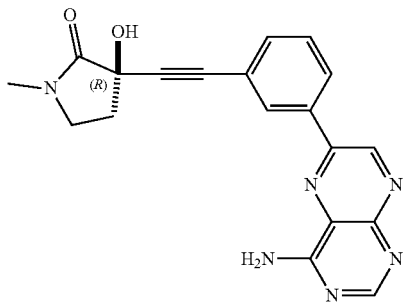

Step A: 2-(3-Bromophenyl)-2-oxoacetaldehyde. A 10 mL round-bottomed flask was charged with 3-bromophenacyl bromide (5.6 g, 20 mmol), DMSO (1.4 mL) and water (0.7 mL). The mixture was then heated to 50° C. for 2.5 h. The resulting mixture was diluted with water (50 mL) and ethyl acetate (50 mL). The organic layer was separated, and the aqueous layer was further extracted with ethyl acetate (3×25 mL). The combined organic extracts were washed with brine (50 mL), dried over anhydrous $Na_2SO_4$, filtered, and concentrated to dryness to afford 2-(3-bromophenyl)-2-oxoacetaldehyde. The resulting pale yellow solid, 2-(3-bromophenyl)-2-oxoacetaldehyde, (4.2 g, 99%) was used without further purification in the next step.

Step B: 2-(3-Bromophenyl)-2-oxoacetaldehyde oxime. A 100 mL round-bottomed flask was charged with 2-(3-bromophenyl)-2-oxoacetaldehyde (4.2 g, 20 mmol), THF (40 mL) and hydroxylamine HCl (1.4 g, 20 mmol). The mixture was stirred for 16 h at rt under a nitrogen atmosphere. The resulting mixture was concentrated to dryness and purified by FCC (gradient of ethyl acetate:heptane=0 to 100%) to provide 2-(3-bromophenyl)-2-oxoacetaldehyde oxime (2.7 g, 60%). MS (ESI): mass calcd. for $C_8H_6BrNO_2$, 226.96; m/z. found, 228.0 [M+H]$^+$.

Step C: 6-(3-Bromophenyl)pteridin-4-amine. A sealable vial was charged with pyrimidine-4,5,6-triamine (549 mg, 4.40 mmol) and HCl (8.80 mL, 11.0 mmol, 1.25 M in ethanol). The resulting suspension was pre-heated to 70° C. followed by dropwise addition of a solution of 2-(3-bromophenyl)-2-oxoacetaldehyde oxime (1.00 g, 4.40 mmol) in EtOH (11 mL). The reaction mixture was then heated at 80° C. for 2 h. The resulting mixture was cooled to rt and $NH_4OH$ (1 mL, 28% aqueous) was added with stirring. After 30 min, water (50 mL) was added and the resulting solid was collected by filtration. The solid was washed with water (25 mL) and then dried under high vacuum. The resulting solid was triturated with ethyl acetate (15 ml) and MeOH (2 mL) and collected by vacuum filtration to provide 6-(3-bromophenyl)pteridin-4-amine (516 mg, 39%) as an off-white solid. MS (ESI): mass calcd. for $C_{12}H_8BrN_5$, 301.00; m/z. found, 302.0 [M+H]$^+$. $^1$H NMR (400 MHz, DMSO-$d_6$) δ 9.76 (s, 1H), 8.79 (t, J=1.8 Hz, 1H), 8.68 (br s, 1H), 8.55 (s, 1H), 8.52-8.46 (m, 1H), 8.38 (br s, 1H), 7.74 (app ddd, J=8.0, 2.0, 0.9 Hz, 1H), 7.54 (t, J=7.9 Hz, 1H).

Step D: (R)-3-[2-[3-(4-Aminopteridin-6-yl)phenyl]ethynyl]-3-hydroxy-1-methyl-pyrrolidin-2-one. A 10 mL sealable vial was charged with 6-(3-bromophenyl)pteridin-4-amine (71.0 mg, 0.24 mmol), (R)-3-ethynyl-3-hydroxy-1-methylpyrrolidin-2-one (50.0 mg, 0.35 mmol), CuI (4.5 mg, 0.024 mmol) and $PdCl_2(PPh_3)_2$ (16.5 mg, 0.02 mmol). The vessel was evacuated and backfilled with argon three times. The vial was then charged with degassed anhydrous DMF (2 mL) and DIEA (122 µL, 0.71 mmol). Then the vessel was placed in a heating block at 90° C., for 1 h. The resulting mixture was cooled to rt and concentrated to dryness. The residue was purified by FCC (MeOH in DCM 0 to 10% gradient) to provide a solid that was triturated with MeCN (5 mL) to afford (R)-3-[2-[3-(4-aminopteridin-6-yl)phenyl] ethynyl]-3-hydroxy-1-methyl-pyrrolidin-2-one (31 mg, 36%). MS (ESI): mass calcd. for $C_{19}H_{16}N_6O_2$, 360.13; m/z. found, 361.2 [M+H]$^+$. $^1$H NMR (400 MHz, $CD_3OD$) δ 9.62 (s, 1H), 8.55 (s, 1H), 8.49 (s, 1H), 8.35 (d, J=7.7 Hz, 1H), 7.63 (d, J=7.8 Hz, 1H), 7.60-7.54 (m, 1H), 3.54-3.43 (m, 2H), 2.94 (s, 3H), 2.68-2.57 (m, 1H), 2.38-2.26 (m, 1H).

Example 16: (R)-3-[2-[3-(4-Aminoquinazolin-6-yl) phenyl]ethynyl]-3-hydroxy-1-methyl-pyrrolidin-2-one

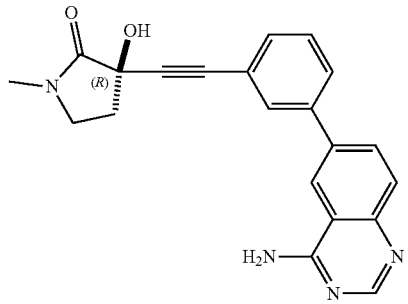

A 20 mL microwave vial was charged with 6-bromoquinazolin-4-amine (150 mg, 0.67 mmol), (R)-3-hydroxy-1-methyl-3-((3-(4,4,5,5-tetramethyl-1,3,2-dioxaborolan-2-yl) phenyl)ethynyl)pyrrolidin-2-one (297 mg, 0.87 mmol), $Na_2CO_3$ (1.3 mL, 2M in $H_2O$), and THF (6.7 mL). The resulting reaction mixture was purged with nitrogen for 10 minutes and 1,1'-bis[di t-butylphosphino)ferrocene]palladium (8 mg, 0.013 mmol) was added. The vial was then sealed and heated to 50° C. After 16 h, the resulting mixture was cooled to rt and partitioned between ethyl acetate (10 mL) and water (10 mL). The organic layer was separated and the aqueous was extracted with ethyl acetate (2×20 mL). The combined organic extracts were concentrated and purified by preparative HPLC (XBridge OBD C18 5 µm, 50×100 mm column using a 0 to 95% gradient of ACN/20 mM $NH_4OH$ in $H_2O$ over 16 min. Detection, UV at λ=220-254 nM) to afford (R)-3-[2-[3-(4-aminoquinazolin-6-yl)phenyl] ethynyl]-3-hydroxy-1-methyl-pyrrolidin-2-one (92 mg, 38%) as a colorless solid. MS (ESI): mass calcd. for $C_{21}H_{18}N_4O_2$, 358.1; m/z. found, 359.1 [M+H]$^+$. $^1$H NMR (500 MHz, $CDCl_3$) δ 8.60 (s, 1H), 7.81 (d, J=8.5 Hz, 1H), 7.70-7.65 (m, 2H), 7.45-7.42 (m, 1H), 7.34-7.23 (m, 3H), 6.22 (s, 2H), 3.46-3.32 (m, 2H), 2.91 (s, 3H), 2.66-2.54 (m, 1H), 2.40-2.31 (m, 2H).

Example 17: (R)-7-[2-[3-(8-Aminopyrido[3,4-d]pyrimidin-2-yl)phenyl]ethynyl]-5,6-dihydropyrrolo[1,2-a]imidazol-7-ol

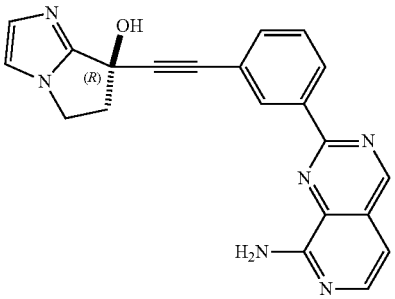

The title compound (51 mg, 48%) was prepared with analogous conditions described in Example 1 using 2-(3-iodophenyl)pyrido[3,4-d]pyrimidin-8-amine and (R)-7-ethynyl-6,7-dihydro-5H-pyrrolo[1,2-a]imidazol-7-ol in THF. MS (ESI): mass calcd. for $C_{21}H_{16}N_6O$, 368.4; m/z. found, 369.2 [M+H]$^+$. $^1$H NMR (500 MHz, DMSO-$d_6$) δ 8.63 (s, 1H), 8.00-7.93 (m, 1H), 7.84 (d, J=7.9 Hz, 1H), 7.15 (d, J=5.8 Hz, 1H), 6.84 (d, J=7.6 Hz, 1H), 6.76-6.66 (m, 1H), 6.34 (d, J=7.1 Hz, 2H), 6.27 (d, J=5.8 Hz, 1H), 3.88 (s, 1H), 3.54-3.22 (m, 2H), 2.46-2.36 (m, 1H), 2.24-1.94 (m, 1H).

Example 18: (R)-4-[3-(8-Aminopyrido[3,4-d]pyrimidin-2-yl)phenyl]-2-(5-methyl-1,3,4-oxadiazol-2-yl)but-3-yn-2-ol

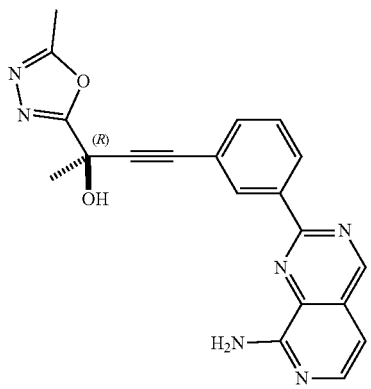

The title compound (46 mg, 36%) was prepared with analogous conditions described in Example 1 using 2-(3-iodophenyl)pyrido[3,4-d]pyrimidin-8-amine and (R)-2-(5-methyl-1,3,4-oxadiazol-2-yl)but-3-yn-2-ol. MS (ESI): mass calcd. for $C_{20}H_{16}N_6O_2$, 372.4; m/z. found, 373.2 [M+H]$^+$. $^1$H NMR (500 MHz, CDCl$_3$) δ 9.31 (s, 1H), 8.61-8.57 (m, 1H), 8.56-8.50 (m, 1H), 8.10 (d, J=5.7 Hz, 1H), 7.61-7.54 (m, 1H), 7.52-7.43 (m, 1H), 7.00 (d, J=5.7 Hz, 1H), 6.15 (s, 2H), 4.19 (s, 1H), 2.63 (s, 3H), 2.12 (s, 3H).

Example 19: (R)-3-[2-[3-(8-Amino-1,7-naphthyridin-2-yl)phenyl]ethynyl]-3-hydroxy-1-methyl-pyrrolidin-2-one

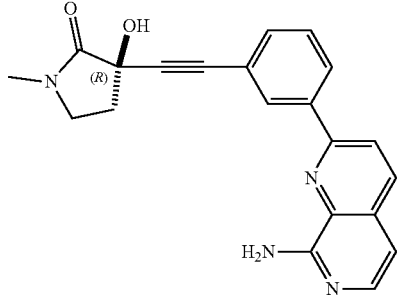

The title compound was prepared with analogous conditions described in Example 1 using 2-(3-iodophenyl)-1,7-naphthyridin-8-amine and (R)-7-ethynyl-6,7-dihydro-5H-pyrrolo[1,2-a]imidazol-7-ol in THF. The resulting compound was purified by preparative HPLC (XBridge Prep C18 5 µm, 50×250 mm column using a 0 to 100% gradient of MeCN/20 mM NH$_4$OH in H$_2$O over 35 min. Detection, UV at λ=220-254 nM) to afford (R)-3-[2-[3-(8-amino-1,7-naphthyridin-2-yl)phenyl]ethynyl]-3-hydroxy-1-methyl-pyrrolidin-2-one as a colorless solid (19 mg, 42%). MS (ESI): mass calcd. for $C_{21}H_{18}N_4O_2$, 358.4; m/z. found, 359.1 [M+H]$^+$. $^1$H NMR (400 MHz, DMSO-$d_6$) δ 8.46-8.41 (m, 1H), 8.40-8.37 (m, 1H), 8.33 (d, J=8.7 Hz, 1H), 8.25 (d, J=8.7 Hz, 1H), 7.87 (d, J=5.7 Hz, 1H), 7.60-7.50 (m, 2H), 7.14 (s, 2H), 6.95 (d, J=5.8 Hz, 1H), 6.48 (s, 1H), 3.43-3.35 (m, 2H), 2.82 (s, 3H), 2.49-2.45 (m, 1H), 2.26-2.15 (m, 1H).

Example 20: (R)-3-((3-(8-Amino-3,4-dihydro-2,7-naphthyridin-2(1H)-yl)phenyl)ethynyl)-3-hydroxy-1-methylpyrrolidin-2-one

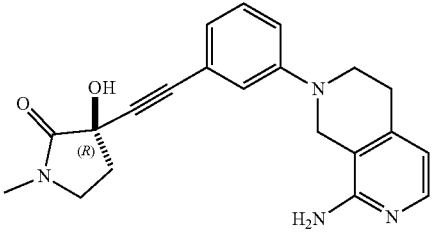

A 10 mL microwave vial was charged with 7-(3-iodophenyl)-5,6,7,8-tetrahydro-2,7-naphthyridin-1-amine (260 mg, 0.74 mmol), (R)-3-ethynyl-3-hydroxy-1-methylpyrrolidin-2-one (90.0 mg, 0.65 mmol), Et$_3$N (4 mL), and DMF (4 mL). The mixture was purged with argon for 5 min and then treated with Pd(PPh$_3$)$_2$Cl$_2$ (54.0 mg, 0.08 mmol) and CuI (27 mg, 0.14 mmol). The mixture was purged with argon for another 5 min and then subjected to microwave irradiation for 2 h at 70° C. The resulting mixture was cooled to rt, poured into a LiCl solution (20 mL, 4% aqueous), and extracted with ethyl acetate (20 mL×4). The combined organic extracts were washed with brine (50 mL), dried over anhydrous Na$_2$SO$_4$, filtered and concentrated to dryness. The resulting residue was purified by preparative HPLC (Boston Green ODS 5 µm, 150×30 mm column, eluent: 25% to 55% (v/v) CH$_3$CN and H$_2$O with (0.04% NH$_3$H$_2$O+10 mM NH$_4$HCO$_3$. Detection, UV at λ=220-254 nM) to afford (R)-3-((3-(8-amino-3,4-dihydro-2,7-naphthyridin-2(1H)-yl)phenyl)ethynyl)-3-hydroxy-1-methylpyrrolidin-2-one (67.2 mg, 25%) as a yellow solid. MS (ESI): mass calcd. for C$_{21}$H$_{22}$N$_4$O$_2$ 362.17 m/z, found 363.2 [M+H]$^+$. $^1$H NMR (400 MHz, DMSO-d$_6$) δ 7.90-7.59 (m, 1H), 7.28-7.20 (m, 1H), 7.18-7.07 (m, 2H), 6.81 (d, J=7.3 Hz, 1H), 6.47-6.32 (m, 2H), 5.91 (br s, 2H), 3.97 (s, 2H), 3.48 (t, J=5.6 Hz, 2H), 3.39-3.36 (m, 1H), 3.34-3.31 (m, 1H), 2.84-2.71 (m, 5H), 2.46-2.38 (m, 1H), 2.23-2.13 (m, 1H).

Example 21: (R)-3-[2-[3-(3-Amino-1-methyl-pyrazolo[4,3-b]pyridin-5-yl)phenyl]ethynyl]-3-hydroxy-1-methyl-pyrrolidin-2-one

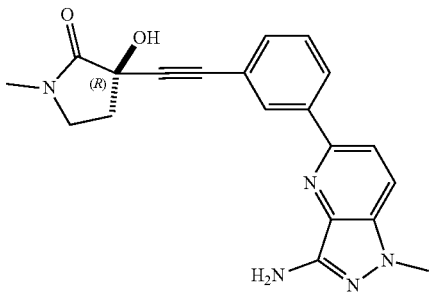

The title compound was prepared with analogous conditions described in Example 1 using 5-(3-Iodophenyl)-1-methyl-1H-pyrazolo[4,3-b]pyridin-3-amine and (R)-3-ethynyl-3-hydroxy-1-methylpyrrolidin-2-one in THF. The resulting compound was purified by preparative HPLC (XBridge Prep C18 5 μm, 50×250 mm column using a 0 to 100% gradient of ACN/20 mM NH$_4$OH in H$_2$O over 35 min. Detection, UV at λ=220-254 nM) to afford (R)-3-[2-[3-(3-amino-1-methyl-pyrazolo[4,3-b]pyridin-5-yl)phenyl]ethynyl]-3-hydroxy-1-methyl-pyrrolidin-2-one as a colorless solid (36 mg, 36%). MS (ESI): mass calcd. for C$_{20}$H$_{19}$N$_5$O$_2$, 361.4; m/z. found, 362.1 [M+H]$^+$. $^1$H NMR (500 MHz, DMSO-d$_6$) δ 8.24-8.20 (m, 1H), 8.16-8.09 (m, 1H), 7.97-7.86 (m, 2H), 7.53-7.47 (m, 1H), 7.45-7.36 (m, 1H), 6.48 (s, 1H), 5.57 (s, 2H), 3.80 (s, 3H), 3.40-3.35 (m, 2H), 2.82 (s, 3H), 2.49-2.41 (m, 1H), 2.25-2.12 (m, 1H).

Example 22: (R)-3-[2-[3-(3-Amino-1H-pyrazolo[4,3-b]pyridin-5-yl)phenyl]ethynyl]-3-hydroxy-1-methyl-pyrrolidin-2-one

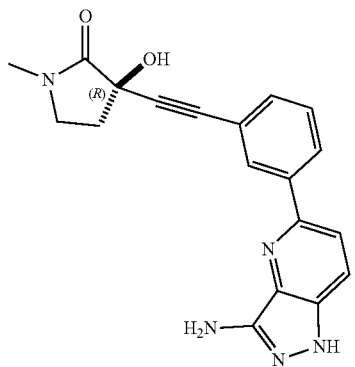

The title compound was prepared using analogous conditions described in Example 1 using 5-(3-iodophenyl)-1H-pyrazolo[4,3-b]pyridin-3-amine and (R)-3-ethynyl-3-hydroxy-1-methylpyrrolidin-2-one in THF. The resulting compound was purified by preparative HPLC (XBridge Prep C18 5 μm, 50×250 mm column using a 0 to 100% gradient of ACN/20 mM NH$_4$OH in H$_2$O over 35 min. Detection, UV at λ=220-254 nM) to afford (R)-3-[2-[3-(3-amino-1H-pyrazolo[4,3-b]pyridin-5-yl)phenyl]ethynyl]-3-hydroxy-1-methyl-pyrrolidin-2-one (39 mg, 38%) as a colorless solid. MS (ESI): mass calcd. for C$_{19}$H$_{17}$N$_5$O$_2$, 347.4; m/z. found, 348.1 [M+H]$^+$. $^1$H NMR (500 MHz, DMSO-d$_6$) δ 11.73 (s, 1H), 8.26-8.15 (m, 1H), 8.16-8.04 (m, 1H), 7.89 (d, J=8.9 Hz, 1H), 7.79 (d, J=8.8 Hz, 1H), 7.54-7.47 (m, 1H), 7.46-7.39 (m, 1H), 6.49 (s, 1H), 5.47 (s, 2H), 3.41-3.35 (m, 2H), 2.82 (s, 3H), 2.49-2.37 (m, 1H), 2.26-2.11 (m, 1H).

Example 23: (R)-3-Hydroxy-1-methyl-3-((3-(4-methylpyrido[3,2-d]pyrimidin-6-yl)phenyl)ethynyl)pyrrolidin-2-one

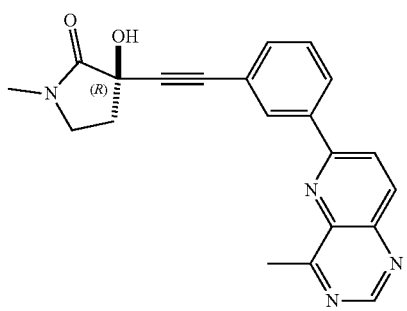

A 20 mL microwave vial was charged with 6-chloro-4-methylpyrido[3,2-d]pyrimidine (100 mg, 0.56 mmol), (R)-3-hydroxy-1-methyl-3-((3-(4,4,5,5-tetramethyl-1,3,2-dioxaborolan-2-yl)phenyl)ethynyl)pyrrolidin-2-one (190 mg, 0.56 mmol), K$_3$PO$_4$ (350 mg, 0.17 mmol), 1,4-dioxane (8 mL), and H$_2$O (2 mL). The resulting mixture was sparged with argon for 5 min, treated with [1,1'-bis(di-tert butylphosphino) ferrocene]dichloropalladium(II) (50 mg, 0.08 mmol) and then sparged with argon for another 5 min. The resulting mixture was subjected to microwave irradiation at 100° C. for 1 h before cooling to rt. The resulting suspension was filtered through a pad of diatomaceous earth, such as Celite® and the pad washed with ethyl acetate (10 mL). The filtrate was concentrated to dryness and the residue was sequentially purified by FCC (petroleum ether:ethyl acetate=1:0 to 0:1, then dichloromethane:methanol=1:0, to 5:1), preparative HPLC [(YMC-Triart Prep C18 10 μm, 250 mm×50 mm, eluent: 28% to 58% (v/v) CH$_3$CN and H$_2$O with 0.04% NH$_3$H$_2$O+10 mM NH$_4$HCO$_3$, Detection, UV at λ=220-254 nM)] to afford (R)-3-hydroxy-1-methyl-3-((3-(4-methylpyrido[3,2-d]pyrimidin-6-yl)phenyl)ethynyl)pyrrolidin-2-one (45.5 mg, 23%) as a yellow solid. MS (ESI): mass calcd. for C$_{21}$H$_{18}$N$_4$O$_2$ 358.14 m/z found 359.2 [M+H]$^+$. $^1$H NMR (400 MHz, DMSO-d$_6$) δ 9.21 (s, 1H), 8.68 (d, J=9.0 Hz, 1H), 8.49 (d, J=8.8 Hz, 1H), 8.39-8.34 (m, 2H), 7.66-7.60 (m, 2H), 6.56 (s, 1H), 3.41-3.37 (m, 2H), 3.11-3.04 (m, 3H), 2.83 (s, 3H), 2.48-2.45 (m, 1H), 2.27-2.17 (m, 1H).

Example 24: (R)-3-((3-(4-Ethoxypyrido[3,2-d]pyrimidin-6-yl)phenyl)ethynyl)-3-hydroxy-1-methylpyrrolidin-2-one

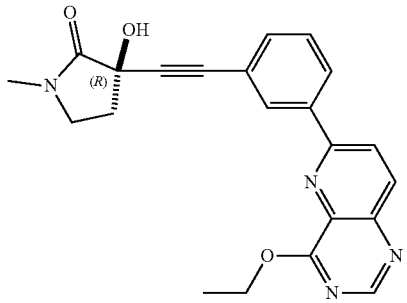

The title compound was prepared using analogous conditions described in Example 23 using 6-chloro-4-ethoxypyrido[3,2-d]pyrimidine and (R)-3-hydroxy-1-methyl-3-((3-(4,4,5,5-tetramethyl-1,3,2-dioxaborolan-2-yl)phenyl)ethynyl)pyrrolidin-2-one. The resulting compound was purified by preparative HPLC (Xtimate C18 10 μm, 250 mm×50 mm, eluent: 31% to 61% (v/v) CH$_3$CN and H$_2$O with 0.04% NH$_3$H$_2$O+10 mM NH$_4$HCO$_3$. Detection, UV at λ=220-254 nM) to afford (R)-3-((3-(4-ethoxypyrido[3,2-d]pyrimidin-6-yl)phenyl)ethynyl)-3-hydroxy-1-methylpyrrolidin-2-one (94.6 mg, 40%) as a white solid. MS (ESI): mass calcd. for C$_{22}$H$_{20}$N$_4$O$_3$ 388.15 m/z found 389.2 [M+H]$^+$. $^1$H NMR (400 MHz, DMSO-d$_6$) δ 8.86 (s, 1H), 8.60 (d, J=9.0 Hz, 1H), 8.40 (d, J=9.0 Hz, 1H), 8.31-8.25 (m, 2H), 7.64-7.57 (m, 2H), 6.55 (s, 1H), 4.72 (q, J=7.0 Hz, 2H), 3.40-3.36 (m, 2H), 2.82 (s, 3H), 2.49-2.45 (m, 1H), 2.27-2.17 (m, 1H), 1.51 (t, J=7.0 Hz, 3H).

Example 25: (R)-3-((3-(4-(Dimethylamino)pyrido[3,2-d]pyrimidin-6-yl)phenyl)ethynyl)-3-hydroxy-1-methylpyrrolidin-2-one

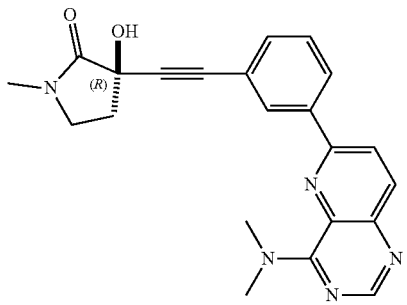

A 20 mL vial containing 1,4-dioxane (11 mL) and K$_2$CO$_3$ (1.3 mL, 2M in H$_2$O) was degassed with nitrogen for 15 min. To the resulting solution was added to 6-chloro-N,N-dimethylpyrido[3,2-d]pyrimidin-4-amine (135 mg, 0.65 mmol), (R)-3-hydroxy-1-methyl-3-((3-(4,4,5,5-tetramethyl-1,3,2-dioxaborolan-2-yl)phenyl)ethynyl)pyrrolidin-2-one (161 mg, 0.47 mmol) and Pd(PPh$_3$)$_4$ (16 mg, 0.01 mmol). The vial was sealed, evacuated, and purged with nitrogen 3 times before heating at 100° C. After 1.5 h, the contents were cooled to rt, filtered through a diatomaceous earth, such as Celite©, and the pad was washed THF (25 mL) and ethyl acetate (25 mL). The filtrate was concentrated to dryness, loaded onto a pad of diatomaceous earth, such as Celite® (2.5 g) using CHCl$_3$-MeOH, and purified by FCC (100% DCM increasing to 5% 2M NH$_3$-MeOH/DCM) to afford (R)-3-((3-(4-(dimethylamino)pyrido[3,2-d]pyrimidin-6-yl)phenyl)ethynyl)-3-hydroxy-1-methylpyrrolidin-2-one (220 mg, 87%) as an amber solid. MS (ESI): mass calcd. For C$_{22}$H$_{21}$N$_5$O$_2$, 387.44; m/z. found, 388.10 [M+H]$^+$. $^1$H NMR (500 MHz, CD$_3$OD) δ 8.40 (s, 1H), 8.22 (d, J=8.9 Hz, 1H), 8.16-8.11 (m, 1H), 8.12-8.02 (m, 2H), 7.58-7.42 (m, 2H), 3.55-3.85 (m, 6H), 3.51-3.45 (m, 2H), 2.94 (s, 3H), 2.57-2.65 (m, 1H), 2.38-2.26 (m, 1H).

Example 26: (R)-3-((3-(4-(Azetidin-1-yl)pyrido[3,2-d]pyrimidin-6-yl)phenyl)ethynyl)-3-hydroxy-1-methylpyrrolidin-2-one

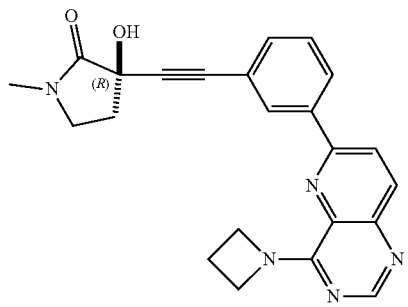

The title compound was prepared using analogous conditions described in Example 25 using 4-(azetidin-1-yl)-6-chloropyrido[3,2-d]pyrimidine and (R)-3-hydroxy-1-methyl-3-((3-(4,4,5,5-tetramethyl-1,3,2-dioxaborolan-2-yl)phenyl)ethynyl)pyrrolidin-2-one to afford a yellow solid (220 mg, 90%). MS (ESI): mass calcd. For C$_{23}$H$_{21}$N$_5$O$_2$, 399.45; m/z. found, 400.05 [M+H]$^+$. $^1$H NMR (400 MHz, CD$_3$OD) δ 8.29 (s, 1H), 8.13 (d, J=8.9 Hz, 1H), 8.04 (t, J=1.6 Hz, 1H), 7.99 (dt, J=7.7, 1.5 Hz, 1H), 7.94 (d, J=8.9 Hz, 1H), 7.56-7.39 (m, 2H), 4.88 (t, J=7.7 Hz, 2H), 4.33 (t, J=7.8 Hz, 2H), 3.55-3.42 (m, 2H), 2.95 (s, 3H), 2.58-2.62 (m, 1H), 2.56-2.45 (m, 2H), 2.30-2.38 (m, 1H).

Example 27: (R)-3-Hydroxy-1-methyl-3-((3-(4-(methylamino)pyrido[3,2-d]pyrimidin-6-yl)phenyl)ethynyl)pyrrolidin-2-one

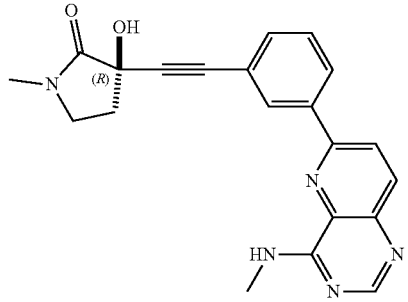

A 20 mL microwave vial was charged with 6-chloro-N-methylpyrido[3,2-d]pyrimidin-4-amine (100 mg, 0.51 mmol), (R)-3-hydroxy-1-methyl-3-((3-(4,4,5,5-tetramethyl- 1,3,2-dioxaborolan-2-yl)phenyl)ethynyl)pyrrolidin-2-one (180 mg, 0.53 mmol), $K_3PO_4$ (327 mg, 1.54 mmol), 1,4-dioxane (8 mL), and $H_2O$ (2 mL). The resulting mixture was sparged with argon for 5 min followed by addition of [1,1'-bis(di-tert butylphosphino) ferrocene] dichloropalladium(II) (33.0 mg, 0.05 mmol). The resulting mixture was sparged with argon for another 5 minutes and then subjected to microwave irradiation 90° C. for 1 h before cooling to rt. The mixture was filtered through a pad of diatomaceous earth, such as Celite® and the pad was washed with MeOH (20 mL). The filtrate was concentrated and purified sequentially by FCC (petroleum ether:ethyl acetate=1:0 to 0:1, then dichloromethane:methanol=1:0 to 10:1) and preparative HPLC (Xtimate C18 250 mm×50 mm×10 μm (eluent: 25% to 55% (v/v) $CH_3CN$ and $H_2O$ with 0.04% $NH_3 \cdot H_2O$ and 10 mM $NH_4HCO_3$). Detection, UV at λ=220-254 nM) to afford (R)-3-hydroxy-1-methyl-3-((3-(4-(methylamino)pyrido[3,2-d]pyrimidin-6-yl)phenyl)ethynyl)pyrrolidin-2-one (76.5 mg, 40%) as a white solid. MS (ESI): mass calcd. For $C_{21}H_{19}N_5O_2$ 373.2 m/z found 374.2 [M+H]$^+$. $^1$H NMR (400 MHz, DMSO-d$_6$) δ 8.73-8.66 (m, 1H), 8.52-8.40 (m, 4H), 8.15 (d, J=8.8 Hz, 1H), 7.62-7.51 (m, 2H), 6.51 (s, 1H), 3.41-3.39 (m, 2H), 3.09 (d, J=4.8 Hz, 3H), 2.83 (s, 3H), 2.50-2.46 (m, 1H), 2.27-2.18 (m, 1H).

Example 28: (R)-3-((3-(4-Amino-8-methylpyrido[3,2-d]pyrimidin-6-yl)phenyl)ethynyl)-3-hydroxy-1-methylpyrrolidin-2-one, and its trifluoroacetate

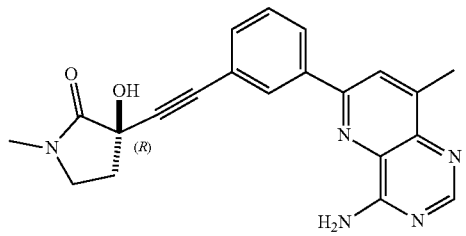

(R)-3-((3-(4-Amino-8-methylpyrido[3,2-d]pyrimidin-6-yl)phenyl)ethynyl)-3-hydroxy-1-methylpyrrolidin-2-one was prepared using conditions analogous to those described in Example 1, utilizing 6-(3-iodophenyl)-8-methylpyrido[3,2-d]pyrimidin-4-amine and (R)-3-ethynyl-3-hydroxy-1-methylpyrrolidin-2-one. This compound was then purified by preparative HPLC (Phenomenex Luna C18 100×30 mm, 5 μm; Gradient, 95:5 to 5:95 water (0.1% TFA)/$CH_3CN$ (0.1% TFA) over 15 minutes; Flow rate, 50 mL/min; Detection, UV at λ=254 nM) to afford (R)-3-((3-(4-amino-8-methylpyrido[3,2-d]pyrimidin-6-yl)phenyl)ethynyl)-3-hydroxy-1-methylpyrrolidin-2-one trifluoroacetate (19 mg, 27%). MS (ESI): mass calcd. for $C_{21}H_{19}N_5O_2$, 373.15; m/z. found, 374.3 [M+H]$^+$. $^1$H NMR (400 MHz, CD$_3$OD) δ 8.64 (s, 1H), 8.46 (d, J=8.0 Hz, 2H), 8.32 (d, J=7.7 Hz, 1H), 7.60 (d, J=7.6 Hz, 1H), 7.54 (t, J=7.7 Hz, 1H), 3.50 (t, J=6.4 Hz, 2H), 2.95 (s, 3H), 2.73 (s, 3H), 2.66-2.56 (m, 1H), 2.39-2.29 (m, 1H).

Example 29: (R)-3-((3-(4-aminopyrido[3,2-d]pyrimidin-6-yl-2-d)-4-(trifluoromethoxy)phenyl)ethynyl)-3-hydroxy-1-methylpyrrolidin-2-one

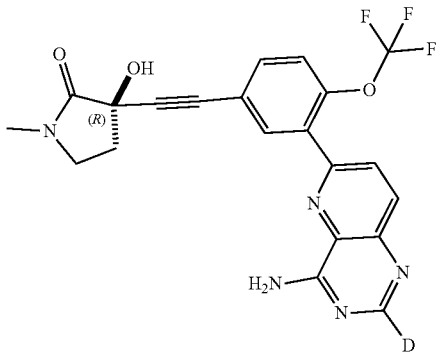

The title compound (69 mg, 47%) was prepared using analogous conditions described in Example 6 using (R)-3-hydroxy-1-methyl-3-((3-(4,4,5,5-tetramethyl-1,3,2-dioxaborolan-2-yl)-4-(trifluoromethoxy)phenyl)ethynyl)pyrrolidin-2-one and 6-chloropyrido[3,2-d]pyrimidin-2-d-4-amine. MS (ESI): mass calcd. for $C_{21}H_{15}DF_3N_5O_3$, 444.13; m/z. found, 445.0 [M+H]$^+$. $^1$H NMR (400 MHz, CD$_3$OD) δ 8.26 (d, J=8.8 Hz, 1H), 8.22 (d, J=8.8 Hz, 1H), 8.17 (d, J=2.1 Hz, 1H), 7.71 (dd, J=8.6, 2.2 Hz, 1H), 7.56-7.48 (m, 1H), 3.52-3.47 (m, 2H), 2.95 (s, 3H), 2.65-2.57 (m, 1H), 2.39-2.29 (m, 1H).

Example 30: (R)-2-[3-[2-(3-Hydroxy-1-methyl-2-oxo-pyrrolidin-3-yl)ethynyl]phenyl]-7H-pyrido[3,4-d]pyrimidin-8-one

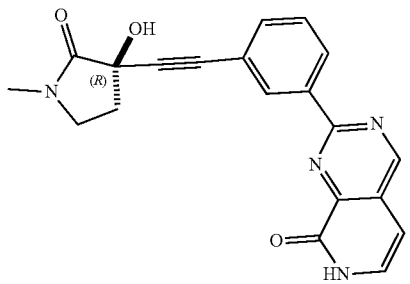

A flask was charged with 2-(3-bromophenyl)pyrido[3,4-d]pyrimidin-8(7H)-one (Intermediate 29, 1.0 g, 3.3 mmol), TEA (10 mL, 73 mmol), ACN (10 mL), DMF (20 mL), 3-ethynyl-3-hydroxy-1-methylpyrrolidin-2-one (690 mg, 4.96 mmol), CuI (32 mg, 0.17 mmol), and Pd(PPh$_3$)$_2$Cl$_2$ (230 mg, 0.33 mmol). The resulting mixture was sparged with nitrogen for 10 min and heated to 80° C. After 4 h, the resulting mixture was diluted with water (50 mL) and extracted with ethyl acetate (50 mL×2). The organic layers were combined and concentrated to dryness. The resulting residue was purified by FCC to afford racemic 2-[3-[2-(3-hydroxy-1-methyl-2-oxo-pyrrolidin-3-yl)ethynyl]phenyl]-7H-pyrido[3,4-d]pyrimidin-8-one which was further purified by chiral HPLC (Chirapak IC-3, 10×0.46 cm, 3.0 μm; mobile phase: 85/15 hexanes (0.1% diethylamine):EtOH) to afford (R)-2-[3-[2-(3-hydroxy-1-methyl-2-oxo-pyrrolidin- 3-yl)ethynyl]phenyl]-7H-pyrido[3,4-d]pyrimidin-8-one (209 mg, 17.5%) as a white solid and (S)-2-[3-[2-(3-hydroxy-1-methyl-2-oxo-pyrrolidin-3-yl)ethynyl]phenyl]-7H-pyrido[3,4-d]pyrimidin-8-one (Example 31, 222 mg, 19%). Data for (R)-2-[3-[2-(3-hydroxy-1-methyl-2-oxo-pyrrolidin-3-yl)ethynyl]phenyl]-7H-pyrido[3,4-d]pyrimidin-8-one: MS (ESI): mass calcd. for $C_{20}H_{16}N_4O_3$, 360.1; m/z. found, 360.9 [M+H]$^+$. $^1$H NMR (300 MHz, DMSO-$d_6$): δ 11.98 (s, 1H), 9.49 (s, 1H), 8.58-8.44 (m, 2H), 7.64-7.56 (m, 2H), 7.42 (d, J=7.1 Hz, 1H), 6.70 (d, J=7.0 Hz, 1H), 6.55 (s, 1H), 3.38 (t, J=6.5 Hz, 2H), 2.82 (s, 3H), 2.46 (d, J=5.9 Hz, 1H), 2.29-2.15 (m, 1H).

Example 31: (S)-2-[3-[2-(3-Hydroxy-1-methyl-2-oxo-pyrrolidin-3-yl)ethynyl]phenyl]-7H-pyrido[3,4-d]pyrimidin-8-one

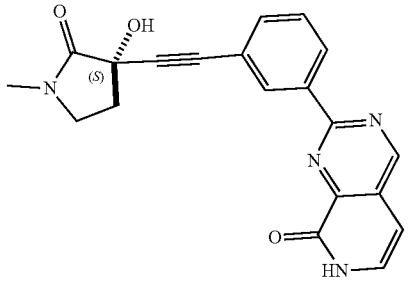

The title compound (222 mg, 19%) was prepared as described in Example 30, as the second eluting (S)-enantiomer. MS (ESI): mass calcd. for $C_{20}H_{16}N_4O_3$, 360.1; m/z found, 361.0 [M+H]$^+$. $^1$H NMR (300 MHz, DMSO-$d_6$): δ 11.96 (s, 1H), 9.49 (s, 1H), 8.57-8.44 (m, 2H), 7.60 (d, J=4.8 Hz, 2H), 7.42 (d, J=7.0 Hz, 1H), 6.69 (d, J=6.9 Hz, 1H), 6.55 (s, 1H), 3.54-3.34 (m, 2H), 2.82 (s, 3H), 2.46 (d, J=5.9 Hz, 1H), 2.29-2.15 (m, 1H).

Example 32: (R)-4-[3-(8-Aminopyrido[3,4-d]pyrimidin-2-yl)phenyl]-2-thiazol-2-yl-but-3-yn-2-ol

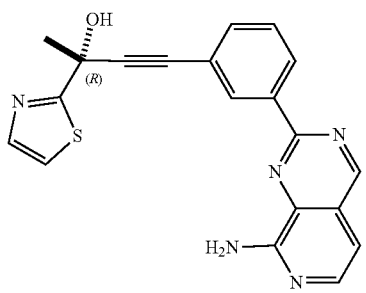

In a sealable vial were added Intermediate 28: [2-(3-bromophenyl)pyrido[3,4-d]pyrimidin-8-amine (80 mg, 0.26 mmol)], Intermediate 30: [(R)-2-thiazol-2-ylbut-3-yn-2-ol (62 mg, 0.39 mmol)], CuI (5 mg, 0.026 mmol), and PdCl$_2$(PPh$_3$)$_2$ (9 mg, 0.013 mmol). The vial was then charged with degassed anhydrous DMF (1.6 mL) followed by addition of TEA (80 μL, 5.7 mmol). The vial was sealed and heated to 80° C. for 16 h, cooled to rt, and then partitioned between DCM (10 mL) and water (10 mL). The organic layer was separated and concentrated to dryness. The resulting residue was purified by FCC (gradient of ethyl acetate: 10% MeOH in hexanes 0 to 80%) followed by purification by preparative HPLC (XBridge Prep C18 5 μm (100×50 mm); Gradient 5 to 99% ACN/ammonium hydroxide 20 mM over 12 min; Flow rate, 40 mL/min; Detection, UV at λ=254 nM) to afford (R)-4-[3-(8-amminopyrido[3,4-d]pyrimidin-2-yl)phenyl]-2-thiazol-2-yl-but-3-yn-2-ol (23 mg, 23%) as a colorless solid. MS (ESI): mass calcd. for $C_{20}H_{15}N_5OS$, 373.4; m/z. found, 374.1 [M+H]$^+$. $^1$H NMR (500 MHz, CDCl$_3$) δ 9.34 (s, 1H), 8.70-8.64 (m, 1H), 8.57-8.50 (m, 1H), 8.10 (d, J=5.7 Hz, 1H), 7.82 (d, J=3.2 Hz, 1H), 7.62 (dt, J=7.6, 1.4 Hz, 1H), 7.49 (td, J=7.8, 0.6 Hz, 1H), 7.39 (d, J=3.2 Hz, 1H), 7.02 (d, J=5.7 Hz, 1H), 6.06 (s, 2H), 3.87 (s, 1H), 2.11 (s, 3H).

Example 33: 1-[2-[3-(8-Aminopyrido[3,4-d]pyrimidin-2-yl)phenyl]ethynyl]cyclopentanol

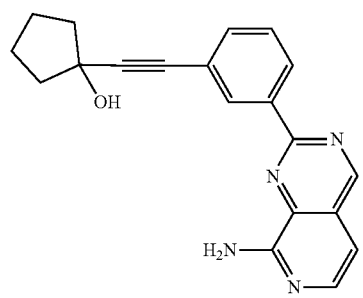 [SMILES: Nc1nccc2cnc(-c3cccc(C#CC4(O)CCCC4)c3)nc12]

The title compound was prepared using analogous conditions described in Example 32 [(R)-4-[3-(8-aminopyrido[3,4-d]pyrimidin-2-yl)phenyl]-2-thiazol-2-yl-but-3-yn-2-ol using 1-ethynylcyclopentan-1-ol] to afford 1-[2-[3-(8-aminopyrido[3,4-d]pyrimidin-2-yl)phenyl]ethynyl]cyclopentanol (34 mg, 26%) as colorless solid. MS (ESI): mass calcd. for $C_{20}H_{18}N_4O$, 330.4; m/z. found, 331.0 [M+H]$^+$. $^1$H NMR (500 MHz, CDCl$_3$) δ 9.35 (s, 1H), 8.66-8.60 (m, 1H), 8.56-8.44 (m, 1H), 8.10 (d, J=5.7 Hz, 1H), 7.58 (dt, J=7.7, 1.4 Hz, 1H), 7.49 (t, J=7.7 Hz, 1H), 7.02 (d, J=5.7 Hz, 1H), 6.06 (s, 2H), 2.19-2.03 (m, 5H), 1.98-1.79 (m, 4H).

Example 34: (R)-4-[3-(8-Aminopyrido[3,4-d]pyrimidin-2-yl)phenyl]-2-(5-methylisoxazol-3-yl)but-3-yn-2-ol

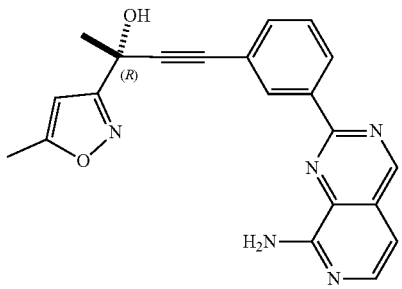

The title compound was prepared using analogous conditions described in Example 1 [(R)-3-[2-[3-(8-aminopyrido[3,4-d]pyrimidin-2-yl)phenyl]ethynyl]-3-hydroxy-1-methyl-pyrrolidin-2-one] using Intermediate 1 [2-(3-iodophenyl)pyrido[3,4-d]pyrimidin-8-amine] and Intermediate 32 [(R)-2-(5-methylisoxazol-3-yl)but-3-yn-2-ol] to afford (R)-4-[3-(8-aminopyrido[3,4-d]pyrimidin-2-yl)phenyl]-2-(5-methylisoxazol-3-yl)but-3-yn-2-ol (68 mg, 53%) as a colorless solid. MS (ESI): mass calcd. for $C_{21}H_{17}N_5O_2$, 371.4; m/z. found, 354.1 [M+H]$^+$. $^1$H NMR (400 MHz, CDCl$_3$) δ 9.32 (s, 1H), 8.61 (t, J=1.7 Hz, 1H), 8.52 (dt, J=7.8, 1.5 Hz, 1H), 8.10 (d, J=5.7 Hz, 1H), 7.59 (dt, J=7.7, 1.5 Hz, 1H), 7.48 (t, J=7.7 Hz, 1H), 7.30 (s, 1H), 7.01 (d, J=5.8 Hz, 1H), 6.27-6.24 (m, 1H), 6.19 (s, 2H), 2.50 (s, 3H), 2.04 (s, 3H).

Example 35: 4-[3-(8-Aminopyrido[3,4-d]pyrimidin-2-yl)phenyl]-2-methyl-but-3-yn-2-ol

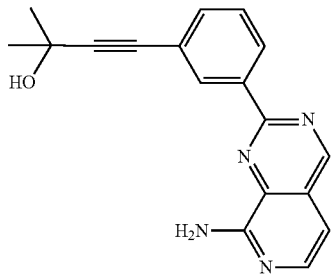 [SMILES: CC(C)(O)C#Cc1cccc(-c2ncc3ccnc(N)c3n2)c1]

The title compound was prepared using analogous conditions described in Example 1 [(R)-3-[2-[3-(8-aminopyrido[3,4-d]pyrimidin-2-yl)phenyl]ethynyl]-3-hydroxy-1-methyl-pyrrolidin-2-one] using Intermediate 1 [2-(3-iodophenyl)pyrido[3,4-d]pyrimidin-8-amine] and 2-methylbut-3-yn-2-ol to afford 4-[3-(8-aminopyrido[3,4-d]pyrimidin-2-yl)phenyl]-2-methyl-but-3-yn-2-ol (55 mg, 52%) as colorless solid. MS (ESI): mass calcd. for $C_{18}H_{16}N_4O$, 304.4; m/z. found, 306.1 [M+H]$^+$. $^1$H NMR (500 MHz, CDCl$_3$) δ 9.36 (s, 1H), 8.67-8.61 (m, 1H), 8.56-8.51 (m, 1H), 8.11 (d, J=5.7 Hz, 1H), 7.60-7.56 (m, 1H), 7.52-7.45 (m, 1H), 7.03 (d, J=5.7 Hz, 1H), 6.03 (s, 2H), 2.14 (s, 1H), 1.69 (s, 6H).

Example 36: (R)-3-[2-[3-(1-Amino-7-isoquinolyl)phenyl]ethynyl]-3-hydroxy-1-methyl-pyrrolidin-2-one

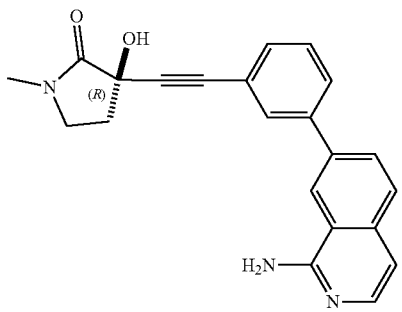

The title compound was prepared using analogous conditions described in Example 16 [(R)-3-[2-[3-(4-aminoquinazolin-6-yl)phenyl]ethynyl]-3-hydroxy-1-methyl-pyrrolidin-2-one] using 7-bromoisoquinolin-1-amine to afford (R)-3-[2-[3-(1-Amino-7-isoquinolyl)phenyl]ethynyl]-3-hydroxy-1-methyl-pyrrolidin-2-one (9 mg, 11%) as a colorless solid. MS (ESI): mass calcd. for $C_{22}H_{19}N_3O_2$, 357.4; m/z. found, 358.2 [M+H]$^+$. $^1$H NMR (400 MHz, DMSO-d$_6$) δ 8.56 (s, 1H), 7.99 (dd, J=8.5, 1.7 Hz, 1H), 7.93-7.85 (m, 2H), 7.84-7.74 (m, 2H), 7.54 (t, J=7.7 Hz, 1H), 7.45 (dt, J=7.7, 1.3 Hz, 1H), 7.02 (s, 2H), 6.94 (d, J=5.8 Hz, 1H), 6.50 (s, 1H), 3.40-3.35 (m, 2H), 2.82 (s, 3H), 2.48-2.43 (m, 1H), 2.25-2.16 (m, 1H).

Example 37: (R)-3-((3-(8-Amino-4-methylpyrido[3,4-d]pyrimidin-2-yl)phenyl)ethynyl)-3-hydroxy-1-methylpyrrolidin-2-one, and its trifluoroacetate

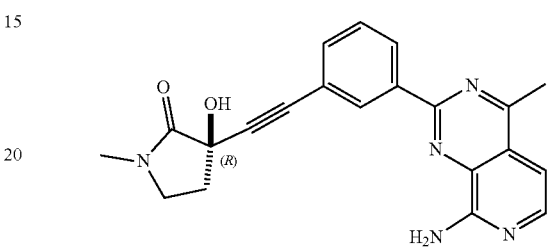

(R)-3-((3-(8-Amino-4-methylpyrido[3,4-d]pyrimidin-2-yl)phenyl)ethynyl)-3-hydroxy-1-methylpyrrolidin-2-one was prepared using conditions analogous to those described in Example 1 using Intermediate 34 [2-(3-iodophenyl)-4-methylpyrido[3,4-d]pyrimidin-8-amine]. It was then purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100% 5 min. Detection, UV at λ=220-254 nM to afford (R)-3-((3-(8-amino-4-methylpyrido[3,4-d]pyrimidin-2-yl)phenyl)ethynyl)-3-hydroxy-1-methylpyrrolidin-2-one trifluoroacetate. MS (ESI): mass calcd. for $C_{21}H_{19}N_5O_2$, 373.15; m/z. found, 374.2 [M+H]$^+$. $^1$H NMR (400 MHz, CD$_3$OD) δ 8.76-8.71 (m, 1H), 8.69-8.62 (m, 1H), 7.68 (d, J=7.1 Hz, 1H), 7.63-7.57 (m, 1H), 7.51 (t, J=7.7 Hz, 1H), 7.33 (d, J=7.1 Hz, 1H), 3.54-3.47 (m, 2H), 2.96 (s, 6H), 2.67-2.58 (m, 1H), 2.40-2.30 (m, 1H).

Example 38: (R)-3-((3-(8-Amino-4-(trifluoromethyl)pyrido[3,4-d]pyrimidin-2-yl)phenyl)ethynyl)-3-hydroxy-1-methylpyrrolidin-2-one, and its trifluoroacetate

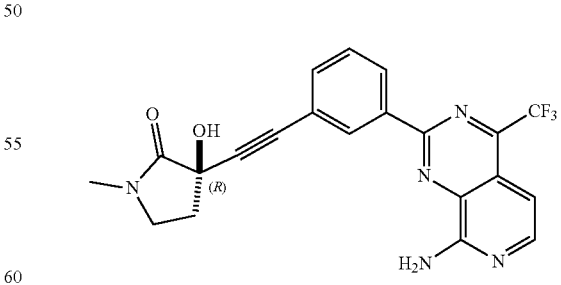

To a vial were added Intermediate 35 [2-(3-bromophenyl)-4-(trifluoromethyl)pyrido[3,4-d]pyrimidin-8-amine (0.199 g, 0.539 mmol)], Intermediate 2 [(R)-3-ethynyl-3-hydroxy-1-methylpyrrolidin-2-one (0.113 g, 0.812 mmol), CuI (0.011 g, 0.058 mmol)], and bis(triphenylphosphine)palladium(II) dichloride (0.040 g, 0.057 mmol). The vial was sealed with a septum, evacuated, and then purged with N₂ (3×). The vial was charged with dry DMF (4 mL) followed by DIPEA (0.3 mL, 1.741 mmol) and placed in a heating block that had been pre-heated at 100° C. After 1 h, the resulting mixture was cooled to rt, filtered through a PTFE membrane filter (0.45 μm) to provide (R)-3-((3-(8-amino-4-(trifluoromethyl)pyrido[3,4-d]pyrimidin-2-yl)phenyl)ethynyl)-3-hydroxy-1-methylpyrrolidin-2-one which was then purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100% 5 min. Detection, UV at λ=220-254 nM to afford (R)-3-((3-(8-amino-4-(trifluoromethyl)pyrido[3,4-d]pyrimidin-2-yl) phenyl)ethynyl)-3-hydroxy-1-methylpyrrolidin-2-one trifluoroacetate (183 mg, 63%). MS (ESI): mass calcd. for $C_{21}H_{16}F_3N_5O_2$, 427.13; m/z. found, 428.1 [M+H]⁺. ¹H NMR (400 MHz, CD₃OD) δ 8.83-8.79 (m, 1H), 8.72-8.67 (m, 1H), 7.83 (d, J=7.1 Hz, 1H), 7.71-7.65 (m, 1H), 7.58 (t, J=7.8 Hz, 1H), 7.31-7.25 (m, 1H), 3.53-3.47 (m, 2H), 2.95 (s, 3H), 2.67-2.59 (m, 1H), 2.40-2.30 (m, 1H).

Example 39: (R)-3-((3-(8-Amino-5-methylpyrido[3,4-d]pyrimidin-2-yl)phenyl)ethynyl)-3-hydroxy-1-methylpyrrolidin-2-one, and its trifluoroacetate

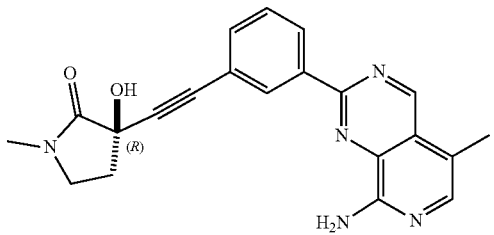

(R)-3-((3-(8-Amino-5-methylpyrido[3,4-d]pyrimidin-2-yl)phenyl)ethynyl)-3-hydroxy-1-methylpyrrolidin-2-one was prepared using conditions analogous to those described in Example 38 using Intermediate 36 [2-(3-bromophenyl)-5-methylpyrido[3,4-d]pyrimidin-8-amine] and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100% 5 min. Detection, UV at λ=220-254 nM to afford (R)-3-((3-(8-amino-5-methylpyrido[3,4-d]pyrimidin-2-yl)phenyl)ethynyl)-3-hydroxy-1-methylpyrrolidin-2-one trifluoroacetate. MS (ESI): mass calcd. for $C_{21}H_{19}N_5O_2$, 373.15; m/z. found, 374.1 [M+H]⁺. ¹H NMR (400 MHz, CD₃OD) δ 9.70 (s, 1H), 8.83-8.77 (m, 1H), 8.72-8.67 (m, 1H), 7.67-7.62 (m, 1H), 7.57-7.52 (m, 1H), 7.51-7.47 (m, 1H), 3.54-3.46 (m, 2H), 2.96 (s, 3H), 2.67-2.59 (m, 1H), 2.57-2.52 (m, 3H), 2.39-2.30 (m, 1H).

Example 40: (R)-3-((5-(8-Aminopyrido[3,4-d]pyrimidin-2-yl)-2-methylphenyl)ethynyl)-3-hydroxy-1-methylpyrrolidin-2-one, and its trifluoroacetate

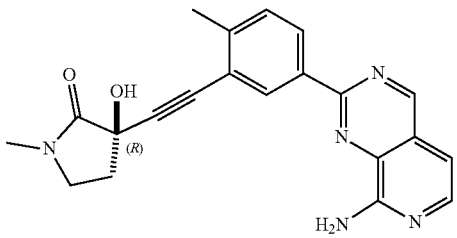

Step A: 2-(3-Bromo-4-methylphenyl)-8-chloropyrido[3,4-d]pyrimidine. A heterogenous mixture of 3-amino-2-chloroisonicotinaldehyde (0.21 g, 1.33 mmol), (3-bromo-4-methylphenyl)methanamine (0.51 g, 2.56 mmol) and ceric ammonium nitrate (0.07 g, 0.13 mmol) in MeCN (5 mL) was treated with tert-butyl hydroperoxide (1.1 mL, 5.9 M in decane). The reaction vessel was sealed with a septum and then placed in a heating block that had been pre-heated at 80° C. After 16 hours, the resulting mixture was cooled to rt, diluted with DCM (5 mL), and filtered through a pad of diatomaceous earth. The filtrate was concentrated to near dryness and then purified via FCC to yield 2-(3-bromo-4-methylphenyl)-8-chloropyrido[3,4-d]pyrimidine (130 mg, 29%). MS (ESI): mass calcd. for $C_{14}H_9BrClN_3$, 332.97; m/z. found, 334.0 [M+H]⁺. ¹H NMR (400 MHz, CDCl₃) δ 9.52 (s, 1H), 8.82 (d, J=1.7 Hz, 1H), 8.53-8.47 (m, 2H), 7.69 (d, J=5.4 Hz, 1H), 7.40 (d, J=8.0 Hz, 1H), 2.50 (s, 3H).

Step B: 2-(3-Bromo-4-methylphenyl)pyrido[3,4-d]pyrimidin-8-amine. In a 10 mL microwave vial, a homogeneous solution of 2-(3-bromo-4-methylphenyl)-8-chloropyrido[3,4-d]pyrimidine (0.13 g, 0.39 mmol) in THF (2 mL) was treated with NH₃ in MeOH (2 mL, 7N). The vial was crimp-sealed and heated in a microwave reactor at 150° C. for 2 h. The reaction mixture was concentrated to near dryness and further dried under high-vacuum to yield 2-(3-bromo-4-methylphenyl)pyrido[3,4-d]pyrimidin-8-amine (123 mg, 99%) which was used without further purification. MS (ESI): mass calcd. for $C_{14}H_{11}BrN_4$, 314.02; m/z. found, 315.0 [M+H]⁺.

Step C: (R)-3-((5-(8-aminopyrido[3,4-d]pyrimidin-2-yl)-2-methylphenyl)ethynyl)-3-hydroxy-1-methylpyrrolidin-2-one was prepared using conditions analogous to those described in Example 38 using 2-(3-bromo-4-methylphenyl)pyrido[3,4-d]pyrimidin-8-amine and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100% 5 min. Detection, UV at λ=220-254 nM to afford (R)-3-((5-(8-aminopyrido[3,4-d]pyrimidin-2-yl)-2-methylphenyl)ethynyl)-3-hydroxy-1-methylpyrrolidin-2-one trifluoroacetate (61 mg, 32%) as white solid. MS (ESI): mass calcd. for $C_{21}H_{19}N_5O_2$, 373.15; m/z. found, 374.3 [M+H]⁺. ¹H NMR (400 MHz, CD₃OD) δ 9.55 (s, 1H), 8.74 (d, J=1.8 Hz, 1H), 8.60-8.53 (m, 1H), 7.68 (d, J=6.9 Hz, 1H), 7.43 (d, J=8.1 Hz, 1H), 7.25 (d, J=6.9 Hz, 1H), 3.55-3.48 (m, 2H), 2.96 (s, 3H), 2.68-2.59 (m, 1H), 2.51 (s, 3H), 2.42-2.34 (m, 1H).

Example 41: (R)-3-((3-(8-Aminopyrido[3,4-d]pyrimidin-2-yl)-2-methylphenyl)ethynyl)-3-hydroxy-1-methylpyrrolidin-2-one, and its trifluoroacetate

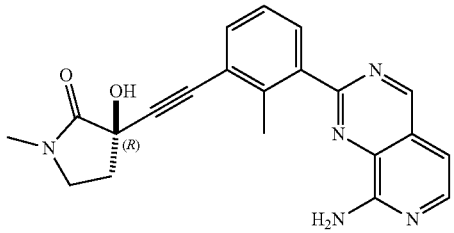

(R)-3-((3-(8-Aminopyrido[3,4-d]pyrimidin-2-yl)-2-methylphenyl)ethynyl)-3-hydroxy-1-methylpyrrolidin-2-one was prepared using conditions analogous to those described in Example 40, using (3-bromo-2-methylphenyl)methanamine in Step A and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100% 5 min. Detection, UV at λ=220-254 nM to afford (R)-3-((3-(8-aminopyrido[3,4-d]pyrimidin-2-yl)-2-methylphenyl)ethynyl)-3-hydroxy-1-methylpyrrolidin-2-one trifluoroacetate (14 mg, 17%) as a white solid. MS (ESI): mass calcd. for $C_{21}H_{19}N_5O_2$, 373.15; m/z. found, 374.1 [M+H]$^+$. $^1$H NMR (400 MHz, CD$_3$OD) δ 9.64 (s, 1H), 7.92 (d, J=7.7 Hz, 1H), 7.74 (d, J=6.9 Hz, 1H), 7.62 (d, J=7.6 Hz, 1H), 7.40-7.31 (m, 2H), 3.52-3.45 (m, 2H), 2.93 (s, 3H), 2.67 (s, 3H), 2.64-2.55 (m, 1H), 2.37-2.32 (m, 1H).

Example 42: (R)-3-((3-(8-Aminopyrido[3,4-d]pyrimidin-2-yl)-5-methylphenyl)ethynyl)-3-hydroxy-1-methylpyrrolidin-2-one, and its trifluoroacetate

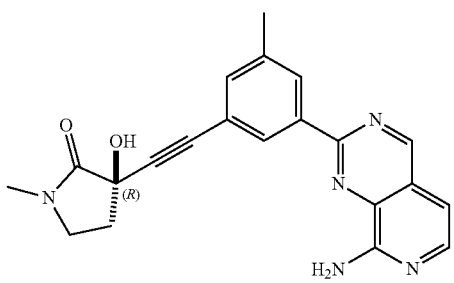

(R)-3-((3-(8-aminopyrido[3,4-d]pyrimidin-2-yl)-5-methylphenyl)ethynyl)-3-hydroxy-1-methylpyrrolidin-2-one was prepared using conditions analogous to those described in Example 40 using (3-bromo-5-methylphenyl)methanamine in Step A and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100% 5 min. Detection, UV at λ=220-254 nM to afford (R)-3-((3-(8-aminopyrido[3,4-d]pyrimidin-2-yl)-5-methylphenyl)ethynyl)-3-hydroxy-1-methylpyrrolidin-2-one trifluoroacetate (130 mg, 55%) as a white solid. MS (ESI): mass calcd. for $C_{21}H_{19}N_5O_2$, 373.15; m/z. found, 374.3 [M+H]$^+$. $^1$H NMR (400 MHz, CD$_3$OD) δ 9.55 (s, 1H), 8.52 (d, J=7.9 Hz, 2H), 7.70 (d, J=6.9 Hz, 1H), 7.42 (s, 1H), 7.26 (d, J=6.9 Hz, 1H), 3.54-3.47 (m, 2H), 2.96 (s, 3H), 2.66-2.57 (m, 1H), 2.44 (s, 3H), 2.39-2.32 (m, 1H).

Example 43: (R)-3-((3-(8-Aminopyrido[3,4-d]pyrimidin-2-yl)-4-methylphenyl)ethynyl)-3-hydroxy-1-methylpyrrolidin-2-one, and its trifluoroacetate

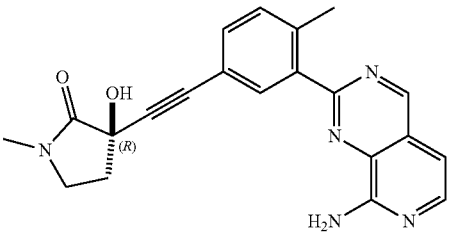

(R)-3-((3-(8-Aminopyrido[3,4-d]pyrimidin-2-yl)-4-methylphenyl)ethynyl)-3-hydroxy-1-methylpyrrolidin-2-one was prepared using conditions analogous to those described in Example 40 using (5-bromo-2-methylphenyl)methanamine in Step A and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-3-((3-(8-aminopyrido[3,4-d]pyrimidin-2-yl)-4-methylphenyl)ethynyl)-3-hydroxy-1-methylpyrrolidin-2-one trifluoroacetate (76 mg, 42%) as a white solid. MS (ESI): mass calcd. for $C_{21}H_{19}N_5O_2$, 373.15; m/z. found, 374.1 [M+H]$^+$. $^1$H NMR (400 MHz, CD$_3$OD) δ 9.63 (s, 1H), 8.17 (d, J=1.6 Hz, 1H), 7.74 (d, J=6.9 Hz, 1H), 7.52-7.48 (m, 1H), 7.37 (d, J=8.0 Hz, 1H), 7.31 (d, J=6.9 Hz, 1H), 3.51-3.43 (m, 2H), 2.93 (s, 3H), 2.66 (s, 3H), 2.63-2.54 (m, 3H), 2.35-2.28 (m, 1H).

Example 44: (R)-3-((3-(8-Amino-6-methylpyrido[3,4-d]pyrimidin-2-yl)phenyl)ethynyl)-3-hydroxy-1-methylpyrrolidin-2-one, and its trifluoroacetate

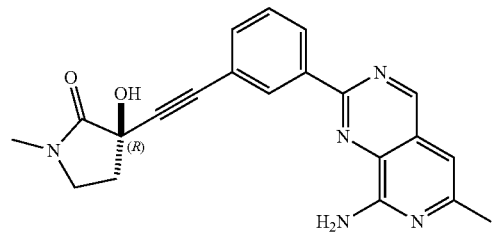

(R)-3-((3-(8-Amino-6-methylpyrido[3,4-d]pyrimidin-2-yl)phenyl)ethynyl)-3-hydroxy-1-methylpyrrolidin-2-one was prepared using conditions analogous to those described in Example 1, using Intermediate 37 [2-(3-iodophenyl)-6-methylpyrido[3,4-d]pyrimidin-8-amine] and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-3-((3-(8-amino-6-methylpyrido[3,4-d]pyrimidin-2-yl)phenyl)ethynyl)-3-hydroxy-1-methylpyrrolidin-2-one trifluoroacetate (92 mg, 34%) as a white solid. MS (ESI): mass calcd. for C$_{21}$H$_{19}$N$_{5}$O$_{2}$, 373.15; m/z. found, 374.3 [M+H]$^{+}$. $^{1}$H NMR (400 MHz, CD$_{3}$OD) δ 9.42 (s, 1H), 8.67 (t, J=1.5 Hz, 1H), 8.62-8.57 (m, 1H), 7.61-7.55 (m, 1H), 7.49 (t, J=7.8 Hz, 1H), 7.00 (d, J=1.0 Hz, 1H), 3.55-3.48 (m, 2H), 2.97 (s, 3H), 2.67-2.59 (m, 1H), 2.56 (s, 3H), 2.41-2.31 (m, 1H).

Example 45: (R)-7-[2-[3-(8-Aminopyrido[3,4-d] pyrimidin-2-yl)phenyl]ethynyl]-5,6-dihydrocyclopenta[b]pyridin-7-ol

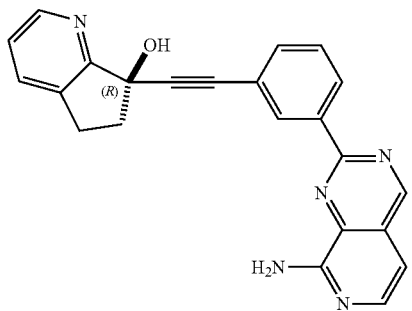

(R)-7-[2-[3-(8-aminopyrido[3,4-d]pyrimidin-2-yl)phenyl]ethynyl]-5,6-dihydrocyclopenta[b]pyridin-7-ol was prepared using analogous conditions described in Example 1 using Intermediate 38 [(R)-7-ethynyl-6,7-dihydro-5H-cyclopenta[b]pyridin-7-ol] to afford (R)-7-[2-[3-(8-aminopyrido[3,4-d]pyrimidin-2-yl)phenyl]ethynyl]-5,6-dihydrocyclopenta[b]pyridin-7-ol (59 mg, 43%) a white solid. MS (ESI): mass calcd. for C$_{23}$H$_{17}$N$_{5}$O, 379.4; m/z. found, 380.1 [M+H]$^{+}$. $^{1}$H NMR (500 MHz, DMSO-d$_{6}$) δ 9.52 (s, 1H), 8.71-8.68 (m, 1H), 8.67-8.65 (m, 1H), 8.50-8.43 (m, 1H), 8.00 (d, J=5.6 Hz, 1H), 7.80-7.71 (m, 1H), 7.60-7.54 (m, 2H), 7.44 (s, 2H), 7.31-7.26 (m, 1H), 7.02 (d, J=5.6 Hz, 1H), 6.25 (s, 1H), 3.09-2.88 (m, 2H), 2.67-2.58 (m, 1H), 2.46-2.35 (m, 1H).

Example 46: (S)-7-[2-[3-(8-Aminopyrido[3,4-d] pyrimidin-2-yl)phenyl]ethynyl]-5,6-dihydrocyclopenta[b]pyridin-7-ol

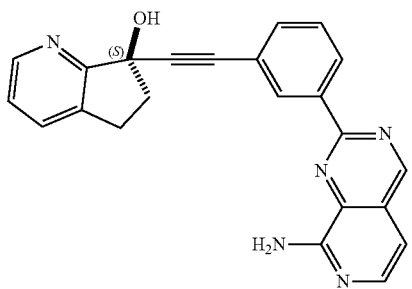

The title compound was prepared using analogous conditions described in Example 1 using Intermediate 39 [(S)-7-ethynyl-6,7-dihydro-5H-cyclopenta[b]pyridin-7-ol] to afford (S)-7-[2-[3-(8-aminopyrido[3,4-d]pyrimidin-2-yl) phenyl]ethynyl]-5,6-dihydrocyclopenta[b]pyridin-7-ol (47 mg, 35%). MS (ESI): mass calcd. for C$_{23}$H$_{17}$N$_{5}$O, 379.4; m/z. found, 380.1 [M+H]$^{+}$. $^{1}$H NMR (500 MHz, DMSO-d$_{6}$) δ 9.52 (s, 1H), 8.72-8.68 (m, 1H), 8.68-8.66 (m, 1H), 8.49-8.45 (m, 1H), 8.01 (d, J=5.6 Hz, 1H), 7.77-7.70 (m, 1H), 7.59-7.53 (m, 2H), 7.44 (s, 2H), 7.35-7.27 (m, 1H), 7.02 (d, J=5.6 Hz, 1H), 6.25 (s, 1H), 3.08-2.98 (m, 1H), 2.97-2.87 (m, 1H), 2.65-2.56 (m, 1H), 2.47-2.33 (m, 1H).

Example 47: (R)-2-[3-[2-(7-Hydroxy-5,6-dihydrocyclopenta[b]pyridin-7-yl)ethynyl]phenyl]-7H-pyrido[3,4-d]pyrimidin-8-one

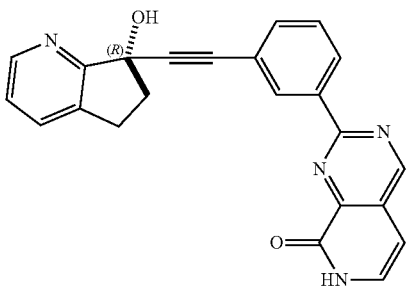

To a flask were added Intermediate 40 [2-(3-iodophenyl) pyrido[3,4-d]pyrimidin-8(7H)-one (100 mg, 0.286 mmol)], Intermediate 38 [(R)-7-ethynyl-6,7-dihydro-5H-cyclopenta[b]pyridin-7-ol (115 mg, 0.722 mmol)], Et$_{3}$N (290 mg, 2.87 mmol), copper(I) iodide (7 mg, 0.06 mmol) and THF (2 mL). The mixture was sparged with N$_{2}$ for 5 min and then Pd(PPh$_{3}$)Cl$_{2}$ (20 mg, 0.028 mmol) was added. The mixture was sparged with N2 for 5 min and then stirred at 50° C. for 16 h. The resulting suspension was filtered through a pad of diatomaceous earth and the filtrate was concentrated to dryness. The residue was purified by preparative HPLC (Xtimate C18, 150×25 mm×5 µm column (eluent: 26% to 56% (v/v) CH$_{3}$CN and H$_{2}$O with 0.225 HCOOH)). This material was further purified by SFC (YMC CHIRAL Amylose-C (250 mm×30 mm×10 µm) (eluent: 50% to 50% (v/v) H$_{2}$O/IPA with 0.1% NH$_{3}$)) to provide (R)-2-[3-[2-(7-hydroxy-5,6-dihydrocyclopenta[b]pyridin-7-yl)ethynyl]phenyl]-7H-pyrido[3,4-d]pyrimidin-8-one (56.9 mg, 51%) as a white solid. MS (ESI): mass calcd. for C$_{23}$H$_{16}$N$_{4}$O$_{2}$, 380.1; m/z. found, 381.0 [M+H]$^{+}$. $^{1}$H NMR (400 MHz, DMSO-d$_{6}$): δ 11.99 (br. s, 1H), 9.48 (s, 1H), 8.52 (s, 1H), 8.50-8.41 (m, 2H), 7.74 (d, J=7.5 Hz, 1H), 7.57 (d, J=4.9 Hz, 2H), 7.41 (br. d, J=6.8 Hz, 1H), 7.33-7.26 (m, 1H), 6.69 (d, J=6.8 Hz, 1H), 6.33 (br. s, 1H), 3.07-2.97 (m, 1H), 2.97-2.87 (m, 1H), 2.64-2.55 (m, 1H), 2.44-2.36 (m, 1H).

Example 48: (R)-4-(3-(8-Amino-4-methylpyrido[3, 4-d]pyrimidin-2-yl)phenyl)-2-(thiazol-2-yl)but-3-yn-2-ol, and its trifluoroacetate

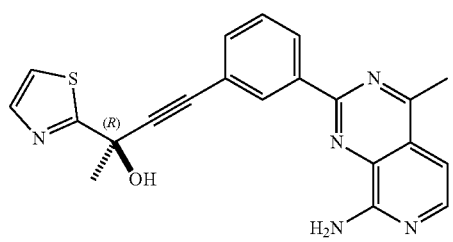

(R)-4-(3-(8-Amino-4-methylpyrido[3,4-d]pyrimidin-2-yl)phenyl)-2-(thiazol-2-yl)but-3-yn-2-ol was prepared using conditions analogous to those described in Example 1 utilizing Intermediate 34 [2-(3-iodophenyl)-4-methylpyrido[3,4-d]pyrimidin-8-amine] and Intermediate 30 [(R)-2-thiazol-2-ylbut-3-yn-2-ol] and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-4-(3-(8-amino-4-methylpyrido[3,4-d]pyrimidin-2-yl)phenyl)-2-(thiazol-2-yl)but-3-yn-2-ol trifluoroacetate (70 mg, 49%). MS (ESI): mass calcd. for $C_{21}H_{17}N_5OS$, 387.12; m/z found, 388.2 [M+H]$^+$. $^1$H NMR (400 MHz, CD$_3$OD) δ 8.82 (t, J=1.5 Hz, 1H), 8.73-8.67 (m, 1H), 7.80 (d, J=3.3 Hz, 1H), 7.70-7.63 (m, 2H), 7.59 (d, J=3.3 Hz, 1H), 7.54 (t, J=7.8 Hz, 1H), 7.37 (d, J=7.1 Hz, 1H), 2.99 (s, 3H), 1.99 (s, 3H).

Example 49: (R)-4-(3-(8-Amino-4-(trifluoromethyl)pyrido[3,4-d]pyrimidin-2-yl)phenyl)-2-(thiazol-2-yl)but-3-yn-2-ol, and its trifluoroacetate

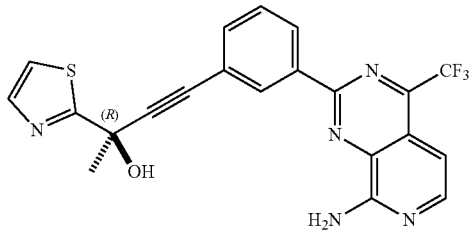

(R)-4-(3-(8-Amino-4-(trifluoromethyl)pyrido[3,4-d]pyrimidin-2-yl)phenyl)-2-(thiazol-2-yl)but-3-yn-2-ol was prepared using conditions analogous to those described in Example 1, utilizing Intermediate 35 [2-(3-bromophenyl)-4-(trifluoromethyl)pyrido[3,4-d]pyrimidin-8-amine] and Intermediate 30 [(R)-2-thiazol-2-ylbut-3-yn-2-ol] and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-4-(3-(8-amino-4-(trifluoromethyl)pyrido[3,4-d]pyrimidin-2-yl)phenyl)-2-(thiazol-2-yl)but-3-yn-2-ol trifluoroacetate (74 mg, 49%). MS (ESI): mass calcd. for $C_{21}H_{14}F_3N_5OS$, 441.09; m/z. found, 442.2 [M+H]$^+$. $^1$H NMR (400 MHz, CD$_3$OD) δ 8.87 (t, J=1.5 Hz, 1H), 8.75-8.70 (m, 1H), 7.84-7.77 (m, 2H), 7.74-7.69 (m, 1H), 7.63-7.56 (m, 2H), 7.33-7.28 (m, 1H), 1.99 (s, 3H).

Example 50: (R)-4-(3-(8-Amino-5-methylpyrido[3,4-d]pyrimidin-2-yl)phenyl)-2-(thiazol-2-yl)but-3-yn-2-ol, and its trifluoroacetate

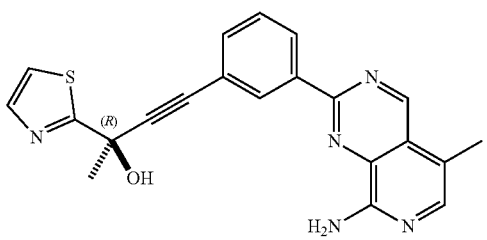

(R)-4-(3-(8-Amino-5-methylpyrido[3,4-d]pyrimidin-2-yl)phenyl)-2-(thiazol-2-yl)but-3-yn-2-ol was prepared using conditions analogous to those described in Example 1 utilizing Intermediate 36 [2-(3-bromophenyl)-5-methylpyrido[3,4-d]pyrimidin-8-amine] and Intermediate 30 [(R)-2-thiazol-2-ylbut-3-yn-2-ol] and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-4-(3-(8-amino-5-methylpyrido[3,4-d]pyrimidin-2-yl)phenyl)-2-(thiazol-2-yl)but-3-yn-2-ol trifluoroacetate (59 mg, 38%). MS (ESI): mass calcd. for $C_{21}H_{17}N_5OS$, 387.12; m/z found, 388.2 [M+H]$^+$. $^1$H NMR (400 MHz, CD$_3$OD) δ 9.71 (s, 1H), 8.83 (t, J=1.5 Hz, 1H), 8.73-8.68 (m, 1H), 7.80 (d, J=3.3 Hz, 1H), 7.68-7.63 (m, 1H), 7.59 (d, J=3.3 Hz, 1H), 7.55 (t, J=7.8 Hz, 1H), 7.49 (d, J=1.2 Hz, 1H), 2.55 (d, J=1.1 Hz, 3H), 1.99 (s, 3H).

Example 51: (R)-4-(3-(8-Amino-6-methylpyrido[3,4-d]pyrimidin-2-yl)phenyl)-2-(thiazol-2-yl)but-3-yn-2-ol, and its trifluoroacetate

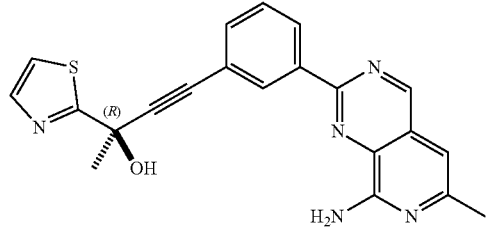

(R)-4-(3-(8-Amino-6-methylpyrido[3,4-d]pyrimidin-2-yl)phenyl)-2-(thiazol-2-yl)but-3-yn-2-ol was prepared using conditions analogous to those described in Example 1, utilizing Intermediate 37 [2-(3-iodophenyl)-6-methylpyrido[3,4-d]pyrimidin-8-amine] and Intermediate 30 [(R)-2-thiazol-2-ylbut-3-yn-2-ol] and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-4-(3-(8-amino-6-methylpyrido[3,4-d]pyrimidin-2-yl)phenyl)-2-(thiazol-2-yl)but-3-yn-2-ol trifluoroacetate (75 mg, 55%). MS (ESI): mass calcd. for $C_{21}H_{17}N_5OS$, 387.12; m/z found, 388.2 [M+H]$^+$. $^1$H NMR (400 MHz, CD$_3$OD) δ 9.49 (s, 1H), 8.80 (t, J=1.5 Hz, 1H), 8.70-8.65 (m, 1H), 7.80 (d, J=3.3 Hz, 1H), 7.67-7.62 (m, 1H), 7.59 (d, J=3.3 Hz, 1H), 7.54 (t, J=7.8 Hz, 1H), 7.05 (d, J=1.0 Hz, 1H), 2.56 (d, J=0.8 Hz, 3H), 1.99 (s, 3H).

Example 52: (R)-7-[2-[3-(8-Aminopyrido[3,4-d]pyrimidin-2-yl)-5-methyl-phenyl]ethynyl]-5,6-dihydrocyclopenta[b]pyridin-7-ol

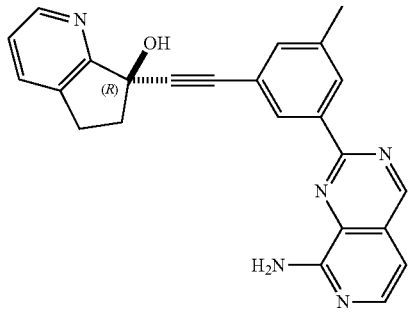

Example 53: (R)-3-((3-(8-Aminopyrido[3,4-d]pyrimidin-2-yl)-4-methoxyphenyl)ethynyl)-3-hydroxy-1-methylpyrrolidin-2-one, and its trifluoroacetate

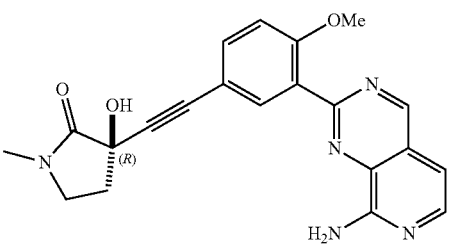

Step A: 2-(3-bromo-5-methylphenyl)pyrido[3,4-d]pyrimidin-8-amine. To a sealable vial were added Intermediate 41 [2-methylsulfanylpyrido[3,4-d]pyrimidin-8-amine (100 mg, 0.52 mmol)], (3-bromo-5-methylphenyl)boronic acid (122 mg, 0.57 mmol), Pd(PPh$_3$)$_4$ (60 mg, 0.05 mmol), and copper(I)thiophene-2-carboxylate (109 mg, 0.57 mmol). The vial was evacuated and backfilled with argon (3×). Then degassed, anhydrous THF (4 mL) was added and the reaction mixture was heated at 80° C. for 16 h. Then. the reaction progression was checked by LCMS and it was determined that no 2-methylsulfanylpyrido[3,4-d]pyrimidin-8-amine remained. The reaction mixture was diluted with ethyl acetate (20 mL) and 10% aqueous. ammonium hydroxide (20 mL). The organic layer was extracted with 10% aqueous ammonium hydroxide (20 mL×3). The combined organic layers were washed with brine (20 mL), dried over sodium sulfate, filtered and concentrated to dryness. The residue was purified by FCC (0 to 50% gradient, ethyl acetate/DCM) to afford 2-(3-bromo-5-methylphenyl)pyrido[3,4-d]pyrimidin-8-amine (29 mg). MS (ESI): mass calcd. for C$_{14}$H$_{11}$BrN$_4$, 314.02; m/z. found, 315.0 [M+H]$^+$.

Step B: (R)-7-[2-[3-(8-Aminopyrido[3,4-d]pyrimidin-2-yl)-5-methyl-phenyl]ethynyl]-5,6-dihydrocyclopenta[b]pyridin-7-ol. To a sealable vial were added 2-(3-bromo-5-methylphenyl) pyrido[3,4-d]pyrimidin-8-amine (39 mg, 0.12 mmol), Intermediate 38 [(R)-7-ethynyl-6,7-dihydro-5H-cyclopenta[b]pyridin-7-ol (36 mg, 0.22 mmol)], CuI (2.4 mg, 0.01 mmol), and PdCl$_2$(PPh$_3$)$_2$ (8.7 mg, 0.01 mmol). The vessel was evacuated and then backfilled with argon (3×). The vial was then charged with degassed anhydrous DMF (2 mL) and DIEA (64 µL, 0.37 mmol). The vessel was then placed in a pre-heated heating block at 90° C. for 16 hr. The reaction was then cooled to rt, concentrated to dryness and purified by FCC using a 0 to 10% MeOH in DCM gradient. The material was then triturated with MeCN (5 mL), filtered, and dried to afford (R)-7-[2-[3-(8-aminopyrido[3,4-d]pyrimidin-2-yl)-5-methyl-phenyl]ethynyl]-5,6-dihydrocyclopenta[b]pyridin-7-ol (19 mg, 38%) as an off-white solid. MS (ESI): mass calcd. for C$_{24}$H$_{19}$N$_5$O, 393.16; m/z. found, 394.2 [M+H]$^+$. $^1$H NMR (400 MHz, DMSO-d$_6$) δ 9.50 (s, 1H), 8.55 (s, 1H), 8.47 (d, J=4.8 Hz, 2H), 8.00 (d, J=5.6 Hz, 1H), 7.75 (d, J=7.7 Hz, 1H), 7.48 (s, 2H), 7.39 (s, 1H), 7.33-7.26 (m, 1H), 7.02 (d, J=5.6 Hz, 1H), 6.25 (s, 1H), 3.34 (s, 3H), 3.08-2.98 (m, 1H), 2.97-2.87 (m, 1H), 2.71-2.54 (m, 1H), 2.40-2.23 (m, 1H).

Step A: 2-(5-Bromo-2-methoxyphenyl)-8-chloropyrido[3,4-d]pyrimidine. A mixture of 3-amino-2-chloroisonicotinaldehyde (1.0 g, 6.4 mmol), (5-bromo-2-methoxyphenyl) methanamine (1.5 g, 6.7 mmol), and 4-hydroxy-tempo (0.3 g, 1.8 mmol) were heated for 30 minutes at 120° C. The resulting mixture was then treated with tert-butyl hydroperoxide (3 mL, 17.67 mmol, 5.9 M in decane) and stirred for another 90 min at 120° C. The mixture was cooled to rt and diluted with MeCN (5 mL). A solid precipitated and was removed via filtration. The filtrate was concentrated to dryness and purified by FCC to afford 2-(5-bromo-2-methoxyphenyl)-8-chloropyrido[3,4-d]pyrimidine (0.29 g, 13%). MS (ESI): mass calcd. for C$_{14}$H$_9$BrClN$_3$O, 348.96; m/z. found, 350.0 [M+H]$^+$.

Step B: 2-(5-Bromo-2-methoxyphenyl)pyrido[3,4-d]pyrimidin-8-amine. 2-(5-bromo-2-methoxyphenyl)-8-chloropyrido[3,4-d]pyrimidine (0.27 g, 0.77 mmol) was suspended NH$_3$ in IPA (3 mL, 2N). The vial was crimp-sealed and heated in a microwave reactor at 150° C. for 10 h. The resulting mixture was concentrated to near dryness to afford 2-(5-bromo-2-methoxyphenyl)pyrido[3,4-d]pyrimidin-8-amine (0.32 g, 99%) which was used directly in the next step without further purification. MS (ESI): mass calcd. for C$_{14}$H$_{11}$BrN$_4$O, 330.01; m/z. found, 331.0 [M+H]$^+$.

Step C: (R)-3-((3-(8-Aminopyrido[3,4-d]pyrimidin-2-yl)-4-methoxyphenyl)ethynyl)-3-hydroxy-1-methylpyrrolidin-2-one was prepared using conditions analogous to those described in Example 1, utilizing Intermediate 2 [(R)-3-ethynyl-3-hydroxy-1-methylpyrrolidin-2-one] and 2-(5-bromo-2-methoxyphenyl)pyrido[3,4-d]pyrimidin-8-amine and purified by acidic preparative reverse phase HPLC using either a Phenomenex Luna C18 250×50 mm, 5 µm or Welch Xtimate C18 250×50 mm, 10 µm; mobile phase: [water (0.1% TFA)-ACN]; B %: 10%-60%, 20 min, 100%, 5 min. Detection, UV at λ=220-254 nM to afford (R)-3-((3-(8-aminopyrido[3,4-d]pyrimidin-2-yl)-4-methoxyphenyl)ethynyl)-3-hydroxy-1-methylpyrrolidin-2-one trifluoroacetate (42 mg, 34%). MS (ESI): mass calcd. for C$_{21}$H$_{19}$N$_5$O$_3$, 389.1; m/z. found, 390.1 [M+H]$^+$. $^1$H NMR (400 MHz, CD$_3$OD) δ 9.59 (s, 1H), 8.01 (d, J=2.2 Hz, 1H), 7.74 (d, J=6.9 Hz, 1H), 7.64-7.60 (m, 1H), 7.30 (d, J=6.9 Hz, 1H), 7.20 (d, J=8.7 Hz, 1H), 3.90 (s, 3H), 3.49-3.43 (m, 2H), 2.92 (s, 3H), 2.61-2.52 (m, 1H), 2.35-2.26 (m, 1H).

Example 54: (R)-3-((3-(8-Aminopyrido[3,4-d]pyrimidin-2-yl)-4-isobutylphenyl)ethynyl)-3-hydroxy-1-methylpyrrolidin-2-one

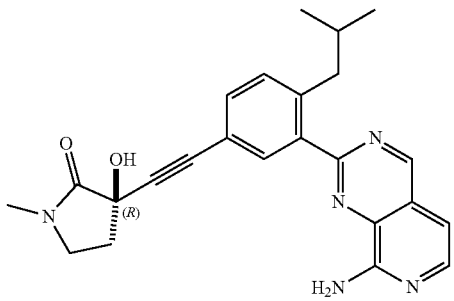

The title compound was prepared using conditions analogous to those described in Example 1, utilizing Intermediate 2 [(R)-3-ethynyl-3-hydroxy-1-methylpyrrolidin-2-one] and Intermediate 42 [2-(5-bromo-2-isobutylphenyl)pyrido[3,4-d]pyrimidin-8-amine]. Purification by FCC afforded (R)-3-((3-(8-aminopyrido[3,4-d]pyrimidin-2-yl)-4-isobutylphenyl)ethynyl)-3-hydroxy-1-methylpyrrolidin-2-one (0.1 g, 60%). MS (ESI): mass calcd. for $C_{24}H_{25}N_5O_2$, 415.20; m/z. found, 416.3 [M+H]$^+$. $^1$H NMR (400 MHz, CDCl$_3$) δ 9.16 (s, 1H), 8.12 (d, J=5.8 Hz, 1H), 7.34-7.30 (m, 1H), 7.13 (d, J=7.9 Hz, 1H), 7.06 (d, J=1.6 Hz, 1H), 7.00 (d, J=5.8 Hz, 1H), 3.55-3.44 (m, 2H), 3.17-3.08 (m, 1H), 2.98 (s, 3H), 2.68-2.59 (m, 1H), 2.58-2.50 (m, 1H), 2.48-2.38 (m, 1H), 1.51-1.39 (m, 1H), 0.70-0.60 (m, 6H).

Example 55: (R)-8-Amino-2-(3-((3-hydroxy-1-methyl-2-oxopyrrolidin-3-yl)ethynyl)phenyl)pyrido[3,4-d]pyrimidin-4(3H)-one

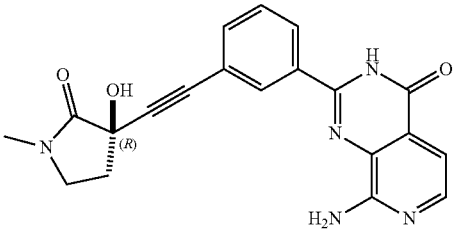

The title compound was prepared using conditions analogous to those described in Example 1, utilizing Intermediate 2 [(R)-3-ethynyl-3-hydroxy-1-methylpyrrolidin-2-one] and Intermediate 43 [8-amino-2-(3-iodophenyl)pyrido[3,4-d]pyrimidin-4(3H)-one]. Purification via FCC yielded (R)-8-amino-2-(3-((3-hydroxy-1-methyl-2-oxopyrrolidin-3-yl)ethynyl)phenyl)pyrido[3,4-d]pyrimidin-4(3H)-one (44 mg, 42%). MS (ESI): mass calcd. for $C_{20}H_{17}N_5O_3$, 375.13; m/z. found, 376.2 [M+H]$^+$. $^1$H NMR (400 MHz, CD$_3$OD) δ 8.42-8.37 (m, 1H), 8.25-8.20 (m, 1H), 7.75-7.68 (m, 2H), 7.58 (t, J=7.8 Hz, 1H), 7.35 (d, J=6.7 Hz, 1H), 3.52-3.45 (m, 2H), 2.93 (s, 3H), 2.64-2.55 (m, 1H), 2.38-2.28 (m, 1H).

Example 56: (R)-3-((3-(8-Aminopyrido[3,4-d]pyrimidin-2-yl)-4-(trifluoromethoxy)phenyl)ethynyl)-3-hydroxy-1-methylpyrrolidin-2-one, and its Trifluoroacetate

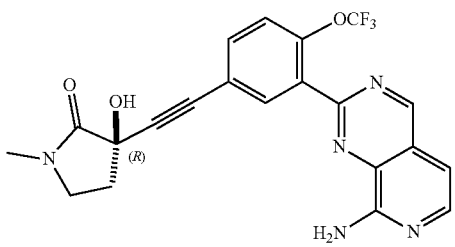

(R)-3-((3-(8-Aminopyrido[3,4-d]pyrimidin-2-yl)-4-(trifluoromethoxy)phenyl)ethynyl)-3-hydroxy-1-methylpyrrolidin-2-one was prepared in a manner analogous to Example 40, utilizing (5-bromo-2-(trifluoromethoxy)phenyl)methanamine in Step A and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-3-((3-(8-aminopyrido[3,4-d]pyrimidin-2-yl)-4-(trifluoromethoxy)phenyl)ethynyl)-3-hydroxy-1-methylpyrrolidin-2-one trifluoroacetate (30 mg, 40%). MS (ESI): mass calcd. for $C_{21}H_{16}F_3N_5O_3$, 443.12; m/z. found, 444.1 [M+H]$^+$. $^1$H NMR (400 MHz, CD$_3$OD) δ 9.67 (s, 1H), 8.40 (d, J=2.1 Hz, 1H), 7.81-7.72 (m, 2H), 7.55-7.50 (m, 1H), 7.33 (d, J=6.9 Hz, 1H), 3.51-3.44 (m, 2H), 2.93 (s, 3H), 2.64-2.55 (m, 1H), 2.37-2.28 (m, 1H).

Example 57: (R)-3-((3-(8-Amino-4-morpholinopyrido[3,4-d]pyrimidin-2-yl)phenyl)ethynyl)-3-hydroxy-1-methylpyrrolidin-2-one, and its trifluoroacetate

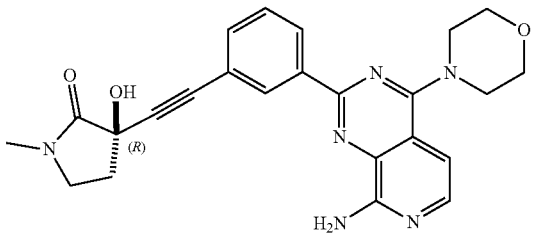

Step A: 4-(8-Chloro-2-(3-iodophenyl)pyrido[3,4-d]pyrimidin-4-yl)morpholine. To flask were added Intermediate 44 [4,8-dichloro-2-(3-iodophenyl)pyrido[3,4-d]pyrimidine (0.3 g, 0.5 mmol)] and 1,4-dioxane (5 mL), followed by DIPEA (0.4 mL, 2.3 mmol) and morpholine (0.3 mL, 3.4 mmol) at rt. After 30 min, the resulting mixture was diluted with ethyl acetate (50 mL) and washed with brine (50 mL×5). The organic layer was dried (MgSO$_4$), filtered, and concentrated to dryness. The residue was purified via FCC to afford 4-(8-chloro-2-(3-iodophenyl)pyrido[3,4-d]pyrimidin-4-yl)morpholine (0.23 g, 97%) as a white solid. MS (ESI): mass calcd. for $C_{17}H_{14}ClIN_4O$, 451.99; m/z. found, 453.0 [M+H]$^+$. $^1$H NMR (400 MHz, DMSO-d$_6$) δ 8.80-8.75

(d, J=1.5 Hz, 1H), 8.49 (d, J=7.9 Hz, 1H), 8.31 (d, J=5.6 Hz, 1H), 7.95-7.88 (m, 2H), 7.37 (t, J=7.8 Hz, 1H), 4.00-3.91 (m, 4H), 3.87-3.76 (m, 4H).

Step B: 2-(3-Iodophenyl)-4-morpholinopyrido[3,4-d]pyrimidin-8-amine was prepared using conditions analogous to those described in Step B of Example 40, utilizing 4-(8-chloro-2-(3-iodophenyl)pyrido[3,4-d]pyrimidin-4-yl)morpholine. MS (ESI): mass calcd. for $C_{17}H_{16}IN_5O$, 433.04; m/z. found, 434.1 $[M+H]^+$.

Step C: (R)-3-((3-(8-Amino-4-morpholinopyrido[3,4-d]pyrimidin-2-yl)phenyl)ethynyl)-3-hydroxy-1-methylpyrrolidin-2-one was prepared using conditions analogous to those described in Example 1, utilizing Intermediate 2 [(R)-3-ethynyl-3-hydroxy-1-methylpyrrolidin-2-one] and 2-(3-iodophenyl)-4-morpholinopyrido[3,4-d]pyrimidin-8-amine and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-3-((3-(8-amino-4-morpholinopyrido[3,4-d]pyrimidin-2-yl)phenyl)ethynyl)-3-hydroxy-1-methylpyrrolidin-2-one trifluoroacetate (28 mg, 40%). MS (ESI): mass calcd. for $C_{24}H_{24}N_6O_3$, 444.19; m/z. found, 445.3 $[M+H]^+$. $^1H$ NMR (400 MHz, $CD_3OD$) δ 8.67 (t, J=1.5 Hz, 1H), 8.61-8.56 (m, 1H), 7.63-7.58 (m, 1H), 7.57-7.46 (m, 2H), 7.16 (d, J=7.2 Hz, 1H), 3.98-3.86 (m, 8H), 3.54-3.46 (m, 2H), 2.95 (s, 3H), 2.65-2.57 (m, 1H), 2.39-2.29 (m, 1H).

Example 58: (R)-3-((3-(8-Amino-4-(dimethylamino)pyrido[3,4-d]pyrimidin-2-yl)phenyl)ethynyl)-3-hydroxy-1-methylpyrrolidin-2-one, and its trifluoroacetate

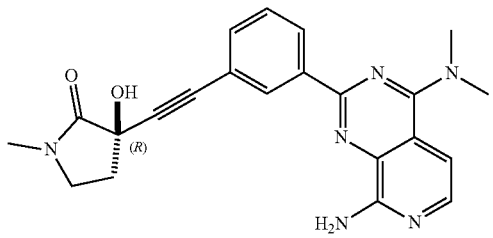

(R)-3-((3-(8-Amino-4-(dimethylamino)pyrido[3,4-d]pyrimidin-2-yl)phenyl)ethynyl)-3-hydroxy-1-methylpyrrolidin-2-one, and its trifluoroacetate were prepared in a manner analogous to Example 57 utilizing dimethylamine (2M in THF) in Step A to afford (R)-3-((3-(8-amino-4-(dimethylamino)pyrido[3,4-d]pyrimidin-2-yl)phenyl)ethynyl)-3-hydroxy-1-methylpyrrolidin-2-one trifluoroacetate (33 mg, 49%). MS (ESI): mass calcd. for $C_{22}H_{22}N_6O_2$, 402.18; m/z. found, 403.2 $[M+H]^+$. $^1H$ NMR (400 MHz, $CD_3OD$) δ 8.67 (t, J=1.5 Hz, 1H), 8.61-8.57 (m, 1H), 7.61-7.57 (m, 1H), 7.52-7.45 (m, 2H), 7.39 (d, J=7.3 Hz, 1H), 3.53-3.45 (m, 8H), 2.95 (s, 3H), 2.65-2.57 (m, 1H), 2.39-2.29 (m, 1H).

Example 59: (R)-3-[2-[3-(4-Amino-1H-imidazo[4,5-c]pyridin-2-yl)phenyl]ethynyl]-3-hydroxy-1-methyl-pyrrolidin-2-one

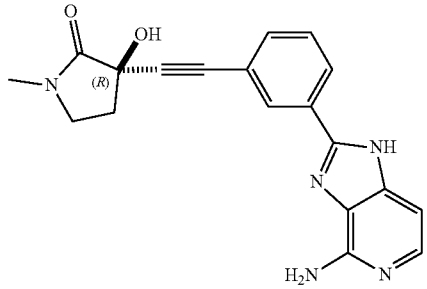

Step A: 2-(3-Bromophenyl)-4-chloro-1H-imidazo[4,5-c]pyridine. To a sealable pressure tube were added 4-amino-2-chloro-3-nitropyridine (500 mg, 2.9 mmol), 3-bromobenzaldehyde (0.35 mL, 3.0 mmol), sodium hydrosulfite (649 mg, 3.2 mmol), and ethanol (5.8 mL). The solution was heated at 80° C. for 16 h. Then additional sodium hydrosulfite (353 mg, 2.0 mmol) was added, and heating was continued for 6 h. The reaction mixture was then cooled to rt, then diluted with water (20 mL) and extracted with ethyl acetate (50 mL×3). The combined organic layers were dried over sodium sulfate, filtered, and concentrated to dryness. The residue was purified by FCC (0 to 100% gradient using ethyl acetate in heptane) to provide 2-(3-bromophenyl)-4-chloro-1H-imidazo[4,5-c]pyridine (203 mg). MS (ESI): mass calcd. for $C_{12}H_7BrClN_3$, 306.95; m/z. found, 308.0 $[M+H]^+$.

Step B: 2-(3-Bromophenyl)-N-(2,4-dimethoxybenzyl)-1H-imidazo[4,5-c]pyridin-4-amine. To a sealable vial were added 2-(3-bromophenyl)-4-chloro-1H-imidazo[4,5-c]pyridine (247 mg, 0.8 mmol), 2,4-dimethoxybenzylamine (1.1 mL, 7.1 mmol), DIEA (0.6 mL, 3.2 mmol), and n-butanol (9 mL). The vial was sealed and heated at 190° C. in a microwave reactor for 30 min. The solution was then concentrated to dryness and purified by FCC (0 to 10% gradient using MeOH in DCM) to provide 2-(3-bromophenyl)-N-(2,4-dimethoxybenzyl)-1H-imidazo[4,5-c]pyridin-4-amine (70 mg). MS (ESI): mass calcd. for $C_{21}H_{19}BrN_4O_2$, 438.07; m/z. found, 439.2 $[M+H]^+$.

Step C: 2-(3-Bromophenyl)-1H-imidazo[4,5-c]pyridin-4-amine. To a sealable vial were added 2-(3-bromophenyl)-N-(2,4-dimethoxybenzyl)-1H-imidazo[4,5-c]pyridin-4-amine (70 mg, 0.16 mmol) and DCM (1 mL). To this solution was then added TFA (2.5 mL), dropwise. The reaction was stirred at rt for 1 h. The resulting mixture was concentrated to dryness then partitioned between ethyl acetate (25 mL) and saturated aqueous $NaHCO_3$ (25 mL). The organic layer was separated and the aqueous layer was extracted with additional ethyl acetate (50 mL). The combined organic layers were dried over sodium sulfate, filtered, concentrated to dryness, and used without further purification to afford 2-(3-bromophenyl)-1H-imidazo[4,5-c]pyridin-4-amine (46 mg). MS (ESI): mass calcd. for $C_{12}H_9BrN_4$, 288.00; m/z. found, 289.0 $[M+H]^+$.

Step D: (R)-3-[2-[3-(4-Amino-1H-imidazo[4,5-c]pyridin-2-yl)phenyl]ethynyl]-3-hydroxy-1-methyl-pyrrolidin-2-one. In sealable vial were added 2-(3-bromophenyl)-1H-imidazo[4,5-c]pyridin-4-amine (46 mg, 0.16 mmol), (R)-3-ethynyl-3-hydroxy-1-methylpyrrolidin-2-one (45 mg, 0.32 mmol), CuI (3 mg, 0.016 mmol), and PdCl$_2$(PPh$_3$)$_2$ (11 mg, 0.016 mmol). The vessel was evacuated and then backfilled with argon (3×). The vial was then charged with degassed anhydrous DMF (2 mL), and DIEA (82 µL, 0.48 mmol) and the reaction vessel was heated in a heating block at 100° C., for 3 h (The heating block had been preheated to 100° C.). The resulting mixture was cooled to rt, concentrated to dryness, and purified preparative reverse phase HPLC (Phenomonex Luna 5u C18(2) 100A, AXIA, 100×30 mm column using a 5 to 90% gradient of MeCN in water (both phases containing 0.1% TFA)). The pure fractions containing the title compound were combined and treated with saturated aqueous NaHCO$_3$ and extracted with ethyl acetate (25 mL×3). The combined organic layers were dried over sodium sulfate, filtered, and concentrated to dryness to afford (R)-3-[2-[3-(4-amino-1H-imidazo[4,5-c]pyridin-2-yl)phenyl]ethynyl]-3-hydroxy-1-methyl-pyrrolidin-2-one (23 mg, 42%) as a white solid. MS (ESI): mass calcd. for C$_{19}$H$_{17}$N$_5$O$_2$, 347.14; m/z. found, 348.1 [M+H]$^+$. $^1$H NMR (400 MHz, CD$_3$OD) δ 8.17 (t, J=1.7 Hz, 1H), 8.09-8.04 (m, 1H), 7.62 (d, J=6.1 Hz, 1H), 7.60-7.55 (m, 1H), 7.53 (t, J=7.6 Hz, 1H), 6.90 (d, J=6.1 Hz, 1H), 3.55-3.41 (m, 2H), 2.94 (s, 3H), 2.64-2.56 (m, 1H), 2.38-2.28 (m, 1H).

Example 60: (R)-7-((3-(8-Amino-4-methylpyrido[3,4-d]pyrimidin-2-yl)phenyl)ethynyl)-6,7-dihydro-5H-cyclopenta[b]pyridin-7-ol, and its trifluoroacetate

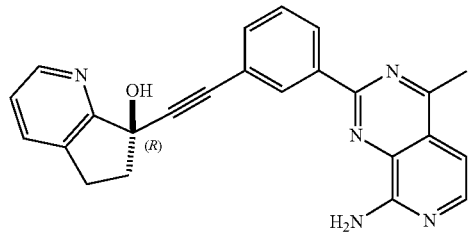

(R)-7-((3-(8-amino-4-methylpyrido[3,4-d]pyrimidin-2-yl)phenyl)ethynyl)-6,7-dihydro-5H-cyclopenta[b]pyridin-7-ol was prepared using conditions analogous to those described in Example 1 using Intermediate 34 [2-(3-iodophenyl)-4-methylpyrido[3,4-d]pyrimidin-8-amine] and Intermediate 38 [(R)-7-ethynyl-6,7-dihydro-5H-cyclopenta[b]pyridin-7-ol] and purified by acidic preparative reverse phase HPLC using either a Phenomenex Luna C18 250×50 mm, 5 µm or Welch Xtimate C18 250×50 mm, 10 µm; mobile phase: [water (0.1% TFA)-ACN]; B %: 10%-60%, 20 min, 100%, 5 min. Detection, UV at λ=220-254 nM to afford (R)-7-((3-(8-amino-4-methylpyrido[3,4-d]pyrimidin-2-yl)phenyl)ethynyl)-6,7-dihydro-5H-cyclopenta[b]pyridin-7-ol trifluoroacetate (67 mg, 78%) as a white solid. MS (ESI): mass calcd. for C$_{24}$H$_{19}$N$_5$O, 393.16; m/z. found, 394.2 [M+H]$^+$. $^1$H NMR (400 MHz, CD$_3$OD) δ 8.77 (s, 1H), 8.66 (d, J=8.0 Hz, 1H), 8.54 (d, J=4.6 Hz, 1H), 7.99 (d, J=7.6 Hz, 1H), 7.68 (d, J=7.1 Hz, 1H), 7.62 (d, J=7.7 Hz, 1H), 7.55-7.48 (m, 2H), 7.34 (d, J=7.1 Hz, 1H), 3.25-3.16 (m, 1H), 3.14-3.05 (m, 1H), 2.97 (s, 3H), 2.85-2.75 (m, 1H), 2.62-2.52 (m, 1H).

Example 61: (R)-7-((3-(8-Amino-4-(trifluoromethyl)pyrido[3,4-d]pyrimidin-2-yl)phenyl)ethynyl)-6,7-dihydro-5H-cyclopenta[b]pyridin-7-ol, and its trifluoroacetate

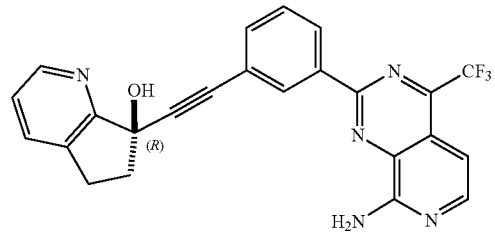

(R)-7-((3-(8-amino-4-(trifluoromethyl)pyrido[3,4-d]pyrimidin-2-yl)phenyl)ethynyl)-6,7-dihydro-5H-cyclopenta[b]pyridin-7-ol was prepared using conditions analogous to those described in Example 1, utilizing Intermediate 35 [2-(3-bromophenyl)-4-(trifluoromethyl)pyrido[3,4-d]pyrimidin-8-amine] and Intermediate 38 [(R)-7-ethynyl-6,7-dihydro-5H-cyclopenta[b]pyridin-7-ol] and purified by acidic preparative reverse phase HPLC using either a Phenomenex Luna C18 250×50 mm, 5 µm or Welch Xtimate C18 250×50 mm, 10 µm; mobile phase: [water (0.1% TFA)-ACN]; B %: 10%-60%, 20 min, 100%, 5 min. Detection, UV at λ=220-254 nM to afford (R)-7-((3-(8-amino-4-(trifluoromethyl)pyrido[3,4-d]pyrimidin-2-yl)phenyl)ethynyl)-6,7-dihydro-5H-cyclopenta[b]pyridin-7-ol trifluoroacetate (52 mg, 63%) as a white solid. MS (ESI): mass calcd. for C$_{24}$H$_{16}$F$_3$N$_5$O, 447.13; m/z. found, 448.2 [M+H]$^+$. $^1$H NMR (400 MHz, CD$_3$OD) δ 8.86 (s, 1H), 8.71 (d, J=8.0 Hz, 1H), 8.52 (d, J=4.7 Hz, 1H), 7.97 (d, J=7.6 Hz, 1H), 7.80 (d, J=7.2 Hz, 1H), 7.70 (d, J=7.7 Hz, 1H), 7.58 (t, J=7.8 Hz, 1H), 7.53-7.47 (m, 1H), 7.33-7.27 (m, 1H), 3.25-3.15 (m, 1H), 3.13-3.05 (m, 1H), 2.85-2.75 (m, 1H), 2.61-2.53 (m, 1H).

Example 62: (R)-7-((3-(8-Amino-5-methylpyrido[3,4-d]pyrimidin-2-yl)phenyl)ethynyl)-6,7-dihydro-5H-cyclopenta[b]pyridin-7-ol, and its trifluoroacetate

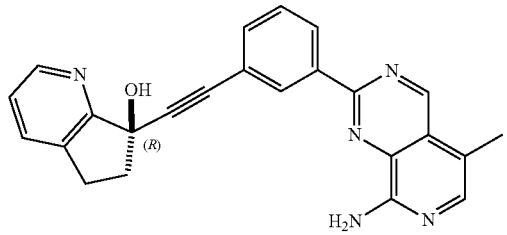

(R)-7-((3-(8-Amino-5-methylpyrido[3,4-d]pyrimidin-2-yl)phenyl)ethynyl)-6,7-dihydro-5H-cyclopenta[b]pyridin-7-ol was prepared using conditions analogous to those described in Example 1 using Intermediate 36 [2-(3-bromophenyl)-5-methylpyrido[3,4-d]pyrimidin-8-amine] and Intermediate 38 [(R)-7-ethynyl-6,7-dihydro-5H-cyclopenta[b]pyridin-7-ol] and purified by acidic preparative reverse phase HPLC using either a Phenomenex Luna C18 250×50 mm, 5 µm or Welch Xtimate C18 250×50 mm, 10 µm; mobile phase: [water (0.1% TFA)-ACN]; B %: 10%-60%, 20 min, 100%, 5 min. Detection, UV at λ=220-254 nM to afford (R)-7-((3-(8-amino-5-methylpyrido[3,4-d]pyrimidin-2-yl)phenyl)ethynyl)-6,7-dihydro-5H-cyclopenta[b]pyridin-7-ol trifluoroacetate (42 mg, 47%) as white solid. MS (ESI): mass calcd. for $C_{24}H_{19}N_5O$, 393.16; m/z. found, 394.2 [M+H]$^+$. $^1$H NMR (400 MHz, CD$_3$OD) δ 9.70 (s, 1H), 8.82 (t, J=1.5 Hz, 1H), 8.71-8.66 (m, 1H), 8.53 (d, J=4.6 Hz, 1H), 7.96 (d, J=7.7 Hz, 1H), 7.67-7.62 (m, 1H), 7.56-7.46 (m, 3H), 3.24-3.15 (m, 1H), 3.13-3.04 (m, 1H), 2.84-2.75 (m, 1H), 2.61-2.52 (m, 4H).

Example 63: (R)-7-((3-(8-amino-6-methylpyrido[3,4-d]pyrimidin-2-yl)phenyl)ethynyl)-6,7-dihydro-5H-cyclopenta[b]pyridin-7-ol, and its trifluoroacetate

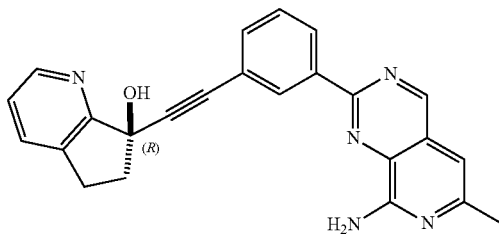

(R)-7-((3-(8-amino-6-methylpyrido[3,4-d]pyrimidin-2-yl)phenyl)ethynyl)-6,7-dihydro-5H-cyclopenta[b]pyridin-7-ol was prepared using conditions analogous to those described in Example 1 utilizing Intermediate 37 [2-(3-iodophenyl)-6-methylpyrido[3,4-d]pyrimidin-8-amine] and Intermediate 38 [(R)-7-ethynyl-6,7-dihydro-5H-cyclopenta[b]pyridin-7-ol] and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-7-((3-(8-amino-6-methylpyrido[3,4-d]pyrimidin-2-yl)phenyl)ethynyl)-6,7-dihydro-5H-cyclopenta[b]pyridin-7-ol trifluoroacetate (58 mg, 79%) as a white solid. MS (ESI): mass calcd. for $C_{24}H_{19}N_5O$, 393.16; m/z. found, 394.2 [M+H]$^+$. $^1$H NMR (400 MHz, CD$_3$OD) δ 9.48 (s, 1H), 8.79 (s, 1H), 8.69-8.62 (m, 1H), 8.53 (d, J=4.4 Hz, 1H), 7.98 (d, J=7.6 Hz, 1H), 7.64 (d, J=7.7 Hz, 1H), 7.56-7.47 (m, 2H), 7.04 (d, J=1.0 Hz, 1H), 3.24-3.15 (m, 1H), 3.14-3.05 (m, 1H), 2.85-2.75 (m, 1H), 2.61-2.52 (m, 4H).

Example 64: (S)-7-[2-[3-(8-Aminopyrido[3,4-d]pyrimidin-2-yl)phenyl]ethynyl]-5,6-dihydropyrrolo[1,2-a]imidazol-7-ol

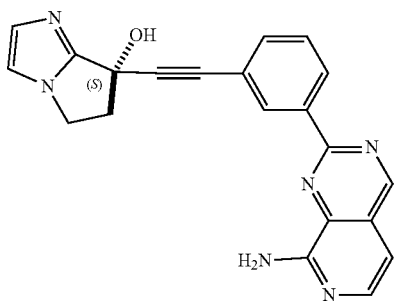

The title compound was prepared using analogous conditions described in Example 1 using Intermediate 11 [(S)-7-Ethynyl-6,7-dihydro-5H-pyrrolo[1,2-a]imidazol-7-ol] to afford (S)-7-[2-[3-(8-aminopyrido[3,4-d]pyrimidin-2-yl)phenyl]ethynyl]-5,6-dihydropyrrolo[1,2-a]imidazol-7-ol (51 mg, 48%) as white solid. MS (ESI): mass calcd. for $C_{21}H_{16}N_6O$, 368.4; m/z. found, 369.1 [M+H]$^+$. $^1$H NMR (500 MHz, CDCl$_3$) δ 8.62 (s, 1H), 7.99-7.91 (m, 1H), 7.83 (d, J=7.9 Hz, 1H), 7.14 (d, J=5.9 Hz, 1H), 6.83 (d, J=7.6 Hz, 1H), 6.73 (t, J=7.8 Hz, 1H), 6.34 (d, J=7.1 Hz, 2H), 6.26 (d, J=5.7 Hz, 1H), 3.88 (s, 1H), 3.48-3.33 (m, 2H), 2.47-2.39 (m, 1H), 2.21-2.10 (m, 1H).

Example 65: (R)-3-[2-[3-(8-Amino-5-methyl-pyrido[3,4-d]pyrimidin-2-yl)-4-methyl-phenyl]ethynyl]-3-hydroxy-1-methyl-pyrrolidin-2-one

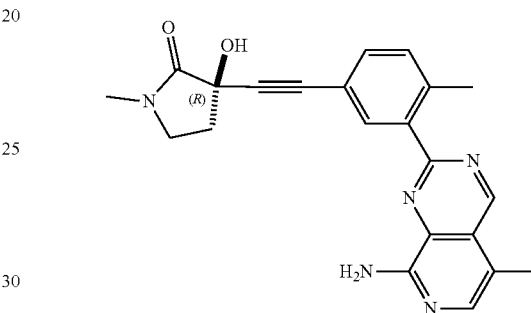

Step A: N-(4-Methoxybenzyl)-5-methyl-2-(methylthio)pyrido[3,4-d]pyrimidin-8-amine. To a sealable vial were added 8-chloro-5-methyl-2-(methylthio)pyrido[3,4-d]pyrimidine (100 mg, 0.44 mmol), Pd(OAc)$_2$ (5 mg, 0.02 mmol), BINAP (14 mg, 0.02 mmol), and K$_2$CO$_3$ (214 mg, 1.6 mmol). The vial was sealed, then evacuated and backfilled with argon (3×). To this vial was added degassed anhydrous toluene (2.2 mL), then the 4-methoxybenzylamine (70 μL, 0.53 mmol). The reaction was then heated at 130° C. for 16 h. The resulting mixture was concentrated to dryness and purified by FCC (0 to 100% gradient using ethyl acetate in heptane) to afford N-(4-methoxybenzyl)-5-methyl-2-(methylthio)pyrido[3,4-d]pyrimidin-8-amine (101 mg) as a yellow solid. MS (ESI): mass calcd. for $C_{17}H_{18}N_4OS$, 326.12; m/z. found, 327.1 [M+H]$^+$.

Step B: 2-(5-Bromo-2-methylphenyl)-N-(4-methoxybenzyl)-5-methylpyrido[3,4-d]pyrimidin-8-amine. To a sealable vial were added N-(4-methoxybenzyl)-5-methyl-2-(methylthio)pyrido[3,4-d]pyrimidin-8-amine (105 mg, 0.32 mmol), 5-bromo-2-methylphenylboronic acid (104 mg, 0.48 mmol), Pd(PPh$_3$)$_4$ (37 mg, 0.03 mmol), and copper(I)thiophene-2-carboxylate (184 mg, 0.97 mmol). The vial was evacuated and backfilled with argon (3×). Then degassed, anhydrous THF (2.5 mL) was added and the reaction was heated at 80° C. for 16 h. The resulting mixture was then cooled to rt, diluted with ethyl acetate (50 mL) and then extracted with 10% aqueous NH$_4$OH (50 mL). The organic layer was separated and the aqueous layer was washed with ethyl acetate (20 mL×3). The combined organic layers were dried over sodium sulfate, filtered and concentrated to dryness. The resulting residue was purified by FCC (100% DCM for 4 minutes and then a 0 to 50% gradient using ethyl acetate in DCM) to afford 2-(5-bromo-2-methylphenyl)-N-(4-methoxybenzyl)-5-methylpyrido[3,4-d]pyrimidin-8-amine (92 mg) a yellow oil. MS (ESI): mass calcd. for $C_{23}H_{21}BrN_4O$, 448.09; m/z. found, 449.2 [M+H]$^+$.

Step C: 2-(5-Bromo-2-methylphenyl)-5-methylpyrido[3,4-d]pyrimidin-8-amine. To a sealable vial were added 2-(5-bromo-2-methylphenyl)-N-(4-methoxybenzyl)-5-methylpyrido[3,4-d]pyrimidin-8-amine (92 mg, 0.21 mmol), and DCM (1.5 mL). To this solution was added TFA (1.5 mL). The vial was sealed, heated at 65° C. for 16 h, and then concentrated to dryness. To the resulting residue was added 50 mL of 10% 2N methanolic $NH_3$ in DCM. The resulting solution was concentrated to dryness and the residue was purified FCC (0 to 100% gradient using ethyl acetate in DCM) to afford 2-(5-bromo-2-methylphenyl)-5-methylpyrido[3,4-d]pyrimidin-8-amine (55 mg) as an off-white solid. MS (ESI): mass calcd. for $C_{15}H_{13}BrN_4$, 328.03; m/z. found, 329.1 [M+H]$^+$.

Step D: (R)-3-[2-[3-(8-Amino-5-methyl-pyrido[3,4-d]pyrimidin-2-yl)-4-methyl-phenyl]ethynyl]-3-hydroxy-1-methyl-pyrrolidin-2-one. In sealable vial were added 2-(5-bromo-2-methylphenyl)-5-methylpyrido[3,4-d]pyrimidin-8-amine (55 mg, 0.17 mmol), Intermediate 2 [(R)-3-ethynyl-3-hydroxy-1-methylpyrrolidin-2-one (43 mg, 0.30 mmol)], CuI (3 mg, 0.017 mmol), and $PdCl_2(PPh_3)_2$ (11 mg, 0.017 mmol). The vessel was evacuated and then backfilled with argon (3×). The vial was then charged with degassed anhydrous DMF (2 mL) and DIEA (87 μL, 0.50 mmol). It was then placed vessel in a heating block at 90° C. for 16 h. (The heating block had been preheated to 90° C.) The reaction mixture was cooled to rt, concentrated to dryness, and purified by FCC (0 to 10% gradient using MeOH in DCM) to afford the title compound which further purified on preparative reverse phase HPLC (Phenomonex Luna 5p C18(2) 100A, 100×30 mm column using a 5 to 90% gradient of ACN in water (both phases containing 0.1% TFA)). The fractions containing (R)-3-[2-[3-(8-amino-5-methyl-pyrido[3,4-d]pyrimidin-2-yl)-4-methyl-phenyl]ethynyl]-3-hydroxy-1-methyl-pyrrolidin-2-one were combined and treated with saturated aqueous $NaHCO_3$ and extracted with ethyl acetate (25 mL×3). The combined organic fractions were dried over sodium sulfate, filtered, and concentrated to dryness to provide (R)-3-[2-[3-(8-amino-5-methyl-pyrido[3,4-d]pyrimidin-2-yl)-4-methyl-phenyl]ethynyl]-3-hydroxy-1-methyl-pyrrolidin-2-one (13 mg, as a pale yellow solid (12.8 mg, 20%). MS (ESI): mass calcd. for $C_{22}H_{21}N_5O_2$, 387.17; m/z. found, 388.2 [M+H]$^+$. $^1$H NMR (400 MHz, $CD_3OD$) δ 9.59 (s, 1H), 8.07 (d, J=1.7 Hz, 1H), 7.77 (s, 1H), 7.45 (dd, J=7.9, 1.8 Hz, 1H), 7.34 (d, J=7.9 Hz, 1H), 3.51-3.43 (m, 2H), 2.93 (s, 3H), 2.63 (s, 3H), 2.61-2.55 (m, 1H), 2.52 (s, 3H), 2.36-2.25 (m, 1H).

Example 66: (R)-3-[2-[3-(8-Aminopyrido[3,4-d]pyrimidin-2-yl)phenyl]ethynyl]-3-hydroxy-1-(trideuteriomethyl)pyrrolidin-2-one

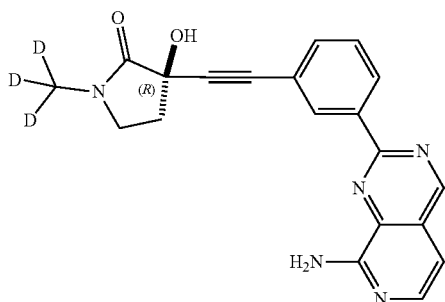

The title compound was prepared using analogous conditions described in Example 1 utilizing Intermediate 45, [(R)-3-ethynyl-3-hydroxy-1-(methyl-d$_3$)pyrrolidin-2-one] to afford (R)-3-[2-[3-(8-aminopyrido[3,4-d]pyrimidin-2-yl)phenyl]ethynyl]-3-hydroxy-1-(trideuteriomethyl)pyrrolidin-2-one (19 mg, 18%) as a white solid. MS (ESI): mass calcd. for $C_{20}H_{14}D_3N_5O_2$, 362.4; m/z. found, 363.1 [M+H]$^+$. $^1$H NMR (500 MHz, DMSO-d$_6$) δ 9.46 (s, 1H), 8.68-8.64 (m, 1H), 8.64-8.62 (m, 1H), 7.94 (d, J=5.6 Hz, 1H), 7.53-7.47 (m, 2H), 7.42 (s, 2H), 6.96 (d, J=5.6 Hz, 1H), 6.46 (s, 1H), 3.33-3.29 (m, 2H), 2.42-2.37 (m, 1H), 2.17-2.09 (m, 1H).

Example 67: (S)-3-[2-[3-(8-Aminopyrido[3,4-d]pyrimidin-2-yl)phenyl]ethynyl]-3-hydroxy-1-(trideuteriomethyl)pyrrolidin-2-one

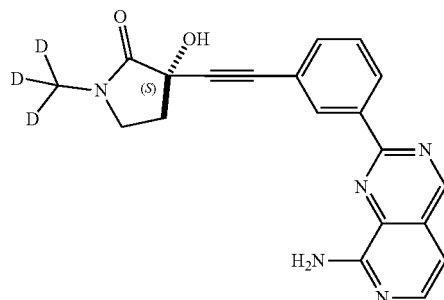

The title compound was prepared using analogous conditions described in Example 1 utilizing Intermediate 46 [(S)-3-ethynyl-3-hydroxy-1-(methyl-d$_3$)pyrrolidin-2-one] to afford (S)-3-[2-[3-(8-Aminopyrido[3,4-d]pyrimidin-2-yl)phenyl]ethynyl]-3-hydroxy-1-(trideuteriomethyl)pyrrolidin-2-one (36 mg, 35%) as a white solid. MS (ESI): mass calcd. for $C_{20}H_{14}D_3N_5O_2$, 362.4; m/z. found, 363.2 [M+H]$^+$. $^1$H NMR (400 MHz, DMSO-d$_6$) δ 9.46 (s, 1H), 8.69-8.57 (m, 2H), 7.94 (d, J=5.6 Hz, 1H), 7.56-7.46 (m, 2H), 7.37 (s, 2H), 6.96 (d, J=5.6 Hz, 1H), 6.42 (s, 1H), 3.35-3.28 (m, 2H), 2.41-2.37 (m, 1H), 2.19-2.07 (m, 1H).

Example 68: (R)-4-[3-(1-Amino-7-isoquinolyl)-4-methyl-phenyl]-2-thiazol-2-yl-but-3-yn-2-ol

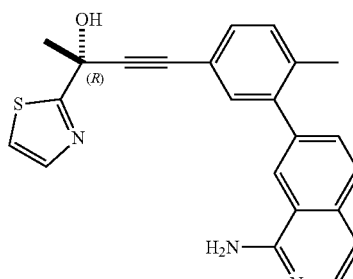

The title compound was prepared using analogous conditions described in Example 1 utilizing Intermediate 47 [7-(5-Iodo-2-methylphenyl)isoquinolin-1-amine] and Intermediate 30 [(R)-2-thiazol-2-ylbut-3-yn-2-ol] to afford (R)-4-[3-(1-amino-7-isoquinolyl)-4-methyl-phenyl]-2-thiazol-2-yl-but-3-yn-2-ol (46 mg, 53%) as a colorless solid. MS (ESI): mass calcd. for $C_{23}H_{19}N_3OS$, 385.5; m/z. found, 386.1 [M+H]⁺. ¹H NMR (500 MHz, DMSO-d₆) δ 8.12 (s, 1H), 7.77-7.71 (m, 1H), 7.70 (d, J=3.3 Hz, 1H), 7.67 (d, J=8.4 Hz, 1H), 7.61 (d, J=3.2 Hz, 1H), 7.55 (dd, J=8.3, 1.6 Hz, 1H), 7.30 (d, J=1.2 Hz, 2H), 7.27-7.23 (m, 1H), 6.97 (s, 1H), 6.87 (d, J=5.7 Hz, 1H), 6.77 (s, 2H), 2.22 (s, 3H), 1.80 (s, 3H).

Example 69: (R)-4-(3-(8-Aminopyrido[3,4-d]pyrimidin-2-yl)-4-methylphenyl)-2-(thiazol-2-yl)but-3-yn-2-ol

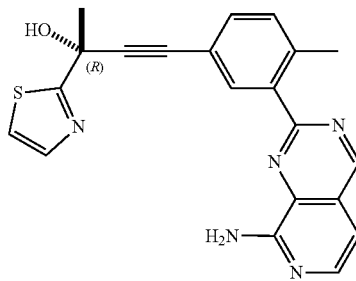

To a vial containing Intermediate 48 [2-(5-bromo-2-methylphenyl)pyrido[3,4-d]pyrimidin-8-amine (125 mg, 0.40 mmol)] and Intermediate 30 [(R)-2-(thiazol-2-yl)but-3-yn-2-ol (121 mg, 0.79 mmol)] was added PdCl₂(PPh₃)₂ (30 mg, 0.044 mmol), CuI (8.3 mg, 0.44 mmol), followed by DMF (15 mL) and Et₃N (0.55 mL, 3.97 mmol). The vial was sealed, evacuated/purged with nitrogen 3 times, and placed in a pre-heated aluminum heating mantle at 105° C. After 3.5 h, the contents were diluted with ethyl acetate and filtered through a diatomaceous earth pad which was rinsed further with ethyl acetate. The filtrate was concentrated onto diatomaceous earth (2.5 g), dried, and purified by FCC (100% DCM increasing to 50% ethyl acetate-DCM) to give (R)-4-(3-(8-aminopyrido[3,4-d]pyrimidin-2-yl)-4-methylphenyl)-2-(thiazol-2-yl)but-3-yn-2-ol (97 mg, 63%) as an amber solid. MS (ESI): mass calcd. For C₂₁H₁₇N₅OS, 387.12; m/z. found, 388.1 [M+H]⁺. ¹H NMR (400 MHz, MeOD) δ 9.43 (s, 1H), 8.06 (s, 1H), 7.96-8.00 (m, 1H), 7.77 (d, J=3.3 Hz, 1H), 7.55 (d, J=3.3 Hz, 1H), 7.46 (d, J=7.9 Hz, 1H), 7.33 (d, J=7.9 Hz, 1H), 7.07 (d, J=5.6 Hz, 1H), 2.62 (s, 3H), 1.96 (s, 3H).

Example 70: (R)-3-[2-[3-(1-Amino-7-isoquinolyl)-4-methyl-phenyl]ethynyl]-3-hydroxy-1-(trideuteriomethyl)pyrrolidin-2-one

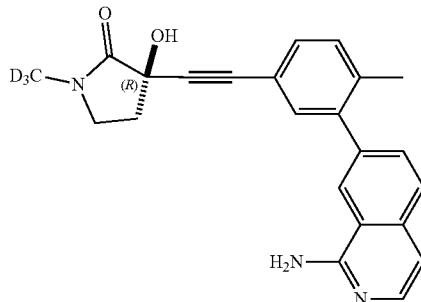

The title compound was prepared using analogous conditions described in Example 1 utilizing Intermediate 47 [7-(5-Iodo-2-methylphenyl)isoquinolin-1-amine] and [(R)-3-ethynyl-3-hydroxy-1-(methyl-d₃)pyrrolidin-2-one] to afford (R)-3-[2-[3-(1-amino-7-isoquinolyl)-4-methyl-phenyl]ethynyl]-3-hydroxy-1-(trideuteriomethyl)pyrrolidin-2-one (41 mg, 39%) as a colorless solid. MS (ESI): mass calcd. for C₂₃H₁₈D₃N₃O₂, 374.4; m/z found, 375.2 [M+H]⁺. ¹H NMR (500 MHz, DMSO-d₆) δ 8.19 (s, 1H), 7.83 (s, 1H), 7.74 (d, J=8.4 Hz, 1H), 7.62 (dd, J=8.3, 1.6 Hz, 1H), 7.38-7.31 (m, 3H), 6.95 (s, 1H), 6.84 (s, 2H), 6.45 (s, 1H), 3.33 (d, J=3.3 Hz, 2H), 2.45-2.37 (m, 1H), 2.29 (s, 3H), 2.21-2.10 (m, 1H).

Example 71: (S)-3-[2-[3-(1-Amino-7-isoquinolyl)-4-methyl-phenyl]ethynyl]-3-hydroxy-1-(trideuteriomethyl)pyrrolidin-2-one

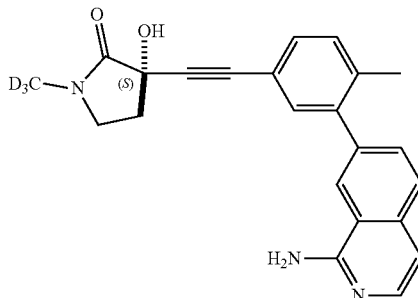

The title compound was prepared using analogous conditions described in Example 1 utilizing Intermediate 47 [7-(5-Iodo-2-methylphenyl)isoquinolin-1-amine] and Intermediate 46 [(S)-3-ethynyl-3-hydroxy-1-(methyl-d₃)pyrrolidin-2-one] to afford (S)-3-[2-[3-(1-Amino-7-isoquinolyl)-4-methyl-phenyl]ethynyl]-3-hydroxy-1-(trideuteriomethyl) pyrrolidin-2-one (33 mg, 32%) as a colorless solid. MS (ESI): mass calcd. for C₂₃H₁₈D₃N₃O₂, 374.4; m/z. found, 375.2 [M+H]⁺. ¹H NMR (500 MHz, DMSO-d₆) δ 8.19 (d, J=1.7 Hz, 1H), 7.83 (s, 1H), 7.74 (d, J=8.4 Hz, 1H), 7.62 (dd, J=8.4, 1.6 Hz, 1H), 7.41-7.32 (m, 3H), 6.96 (s, 1H), 6.84 (s, 2H), 6.46 (s, 1H), 3.34-3.20 (m, 2H), 2.44-2.38 (m, 1H), 2.29 (s, 3H), 2.21-2.12 (m, 1H).

Example 72: (R)-3-[2-[3-(8-Aminopyrido[3,4-d]pyrimidin-2-yl)phenyl]ethynyl]-3-hydroxy-1-(2,2,2-trifluoroethyl)pyrrolidin-2-one

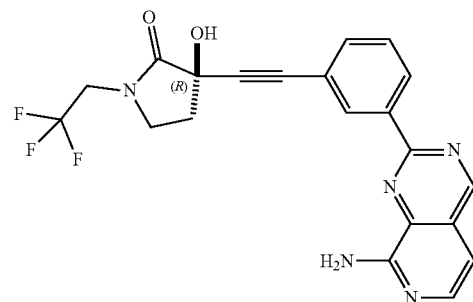

The title compound was prepared using analogous conditions described for Example 1 utilizing Intermediate 49 [(R)-3-ethynyl-3-hydroxy-1-(2,2,2-trifluoroethyl)pyrrolidin-2-one] and was purified by reverse phase preparative HPLC (XBridge Prep C18 5 μm, 50×250 mm column using a 0 to 100% gradient of ACN/20 mM NH₄OH in H₂O; 35 min gradient) to afford (R)-3-[2-[3-(8-aminopyrido[3,4-d]pyrimidin-2-yl)phenyl]ethynyl]-3-hydroxy-1-(2,2,2-trifluoroethyl)pyrrolidin-2-one (70 mg, 57%) as a colorless solid. MS (ESI): mass calcd. for $C_{21}H_{16}F_3N_5O_2$, 427.4; m/z. found, 428.1 [M+H]⁺. ¹H NMR (500 MHz, DMSO-$d_6$) δ 9.53 (s, 1H), 8.78-8.71 (m, 1H), 8.71-8.65 (m, 1H), 8.01 (d, J=5.6 Hz, 1H), 7.62-7.56 (m, 2H), 7.48 (s, 2H), 7.03 (d, J=5.6 Hz, 1H), 6.77 (s, 1H), 4.25-4.06 (m, 2H), 3.57-3.47 (m, 2H), 2.58-2.51 (m, 1H), 2.31-2.20 (m, 1H).

Example 73: (S)-3-[2-[3-(8-Aminopyrido[3,4-d]pyrimidin-2-yl)phenyl]ethynyl]-3-hydroxy-1-(2,2,2-trifluoroethyl)pyrrolidin-2-one

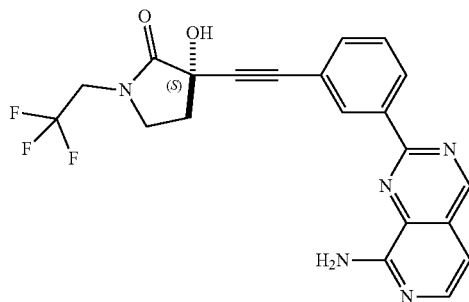

The title compound was prepared using analogous conditions described for Example 1 utilizing Intermediate 50 [(S)-3-ethynyl-3-hydroxy-1-(2,2,2-trifluoroethyl)pyrrolidin-2-one] and was purified by reverse phase preparative HPLC (XBridge Prep C18 5 μm, 50×250 mm column using a 0 to 100% gradient of ACN/20 mM NH₄OH in H₂O; 35 min gradient) to afford (S)-3-[2-[3-(8-aminopyrido[3,4-d]pyrimidin-2-yl)phenyl]ethynyl]-3-hydroxy-1-(2,2,2-trifluoroethyl)pyrrolidin-2-one (70 mg, 57%) as a colorless solid. MS (ESI): mass calcd. for $C_{21}H_{16}F_3N_5O_2$, 427.4; m/z. found, 428.1 [M+H]⁺. ¹H NMR (500 MHz, DMSO-$d_6$) δ 9.57 (s, 1H), 8.80-8.73 (m, 1H), 8.73-8.67 (m, 1H), 7.97 (d, J=5.9 Hz, 1H), 7.93 (s, 2H), 7.65-7.53 (m, 2H), 7.09 (d, J=5.9 Hz, 1H), 6.77 (s, 1H), 4.25-4.07 (m, 2H), 3.58-3.47 (m, 2H), 2.57-2.52 (m, 1H), 2.32-2.22 (m, 1H).

Example 74: (R)-4-(3-(8-Aminopyrido[3,4-d]pyrimidin-2-yl)-4-methylphenyl)-2-(5-methyl-1,3,4-oxadiazol-2-yl)but-3-yn-2-ol

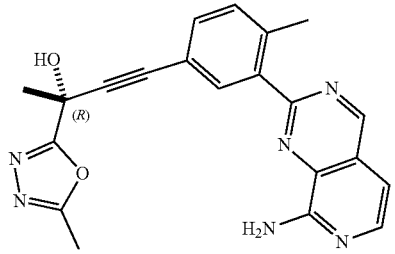

The title compound was prepared using conditions analogous to those described in Example 40, Step A using (5-bromo-2-methylphenyl)methanamine and Intermediate 14 [(R)-2-(5-methyl-1,3,4-oxadiazol-2-yl)but-3-yn-2-ol] to afford (R)-4-(3-(8-aminopyrido[3,4-d]pyrimidin-2-yl)-4-methylphenyl)-2-(5-methyl-1,3,4-oxadiazol-2-yl)but-3-yn-2-ol (84 mg, 70%) as a light amber solid. MS (ESI): mass calcd. For $C_{21}H_{18}N_6O_2$, 386.15; m/z. found, 387.1 [M+H]⁺. ¹H NMR (400 MHz, CDCl₃) δ 9.25 (s, 1H), 8.07 (d, J=5.8 Hz, 1H), 8.01-7.88 (m, 1H), 7.36-7.40 (m, 1H), 7.23 (d, J=7.9 Hz, 1H), 6.95 (d, J=5.8 Hz, 1H), 6.33 (br s, 2H), 2.59 (s, 3H), 2.58 (s, 3H), 2.08 (s, 3H).

Example 75: (R)-7-((3-(8-Aminopyrido[3,4-d]pyrimidin-2-yl)-4-methylphenyl)ethynyl)-6,7-dihydro-5H-cyclopenta[b]pyridin-7-ol

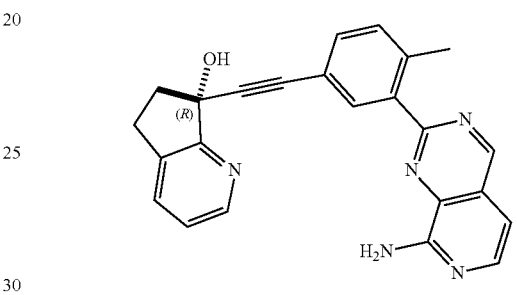

The title compound was prepared using conditions analogous to those described in Example 40, Step A using (5-bromo-2-methylphenyl)methanamine and Intermediate 38 [(R)-7-ethynyl-6,7-dihydro-5H-cyclopenta[b]pyridin-7-ol] to afford (R)-7-((3-(8-aminopyrido[3,4-d]pyrimidin-2-yl)-4-methylphenyl)ethynyl)-6,7-dihydro-5H-cyclopenta[b]pyridin-7-ol (81 mg, 68%) as a tan solid. MS (ESI): mass calcd. For $C_{24}H_{19}N_5O$, 393.16; m/z. found, 394.1 [M+H]⁺ ¹H NMR (400 MHz, DMSO, 80° C.) δ 9.54 (s, 1H), 8.62-8.37 (m, 1H), 8.16-7.98 (m, 2H), 7.82-7.65 (m, 1H), 7.57-6.96 (m, 4H), 6.19 (s, 1H), 3.15-2.79 (m, 2H), 2.75-2.16 (m, 5H). ¹H NMR (400 MHz, CD₃OD) δ 9.43 (s, 1H), 8.43 (s, 1H), 7.80-8.20 (m, 2H), 7.73-7.77 (m, 2H), 7.40-7.46 (m, 1H), 7.30-7.33 (m, 2H), 7.09 (s, 1H), 2.90-3.15 (m, 2H), 2.35-2.80 (m, 5H).

Example 76: (R)-3-[2-[3-(8-Amino-5-methyl-pyrido[3,4-d]pyrimidin-2-yl)-5-methyl-phenyl]ethynyl]-3-hydroxy-1-methyl-pyrrolidin-2-one

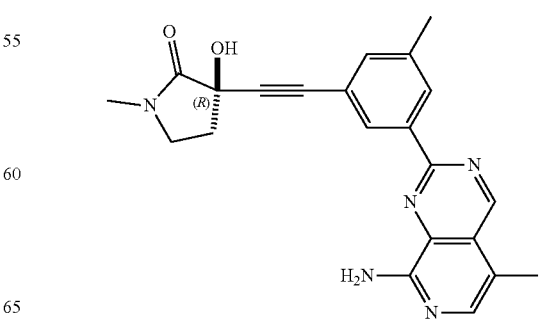

The title compound was prepared using analogous conditions described for Example 65 utilizing 3-bromo-5-methylphenylboronic acid in Step B to afford (R)-3-[2-[3-(8-amino-5-methyl-pyrido[3,4-d]pyrimidin-2-yl)-5-methyl-phenyl]ethynyl]-3-hydroxy-1-methyl-pyrrolidin-2-one (35 mg, 41%) as yellow solid. MS (ESI): mass calcd. for $C_{22}H_{21}N_5O_2$, 387.17; m/z. found, 388.2 [M+H]$^+$. $^1$H NMR (400 MHz, CD$_3$OD) δ 9.55 (s, 1H), 8.50 (s, 1H), 8.46 (s, 1H), 7.72 (s, 1H), 7.42 (s, 1H), 3.57-3.41 (m, 2H), 2.95 (s, 4H), 2.65-2.55 (m, 1H), 2.51 (s, 2H), 2.45 (s, 3H), 2.38-2.29 (m, 1H).

Example 77: (R)-3-[2-[3-(1-Amino-7-isoquinolyl)-4-methyl-phenyl]ethynyl]-3-hydroxy-1-(2,2,2-trifluoroethyl)pyrrolidin-2-one

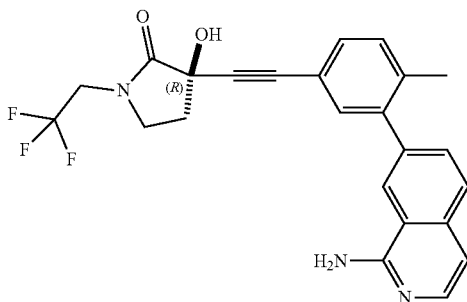

The title compound was prepared using analogous conditions described in Example 1 utilizing Intermediate 47 [7-(5-iodo-2-methylphenyl)isoquinolin-1-amine] and Intermediate 49 [(R)-3-ethynyl-3-hydroxy-1-(2,2,2-trifluoroethyl)pyrrolidin-2-one] to afford (R)-3-[2-[3-(1-amino-7-isoquinolyl)-4-methyl-phenyl]ethynyl]-3-hydroxy-1-(2,2,2-trifluoroethyl)pyrrolidin-2-one. (44 mg, 45%) as a colorless solid. MS (ESI): mass calcd. for $C_{24}H_{20}F_3N_3O_2$, 439.4; m/z. found, 440.1 [M+H]$^+$. $^1$H NMR (500 MHz, DMSO-d$_6$) δ 8.12 (s, 1H), 7.75 (d, J=5.8 Hz, 1H), 7.68 (d, J=8.3 Hz, 1H), 7.54 (dd, J=8.3, 1.6 Hz, 1H), 7.34-7.28 (m, 2H), 7.27 (s, 1H), 6.87 (dd, J=5.9, 0.8 Hz, 1H), 6.76 (s, 2H), 6.61 (s, 1H), 4.15-3.97 (m, 2H), 3.47-3.36 (m, 2H), 2.42-2.36 (m, 1H), 2.22 (s, 3H), 2.19-2.11 (m, 1H).

Example 78: (R)-4-[3-(1-Amino-7-isoquinolyl)-4-methyl-phenyl]-2-(5-methyl-1,3,4-oxadiazol-2-yl)but-3-yn-2-ol

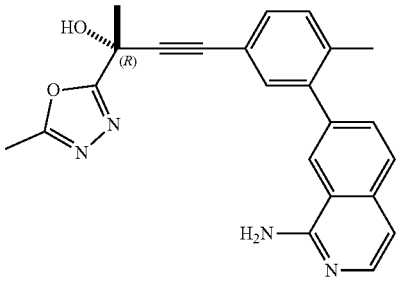

The title compound was prepared using analogous conditions described in Example 1 utilizing Intermediate 47 [7-(5-iodo-2-methylphenyl)isoquinolin-1-amine] and Intermediate 14 [(R)-2-(5-methyl-1,3,4-oxadiazol-2-yl)but-3-yn-2-ol] to afford (R)-4-[3-(1-amino-7-isoquinolyl)-4-methyl-phenyl]-2-(5-methyl-1,3,4-oxadiazol-2-yl)but-3-yn-2-ol (30 mg, 35%) as a colorless solid. MS (ESI): mass calcd. for $C_{23}H_{20}N_4O_2$, 384.4; m/z. found, 385.2 [M+H]$^+$. $^1$H NMR (400 MHz, DMSO-d$_6$) δ 8.19 (s, 1H), 7.83 (d, J=5.8 Hz, 1H), 7.75 (d, J=8.4 Hz, 1H), 7.62 (dd, J=8.4, 1.6 Hz, 1H), 7.44-7.35 (m, 3H), 6.97 (s, 1H), 6.95 (d, J=5.9 Hz, 1H), 6.82 (s, 2H), 2.53 (s, 3H), 2.30 (s, 3H), 1.90 (s, 3H).

Example 79: (R)-4-[3-(1-Amino-7-isoquinolyl)-4-methyl-phenyl]-2-(5-methylisoxazol-3-yl)but-3-yn-2-ol

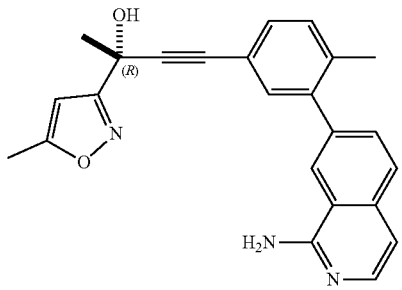

The title compound was prepared using analogous conditions described in Example 1 utilizing Intermediate 47 [7-(5-iodo-2-methylphenyl)isoquinolin-1-amine] and Intermediate 32 [(R)-2-(5-methylisoxazol-3-yl)but-3-yn-2-ol] to afford (R)-4-[3-(1-amino-7-isoquinolyl)-4-methyl-phenyl]-2-(5-methylisoxazol-3-yl)but-3-yn-2-ol (21 mg, 25%) as a colorless solid. MS (ESI): mass calcd. for $C_{24}H_{21}N_3O_2$, 383.4; m/z. found, 384.1 [M+H]$^+$. $^1$H NMR (500 MHz, DMSO-d$_6$) δ 8.12 (s, 1H), 7.75 (s, 1H), 7.67 (d, J=8.3 Hz, 1H), 7.54 (dd, J=8.3, 1.6 Hz, 1H), 7.32-7.27 (m, 2H), 7.27-7.25 (m, 1H), 6.87 (d, J=5.7 Hz, 1H), 6.75 (s, 2H), 6.41 (s, 1H), 6.31-6.21 (m, 1H), 2.32 (d, J=0.9 Hz, 3H), 2.22 (s, 3H), 1.71 (s, 3H).

Example 80: (R)-7-[2-[3-(1-Amino-7-isoquinolyl)-4-methyl-phenyl]ethynyl]-5,6-dihydrocyclopenta[b]pyridin-7-ol

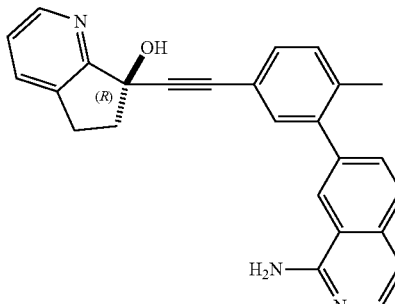

The title compound was prepared using analogous conditions described in Example 1 utilizing Intermediate 47 [7-(5-iodo-2-methylphenyl)isoquinolin-1-amine] and Intermediate 38 [(R)-7-ethynyl-6,7-dihydro-5H-cyclopenta[b]pyridin-7-ol] to afford (R)-7-[2-[3-(1-amino-7-isoquinolyl)-

4-methyl-phenyl]ethynyl]-5,6-dihydrocyclopenta[b]pyridin-7-ol (29 mg, 33%) as a colorless solid. MS (ESI): mass calcd. for C$_{26}$H$_{21}$N$_3$O, 391.5; m/z. found, 392.1 [M+H]$^+$. $^1$H NMR (500 MHz, DMSO-d$_6$) δ 8.37 (d, J=4.8 Hz, 1H), 8.14-8.06 (m, 1H), 7.75 (d, J=5.7 Hz, 1H), 7.68-7.62 (m, 2H), 7.54 (dd, J=8.3, 1.7 Hz, 1H), 7.28 (d, J=1.2 Hz, 2H), 7.24 (d, J=1.1 Hz, 1H), 7.20 (dd, J=7.7, 4.8 Hz, 1H), 6.87 (d, J=5.7 Hz, 1H), 6.75 (s, 2H), 6.12 (s, 1H), 2.96-2.88 (m, 1H), 2.86-2.75 (m, 1H), 2.51-2.45 (m, 1H), 2.34-2.26 (m, 1H), 2.21 (s, 3H).

Example 81: (R)-7-[2-[3-(1-Amino-7-isoquinolyl)-4-methyl-phenyl]ethynyl]-5,6-dihydropyrrolo[1,2-a]imidazol-7-ol

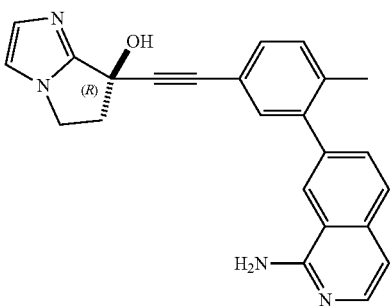

The title compound was prepared using analogous conditions described in Example 1 utilizing Intermediate 47 [7-(5-iodo-2-methylphenyl)isoquinolin-1-amine] and Intermediate 10 [(R)-7-ethynyl-6,7-dihydro-5H-pyrrolo[1,2-a]imidazol-7-ol] to afford (R)-7-[2-[3-(1-amino-7-isoquinolyl)-4-methyl-phenyl]ethynyl]-5,6-dihydropyrrolo[1,2-a]imidazol-7-ol (29 mg, 33%) as a colorless solid. MS (ESI): mass calcd. for C$_{24}$H$_{20}$N$_4$O, 380.4; m/z. found, 381.1 [M+H]$^+$. $^1$H NMR (500 MHz) δ 9.00 (s, 1H), 8.63 (s, 1H), 8.55 (d, J=8.4 Hz, 1H), 8.44 (dd, J=8.3, 1.6 Hz, 1H), 8.24-8.13 (m, 3H), 7.93 (s, 1H), 7.79 (s, 1H), 7.75 (d, J=5.6 Hz, 1H), 7.63 (s, 2H), 7.31 (s, 1H), 4.92-4.76 (m, 2H), 3.88-3.76 (m, 1H), 3.64-3.49 (m, 1H), 3.11 (s, 3H).

Example 82: (R)-4-(3-(8-Aminopyrido[3,4-d]pyrimidin-2-yl)-4-methylphenyl)-2-(5-methylisoxazol-3-yl)but-3-yn-2-ol

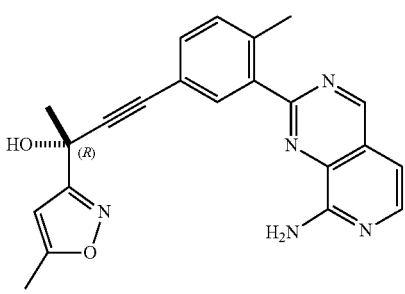

The title compound was prepared using conditions analogous to those described in Example 40, Step A using (5-bromo-2-methylphenyl)methanamine and Intermediate 32 [(R)-2-(5-methylisoxazol-3-yl)but-3-yn-2-ol] to afford (R)-4-(3-(8-aminopyrido[3,4-d]pyrimidin-2-yl)-4-methylphenyl)-2-(5-methylisoxazol-3-yl)but-3-yn-2-ol (64 mg, 71%) as an amber solid. MS (ESI): mass calcd. For C$_{22}$H$_{19}$N$_5$O$_2$, 385.15; m/z. found, 386.1 [M+H]$^+$. $^1$H NMR (500 MHz, CD$_3$OD) δ 9.44 (s, 1H), 8.05 (d, J=1.9 Hz, 1H), 7.97 (d, J=5.8 Hz, 1H), 7.45 (dd, J=7.9, 1.9 Hz, 1H), 7.33 (d, J=7.9 Hz, 1H), 7.08 (d, J=5.8 Hz, 1H), 6.31 (s, 1H), 2.62 (s, 3H), 2.43 (s, 3H), 1.88 (s, 3H).

Example 83: (R)-3-((3-(8-Amino-4-methylpyrido[3,4-d]pyrimidin-2-yl)phenyl)ethynyl)-3-hydroxy-1-(methyl-d$_3$)pyrrolidin-2-one

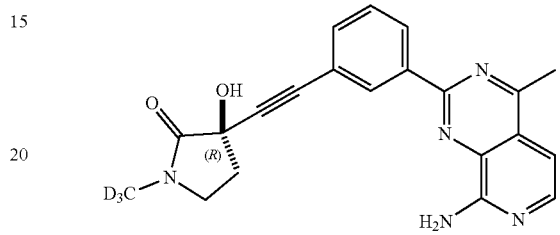

The title compound was prepared using conditions analogous to those described in Example 1 utilizing Intermediate 34 [2-(3-iodophenyl)-4-methylpyrido[3,4-d]pyrimidin-8-amine] and Intermediate 45 [(R)-3-ethynyl-3-hydroxy-1-(methyl-d$_3$)pyrrolidin-2-one] to afford (R)-3-((3-(8-amino-4-methylpyrido[3,4-d]pyrimidin-2-yl)phenyl)ethynyl)-3-hydroxy-1-(methyl-d$_3$)pyrrolidin-2-one (68 mg, 64%) as a white solid. MS (ESI): mass calcd. for C$_{21}$H$_{16}$D$_3$N$_5$O$_2$, 376.17; m/z. found, 377.3 [M+H]$^+$. $^1$H NMR (400 MHz, DMSO-d$_6$) δ 8.75-8.70 (m, 1H), 8.69-8.64 (m, 1H), 7.99 (d, J=5.6 Hz, 1H), 7.61-7.53 (m, 2H), 7.42 (s, 2H), 7.08 (d, J=5.8 Hz, 1H), 6.53 (s, 1H), 3.41-3.36 (m, 2H), 2.87 (s, 3H), 2.49-2.44 (m, 1H), 2.26-2.16 (m, 1H).

Example 84: (R)-7-((3-(8-Amino-4-methylpyrido[3,4-d]pyrimidin-2-yl)phenyl)ethynyl)-6,7-dihydro-5H-pyrrolo[1,2-a]imidazol-7-ol

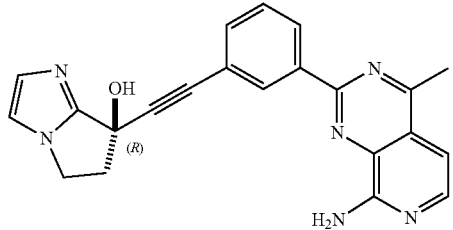

The title compound was prepared using conditions analogous to those described in Example 1 utilizing Intermediate 34 [2-(3-iodophenyl)-4-methylpyrido[3,4-d]pyrimidin-8-amine] and Intermediate 10 [(R)-7-ethynyl-6,7-dihydro-5H-pyrrolo[1,2-a]imidazol-7-ol] to afford (R)-7-((3-(8-Amino-4-methylpyrido[3,4-d]pyrimidin-2-yl)phenyl)ethynyl)-6,7-dihydro-5H-pyrrolo[1,2-a]imidazol-7-ol (71 mg, 67%) as a white solid. MS (ESI): mass calcd. for C$_{22}$H$_{18}$N$_6$O, 382.15; m/z. found, 383.3 [M+H]$^+$. $^1$H NMR (400 MHz, DMSO-d$_6$) δ 8.79-8.66 (m, 2H), 7.99 (d, J=5.8 Hz, 1H), 7.62-7.53 (m, 2H), 7.41 (s, 2H), 7.16 (s, 1H), 7.07 (d, J=5.8 Hz, 1H), 7.01 (s, 1H), 6.59 (s, 1H), 4.12-4.04 (m, 2H), 3.13-3.04 (m, 1H), 2.91-2.78 (m, 4H).

Example 85: (R)-3-((3-(8-Amino-4-(methylamino) pyrido[3,4-d]pyrimidin-2-yl)phenyl)ethynyl)-3-hydroxy-1-methylpyrrolidin-2-one, and its trifluoroacetate

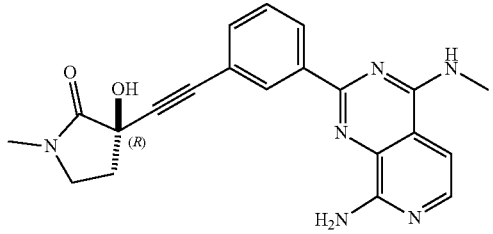

(R)-3-((3-(8-Amino-4-(methylamino)pyrido[3,4-d]pyrimidin-2-yl)phenyl)ethynyl)-3-hydroxy-1-methylpyrrolidin-2-one was prepared in a manner analogous to Example 57 utilizing methylamine (2M in THF) in Step A and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-3-((3-(8-Amino-4-(methylamino)pyrido[3,4-d]pyrimidin-2-yl)phenyl)ethynyl)-3-hydroxy-1-methylpyrrolidin-2-one trifluoroacetate (19 mg, 19%) as a white solid. MS (ESI): mass calcd. for $C_{21}H_{20}N_6O_2$, 388.16; m/z. found, 389.3 [M+H]$^+$. $^1$H NMR (400 MHz, CD$_3$OD) δ 8.69 (t, J=1.5 Hz, 1H), 8.64-8.60 (m, 1H), 7.60-7.55 (m, 2H), 7.48 (t, J=7.8 Hz, 1H), 7.24 (d, J=7.1 Hz, 1H), 3.53-3.47 (m, 2H), 3.24 (s, 3H), 2.95 (s, 3H), 2.66-2.58 (m, 1H), 2.39-2.30 (m, 1H).

Example 86: (R)-7-[2-[3-(8-Amino-5-methyl-pyrido[3,4-d]pyrimidin-2-yl)phenyl]ethynyl]-6-dihydropyrrolo[1,2-a]imidazol-7-ol

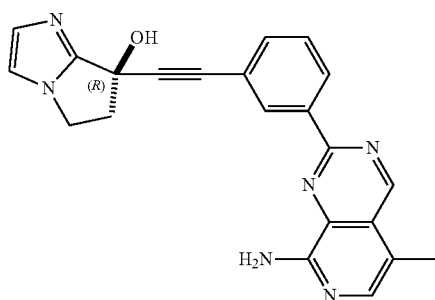

The title compound was prepared using conditions analogous to those described in Example 1 using Intermediate 36 [2-(3-bromophenyl)-5-methylpyrido[3,4-d]pyrimidin-8-amine] and Intermediate 10 [(R)-7-ethynyl-6,7-dihydro-5H-pyrrolo[1,2-a]imidazol-7-ol] to afford (R)-7-[2-[3-(8-amino-5-methyl-pyrido[3,4-d]pyrimidin-2-yl)phenyl]ethynyl]-5,6-dihydropyrrolo[1,2-a]imidazol-7-ol (30 mg, 25%) as a yellow solid. MS (ESI): mass calcd. for $C_{22}H_{18}N_6O$, 382.15; m/z. found, 383.3 [M+H]$^+$. $^1$H NMR (400 MHz, DMSO-d$_6$) δ 9.62 (s, 1H), 8.85-8.65 (m, 2H), 7.82 (s, 1H), 7.72-7.49 (m, 2H), 7.24 (br s, 2H), 7.15 (s, 1H), 7.01 (s, 1H), 6.58 (s, 1H), 4.08 (t, J=6.8 Hz, 2H), 3.12-3.00 (m, 1H), 2.87-2.73 (m, 1H), 2.46 (s, 3H).

Example 87: (R)-3-[2-[3-(8-Amino-5-methyl-pyrido[3,4-d]pyrimidin-2-yl)phenyl]ethynyl]-3-hydroxy-1-(trideuteriomethyl)pyrrolidin-2-one

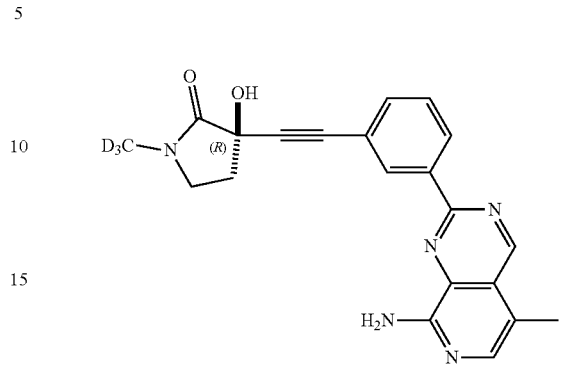

The title compound was prepared using conditions analogous to those described in Example 1 using Intermediate 36 [2-(3-bromophenyl)-5-methylpyrido[3,4-d]pyrimidin-8-amine and Intermediate 45 [(R)-3-ethynyl-3-hydroxy-1-(methyl-d$_3$)pyrrolidin-2-one] to afford (R)-3-[2-[3-(8-amino-5-methyl-pyrido[3,4-d]pyrimidin-2-yl)phenyl]ethynyl]-3-hydroxy-1-(trideuteriomethyl)pyrrolidin-2-one (9 mg, 6%). MS (ESI): mass calcd. for $C_{21}H_{16}D_3N_5O_2$, 376.17; m/z. found, 377.3 [M+H]$^+$. $^1$H NMR (400 MHz, CD$_3$OD) δ 9.71 (s, 1H), 8.82 (d, J=1.8 Hz, 1H), 8.74-8.67 (m, 1H), 7.67-7.62 (m, 1H), 7.59-7.48 (m, 1H), 7.51-7.50 (m, 1H), 3.54-3.48 (m, 2H), 2.67-2.58 (m, 1H), 2.55 (s, 3H), 2.39-2.29 (m, 1H).

Example 88: (R)-4-[3-(8-Amino-1,7-naphthyridin-2-yl)phenyl]-2-(5-methyl-1,3,4-oxadiazol-2-yl)but-3-yn-2-ol

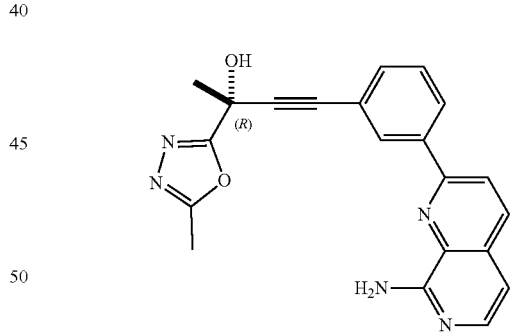

The title compound was prepared using conditions analogous to those described in Example 19 utilizing Intermediate 14 [(R)-2-(5-methyl-1,3,4-oxadiazol-2-yl)but-3-yn-2-ol] to afford (R)-4-[3-(8-amino-1,7-naphthyridin-2-yl)phenyl]-2-(5-methyl-1,3,4-oxadiazol-2-yl)but-3-yn-2-ol (33 mg, 42%) as a colorless solid. MS (ESI): mass calcd. for $C_{21}H_{17}N_5O_2$, 371.4; m/z. found, 372.1 [M+H]$^+$. $^1$H NMR (500 MHz, DMSO-d$_6$) δ 8.43-8.37 (m, 1H), 8.36 (s, 1H), 8.26 (d, J=8.6 Hz, 1H), 8.17 (d, J=8.7 Hz, 1H), 7.80 (d, J=5.6 Hz, 1H), 7.54-7.45 (m, 2H), 7.04 (s, 2H), 6.97 (s, 1H), 6.87 (d, J=5.7 Hz, 1H), 2.49 (s, 3H), 1.88 (s, 3H).

Example 89: (R)-4-[3-(8-Amino-1,7-naphthyridin-2-yl)phenyl]-2-(5-methylisoxazol-3-yl)but-3-yn-2-ol

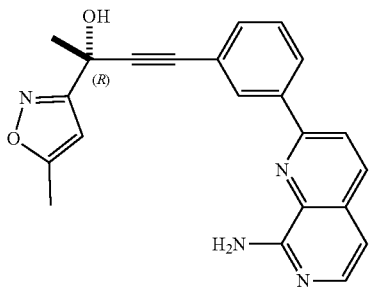

The title compound was prepared using conditions analogous to those described in Example 19 utilizing Intermediate 32 [(R)-2-(5-methylisoxazol-3-yl)but-3-yn-2-ol] to afford (R)-4-[3-(8-amino-1,7-naphthyridin-2-yl)phenyl]-2-(5-methylisoxazol-3-yl)but-3-yn-2-ol (27 mg, 34%) as a colorless solid. MS (ESI): mass calcd. for $C_{22}H_{18}N_4O_2$, 370.4; m/z. found, 371.0 [M+H]$^+$. $^1$H NMR (500 MHz, DMSO-d$_6$) δ 8.40-8.34 (m, 1H), 8.33-8.29 (m, 1H), 8.25 (d, J=8.7 Hz, 1H), 8.17 (d, J=8.7 Hz, 1H), 7.79 (d, J=5.7 Hz, 1H), 7.52-7.40 (m, 2H), 7.02 (s, 2H), 6.87 (d, J=5.7 Hz, 1H), 6.47 (s, 1H), 6.38-6.24 (m, 1H), 2.35 (d, J=0.9 Hz, 3H), 1.77 (s, 3H).

Example 90: (R)-4-[3-(8-Amino-1,7-naphthyridin-2-yl)phenyl]-2-thiazol-2-yl-but-3-yn-2-ol

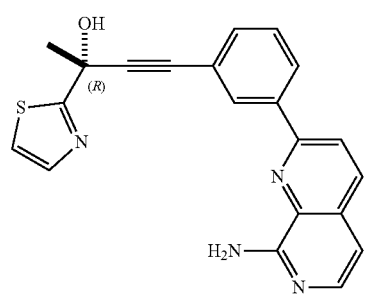

The title compound was prepared using conditions analogous to those described in Example 19 utilizing Intermediate 30 [(R)-2-(thiazol-2-yl)but-3-yn-2-ol] to afford (R)-4-[3-(8-amino-1,7-naphthyridin-2-yl)phenyl]-2-thiazol-2-yl-but-3-yn-2-ol (20 mg, 25%) as a colorless solid. MS (ESI): mass calcd. for $C_{21}H_{16}N_4OS$, 372.5; m/z. found, 373.0 [M+H]$^+$. $^1$H NMR (500 MHz, DMSO-d$_6$) δ 8.40-8.33 (m, 1H), 8.31-8.28 (m, 1H), 8.25 (d, J=8.6 Hz, 1H), 8.16 (d, J=8.7 Hz, 1H), 7.79 (d, J=5.7 Hz, 1H), 7.72 (d, J=3.2 Hz, 1H), 7.63 (d, J=3.2 Hz, 1H), 7.52-7.42 (m, 2H), 7.05-6.95 (m, 3H), 6.86 (d, J=5.8 Hz, 1H), 1.86 (s, 3H).

Example 91: (R)-7-[2-[3-(8-Amino-1,7-naphthyridin-2-yl)phenyl]ethynyl]-5,6-dihydropyrrolo[1,2-a]imidazol-7-ol

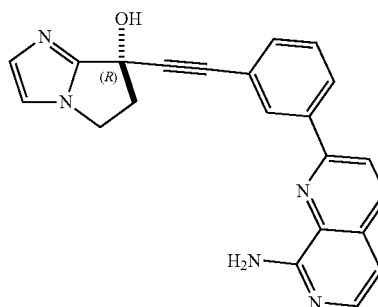

The title compound was prepared using conditions analogous to those described in Example 19 utilizing Intermediate 10 [(R)-7-ethynyl-6,7-dihydro-5H-pyrrolo[1,2-a]imidazol-7-ol] to afford (R)-7-[2-[3-(8-amino-1,7-naphthyridin-2-yl)phenyl]ethynyl]-5,6-dihydropyrrolo[1,2-a]imidazol-7-ol (18 mg, 78%) as a colorless solid. MS (ESI): mass calcd. for $C_{22}H_{17}N_5O$, 367.4; m/z. found, 368.1 [M+H]$^+$. $^1$H NMR (500 MHz, DMSO-d$_6$) δ 8.37-8.34 (m, 1H), 8.34-8.32 (m, 1H), 8.25 (d, J=8.6 Hz, 1H), 8.17 (d, J=8.7 Hz, 1H), 7.79 (d, J=5.7 Hz, 1H), 7.53-7.45 (m, 2H), 7.07 (d, J=1.2 Hz, 1H), 7.02 (s, 2H), 6.94 (d, J=1.2 Hz, 1H), 6.86 (d, J=5.7 Hz, 1H), 6.49 (s, 1H), 4.07-3.89 (m, 2H), 3.07-2.94 (m, 1H), 2.81-2.65 (m, 1H).

Example 92: (R)-3-[2-[3-(8-Amino-4-methyl-pyrido[3,4-d]pyrimidin-2-yl)phenyl]ethynyl]-3-hydroxy-1-(2,2,2-trifluoroethyl)pyrrolidin-2-one

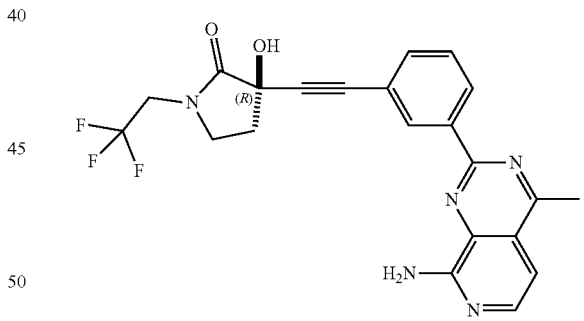

The title compound was prepared using conditions analogous to those described in Example 1 utilizing Intermediate 34 [2-(3-iodophenyl)-4-methylpyrido[3,4-d]pyrimidin-8-amine] and Intermediate 49 [(R)-3-ethynyl-3-hydroxy-1-(2,2,2-trifluoroethyl)pyrrolidin-2-one] to afford (R)-3-[2-[3-(8-amino-4-methyl-pyrido[3,4-d]pyrimidin-2-yl)phenyl]ethynyl]-3-hydroxy-1-(2,2,2-trifluoroethyl)pyrrolidin-2-one (49 mg, 41%) as a colorless solid. MS (ESI): mass calcd. for $C_{22}H_{18}F_3N_5O_2$, 441.4; m/z. found, 422.2 [M+H]$^+$. $^1$H NMR (400 MHz, DMSO-d$_6$) δ 8.77-8.71 (m, 1H), 8.70-8.64 (m, 1H), 8.00 (d, J=5.8 Hz, 1H), 7.61-7.52 (m, 2H), 7.38 (s, 2H), 7.08 (d, J=5.8 Hz, 1H), 6.74 (s, 1H), 4.26-4.06 (m, 2H), 3.59-3.48 (m, 2H), 2.88 (s, 3H), 2.59-2.52 (m, 1H), 2.35-2.22 (m, 1H).

Example 93: (R)-4-(3-(4-Aminopyrido[3,2-d]pyrimidin-6-yl)phenyl)-2-(thiazol-2-yl)but-3-yn-2-ol

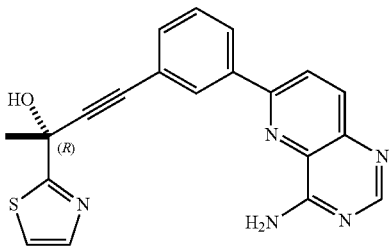

The title compound was prepared using conditions analogous to those described in Example 1 utilizing Intermediate 30 [(R)-2-(thiazol-2-yl)but-3-yn-2-ol] to afford (R)-4-(3-(4-aminopyrido[3,2-d]pyrimidin-6-yl)phenyl)-2-(thiazol-2-yl)but-3-yn-2-ol (60 mg, 23%) as a white solid. MS (ESI): mass calcd. for $C_{20}H_{15}N_5OS$, 373.10; m/z. found, 374.1 $[M+H]^+$. $^1$H NMR (500 MHz, $CD_3OD$) δ 8.45-8.33 (m, 3H), 8.26 (d, J=7.8 Hz, 1H), 8.12 (d, J=8.8 Hz, 1H), 7.79 (d, J=3.3 Hz, 1H), 7.62-7.55 (m, 2H), 7.52 (t, J=7.7 Hz, 1H), 1.98 (s, 3H).

Example 94: (R)-3-((3-(8-Amino-5-bromopyrido[3,4-d]pyrimidin-2-yl)phenyl)ethynyl)-3-hydroxy-1-methylpyrrolidin-2-one

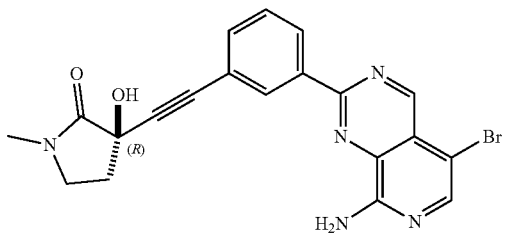

A flask was charged with Example 1 [(R)-3-[2-[3-(8-aminopyrido[3,4-d]pyrimidin-2-yl)phenyl]ethynyl]-3-hydroxy-1-methyl-pyrrolidin-2-one] (0.20 g, 0.56 mmol) and DMF (10 mL). The resulting mixture was heated at 90° C. until the mixture became homogeneous. The resulting solution was then cooled to 0° C. and treated with N-bromosuccinimide (0.11 g, 0.60 mmol) in one portion. The mixture was immediately removed from the ice bath and allowed to begin warming to room temperature. After 15 minutes, the mixture was diluted with MeOH (about 5 mL) and a solid precipitated. The solid was isolated by filtration, rinsed with MeCN (5 mL×2), and dried to afford (R)-3-((3-(8-amino-5-bromopyrido[3,4-d]pyrimidin-2-yl)phenyl)ethynyl)-3-hydroxy-1-methylpyrrolidin-2-one (133 mg, 55%) as a white solid. MS (ESI): mass calcd. for $C_{20}H_{16}BrN_5O_2$, 437.05; m/z. found, 438.1 $[M+H]^+$. $^1$H NMR (400 MHz, DMSO-$d_6$) δ 9.50 (s, 1H), 8.80-8.70 (m, 2H), 8.13 (s, 1H), 7.80 (s, 2H), 7.64-7.57 (m, 2H), 6.54 (s, 1H), 3.42-3.36 (m, 2H), 2.82 (s, 3H), 2.50-2.44 (m, 1H), 2.26-2.16 (m, 1H).

Example 95: (R)-4-(3-(4-Aminopyrido[3,2-d]pyrimidin-6-yl)phenyl)-2-(5-methylisoxazol-3-yl)but-3-yn-2-ol

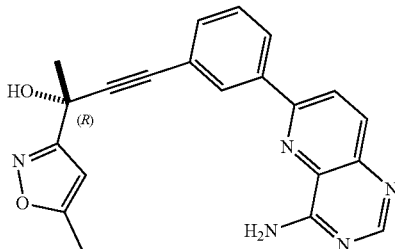

The title compound was prepared using conditions analogous to those described in Example 1 utilizing Intermediate 32 [(R)-2-(5-methylisoxazol-3-yl)but-3-yn-2-ol] to afford (R)-4-(3-(4-aminopyrido[3,2-d]pyrimidin-6-yl)phenyl)-2-(5-methylisoxazol-3-yl)but-3-yn-2-ol (111 mg, 72%) as a white solid. MS (ESI): mass calcd. For $C_{21}H_{17}N_5O_2$, 371.14; m/z. found, 372.10 $[M+H]^+$. $^1$H NMR (500 MHz, Methanol-d4) δ 8.44-8.35 (m, 3H), 8.24-8.28 (m, 1H), 8.13 (d, J=8.9 Hz, 1H), 7.61-7.48 (m, 2H), 6.33 (s, 1H), 2.45 (s, 3H), 1.90 (s, 3H).

Example 96: (R)-3-[2-[3-(4-Aminophthalazin-6-yl)phenyl]ethynyl]-3-hydroxy-1-methyl-pyrrolidin-2-one

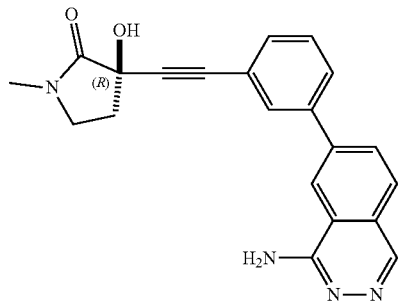

Step A: 7-Bromophthalazin-1-amine. To a sealable microwave vial were added 7-bromo-1-chlorophthalazine (150 mg, 0.62 mmol), NMP (3 mL) and 28% aqueous ammonium hydroxide (416 μL, 6.2 mmol). The reaction vessel was sealed and heated at 140° C. in the microwave reactor for 60 min (at 14 bar). The reaction vessel was then heated at 160° C. in the microwave reactor for 30 min. Additional ammonium hydroxide (416 μL, 6.2 mmol) was then added and the reaction vessel was heated again at 160° C. in the microwave reactor for 30 min. After the vial had cooled to rt, the reaction mixture diluted with water (50 mL) and extracted with ethyl acetate (50 mL×3). The combined organic layers were dried over sodium sulfate, filtered and concentrated to dryness. The resulting residue was purified FCC (0 to 10% gradient using MeOH in DCM) to afford 7-bromophthalazin-1-amine which was used directly in the next step.

Step B: (R)-3-[2-[3-(4-Aminophthalazin-6-yl)phenyl]ethynyl]-3-hydroxy-1-methyl-pyrrolidin-2-one. To a sealable vial were added 7-bromophthalazin-1-amine (40 mg, 0.18 mmol), Intermediate 4 [(R)-3-Hydroxy-1-methyl-3-

((4-methyl-3-(4,4,5,5-tetramethyl-1,3,2-dioxaborolan-2-yl)phenyl)ethynyl)pyrrolidin-2-one (79 mg, 0.23 mmol)], dioxane (1 mL), and 2 M $Na_2CO_3$ (0.36 mL, 7.2 mmol) solution. The mixture was degassed by sparging with argon for 10 min then 1,1'-bis(di-tert-butylphosphino)ferrocene palladium dichloride was added. The vial was then sealed and heated at 40° C. for 2 h. The resulting mixture was cooled to rt and partitioned between ethyl acetate (25 mL) and water (25 mL). The organic layer was separated, and the aqueous layer was further extracted with ethyl acetate (25 mL×2). The combined organic layers were dried over sodium sulfate, filtered, and concentrated to dryness. The resulting residue was purified by FCC (0 to 10% gradient using MeOH in DCM) to afford (R)-3-[2-[3-(4-aminophthalazin-6-yl)phenyl]ethynyl]-3-hydroxy-1-methyl-pyrrolidin-2-one (18 mg, 27%) as an off-white solid. MS (ESI): mass calcd. for $C_{21}H_{18}N_4O_2$, 358.14; m/z. found, 359.2 $[M+H]^+$. $^1H$ NMR (400 MHz, $CD_3OD$) δ 8.87 (s, 1H), 8.50 (s, 1H), 8.18 (dd, J=8.4, 1.7 Hz, 1H), 8.02 (d, J=8.4 Hz, 1H), 7.92-7.91 (m, 1H), 7.85-7.78 (m, 1H), 7.55-7.48 (m, 2H), 3.55-3.42 (m, 2H), 2.94 (s, 3H), 2.64-2.55 (m, 1H), 2.39-2.26 (m, 1H).

Example 97: (R)-4-(3-(4-Aminopyrido[3,2-d]pyrimidin-6-yl)phenyl)-2-(5-methyl-1,3,4-oxadiazol-2-yl)but-3-yn-2-ol

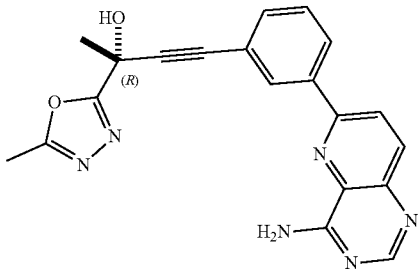

The title compound was prepared using conditions analogous to those described in Example 1 utilizing Intermediate 14 [(R)-2-(5-methyl-1,3,4-oxadiazol-2-yl)but-3-yn-2-ol] to afford (R)-4-(3-(4-aminopyrido[3,2-d]pyrimidin-6-yl)phenyl)-2-(5-methyl-1,3,4-oxadiazol-2-yl)but-3-yn-2-ol (91 mg, 80%). MS (ESI): mass calcd. For $C_{20}H_{16}N_6O_2$, 372.13; m/z. found, 373.1 $[M+H]^+$. $^1H$ NMR (400 MHz, $CD_3OD$) δ 8.42-8.38 (m, 2H), 8.35 (d, J=8.9 Hz, 1H), 8.25-8.28 (m, 1H), 8.12 (d, J=8.8 Hz, 1H), 7.64-7.47 (m, 2H), 2.59 (s, 3H), 2.01 (s, 3H).

Example 98: (R)-3-((3-(8-Amino-4-isopropylpyrido[3,4-d]pyrimidin-2-yl)phenyl)ethynyl)-3-hydroxy-1-methylpyrrolidin-2-one, and its trifluoroacetate

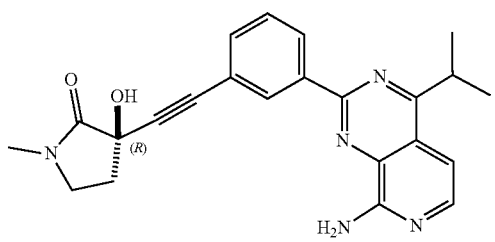

(R)-3-((3-(8-Amino-4-isopropylpyrido[3,4-d]pyrimidin-2-yl)phenyl)ethynyl)-3-hydroxy-1-methylpyrrolidin-2-one was prepared using conditions analogous to those described in Example 1 utilizing Intermediate 51 [2-(3-Iodophenyl)-4-isopropylpyrido[3,4-d]pyrimidin-8-amine] and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-3-((3-(8-Amino-4-isopropylpyrido[3,4-d]pyrimidin-2-yl)phenyl)ethynyl)-3-hydroxy-1-methylpyrrolidin-2-one trifluoroacetate (39 mg, 43%) as a white solid. MS (ESI): mass calcd. for $C_{23}H_{23}N_5O_2$, 401.19; m/z. found, 402.3 $[M+H]^+$. $^1H$ NMR (400 MHz, $CD_3OD$) δ 8.81 (s, 1H), 8.72 (d, J=8.0 Hz, 1H), 7.69 (d, J=7.2 Hz, 1H), 7.65-7.61 (m, 1H), 7.54 (t, J=7.7 Hz, 1H), 7.44 (d, J=7.3 Hz, 1H), 3.88 (p, J=6.7 Hz, 1H), 3.54-3.47 (m, 2H), 2.96 (s, 3H), 2.67-2.59 (m, 1H), 2.40-2.30 (m, 1H), 1.49 (d, J=6.7 Hz, 6H).

Example 99: (R)-3-[2-[3-[8-Amino-5-(trifluoromethyl)pyrido[3,4-d]pyrimidin-2-yl]phenyl]ethynyl]-3-hydroxy-1-methyl-pyrrolidin-2-one

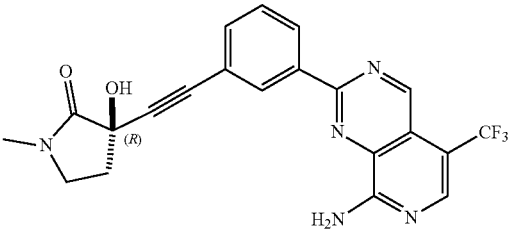

(R)-3-[2-[3-[8-Amino-5-(trifluoromethyl)pyrido[3,4-d]pyrimidin-2-yl]phenyl]ethynyl]-3-hydroxy-1-methyl-pyrrolidin-2-one was prepared using conditions analogous to those described in Example 1 utilizing Intermediate 204 [2-(3-iodophenyl)-5-(trifluoromethyl)pyrido[3,4-d]pyrimidin-8-amine]. MS (ESI): mass calcd. for $C_{21}H_{16}F_3N_5O_2$, 427.1; m/z. found, 428.1 $[M+H]^+$. $^1H$ NMR (400 MHz, DMSO-$d_6$): δ9.59-9.50 (m, 1H), 8.80-8.72 (m, 1H), 8.75 (s, 1H), 8.50 (br s., 1H), 8.34 (s, 1H), 8.29 (br. s., 1H), 7.65-7.57 (m, 2H), 6.54 (s, 1H), 3.41-3.35 (m, 2H), 2.82 (s, 3H), 2.49-2.41 (m, 1H), 2.27-2.17 (m, 1H).

Example 100: (R)-8-Amino-2-(3-((3-hydroxy-1-methyl-2-oxopyrrolidin-3-yl)ethynyl)phenyl)pyrido[3,4-d]pyrimidine-5-carbonitrile and its trifluoroacetate

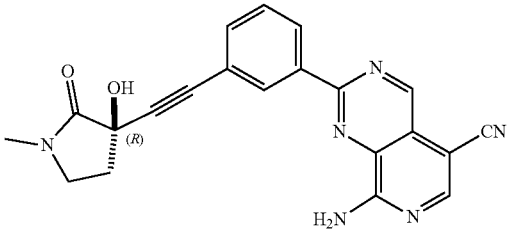

To a vial were added Example 94 [(R)-3-((3-(8-amino-5-bromopyrido[3,4-d]pyrimidin-2-yl)phenyl)ethynyl)-3-hydroxy-1-methylpyrrolidin-2-one (0.05 g, 0.11 mmol)], zinc cyanide (0.04 g, 0.32 mmol), zinc powder (0.04 g, 0.57 mmol), and chloro(2-dicyclohexylphosphino-2',4',6'-triisopropyl-1,1'-biphenyl)[2-(2'-amino-1,1'-biphenyl)]palladium (II) (0.01 g, 0.01 mmol). The vial was sealed with a septum, the atmosphere was evacuated, and then purged with nitrogen (3×). The vial was then charged with dry DMF (2 mL) and then placed in a heating block that had been pre-heated at 100° C. After 1 h, the resulting mixture was cooled to rt and concentrated to dryness to afford (R)-8-amino-2-(3-((3-hydroxy-1-methyl-2-oxopyrrolidin-3-yl)ethynyl)phenyl) pyrido[3,4-d]pyrimidine-5-carbonitrile. The residue was re-dissolved in DCM (about 2 mL) and purified via FCC followed by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-8-amino-2-(3-((3-hydroxy-1-methyl-2-oxopyrrolidin-3-yl)ethynyl)phenyl)pyrido[3,4-d]pyrimidine-5-carbonitrile trifluoroacetate (9 mg, 16%) as a white solid. MS (ESI): mass calcd. for $C_{21}H_{16}N_6O_2$, 384.13; m/z. found, 385.2 [M+H]$^+$. $^1$H NMR (400 MHz, DMSO-d$_6$) δ 9.50 (s, 1H), 8.81-8.71 (m, 3H), 8.52 (s, 1H), 7.66-7.57 (m, 2H), 6.54 (s, 1H), 3.41-3.37 (m, 2H), 2.82 (s, 3H), 2.48-2.44 (m, 1H), 2.26-2.17 (m, 1H).

Example 101: (R)-3-((3-(7-Aminothiazolo[5,4-d] pyrimidin-2-yl)phenyl)ethynyl)-3-hydroxy-1-methylpyrrolidin-2-one, and its trifluoroacetate

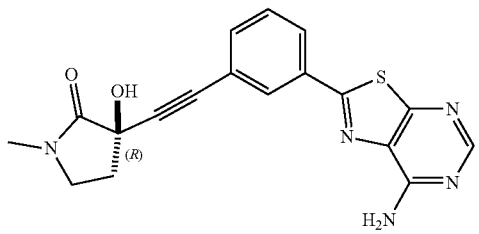

(R)-3-((3-(7-Aminothiazolo[5,4-d]pyrimidin-2-yl)phenyl)ethynyl)-3-hydroxy-1-methylpyrrolidin-2-one was prepared using conditions analogous to those described in Example 1 utilizing Intermediate 52 [2-(3-iodophenyl)thiazolo[5,4-d]pyrimidin-7-amine] and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-3-((3-(7-aminothiazolo[5,4-d]pyrimidin-2-yl)phenyl)ethynyl)-3-hydroxy-1-methylpyrrolidin-2-one trifluoroacetate (38 mg, 25%) as a white solid. MS (ESI): mass calcd. for $C_{18}H_{15}N_5O_2S$, 365.09; m/z. found, 366.1 [M+H]$^+$. $^1$H NMR (400 MHz, CD$_3$OD) δ 8.38 (s, 1H), 8.24-8.20 (m, 1H), 8.13-8.08 (m, 1H), 7.67-7.62 (m, 1H), 7.55 (t, J=7.8 Hz, 1H), 3.52-3.46 (m, 2H), 2.94 (s, 3H), 2.64-2.56 (m, 1H), 2.37-2.28 (m, 1H).

Example 102: (R)-3-((3-(8-Amino-5-iodopyrido[3, 4-d]pyrimidin-2-yl)phenyl)ethynyl)-3-hydroxy-1-methylpyrrolidin-2-one

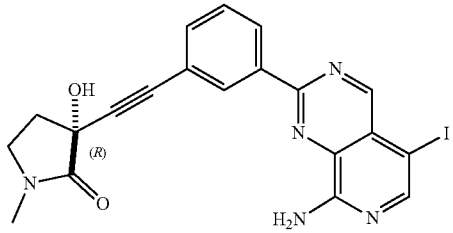

To a 50 mL round-bottomed flask were added Example 1 [(R)-3-[2-[3-(8-aminopyrido[3,4-d]pyrimidin-2-yl)phenyl]ethynyl]-3-hydroxy-1-methyl-pyrrolidin-2-one (784 mg, 2.18 mmol)], N-iodosuccinimide (523 mg, 2.32 mmol), and DMF (30 mL). The resulting yellow suspension was heated at 70° C. under argon for 45 min. The mixture was then concentrated to dryness and purified by FCC to provide (R)-3-((3-(8-amino-5-iodopyrido[3,4-d]pyrimidin-2-yl)phenyl)ethynyl)-3-hydroxy-1-methylpyrrolidin-2-one (448 mg, 42%) as a white solid. MS (ESI): mass calcd. for $C_{20}H_{16}IN_5O_2$, 485.04; m/z. found, 486.1 [M+H]$^+$. $^1$H NMR (400 MHz, DMSO-d$_6$) δ 9.30 (s, 1H), 8.76 (ddd, J=1.71, 2.69, 6.36 Hz, 1H), 8.71-8.73 (m, 1H), 8.26 (s, 1H), 7.77 (br s, 2H), 7.56-7.64 (m, 2H), 6.54 (s, 1H), 2.82 (s, 3H), 2.46-2.53 (m, 3H), 2.21 (dt, J=12.96, 6.97 Hz, 1H).

Example 103: (R)-3-((3-(8-Amino-5-chloropyrido [3,4-d]pyrimidin-2-yl)phenyl)ethynyl)-3-hydroxy-1-methylpyrrolidin-2-one, and its trifluoroacetate

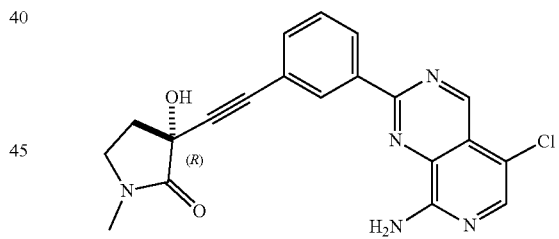

(R)-3-((3-(8-Amino-5-chloropyrido[3,4-d]pyrimidin-2-yl)phenyl)ethynyl)-3-hydroxy-1-methylpyrrolidin-2-one was prepared using conditions analogous to those described in Example 102 utilizing N-chlorosuccinimide with heating at 90° C. under argon for 1 h and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-3-((3-(8-amino-5-chloropyrido[3,4-d]pyrimidin-2-yl)phenyl)ethynyl)-3-hydroxy-1-methylpyrrolidin-2-one trifluoroacetate (51 mg, 18%). MS (ESI): mass calcd. for $C_{20}H_{16}ClN_5O_2$, 393.099; m/z. found, 394.2 [M+H]$^+$. $^1$H NMR (400 MHz, DMSO-d$_6$) δ 9.63 (s, 1H), 8.78-8.75 (m, 1H), 8.74 (s, 1H), 8.06 (s, 1H), 8.04-7.77 (m, 2H), 7.64-7.58 (m, 3H), 3.36-3.33 (m, 2H), 2.82 (s, 3H), 2.49-2.46 (m, 1H), 2.21 (td, J=7.3, 12.7 Hz, 1H).

Example 104: (R)-4-[3-(4-Aminoquinazolin-6-yl)phenyl]-2-(5-methylisoxazol-3-yl)but-3-yn-2-ol

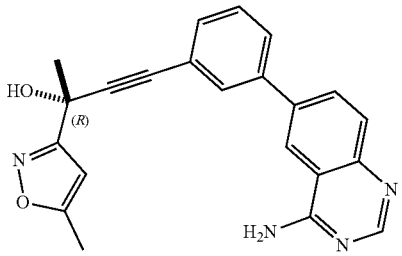

The title compound was prepared using conditions analogous to those described in Example 12 utilizing 6-bromoquinazolin-4-amine and Intermediate 53 [(R)-2-(5-methylisoxazol-3-yl)-4-(3-(4,4,5,5-tetramethyl-1,3,2-dioxaborolan-2-yl)phenyl)but-3-yn-2-ol] to afford (R)-4-[3-(4-aminoquinazolin-6-yl)phenyl]-2-(5-methylisoxazol-3-yl)but-3-yn-2-ol (15 mg, 78%) as a colorless solid (ESI): mass calcd. for $C_{22}H_{18}N_4O_2$, 370.4; m/z found, 371.1 [M+H]$^+$. $^1$H NMR (500 MHz, DMSO-d$_6$) δ 8.59 (d, J=2.1 Hz, 1H), 8.40 (s, 1H), 8.13 (dd, J=8.7, 2.0 Hz, 1H), 7.90-7.84 (m, 2H), 7.74 (d, J=8.7 Hz, 1H), 7.54 (t, J=7.7 Hz, 1H), 7.46 (dt, J=7.6, 1.3 Hz, 1H), 6.54 (s, 1H), 6.38 (d, J=1.1 Hz, 1H), 2.42 (d, J=0.9 Hz, 3H), 1.83 (s, 3H).

Example 105: (R)-4-[3-(4-Aminoquinazolin-6-yl)phenyl]-2-thiazol-2-yl-but-3-yn-2-ol

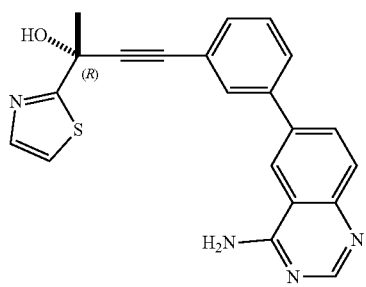

The title compound was prepared using conditions analogous to those described in Example 12 utilizing 6-bromoquinazolin-4-amine and Intermediate 54 [(R)-4-(3-(4,4,5,5-tetramethyl-1,3,2-dioxaborolan-2-yl)phenyl)-2-(thiazol-2-yl)but-3-yn-2-ol] to afford (R)-4-[3-(4-aminoquinazolin-6-yl)phenyl]-2-thiazol-2-yl-but-3-yn-2-ol (14 mg, 27%) as a colorless solid. MS (ESI): mass calcd. for $C_{21}H_{16}N_4OS$, 372.5; m/z. found, 373.0 [M+H]$^+$. $^1$H NMR (500 MHz, DMSO-d$_6$) δ 8.52 (d, J=2.1 Hz, 1H), 8.32 (s, 1H), 8.09-8.03 (m, 1H), 7.82-7.77 (m, 2H), 7.72 (d, J=3.2 Hz, 1H), 7.66 (d, J=8.7 Hz, 1H), 7.63 (d, J=3.2 Hz, 1H), 7.47 (t, J=7.7 Hz, 1H), 7.39 (dt, J=7.6, 1.3 Hz, 1H), 7.00 (s, 1H), 1.84 (s, 3H).

Example 106: (R)-4-[3-(4-Aminoquinazolin-6-yl)phenyl]-2-(5-methyl-1,3,4-oxadiazol-2-yl)but-3-yn-2-ol

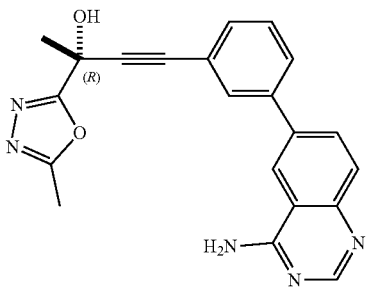

The title compound was prepared using conditions analogous to those described in Example 12 utilizing 6-bromoquinazolin-4-amine and Intermediate 55 [(R)-2-(5-methyl-1,3,4-oxadiazol-2-yl)-4-(3-(4,4,5,5-tetramethyl-1,3,2-dioxaborolan-2-yl)phenyl)but-3-yn-2-ol] to afford (R)-4-[3-(4-aminoquinazolin-6-yl)phenyl]-2-(5-methyl-1,3,4-oxadiazol-2-yl)but-3-yn-2-ol (10 mg, 19%) as a colorless solid. MS (ESI): mass calcd. for $C_{21}H_{17}N_5O_2$, 371.4; m/z. found, 372.1 [M+H]$^+$. $^1$H NMR (400 MHz, DMSO-d$_6$) δ 8.53 (d, J=2.1 Hz, 1H), 8.33 (s, 1H), 8.06 (dd, J=8.7, 2.0 Hz, 1H), 7.85 (t, J=1.7 Hz, 1H), 7.82 (dt, J=7.6, 1.5 Hz, 1H), 7.67 (d, J=8.7 Hz, 1H), 7.49 (t, J=7.7 Hz, 1H), 7.43 (dt, J=7.7, 1.4 Hz, 1H), 6.96 (s, 1H), 2.48 (s, 3H), 1.87 (s, 3H).

Example 107: 2-(3-((1H-Pyrazol-5-yl)ethynyl)phenyl)-4-methylpyrido[3,4-d]pyrimidin-8-amine

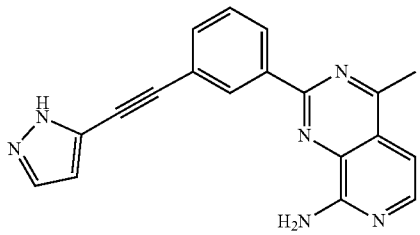 [SMILES: Cc1nc(-c2cccc(C#Cc3ccn[nH]3)c2)nc2c(N)nccc12]

2-(3-((1H-Pyrazol-5-yl)ethynyl)phenyl)-4-methylpyrido[3,4-d]pyrimidin-8-amine was prepared using conditions analogous to those described in Example 1 utilizing Intermediate 34 [2-(3-Iodophenyl)-4-methylpyrido[3,4-d]pyrimidin-8-amine and 5-ethynyl-1H-pyrazole]. MS (ESI): mass calcd. for $C_{19}H_{14}N_6$, 326.13; m/z. found, 327.1 [M+H]$^+$. $^1$H NMR (400 MHz, DMSO-d$_6$) δ 8.84 (s, 1H), 8.72 (d, J=7.6 Hz, 1H), 7.99 (d, J=5.8 Hz, 1H), 7.87 (s, 1H), 7.74-7.58 (m, 2H), 7.09 (d, J=5.8 Hz, 1H), 6.62 (s, 1H), 2.89 (s, 3H).

Example 108. (R)-4-(3-(4-Aminopyrido[2,3-d]pyrimidin-6-yl)phenyl)-2-(thiazol-2-yl)but-3-yn-2-ol

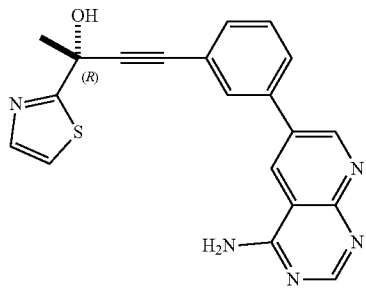

(R)-3-((3-(4-Aminopyrido[2,3-d]pyrimidin-6-yl)phenyl)ethynyl)-3-hydroxy-1-methylpyrrolidin-2-one was prepared using conditions analogous to those described in Example 12 using Intermediate 56 [6-bromopyrido[2,3-d]pyrimidin-4-amine] and Intermediate 54 [(R)-4-(3-(4,4,5,5-tetramethyl-1,3,2-dioxaborolan-2-yl)phenyl)-2-(thiazol-2-yl)but-3-yn-2-ol] to afford (R)-4-(3-(4-aminopyrido[2,3-d]pyrimidin-6-yl)phenyl)-2-(thiazol-2-yl)but-3-yn-2-ol (86 mg, 52%) as an amber solid. MS (ESI): mass calcd. for $C_{20}H_{15}N_5OS$ 373.1 m/z found 374.1 [M+H]$^+$. $^1$H NMR (500 MHz, CD$_3$OD) δ 9.29 (d, J=2.5 Hz, 1H), 8.93 (d, J=2.5 Hz, 1H), 8.54 (s, 1H), 7.94-7.90 (m, 1H), 7.85-7.75 (m, 2H), 7.61-7.47 (m, 3H), 1.97 (s, 3H).

Example 109: (R)-3-((3-(4-Aminopyrido[2,3-d]pyrimidin-6-yl)phenyl)ethynyl)-3-hydroxy-1-methylpyrrolidin-2-one

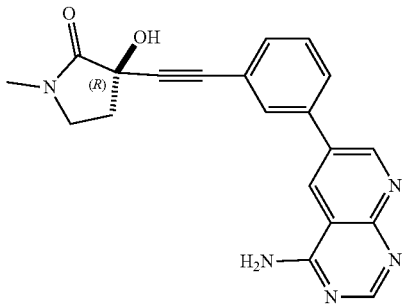

(R)-3-((3-(4-Aminopyrido[2,3-d]pyrimidin-6-yl)phenyl)ethynyl)-3-hydroxy-1-methylpyrrolidin-2-one was prepared using conditions analogous to those described in Example 12 using Intermediate 56 [6-bromopyrido[2,3-d]pyrimidin-4-amine] to afford (R)-3-((3-(4-aminopyrido[2,3-d]pyrimidin-6-yl)phenyl)ethynyl)-3-hydroxy-1-methylpyrrolidin-2-one (79 mg, 66%) as a yellow solid. MS (ESI): mass calcd. for $C_{20}H_{17}N_5O_2$ 359.39 m/z found 360.10 [M+H]$^+$. $^1$H NMR (400 MHz, DMSO-d$_6$) δ 9.36 (d, J=2.4 Hz, 1H), 9.04 (s, 1H), 8.55 (s, 1H), 8.23 (m, 2H), 8.02-7.79 (m, 2H), 7.71-7.42 (m, 2H), 6.50 (s, 1H), 3.38 (m, 1H), 2.82 (s, 3H), 2.46 (m, 1H), 2.32-2.10 (m, 1H).

Example 110: (R)-3-((3-(4-Amino-8-methylquinazolin-6-yl)phenyl)ethynyl)-3-hydroxy-1-methylpyrrolidin-2-one

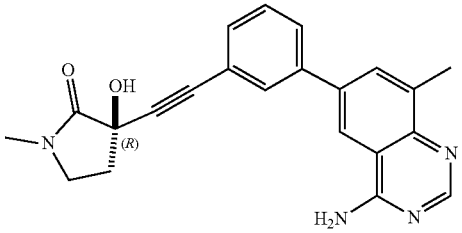

The title compound was prepared using conditions analogous to those described in Example 12 using Intermediate 57 [6-bromo-8-methylquinazolin-4-amine] to afford (R)-3-((3-(4-amino-8-methylquinazolin-6-yl)phenyl)ethynyl)-3-hydroxy-1-methylpyrrolidin-2-one (57 mg, 65%) as a white solid. MS (ESI): mass calcd. for $C_{22}H_{20}N_4O_2$, 372.16; m/z. found, 373.2 [M+H]$^+$. $^1$H NMR (400 MHz, CDCl$_3$) δ 8.58 (s, 1H), 7.66 (s, 1H), 7.45 (s, 1H), 7.38-7.32 (m, 2H), 7.24-7.15 (m, 2H), 3.59-3.43 (m, 2H), 2.99 (s, 3H), 2.71-2.62 (m, 1H), 2.58 (s, 3H), 2.53-2.44 (m, 1H).

Example 111: (R)-3-[2-[3-(4-Aminopyrido[3,4-d]pyrimidin-6-yl)phenyl]ethynyl]-3-hydroxy-1-methyl-pyrrolidin-2-one

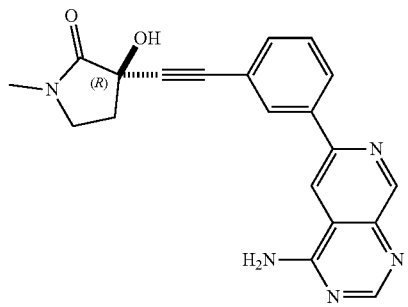

The title compound was prepared using conditions analogous to those described in Example 12 utilizing Intermediate 58 [6-chloropyrido[3,4-d]pyrimidin-4-amine] to afford (R)-3-[2-[3-(4-aminopyrido[3,4-d]pyrimidin-6-yl)phenyl]ethynyl]-3-hydroxy-1-methyl-pyrrolidin-2-one (38 mg, 34%) of as a colorless solid. MS (ESI): mass calcd. for $C_{20}H_{17}N_5O_2$, 359.4; m/z. found, 360.1 [M+H]$^+$. $^1$H NMR (400 MHz, DMSO-d$_6$) δ 9.07 (s, 1H), 8.70 (s, 1H), 8.47-8.42 (m, 1H), 8.26 (s, 1H), 8.17 (dt, J=7.9, 1.5 Hz, 2H), 8.10 (s, 1H), 7.50 (td, J=7.5, 1.1 Hz, 1H), 7.43 (dt, J=7.6, 1.4 Hz, 1H), 6.43 (s, 1H), 3.31 (dd, J=7.5, 5.5 Hz, 2H), 2.75 (s, 3H), 2.41-2.36 (m, 1H), 2.19-2.09 (m, 1H).

Example 112: (R)-3-[2-[3-(8-Amino-5-bromo-1,7-naphthyridin-2-yl)phenyl]ethynyl]-3-hydroxy-1-methyl-pyrrolidin-2-one

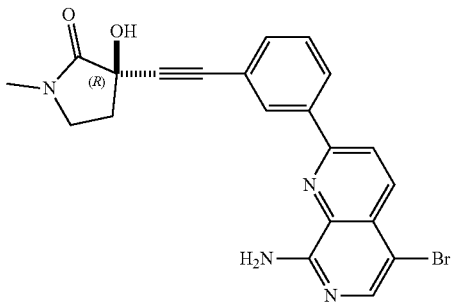

To a flask were added Example 19 [(R)-3-[2-[3-(8-amino-1,7-naphthyridin-2-yl)phenyl]ethynyl]-3-hydroxy-1-methyl-pyrrolidin-2-one (5.60 g, 15.6 mmol)], and DCM (90 mL). The reaction mixture was cooled to 0° C., and TFA (0.60 mL, 1.40 mmol) was added. The resulting mixture was stirred until the mixture became homogeneous. The solution was then treated with N-bromosuccinimide (2.90 g, 16.4 mmol) at 0° C. After 1 h, the resulting solid was collected by filtration to afford (R)-3-[2-[3-(8-amino-5-bromo-1,7-naphthyridin-2-yl)phenyl]ethynyl]-3-hydroxy-1-methyl-pyrrolidin-2-one (4.6 g, 67%) as a yellow solid. MS (ESI): mass calcd. for $C_{21}H_{17}BrN_4O_2$, 437.3; m/z. found, 437.1 [M+H]$^+$. $^1$H NMR (500 MHz, DMSO-d$_6$) δ 8.51-8.45 (m, 2H), 8.44-8.38 (m, 1H), 8.28 (d, J=8.8 Hz, 1H), 8.05 (s, 1H), 7.60-7.52 (m, 2H), 7.43 (s, 2H), 6.49 (s, 1H), 3.42-3.36 (m, 2H), 2.49-2.45 (m, 1H), 2.26-2.11 (m, 1H).

Example 113: (R)-3-[2-[3-(4-Amino-8-fluoro-quinazolin-6-yl)phenyl]ethynyl]-3-hydroxy-1-methyl-pyrrolidin-2-one

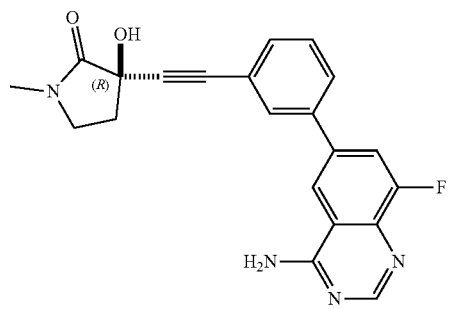

The title compound was prepared using conditions analogous to those described in Example 16 utilizing 6-bromo-8-fluoroquinazolin-4-amine to afford (R)-3-[2-[3-(4-amino-8-fluoro-quinazolin-6-yl)phenyl]ethynyl]-3-hydroxy-1-methyl-pyrrolidin-2-one (25 mg, 20%) of as a colorless solid. MS (ESI): mass calcd. for $C_{21}H_{17}FN_4O_2$, 376.4; m/z found, 377.1 [M+H]$^+$. $^1$H NMR (500 MHz, DMSO-d$_6$) δ 8.46-8.44 (m, 1H), 8.43 (s, 1H), 8.05 (dd, J=12.0, 1.8 Hz, 1H), 7.92-7.90 (m, 1H), 7.90-7.85 (m, 1H), 7.58-7.51 (m, 1H), 7.47 (dt, J=7.7, 1.3 Hz, 1H), 6.48 (s, 1H), 3.40-3.35 (m, 2H), 2.81 (s, 3H), 2.49-2.41 (m, 1H), 2.26-2.16 (m, 1H).

Example 114: (R)-3-((3-(4-Amino-8-methoxyquinazolin-6-yl)phenyl)ethynyl)-3-hydroxy-1-methylpyrrolidin-2-one

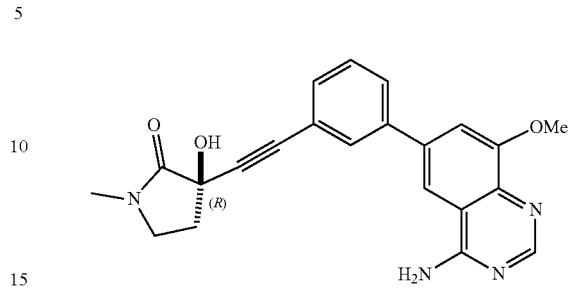

The title compound was prepared using conditions analogous to those described in Example 12 utilizing Intermediate 59 [6-bromo-8-methoxyquinazolin-4-amine] to afford (R)-3-((3-(4-amino-8-methoxyquinazolin-6-yl)phenyl)ethynyl)-3-hydroxy-1-methylpyrrolidin-2-one (62 mg, 60%) as a white solid. MS (ESI): mass calcd. for $C_{22}H_{20}N_4O_3$, 388.15; m/z. found, 389.3 [M+H]$^+$. $^1$H NMR (400 MHz, CD$_3$OD) δ 8.36 (s, 1H), 7.95 (d, J=1.5 Hz, 1H), 7.86 (s, 1H), 7.81-7.74 (m, 1H), 7.51-7.44 (m, 3H), 4.07 (s, 3H), 3.53-3.44 (m, 2H), 2.94 (s, 3H), 2.64-2.55 (m, 1H), 2.37-2.27 (m, 1H).

Example 115: (R)-3-((3-(4-Amino-8-(trifluoromethyl)quinazolin-6-yl)phenyl)ethynyl)-3-hydroxy-1-methylpyrrolidin-2-one

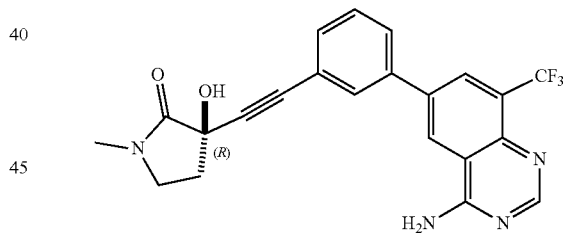

The title compound was prepared in a manner analogous to Example 114 and utilizing 6-bromo-8-(trifluoromethyl)quinazolin-4-amine to afford (R)-3-((3-(4-amino-8-(trifluoromethyl)quinazolin-6-yl)phenyl)ethynyl)-3-hydroxy-1-methylpyrrolidin-2-one (83 mg, 46%) as a white solid. MS (ESI): mass calcd. for $C_{22}H_{17}F_3N_4O_2$, 426.13; m/z. found, 427.2 [M+H]$^+$. $^1$H NMR (400 MHz, CDCl$_3$) δ 8.53 (s, 1H), 8.22-8.13 (m, 1H), 7.98 (s, 1H), 7.65 (s, 1H), 7.23 (s, 1H), 7.08-6.99 (m, 2H), 3.63-3.48 (m, 2H), 3.05 (s, 3H), 2.71-2.60 (m, 1H), 2.56-2.45 (m, 1H). 6-Bromo-8-(trifluoromethyl)quinazolin-4-amine was made in a manner analogous to Intermediate 59 using methyl 2-amino-3-(trifluoromethyl)benzoate in place of methyl 2-amino-3-methoxybenzoate in Step A.

Example 116: (R)-3-((3-(4-Aminothiazolo[4,5-c]pyridin-2-yl)phenyl)ethynyl)-3-hydroxy-1-methylpyrrolidin-2-one, and its trifluoroacetate

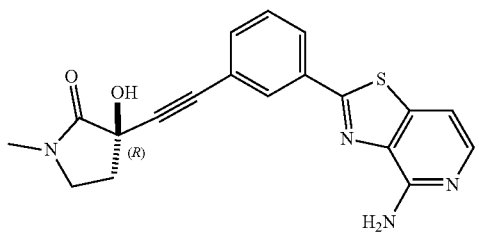

(R)-3-((3-(4-Aminothiazolo[4,5-c]pyridin-2-yl)phenyl)ethynyl)-3-hydroxy-1-methylpyrrolidin-2-one was prepared using conditions analogous to those described in Example 1 utilizing Intermediate 60 [2-(3-iodophenyl)thiazolo[4,5-c]pyridin-4-amine]. (R)-3-((3-(4-aminothiazolo[4,5-c]pyridin-2-yl)phenyl)ethynyl)-3-hydroxy-1-methylpyrrolidin-2-one and purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM to afford (R)-3-((3-(4-aminothiazolo[4,5-c]pyridin-2-yl)phenyl)ethynyl)-3-hydroxy-1-methylpyrrolidin-2-one trifluoroacetate (31 mg, 55%) as a white solid. MS (ESI): mass calcd. for $C_{19}H_{16}N_4O_2S$, 364.10; m/z. found, 365.1 [M+H]$^+$. $^1$H NMR (400 MHz, DMSO-$d_6$) δ 8.61 (s, 2H), 8.25 (s, 1H), 8.15-8.10 (m, 1H), 7.86 (d, J=6.7 Hz, 1H), 7.70-7.60 (m, 3H), 6.57 (s, 1H), 3.54-3.45 (m, 2H), 2.82 (s, 3H), 2.48-2.42 (m, 1H), 2.26-2.18 (m, 1H).

Example 117: (R)-3-((3-(4-Amino-8-chloroquinazolin-6-yl)phenyl)ethynyl)-3-hydroxy-1-methylpyrrolidin-2-one, and its trifluoroacetate

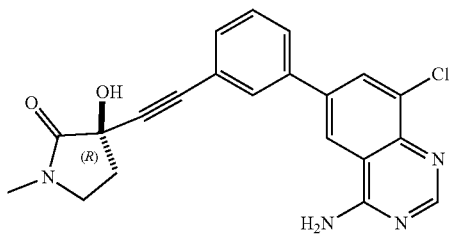

(R)-3-((3-(4-Amino-8-chloroquinazolin-6-yl)phenyl)ethynyl)-3-hydroxy-1-methylpyrrolidin-2-one was prepared in a manner analogous to Example 12 utilizing 6-bromo-8-chloroquinazolin-4-amine. (R)-3-((3-(4-Amino-8-chloroquinazolin-6-yl)phenyl)ethynyl)-3-hydroxy-1-methylpyrrolidin-2-one was then purified by acidic preparative reverse phase HPLC using either a Phenomenex Luna C18 250×50 mm, 5 μm or Welch Xtimate C18 250×50 mm, 10 μm; mobile phase: [water (0.1% TFA)-ACN]; B %: 10%-60%, 20 min, 100%, 5 min. Detection, UV at λ=220-254 nM in Example 12 to afford (R)-3-((3-(4-amino-8-chloroquinazolin-6-yl)phenyl)ethynyl)-3-hydroxy-1-methylpyrrolidin-2-one trifluoroacetate (61 mg, 35%) as a white solid. MS (ESI): mass calcd. for $C_{21}H_{17}ClN_4O_2$, 392.10; m/z. found, 393.1 [M+H]$^+$. $^1$H NMR (400 MHz, CD$_3$OD) δ 8.69-8.60 (m, 2H), 8.49 (d, J=1.8 Hz, 1H), 7.96-7.91 (m, 1H), 7.84-7.79 (m, 1H), 7.59-7.51 (m, 2H), 3.52-3.44 (m, 2H), 2.93 (s, 3H), 2.64-2.55 (m, 1H), 2.38-2.27 (m, 1H). 6-Bromo-8-chloroquinazolin-4-amine was made in a manner analogous to Intermediate 59 using methyl 2-amino-3-chlorobenzoate in place of methyl 2-amino-3-methoxybenzoate in Step A.

Example 118: (R)-8-Amino-2-[3-[2-(3-hydroxy-1-methyl-2-oxo-pyrrolidin-3-yl)ethynyl]phenyl]-1,7-naphthyridine-5-carbonitrile

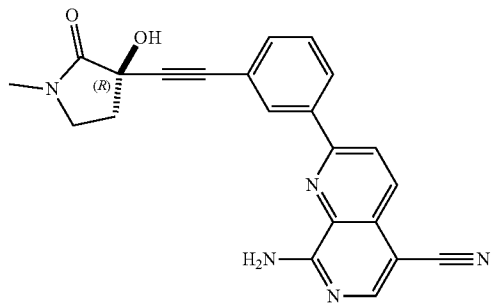

To a microwave vial, were added Example 112 [(R)-3-[2-[3-(8-amino-5-bromo-1,7-naphthyridin-2-yl)phenyl]ethynyl]-3-hydroxy-1-methyl-pyrrolidin-2-one (50 mg, 0.11 mmol)], zinc cyanide (30 mg, 0.25 mmol), Pd(PPh$_3$)$_4$ (32 mg, 0.028 mmol), and DMF (1 mL). The vial was sealed and heated at 120° C. After 16 h, the resulting mixture was cooled to rt and additional zinc cyanide (30 mg, 0.25 mmol) and Pd(PPh$_3$)$_4$ (32 mg, 0.028 mmol) were added. The vial was sealed heated at 120° C. for 4 h. The mixture was again cooled to rt and zinc cyanide (30 mg, 0.25 mmol) and Pd(PPh$_3$)$_4$ (32 mg, 0.028 mmol) were added. The vial was sealed and stirred at 120° C. After 16 h, the mixture was cooled to rt and the mixture was partitioned between DCM (10 mL) and water (10 mL). The organic layer was separate and concentrated to dryness. The resulting residue was purified by reverse phase preparative HPLC (XBridge Prep C18 5 μm, 50×250 mm column using a 0 to 100% gradient of MeCN/20 mM NH$_4$OH in H$_2$O over 35 min) to afford (R)-8-amino-2-[3-[2-(3-hydroxy-1-methyl-2-oxo-pyrrolidin-3-yl)ethynyl]phenyl]-1,7-naphthyridine-5-carbonitrile (18 mg, 41%) as a colorless solid. MS (ESI): mass calcd. for $C_{22}H_{17}N_5O_2$, 383.4; m/z. found, 384.1 [M+H]$^+$. $^1$H NMR (500 MHz, DMSO-$d_6$) δ 8.46 (d, J=8.8 Hz, 1H), 8.44-8.41 (m, 1H), 8.39-8.36 (m, 1H), 8.35 (s, 1H), 8.31 (s, 1H), 8.17 (d, J=8.7 Hz, 1H), 8.15 (s, 1H), 7.53-7.46 (m, 2H), 6.41 (s, 1H), 3.34-3.28 (m, 2H), 2.75 (s, 3H), 2.42-2.38 (m, 1H), 2.18-2.10 (m, 1H).

Example 119: (R)-3-[2-[3-(5-Amino-2,6-naphthyridin-3-yl)phenyl]ethynyl]-3-hydroxy-1-methyl-pyrrolidin-2-one

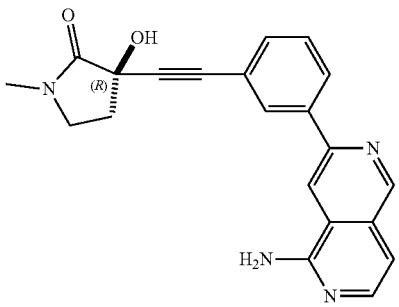

The title compound was prepared using conditions analogous to those described in Example 1 utilizing Intermediate 62 [7-(3-iodophenyl)-2,6-naphthyridin-1-amine] to afford (R)-3-[2-[3-(5-amino-2,6-naphthyridin-3-yl)phenyl]ethynyl]-3-hydroxy-1-methyl-pyrrolidin-2-one (17 mg, 16%) as a colorless solid. MS (ESI): mass calcd. for $C_{21}H_{18}N_4O_2$, 358.4; m/z. found, 359.1 [M+H]$^+$. $^1$H NMR (500 MHz, DMSO-$d_6$) δ 9.14 (d, J=0.8 Hz, 1H), 8.66 (s, 1H), 8.25-8.18 (m, 2H), 7.90 (d, J=5.7 Hz, 1H), 7.49 (t, J=7.7 Hz, 1H), 7.41 (dt, J=7.6, 1.4 Hz, 1H), 7.20 (s, 2H), 6.99 (dd, J=5.8, 0.8 Hz, 1H), 6.43 (s, 1H), 3.34-3.28 (m, 2H), 2.75 (s, 3H), 2.43-2.37 (m, 1H), 2.18-2.11 (m, 1H).

Example 120: (R)-3-[2-[3-(8-Amino-5-methyl-1,7-naphthyridin-2-yl)phenyl]ethynyl]-3-hydroxy-1-methyl-pyrrolidin-2-one

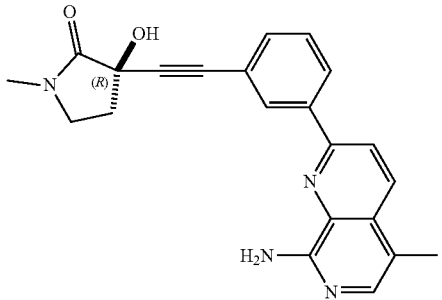

2,4,6-Trimethyl-1,3,5,2,4,6-trioxatriborinane (0.33 mL, 0.23 mmol) and aqueous tribasic potassium phosphate (1.1 mL, 0.57 mmol) were added to a suspension of Example 112 [(R)-3-[2-[3-(8-amino-5-bromo-1,7-naphthyridin-2-yl)phenyl]ethynyl]-3-hydroxy-1-methyl-pyrrolidin-2-one (50 mg, 0.11 mmol)], and (2-dicyclohexylphosphino-2',6'-diisopropoxy-1,1'-biphenyl)[2-(2'-amino-1,1'-biphenyl)]palladium(II) methanesulfonate (9.0 mg, 0.01 mmol) in dioxane (1.1 mL). The reaction vessel was sealed and heated at 90° C. for 1.5 h. The reaction mixture was then cooled to rt and partitioned between ethyl acetate (10 mL) and water (10 mL). The organic layer was separated, concentrated to dryness, and purified by reverse phase preparative HPLC (XBridge Prep C18 5 μm, 50×100 mm column using a 5 to 99% gradient of CH$_3$CN/20 mM NH$_4$OH in H$_2$O for 12 min) to afford (R)-3-[2-[3-(8-amino-5-methyl-1,7-naphthyridin-2-yl)phenyl]ethynyl]-3-hydroxy-1-methyl-pyrrolidin-2-one (8.4 mg, 20%) as a colorless solid. MS (ESI): mass calcd. for $C_{22}H_{20}N_4O_2$, 372.4; m/z. found, 373.1 [M+H]$^+$. $^1$H NMR (500 MHz, DMSO-$d_6$) δ 8.37 (dt, J=7.6, 1.7 Hz, 1H), 8.30 (d, J=8.8 Hz, 1H), 8.23 (d, J=8.8 Hz, 1H), 7.65 (d, J=1.2 Hz, 2H), 7.51-7.44 (m, 2H), 6.81 (s, 2H), 6.42 (s, 1H), 3.35-3.28 (m, 2H), 2.75 (s, 3H), 2.42-2.39 (m, 1H), 2.33-2.27 (m, 3H), 2.20-2.09 (m, 1H).

Example 121: (R)-3-((3-(8-Amino-5-phenylpyrido[3,4-d]pyrimidin-2-yl)phenyl)ethynyl)-3-hydroxy-1-methylpyrrolidin-2-one, and its trifluoroacetate

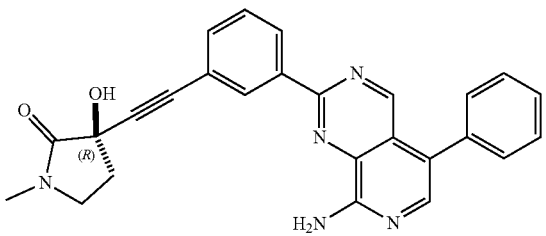

To a vial were added Example 102 [(R)-3-((3-(8-amino-5-iodopyrido[3,4-d]pyrimidin-2-yl)phenyl)ethynyl)-3-hydroxy-1-methylpyrrolidin-2-one, (0.025 g, 0.052 mmol)], phenyl boronic acid (0.011 g, 0.086 mmol), and tetrakis(triphenylphosphine)palladium(0) (0.007 g, 0.006 mmol). The vial was sealed with a septum, the atmosphere was evacuated, and then purged with N$_2$ (3×). The vial was charged with degassed 1,4-dioxane (1.5 mL) and degassed aqueous K$_2$CO$_3$ solution (0.5 mL, 2M) and then placed in a heating block that had been pre-heated at 100° C. After 30 min, the resulting mixture was cooled to rt and concentrated to dryness to afford (R)-3-((3-(8-amino-5-phenylpyrido[3,4-d]pyrimidin-2-yl)phenyl)ethynyl)-3-hydroxy-1-methylpyrrolidin-2-one. This residue was purified via preparative reverse phase HPLC (Phenomonex Luna 5 μm C18(2) 100A, AXIA, 100×30 mm column using a 5 to 90% gradient of MeCN in water (both phases containing 0.1% TFA) over 15 min) to afford (R)-3-((3-(8-amino-5-phenylpyrido[3,4-d]pyrimidin-2-yl)phenyl)ethynyl)-3-hydroxy-1-methylpyrrolidin-2-one trifluoroacetate (14 mg, 49%). MS (ESI): mass calcd. for $C_{26}H_{21}N_5O_2$, 435.17; m/z. found, 436.2 [M+H]$^+$. $^1$H NMR (400 MHz, CD$_3$OD) δ 9.47 (s, 1H), 8.84 (s, 1H), 8.74-8.69 (m, 1H), 7.69-7.53 (m, 7H), 3.53-3.46 (m, 2H), 2.95 (s, 3H), 2.67-2.57 (m, 1H), 2.39-2.29 (m, 1H).

Example 122: (R)-3-[2-[3-[8-Amino-5-(1-methylpyrazol-4-yl)pyrido[3,4-d]pyrimidin-2-yl]phenyl]ethynyl]-3-hydroxy-1-methyl-pyrrolidin-2-one

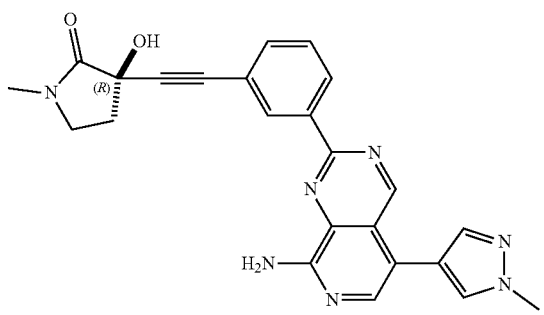

The title compound was prepared using analogous conditions described in Example 121 utilizing 1-methyl-4-(4,4,5,5-tetramethyl-1,3,2-dioxaborolan-2-yl)-1H-pyrazole to afford (R)-3-[2-[3-[8-amino-5-(1-methylpyrazol-4-yl)pyrido[3,4-d]pyrimidin-2-yl]phenyl]ethynyl]-3-hydroxy-1-methyl-pyrrolidin-2-one (17 mg, 38%) as a yellow solid. MS (ESI): mass calcd. for C$_{24}$H$_{21}$N$_7$O$_2$, 439.18; m/z. found, 440.3 [M+H]$^+$. $^1$H NMR (400 MHz, CD$_3$OD) δ 9.58 (s, 1H), 8.76-8.72 (m, 1H), 8.68-8.61 (m, 1H), 7.96 (s, 1H), 7.93 (s, 1H), 7.77 (d, J=0.8 Hz, 1H), 7.63-7.57 (m, 1H), 7.57-7.49 (m, 1H), 4.01 (s, 3H), 3.55-3.43 (m, 2H), 2.95 (s, 3H), 2.67-2.56 (m, 1H), 2.39-2.28 (m, 1H).

Example 123: (R)-3-[2-[3-[8-Amino-5-[1-(2-hydroxy-2-methyl-propyl)pyrazol-4-yl]pyrido[3,4-d]pyrimidin-2-yl]phenyl]ethynyl]-3-hydroxy-1-methyl-pyrrolidin-2-one

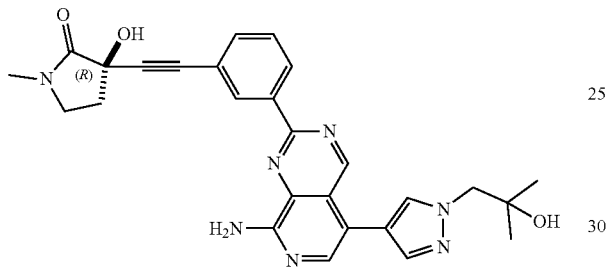

The title compound was prepared using analogous conditions described Example 121 utilizing 2-methyl-1-(4-(4,4,5,5-tetramethyl-1,3,2-dioxaborolan-2-yl)-1H-pyrazol-1-yl)propan-2-ol to afford (R)-3-[2-[3-[8-amino-5-[1-(2-hydroxy-2-methyl-propyl)pyrazol-4-yl]pyrido[3,4-d]pyrimidin-2-yl]phenyl]ethynyl]-3-hydroxy-1-methyl-pyrrolidin-2-one (13 mg, 25%) as a yellow solid. MS (ESI): mass calcd. for C$_{27}$H$_{27}$N$_7$O$_3$, 497.22; m/z. found, 498.3 [M+H]$^+$. $^1$H NMR (400 MHz, CD$_3$OD) δ 9.60 (s, 1H), 8.76-8.72 (m, 1H), 8.67-8.62 (m, 1H), 7.99 (s, 1H), 7.96 (s, 1H), 7.79 (s, 1H), 7.63-7.58 (m, 1H), 7.55-7.49 (m, 1H), 4.21 (s, 2H), 3.54-3.43 (m, 2H), 2.95 (s, 3H), 2.66-2.56 (m, 1H), 2.39-2.26 (m, 1H), 1.25 (s, 6H).

Example 124: (R)-3-[2-[3-[8-Amino-5-(1H-pyrazol-4-yl)pyrido[3,4-d]pyrimidin-2-yl]phenyl]ethynyl]-3-hydroxy-1-methyl-pyrrolidin-2-one

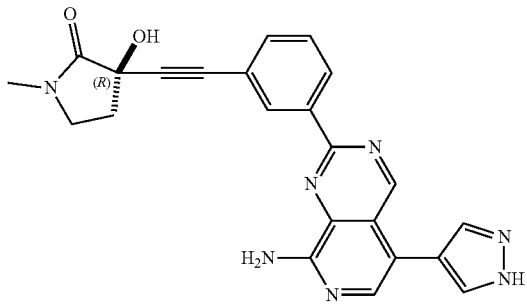

To a sealable vial were added Example 102 [(R)-3-((3-(8-amino-5-iodopyrido[3,4-d]pyrimidin-2-yl)phenyl)ethynyl)-3-hydroxy-1-methylpyrrolidin-2-one (50 mg, 0.10 mmol)], 4-(4,4,5,5-tetramethyl-1,3,2-dioxaborolan-2-yl)-1H-pyrazole (22 mg, 0.11 mmol), dioxane (0.9 mL), aqueous Na$_2$CO$_3$ solution (0.2 mL, 2M). The mixture was sparged with argon for 10 min and then [1,1'-bis(diphenylphoshino)ferrocene]dichloropalladium(II) (7.5 mg, 0.01 mmol) was added. The vial was sealed and heated at 80° C. After 16 h, the resulting mixture was cooled to rt, diluted with ethyl acetate (25 mL) and water (25 mL) and extracted with ethyl acetate (25 mL×3). The combined organic layers were dried over sodium sulfate, filtered, and concentrated to dryness. The residue was purified by FCC (0 to 10% gradient using MeOH in DCM) to afford (R)-3-[2-[3-[8-amino-5-(1H-pyrazol-4-yl)pyrido[3,4-d]pyrimidin-2-yl]phenyl]ethynyl]-3-hydroxy-1-methyl-pyrrolidin-2-one (12.6 mg, 24.6%) as a pale yellow solid. MS (ESI): mass calcd. for C$_{23}$H$_{19}$N$_7$O$_2$, 425.16; m/z found, 426.3 [M+H]$^+$. $^1$H NMR (400 MHz, CD$_3$OD) δ 9.44 (s, 1H), 8.61-8.56 (m, 1H), 8.57-8.48 (m, 1H), 7.98 (br s, 1H), 7.88 (s, 1H), 7.85 (br s, 1H), 7.59-7.48 (m, 1H), 7.48-7.35 (m, 1H), 3.61-3.44 (m, 2H), 2.96 (s, 3H), 2.70-2.55 (m, 1H), 2.40-2.24 (m, 1H).

Example 125: (R)-3-[2-[3-[8-Amino-5-(3,5-dimethyl-1H-pyrazol-4-yl)pyrido[3,4-d]pyrimidin-2-yl]phenyl]ethynyl]-3-hydroxy-1-methyl-pyrrolidin-2-one

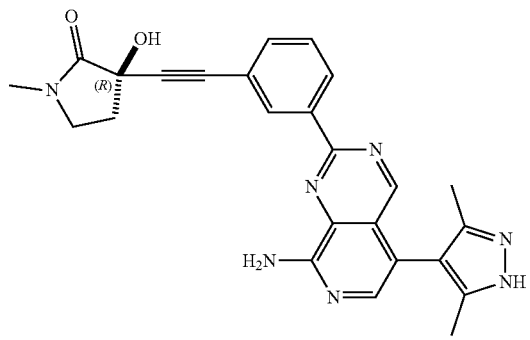

The title compound was prepared using analogous conditions described Example 121 utilizing 3,5-dimethyl-4-(4,4,5,5-tetramethyl-1,3,2-dioxaborolan-2-yl)-1H-pyrazole to afford (R)-3-[2-[3-[8-amino-5-(3,5-dimethyl-1H-pyrazol-4-yl)pyrido[3,4-d]pyrimidin-2-yl]phenyl]ethynyl]-3-hydroxy-1-methyl-pyrrolidin-2-one (10 mg, 22%) as a yellow solid. MS (ESI): mass calcd. for C$_{25}$H$_{23}$N$_7$O$_2$, 453.19; m/z. found, 454.4 [M+H]$^+$. $^1$H NMR (400 MHz, CD$_3$OD) δ 9.05 (s, 1H), 8.76-8.70 (m, 1H), 8.67-8.59 (m, 1H), 7.76 (s, 1H), 7.62-7.56 (m, 1H), 7.54-7.47 (m, 1H), 3.56-3.44 (m, 2H), 2.95 (s, 3H), 2.66-2.57 (m, 1H), 2.38-2.28 (m, 1H), 2.14 (s, 6H).

Example 126: (R)-4-Amino-6-(3-((3-hydroxy-1-methyl-2-oxopyrrolidin-3-yl)ethynyl)phenyl)quinazoline-8-carbonitrile

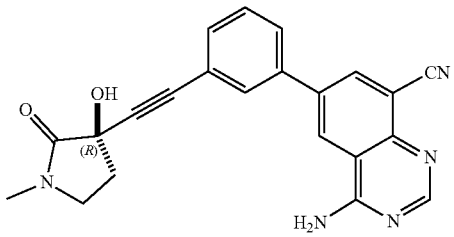

The title compound was prepared using conditions analogous to those described in Example 12 utilizing 4-amino-6-bromoquinazoline-8-carbonitrile to afford (R)-4-amino-6-(3-((3-hydroxy-1-methyl-2-oxopyrrolidin-3-yl)ethynyl)phenyl)quinazoline-8-carbonitrile (48 mg, 27%) as a white solid. MS (ESI): mass calcd. for $C_{22}H_{17}N_5O_2$, 383.14; m/z found, 384.1 [M+H]$^+$. $^1$H NMR (400 MHz, CD$_3$OD) δ 8.76 (s, 1H), 8.56 (s, 1H), 8.48 (s, 1H), 7.93 (s, 1H), 7.81 (s, 1H), 7.53 (s, 2H), 3.53-3.43 (m, 2H), 2.93 (s, 3H), 2.65-2.54 (m, 1H), 2.38-2.26 (m, 1H).

Example 127: (R)-3-[2-[3-[8-Amino-5-(5-methyl-1H-pyrazol-4-yl)pyrido[3,4-d]pyrimidin-2-yl]phenyl]ethynyl]-3-hydroxy-1-methyl-pyrrolidin-2-one

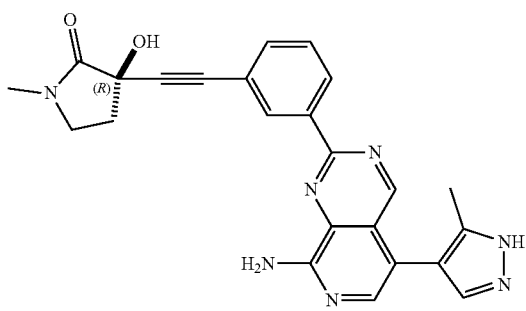

The title compound was prepared using analogous conditions described in Example 121 utilizing 3-methyl-4-(4,4,5,5-tetramethyl-1,3,2-dioxaborolan-2-yl)-1H-pyrazole to afford (R)-3-[2-[3-[8-amino-5-(5-methyl-1H-pyrazol-4-yl)pyrido[3,4-d]pyrimidin-2-yl]phenyl]ethynyl]-3-hydroxy-1-methyl-pyrrolidin-2-one (11 mg, 45%) as a yellow solid. MS (ESI): mass calcd. for $C_{24}H_{21}N_7O_2$, 439.18; m/z found, 440.3 [M+H]$^+$. $^1$H NMR (400 MHz, CD$_3$OD) δ 9.24 (s, 1H), 8.72-8.65 (m, 1H), 8.64-8.57 (m, 1H), 7.81 (s, 1H), 7.72 (s, 1H), 7.61-7.54 (m, 1H), 7.54-7.44 (m, 1H), 3.57-3.43 (m, 2H), 2.95 (s, 3H), 2.66-2.56 (m, 1H), 2.38-2.28 (m, 1H), 2.26 (s, 3H).

Example 128: (R)-Phenyl 8-amino-2-[3-[2-(3-hydroxy-1-methyl-2-oxo-pyrrolidin-3-yl)ethynyl]phenyl]pyrido[3,4-d]pyrimidine-5-carboxylate

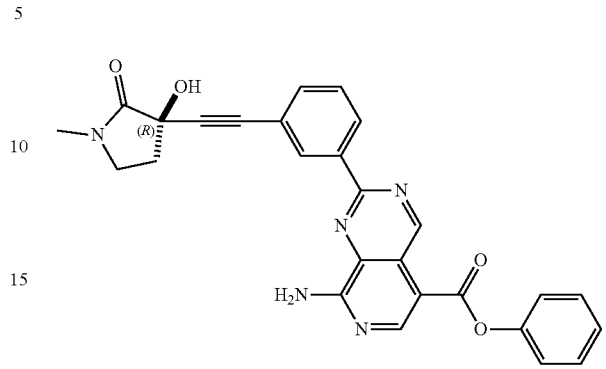

In a sealable vial, were added Example 94 [(R)-3-((3-(8-Amino-5-bromopyrido[3,4-d]pyrimidin-2-yl)phenyl)ethynyl)-3-hydroxy-1-methylpyrrolidin-2-one (100 mg, 0.23 mmol)] and MeCN (2.3 mL). The solution was degassed with N$_2$ for 10 min, then charged with phenyl formate (0.05 ml, 0.46 mmol), tri-tert-butylphosphonium tetrafluoroborate (7.9 mg, 0.03 mmol), palladium(II) acetate (1.5 mg, 0.007 mmol), and TEA (0.06 ml, 0.46 mmol). The vial was sealed and heated at 85° C. After 72 h, the resulting mixture was cooled to rt, and partitioned between ethyl acetate (20 mL) and water (10 mL). The organic layer was separated, concentrated to dryness, and the residue was reverse phase preparative HPLC (XBridge Prep C18 5 μm, 50×100 mm column using a 5 to 99% gradient of CH$_3$CN/20 mM NH$_4$OH in H$_2$O over 12 min) to afford (R)-phenyl 8-amino-2-[3-[2-(3-hydroxy-1-methyl-2-oxo-pyrrolidin-3-yl)ethynyl]phenyl]pyrido[3,4-d]pyrimidine-5-carboxylate (12 mg, 11%) as a colorless solid. MS (ESI): mass calcd. for $C_{27}H_{21}N_5O_4$, 479.5; m/z. found, 480.1 [M+H]$^+$. $^1$H NMR (500 MHz, DMSO-d$_6$) δ 10.28 (s, 1H), 8.87 (s, 1H), 8.75-8.66 (m, 2H), 8.49 (s, 1H), 7.56-7.48 (m, 2H), 7.47-7.38 (m, 2H), 7.32-7.19 (m, 3H), 6.43 (s, 1H), 3.33-3.28 (m, 2H), 2.75 (s, 3H), 2.42-2.37 (m, 1H), 2.19-2.08 (m, 1H).

Example 129: (R)-3-((3-(8-Amino-5-ethylpyrido[3,4-d]pyrimidin-2-yl)phenyl)ethynyl)-3-hydroxy-1-methylpyrrolidin-2-one

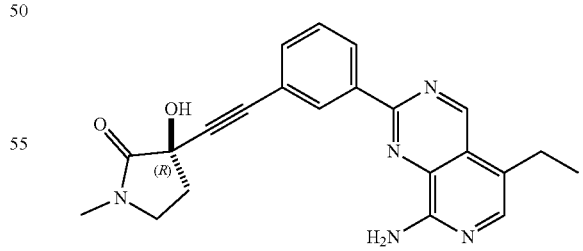

A vial was charged with Example 102, [(R)-3-((3-(8-amino-5-iodopyrido[3,4-d]pyrimidin-2-yl)phenyl)ethynyl)-3-hydroxy-1-methylpyrrolidin-2-one (54.0 mg, 0.11 mmol)], palladium(II) acetate (2.60 mg, 0.01 mmol), 2-dicyclohexylphosphino-2',6'-dimethoxy-1,1'-biphenyl (9.50 mg, 0.02 mmol), and THF (1 mL). The vial was sealed, evacuated, and re-filled with argon three times. Ethylzinc bromide (0.67 mL, 0.34 mmol, 0.5 M in THF) was added. The resulting solution was stirred at rt for 1 h. The reaction mixture was partitioned between ethyl acetate (5 mL) and water (5 mL). The aqueous phase was extracted with ethyl acetate (5 mL×3). The combined organic layers were washed with brine (10 mL), dried with $Na_2SO_4$, filtered, and concentrated to dryness. The resulting residue was purified by FCC to afford (R)-3-((3-(8-amino-5-ethylpyrido[3,4-d]pyrimidin-2-yl)phenyl)ethynyl)-3-hydroxy-1-methylpyrrolidin-2-one (14 mg, 32%) as a white solid. MS (ESI): mass calcd. for $C_{22}H_{21}N_5O_2$, 387.17; m/z. found, 388.2 [M+H]$^+$. $^1$H NMR (400 MHz, DMSO-d$_6$) δ 9.68 (s, 1H), 8.68-8.75 (m, 2H), 7.85 (s, 1H), 7.56-7.61 (m, 2H), 7.27 (br s, 2H), 6.54 (s, 1H), 2.92 (q, J=7.50 Hz, 2H), 2.82 (s, 3H), 2.45-2.53 (m, 3H), 2.17-2.26 (m, 1H), 1.27 (t, J=7.58 Hz, 3H).

Example 130: (R)-3-((3-(8-Amino-5-isobutylpyrido[3,4-d]pyrimidin-2-yl)phenyl)ethynyl)-3-hydroxy-1-methylpyrrolidin-2-one

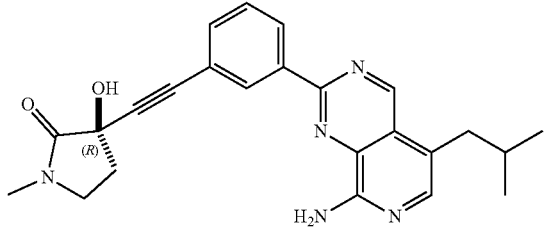

The title compound was prepared using analogous conditions described in Example 129 utilizing 2-methylpropylzinc bromide to afford (R)-3-((3-(8-amino-5-isobutylpyrido[3,4-d]pyrimidin-2-yl)phenyl)ethynyl)-3-hydroxy-1-methylpyrrolidin-2-one (8.5 mg, 25%) as a white solid. MS (ESI): mass calcd. for $C_{24}H_{25}N_5O_2$, 415.20; m/z found, 416.3 [M+H]$^+$. $^1$H NMR (400 MHz, DMSO-d$_6$) δ 9.67 (s, 1H), 8.68-8.75 (m, 2H), 7.80 (s, 1H), 7.59 (d, J=5.38 Hz, 2H), 7.29 (br s, 2H), 6.54 (s, 1H), 2.82 (s, 3H), 2.75 (d, J=6.85 Hz, 2H), 2.44-2.50 (m, 3H), 2.21 (dt, J=12.72, 7.34 Hz, 1H), 1.82-1.94 (m, 1H), 0.92 (d, J=6.85 Hz, 6H).

Example 131: (R)-2-[2-[3-(4-Aminopyrido[3,2-d]pyrimidin-6-yl)phenyl]ethynyl]-2-hydroxy-5,5-dimethyl-cyclopentanone

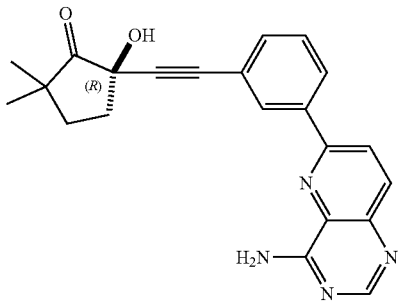

The title compound was prepared using conditions analogous to those described in Example 12 utilizing Intermediate 66 [(R)-2-hydroxy-5,5-dimethyl-2-((3-(4,4,5,5-tetramethyl-1,3,2-dioxaborolan-2-yl)phenyl)ethynyl)cyclopentan-1-one] and Intermediate 56 [6-bromopyrido[2,3-d]pyrimidin-4-amine] to afford (R)-2-[2-[3-(4-aminopyrido[3,2-d]pyrimidin-6-yl)phenyl]ethynyl]-2-hydroxy-5,5-dimethyl-cyclopentanone (38 mg, 50%) as a colorless solid. MS (ESI): mass calcd. for $C_{22}H_{20}N_4O_2$, 372.4; m/z. found, 373.2 [M+H]$^+$. $^1$H NMR (500 MHz, DMSO-d$_6$) δ 8.49-8.44 (m, 2H), 8.42-8.36 (m, 2H), 8.19 (s, 1H), 8.13 (d, J=8.8 Hz, 1H), 7.98 (s, 1H), 7.59-7.49 (m, 2H), 6.47 (s, 1H), 2.36-2.26 (m, 1H), 2.13-2.03 (m, 1H), 1.93-1.84 (m, 2H), 1.15 (s, 3H), 1.09 (s, 3H).

Example 132: (S)-2-[2-[3-(4-Aminopyrido[3,2-d]pyrimidin-6-yl)phenyl]ethynyl]-2-hydroxy-5,5-dimethyl-cyclopentanone

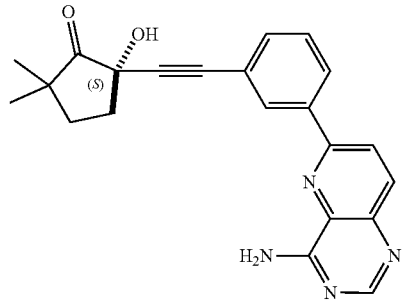

The title compound was prepared using conditions analogous to those described in Example 12 utilizing Intermediate 67 [(S)-2-hydroxy-5,5-dimethyl-2-((3-(4,4,5,5-tetramethyl-1,3,2-dioxaborolan-2-yl)phenyl)ethynyl)cyclopentan-1-one] and Intermediate 56 [6-bromopyrido[2,3-d]pyrimidin-4-amine] to afford (S)-2-[2-[3-(4-aminopyrido[3,2-d]pyrimidin-6-yl)phenyl]ethynyl]-2-hydroxy-5,5-dimethyl-cyclopentanone (36 mg, 47%) as a colorless solid. MS (ESI): mass calcd. for $C_{22}H_{20}N_4O_2$, 372.4; m/z. found, 373.1 [M+H]$^+$. $^1$H NMR (500 MHz, DMSO-d$_6$) δ 8.49-8.44 (m, 2H), 8.42-8.36 (m, 2H), 8.19 (s, 1H), 8.13 (d, J=8.8 Hz, 1H), 7.98 (s, 1H), 7.59-7.49 (m, 2H), 6.47 (s, 1H), 2.36-2.26 (m, 1H), 2.13-2.03 (m, 1H), 1.93-1.84 (m, 2H), 1.15 (s, 3H), 1.09 (s, 3H).

Example 133: (R)-3-[2-[3-[8-Amino-5-(pyrrolidin-1-ylmethyl)pyrido[3,4-d]pyrimidin-2-yl]phenyl]ethynyl]-3-hydroxy-1-methyl-pyrrolidin-2-one

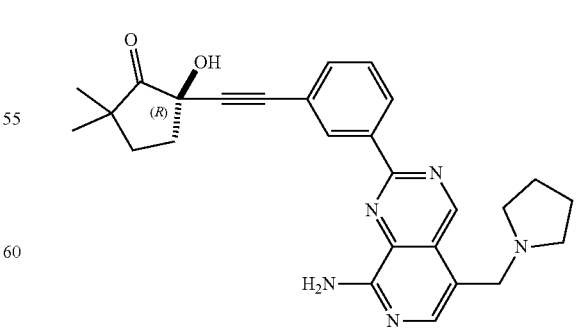

A sealable vial was charged with Example 94 [(R)-3-((3-(8-amino-5-bromopyrido[3,4-d]pyrimidin-2-yl)phenyl)ethynyl)-3-hydroxy-1-methylpyrrolidin-2-one (50 mg, 0.11 mmol)], potassium (pyrrolidin-1-yl)methyltrifluoroborate (24 mg, 0.13 mmol), cesium carbonate (112 mg, 0.34 mmol) and chloro(2-dicyclohexylphosphino-2',4',6'-triisopropyl-1,1'-biphenyl)[2-(2'-amino-1,1'-biphenyl)]palladium(II) (5 mg, 0.007 mmol). The vial was sealed, evacuated, and flushed with nitrogen three times. To the mixture was added THF/water (0.5 mL, 10:1) and the vial was heated at 80° C. After 2 h, the reaction mixture was cooled to rt and partitioned between DCM (10 mL) and water (10 mL). The organic layer was separated and concentrated to dryness. The residue was purified using reverse phase preparative HPLC (XBridge Prep C18 5 μm, 50×100 mm column using a 5 to 99% gradient of ACN/20 mM $NH_4OH$ in $H_2O$ over 12 min) to afford (R)-3-[2-[3-[8-amino-5-(pyrrolidin-1-ylmethyl)pyrido[3,4-d]pyrimidin-2-yl]phenyl]ethynyl]-3-hydroxy-1-methyl-pyrrolidin-2-one (16 mg, 32%) as a colorless solid. MS (ESI): mass calcd. for $C_{25}H_{26}N_6O_2$, 442.5; m/z. found, 443.3 [M+H]+. 1H NMR (500 MHz, DMSO-$d_6$) δ 9.73 (s, 1H), 8.68-8.59 (m, 2H), 7.79 (s, 1H), 7.55-7.47 (m, 2H), 7.31 (s, 2H), 6.43 (s, 1H), 3.75 (s, 2H), 3.35-3.29 (m, 3H), 2.75 (s, 3H), 2.41-2.36 (m, 4H), 2.20-2.09 (m, 1H), 1.64-1.56 (m, 4H).

Example 134: (R)-3-[2-[3-[8-Amino-5-[1-(2-aminoethyl)pyrazol-4-yl]pyrido[3,4-d]pyrimidin-2-yl]phenyl]ethynyl]-3-hydroxy-1-methyl-pyrrolidin-2-one as a hydrochloride salt

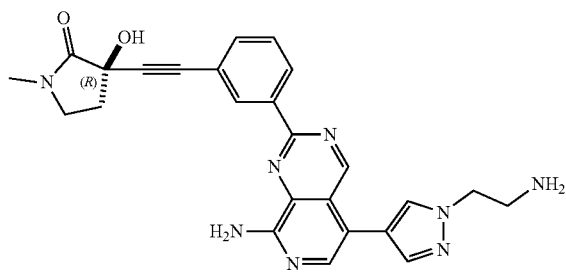

Step A: tert-Butyl-(R)-(2-(4-(8-amino-2-(3-((3-hydroxy-1-methyl-2-oxopyrrolidin-3-yl)ethynyl)phenyl)pyrido[3,4-d]pyrimidin-5-yl)-1H-pyrazol-1-yl)ethyl)carbamate was prepared using analogous conditions described in Example 121 utilizing tert-butyl(2-(4-(4,4,5,5-tetramethyl-1,3,2-dioxaborolan-2-yl)-1H-pyrazol-1-yl)ethyl)carbamate.

Step B: (R)-3-[2-[3-[8-Amino-5-[1-(2-aminoethyl)pyrazol-4-yl]pyrido[3,4-d]pyrimidin-2-yl]phenyl]ethynyl]-3-hydroxy-1-methyl-pyrrolidin-2-one as a hydrochloride salt. To a sealable vial were added tert-butyl-(R)-(2-(4-(8-amino-2-(3-((3-hydroxy-1-methyl-2-oxopyrrolidin-3-yl)ethynyl)phenyl)pyrido[3,4-d]pyrimidin-5-yl)-1H-pyrazol-1-yl)ethyl)carbamate (31 mg, 0.05 mmol) and DCM (1.1 mL). To this solution was added HCl (0.3 mL, 4N HCl in dioxane) in a dropwise manner. After 1 h, the resulting mixture was concentrated to dryness. The resulting solid was triturated with DCM (5 mL), filtered and dried to afford (R)-3-[2-[3-[8-amino-5-[1-(2-aminoethyl)pyrazol-4-yl]pyrido[3,4-d]pyrimidin-2-yl]phenyl]ethynyl]-3-hydroxy-1-methyl-pyrrolidin-2-one as a hydrochloride salt (20 mg, 100%) as a yellow solid. MS (ESI): mass calcd. for $C_{25}H_{24}N_8O_2$, 468.20; m/z. found, 469.3 [M+H]+. 1H NMR (400 MHz, $CD_3OD$) δ 9.72 (s, 1H), 8.86 (d, J=2.1 Hz, 1H), 8.74 (d, J=7.9 Hz, 1H), 8.19 (s, 1H), 7.95 (s, 1H), 7.72-7.65 (m, 2H), 7.57 (t, J=7.8 Hz, 1H), 4.60 (t, J=5.7 Hz, 2H), 3.55 (t, J=5.8 Hz, 2H), 3.53-3.47 (m, 2H), 2.95 (s, 3H), 2.66-2.56 (m, 1H), 2.45-2.27 (m, 1H). (R)-3-[2-[3-[8-Amino-5-[1-(2-aminoethyl)pyrazol-4-yl]pyrido[3,4-d]pyrimidin-2-yl]phenyl]ethynyl]-3-hydroxy-1-methyl-pyrrolidin-2-one hydrochloride can be converted to its respective free base by following the below procedure: (R)-3-[2-[3-[8-amino-5-[1-(2-aminoethyl)pyrazol-4-yl]pyrido[3,4-d]pyrimidin-2-yl]phenyl]ethynyl]-3-hydroxy-1-methyl-pyrrolidin-2-one hydrochloride is partitioned between ethyl acetate and saturated aqueous sodium bicarbonate. The organic layer is separated, and the aqueous layer is extracted twice with ethyl acetate. The combined organic extracts are washed with brine and concentrated to dryness to provide (R)-3-[2-[3-[8-amino-5-[1-(2-aminoethyl)pyrazol-4-yl]pyrido[3,4-d]pyrimidin-2-yl]phenyl]ethynyl]-3-hydroxy-1-methyl-pyrrolidin-2-one.

Example 135: (R)-3-[2-[3-[8-Amino-5-(dimethylaminomethyl)pyrido[3,4-d]pyrimidin-2-yl]phenyl]ethynyl]-3-hydroxy-1-methyl-pyrrolidin-2-one

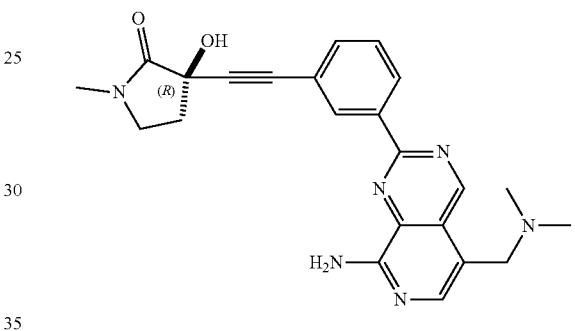

The title compound was prepared using conditions analogous to those described in Example 133 utilizing potassium ((dimethylamino)methyl)trifluoroborate to afford (R)-3-[2-[3-[8-amino-5-(dimethylaminomethyl)pyrido[3,4-d]pyrimidin-2-yl]phenyl]ethynyl]-3-hydroxy-1-methyl-pyrrolidin-2-one (12 mg, 17%) as a colorless solid. MS (ESI): mass calcd. for $C_{23}H_{24}N_6O_2$, 416.5; m/z. found, 417.2 [M+H]+. 1H NMR (500 MHz, DMSO-$d_6$) δ 9.76 (s, 1H), 8.74-8.68 (m, 1H), 7.82 (s, 1H), 7.61-7.54 (m, 2H), 7.41 (s, 2H), 6.51 (s, 1H), 3.61 (s, 2H), 3.40-3.35 (m, 2H), 2.82 (s, 3H), 2.49-2.46 (m, 2H), 2.25-2.19 (m, 1H), 2.18 (s, 6H).

Example 136: (R)-3-[2-[3-(4-Amino-8-methylpyrido[3,4-d]pyrimidin-6-yl)phenyl]ethynyl]-3-hydroxy-1-methyl-pyrrolidin-2-one

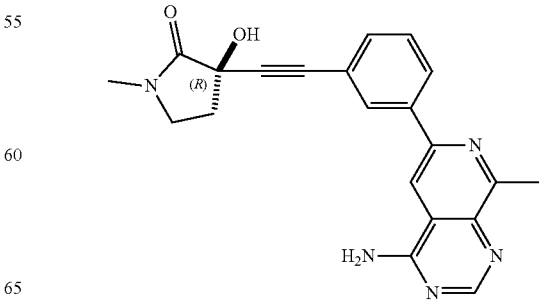

The title compound was prepared using conditions analogous to those described in Example 1 utilizing Intermediate 68 [6-(3-iodophenyl)-8-methylpyrido[3,4-d]pyrimidin-4-amine] to afford (R)-3-[2-[3-(4-amino-8-methyl-pyrido[3,4-d]pyrimidin-6-yl)phenyl]ethynyl]-3-hydroxy-1-methyl-pyrrolidin-2-one (18 mg, 19%) as a light brown solid. MS (ESI): mass calcd. for $C_{21}H_{19}N_5O_2$, 373.15; m/z. found, 374.1 [M+H]$^+$. $^1$H NMR (400 MHz, CD$_3$OD) δ 8.50 (s, 1H), 8.40 (s, 1H), 8.25 (d, J=2.0 Hz, 1H), 8.17-8.11 (m, 1H), 7.54-7.41 (m, 2H), 3.56-3.41 (m, 2H), 2.94 (s, 3H), 2.93 (s, 3H), 2.68-2.56 (m, 1H), 2.39-2.26 (m, 1H).

Example 137: (R)-4-(3-(8-Aminopyrimido[5,4-d]pyrimidin-2-yl)phenyl)-2-(thiazol-2-yl)but-3-yn-2-ol

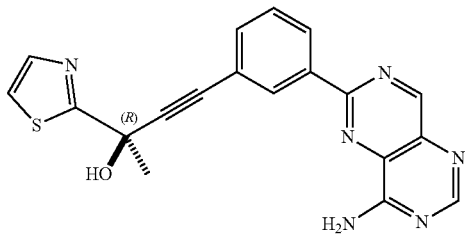

In one portion, DDQ (104 mg, 0.458 mmol) was added to a suspension of Intermediate 69 [(R)-4-(3-(8-((2,4-dimethoxybenzyl)amino)pyrimido[5,4-d]pyrimidin-2-yl)phenyl)-2-(thiazol-2-yl)but-3-yn-2-ol (200 mg, 0.381 mmol)], dichloromethane (40 mL), and H$_2$O (8 mL). The resultant mixture was stirred at rt for 30 min before treating with another batch of DDQ (52 mg, 0.23 mmol). The resultant mixture was stirred at rt for another 20 min before it was concentrated to dryness. The resulting residue was diluted with ethyl acetate (30 mL) and the pH was adjusted to pH=8 with saturated aqueous NaHCO$_3$. The resulting solution was extracted with ethyl acetate (30 mL×3). The combined organic extracts were washed with H$_2$O (30 mL), dried over anhydrous Na$_2$SO$_4$, filtered, and concentrated to dryness. The residue was purified by FCC (1:0 to 1:5 gradient, petroleum ether/ethyl acetate (containing 10% methanol)) to afford (R)-4-(3-(8-aminopyrimido[5,4-d]pyrimidin-2-yl)phenyl)-2-(thiazol-2-yl)but-3-yn-2-ol (44.9 mg, 30%) as a yellow solid. MS (ESI): mass calcd. for $C_{19}H_{14}N_6OS$ 374.1 m/z found 375.0 [M+H]$^+$. $^1$H NMR (400 MHz, DMSO-d$_6$) δ 9.42 (s, 1H), 8.72-8.67 (m, 2H), 8.61 (br. s., 1H), 8.52 (s, 1H), 8.36 (br s, 1H), 7.79 (d, J=3.3 Hz, 1H), 7.70 (d, J=3.3 Hz, 1H), 7.61-7.56 (m, 2H), 7.09 (s, 1H), 1.92 (s, 3H).

Example 138: (R)-3-((3-(8-Amino-4,5-dimethylpyrido[3,4-d]pyrimidin-2-yl)phenyl)ethynyl)-3-hydroxy-1-methylpyrrolidin-2-one

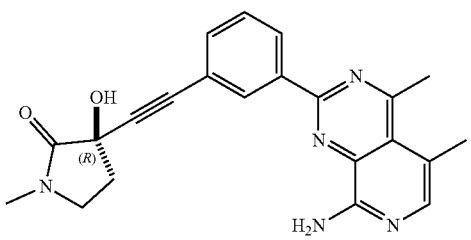

Intermediate 71 [2-(3-bromophenyl)-4,5-dimethylpyrido[3,4-d]pyrimidin-8-amine](230 mg, 0.699 mmol), Intermediate 2 [(R)-3-ethynyl-3-hydroxy-1-methylpyrrolidin-2-one (120 mg, 0.862 mmol)], TEA (2 mL), and DMF (2 mL) were combined. The mixture was sparged with Ar for 5 min and then treated with Pd(PPh$_3$)$_2$Cl$_2$ (49 mg, 0.070 mmol) and CuI (27 mg, 0.14 mmol). The mixture was sparged with Ar for another 5 min and then heated at 100° C. for 1 h. The reaction mixture was then cooled to rt and concentrated to dryness. The resulting residue was purified by FCC (1:0 to 0:1 gradient, petroleum ether/ethyl acetate (containing 10% methanol)) followed by further purification by preparative SFC (DAICEL CHIRALCEL OJ-H 250×30 mm, 5 μm (eluent: 40% to 40% (v/v) supercritical CO$_2$ in EtOH and H$_2$O with 0.1% NH$_3$) to afford (R)-3-((3-(8-amino-4,5-dimethylpyrido[3,4-d]pyrimidin-2-yl)phenyl)ethynyl)-3-hydroxy-1-methylpyrrolidin-2-one (55 mg, 20%) as a yellow solid. MS (ESI): mass calcd. for $C_{22}H_{21}N_5O_2$ 387.2 m/z found 388.2 [M+H]$^+$. $^1$H NMR (400 MHz, DMSO-d$_6$) δ 8.73-8.68 (m, 1H), 8.65 (s, 1H), 7.78 (s, 1H), 7.58-7.54 (m, 2H), 7.11 (s, 2H), 6.53 (br. s, 1H), 3.39-3.36 (m, 2H), 3.08 (s, 3H), 2.82 (s, 3H), 2.60 (s, 3H), 2.48-2.43 (m, 1H), 2.25-2.16 (m, 1H).

Example 139: (R)-3-((3-(4-Aminopyrido[3,2-d]pyrimidin-6-yl)-4-methoxyphenyl)ethynyl)-3-hydroxy-1-methylpyrrolidin-2-one

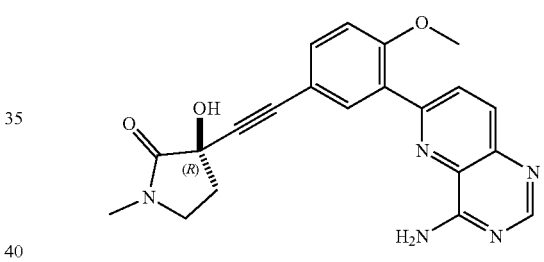

Intermediate 73 [6-bromopyrido[3,2-d]pyrimidin-4-amine (110 mg, 0.489 mmol)], Intermediate 72 [(R)-3-hydroxy-3-((4-methoxy-3-(4,4,5,5-tetramethyl-1,3,2-dioxaborolan-2-yl)phenyl)ethynyl)-1-methylpyrrolidin-2-one (145 mg, 0.391 mmol)], K$_3$PO$_4$ (259 mg, 1.22 mmol), 1,4-dioxane (3 mL), and H$_2$O (0.6 mL) were combined. The mixture was sparged with Ar for 5 min and then treated with Pd(dtbpf)Cl$_2$ (32 mg, 0.05 mmol). The mixture was sparged with Ar for another 5 min and the resultant mixture was then subjected to microwave irradiation at 90° C. in for 1 h. After the reaction mixture was allowed to cool to rt, water (80 mL) was added. The resulting mixture was extracted with ethyl acetate (60 mL×3). The combined organic extracts were dried over anhydrous Na$_2$SO$_4$, filtered, and concentrated to dryness. The resulting residue was purified by preparative reverse phase HPLC (Xtimate C18 250 mm×50 mm×10 μm column (eluent: 17% to 47% (v/v) CH$_3$CN and H$_2$O with 0.04% NH$_3$ and 10 mM NH$_4$HCO$_3$) to afford (R)-3-((3-(4-aminopyrido[3,2-d]pyrimidin-6-yl)-4-methoxyphenyl)ethynyl)-3-hydroxy-1-methylpyrrolidin-2-one (36 mg, 19%) as a pale yellow solid. MS (ESI): mass calcd. for $C_{21}H_{19}N_5O_3$ 389.2 m/z. found 390.2 [M+1]$^+$. $^1$H NMR (400 MHz, DMSO-d$_6$) δ 8.42 (s, 1H), 8.20 (d, J=8.8 Hz, 1H), 8.07 (d, J=8.8 Hz, 1H), 7.99-7.88 (m, 3H), 7.56-7.49 (m, 1H), 7.22 (d, J=8.8 Hz, 1H), 6.40 (s, 1H), 3.90 (s, 3H), 3.38-3.33 (m, 2H), 2.79 (s, 3H), 2.47-2.39 (m, 1H), 2.22-2.12 (m, 1H).

Example 140: (R)-4-[4-[8-Amino-2-[3-[2-(3-hydroxy-1-methyl-2-oxo-pyrrolidin-3-yl)ethynyl]phenyl]pyrido[3,4-d]pyrimidin-5-yl]pyrazol-1-yl]butanenitrile

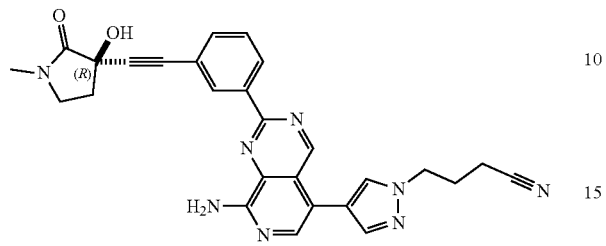

The title compound was prepared using analogous conditions described in Example 121 utilizing 4-(4-(4,4,5,5-tetramethyl-1,3,2-dioxaborolan-2-yl)-1H-pyrazol-1-yl)butanenitrile to afford (R)-4-[4-[8-amino-2-[3-[2-(3-hydroxy-1-methyl-2-oxo-pyrrolidin-3-yl)ethynyl]phenyl]pyrido[3,4-d]pyrimidin-5-yl]pyrazol-1-yl]butanenitrile (19 mg, 38%) as a white solid. MS (ESI): mass calcd. for $C_{27}H_{24}N_8O_2$, 492.20; m/z. found, 493.3 [M+H]+. 1H NMR (400 MHz, $CD_3OD$) δ 9.60 (s, 1H), 8.75 (s, 1H), 8.66 (d, J=7.9 Hz, 1H), 8.04 (s, 1H), 7.95 (s, 1H), 7.82 (s, 1H), 7.63-7.58 (m, 1H), 7.53 (t, J=7.7 Hz, 1H), 4.39 (t, J=6.6 Hz, 2H), 3.57-3.42 (m, 2H), 2.95 (s, 3H), 2.67-2.58 (m, 1H), 2.54 (t, J=7.1 Hz, 2H), 2.39-2.24 (m, 3H).

Example 141: (R)-3-((3-(4-Aminothieno[2,3-d]pyrimidin-6-yl)phenyl)ethynyl)-3-hydroxy-1-methylpyrrolidin-2-one

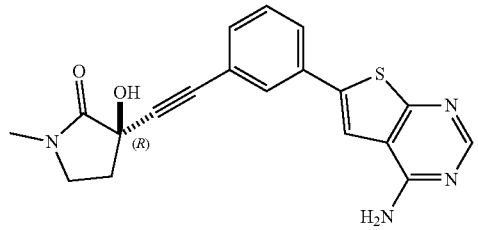

The title compound was prepared using analogous conditions described in Example 12 utilizing 6-bromothieno[2,3-d]pyrimidin-4-amine to afford (R)-3-((3-(4-aminothieno[2,3-d]pyrimidin-6-yl)phenyl)ethynyl)-3-hydroxy-1-methylpyrrolidin-2-one (84 mg, 27%) as a white solid. MS (ESI): mass calcd. for $C_{19}H_{16}N_4O_2S$, 364.10; m/z. found, 365.1 [M+H]+. 1H NMR (400 MHz, $CD_3OD$) δ 8.39 (s, 1H), 7.91 (s, 1H), 7.82 (s, 1H), 7.76-7.71 (m, 1H), 7.54-7.46 (m, 2H), 3.52-3.45 (m, 2H), 2.94 (s, 3H), 2.64-2.55 (m, 1H), 2.38-2.28 (m, 1H).

Example 142: (R)-3-((3-(7-Aminooxazolo[5,4-d]pyrimidin-2-yl)phenyl)ethynyl)-3-hydroxy-1-methylpyrrolidin-2-one

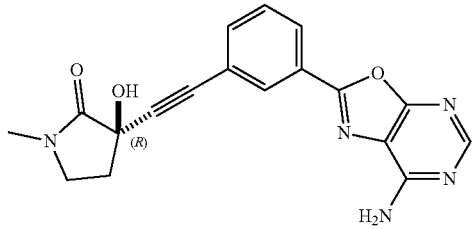

The title compound was prepared using analogous conditions described in Example 12 utilizing Intermediate 74 [2-(3-iodophenyl)oxazolo[5,4-d]pyrimidin-7-amine] to afford (R)-3-((3-(7-aminooxazolo[5,4-d]pyrimidin-2-yl)phenyl)ethynyl)-3-hydroxy-1-methylpyrrolidin-2-one (41 mg, 44%) as a white solid. MS (ESI): mass calcd. for $C_{18}H_{15}N_5O_3$, 349.12; m/z. found, 350.1 [M+H]+. 1H NMR (400 MHz, 4:1 CD3OD/$CDCl_3$) δ 8.30-8.23 (m, 2H), 8.17 (d, J=7.9 Hz, 1H), 7.66 (d, J=7.8 Hz, 1H), 7.55 (t, J=7.8 Hz, 1H), 3.56-3.45 (m, 2H), 2.96 (s, 3H), 2.68-2.58 (m, 1H), 2.41-2.30 (m, 1H).

Example 143: (R)-3-((3-(6-Amino-9-methyl-9H-purin-8-yl)phenyl)ethynyl)-3-hydroxy-1-methylpyrrolidin-2-one

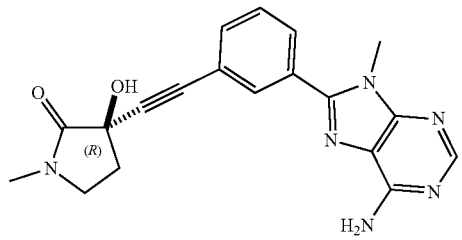

Step A: 8-Bromo-N-(2,4-dimethoxybenzyl)-9-methyl-9H-purin-6-amine. A suspension of 8-bromo-6-chloro-9-methyl-9H-purine (0.126 g, 0.509 mmol), (2,4-dimethoxyphenyl)methanamine (0.128 g, 0.764 mmol), and DIPEA (0.2 mL, 1.161 mmol) in EtOH (5 mL) was heated for 30 minutes at 40° C., 30 minutes at 60° C., and then 30 minutes at 80° C. The resulting mixture was then cooled to rt and concentrated to dryness. The resulting residue was purified via FCC to afford the desired 8-bromo-N-(2,4-dimethoxybenzyl)-9-methyl-9H-purin-6-amine (95 mg, 49%) as a white solid. MS (ESI): mass calcd. for $C_{15}H_{16}BrN_5O_2$, 377.05; m/z. found, 378.1 [M+H]+. 1H NMR (400 MHz, $CDCl_3$) δ 8.38 (s, 1H), 7.31-7.27 (m, 1H), 6.46 (d, J=2.3 Hz, 1H), 6.44-6.39 (m, 1H), 6.10-6.01 (m, 1H), 4.73 (br s, 2H), 3.84 (s, 3H), 3.79 (s, 3H), 3.75 (s, 3H). 6-Chloro-N-(2,4-dimethoxybenzyl)-9-methyl-9H-purin-8-amine (75 mg, 44%) was also isolated as a white solid. MS (ESI): mass calcd. for $C_{15}H_{1}ClN_5O_2$, 333.10; m/z. found, 334.1 [M+H]+. 1H NMR (400 MHz, $CDCl_3$) δ 8.40 (s, 1H), 7.32 (d, J=8.0 Hz, 1H), 6.51-6.41 (m, 2H), 5.25-5.18 (m, 1H), 4.72 (d, J=5.5 Hz, 2H), 3.86 (s, 3H), 3.80 (s, 3H), 3.55 (s, 3H).

Step B: 8-Bromo-9-methyl-9H-purin-6-amine. 8-Bromo-9-methyl-9H-purin-6-amine was prepared using conditions analogous to those described in Step E of Intermediate 42 utilizing 8-bromo-N-(2,4-dimethoxybenzyl)-9-methyl-9H-purin-6-amine. MS (ESI): mass calcd. for $C_6H_6BrN_5$, 226.98; m/z. found, 228.0 [M+H]$^+$.

Step C: (R)-3-((3-(6-Amino-9-methyl-9H-purin-8-yl)phenyl)ethynyl)-3-hydroxy-1-methylpyrrolidin-2-one. (R)-3-((3-(6-Amino-9-methyl-9H-purin-8-yl)phenyl)ethynyl)-3-hydroxy-1-methylpyrrolidin-2-one was prepared using conditions analogous to those described in Example 12 utilizing 8-bromo-9-methyl-9H-purin-6-amine and chloro(2-dicyclohexylphosphino-2',4',6'-triisopropyl-1,1'-biphenyl)[2-(2'-amino-1,1'-biphenyl)]palladium(II) to afford (42 mg, 47%) a white solid. MS (ESI): mass calcd. for $C_{19}H_{18}N_6O_2$, 362.15; m/z. found, 363.1 [M+H]$^+$. $^1$H NMR (400 MHz, 20% CD30D/CDCl$_3$) δ 8.31 (s, 1H), 7.79 (s, 1H), 7.74-7.68 (m, 1H), 7.67-7.60 (m, 1H), 7.54 (t, J=7.7 Hz, 1H), 3.87 (s, 3H), 3.52-3.43 (m, 2H), 2.96 (s, 3H), 2.67-2.59 (m, 1H), 2.44-2.34 (m, 1H).

Example 144: (R)-7-((3-(8-Aminopyrimido[5,4-d]pyrimidin-2-yl)phenyl)ethynyl)-6,7-dihydro-5H-cyclopenta[b]pyridin-7-ol

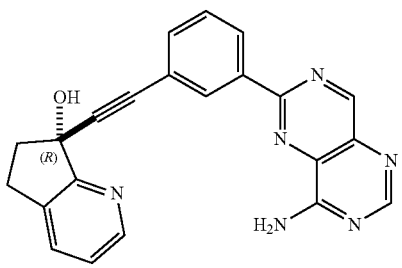

The title compound was prepared using analogous conditions described in Example 137 utilizing Intermediate 75 [(R)-7-((3-(8-((2,4-dimethoxybenzyl)amino)pyrimido[5,4-d]pyrimidin-2-yl)phenyl)ethynyl)-6,7-dihydro-5H-cyclopenta[b]pyridin-7-ol] to afford (R)-7-((3-(8-aminopyrimido[5,4-d]pyrimidin-2-yl)phenyl)ethynyl)-6,7-dihydro-5H-cyclopenta[b]pyridin-7-ol (27 mg, 31%) as a yellow solid. MS (ESI): mass calcd. for $C_{22}H_{16}N_6O$, 380.1 m/z found 381.1 [M+H]$^+$. $^1$H NMR (400 MHz, DMSO-d$_6$) δ 9.41 (s, 1H), 8.69-8.64 (m, 2H), 8.59 (s, 1H), 8.52 (s, 1H), 8.47 (d, J=4.9 Hz, 1H), 8.35 (s, 1H), 7.74 (d, J=7.8 Hz, 1H), 7.60-7.54 (m, 2H), 7.32-7.28 (m, 1H), 6.26 (s, 1H), 3.08-2.98 (m, 1H), 2.98-2.88 (m, 1H), 2.65-2.56 (m, 1H), 2.45-2.36 (m, 1H).

Example 145: (R)-3-[2-[3-[8-Amino-5-(1-piperidylmethyl)pyrido[3,4-d]pyrimidin-2-yl]phenyl]ethynyl]-3-hydroxy-1-methyl-pyrrolidin-2-one

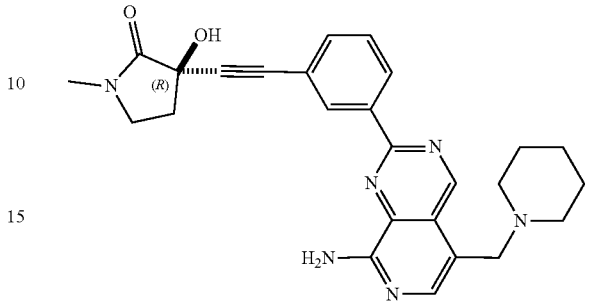

The title compound was prepared using conditions analogous to those described in Example 133 utilizing potassium (piperidin-1-yl)methyltrifluoroborate to afford (R)-3-[2-[3-[8-amino-5-(1-piperidylmethyl)pyrido[3,4-d]pyrimidin-2-yl]phenyl]ethynyl]-3-hydroxy-1-methyl-pyrrolidin-2-one (13 mg, 17%) as a colorless solid. MS (ESI): mass calcd. for $C_{26}H_{28}N_6O_2$, 456.5; m/z. found, 457.2 [M+H]$^+$. $^1$H NMR (500 MHz, DMSO-d$_6$) δ 9.74 (s, 1H), 8.66-8.58 (m, 2H), 7.74 (s, 1H), 7.54-7.46 (m, 2H), 7.32 (s, 2H), 6.44 (s, 1H), 3.58 (s, 2H), 3.35-3.28 (m, 2H), 2.75 (s, 3H), 2.43-2.39 (m, 1H), 2.31 (s, 4H), 2.20-2.11 (m, 1H), 1.43-1.26 (m, 6H).

Example 146: (R)-7-[2-[3-(4-Aminopyrimido[5,4-d]pyrimidin-6-yl)phenyl]ethynyl]-5,6-dihydropyrrolo[1,2-a]imidazol-7-ol

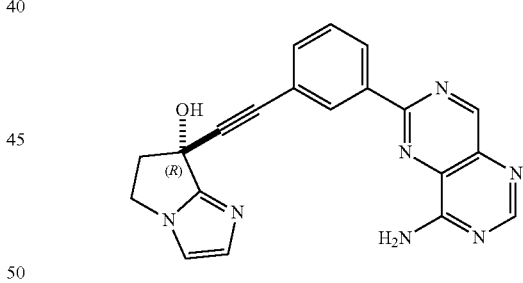

The title compound was prepared using analogous conditions described in Example 137 utilizing Intermediate 76 [(R)-7-((3-(8-((2,4-dimethoxybenzyl)amino)pyrimido[5,4-d]pyrimidin-2-yl)phenyl)ethynyl)-6,7-dihydro-5H-pyrrolo[1,2-a]imidazol-7-ol] to afford (R)-7-[2-[3-(4-aminopyrimido[5,4-d]pyrimidin-6-yl)phenyl]ethynyl]-5,6-dihydropyrrolo[1,2-a]imidazol-7-ol (15.4 mg, 35%) as a light yellow solid. MS (ESI): mass calcd. for $C_{20}H_{15}N_7O$, 369.1 m/z found 370.1 [M+H]$^+$. $^1$H NMR (400 MHz, DMSO-d$_6$) δ 9.42 (s, 1H), 8.76-8.66 (m, 2H), 8.61 (s, 1H), 8.52 (s, 1H), 8.36 (s, 1H), 7.64-7.56 (m, 2H), 7.27-6.93 (m, 2H), 6.59 (br. s, 1H), 4.12-4.03 (m, 2H), 3.12-3.03 (m, 1H), 2.86-2.78 (m, 1H).

Example 147: (R)-3-[2-[3-[8-Amino-5-[6-(trifluoromethyl)-3-pyridyl]pyrido[3,4-d]pyrimidin-2-yl]phenyl]ethynyl]-3-hydroxy-1-methyl-pyrrolidin-2-one

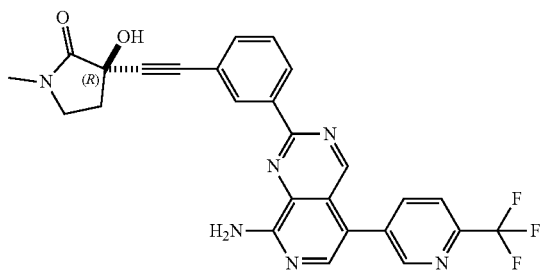

The title compound was prepared using analogous conditions described in Example 121 utilizing 5-(4,4,5,5-tetramethyl-1,3,2-dioxaborolan-2-yl)-2-(trifluoromethyl)pyridine to afford (R)-3-[2-[3-[8-amino-5-[6-(trifluoromethyl)-3-pyridyl]pyrido[3,4-d]pyrimidin-2-yl]phenyl]ethynyl]-3-hydroxy-1-methyl-pyrrolidin-2-one (22 mg, 42%) as a yellow solid. MS (ESI): mass calcd. for $C_{26}H_{19}F_3N_6O_2$, 504.15; m/z found, 505.2 [M+H]$^+$. $^1$H NMR (400 MHz, CD$_3$OD) δ 9.17 (s, 1H), 8.85 (d, J=2.0 Hz, 1H), 8.41-8.38 (m, 1H), 8.35 (d, J=7.9 Hz, 1H), 8.18 (dd, J=8.1, 2.1 Hz, 1H), 7.96 (d, J=8.1 Hz, 1H), 7.86 (s, 1H), 7.41 (d, J=7.6 Hz, 1H), 7.31 (t, J=7.7 Hz, 1H), 3.53-3.46 (m, 2H), 2.95 (s, 3H), 2.62-2.53 (m, 1H), 2.37-2.28 (m, 1H).

Example 148: (R)-3-[2-[3-(4-Amino-2-methyl-pteridin-6-yl)phenyl]ethynyl]-3-hydroxy-1-methyl-pyrrolidin-2-one

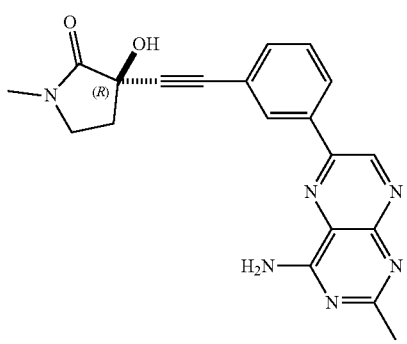

The title compound was prepared using analogous conditions described in Example 1 utilizing Intermediate 77 [6-(3-iodophenyl)-2-methylpteridine-4-amine] to afford (R)-3-[2-[3-(4-amino-2-methyl-pteridin-6-yl)phenyl]ethynyl]-3-hydroxy-1-methyl-pyrrolidin-2-one (23 mg, 14%) as a white solid. MS (ESI): mass calcd. for $C_{20}H_{18}N_6O_2$, 374.15; m/z. found, 375.2 [M+H]$^+$. $^1$H NMR (400 MHz, CD$_3$OD) δ 9.56 (s, 1H), 8.46 (s, 1H), 8.32 (d, J=7.6 Hz, 1H), 7.66-7.48 (m, 2H), 3.56-3.41 (m, 2H), 2.94 (s, 3H), 2.63 (dd, J=7.6, 5.3 Hz, 1H), 2.59 (s, 3H), 2.38-2.26 (m, 1H).

Example 149: (R)-3-((3-(4-Aminopyrido[3,2-d]pyrimidin-6-yl-2-d)-4-methylphenyl)ethynyl)-3-hydroxy-1-methylpyrrolidin-2-one

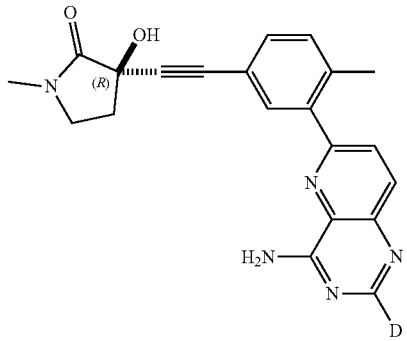

The title compound was prepared using analogous conditions described in Example 8 utilizing Intermediate 6 [(R)-3-hydroxy-1-methyl-3-((4-methyl-3-(4,4,5,5-tetramethyl-1,3,2-dioxaborolan-2-yl)phenyl)ethynyl)pyrrolidin-2-one] to afford (R)-3-((3-(4-aminopyrido[3,2-d]pyrimidin-6-yl-2-d)-4-methylphenyl)ethynyl)-3-hydroxy-1-methylpyrrolidin-2-one (32 mg, 31%) as a brown solid. MS (ESI): mass calcd. for $C_{21}H_{18}DN_5O_2$ 374.2 m/z found 375.2 [M+H]$^+$. $^1$H NMR (400 MHz, DMSO-d$_6$) δ 8.13 (d, J=8.6 Hz, 1H), 7.98 (d, J=8.6 Hz, 1H), 7.93 (br. s, 1H), 7.87 (br. s, 1H), 7.58-7.54 (m, 1H), 7.45-7.36 (m, 2H), 6.45 (s, 1H), 3.33-3.30 (m, 2H), 2.79 (s, 3H), 2.42 (s, 3H), 2.46-2.38 (m, 1H), 2.20-2.13 (m, 1H). The $^1$H NMR for (R)-3-((3-(4-aminopyrido[3,2-d]pyrimidin-6-yl-2-d)-4-methylphenyl)ethynyl)-3-hydroxy-1-methylpyrrolidin-2-one was also taken in an alternative solvent (CDCl$_3$) and the data is as follows: $^1$H NMR (400 MHz, CDCl$_3$) δ 8.30 (br s, 1H), 8.05 (d, J=8.8 Hz, 1H), 7.74 (br s, 1H), 7.36 (d, J=8.8 Hz, 1H), 7.32-7.28 (m, 1H), 7.18 (d, J=7.8 Hz, 1H), 7.00 (br. s, 1H), 6.59 (s, 1H), 3.52 (t, J=6.5 Hz, 2H), 2.99 (s, 3H), 2.69-2.61 (m, 1H), 2.51-2.42 (m, 1H), 2.33 (s, 3H).

Example 150: (R)-3-((3-(4-Amino-2-methylpyrido[3,2-d]pyrimidin-6-yl)-4-methylphenyl)ethynyl)-3-hydroxy-1-methylpyrrolidin-2-one

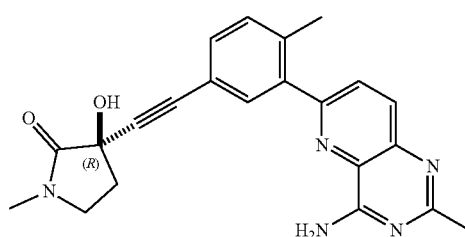

The title compound was prepared using analogous conditions described in Example 6 utilizing Intermediate 6 [(R)-3-hydroxy-1-methyl-3-((4-methyl-3-(4,4,5,5-tetramethyl-1,3,2-dioxaborolan-2-yl)phenyl)ethynyl)pyrrolidin-2-one] to afford (R)-3-((3-(4-amino-2-methylpyrido[3,2-d]pyrimidin-6-yl)-4-methylphenyl)ethynyl)-3-hydroxy-1-methylpyrrolidin-2-one (60 mg, 36%) as a brown solid. MS (ESI): mass calcd. for $C_{22}H_{21}N_5O_2$ 387.2 m/z found 388.2

[M+H]⁺. ¹H NMR (400 MHz, CDCl₃) δ 8.00 (d, J=8.5 Hz, 1H), 7.89 (br s, 1H), 7.38 (d, J=8.8 Hz, 1H), 7.33-7.27 (m, 2H), 7.19 (d, J=8.0 Hz, 1H), 6.99 (bs., 1H), 6.72 (s, 1H), 3.58-3.42 (m, 2H), 2.98 (s, 3H), 2.72 (s, 3H), 2.69-2.60 (m, 1H), 2.50-2.40 (m, 1H), 2.32 (s, 3H).

Example 151: (R)-3-((3-(8-Amino-5-neopentylpyrido[3,4-d]pyrimidin-2-yl)phenyl)ethynyl)-3-hydroxy-1-methylpyrrolidin-2-one

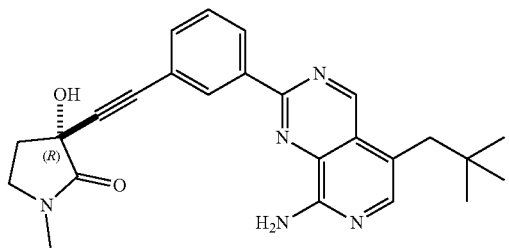

The title compound was prepared using analogous conditions described in Example 129 utilizing neopentylzinc bromide to afford (R)-3-((3-(8-amino-5-neopentylpyrido[3,4-d]pyrimidin-2-yl)phenyl)ethynyl)-3-hydroxy-1-methylpyrrolidin-2-one (26.5 mg, 55%) as a white solid. MS (ESI): mass calcd. for C₂₅H₂₇N₅O₂, 429.22; m/z found, 430.4 [M+H]⁺. ¹H NMR (400 MHz, CDCl₃) δ 9.42 (s, 1H), 8.48 (t, J=1.5 Hz, 1H), 8.39 (td, J=7.8, 1.5 Hz, 1H), 7.81 (s, 1H), 7.42-7.47 (m, 1H), 7.36 (t, J=7.8 Hz, 1H), 6.64 (br s, 2H), 3.49-3.57 (m, 1H), 3.40-3.48 (m, 1H), 3.02 (s, 3H), 2.70-2.81 (m, 2H), 2.67 (ddd, J=9.9, 6.7, 3.4 Hz, 1H), 2.44 (dt, J=8.1, 12.7 Hz, 1H), 0.94 (s, 9H).

Example 152: (R)-3-((5-(7-Aminothiazolo[5,4-d]pyrimidin-2-yl)-2-methylphenyl)ethynyl)-3-hydroxy-1-methylpyrrolidin-2-one

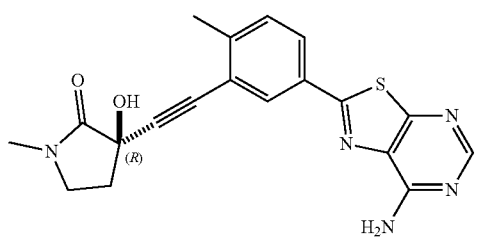

The title compound was prepared using conditions analogous to those described in Example 1 utilizing 3-iodo-4-methylbenzoyl chloride in Step A of Intermediate 52 to afford (R)-3-((5-(7-aminothiazolo[5,4-d]pyrimidin-2-yl)-2-methylphenyl)ethynyl)-3-hydroxy-1-methylpyrrolidin-2-one (43 mg, 27%) as a white solid. MS (ESI): mass calcd. for C₁₉H₁₇N₅O₂S, 379.11; m/z found, 380.1 [M+H]⁺. ¹H NMR (400 MHz, DMSO-d₆) δ 8.31 (s, 1H), 8.12 (s, 1H), 7.94 (d, J=7.9 Hz, 1H), 7.50 (d, J=8.1 Hz, 1H), 3.40-3.32 (m, 2H), 2.82 (s, 3H), 2.49-2.40 (m, 4H), 2.27-2.17 (m, 1H).

Example 153: (R)-3-((3-(7-Aminothiazolo[5,4-d]pyrimidin-2-yl)-5-methylphenyl)ethynyl)-3-hydroxy-1-methylpyrrolidin-2-one

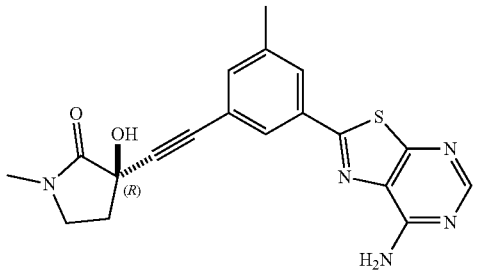

Step A: N-(4-Amino-6-oxo-1,6-dihydropyrimidin-5-yl)-3-bromo-5-methylbenzamide. A suspension of 5,6-diaminopyrimidin-4(3H)-one (0.5 g, 3.9 mmol) and 3-bromo-5-methylbenzoic acid (0.9 g, 4.3 mmol) in DMF (15 mL) was treated with DIPEA (2 mL, 12 mmol) followed by 1-[bis(dimethylamino)methylene]-1H-1,2,3-triazolo[4,5-b]pyridinium 3-oxide hexafluorophosphate (1.6 g, 4.2 mmol) and allowed to stir at rt. After 30 min, the mixture was diluted with MeCN (100 mL) and briefly sonicated. The resulting solid was isolated via filtration and dried to afford N-(4-amino-6-oxo-1,6-dihydropyrimidin-5-yl)-3-bromo-5-methylbenzamide (1.1 g, 82%) as a white solid. MS (ESI): mass calcd. for C₁₂H₁₁BrN₄O₂, 322.01; m/z. found, 323.0 [M+H]⁺. ¹H NMR (400 MHz, DMSO-d₆) δ 11.74 (s, 1H), 9.12 (s, 1H), 8.02-7.51 (m, 4H), 6.41 (s, 2H), 2.37 (s, 3H).

Step B: (R)-3-((3-(7-Aminothiazolo[5,4-d]pyrimidin-2-yl)-5-methylphenyl)ethynyl)-3-hydroxy-1-methylpyrrolidin-2-one was prepared using conditions analogous to those described in Example 1 utilizing N-(4-amino-6-oxo-1,6-dihydropyrimidin-5-yl)-3-bromo-5-methylbenzamide in Step B of Intermediate 52 to afford (R)-3-((3-(7-aminothiazolo[5,4-d]pyrimidin-2-yl)-5-methylphenyl)ethynyl)-3-hydroxy-1-methylpyrrolidin-2-one (104 mg, 58%) as a white solid. MS (ESI): mass calcd. for C₁₂H₉BrN₄S, 319.97; m/z. found, 321.0 [M+H]⁺. ¹H NMR (400 MHz, DMSO-d₆) δ 8.32 (s, 1H), 8.10 (s, 1H), 7.88-7.79 (m, 3H), 7.63 (s, 1H), 2.42 (s, 3H).

Example 154: (R)-3-((3-(7-Aminothiazolo[5,4-d]pyrimidin-2-yl)-2-methylphenyl)ethynyl)-3-hydroxy-1-methylpyrrolidin-2-one

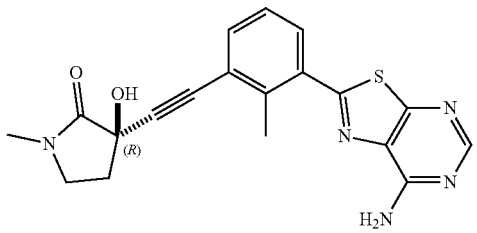

The title compound was prepared using conditions analogous to those described in Example 1 utilizing 3-bromo-2-methylbenzoyl chloride in Step A of Intermediate 52 to afford (R)-3-((3-(7-aminothiazolo[5,4-d]pyrimidin-2-yl)-2-methylphenyl)ethynyl)-3-hydroxy-1-methylpyrrolidin-2- one (85 mg, 35%) as a white solid. MS (ESI): mass calcd. for $C_{19}H_{17}N_5O_2S$, 379.11; m/z. found, 380.1 [M+H]$^+$. $^1$H NMR (400 MHz, CD$_3$OD) δ 8.43 (s, 1H), 7.75 (d, J=8.1 Hz, 1H), 7.63 (d, J=7.5 Hz, 1H), 7.36 (t, J=7.7 Hz, 1H), 3.53-3.44 (m, 2H), 2.93 (s, 3H), 2.74 (s, 3H), 2.64-2.56 (m, 1H), 2.39-2.29 (m, 1H).

Example 155: (S)-7-((3-(8-Aminopyrimido[5,4-d]pyrimidin-2-yl)phenyl)ethynyl)-6,7-dihydro-5H-cyclopenta[b]pyridin-7-ol

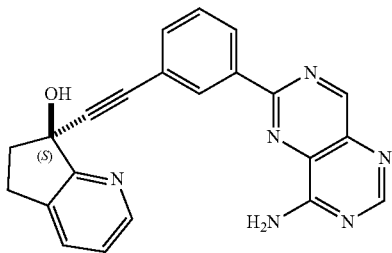

The title compound was prepared using analogous conditions described in Example 137 and Intermediate 69 utilizing Intermediate 39 [(S)-7-ethynyl-6,7-dihydro-5H-cyclopenta[b]pyridin-7-ol] to afford (S)-7-((3-(8-aminopyrimido[5,4-d]pyrimidin-2-yl)phenyl)ethynyl)-6,7-dihydro-5H-cyclopenta[b]pyridin-7-ol (33.0 mg, 28%) as a yellow solid. MS (ESI): mass calcd. for $C_{22}H_{16}N_6O$, 380.1 m/z found 381.2 [M+H]$^+$. $^1$H NMR (400 MHz, DMSO-d$_6$) δ 9.41 (s, 1H), 8.69-8.64 (m, 2H), 8.59 (s, 1H), 8.52 (s, 1H), 8.47 (d, J=4.2 Hz, 1H), 8.35 (s, 1H), 7.74 (d, J=7.6 Hz, 1H), 7.59-7.55 (m, 2H), 7.32-7.27 (m, 1H), 6.26 (s, 1H), 3.07-2.98 (m, 1H), 2.98-2.88 (m, 1H), 2.65-2.56 (m, 1H), 2.45-2.37 (m, 1H).

Example 156: (R)-3-((3-(8-Amino-4,6-dimethylpyrimido[5,4-d]pyrimidin-2-yl)phenyl)ethynyl)-3-hydroxy-1-methylpyrrolidin-2-one

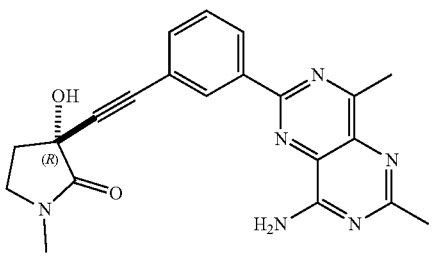

The title compound was prepared using analogous conditions as described in Example 6 utilizing Intermediate 78 [6-chloro-2,8-dimethylpyrimido[5,4-d]pyrimidin-4-amine] to afford (R)-3-((3-(8-amino-4,6-dimethylpyrimido[5,4-d]pyrimidin-2-yl)phenyl)ethynyl)-3-hydroxy-1-methylpyrrolidin-2-one (52.8 mg, 18%) as a white solid. MS (ESI): mass calcd. for $C_{21}H_{20}N_6O_2$ 388.2 m/z found 389.2 [M+H]$^+$. $^1$H NMR (400 MHz, CDCl$_3$) δ 8.36-8.27 (m, 2H), 7.82 (br. s., 1H), 7.39-7.35 (m, 1H), 7.33-7.28 (m, 1H), 7.13 (br. s., 1H), 3.58-3.42 (m, 2H), 3.04 (s, 3H), 2.85 (s, 3H), 2.67 (s, 3H), 2.71-2.63 (m, 1H), 2.52-2.41 (m, 1H).

Example 157: (S)-4-(3-(4-Amino-2-methylpyrido[3,2-d]pyrimidin-6-yl)phenyl)-2-(2-methylthiazol-5-yl)but-3-yn-2-ol

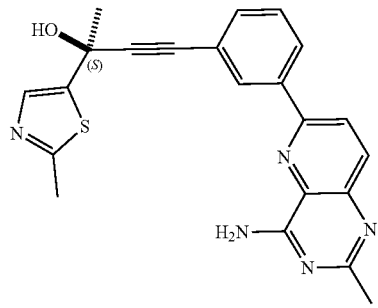

The title compound was prepared using analogous conditions as described in Example 1 utilizing Intermediate 80 [(S)-2-(2-methylthiazol-5-yl)-4-(3-(4,4,5,5-tetramethyl-1,3,2-dioxaborolan-2-yl)phenyl)but-3-yn-2-ol] to afford (S)-4-(3-(4-amino-2-methylpyrido[3,2-d]pyrimidin-6-yl)phenyl)-2-(2-methylthiazol-5-yl)but-3-yn-2-ol (184 mg, 67%) as a tan solid. MS (ESI): mass calcd. for $C_{22}H_{19}N_5OS$, 401.1; m/z. found, 402.1 [M+H]$^+$. $^1$H NMR (400 MHz, CDCl$_3$) δ 8.10 (d, J=8.8 Hz, 1H), 8.06-7.90 (m, 3H), 7.74 (s, 1H), 7.54-7.38 (m, 2H), 2.70 (s, 3H), 2.63 (s, 3H), 2.00 (s, 3H).

Example 158: (R)-4-(3-(4-Amino-2-methylpyrido[3,2-d]pyrimidin-6-yl)phenyl)-2-(2-methylthiazol-5-yl)but-3-yn-2-ol

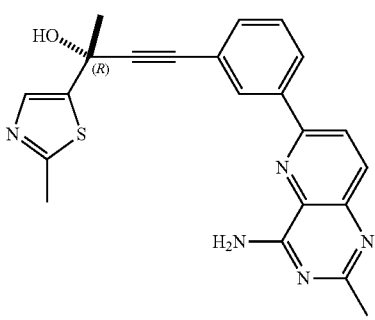

The title compound was prepared using analogous conditions as described in Example 1 utilizing Intermediate 82 [(R)-2-(2-methylthiazol-5-yl)-4-(3-(4,4,5,5-tetramethyl-1,3,2-dioxaborolan-2-yl)phenyl)but-3-yn-2-ol] to afford (R)-4-(3-(4-amino-2-methylpyrido[3,2-d]pyrimidin-6-yl)phenyl)-2-(2-methylthiazol-5-yl)but-3-yn-2-ol (162 mg, 58%) as a tan solid. MS (ESI): mass calcd. for $C_{22}H_{19}N_5OS$, 401.1; m/z. found, 402.1 [M+H]$^+$. $^1$H NMR (400 MHz, CDCl$_3$) δ 8.11 (d, J=8.8 Hz, 1H), 8.07-7.95 (m, 3H), 7.74 (s, 1H), 7.55-7.38 (m, 2H), 2.70 (s, 3H), 2.63 (s, 3H), 2.01 (s, 3H).

Example 159: (R)-3-((3-(4-Amino-7,8-dihydropyrido[4,3-d]pyrimidin-6(5H)-yl)phenyl)ethynyl)-3-hydroxy-1-methylpyrrolidin-2-one

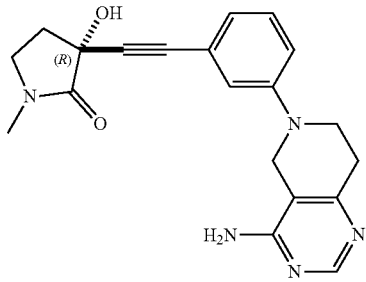

The title compound was prepared analogously to that of Example 1 utilizing Intermediate 83 [6-(3-iodophenyl)-5,6,7,8-tetrahydropyrido[4,3-d]pyrimidin-4-amine] to afford (R)-3-((3-(4-amino-7,8-dihydropyrido[4,3-d]pyrimidin-6(5H)-yl)phenyl)ethynyl)-3-hydroxy-1-methylpyrrolidin-2-one (26 mg, 15%) as a pale yellow solid. MS (ESI): mass calcd. for $C_{20}H_{21}N_5O_2$ 363.2 m/z found 364.2 [M+H]$^+$. $^1$H NMR (400 MHz, DMSO-d$_6$) δ 8.20 (s, 1H), 7.28-7.20 (m, 1H), 7.15-7.07 (m, 2H), 6.84 (d, J=7.5 Hz, 1H), 6.55 (br. s, 2H), 6.06 (br s, 1H), 4.03 (s, 2H), 3.56 (t, J=5.8 Hz, 2H), 3.38-3.32 (m, 2H), 2.81 (s, 3H), 2.78 (t, J=5.8 Hz, 2H), 2.48-2.40 (m, 1H), 2.25-2.17 (m, 1H).

Example 160: (R)-3-((3-(4-Aminopyrido[3,2-d]pyrimidin-6-yl-2-d)-4-methoxyphenyl)ethynyl)-3-hydroxy-1-methylpyrrolidin-2-one

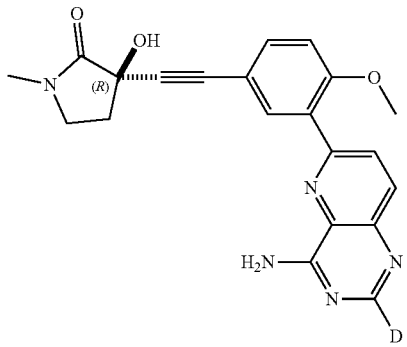

The title compound was prepared using analogous conditions as described in Example 8 utilizing Intermediate 72 [(R)-3-hydroxy-3-((4-methoxy-3-(4,4,5,5-tetramethyl-1,3,2-dioxaborolan-2-yl)phenyl)ethynyl)-1-methylpyrrolidin-2-one] to afford (R)-3-((3-(4-aminopyrido[3,2-d]pyrimidin-6-yl-2-d)-4-methoxyphenyl)ethynyl)-3-hydroxy-1-methylpyrrolidin-2-one (31 mg, 28%) as a white solid. MS (ESI): mass calcd. for $C_{21}H_{18}DN_5O_3$ 390.2 m/z found 391.2 [M+H]$^+$. $^1$H NMR (400 MHz, DMSO-d$_6$) δ 8.20 (d, J=8.8 Hz, 1H), 8.07 (d, J=8.8 Hz, 1H), 8.00-7.88 (m, 3H), 7.53 (dd, J=2.2, 8.6 Hz, 1H), 7.22 (d, J=8.6 Hz, 1H), 6.40 (s, 1H), 3.90 (s, 3H), 3.33-3.32 (m, 2H), 2.79 (s, 3H), 2.47-2.39 (m, 1H), 2.21-2.13 (m, 1H).

Example 161: (R)-3-((3-(4-Amino-2-methylpyrido[3,2-d]pyrimidin-6-yl)-4-methoxyphenyl)ethynyl)-3-hydroxy-1-methylpyrrolidin-2-one

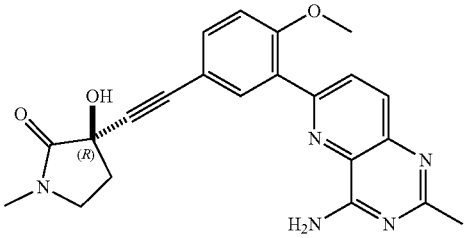

The title compound was prepared using analogous conditions as described in Example 6 utilizing Intermediate 72 [(R)-3-hydroxy-3-((4-methoxy-3-(4,4,5,5-tetramethyl-1,3,2-dioxaborolan-2-yl)phenyl)ethynyl)-1-methylpyrrolidin-2-one] to afford (R)-3-((3-(4-amino-2-methylpyrido[3,2-d]pyrimidin-6-yl)-4-methoxyphenyl)ethynyl)-3-hydroxy-1-methylpyrrolidin-2-one (36 mg, 35%) as a brown solid. MS (ESI): mass calcd. for $C_{22}H_{21}N_5O_3$ 403.2 m/z found 404.2 [M+H]$^+$. $^1$H NMR (400 MHz, DMSO-d$_6$) δ 8.16 (d, J=8.8 Hz, 1H), 7.97 (d, J=8.8 Hz, 1H), 7.93 (d, J=2.2 Hz, 1H), 7.84 (br s, 2H), 7.51 (dd, J=2.2, 8.6 Hz, 1H), 7.21 (d, J=8.6 Hz, 1H), 6.40 (s, 1H), 3.89 (s, 3H), 3.37-3.34 (m, 2H), 2.79 (s, 3H), 2.46 (s, 3H), 2.45-2.39 (m, 1H), 2.21-2.12 (m, 1H).

Example 162: (S)-4-(3-(4-Amino-2-methylpyrido[3,2-d]pyrimidin-6-yl)phenyl)-2-(4-methylthiazol-5-yl)but-3-yn-2-ol

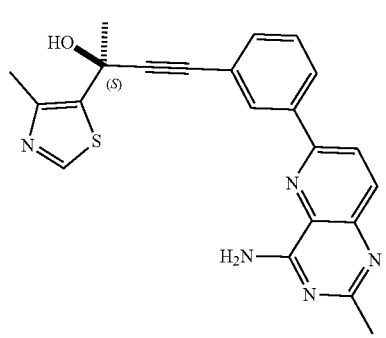

The title compound was prepared using analogous conditions described in Example 6 utilizing Intermediate 86 [(S)-2-(4-methylthiazol-5-yl)-4-(3-(4,4,5,5-tetramethyl-1,3,2-dioxaborolan-2-yl)phenyl)but-3-yn-2-ol] to afford (S)-4-(3-(4-amino-2-methylpyrido[3,2-d]pyrimidin-6-yl)phenyl)-2-(4-methylthiazol-5-yl)but-3-yn-2-ol (251 mg, 93%) as a yellow solid. MS (ESI): mass calcd. for $C_{22}H_{19}N_5OS$ 401.1; m/z. found, 402.1 [M+H]$^+$. $^1$H NMR (400 MHz, CD$_3$OD) δ 8.75 (s, 1H), 8.35-8.29 (m, 2H), 8.26 (dt, J=7.4, 1.7 Hz, 1H), 8.05 (d, J=8.9 Hz, 1H), 7.61-7.46 (m, 2H), 2.64 (s, 3H), 2.55 (s, 3H), 1.93 (s, 3H).

Example 163: (R)-4-(3-(4-Amino-2-methylpyrido[3,2-d]pyrimidin-6-yl)phenyl)-2-(4-methylthiazol-5-yl)but-3-yn-2-ol

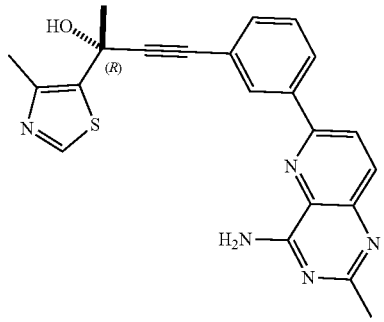

The title compound was prepared using analogous conditions described in Example 6 utilizing Intermediate 87 [(R)-2-(4-methylthiazol-5-yl)-4-(3-(4,4,5,5-tetramethyl-1,3,2-dioxaborolan-2-yl)phenyl)but-3-yn-2-ol] to afford (R)-4-(3-(4-amino-2-methylpyrido[3,2-d]pyrimidin-6-yl)phenyl)-2-(4-methylthiazol-5-yl)but-3-yn-2-ol (240 mg, 88%) as a yellow solid. MS (ESI): mass calcd. for $C_{22}H_{19}N_5OS$, 401.1; m/z. found, 402.1 [M+H]$^+$. $^1$H NMR (400 MHz, CD$_3$OD) δ 8.75 (s, 1H), 8.35-8.30 (m, 2H), 8.26 (dt, J=7.4, 1.8 Hz, 1H), 8.05 (d, J=8.9 Hz, 1H), 7.63-7.43 (m, 2H), 2.64 (s, 3H), 2.55 (s, 3H), 1.93 (s, 3H).

Example 164: (R)-4-(3-(4-Amino-2-methylpyrido[3,2-d]pyrimidin-6-yl)phenyl)-2-(thiazol-2-yl)but-3-yn-2-ol

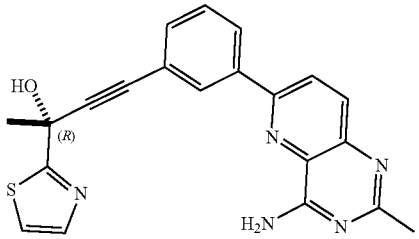

The title compound was prepared using analogous conditions described in Example 6 utilizing Intermediate 54 [(R)-4-(3-(4,4,5,5-tetramethyl-1,3,2-dioxaborolan-2-yl)phenyl)-2-(thiazol-2-yl)but-3-yn-2-ol] to afford (R)-4-(3-(4-amino-2-methylpyrido[3,2-d]pyrimidin-6-yl)phenyl)-2-(thiazol-2-yl)but-3-yn-2-ol (228 mg, 76%) as a yellow solid. MS (ESI): mass calcd. for $C_{21}H_{17}N_5OS$, 387.1; m/z. found, 388.1 [M+H]$^+$. $^1$H NMR (400 MHz, CD$_3$OD) δ 8.40-8.34 (m, 1H), 8.31 (d, J=8.9 Hz, 1H), 8.22-8.25 (m, 1H), 8.04 (d, J=8.9 Hz, 1H), 7.79 (d, J=3.3 Hz, 1H), 7.63-7.43 (m, 3H), 2.54 (s, 3H), 1.98 (s, 3H).

Example 165: racemic-8-((3-(4-Amino-2-methylpyrido[3,2-d]pyrimidin-6-yl)phenyl)ethynyl)-5,6,7,8-tetrahydroquinolin-8-ol

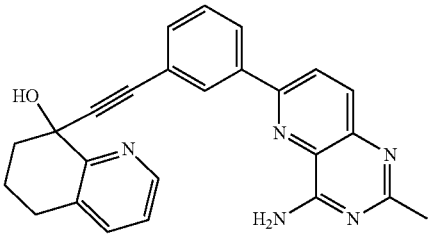 [SMILES: Cc1nc(N)c2nc(-c3cccc(C#CC4(O)CCCc5cccnc54)c3)ccc2n1]

The title compound was prepared using analogous conditions described in Example 6 utilizing Intermediate 89 [racemic-8-((3-(4,4,5,5-tetramethyl-1,3,2-dioxaborolan-2-yl)phenyl)ethynyl)-5,6,7,8-tetrahydroquinolin-8-ol] to afford racemic-8-((3-(4-amino-2-methylpyrido[3,2-d]pyrimidin-6-yl)phenyl)ethynyl)-5,6,7,8-tetrahydroquinolin-8-ol (11 mg, 4%) as a tan solid. MS (ESI): mass calcd. for $C_{25}H_{21}N_5O$, 407.2; m/z. found, 408.1 [M+H]$^+$. $^1$H NMR (400 MHz, CD$_3$OD) δ 8.49-8.41 (m, 1H), 8.36-8.26 (m, 2H), 8.18-8.21 (m, 1H), 8.03 (d, J=8.9 Hz, 1H), 7.58-7.62 (m, 1H), 7.56-7.41 (m, 2H), 7.27-7.31 (m, 1H), 2.91 (t, J=6.4 Hz, 2H), 2.54 (s, 3H), 2.50-2.38 (m, 1H), 2.35-2.23 (m, 1H), 2.08-2.12 (m, 2H).

Example 166: (S)-4-(3-(4-Amino-2-methylpyrido[3,2-d]pyrimidin-6-yl)phenyl)-2-(5-methylthiazol-2-yl)but-3-yn-2-ol

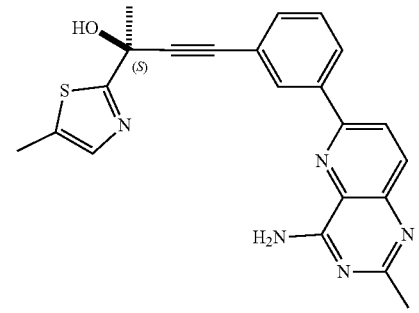

The title compound was prepared using analogous conditions as described in Example 6 utilizing Intermediate 93 [(S)-2-(5-methylthiazol-2-yl)-4-(3-(4,4,5,5-tetramethyl-1,3,2-dioxaborolan-2-yl)phenyl)but-3-yn-2-ol] to afford (S)-4-(3-(4-amino-2-methylpyrido[3,2-d]pyrimidin-6-yl)phenyl)-2-(5-methylthiazol-2-yl)but-3-yn-2-ol (448 mg, 86%) as a tan solid. MS (ESI): mass calcd. for $C_{22}H_{19}N_5OS$, 401.1; m/z. found, 402.2 [M+H]$^+$. $^1$H NMR (400 MHz, CDCl$_3$) δ 8.09 (d, J=8.8 Hz, 2H), 8.02 (dd, J=8.8, 1.1 Hz, 1H), 7.97 (ddt, J=7.9, 2.2, 1.1 Hz, 1H), 7.52 (dt, J=7.8, 1.4 Hz, 1H), 7.46-7.34 (m, 2H), 3.49 (s, 3H), 2.66 (s, 3H), 2.48 (d, J=1.3 Hz, 3H), 2.05 (s, 3H).

Example 167: (R)-4-(3-(4-Amino-2-methylpyrido[3,2-d]pyrimidin-6-yl)phenyl)-2-(5-methylthiazol-2-yl)but-3-yn-2-ol

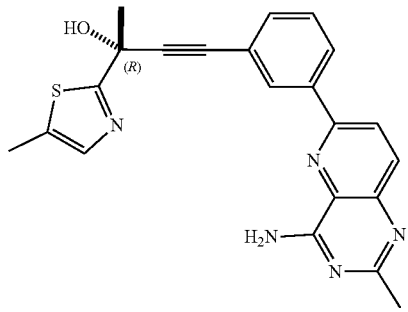

The title compound was prepared using analogous conditions described in Example 6 utilizing Intermediate 92 [(R)-2-(5-methylthiazol-2-yl)-4-(3-(4,4,5,5-tetramethyl-1,3,2-dioxaborolan-2-yl)phenyl)but-3-yn-2-ol] to afford (R)-4-(3-(4-amino-2-methylpyrido[3,2-d]pyrimidin-6-yl)phenyl)-2-(5-methylthiazol-2-yl)but-3-yn-2-ol (404 mg, 78%) as a tan solid. MS (ESI): mass calcd. for $C_{22}H_{19}N_5OS$, 401.1; m/z. found, 402.2 [M+H]$^+$. $^1$H NMR (400 MHz, CDCl$_3$) δ 8.09 (d, J=8.8 Hz, 2H), 8.02 (dd, J=8.8, 1.1 Hz, 1H), 7.97 (ddt, J=7.9, 2.2, 1.1 Hz, 1H), 7.52 (dt, J=7.8, 1.4 Hz, 1H), 7.46-7.34 (m, 2H), 3.49 (s, 3H), 2.66 (s, 3H), 2.48 (d, J=1.3 Hz, 3H), 2.05 (s, 3H).

Example 168: (R)-3-((3-(8-Amino-4-methylpyrimido[5,4-d]pyrimidin-2-yl-6-d)phenyl)ethynyl)-3-hydroxy-1-methylpyrrolidin-2-one

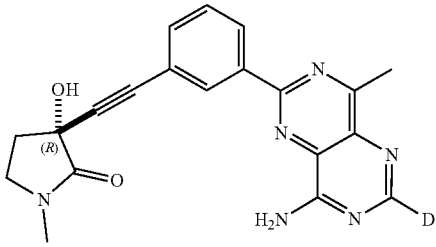

The title compound was prepared using analogous conditions described in Example 8 utilizing Intermediate 94 [6-chloro-8-methylpyrimido[5,4-d]pyrimidin-4-amine-2-d] to afford (R)-3-((3-(8-amino-4-methylpyrimido[5,4-d]pyrimidin-2-yl-6-d)phenyl)ethynyl)-3-hydroxy-1-methylpyrrolidin-2-one (4.1 mg, 8%) as a yellow solid. MS (ESI): mass calcd. for $C_{20}H_{17}DN_6O_2$ 375.2 m/z found 376.2 [M+H]$^+$. $^1$H NMR (400 MHz, DMSO-d$_6$) δ 8.72-8.68 (m, 1H), 8.67 (s, 1H), 8.48 (s, 1H), 8.27 (s, 1H), 7.60-7.55 (m, 2H), 6.51 (s, 1H), 3.40-3.37 (m, 2H), 2.88 (s, 3H), 2.82 (s, 3H), 2.47-2.44 (m, 1H), 2.25-2.17 (m, 1H).

Example 169: (R)-tert-Butyl 3-amino-5-[3-[2-(3-hydroxy-1-methyl-2-oxo-pyrrolidin-3-yl)ethynyl]phenyl]indazole-1-carboxylate

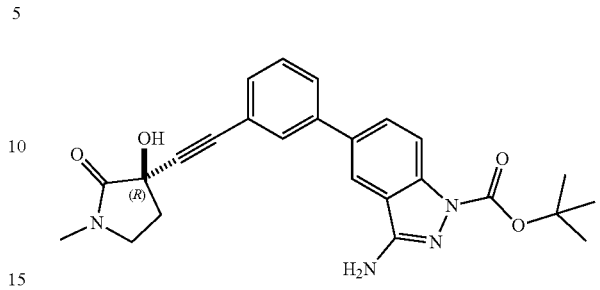

The title compound was prepared using analogous conditions described in Example 1 utilizing tert-Butyl 3-amino-5-(3-iodophenyl)-1H-indazole-1-carboxylate from Step D in Intermediate 95 to afford (R)-tert-butyl 3-amino-5-[3-[2-(3-hydroxy-1-methyl-2-oxo-pyrrolidin-3-yl)ethynyl]phenyl]indazole-1-carboxylate (20 mg, 28%) as a colorless solid. MS (ESI): mass calcd. for $C_{25}H_{26}N_4O_4$, 446.5; m/z. found, 391.2 [M+H]$^+$. $^1$H NMR (500 MHz, DMSO-d$_6$) δ 8.25 (dd, J=1.8, 0.8 Hz, 1H), 8.01 (d, J=8.7 Hz, 1H), 7.87 (dd, J=8.7, 1.8 Hz, 1H), 7.76-7.72 (m, 2H), 7.55-7.49 (m, 1H), 7.45-7.40 (m, 1H), 6.47 (s, 1H), 6.40 (s, 2H), 3.39-3.35 (m, 2H), 2.81 (s, 3H), 2.49-2.41 (m, 1H), 2.24-2.15 (m, 1H), 1.60 (s, 9H).

Example 170: (R)-3-((3-(4-Amino-2-(fluoromethyl)pyrido[3,2-d]pyrimidin-6-yl)phenyl)ethynyl)-3-hydroxy-1-methylpyrrolidin-2-one

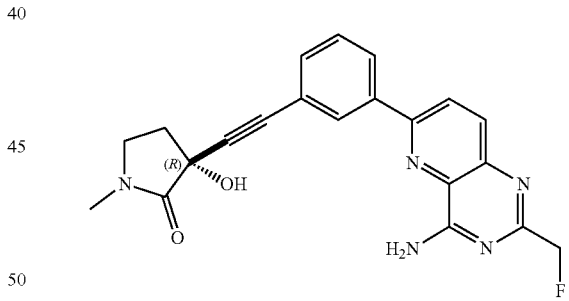

The title compound was prepared using analogous conditions described in Example 6 utilizing Intermediate 96 [6-chloro-2-(fluoromethyl)pyrido[3,2-d]pyrimidin-4-amine] to afford (R)-3-((3-(4-amino-2-(fluoromethyl)pyrido[3,2-d]pyrimidin-6-yl)phenyl)ethynyl)-3-hydroxy-1-methylpyrrolidin-2-one (303 mg, 73%) as an off-white solid. MS (ESI): mass calcd. for $C_{21}H_{18}FN_5O_2$, 391.2; m/z. found, 392.2 [M+H]$^+$. $^1$H NMR (500 MHz, CD$_3$OD) δ 8.58 (d, J=8.9 Hz, 1H), 8.52-8.44 (m, 1H), 8.41-8.23 (m, 2H), 7.65-7.47 (m, 2H), 5.70 (s, 1H), 5.61 (s, 1H), 3.46-3.55 (m, 2H), 2.95 (s, 3H), 2.71-2.55 (m, 1H), 2.30-2.36 (m, 1H). $^{19}$F NMR (376 MHz, CD$_3$OD) δ −77.32.

Example 171: (R)-3-[2-[3-[8-Amino-5-(pyrrolidin-1-ylmethyl)-1,7-naphthyridin-2-yl]phenyl]ethynyl]-3-hydroxy-1-methyl-pyrrolidin-2-one

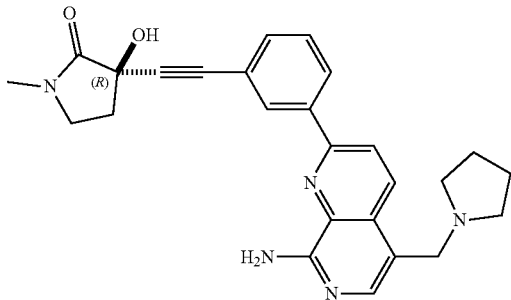

The title compound was prepared using conditions analogous to those described in Example 133 utilizing potassium (pyrrolidin-1-yl)methyltrifluoroborate and (R)-3-[2-[3-(8-amino-5-bromo-1,7-naphthyridin-2-yl)phenyl]ethynyl]-3-hydroxy-1-methyl-pyrrolidin-2-one from Example 112 to afford (R)-3-[2-[3-[8-amino-5-(pyrrolidin-1-ylmethyl)-1,7-naphthyridin-2-yl]phenyl]ethynyl]-3-hydroxy-1-methyl-pyrrolidin-2-one (20 mg, 13%) as a colorless solid. MS (ESI): mass calcd. for $C_{26}H_{27}N_5O_2$, 441.5; m/z. found, 442.2 [M+H]$^+$. $^1$H NMR (500 MHz, DMSO-d$_6$) δ 8.52 (d, J=8.8 Hz, 1H), 8.44-8.40 (m, 1H), 8.38-8.34 (m, 1H), 8.33 (d, J=8.8 Hz, 1H), 7.75 (s, 1H), 7.60-7.48 (m, 2H), 7.03 (s, 2H), 6.49 (s, 1H), 3.74 (s, 2H), 3.42-3.35 (m, 2H), 2.82 (s, 3H), 2.48-2.38 (m, 5H), 2.24-2.17 (m, 1H), 1.66 (d, J=6.1 Hz, 4H).

Example 172: (R)-3-[2-[3-[8-Amino-5-(dimethylaminomethyl)-1,7-naphthyridin-2-yl]phenyl]ethynyl]-3-hydroxy-1-methyl-pyrrolidin-2-one

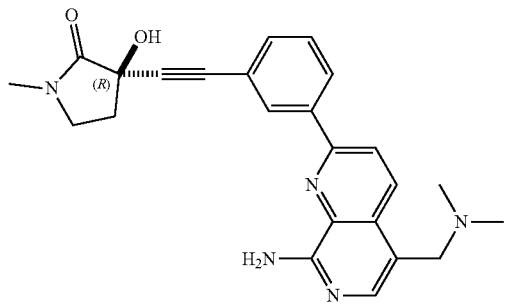

The title compound was prepared using conditions analogous to those described in Example 133 utilizing potassium ((dimethylamino)methyl)trifluoroborate and (R)-3-[2-[3-(8-amino-5-bromo-1,7-naphthyridin-2-yl)phenyl]ethynyl]-3-hydroxy-1-methyl-pyrrolidin-2-one from Example 112 to afford (R)-3-[2-[3-[8-amino-5-(dimethylaminomethyl)-1,7-naphthyridin-2-yl]phenyl]ethynyl]-3-hydroxy-1-methyl-pyrrolidin-2-one (14 mg, 10%) as a colorless solid. MS (ESI): mass calcd. for $C_{24}H_{25}N_5O_2$, 415.5; m/z. found, 416.1 [M+H]$^+$. $^1$H NMR (500 MHz, DMSO-d$_6$) δ 8.50 (d, J=8.9 Hz, 1H), 8.42 (dt, J=7.6, 1.7 Hz, 1H), 8.38-8.35 (m, 1H), 8.33 (d, J=8.8 Hz, 1H), 7.72 (s, 1H), 7.59-7.42 (m, 2H), 7.07 (s, 2H), 6.48 (s, 1H), 3.54 (s, 2H), 3.40-3.34 (m, 2H), 2.82 (s, 3H), 2.49-2.46 (m, 1H), 2.24-2.18 (m, 1H), 2.17 (s, 6H).

Example 173: (R)-3-((3-(4-Amino-2-(hydroxymethyl)pyrido[3,2-d]pyrimidin-6-yl)phenyl)ethynyl)-3-hydroxy-1-methylpyrrolidin-2-one

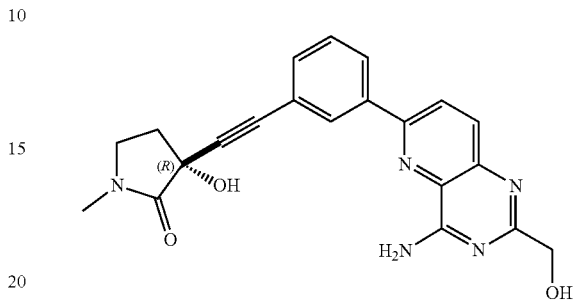

The title compound was prepared using conditions analogous to those described in Example 6 utilizing Intermediate 97 [(4-amino-6-chloropyrido[3,2-d]pyrimidin-2-yl)methanol] to afford (R)-3-((3-(4-amino-2-(hydroxymethyl)pyrido[3,2-d]pyrimidin-6-yl)phenyl)ethynyl)-3-hydroxy-1-methylpyrrolidin-2-one (136 mg, 52%) as a white solid. MS (ESI): mass calcd. for $C_{21}H_{19}N_5O_3$, 389.2; m/z. found, 390.2 [M+H]$^+$. $^1$H NMR (400 MHz, CD$_3$OD) δ 8.36 (br s, 1H), 8.30 (d, J=8.9 Hz, 1H), 8.26-8.19 (m, 1H), 8.12 (d, J=8.9 Hz, 1H), 7.59-7.45 (m, 2H), 4.62 (s, 2H), 3.57-3.41 (m, 2H), 2.94 (s, 3H), 2.58-2.64 (m, 1H), 2.42-2.21 (m, 1H).

Example 174: (R)-3-[2-[3-(3-Amino-1H-indazol-5-yl)phenyl]ethynyl]-3-hydroxy-1-methyl-pyrrolidin-2-one

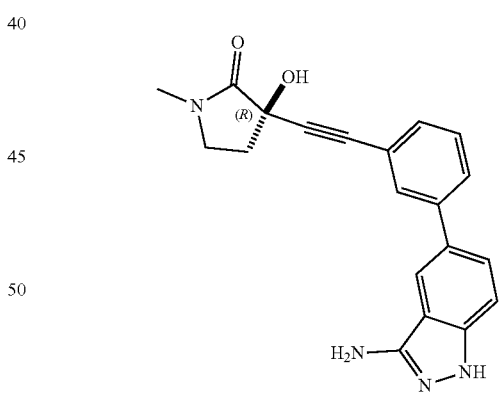

The title compound was prepared using analogous conditions described in Example 1 utilizing Intermediate 95 5-(3-iodophenyl)-1H-indazol-3-amine to afford (R)-3-[2-[3-(3-amino-1H-indazol-5-yl)phenyl]ethynyl]-3-hydroxy-1-methyl-pyrrolidin-2-one (40 mg, 26%) as a colorless solid. MS (ESI): mass calcd. for $C_{20}H_{18}N_4O_2$, 346.4; m/z found, 347.1 [M+H]$^+$. $^1$H NMR (500 MHz, DMSO-d$_6$) δ 11.46 (s, 1H), 8.07 (dd, J=1.7, 0.8 Hz, 1H), 7.71-7.64 (m, 2H), 7.57 (dd, J=8.7, 1.8 Hz, 1H), 7.51-7.44 (m, 1H), 7.37-7.33 (m, 1H), 7.30 (dd, J=8.7, 0.8 Hz, 1H), 6.47 (s, 1H), 5.44 (s, 2H), 3.39-3.34 (m, 2H), 2.84-2.77 (m, 3H), 2.45 (ddd, J=12.8, 6.2, 5.1 Hz, 1H), 2.23-2.15 (m, 1H).

Example 175: (R)-3-((3-(4-Amino-2-cyclopropylpyrido[3,2-d]pyrimidin-6-yl)phenyl)ethynyl)-3-hydroxy-1-methylpyrrolidin-2-one

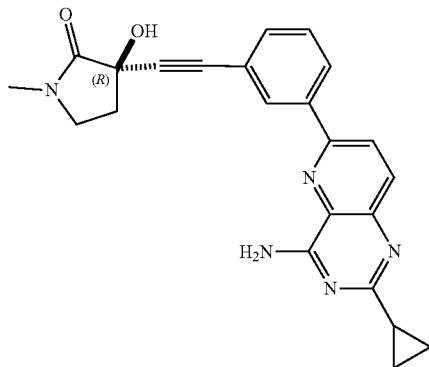

The title compound was prepared using conditions analogous to those described in Example 6 utilizing Intermediate 98 [6-Chloro-2-cyclopropylpyrido[3,2-d]pyrimidin-4-amine] to afford (R)-3-((3-(4-amino-2-cyclopropylpyrido[3,2-d]pyrimidin-6-yl)phenyl)ethynyl)-3-hydroxy-1-methylpyrrolidin-2-one (212 mg, 77%) as a yellow solid. MS (ESI): mass calcd. for $C_{23}H_{21}N_5O_2$, 399.2; m/z. found, 400.2 $[M+H]^+$. $^1$H NMR (400 MHz, $CD_3OD$) δ 8.34 (br s, 1H), 8.26 (d, J=8.9 Hz, 1H), 8.18-8.22 (m, 1H), 8.01 (d, J=8.9 Hz, 1H), 7.56-7.42 (m, 2H), 3.55-3.42 (m, 2H), 2.94 (s, 3H), 2.58-2.62 (m, 1H), 2.44-2.25 (m, 1H), 2.02-2.10 (m, 1H), 1.14-1.18 (m, 2H), 1.06-0.94 (m, 2H).

Example 176: (R)-3-((3-(4-Amino-2-(trifluoromethyl)pyrido[3,2-d]pyrimidin-6-yl)phenyl)ethynyl)-3-hydroxy-1-methylpyrrolidin-2-one

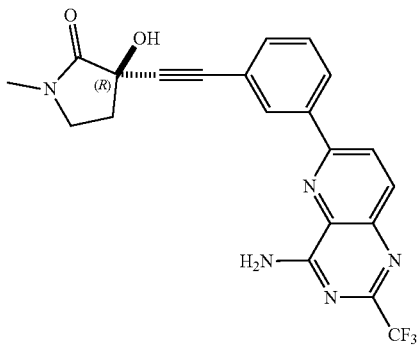

The title compound was prepared using conditions analogous to those described in Example 6 utilizing Intermediate 99 [6-chloro-2-(trifluoromethyl)pyrido[3,2-d]pyrimidin-4-amine] to afford (R)-3-((3-(4-amino-2-(trifluoromethyl)pyrido[3,2-d]pyrimidin-6-yl)phenyl)ethynyl)-3-hydroxy-1-methylpyrrolidin-2-one (80 mg, 30%) as a white solid. MS (ESI): mass calcd. for $C_{21}H_{16}F_3N_5O_2$, 427.1; m/z. found, 428.1 $[M+H]^+$. $^1$H NMR (400 MHz, $CD_3OD$) δ 8.48-8.35 (m, 2H), 8.35-8.18 (m, 2H), 7.63-7.44 (m, 2H), 3.57-3.42 (m, 2H), 2.95 (s, 3H), 2.58-2.66 (m, 1H), 2.30-2.37 (m, 1H).

Example 177: (R)-3-((3-(8-Aminopyrimido[5,4-d]pyrimidin-2-yl)-4-methoxyphenyl)ethynyl)-3-hydroxy-1-methylpyrrolidin-2-one

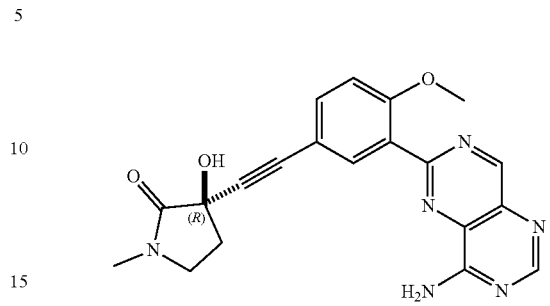

The title compound was prepared using analogous conditions described in Example 137 utilizing Intermediate 101 [(R)-3-((3-(8-(((2,4-dimethoxybenzyl)amino)pyrimido[5,4-d]pyrimidin-2-yl)-4-methoxyphenyl)ethynyl)-3-hydroxy-1-methylpyrrolidin-2-one] to afford (R)-3-((3-(8-aminopyrimido[5,4-d]pyrimidin-2-yl)-4-methoxyphenyl)ethynyl)-3-hydroxy-1-methylpyrrolidin-2-one (8.3 mg, 6.2%) as a white solid. MS (ESI): mass calcd. for $C_{20}H_{18}N_6O_3$ 390.1 m/z found 391.2 $[M+H]^+$. $^1$H NMR (400 MHz, DMSO-$d_6$) δ 9.39 (s, 1H), 8.54 (s, 1H), 8.31 (br s, 1H), 8.17 (br s, 1H), 7.76 (d, J=2.2 Hz, 1H), 7.55 (dd, J=2.1, 8.7 Hz, 1H), 7.21 (d, J=8.8 Hz, 1H), 6.41 (s, 1H), 3.82 (s, 3H), 3.30-3.28 (m, 2H), 2.79 (s, 3H), 2.45-2.36 (m, 1H), 2.20-2.12 (m, 1H).

Example 178: (R)-3-((3-(4-Amino-2,7-dimethylpyrido[3,2-d]pyrimidin-6-yl)phenyl)ethynyl)-3-hydroxy-1-methylpyrrolidin-2-one

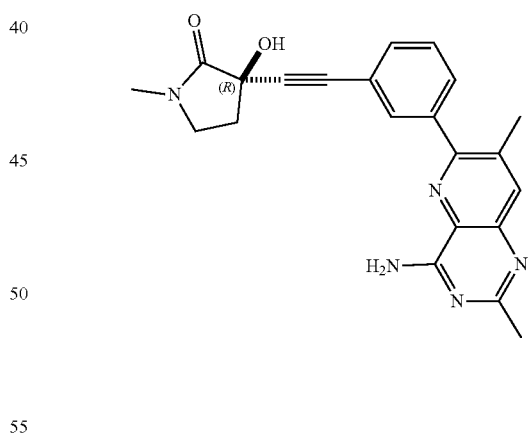

The title compound was prepared using analogous conditions described in Example 6 utilizing 6-chloro-2,7-dimethylpyrido[3,2-d]pyrimidin-4-amine to afford (R)-3-((3-(4-amino-2,7-dimethylpyrido[3,2-d]pyrimidin-6-yl)phenyl)ethynyl)-3-hydroxy-1-methylpyrrolidin-2-one (66 mg, 17%) as a white solid. MS (ESI): mass calcd. for $C_{22}H_{21}N_5O_2$ 387.2 m/z found 388.2 $[M+H]^+$. $^1$H NMR (400 MHz, DMSO-$d_6$) δ 7.91 (s, 1H), 7.76-7.63 (m, 4H), 7.52 (d, J=5.0 Hz, 2H), 6.49 (s, 1H), 3.38-3.35 (m, 2H), 2.80 (s, 3H), 2.48-2.46 (m, 1H), 2.45 (s, 3H), 2.43 (s, 3H), 2.23-2.14 (m, 1H).

Example 179: (R)-3-((3-(4-Amino-2H-pyrazolo[3,4-d]pyrimidin-2-yl)phenyl)ethynyl)-3-hydroxy-1-methylpyrrolidin-2-one

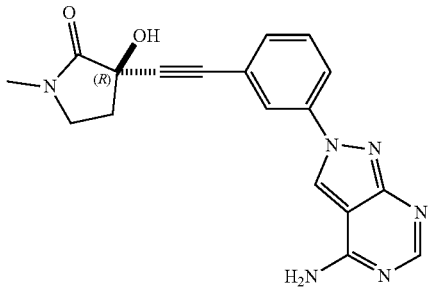

The title compound was prepared using analogous conditions described in Example 1 utilizing Intermediate 102 [2-(3-Bromophenyl)-2H-pyrazolo[4,3-d]pyrimidin-7-amine] to afford (R)-3-((3-(4-amino-2H-pyrazolo[3,4-d]pyrimidin-2-yl)phenyl)ethynyl)-3-hydroxy-1-methylpyrrolidin-2-one (44.1 mg, 14%) as a white solid. MS (ESI): mass calcd. for $C_{18}H_{16}N_6O_2$ 348.1 m/z found 349.2 [M+H]$^+$. $^1$H NMR (400 MHz, DMSO-$d_6$) δ 8.99 (s, 1H), 8.22 (s, 1H), 7.97-7.93 (m, 2H), 7.83 (s, 2H), 7.65-7.59 (m, 1H), 7.52-7.48 (m, 1H), 6.57 (s, 1H), 3.39-3.36 (m, 2H), 2.81 (s, 3H), 2.73-2.67 (m, 1H), 2.23-2.15 (m, 1H).

Example 180: (R)-4-(3-(4-Amino-2-methylpyrido[3,2-d]pyrimidin-6-yl)phenyl)-2-(4-methylthiazol-2-yl)but-3-yn-2-ol

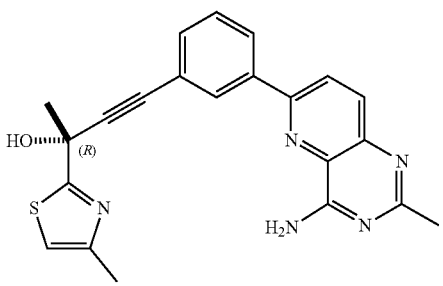

The title compound was prepared using analogous conditions described in Example 1 utilizing Intermediate 104 [(R)-2-(4-methylthiazol-2-yl)but-3-yn-2-ol and 6-(3-iodophenyl)-2-methylpyrido[3,2-d]pyrimidin-4-amine] to afford (R)-4-(3-(4-amino-2-methylpyrido[3,2-d]pyrimidin-6-yl)phenyl)-2-(4-methylthiazol-2-yl)but-3-yn-2-ol (143 mg, 86%) as a tan solid. MS (ESI): mass calcd. for $C_{22}H_{19}N_5OS$, 401.1; m/z. found, 402.1 [M+H]$^+$. $^1$H NMR (400 MHz, CD$_3$OD) δ 8.37 (br s, 1H), 8.30 (d, J=8.9 Hz, 1H), 8.20-8.24 (m, 1H), 8.03 (d, J=8.8 Hz, 1H), 7.61-7.43 (m, 2H), 7.09 (br s, 1H), 2.54 (s, 3H), 2.44 (br s, 3H), 1.97 (s, 3H).

Example 181: (S)-4-(3-(4-Amino-2-methylpyrido[3,2-d]pyrimidin-6-yl)phenyl)-2-(4-methylthiazol-2-yl)but-3-yn-2-ol

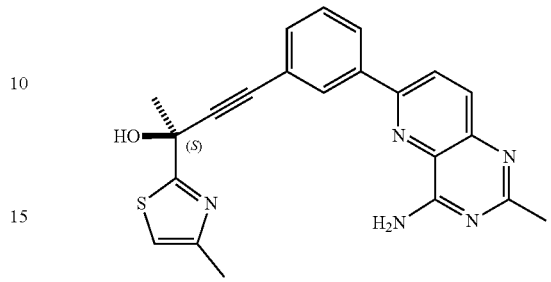

The title compound was prepared using analogous conditions described in Example 1 utilizing Intermediate 103 [(S)-2-(4-methylthiazol-2-yl)but-3-yn-2-ol] and 6-(3-iodophenyl)-2-methylpyrido[3,2-d]pyrimidin-4-amine to afford (S)-4-(3-(4-amino-2-methylpyrido[3,2-d]pyrimidin-6-yl)phenyl)-2-(4-methylthiazol-2-yl)but-3-yn-2-ol (151 mg, 90%) as a tan solid. MS (ESI): mass calcd. for $C_{22}H_{19}N_5OS$, 401.1; m/z. found, 402.1 [M+H]$^+$. $^1$H NMR (400 MHz, CD$_3$OD) δ 8.37 (br s, 1H), 8.30 (d, J=8.9 Hz, 1H), 8.20-8.24 (m, 1H), 8.03 (d, J=8.8 Hz, 1H), 7.61-7.43 (m, 2H), 7.09 (br s, 1H), 2.54 (s, 3H), 2.44 (br s, 3H), 1.97 (s, 3H).

Example 182: (R)-3-[2-[3-(7-Amino-5-methyl-thiazolo[5,4-d]pyrimidin-2-yl)-4-methyl-phenyl]ethynyl]-3-hydroxy-1-methyl-pyrrolidin-2-one

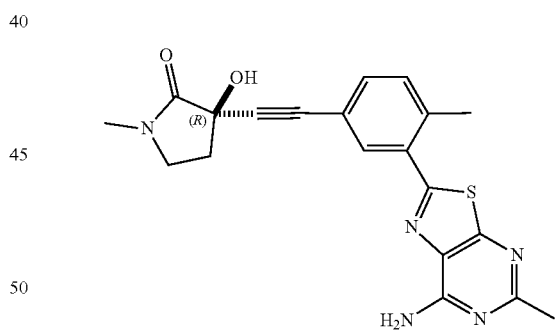

The title compound was prepared using analogous conditions described in Example 1 utilizing 2-(5-iodo-2-methylphenyl)-5-methylthiazolo[5,4-d]pyrimidin-7-amine to afford (R)-3-[2-[3-(7-amino-5-methyl-thiazolo[5,4-d]pyrimidin-2-yl)-4-methyl-phenyl]ethynyl]-3-hydroxy-1-methyl-pyrrolidin-2-one (30 mg, 29%) as a colorless solid. MS (ESI): mass calcd. for $C_{20}H_{19}N_5O_2S$, 393.5; m/z. found, 394.2 [M+H]$^+$. $^1$H NMR (500 MHz, DMSO-$d_6$) δ 7.81 (d, J=1.7 Hz, 1H), 7.66 (s, 2H), 7.48 (dd, J=7.8, 1.8 Hz, 1H), 7.44 (d, J=8.0 Hz, 1H), 6.49 (s, 1H), 3.37-3.34 (m, 1H), 2.80 (s, 3H), 2.63 (s, 3H), 2.48-2.41 (m, 4H), 2.23-2.12 (m, 1H).

Example 183: (R)-7-[2-[3-(7-Aminothiazolo[5,4-d]pyrimidin-2-yl)-4-methyl-phenyl]ethynyl]-5,6-dihydropyrrolo[1,2-a]imidazol-7-ol

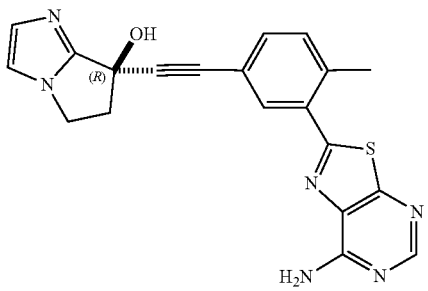

The title compound was prepared using analogous conditions described in Example 10 utilizing Intermediate 10 [(R)-7-ethynyl-6,7-dihydro-5H-pyrrolo[1,2-a]imidazol-7-ol] to afford (R)-7-[2-[3-(7-aminothiazolo[5,4-d]pyrimidin-2-yl)-4-methyl-phenyl]ethynyl]-5,6-dihydropyrrolo[1,2-a]imidazol-7-ol (24 mg, 25%) as a colorless solid. MS (ESI): mass calcd. for $C_{20}H_{16}N_6OS$, 388.5; m/z. found, 389.1 [M+H]$^+$. $^1$H NMR (500 MHz, DMSO-$d_6$) δ 8.33 (s, 1H), 7.86 (d, J=1.8 Hz, 1H), 7.79 (s, 2H), 7.51 (dd, J=7.9, 1.8 Hz, 1H), 7.46 (d, J=8.1 Hz, 1H), 7.14 (d, J=1.1 Hz, 1H), 6.99 (d, J=1.2 Hz, 1H), 6.56 (s, 1H), 4.11-4.00 (m, 2H), 3.09-2.96 (m, 1H), 2.84-2.73 (m, 1H), 2.65 (s, 3H).

Example 184: (R)-7-[2-[3-(7-Aminothiazolo[5,4-d]pyrimidin-2-yl)-4-methyl-phenyl]ethynyl]-5,6-dihydrocyclopenta[b]pyridin-7-ol

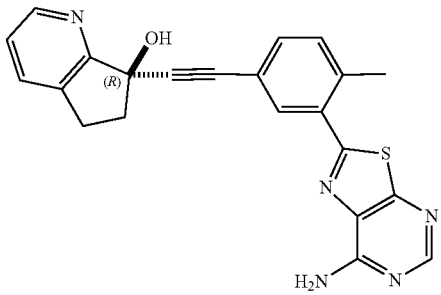

The title compound was prepared using analogous conditions described in Example 10 utilizing Intermediate 38 [(R)-7-ethynyl-6,7-dihydro-5H-cyclopenta[b]pyridin-7-ol] to afford (R)-7-[2-[3-(7-aminothiazolo[5,4-d]pyrimidin-2-yl)-4-methyl-phenyl]ethynyl]-5,6-dihydrocyclopenta[b]pyridin-7-ol (52 mg, 53%) as a colorless solid. MS (ESI): mass calcd. for $C_{22}H_{17}N_5OS$, 399.5; m/z. found, 400.2 [M+H]$^+$. $^1$H NMR (500 MHz, DMSO-$d_6$) δ 8.48-8.42 (m, 1H), 8.33 (s, 1H), 7.82 (d, J=1.7 Hz, 1H), 7.78 (s, 2H), 7.75-7.69 (m, 1H), 7.48 (dd, J=7.8, 1.8 Hz, 1H), 7.43 (d, J=8.0 Hz, 1H), 7.32-7.26 (m, 1H), 6.24 (s, 1H), 3.05-2.96 (m, 1H), 2.95-2.86 (m, 1H), 2.64 (s, 3H), 2.61-2.53 (m, 1H), 2.43-2.30 (m, 1H).

Example 185: 1-[2-[3-(7-Aminothiazolo[5,4-d]pyrimidin-2-yl)-4-methyl-phenyl]ethynyl]cyclopentanol

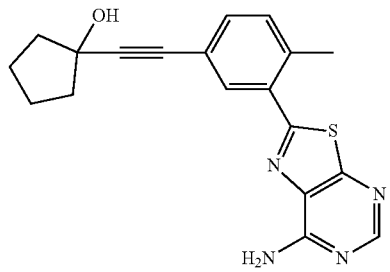 [SMILES: Cc1ccc(C#CC2(O)CCCC2)cc1-c1nc2c(N)ncnc2s1]

The title compound was prepared using analogous conditions described in Example 10 utilizing 1-ethynylcyclopentan-1-ol to afford 1-[2-[3-(7-aminothiazolo[5,4-d]pyrimidin-2-yl)-4-methyl-phenyl]ethynyl]cyclopentanol (25 mg, 29%) as a colorless solid. MS (ESI): mass calcd. for $C_{19}H_{18}N_4OS$, 350.4; m/z. found, 351.1 [M+H]$^+$. $^1$H NMR (500 MHz, DMSO-$d_6$) δ 8.33 (s, 1H), 7.80 (d, J=1.7 Hz, 1H), 7.77 (s, 2H), 7.46 (dd, J=7.9, 1.8 Hz, 1H), 7.43 (d, J=8.0 Hz, 1H), 5.36 (s, 1H), 2.64 (s, 3H), 1.98-1.82 (m, 5H), 1.80-1.62 (m, 3H).

Example 186: (S)-3-((3-(4-Amino-2-methylpyrido[3,2-d]pyrimidin-6-yl)phenyl)ethynyl)-3-hydroxy-1-methylpiperidin-2-one

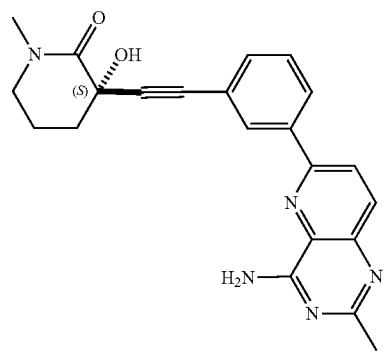

The title compound was prepared using analogous conditions described in Example 1 utilizing Intermediate 107 [(S)-3-ethynyl-3-hydroxy-1-methylpiperidin-2-one] and 6-(3-iodophenyl)-2-methylpyrido[3,2-d]pyrimidin-4-amine to afford (S)-3-((3-(4-amino-2-methylpyrido[3,2-d]pyrimidin-6-yl)phenyl)ethynyl)-3-hydroxy-1-methylpiperidin-2-one (138 mg, 86%) as a tan solid. MS (ESI): mass calcd. for $C_{22}H_{21}N_5O_2$, 387.2; m/z found, 388.2 [M+H]$^+$. $^1$H NMR (400 MHz, CD$_3$OD) δ 8.35 (br s, 1H), 8.31 (d, J=8.9 Hz, 1H), 8.21-8.30 (m, 1H), 8.04 (d, J=8.9 Hz, 1H), 7.57-7.45 (m, 2H), 3.48-3.39 (m, 2H), 2.99 (s, 3H), 2.55 (s, 3H), 2.41-2.31 (m, 1H), 2.31-2.18 (m, 1H), 2.15-1.97 (m, 2H).

Example 187: (R)-3-((3-(4-Amino-2-methylpyrido[3,2-d]pyrimidin-6-yl)phenyl)ethynyl)-3-hydroxy-1-methylpiperidin-2-one

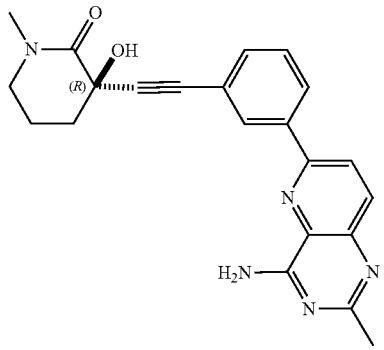

The title compound was prepared using analogous conditions described in Example 1 utilizing Intermediate 106 [(R)-3-ethynyl-3-hydroxy-1-methylpiperidin-2-one] and 6-(3-iodophenyl)-2-methylpyrido[3,2-d]pyrimidin-4-amine to afford (R)-3-((3-(4-amino-2-methylpyrido[3,2-d]pyrimidin-6-yl)phenyl)ethynyl)-3-hydroxy-1-methylpiperidin-2-one (136 mg, 84%) as a tan solid. MS (ESI): mass calcd. for $C_{22}H_{21}N_5O_2$, 387.2; m/z found, 388.2 [M+H]$^+$. $^1$H NMR (400 MHz, CD$_3$OD) δ 8.34 (br s 1H), 8.30 (d, J=8.9 Hz, 1H), 8.20-8.24 (m, 1H), 8.04 (d, J=8.9 Hz, 1H), 7.57-7.44 (m, 2H), 3.50-3.40 (m, 2H), 3.00 (s, 3H), 2.55 (s, 3H), 2.31-2.38 (m, 1H), 2.29-2.17 (m, 1H), 2.16-1.98 (m, 2H).

Example 188: (R)-3-((3-(8-Aminopyrimido[5,4-d]pyrimidin-2-yl)-4-methylphenyl)ethynyl)-3-hydroxy-1-methylpyrrolidin-2-one

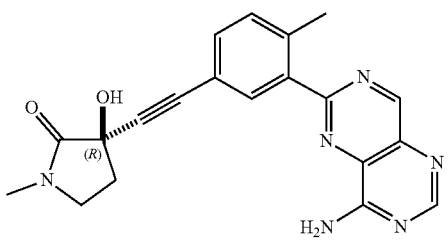

The title compound was prepared using analogous conditions described in Example 137 utilizing Intermediate 109 [(R)-3-((3-(8-((2,4-dimethoxybenzyl)amino)pyrimido[5,4-d]pyrimidin-2-yl)-4-methylphenyl)ethynyl)-3-hydroxy-1-methylpyrrolidin-2-one] to afford (R)-3-((3-(8-aminopyrimido[5,4-d]pyrimidin-2-yl)-4-methylphenyl)ethynyl)-3-hydroxy-1-methylpyrrolidin-2-one (41.5 mg, 25%) as a white solid. MS (ESI): mass calcd. for $C_{20}H_{18}N_6O_2$ 374.2 m/z found 375.3 [M+H]$^+$. $^1$H NMR (400 MHz, DMSO-d$_6$) δ 9.43 (s, 1H), 8.55 (s, 1H), 8.35 (br s, 1H), 8.21 (br s, 1H), 8.00 (d, J=1.5 Hz, 1H), 7.48-7.37 (m, 2H), 6.47 (s, 1H), 3.34-3.33 (m, 2H), 2.79 (s, 3H), 2.60 (s, 3H), 2.46-2.40 (m, 1H), 2.22-2.13 (m, 1H).

Example 189: (R)-3-((3-(4-Amino-7-methylpyrido[3,2-d]pyrimidin-6-yl)phenyl)ethynyl)-3-hydroxy-1-methylpyrrolidin-2-one

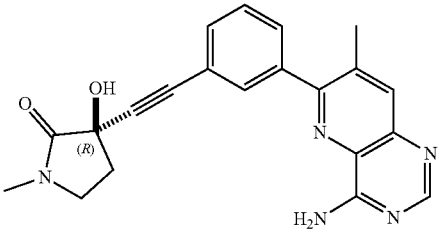

The title compound was prepared using analogous conditions described in Example 12 utilizing 6-chloro-7-methylpyrido[3,2-d]pyrimidin-4-amine to afford (R)-3-((3-(4-amino-7-methylpyrido[3,2-d]pyrimidin-6-yl)phenyl)ethynyl)-3-hydroxy-1-methylpyrrolidin-2-one (87.3 mg, 45%) as a white solid. MS (ESI): mass calcd. for $C_{21}H_{19}N_5O_2$ 373.2 m/z found 374.2 [M+H]$^+$. $^1$H NMR (400 MHz, DMSO-d$_6$) δ 8.40 (s, 1H), 8.01 (s, 1H), 7.89-7.76 (m, 2H), 7.73-7.67 (m, 2H), 7.53 (d, J=4.8 Hz, 2H), 6.51 (s, 1H), 3.36-3.32 (m, 2H), 2.80 (s, 3H), 2.45 (s, 3H), 2.44-2.39 (m, 1H), 2.23-2.14 (m, 1H).

Example 190: (R)-4-[3-(4-Amino-2-methyl-pyrido[3,2-d]pyrimidin-6-yl)phenyl]-2-(2-pyridyl)but-3-yn-2-ol

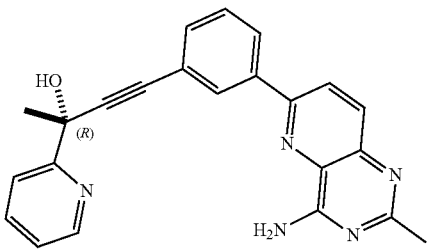

The title compound was prepared using analogous conditions described in Example 1 utilizing Intermediate 110 [6-(3-iodophenyl)-2-methylpyrido[3,2-d]pyrimidin-4-amine] and Intermediate 111 [(R)-2-(pyridin-2-yl)but-3-yn-2-ol] to afford (R)-4-[3-(4-amino-2-methyl-pyrido[3,2-d]pyrimidin-6-yl)phenyl]-2-(2-pyridyl)but-3-yn-2-ol (9 mg, 7%) as a colorless solid. MS (ESI): mass calcd. for $C_{23}H_{19}N_5O$, 381.4; m/z. found, 382.2 [M+H]$^+$. $^1$H NMR (500 MHz, DMSO-d$_6$) δ 8.61-8.54 (m, 1H), 8.42-8.32 (m, 3H), 8.05 (s, 1H), 8.02 (d, J=8.8 Hz, 1H), 7.88-7.83 (m, 2H), 7.83-7.74 (m, 1H), 7.55-7.46 (m, 2H), 7.38-7.29 (m, 1H), 6.37 (s, 1H), 2.46 (s, 3H), 1.85 (s, 3H).

Example 191: (S)-4-[3-(4-Amino-2-methyl-pyrido[3,2-d]pyrimidin-6-yl)phenyl]-2-(2-pyridyl)but-3-yn-2-ol

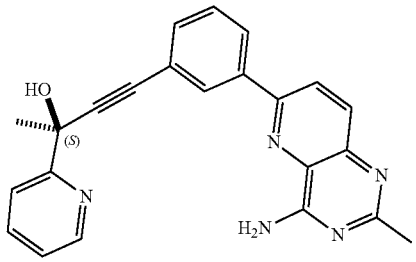

The title compound was prepared using analogous conditions described in Example 1 utilizing Intermediate 110 [6-(3-iodophenyl)-2-methylpyrido[3,2-d]pyrimidin-4-amine] and Intermediate 112 [(S)-2-(pyridin-2-yl)but-3-yn-2-ol] to afford (S)-4-[3-(4-amino-2-methyl-pyrido[3,2-d]pyrimidin-6-yl)phenyl]-2-(2-pyridyl)but-3-yn-2-ol (18 mg, 14%) as a colorless solid. MS (ESI): mass calcd. for $C_{23}H_{19}N_5O$, 381.4; m/z. found, 382.2 [M+H]$^+$. $^1$H NMR (500 MHz, DMSO-$d_6$) δ 8.61-8.51 (m, 1H), 8.42-8.29 (m, 3H), 8.08-7.95 (m, 2H), 7.89-7.77 (m, 3H), 7.55-7.46 (m, 2H), 7.36-7.29 (m, 1H), 6.36 (s, 1H), 2.45 (s, 3H), 1.85 (s, 3H).

Example 192: (R)-4-(3-(4-Amino-2-methylpyrido[3,2-d]pyrimidin-6-yl)phenyl)-2-(4-(trifluoromethyl)thiazol-2-yl)but-3-yn-2-ol

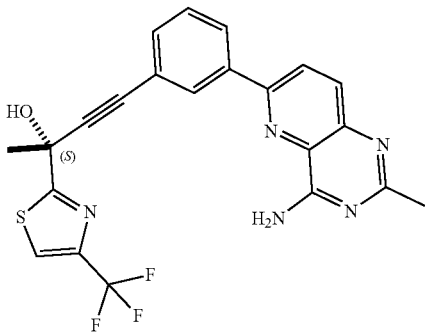

The title compound was prepared using analogous conditions described in Example 1 utilizing Intermediate 110 [6-(3-iodophenyl)-2-methylpyrido[3,2-d]pyrimidin-4-amine] and Intermediate 113 [(R)-2-(4-(trifluoromethyl)thiazol-2-yl)but-3-yn-2-ol] to afford (R)-4-(3-(4-amino-2-methylpyrido[3,2-d]pyrimidin-6-yl)phenyl)-2-(4-(trifluoromethyl)thiazol-2-yl)but-3-yn-2-ol (65 mg, 34%) as a white solid. MS (ESI): mass calcd. for $C_{22}H_{16}F_3N_5OS$, 455.1; m/z. found, 456.1 [M+H]$^+$. $^1$H NMR (400 MHz, CD$_3$OD) δ 8.31 (br s, 1H), 8.27 (d, J=8.9 Hz, 1H), 8.20-8.24 (m, 1H), 8.14 (br s, 1H), 8.01 (d, J=8.9 Hz, 1H), 7.59-7.44 (m, 2H), 2.53 (s, 3H), 2.01 (s, 3H).

Example 193: (S)-4-(3-(4-Amino-2-methylpyrido[3,2-d]pyrimidin-6-yl)phenyl)-2-(4-(trifluoromethyl)thiazol-2-yl)but-3-yn-2-ol

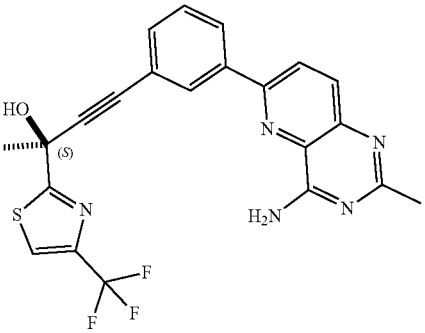

The title compound was prepared using analogous conditions described in Example 1 utilizing Intermediate 110 [6-(3-iodophenyl)-2-methylpyrido[3,2-d]pyrimidin-4-amine] and Intermediate 114 [(S)-2-(4-(trifluoromethyl)thiazol-2-yl)but-3-yn-2-ol] to afford (S)-4-(3-(4-amino-2-methylpyrido[3,2-d]pyrimidin-6-yl)phenyl)-2-(4-(trifluoromethyl)thiazol-2-yl)but-3-yn-2-ol (83 mg, 44%) as a tan solid. MS (ESI): mass calcd. for $C_{22}H_{16}F_3N_5OS$, 455.1; m/z. found, 456.1 [M+H]$^+$. $^1$H NMR (400 MHz, CD$_3$OD) δ 8.31 (br s, 1H), 8.27 (d, J=8.9 Hz, 1H), 8.20-8.24 (m, 1H), 8.14 (br s, 1H), 8.01 (d, J=8.9 Hz, 1H), 7.59-7.44 (m, 2H), 2.53 (s, 3H), 2.01 (s, 3H).

Example 194: (R)-3-((3-(7-Aminothiazolo[5,4-d]pyrimidin-2-yl)-4-methoxyphenyl)ethynyl)-3-hydroxy-1-methylpyrrolidin-2-one

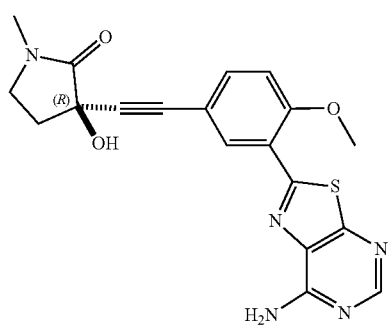

The title compound was prepared using analogous conditions described in Example 1 utilizing Intermediate 115 [2-(5-Iodo-2-methoxyphenyl)thiazolo[5,4-d]pyrimidin-7-amine] to afford (R)-3-((3-(7-aminothiazolo[5,4-d]pyrimidin-2-yl)-4-methoxyphenyl)ethynyl)-3-hydroxy-1-methylpyrrolidin-2-one (24.6 mg, 39%) as a white solid. MS (ESI): mass for $C_{19}H_{17}N_5O_3S$ 395.1 m/z. found 396.1 [M+1]$^+$. $^1$H NMR (400 MHz, DMSO-$d_6$) δ 8.52 (d, J=1.7 Hz, 1H), 8.30 (s, 1H), 7.80 (br s., 2H), 7.64-7.55 (m, 1H), 7.32 (d, J=8.8 Hz, 1H), 6.46 (s, 1H), 4.08 (s, 3H), 3.40-3.36 (m, 2H), 2.81 (s, 3H), 2.47-2.39 (m, 1H), 2.25-2.14 (m, 1H).

Example 195: racemic-1-Allyl-3-((3-(4-amino-2-methylpyrido[3,2-d]pyrimidin-6-yl)phenyl)ethynyl)-3-hydroxypyrrolidin-2-one

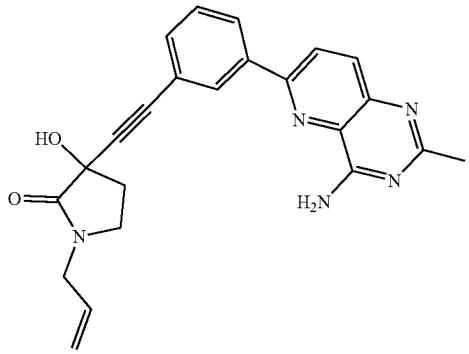 [SMILES: C=CCN1CCC(O)(C#Cc2cccc(-c3ccc4nc(C)nc(N)c4n3)c2)C1=O]

The title compound was prepared using analogous conditions described in Example 1 utilizing Intermediate 110 [6-(3-iodophenyl)-2-methylpyrido[3,2-d]pyrimidin-4-amine] and Intermediate 116 [racemic-1-allyl-3-ethynyl-3-hydroxypyrrolidin-2-one] to afford racemic-1-allyl-3-((3-(4-amino-2-methylpyrido[3,2-d]pyrimidin-6-yl)phenyl)ethynyl)-3-hydroxypyrrolidin-2-one (105 mg, 31%) as a light orange solid. MS (ESI): mass calcd. for $C_{23}H_{21}N_5O_2$, 399.2; m/z. found, 400.2 [M+H]$^+$. $^1$H NMR (400 MHz, CD$_3$OD) δ 8.33 (br s, 1H), 8.27 (d, J=8.9 Hz, 1H), 8.20-8.24 (m, 1H), 8.02 (d, J=8.8 Hz, 1H), 7.59-7.43 (m, 2H), 5.78-5.90 (m, 1H), 5.35-5.15 (m, 2H), 3.95-4.00 (m, 2H), 3.58-3.41 (m, 2H), 2.58-2.65 (m, 1H), 2.54 (s, 3H), 2.28-2.36 (m, 1H).

Example 196: racemic-1-Allyl-3-((3-(4-aminopyrido[3,2-d]pyrimidin-6-yl-2-d)phenyl)ethynyl)-3-hydroxypyrrolidin-2-one

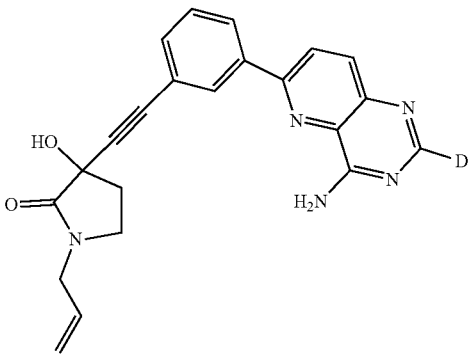 [SMILES: [2H]c1nc(N)c2nc(-c3cccc(C#CC4(O)CCN(CC=C)C4=O)c3)ccc2n1]

The title compound was prepared using analogous conditions described in Example 1 utilizing Intermediate 117 [6-(3-iodophenyl)pyrido[3,2-d]pyrimidin-2-d-4-amine] and Intermediate 116 [racemic-1-allyl-3-ethynyl-3-hydroxypyrrolidin-2-one] to afford (101 mg, 30%) as an orange solid. MS (ESI): mass calcd. for $C_{22}H_{18}DN_5O_2$, 386.2; m/z. found, 387.2 [M+H]$^+$. $^1$H NMR (400 MHz, CD$_3$OD) δ 8.36 (br s, 1H), 8.33 (d, J=8.9 Hz, 1H), 8.20-8.26 (m, 1H), 8.11 (d, J=8.9 Hz, 1H), 7.60-7.44 (m, 2H), 5.78-5.84 (m, 1H), 5.34-5.14 (m, 2H), 3.95-4.00 (m, 2H), 3.56-3.41 (m, 2H), 2.58-2.64 (m, 1H), 2.28-2.36 (m, 1H).

Example 197: (R)-4-[3-(4-Amino-2-methyl-pyrido[3,2-d]pyrimidin-6-yl)phenyl]-2-pyrimidin-2-yl-but-3-yn-2-ol

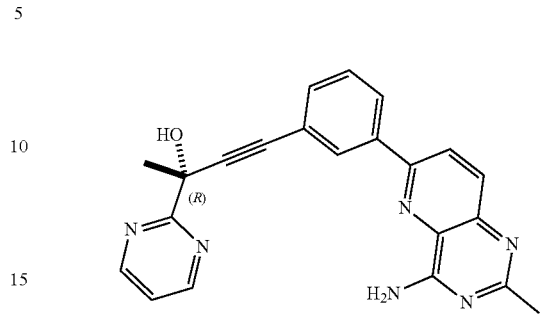

The title compound was prepared using analogous conditions described in Example 1 utilizing Intermediate 110 [6-(3-iodophenyl)-2-methylpyrido[3,2-d]pyrimidin-4-amine] and Intermediate 118 [(R)-2-(pyrimidin-2-yl)but-3-yn-2-ol] to afford (R)-4-[3-(4-amino-2-methyl-pyrido[3,2-d]pyrimidin-6-yl)phenyl]-2-pyrimidin-2-yl-but-3-yn-2-ol (26 mg, 20%) as a colorless solid. MS (ESI): mass calcd. for $C_{22}H_{18}N_6O$, 382.4; m/z. found, 383.1 [M+H]$^+$. $^1$H NMR (500 MHz, DMSO-d$_6$) δ 8.90 (d, J=4.9 Hz, 2H), 8.41-8.36 (m, 2H), 8.36-8.33 (m, 1H), 8.07-7.98 (m, 2H), 7.84 (s, 1H), 7.56-7.40 (m, 3H), 6.19 (s, 1H), 2.45 (s, 3H), 1.91 (s, 3H).

Example 198: (S)-4-[3-(4-Amino-2-methyl-pyrido[3,2-d]pyrimidin-6-yl)phenyl]-2-pyrimidin-2-yl-but-3-yn-2-ol

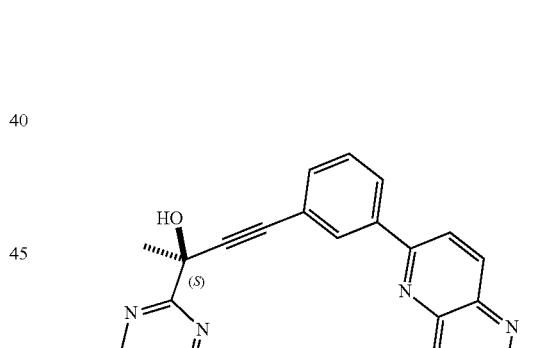

The title compound was prepared using analogous conditions described in Example 1 utilizing Intermediate 110 [6-(3-iodophenyl)-2-methylpyrido[3,2-d]pyrimidin-4-amine] and Intermediate 119 [(S)-2-(pyrimidin-2-yl)but-3-yn-2-ol] to afford (S)-4-[3-(4-amino-2-methyl-pyrido[3,2-d]pyrimidin-6-yl)phenyl]-2-pyrimidin-2-yl-but-3-yn-2-ol (18 mg, 14%) as a colorless solid. MS (ESI): mass calcd. for $C_{22}H_{18}N_6O$, 382.4; m/z. found, 383.1 [M+H]$^+$. $^1$H NMR (500 MHz, DMSO-d$_6$) δ 8.90 (d, J=4.9 Hz, 2H), 8.41-8.36 (m, 2H), 8.36-8.33 (m, 1H), 8.07-7.98 (m, 2H), 7.84 (s, 1H), 7.56-7.40 (m, 3H), 6.19 (s, 1H), 2.45 (s, 3H), 1.91 (s, 3H).

Example 199: (S)-3-((3-(4-Aminopyrido[3,2-d]pyrimidin-6-yl-2-d)phenyl)ethynyl)-3-hydroxy-1-methylpiperidin-2-one

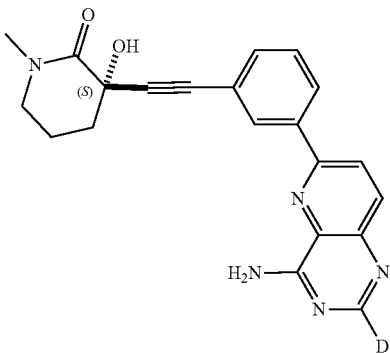

The title compound was prepared using analogous conditions described in Example 1 utilizing Intermediate 107 [(S)-3-ethynyl-3-hydroxy-1-methylpiperidin-2-one] and Intermediate 117 [6-(3-iodophenyl)pyrido[3,2-d]pyrimidin-2-d-4-amine] to afford (S)-3-((3-(4-aminopyrido[3,2-d]pyrimidin-6-yl-2-d)phenyl)ethynyl)-3-hydroxy-1-methylpiperidin-2-one (97 mg, 59%) a tan solid. MS (ESI): mass calcd. for $C_{21}H_{18}DN_5O_2$, 374.2; m/z. found, 375.2 [M+H]$^+$. $^1$H NMR (400 MHz, CD$_3$OD) δ 8.34-8.25 (m, 2H), 8.18-8.22 (m, 1H), 8.08 (d, J=8.8 Hz, 1H), 7.56-7.41 (m, 2H), 3.51-3.40 (m, 2H), 3.00 (s, 3H), 2.31-2.40 (m, 1H), 2.31-2.17 (m, 1H), 2.17-1.97 (m, 2H), 1.92-1.81 (m, 1H).

Example 200: (R)-4-[3-(4-Amino-2-methyl-pyrido[3,2-d]pyrimidin-6-yl)phenyl]-2-pyrazin-2-yl-but-3-yn-2-ol

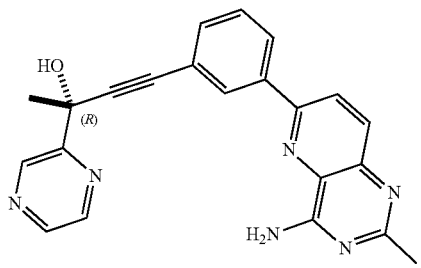

The title compound was prepared using analogous conditions described in Example 1 utilizing Intermediate 110 [6-(3-iodophenyl)-2-methylpyrido[3,2-d]pyrimidin-4-amine] and Intermediate 120 [(R)-2-(pyrazin-2-yl)but-3-yn-2-ol] to afford (R)-4-[3-(4-amino-2-methyl-pyrido[3,2-d]pyrimidin-6-yl)phenyl]-2-pyrazin-2-yl-but-3-yn-2-ol (18 mg, 11%) as a colorless solid. MS (ESI): mass calcd. for $C_{22}H_{18}N_6O$, 382.4; m/z. found, 383.1 [M+H]$^+$. $^1$H NMR (500 MHz, DMSO-d$_6$) δ 9.77 (s, 2H), 9.05 (d, J=1.6 Hz, 1H), 8.69-8.61 (m, 3H), 8.51-8.39 (m, 2H), 8.15 (d, J=8.9 Hz, 1H), 7.61-7.51 (m, 2H), 6.68 (s, 1H), 2.62 (s, 3H), 1.89 (s, 3H).

Example 201: (S)-4-[3-(4-Amino-2-methyl-pyrido[3,2-d]pyrimidin-6-yl)phenyl]-2-pyrazin-2-yl-but-3-yn-2-ol

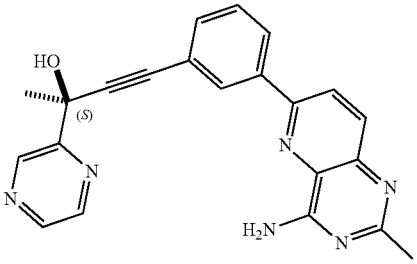

The title compound was prepared using analogous conditions described in Example 1 utilizing Intermediate 110 [6-(3-iodophenyl)-2-methylpyrido[3,2-d]pyrimidin-4-amine] and Intermediate 121 [(S)-2-(pyrazin-2-yl)but-3-yn-2-ol] to afford (S)-4-[3-(4-amino-2-methyl-pyrido[3,2-d]pyrimidin-6-yl)phenyl]-2-pyrazin-2-yl-but-3-yn-2-ol (18 mg, 11%) as a colorless solid. MS (ESI): mass calcd. for $C_{22}H_{18}N_6O$, 382.4; m/z. found, 383.1 [M+H]$^+$. $^1$H NMR (500 MHz, DMSO-d$_6$) δ 9.77 (s, 2H), 9.05 (d, J=1.6 Hz, 1H), 8.69-8.61 (m, 3H), 8.51-8.39 (m, 2H), 8.15 (d, J=8.9 Hz, 1H), 7.61-7.51 (m, 2H), 6.68 (s, 1H), 2.62 (s, 3H), 1.89 (s, 3H).

Example 202: racemic-4-(3-(4-Amino-2-methylpyrido[3,2-d]pyrimidin-6-yl)phenyl)-2-(1H-imidazol-4-yl)but-3-yn-2-ol

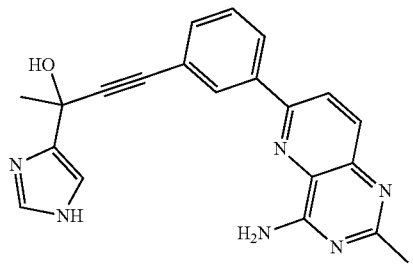 [SMILES: Cc1nc(N)c2nc(-c3cccc(C#CC(C)(O)c4c[nH]cn4)c3)ccc2n1]

The title compound was prepared using analogous conditions described in Example 1 utilizing Intermediate 110 [6-(3-iodophenyl)-2-methylpyrido[3,2-d]pyrimidin-4-amine] and 2-(1H-imidazol-4-yl)but-3-yn-2-ol to afford racemic-4-(3-(4-amino-2-methylpyrido[3,2-d]pyrimidin-6-yl)phenyl)-2-(1H-imidazol-4-yl)but-3-yn-2-ol (18 mg, 14%) as a colorless solid. MS (ESI): mass calcd. for $C_{21}H_{18}N_6O$, 370.4; m/z. found, 371.1 [M+H]$^+$.

Example 203: (R)-3-((3-(2,4-Diaminopyrido[3,2-d]pyrimidin-6-yl)phenyl)ethynyl)-3-hydroxy-1-methylpyrrolidin-2-one

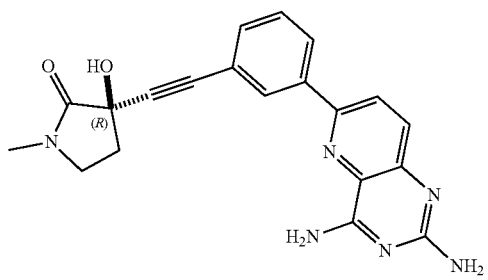

The title compound was prepared using analogous conditions described in Example 1 utilizing Intermediate 122 [6-(3-Bromophenyl)pyrido[3,2-d]pyrimidine-2,4-diamine] to afford (R)-3-((3-(2,4-diaminopyrido[3,2-d]pyrimidin-6-yl)phenyl)ethynyl)-3-hydroxy-1-methylpyrrolidin-2-one (16.3 mg 6.8%) as a white solid. MS (ESI): mass calcd. for $C_{20}H_{18}N_6O_2$ 374.2 m/z found 375.1 [M+H]$^+$. $^1$H NMR (400 MHz, DMSO-d$_6$) δ 8.31 (d, J=7.8 Hz, 1H), 8.28 (s, 1H), 8.20-8.14 (m, 2H), 7.71 (br s, 1H), 7.62 (d, J=8.8 Hz, 1H), 7.54-7.40 (m, 3H), 6.37 (br s, 2H), 3.37 (t, J=6.5 Hz, 2H), 2.81 (s, 3H), 2.47-2.43 (m, 1H), 2.26-2.15 (m, 1H).

Example 204. (R)-3-((3-(4-Aminopyrido[3,2-d]pyrimidin-6-yl)phenyl)ethynyl)-3-(difluoromethyl)-1-methylpyrrolidin-2-one

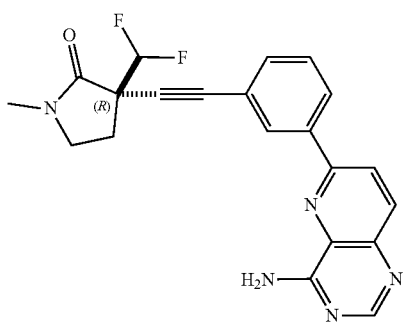

A microwave vial was charged with Intermediate 123 [3-(difluoromethyl)-1-methyl-3-((3-(4,4,5,5-tetramethyl-1,3,2-dioxaborolan-2-yl)phenyl)ethynyl)pyrrolidin-2-one, (360 mg)], 6-chloropyrido[3,2-d]pyrimidin-4-amine (208 mg, 1.15 mmol), Cs$_2$CO$_3$ (936 mg, 2.87 mmol), 1,4-dioxane (8 mL), and H$_2$O (2 mL). The resultant mixture was purged with Ar for 5 min and then treated with chloro(2-dicyclohexylphosphino-2',4',6'-triisopropyl-1,1'-biphenyl)[2-(2'-amino-1,1'-biphenyl)]palladium(II) (80 mg, 0.10 mmol). The resultant mixture was purged with Ar for another 5 min and then heated at 110° C. in a microwave reactor for 1 h before cooling to rt. The mixture was washed with H$_2$O (30 mL) and extracted with ethyl acetate (30 mL×4). The combined organic extracts were washed with brine (80 mL), dried over anhydrous Na$_2$SO$_4$, filtered and concentrated to dryness. The residue was purified by reverse phase preparative HPLC (Xtimate C18 250×50 mm×10 μm, eluent: 20% to 50% (v/v) CH$_3$CN and H$_2$O with (0.04% NH$_3$H$_2$O and 10 mM NH$_4$HCO$_3$)) to afford racemic-3-((3-(4-aminopyrido[3,2-d]pyrimidin-6-yl)phenyl)ethynyl)-3-(difluoromethyl)-1-methylpyrrolidin-2-one (140 mg) as a light yellow solid. MS (ESI): mass calcd. for $C_{21}H_{17}F_2N_5O$, 393.1; m/z. found 394.2 [M+H]$^+$. The enantiomers of racemic 3-((3-(4-aminopyrido[3,2-d]pyrimidin-6-yl)phenyl)ethynyl)-3-(difluoromethyl)-1-methylpyrrolidin-2-one (140 mg) were separated by chiral preparative SFC (DAICEL CHIRALCEL OD-H 250×30 mm×5 μm, (eluent: 25% to 25% (v/v) supercritical CO$_2$ in EtOH and H$_2$O with 0.1% NH$_3$) to afford (R)-3-((3-(4-aminopyrido[3,2-d]pyrimidin-6-yl)phenyl)ethynyl)-3-(difluoromethyl)-1-methylpyrrolidin-2-one (37.9 mg, 27%) as a white solid and (S)-3-((3-(4-aminopyrido[3,2-d]pyrimidin-6-yl)phenyl)ethynyl)-3-(difluoromethyl)-1-methylpyrrolidin-2-one (Example 205, 28.3 mg, 20%) as a white solid. Data for (R)-3-((3-(4-aminopyrido[3,2-d]pyrimidin-6-yl)phenyl)ethynyl)-3-(difluoromethyl)-1-methylpyrrolidin-2-one: MS (ESI): mass calcd. for $C_{21}H_{17}F_2N_5O$, 393.1; m/z. found 394.1 [M+H]$^+$. $^1$H NMR (400 MHz, DMSO-d$_6$) δ 8.55-8.38 (m, 4H), 8.24 (br s, 1H), 8.14 (d, J=8.8 Hz, 1H), 8.01 (br s, 1H), 7.63-7.51 (m, 2H), 6.56-6.23 (m, 1H), 3.61-3.51 (m, 1H), 3.50-3.41 (m, 1H), 2.85 (s, 3H), 2.62-2.54 (m, 1H), 2.43-2.34 (m, 1H).

Example 205: (S)-3-((3-(4-Aminopyrido[3,2-d]pyrimidin-6-yl)phenyl)ethynyl)-3-(difluoromethyl)-1-methylpyrrolidin-2-one

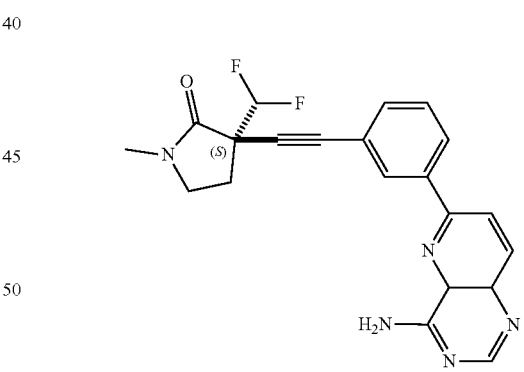

The chiral separation described in Example 204 provided (S)-3-((3-(4-aminopyrido[3,2-d]pyrimidin-6-yl)phenyl)ethynyl)-3-(difluoromethyl)-1-methylpyrrolidin-2-one (28.3 mg, 20%) as a white solid. MS (ESI): mass calcd. for $C_{21}H_{17}F_2N_5O$, 393.1; m/z. found 394.1 [M+H]$^+$. $^1$H NMR (400 MHz, DMSO-d$_6$) δ 8.55-8.38 (m, 4H), 8.24 (br s, 1H), 8.14 (d, J=8.8 Hz, 1H), 8.01 (br s, 1H), 7.63-7.51 (m, 2H), 6.56-6.23 (m, 1H), 3.62-3.52 (m, 1H), 3.50-3.41 (m, 1H), 2.85 (s, 3H), 2.61-2.54 (m, 1H), 2.43-2.34 (m, 1H).

Example 206: (R)-3-((3-(4-Amino-2-(methoxymethyl)pyrido[3,2-d]pyrimidin-6-yl)phenyl)ethynyl)-3-hydroxy-1-methylpyrrolidin-2-one

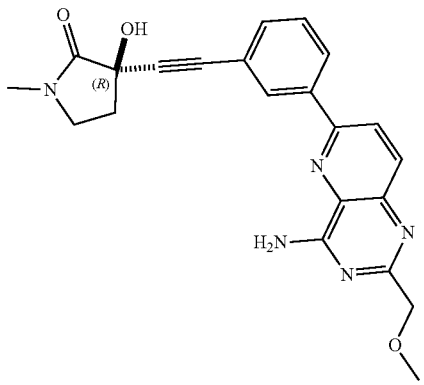

The title compound was prepared using conditions analogous to those described in Example 6 utilizing Intermediate 124 [6-chloro-2-(methoxymethyl)pyrido[3,2-d]pyrimidin-4-amine] to afford (R)-3-((3-(4-amino-2-(methoxymethyl)pyrido[3,2-d]pyrimidin-6-yl)phenyl)ethynyl)-3-hydroxy-1-methylpyrrolidin-2-one (187 mg, 69%) as a yellow solid. MS (ESI): mass calcd. for $C_{22}H_{21}N_5O_3$, 403.2; m/z. found, 404.2 [M+H]$^+$. $^1$H NMR (400 MHz, CD$_3$OD) δ 8.38-8.34 (m, 1H), 8.30 (d, J=8.9 Hz, 1H), 8.20-8.26 (m, 1H), 8.12 (d, J=8.8 Hz, 1H), 7.57-7.44 (m, 2H), 4.50 (s, 2H), 3.54-3.45 (m, 5H), 2.94 (s, 3H), 2.58-2.64 (m, 1H), 2.32-2.38 (m, 1H).

Example 207: (R)-3-((3-(4-Aminopyrido[3,2-d]pyrimidin-6-yl)phenyl)ethynyl)-3-methoxy-1-methylpyrrolidin-2-one

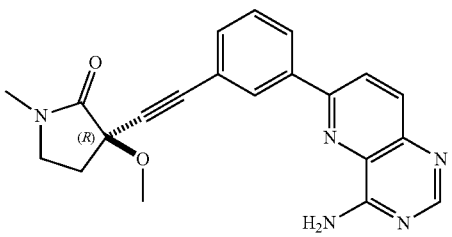

The title compound was prepared using conditions analogous to those described in Example 12 utilizing Intermediate 126 [(R)-3-methoxy-1-methyl-3-((3-(4,4,5,5-tetramethyl-1,3,2-dioxaborolan-2-yl)phenyl)ethynyl)pyrrolidin-2-one] to afford (R)-3-((3-(4-aminopyrido[3,2-d]pyrimidin-6-yl)phenyl)ethynyl)-3-methoxy-1-methylpyrrolidin-2-one (50.9 mg, 24%) as a light-yellow solid. MS (ESI): mass calcd. for $C_{21}H_{19}N_5O_2$ 373.2 m/z found 374.2 [M+H]$^+$. $^1$H NMR (400 MHz, DMSO-d$_6$) δ 8.55-8.45 (m, 3H), 8.41 (s, 1H), 8.25 (br s, 1H), 8.13 (d, J=9.0 Hz, 1H), 8.00 (br s, 1H), 7.62-7.54 (m, 2H), 3.51 (s, 3H), 3.41-3.38 (m, 2H), 2.82 (s, 3H), 2.53-2.52 (m, 1H), 2.37-2.29 (m, 1H).

Example 208: (R)-3-((3-(4-Amino-2-(fluoromethyl)pyrido[3,2-d]pyrimidin-6-yl)phenyl)ethynyl)-3-hydroxy-1-(methyl-d$_3$)pyrrolidin-2-one

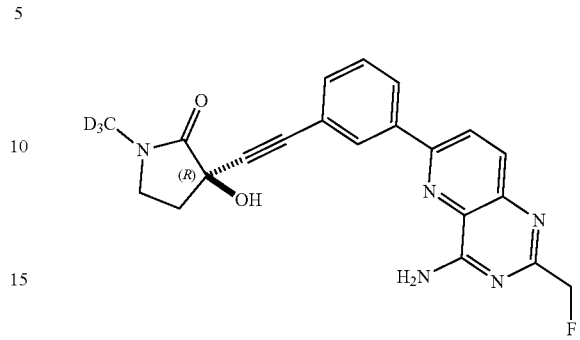

The title compound was prepared using conditions analogous to those described in Example 6 utilizing Intermediate 127 [(R)-3-hydroxy-1-(methyl-d$_3$)-3-((3-(4,4,5,5-tetramethyl-1,3,2-dioxaborolan-2-yl)phenyl)ethynyl)-pyrrolidin-2-one] and Intermediate 96 [6-chloro-2-(fluoromethyl)pyrido[3,2-d]pyrimidin-4-amine] to afford (R)-3-((3-(4-amino-2-(fluoromethyl)pyrido[3,2-d]pyrimidin-6-yl)phenyl)ethynyl)-3-hydroxy-1-(methyl-d$_3$)pyrrolidin-2-one (41 mg, 18%) a tan solid. MS (ESI): mass calcd. for $C_{21}H_{15}D_3FN_5O_2$, 394.2; m/z. found, 395.2 [M+H]$^+$. $^1$H NMR (400 MHz, CD$_3$OD) δ 8.31 (br s, 1H), 8.27 (d, J=8.9 Hz, 1H), 8.18 (dt, J=7.7, 1.6 Hz, 1H), 8.09 (d, J=8.9 Hz, 1H), 7.56-7.42 (m, 2H), 5.40 (s, 1H), 5.28 (s, 1H), 3.59-3.40 (m, 2H), 2.58-2.64 (m, 1H), 2.44-2.25 (m, 1H).

Example 209: (S)-4-[3-(4-Amino-2-methyl-pyrido[3,2-d]pyrimidin-6-yl)phenyl]-2-thiazol-4-yl-but-3-yn-2-ol

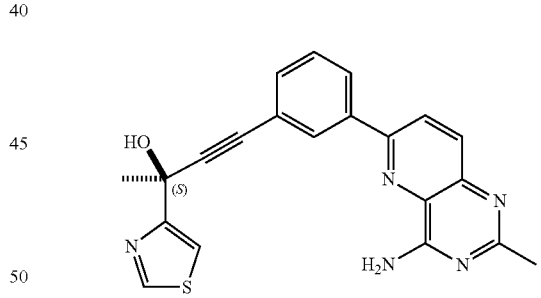

The title compound was prepared using analogous conditions described in Example 1 utilizing Intermediate 110 [6-(3-iodophenyl)-2-methylpyrido[3,2-d]pyrimidin-4-amine] and Intermediate 129 [(S)-2-(thiazol-4-yl)but-3-yn-2-ol] to afford (S)-4-[3-(4-amino-2-methyl-pyrido[3,2-d]pyrimidin-6-yl)phenyl]-2-thiazol-4-yl-but-3-yn-2-ol (24 mg, 18%) as a colorless solid. MS (ESI): mass calcd. for $C_{21}H_{17}N_5OS$, 387.5; m/z. found, 388.1 [M+H]$^+$. $^1$H NMR (500 MHz, DMSO-d$_6$) δ 9.09 (d, J=2.0 Hz, 1H), 8.43-8.36 (m, 3H), 8.06 (s, 1H), 8.03 (d, J=8.8 Hz, 1H), 7.86 (s, 1H), 7.72 (d, J=2.1 Hz, 1H), 7.56-7.50 (m, 2H), 6.34 (s, 1H), 2.46 (s, 3H), 1.87 (s, 3H).

Example 210: (R)-3-((3-(4-Amino-2-ethylpyrido[3,2-d]pyrimidin-6-yl)phenyl)ethynyl)-3-hydroxy-1-methylpyrrolidin-2-one

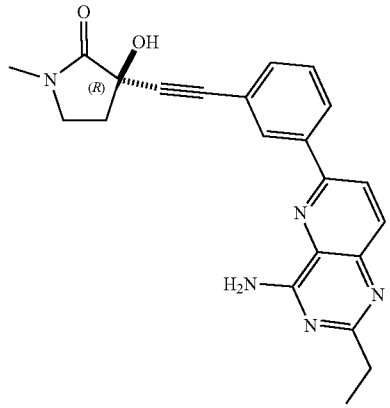

The title compound was prepared using conditions analogous to those described in Example 6 utilizing [6-chloro-2-ethylpyrido[3,2-d]pyrimidin-4-amine] to afford (R)-3-((3-(4-amino-2-ethylpyrido[3,2-d]pyrimidin-6-yl)phenyl)ethynyl)-3-hydroxy-1-methylpyrrolidin-2-one (201 mg, 97%) as an off-white solid. MS (ESI): mass calcd. for $C_{22}H_{21}N_5O_2$, 387.2; m/z. found, 388.2 [M+H]$^+$. $^1$H NMR (400 MHz, CD$_3$OD) δ 8.39-8.34 (m, 1H), 8.30 (d, J=8.9 Hz, 1H), 8.23 (dt, J=7.6, 1.6 Hz, 1H), 8.07 (d, J=8.9 Hz, 1H), 7.58-7.46 (m, 2H), 3.55-3.42 (m, 2H), 2.94 (s, 3H), 2.80 (q, J=7.6 Hz, 2H), 2.57-2.63 (m, 1H), 2.41-2.27 (m, 1H), 1.37 (t, J=7.6 Hz, 3H).

Example 211: (R)-3-((3-(4-Amino-2-hydroxypyrido[3,2-d]pyrimidin-6-yl)phenyl)ethynyl)-3-hydroxy-1-methylpyrrolidin-2-one

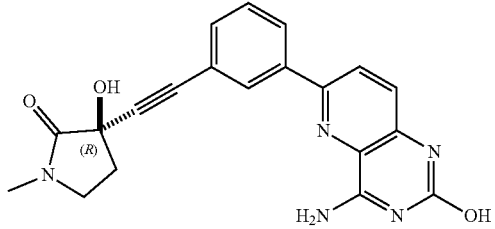

The title compound was prepared using conditions analogous to those described in Example 6 utilizing Intermediate 131 [4-Amino-6-chloropyrido[3,2-d]pyrimidin-2-ol] to afford (R)-3-((3-(4-amino-2-hydroxypyrido[3,2-d]pyrimidin-6-yl)phenyl)ethynyl)-3-hydroxy-1-methylpyrrolidin-2-one (15.4 mg, 8%) as a white solid. MS (ESI): mass calcd. for $C_{20}H_{17}N_5O_3$ 375.1 m/z found 376.0 [M+H]$^+$. $^1$H NMR (400 MHz, DMSO-d$_6$) δ 10.84 (s, 1H), 8.35-8.31 (m, 1H), 8.30-8.26 (m, 2H), 8.18-8.01 (m, 2H), 7.59 (d, J=8.8 Hz, 1H), 7.55-7.45 (m, 2H), 6.49 (s, 1H), 3.39-3.38 (m, 2H), 2.81 (s, 3H), 2.48-2.43 (m, 1H), 2.25-2.16 (m, 1H).

Example 212: (R)-4-[3-(4-Amino-2-methyl-pyrido[3,2-d]pyrimidin-6-yl)phenyl]-2-thiazol-4-yl-but-3-yn-2-ol

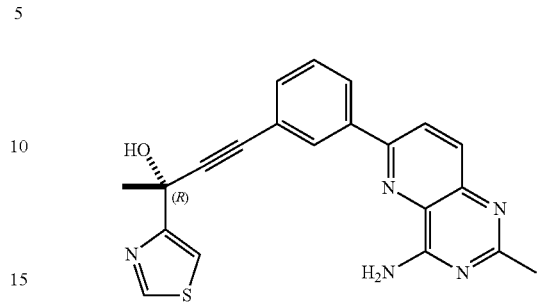

The title compound was prepared using analogous conditions described in Example 1 utilizing Intermediate 110 [6-(3-iodophenyl)-2-methylpyrido[3,2-d]pyrimidin-4-amine] and Intermediate 128 [(R)-2-(thiazol-4-yl)but-3-yn-2-ol] to afford (R)-4-[3-(4-amino-2-methyl-pyrido[3,2-d]pyrimidin-6-yl)phenyl]-2-thiazol-4-yl-but-3-yn-2-ol (22 mg, 16%) as a colorless solid. MS (ESI): mass calcd. for $C_{21}H_{17}N_5OS$, 387.5; m/z. found, 388.1 [M+H]$^+$. $^1$H NMR (500 MHz, DMSO-d$_6$) δ 9.09 (d, J=2.0 Hz, 1H), 8.43-8.36 (m, 3H), 8.06 (s, 1H), 8.03 (d, J=8.8 Hz, 1H), 7.86 (s, 1H), 7.72 (d, J=2.1 Hz, 1H), 7.56-7.50 (m, 2H), 6.34 (s, 1H), 2.46 (s, 3H), 1.87 (s, 3H).

Example 213: (R)-4-(3-(4-Amino-2-methylpyrido[3,2-d]pyrimidin-6-yl)phenyl)-2-(5-methyl-1,3,4-oxadiazol-2-yl)but-3-yn-2-ol

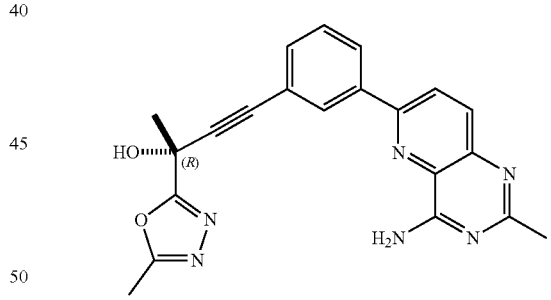

The title compound was prepared using analogous conditions described in Example 1 utilizing Intermediate 110 [6-(3-iodophenyl)-2-methylpyrido[3,2-d]pyrimidin-4-amine] and Intermediate 14 [(R)-2-(5-methyl-1,3,4-oxadiazol-2-yl)but-3-yn-2-ol] to afford (R)-4-(3-(4-amino-2-methylpyrido[3,2-d]pyrimidin-6-yl)phenyl)-2-(5-methyl-1,3,4-oxadiazol-2-yl)but-3-yn-2-ol (75 mg, 46%) as a light grey solid. MS (ESI): mass calcd. for $C_{21}H_{18}N_6O_2$, 386.2; m/z. found, 387.2 [M+H]$^+$. $^1$H NMR (400 MHz, CD$_3$OD) δ 8.39 (br s, 1H), 8.32 (d, J=8.3 Hz, 1H), 8.26 (dt, J=7.8, 1.5 Hz, 1H), 8.04-8.10 (m, 1H), 7.64-7.46 (m, 2H), 2.59 (s, 3H), 2.55 (s, 3H), 2.02 (br s, 3H).

Example 214: (R)-3-((3-(7-Aminothiazolo[4,5-d]pyrimidin-2-yl)phenyl)ethynyl)-3-hydroxy-1-methylpyrrolidin-2-one

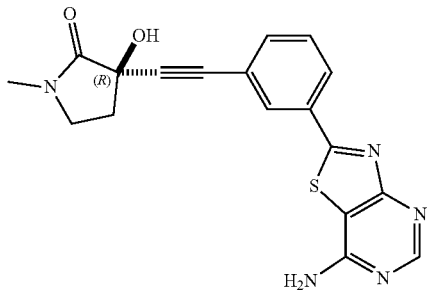

The title compound was prepared using analogous conditions described in Example 1 utilizing Intermediate 132 [2-(3-iodophenyl)thiazolo[4,5-d]pyrimidin-7-amine] to afford (R)-3-((3-(7-aminothiazolo[4,5-d]pyrimidin-2-yl)phenyl)ethynyl)-3-hydroxy-1-methylpyrrolidin-2-one (21.7 mg, 20.4%) as a white solid. MS (ESI): mass calcd. for $C_{18}H_{15}N_5O_2S$ 365.1 m/z found 366.1 [M+H]$^+$. $^1$H NMR (400 MHz, CD$_3$OD) δ 8.46 (s, 1H), 8.23 (s, 1H), 8.16 (d, J=8.1 Hz, 1H), 7.69 (d, J=7.8 Hz, 1H), 7.60-7.52 (m, 1H), 3.54-3.46 (m, 2H), 2.94 (s, 3H), 2.68-2.56 (m, 1H), 2.39-2.28 (m, 1H).

Example 215: (R)-3-((3-(4-Amino-2-methyl-7,8-dihydropyrido[4,3-d]pyrimidin-6(5H)-yl)phenyl)ethynyl)-3-hydroxy-1-methylpyrrolidin-2-one

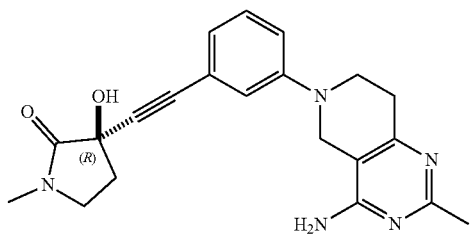

The title compound was prepared using analogous conditions described in Example 1 utilizing Intermediate 133 [6-(3-Iodophenyl)-2-methyl-5,6,7,8-tetrahydropyrido[4,3-d]pyrimidin-4-amine] to afford (R)-3-((3-(4-amino-2-methyl-7,8-dihydropyrido[4,3-d]pyrimidin-6(5H)-yl)phenyl)ethynyl)-3-hydroxy-1-methylpyrrolidin-2-one (21 mg, 20%) as a white solid. MS (ESI): mass calcd. for $C_{21}H_{23}N_5O_2$ 377.2 m/z found 378.1 [M+H]$^+$. $^1$H NMR (400 MHz, DMSO-d$_6$) δ 7.29-7.21 (m, 1H), 7.15-7.11 (m, 1H), 7.10-7.07 (m, 1H), 6.83 (d, J=7.3 Hz, 1H), 6.72 (s, 2H), 6.42 (s, 1H), 3.93 (s, 2H), 3.54 (t, J=5.6 Hz, 2H), 3.33-3.32 (m, 2H), 2.80 (s, 3H), 2.73-2.68 (m, 2H), 2.45-2.38 (m, 1H), 2.27 (s, 3H), 2.22-2.14 (m, 1H).

Example 216: (R)-3-[2-[3-(7-Aminothiazolo[5,4-d]pyrimidin-2-yl)-4-methyl-phenyl]ethynyl]-3-hydroxy-1-(trideuteriomethyl)pyrrolidin-2-one

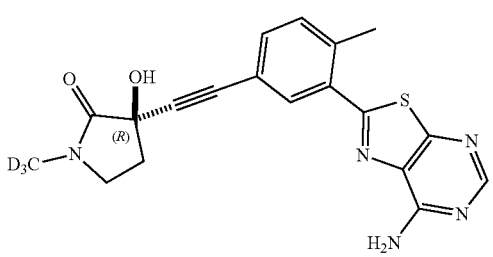

The title compound was prepared using analogous conditions described in Example 10 utilizing Intermediate 45 [(R)-3-ethynyl-3-hydroxy-1-(methyl-d$_3$)pyrrolidin-2-one] to afford (R)-3-[2-[3-(7-aminothiazolo[5,4-d]pyrimidin-2-yl)-4-methyl-phenyl]ethynyl]-3-hydroxy-1-(trideuteriomethyl)pyrrolidin-2-one (21 mg, 22%) as a colorless solid. MS (ESI): mass calcd. for $C_{19}H_{14}D_3N_5O_2S$, 382.4; m/z. found, 383.1 [M+H]$^+$. $^1$H NMR (500 MHz, DMSO-d$_6$) δ 8.33 (s, 1H), 7.84 (d, J=1.7 Hz, 1H), 7.78 (s, 2H), 7.49 (dd, J=7.9, 1.8 Hz, 1H), 7.45 (d, J=8.0 Hz, 1H), 6.48 (s, 1H), 3.38-3.34 (m, 2H), 2.64 (s, 3H), 2.48-2.38 (m, 1H), 2.23-2.12 (m, 1H).

Example 217: (R)-4-[3-(7-Aminothiazolo[5,4-d]pyrimidin-2-yl)-4-methyl-phenyl]-2-(5-methylisoxazol-3-yl)but-3-yn-2-ol

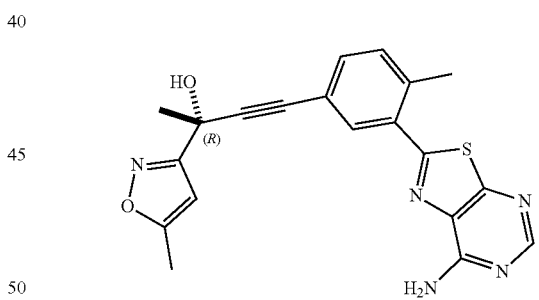

The title compound was prepared using analogous conditions described in Example 10 utilizing Intermediate 32 [(R)-2-(5-methylisoxazol-3-yl)but-3-yn-2-ol] to afford (R)-4-[3-(7-aminothiazolo[5,4-d]pyrimidin-2-yl)-4-methyl-phenyl]-2-(5-methylisoxazol-3-yl)but-3-yn-2-ol (54 mg, 56%) as a colorless solid. MS (ESI): mass calcd. for $C_{20}H_{17}N_5O_2S$, 391.5; m/z. found, 392.1 [M+H]$^+$. $^1$H NMR (500 MHz, DMSO-d$_6$) δ 8.33 (s, 1H), 7.83 (d, J=1.8 Hz, 1H), 7.78 (s, 2H), 7.50 (dd, J=7.8, 1.8 Hz, 1H), 7.45 (d, J=7.9 Hz, 1H), 6.54 (s, 1H), 6.41-6.27 (m, 1H), 2.64 (s, 3H), 2.41 (d, J=0.9 Hz, 3H), 1.80 (s, 3H).

Example 218: (R)-6-[3-[2-(3-Hydroxy-1-methyl-2-oxo-pyrrolidin-3-yl)ethynyl]phenyl]-7H-imidazo[1,5-a]pyrazin-8-one

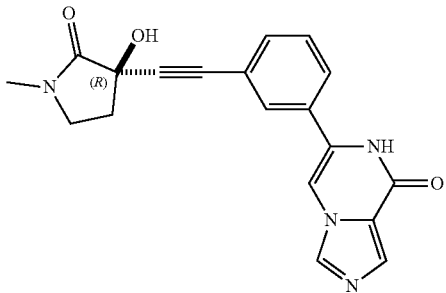

The title compound was prepared using analogous conditions described in Example 1 utilizing Intermediate 134 [5-(3-iodophenyl)-1-methyl-1H-pyrazolo[4,3-b]pyridin-3-amine] to afford (R)-6-[3-[2-(3-hydroxy-1-methyl-2-oxo-pyrrolidin-3-yl)ethynyl]phenyl]-7H-imidazo[1,5-a]pyrazin-8-one (10 mg, 10%) as a colorless solid. MS (ESI): mass calcd. for $C_{19}H_{16}N_4O_3$, 348.4; m/z. found, 349.2 $[M+H]^+$. $^1$H NMR (500 MHz, DMSO-$d_6$) δ 10.34 (s, 1H), 8.25 (d, J=0.8 Hz, 1H), 7.88 (d, J=0.8 Hz, 1H), 7.78-7.75 (m, 2H), 7.72-7.67 (m, 1H), 7.52-7.43 (m, 2H), 6.49 (s, 1H), 3.38-3.34 (m, 2H), 2.81 (s, 3H), 2.48-2.40 (m, 1H), 2.24-2.14 (m, 1H).

Example 219: (R)-3-((3-(8-Amino-1,5-naphthyridin-2-yl)phenyl)ethynyl)-3-hydroxy-1-methylpyrrolidin-2-one

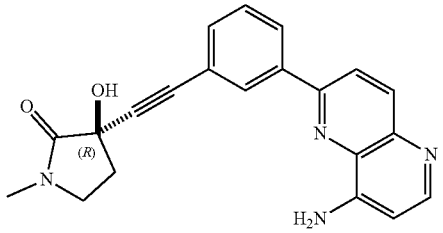

Step A: Intermediate 135 tert-Butyl (6-(3-bromophenyl)-1,5-naphthyridin-4-yl)carbamate (73 mg, 0.18 mmol) was added to a solution of (R)-3-ethynyl-3-hydroxy-1-methylpyrrolidin-2-one (32.8 mg, 0.24 mmol), TEA (1 mL), and DMF (1 mL). The mixture was sparged with Ar for 5 minutes and then treated with Pd(PPh$_3$)$_2$Cl$_2$ (13 mg, 0.02 mmol) and CuI (6.9 mg, 0.04 mmol). The mixture was sparged with Ar for another 5 min and then heated at 100° C. for 2 h before it was allowed to cool to rt. The suspension was filtered through a pad of diatomaceous earth, such as Celite® and the pad washed with methanol (20 mL). The filtrate was concentrated to dryness and the residue was purified by FCC (1:0 to 0:1 gradient, petroleum ether/ethyl acetate, followed by 1:0 to 4:1 gradient, dichloromethane/methanol) to afford tert-butyl-(R)-(6-(3-((3-hydroxy-1-methyl-2-oxopyrrolidin-3-yl)ethynyl)phenyl)-1,5-naphthyridin-4-yl)carbamate (150 mg) as a brown solid. MS (ESI): mass calcd. for $C_{26}H_{26}N_4O_4$ 458.2 m/z found 459.2 $[M+H]^+$.

Step B: A flask was charged with HCl (0.1 mL, 4 M in MeOH), tert-butyl (R)-(6-(3-((3-hydroxy-1-methyl-2-oxopyrrolidin-3-yl)ethynyl)phenyl)-1,5-naphthyridin-4-yl)carbamate (140 mg) and HCOOH (2 mL). The mixture stirred at rt for 2 h. The reaction mixture was concentrated to dryness and the resulting residue was purified by preparative reverse phase HPLC (Xtimate C18 250×50 mm, 10 μm (eluent: 18% to 48% (v/v) CH$_3$CN and H$_2$O with 0.04% NH$_3$·H$_2$O and 10 mM NH$_4$HCO$_3$) to afford (R)-3-((3-(8-amino-1,5-naphthyridin-2-yl)phenyl)ethynyl)-3-hydroxy-1-methylpyrrolidin-2-one (2.0 mg) as a brown solid. MS (ESI): mass calcd. for $C_{21}H_{18}N_4O_2$ 358.1 m/z found 359.1 $[M+H]^+$. $^1$H NMR (400 MHz, DMSO-$d_6$) δ 8.49-8.41 (m, 2H), 8.39 (s, 1H), 8.37-8.32 (m, 1H), 8.30-8.14 (m, 1H), 7.59-7.51 (m, 2H), 7.26 (br s, 2H), 6.80 (s, 1H), 6.50 (s, 1H), 3.41-3.39 (m, 1H), 3.39-3.38 (m, 1H), 2.82 (s, 3H), 2.48-2.46 (m, 1H), 2.26-2.18 (m, 1H).

Example 220: (R)-3-((3-(4-Amino-7,8-dihydropyrido[4,3-d]pyrimidin-6(5H)-yl)-4-methylphenyl)ethynyl)-3-hydroxy-1-methylpyrrolidin-2-one

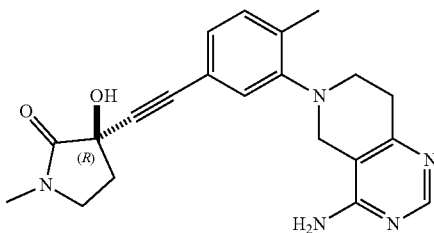

The title compound was prepared using analogous conditions described in Example 1 utilizing Intermediate 136 [6-(5-iodo-2-methylphenyl)-5,6,7,8-tetrahydropyrido[4,3-d]pyrimidin-4-amine] to afford (R)-3-((3-(4-amino-7,8-dihydropyrido[4,3-d]pyrimidin-6(5H)-yl)-4-methylphenyl)ethynyl)-3-hydroxy-1-methylpyrrolidin-2-one (10.6 mg, 14%) as a gray solid. MS (ESI): mass calcd. for $C_{21}H_{23}N_5O_2$ 377.2 m/z found 378.2 $[M+H]^+$. $^1$H NMR (400 MHz, DMSO-$d_6$) δ 8.19 (s, 1H), 7.25-7.16 (m, 2H), 7.09-7.02 (m, 1H), 6.69 (br. s, 2H), 6.40 (s, 1H), 3.75 (s, 2H), 3.33-3.32 (m, 2H), 3.14 (t, J=5.6 Hz, 2H), 2.79 (s, 3H), 2.80-2.72 (m, 2H), 2.44-2.37 (m, 1H), 2.28 (s, 3H), 2.22-2.12 (m, 1H).

Example 221: (R)-6-(3-((3-Hydroxy-1-methyl-2-oxopyrrolidin-3-yl)ethynyl)phenyl)pyrido[3,2-d]pyrimidin-4(3H)-one

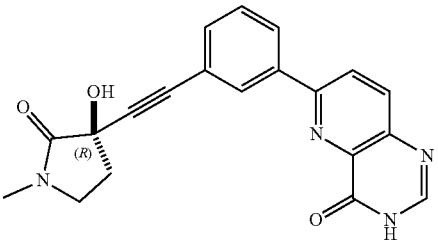

A sealable vial was charged with Intermediate 137 [6-bromopyrido[3,2-d]pyrimidin-4(3H)-one (90 mg, 0.39 mmol)], Intermediate 4 [(R)-3-hydroxy-1-methyl-3-((3-(4,4,5,5-tetramethyl-1,3,2-dioxaborolan-2-yl)phenyl)ethynyl)pyrrolidin-2-one (130 mg, 0.38 mmol)], K$_3$PO$_4$ (246 mg, 1.16 mmol), 1,4-dioxane (12 mL), and H$_2$O (3 mL). The mixture was sparged with Ar for 5 min and then treated with Pd(dtbpf)Cl$_2$ (28 mg, 0.043 mmol). The mixture was sparged with Ar for another 5 min and then subjected to microwave irradiation at 100° C. in for 1 h. The mixture was then concentrated to dryness. The resulting residue was purified by FCC (1:0 to 0:1 gradient, petroleum ether/ethyl acetate) followed by preparative reverse phase HPLC (DuraShell 150×25 mm, 5 μm (eluent: 9% to 37% (v/v) CH$_3$CN and H$_2$O with 0.2% HCOOH) to afford (R)-6-(3-((3-hydroxy-1-methyl-2-oxopyrrolidin-3-yl)ethynyl)phenyl)pyrido[3,2-d]pyrimidin-4(3H)-one (12.5 mg, 9%) as a light yellow solid. MS (ESI): mass calcd. for C$_{20}$H$_{16}$N$_4$O$_3$ 360.1 m/z found 361.2 [M+H]$^+$. $^1$H NMR (400 MHz, DMSO-d$_6$) δ 12.60 (br s., 1H), 8.43 (d, J=8.8 Hz, 1H), 8.29-8.27 (m, 1H), 8.21-8.18 (m, 1H), 8.16-8.12 (m, 2H), 7.57-7.49 (m, 2H), 6.53 (s, 1H), 3.36-3.33 (m, 2H), 2.78 (s, 3H), 2.43-2.41 (m, 1H), 2.21-2.13 (m, 1H).

Example 222: (R)-3-Hydroxy-1-methyl-3-((3-(4-(pyrrolidin-1-yl)pyrido[3,2-d]pyrimidin-6-yl)phenyl)ethynyl)pyrrolidin-2-one

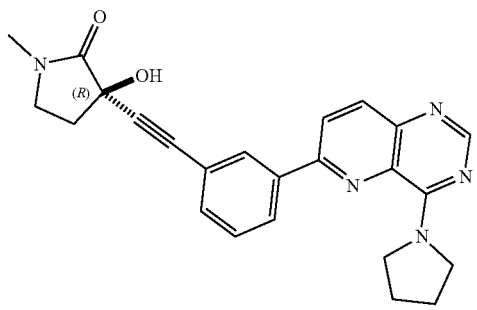

The title compound was prepared using conditions analogous to those described in Example 25 utilizing Intermediate 138 [6-chloro-4-(pyrrolidin-1-yl)pyrido[3,2-d]pyrimidine] to afford (R)-3-hydroxy-1-methyl-3-((3-(4-(pyrrolidin-1-yl)pyrido[3,2-d]pyrimidin-6-yl)phenyl)ethynyl)pyrrolidin-2-one (224, 89%) as a white solid. MS (ESI): mass calcd. for C$_{24}$H$_{23}$N$_5$O$_2$, 413.2; m/z. found, 414.1 [M+H]$^+$. $^1$H NMR (500 MHz, CDCl$_3$) δ 8.58 (s, 1H), 8.14 (d, J=8.8 Hz, 1H), 8.00-7.93 (m, 3H), 7.47 (dt, J=7.7, 1.4 Hz, 1H), 7.40 (td, J=7.7, 0.6 Hz, 1H), 4.38-4.50 (m, 3H), 3.84-3.90 (m, 2H), 3.48-4.52 (m, 1H), 3.38-3.42 (m, 1H), 2.98 (s, 3H), 2.64-2.70 (m, 1H), 2.38-2.42 (m, 1H), 2.10-2.16 (m, 2H), 1.98-2.08 (m, 2H).

Example 223: ((R)-3-Hydroxy-1-methyl-3-((3-(pyrido[3,2-d]pyrimidin-6-yl)phenyl)ethynyl)pyrrolidin-2-one

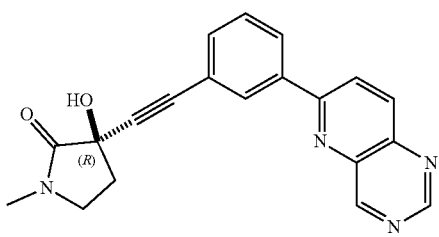

The title compound was prepared using conditions analogous to those described in Example 1 utilizing 6-(3-Iodophenyl)pyrido[3,2-d]pyrimidine to afford ((R)-3-hydroxy-1-methyl-3-((3-(pyrido[3,2-d]pyrimidin-6-yl)phenyl)ethynyl)pyrrolidin-2-one (52.3 mg, 42%) as a white solid. MS (ESI): mass calcd. for C$_{20}$H$_{16}$N$_4$O$_2$ 344.1 m/z found 345.1 [M+H]$^+$. $^1$H NMR (400 MHz, DMSO-d$_6$) δ 9.77 (s, 1H), 9.43 (s, 1H), 8.72 (d, J=9.0 Hz, 1H), 8.56 (d, J=9.0 Hz, 1H), 8.40 (s, 1H), 8.37-8.32 (m, 1H), 7.65-7.61 (m, 2H), 6.56 (s, 1H), 3.41-3.38 (m, 2H), 2.83 (s, 3H), 2.49-2.44 (m, 1H), 2.27-2.17 (m, 1H).

Example 224: (R)-3-((3-(4-Amino-5,7,8,9-tetrahydro-6H-pyrimido[5,4-c]azepin-6-yl)phenyl)ethynyl)-3-hydroxy-1-methylpyrrolidin-2-one

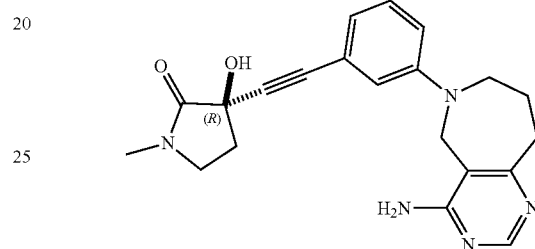

The title compound was prepared using conditions analogous to those described in Example 1 utilizing Intermediate 139 [6-(3-Iodophenyl)-6,7,8,9-tetrahydro-5H-pyrimido[5,4-c]azepin-4-amine] to afford (R)-3-((3-(4-amino-5,7,8,9-tetrahydro-6H-pyrimido[5,4-c]azepin-6-yl)phenyl)ethynyl)-3-hydroxy-1-methylpyrrolidin-2-one (27.5 mg, 43%) as a white solid. MS (ESI): mass calcd. for C$_{21}$H$_{23}$N$_5$O$_2$ 377.2 m/z. found 378.2 [M+1]$^+$. $^1$H NMR (400 MHz, DMSO-d$_6$) δ 8.05 (s, 1H), 7.10-7.00 (m, 1H), 6.85 (s, 2H), 6.74-6.66 (m, 2H), 6.56 (d, J=7.3 Hz, 1H), 6.35 (s, 1H), 4.44 (s, 2H), 3.76-3.62 (m, 2H), 3.29-3.25 (m, 2H), 2.86-2.78 (m, 2H), 2.75 (s, 3H), 2.39-2.31 (m, 1H), 2.15-2.06 (m, 1H), 1.81-1.71 (m, 2H).

Example 225: (R)-3-Hydroxy-1-methyl-3-((3-(4-(piperidin-1-yl)pyrido[3,2-d]pyrimidin-6-yl)phenyl)ethynyl)pyrrolidin-2-one

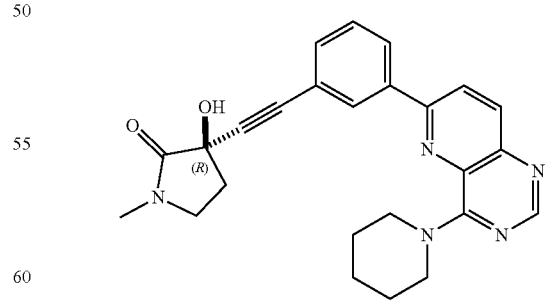

The title compound was prepared using conditions analogous to those described in Example 25 utilizing Intermediate 140 [6-chloro-4-(piperidin-1-yl)pyrido[3,2-d]pyrimidine] to afford (R)-3-hydroxy-1-methyl-3-((3-(4-(piperidin-1-yl)pyrido[3,2-d]pyrimidin-6-yl)phenyl)ethynyl)pyrrolidin-2- one (315 mg, 92%) as a amber solid. MS (ESI): mass calcd. for $C_{25}H_{25}N_5O_2$, 427.2; m/z. found, 428.1 [M+H]+. 1H NMR (500 MHz, CD3OD) δ 8.41 (s, 1H), 8.26 (d, J=8.8 Hz, 1H), 8.19 (t, J=1.8 Hz, 1H), 8.12-8.05 (m, 2H), 7.57-7.44 (m, 2H), 4.47 (br s, 4H), 3.56-3.43 (m, 2H), 2.93 (s, 3H), 2.57-2.62 (m, 1H), 2.28-2.38 (m, 1H), 1.84 (br s, 6H).

Example 226: (R)-3-((3-(4-(3,3-Dimethylazetidin-1-yl)pyrido[3,2-d]pyrimidin-6-yl)phenyl)ethynyl)-3-hydroxy-1-methylpyrrolidin-2-one

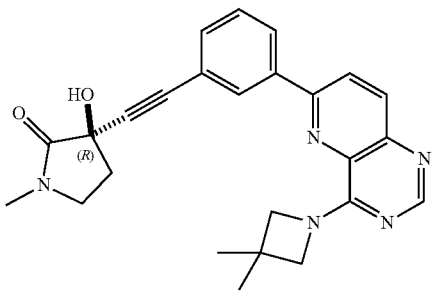

The title compound was prepared using conditions analogous to those described in Example 25 utilizing Intermediate 141 [6-chloro-4-(3,3-dimethylazetidin-1-yl)pyrido[3,2-d]pyrimidine] to afford (R)-3-((3-(4-(3,3-dimethylazetidin-1-yl)pyrido[3,2-d]pyrimidin-6-yl)phenyl)ethynyl)-3-hydroxy-1-methylpyrrolidin-2-one (128 mg, 72%) as a white solid. MS (ESI): mass calcd. for $C_{25}H_{25}N_5O_2$, 427.2; m/z. found, 428.1 [M+H]+. 1H NMR (500 MHz, CD3OD) δ 8.34 (s, 1H), 8.24 (d, J=8.8 Hz, 1H), 8.16-8.13 (m, 1H), 8.08-8.14 (m, 1H), 8.04 (d, J=8.8 Hz, 1H), 7.57-7.41 (m, 2H), 4.71 (s, 2H), 4.06 (s, 2H), 3.53-3.43 (m, 2H), 2.94 (s, 3H), 2.58-2.62 (m, 1H), 2.30-2.36 (m, 1H), 1.43 (s, 6H).

Example 227: (R)-3-((3-(4-(Ethylamino)pyrido[3,2-d]pyrimidin-6-yl)phenyl)ethynyl)-3-hydroxy-1-methylpyrrolidin-2-one

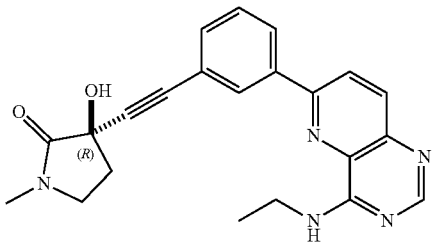

The title compound was prepared using conditions analogous to those described in Example 25 utilizing Intermediate 142 [6-chloro-N-ethylpyrido[3,2-d]pyrimidin-4-amine] to afford (R)-3-((3-(4-(ethylamino)pyrido[3,2-d]pyrimidin-6-yl)phenyl)ethynyl)-3-hydroxy-1-methylpyrrolidin-2-one (182 mg, 94%) as a white solid. MS (ESI): mass calcd. for $C_{22}H_{21}N_5O_2$, 387.2; m/z. found, 388.2 [M+H]+. 1H NMR (500 MHz, CD3OD) δ 8.41 (s, 1H), 8.39-8.34 (m, 1H), 8.27 (d, J=8.8 Hz, 1H), 8.19-8.24 (m, 1H), 8.06 (d, J=8.8 Hz, 1H), 7.59-7.41 (m, 2H), 3.70 (q, J=7.2 Hz, 2H), 3.56-3.42 (m, 2H), 2.94 (s, 3H), 2.58-2.64 (m, 1H), 2.30-2.36 (m, 1H), 1.34 (t, J=7.2 Hz, 3H).

Example 228: (R)-3-Hydroxy-3-((3-(4-(3-hydroxyazetidin-1-yl)pyrido[3,2-d]pyrimidin-6-yl)phenyl)ethynyl)-1-methylpyrrolidin-2-one

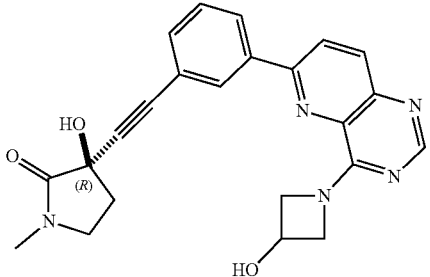

The title compound was prepared using conditions analogous to those described in Example 25 utilizing Intermediate 143 [1-(6-chloropyrido[3,2-d]pyrimidin-4-yl)azetidin-3-ol] to afford (R)-3-hydroxy-3-((3-(4-(3-hydroxyazetidin-1-yl)pyrido[3,2-d]pyrimidin-6-yl)phenyl)ethynyl)-1-methylpyrrolidin-2-one (51 mg, 57%) as a white solid. MS (ESI): mass calcd. for $C_{23}H_{21}N_5O_3$, 415.2; m/z. found, 416.1 [M+H]+. 1H NMR (500 MHz, CD3OD) δ 8.32 (s, 1H), 8.19 (d, J=8.7 Hz, 1H), 8.09 (br s, 1H), 8.06-7.96 (m, 2H), 7.54-7.42 (m, 2H), 5.15-5.22 (m, 1H), 4.82-4.67 (m, 2H), 4.55-4.60 (m, 1H), 4.19-4.06 (m, 1H), 3.56-3.39 (m, 2H), 2.94 (s, 3H), 2.58-2.64 (m, 1H), 2.28-2.36 (m, 1H).

Example 229: (R)-3-Hydroxy-1-methyl-3-((3-(4-(oxetan-3-ylamino)pyrido[3,2-d]pyrimidin-6-yl)phenyl)ethynyl)pyrrolidin-2-one

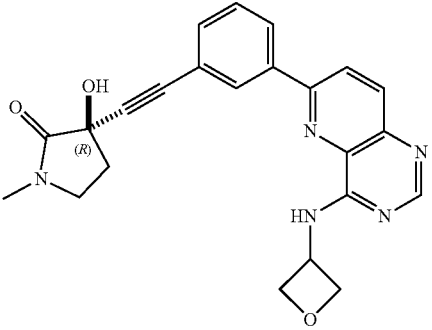

The title compound was prepared using conditions analogous to those described in Example 25 utilizing Intermediate 144 [6-chloro-N-(oxetan-3-yl)pyrido[3,2-d]pyrimidin-4-amine] to afford (R)-3-hydroxy-1-methyl-3-((3-(4-(oxetan-3-ylamino)pyrido[3,2-d]pyrimidin-6-yl)phenyl)ethynyl)pyrrolidin-2-one (68 mg, 77%) as a white solid. MS (ESI): mass calcd. for $C_{23}H_{21}N_5O_3$, 415.2; m/z. found, 416.1 [M+H]+. 1H NMR (500 MHz, CD3OD) δ 8.40 (s, 1H), 8.37-8.32 (m, 1H), 8.23-8.16 (m, 2H), 8.03 (d, J=8.9 Hz, 1H), 7.56-7.40 (m, 2H), 5.29-5.35 (m, 1H), 5.00 (t, J=7.1 Hz, 2H), 4.88 (t, J=6.7 Hz, 2H), 3.55-3.44 (m, 2H), 2.94 (s, 3H), 2.58-2.62 (m, 1H), 2.34 (m, 1H).

Example 230: (R)-3-Hydroxy-3-((3-(4-(3-methoxyazetidin-1-yl)pyrido[3,2-d]pyrimidin-6-yl)phenyl)ethynyl)-1-methylpyrrolidin-2-one

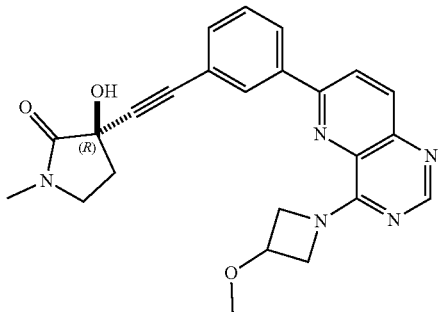

The title compound was prepared using conditions analogous to those described in Example 25 utilizing Intermediate 145 [6-chloro-4-(3-methoxyazetidin-1-yl)pyrido[3,2-d]pyrimidine] to afford (R)-3-hydroxy-3-((3-(4-(3-methoxyazetidin-1-yl)pyrido[3,2-d]pyrimidin-6-yl)phenyl)ethynyl)-1-methylpyrrolidin-2-one (111 mg, 86%) as a white solid. MS (ESI): mass calcd. for $C_{24}H_{23}N_5O_3$, 429.2; m/z. found, 430.2 [M+H]$^+$. $^1$H NMR (500 MHz, CDCl$_3$) δ 8.57 (s, 1H), 8.10-8.15 (m, 1H), 8.07-7.93 (m, 3H), 7.47-7.52 (m, 1H), 7.41 (t, J=8.0 Hz, 1H), 5.24-5.10 (m, 1H), 4.94-4.78 (m, 1H), 4.52-4.60 (m, 1H), 4.40-4.45 (m, 1H), 4.25-4.30 (m, 1H), 4.05-4.10 (m, 1H), 3.57-3.44 (m, 1H), 3.42 (s, 4H), 2.97 (s, 3H), 2.64-2.69 (m, 1H), 2.38-2.44 (m, 1H).

Example 231: (S)-3-((3-(4-(Azetidin-1-yl)pyrido[3,2-d]pyrimidin-6-yl)phenyl)ethynyl)-3-hydroxy-1-methylpyrrolidin-2-one

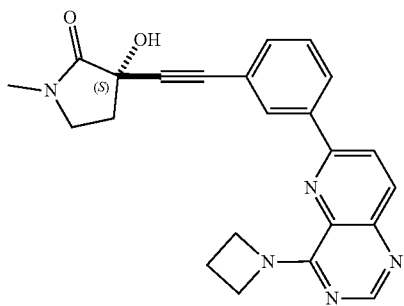

The title compound was prepared using analogous conditions described in Example 25 using 4-(azetidin-1-yl)-6-chloropyrido[3,2-d]pyrimidine and (S)-3-hydroxy-1-methyl-3-((3-(4,4,5,5-tetramethyl-1,3,2-dioxaborolan-2-yl)phenyl)ethynyl)pyrrolidin-2-one to afford (S)-3-((3-(4-(azetidin-1-yl)pyrido[3,2-d]pyrimidin-6-yl)phenyl)ethynyl)-3-hydroxy-1-methylpyrrolidin-2-one (172 mg, 95%) as a yellow solid. MS (ESI): mass calcd. For $C_{23}H_{21}N_5O_2$, 399.45; m/z. found, 400.05 [M+H]$^+$. $^1$H NMR (400 MHz, CD$_3$OD) δ 8.29 (s, 1H), 8.13 (d, J=8.9 Hz, 1H), 8.04 (t, J=1.6 Hz, 1H), 7.99 (dt, J=7.7, 1.5 Hz, 1H), 7.94 (d, J=8.9 Hz, 1H), 7.56-7.39 (m, 2H), 4.88 (t, J=7.7 Hz, 2H), 4.33 (t, J=7.8 Hz, 2H), 3.55-3.42 (m, 2H), 2.95 (s, 3H), 2.58-2.62 (m, 1H), 2.56-2.45 (m, 2H), 2.30-2.38 (m, 1H).

Example 232: (R)-3-((3-(4-(3,3-Difluoroazetidin-1-yl)pyrido[3,2-d]pyrimidin-6-yl)phenyl)ethynyl)-3-hydroxy-1-methylpyrrolidin-2-one

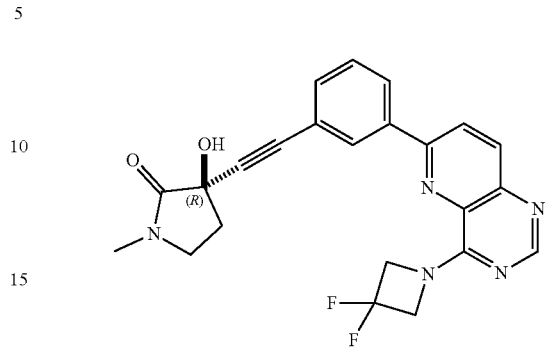

The title compound was prepared using analogous conditions described in Example 25 using Intermediate 146 [6-chloro-4-(3,3-difluoroazetidin-1-yl)pyrido[3,2-d]pyrimidine] to afford (R)-3-((3-(4-(3,3-difluoroazetidin-1-yl)pyrido[3,2-d]pyrimidin-6-yl)phenyl)ethynyl)-3-hydroxy-1-methylpyrrolidin-2-one (128 mg, 75%) as a white solid. MS (ESI): mass calcd. for $C_{23}H_{19}F_2N_5O_2$, 435.2; m/z. found, 436.1 [M+H]$^+$. $^1$H NMR (500 MHz, CDCl$_3$) δ 8.64 (s, 1H), 8.20 (d, J=8.8 Hz, 1H), 8.05 (d, J=8.9 Hz, 1H), 8.00-7.92 (m, 2H), 7.48-7.53 (m, 1H), 7.48-7.39 (m, 1H), 5.27 (br s, 2H), 4.72 (br s, 2H), 4.10 (s, 1H), 3.50-3.55 (m, 1H), 3.40-3.44 (m, 1H), 2.98 (s, 3H), 2.65-2.70 (m, 1H), 2.38-2.42 (m, 1H).

Example 233: (R)-3-((3-(8-(Azetidin-1-yl)-1,7-naphthyridin-2-yl)phenyl)ethynyl)-3-hydroxy-1-methylpyrrolidin-2-one

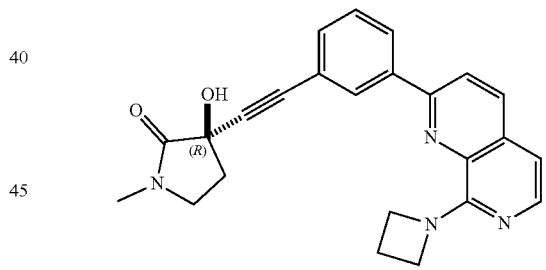

A microwave vial was charged with Intermediate 148 [8-(azetidin-1-yl)-2-(3-bromophenyl)-1,7-naphthyridine (100 mg, 0.29 mmol)], Intermediate 2 [(R)-3-ethynyl-3-hydroxy-1-methylpyrrolidin-2-one (100 mg, 0.72 mmol)], Et$_3$N (5 mL), and DMF (5 mL). The mixture was sparged with Ar for 5 min and then treated with dichlorobis(tricyclohexylphosphine)palladium(II) (40.0 mg, 0.03 mmol) and CuI (20.0 mg, 0.11 mmol). The mixture was sparged with Ar for another 5 min and then subjected to microwave irradiation at 120° C. in for 2 h. After the reaction mixture was allowed to cool to rt, the suspension was filtered through a pad of diatomaceous earth, such as Celite® and the pad washed with ethyl acetate (10 mL). The combined organic extracts was concentrated to dryness and resulting residue was purified by FCC (1:0 to 0:1 gradient, petroleum ether/ ethyl acetate then 1:0, to 5:1 gradient, ethyl acetate/methanol). Further purification by preparative reverse phase HPLC (Xtimate C18 250×50 mm, 10 μm (eluent: 35% to 65% (v/v) CH₃CN and H₂O with 0.04% NH₃H₂O+10 mM NH₄HCO₃) to afford (R)-3-((3-(8-(azetidin-1-yl)-1,7-naphthyridin-2-yl)phenyl)ethynyl)-3-hydroxy-1-methylpyrrolidin-2-one (60.6 mg, 51%) as a yellow solid. MS (ESI): mass calcd. for C₂₄H₂₂N₄O₂ 398.2 m/z found 399.2 [M+H]⁺. ¹H NMR (400 MHz, DMSO-d₆) δ 8.33-8.28 (m, 1H), 8.26-8.19 (m, 3H), 7.96 (d, J=5.5 Hz, 1H), 7.62-7.51 (m, 2H), 6.98 (d, J=5.5 Hz, 1H), 6.53 (s, 1H), 4.55 (s, 4H), 3.42-3.37 (m, 2H), 2.82 (s, 3H), 2.48-2.46 (m, 1H), 2.46-2.41 (m, 2H), 2.26-2.17 (m, 1H).

Example 234: (R)-3-((3-(1-(Azetidin-1-yl)isoquinolin-7-yl)phenyl)ethynyl)-3-hydroxy-1-methylpyrrolidin-2-one

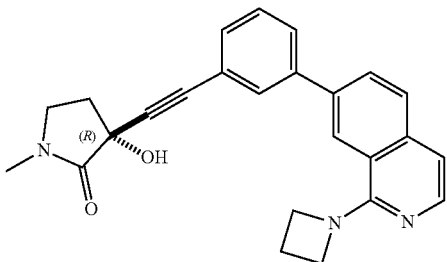

The title compound was prepared using analogous conditions described in Example 221 utilizing Intermediate 149 [1-(azetidin-1-yl)-7-bromoisoquinoline] to afford (R)-3-((3-(1-(azetidin-1-yl)isoquinolin-7-yl)phenyl)ethynyl)-3-hydroxy-1-methylpyrrolidin-2-one (65.7 mg, 43%) as a white solid. MS (ESI): mass calcd. for C₂₅H₂₃N₃O₂ 397.2 m/z found 398.2 [M+H]⁺. ¹H NMR (400 MHz, DMSO-d₆) δ 8.13 (s, 1H), 8.01-7.94 (m, 2H), 7.90-7.84 (m, 1H), 7.84-7.75 (m, 2H), 7.57-7.42 (m, 2H), 7.09 (d, J=5.5 Hz, 1H), 6.51 (s, 1H), 4.43 (t, J=7.5 Hz, 4H), 3.39-3.37 (m, 2H), 2.81 (s, 3H), 2.45-2.43 (m, 1H), 2.40-2.32 (m, 2H), 2.24-2.16 (m, 1H).

Example 235: (R)-3-((3-(4-(Azetidin-1-yl)quinolin-6-yl)phenyl)ethynyl)-3-hydroxy-1-methylpyrrolidin-2-one

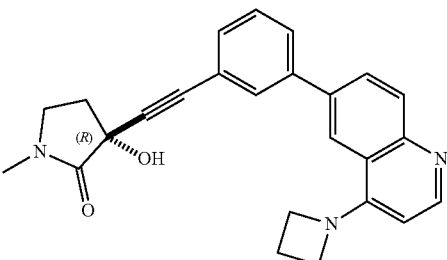

The title compound was prepared using analogous conditions described in Example 221 utilizing Intermediate 150 [4-(azetidin-1-yl)-6-bromoquinoline] to afford (R)-3-((3-(4-(azetidin-1-yl)quinolin-6-yl)phenyl)ethynyl)-3-hydroxy-1-methylpyrrolidin-2-one (12.9 mg, 8%) as a white solid. MS (ESI): mass calcd. for C₂₅H₂₃N₃O₂ 397.2 m/z found 398.2 [M+H]⁺. ¹H NMR (400 MHz, DMSO-d₆) δ 8.42 (d, J=5.3 Hz, 1H), 8.16-8.12 (m, 1H), 7.97-7.87 (m, 2H), 7.81 (d, J=8.0 Hz, 1H), 7.76 (s, 1H), 7.56-7.50 (m, 1H), 7.47-7.42 (m, 1H), 6.51 (s, 1H), 6.29 (d, J=5.3 Hz, 1H), 4.43 (t, J=7.5 Hz, 4H), 3.40-3.36 (m, 2H), 2.81 (s, 3H), 2.49-2.47 (m, 1H), 2.46-2.41 (m, 2H), 2.24-2.16 (m, 1H).

Example 236: (R)-3-((3-(4-(Cyclobutylamino)pyrido[3,2-d]pyrimidin-6-yl)phenyl)ethynyl)-3-hydroxy-1-methylpyrrolidin-2-one

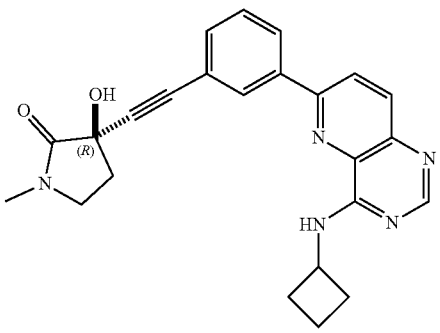

The title compound was prepared using analogous conditions described in Example 25 using Intermediate 151 [6-chloro-N-cyclobutylpyrido[3,2-d]pyrimidin-4-amine] to afford (R)-3-((3-(4-(cyclobutylamino)pyrido[3,2-d]pyrimidin-6-yl)phenyl)ethynyl)-3-hydroxy-1-methylpyrrolidin-2-one (178 mg, 97%) as a white solid. MS (ESI): mass calcd. for C₂₄H₂₃N₅O₂, 413.2; m/z. found, 414.2 [M+H]⁺. ¹H NMR (500 MHz, CD₃OD) δ 8.42 (s, 1H), 8.41-8.36 (m, 1H), 8.29 (d, J=8.8 Hz, 1H), 8.24 (dt, J=7.8, 1.3 Hz, 1H), 8.08 (d, J=8.8 Hz, 1H), 7.61-7.44 (m, 2H), 4.82-4.75 (m, 1H), 3.54-3.42 (m, 2H), 2.94 (s, 3H), 2.58-2.64 (m, 1H), 2.44-2.50 (m, 2H), 2.38-2.22 (m, 3H), 1.78-1.82 (m, 2H).

Example 237: (R)-3-((3-(4-Amino-2-methylpyrido[3,2-d]pyrimidin-6-yl)-4-(trifluoromethoxy)phenyl)ethynyl)-3-hydroxy-1-methylpyrrolidin-2-one

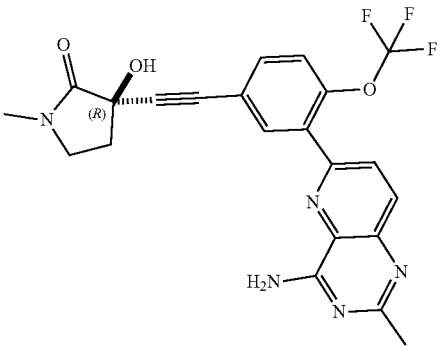

The title compound was prepared using analogous conditions described in Example 6 utilizing Intermediate 127 [(R)-3-hydroxy-1-methyl-3-((3-(4,4,5,5-tetramethyl-1,3,2-dioxaborolan-2-yl)-4-(trifluoromethoxy)phenyl)ethynyl)pyrrolidin-2-one] to afford (R)-3-((3-(4-amino-2-methylpyrido[3,2-d]pyrimidin-6-yl)-4-(trifluoromethoxy)phenyl)ethynyl)-3-hydroxy-1-methylpyrrolidin-2-one (50 mg, 35%) as a white solid. MS (ESI): mass calcd. for C₂₂H₁₈F₃N₅O₃, 457.4; m/z. found, 458.4 [M+H]⁺. ¹H NMR (400 MHz, DMSO-d$_6$) δ 8.09 (d, J=8.8 Hz, 1H), 8.05-8.00 (m, 2H), 7.93-7.83 (m, 2H), 7.66 (dd, J=8.5, 2.2 Hz, 1H), 7.60-7.52 (m, 1H), 6.52 (s, 1H), 3.38-3.33 (m, 2H), 2.80 (s, 3H), 2.48-2.42 (m, 4H), 2.23-2.17 (m, 1H).

Example 238: (R)—N-(6-(3-((3-Hydroxy-1-methyl-2-oxopyrrolidin-3-yl)ethynyl)phenyl)pyrido[3,2-d]pyrimidin-4-yl)acetamide

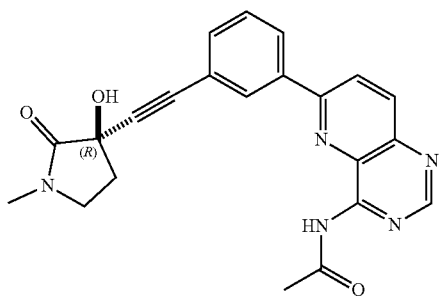

To a vial at rt containing Example 12 [(R)-3-((3-(4-aminopyrido[3,2-d]pyrimidin-6-yl)phenyl)ethynyl)-3-hydroxy-1-methylpyrrolidin-2-one (45 mg, 0.13 mmol)] was added 1,4-dioxane (5 mL), pyridine (25 µL, 0.5 mmol) and acetic anhydride (26 mg, 0.25 mmol), successively. The resulting suspension was stirred at 45° C. and became a colorless homogeneous solution after 2 h. After 17 h, additional acetic anhydride (25 µL) was added and the reaction mixture was heated at 85° C. After 3 h, the reaction mixture was concentrated to dryness and the resulting residue was purified by FCC to afford (R)—N-(6-(3-((3-hydroxy-1-methyl-2-oxopyrrolidin-3-yl)ethynyl)phenyl)pyrido[3,2-d]pyrimidin-4-yl)acetamide (43 mg, 48%) as a white solid. MS (ESI): mass calcd. for C$_{22}$H$_{19}$N$_5$O$_3$, 401.2; m/z. found, 402.1 [M+H]$^+$. $^1$H NMR (400 MHz, CDCl$_3$) δ 9.81 (br s, 1H), 8.96 (br s, 1H), 8.34 (d, J=8.8 Hz, 1H), 8.19 (d, J=8.9 Hz, 1H), 8.14-7.99 (m, 2H), 7.54 (dt, J=7.7, 1.4 Hz, 1H), 7.44 (td, J=7.7, 0.7 Hz, 1H), 3.62-3.33 (m, 2H), 2.97 (s, 3H), 2.79 (s, 3H), 2.65-2.72 (m, 1H), 2.39-2.46 (m, 1H).

Example 239: (R)-3-((3-(4-(3-Fluoroazetidin-1-yl)pyrido[3,2-d]pyrimidin-6-yl)phenyl)ethynyl)-3-hydroxy-1-methylpyrrolidin-2-one

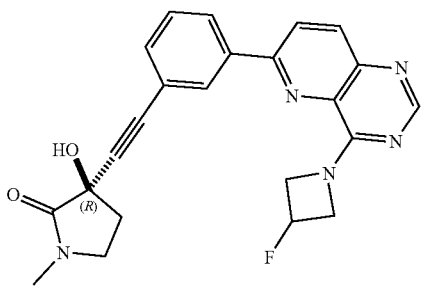

The title compound was prepared using analogous conditions described in Example 25 using Intermediate 152 [6-chloro-4-(3-fluoroazetidin-1-yl)pyrido[3,2-d]pyrimidine] to afford (R)-3-((3-(4-(3-fluoroazetidin-1-yl)pyrido[3,2-d]pyrimidin-6-yl)phenyl)ethynyl)-3-hydroxy-1-methylpyrrolidin-2-one (135 mg, 77%) as a white solid. MS (ESI): mass calcd. for C$_{23}$H$_{20}$FN$_5$O$_2$, 417.2; m/z. found, 418.2 [M+H]$^+$. $^1$H NMR (500 MHz, CDCl$_3$) δ 8.59 (s, 1H), 8.15 (d, J=8.8 Hz, 1H), 8.02 (d, J=8.9 Hz, 1H), 7.99-7.92 (m, 2H), 7.50 (dt, J=7.7, 1.4 Hz, 1H), 7.42 (t, J=7.7 Hz, 1H), 5.58-5.62 (m, 1H), 5.5.44-5.46 (m, 1H), 5.20-5.26 (m, 1H), 5.16-4.91 (m, 1H), 4.66-4.72 (m, 1H), 4.48-4.52 (m, 1H), 4.21-3.96 (m, 1H), 3.50-3.54 (m, 1H), 3.40-3.44 (m, 1H), 2.98 (s, 3H), 2.62-2.70 (m, 1H), 2.40-2.44 (m, 1H).

Example 240: (R)-2-((6-(3-((3-Hydroxy-1-methyl-2-oxopyrrolidin-3-yl)ethynyl)phenyl)pyrido[3,2-d]pyrimidin-4-yl)amino)acetonitrile

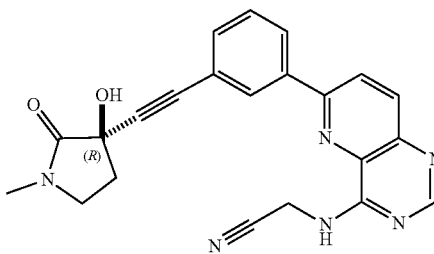

The title compound was prepared using analogous conditions described in Example 25 using Intermediate 153 [2-((6-chloropyrido[3,2-d]pyrimidin-4-yl)amino)acetonitrile] to afford (R)-2-((6-(3-((3-hydroxy-1-methyl-2-oxopyrrolidin-3-yl)ethynyl)phenyl)pyrido[3,2-d]pyrimidin-4-yl)amino)acetonitrile (124 mg, 96%) as a white solid. MS (ESI): mass calcd. for C$_{22}$H$_{18}$N$_6$O$_2$, 398.2; m/z. found, 399.1 [M+H]$^+$. $^1$H NMR (400 MHz, CD$_3$OD) δ 8.60 (s, 1H), 8.41 (d, J=1.9 Hz, 1H), 8.35 (dd, J=9.1, 2.9 Hz, 1H), 8.24 (dt, J=7.8, 1.7 Hz, 1H), 8.16 (dd, J=8.9, 1.9 Hz, 1H), 7.60-7.43 (m, 2H), 4.65 (s, 2H), 3.59-3.43 (m, 2H), 2.95 (s, 3H), 2.62 (ddd, J=12.9, 6.5, 4.6 Hz, 1H), 2.41-2.22 (m, 1H).

Example 241: (R)-3-((3-(4-((2,2-Difluoroethyl)amino)pyrido[3,2-d]pyrimidin-6-yl)phenyl)ethynyl)-3-hydroxy-1-methylpyrrolidin-2-one

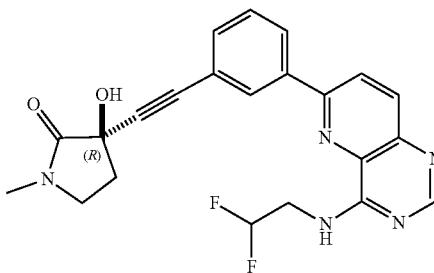

The title compound was prepared using analogous conditions described in Example 25 using Intermediate 154 [6-chloro-N-(2,2-difluoroethyl)pyrido[3,2-d]pyrimidin-4-amine] to afford (R)-3-((3-(4-((2,2-difluoroethyl)amino)pyrido[3,2-d]pyrimidin-6-yl)phenyl)ethynyl)-3-hydroxy-1-methylpyrrolidin-2-one (118 mg, 91%) as a white solid. MS (ESI): mass calcd. for C$_{22}$H$_{19}$F$_2$N$_5$O$_2$, 423.2; m/z. found, 424.1 [M+H]$^+$. $^1$H NMR (500 MHz, CDCl$_3$) δ 8.67 (s, 1H), 8.22 (d, J=8.8 Hz, 1H), 8.13-8.01 (m, 2H), 7.95-8.02 (m, 1H), 7.54-7.44 (m, 2H), 7.38-7.42 (m, 1H), 6.14 (tt, J=56.1, 4.2 Hz, 1H), 4.48-4.58 (m, 1H), 4.08-4.18 (m, 2H), 3.59-3.35 (m, 2H), 2.98 (s, 3H), 2.64-2.70 (m, 1H), 2.39-2.44 (m, 1H).

Example 242: (R)-1-(6-(3-((3-Hydroxy-1-methyl-2-oxopyrrolidin-3-yl)ethynyl)phenyl)pyrido[3,2-d]pyrimidin-4-yl)azetidine-3-carbonitrile

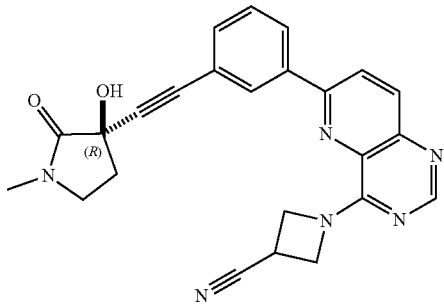

The title compound was prepared using analogous conditions described in Example 25 using Intermediate 155 [1-(6-chloropyrido[3,2-d]pyrimidin-4-yl)azetidine-3-carbonitrile] to afford (R)-1-(6-(3-((3-hydroxy-1-methyl-2-oxopyrrolidin-3-yl)ethynyl)phenyl)pyrido[3,2-d]pyrimidin-4-yl)azetidine-3-carbonitrile (105 mg, 81%) as a white solid. MS (ESI): mass calcd. for $C_{24}H_{20}N_6O_2$, 424.2; m/z. found, 425.1 [M+H]+. 1H NMR (500 MHz, CD3OD) δ 8.39 (s, 1H), 8.15 (d, J=8.9 Hz, 1H), 8.04-7.93 (m, 3H), 7.56-7.35 (m, 2H), 5.24-5.11 (m, 1H), 5.00-5.04 (m, 1H), 4.71-4.56 (m, 1H), 4.45-4.51 (m, 1H), 3.91-4.01 (m, 1H), 3.56-3.40 (m, 2H), 2.95 (s, 3H), 2.58-2.64 (m, 1H), 2.30-2.36 (m, 1H).

Example 243: (R)-3-((3-(4-(Azetidin-1-yl)quinazolin-6-yl)phenyl)ethynyl)-3-hydroxy-1-methylpyrrolidin-2-one

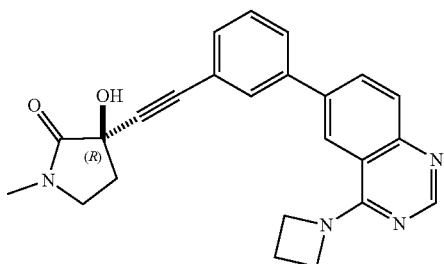

The title compound was prepared using analogous conditions described in Example 221 utilizing Intermediate 156 [4-(azetidin-1-yl)-6-bromoquinazoline] to afford (R)-3-((3-(4-(azetidin-1-yl)quinazolin-6-yl)phenyl)ethynyl)-3-hydroxy-1-methylpyrrolidin-2-one (27 mg, 15%) as a white solid. MS (ESI): mass calcd. for $C_{24}H_{22}N_4O_2$ 398.2 m/z found 399.2 [M+H]+. 1H NMR (400 MHz, DMSO-d6) δ 8.46 (s, 1H), 8.11-8.07 (m, 2H), 7.83-7.79 (m, 1H), 7.79-7.76 (m, 2H), 7.56-7.51 (m, 1H), 7.48-7.44 (m, 1H), 6.51 (s, 1H), 4.60 (br. s., 4H), 3.39-3.37 (m, 2H), 2.81 (s, 3H), 2.49-2.46 (m, 2H), 2.45-2.42 (m, 1H), 2.24-2.16 (m, 1H).

Example 244: (R)-3-((3-(4-(3-Chloroazetidin-1-yl)pyrido[3,2-d]pyrimidin-6-yl)phenyl)ethynyl)-3-hydroxy-1-methylpyrrolidin-2-one

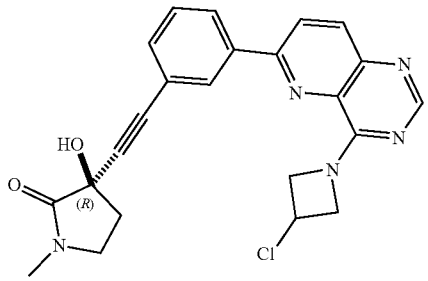

The title compound was prepared using analogous conditions described in Example 25 using Intermediate 157 [6-chloro-4-(3-chloroazetidin-1-yl)pyrido[3,2-d]pyrimidine] to afford (R)-3-((3-(4-(3-chloroazetidin-1-yl)pyrido[3,2-d]pyrimidin-6-yl)phenyl)ethynyl)-3-hydroxy-1-methylpyrrolidin-2-one (160 mg, 94%) as a white solid. MS (ESI): mass calcd. for $C_{23}H_{20}ClN_5O_2$, 433.1; m/z. found, 434.1 [M+H]+. 1H NMR (500 MHz, CDCl3) δ 8.60 (s, 1H), 8.16 (d, J=8.9 Hz, 1H), 7.96 (d, J=30.6 Hz, 3H), 7.54-7.31 (m, 2H), 5.43 (s, 1H), 5.09-4.66 (m, 3H), 4.58-4.31 (m, 2H), 3.49-3.55 (m, 1H), 3.40-3.44 (m, 1H), 2.98 (s, 3H), 2.64-2.72 (m, 1H), 2.40-2.44 (m, 1H).

Example 245: (R)-3-Hydroxy-1-methyl-3-((3-(4-(3-(methylsulfonyl)azetidin-1-yl)pyrido[3,2-d]pyrimidin-6-yl)phenyl)ethynyl)pyrrolidin-2-one

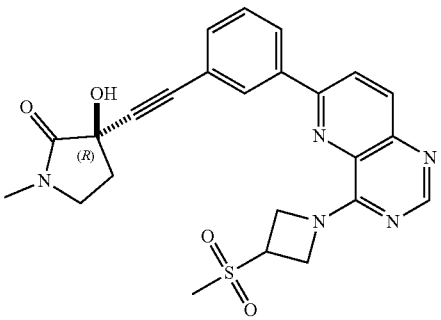

The title compound was prepared using analogous conditions described in Example 25 using Intermediate 158 [6-chloro-4-(3-(methylsulfonyl)azetidin-1-yl)pyrido[3,2-d]pyrimidine] to afford (R)-3-hydroxy-1-methyl-3-((3-(4-(3-(methylsulfonyl)azetidin-1-yl)pyrido[3,2-d]pyrimidin-6-yl)phenyl)ethynyl)pyrrolidin-2-one (138 mg, 86%) as an amber solid. MS (ESI): mass calcd. for $C_{24}H_{23}N_5O_4S$, 477.2; m/z found, 478.1 [M+H]+. 1H NMR (500 MHz, CD3OD) δ 8.42 (s, 1H), 8.26 (s, 1H), 8.19-7.98 (m, 3H), 7.47 (d, J=17.1 Hz, 2H), 5.28 (d, J=20.0 Hz, 2H), 4.75-4.60 (m, 2H), 4.54 (t, J=8.5, 5.3 Hz, 1H), 3.54-3.39 (m, 2H), 3.10 (s, 3H), 2.94 (s, 3H), 2.61 (ddd, J=13.0, 7.0, 3.8 Hz, 1H), 2.32 (dt, J=13.0, 7.6 Hz, 1H).

Example 246: (R)-1-(6-(3-((3-Hydroxy-1-methyl-2-oxopyrrolidin-3-yl)ethynyl)phenyl)pyrido[3,2-d]pyrimidin-4-yl)-N-methylazetidine-3-carboxamide

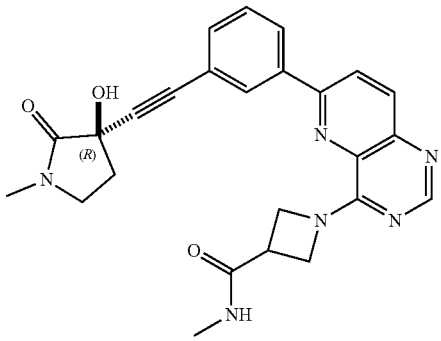

The title compound was prepared using analogous conditions described in Example 25 using Intermediate 159 [1-(6-chloropyrido[3,2-d]pyrimidin-4-yl)-N-methylazetidine-3-carboxamide] to afford (R)-1-(6-(3-((3-hydroxy-1-methyl-2-oxopyrrolidin-3-yl)ethynyl)phenyl)pyrido[3,2-d]pyrimidin-4-yl)-N-methylazetidine-3-carboxamide (111 mg, 68%) as a white solid. MS (ESI): mass calcd. for $C_{25}H_{24}N_6O_3$, 456.2; m/z. found, 457.1 [M+H]$^+$. $^1$H NMR (500 MHz, CD$_3$OD) δ 8.33 (s, 1H), 8.19 (dd, J=8.9, 1.1 Hz, 1H), 8.05-8.08 (m, 1H), 8.07.80-8.20 (m, 2H), 7.52-7.38 (m, 2H), 5.13-4.97 (m, 2H), 4.53-4.37 (m, 2H), 3.60-3.70 (m, 1H), 3.57-3.43 (m, 2H), 2.94 (d, J=3.4 Hz, 3H), 2.82 (s, 3H), 2.58-2.62 (m, 1H), 2.30-2.38 (m, 1H).

Example 247: (R)-3-((3-(8-(Azetidin-1-yl)pyrido[3,4-d]pyrimidin-2-yl)phenyl)ethynyl)-3-hydroxy-1-methylpyrrolidin-2-one

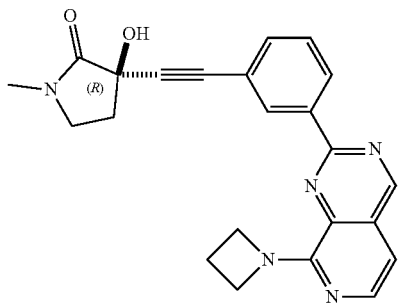

The title compound was prepared using analogous conditions described in Example 1 utilizing Intermediate 160 [8-(azetidin-1-yl)-2-(3-bromophenyl)pyrido[3,4-d]pyrimidine] to afford (R)-3-((3-(8-(azetidin-1-yl)pyrido[3,4-d]pyrimidin-2-yl)phenyl)ethynyl)-3-hydroxy-1-methylpyrrolidin-2-one (53 mg, 45%) as a colorless solid. (MS (ESI): mass calcd. for $C_{23}H_{21}N_5O_2$, 399.17; m/z. found, 400.2 [M+H]$^+$. $^1$H NMR (400 MHz, DMSO-d$_6$) δ 9.50 (s, 1H), 8.40-8.36 (m, 1H), 8.35-8.27 (m, 1H), 7.92 (d, J=6.0 Hz, 1H), 7.58-7.48 (m, 2H), 7.03 (d, J=6.0 Hz, 1H), 6.45 (s, 1H), 4.59 (s, 5H), 3.34-3.29 (m, 2H), 2.75 (s, 3H), 2.51-2.45 (m, 1H), 2.42-2.35 (m, 1H), 2.19-2.08 (m, 1H).

Example 248: (S)-3-((3-(8-(Azetidin-1-yl)pyrido[3,4-d]pyrimidin-2-yl)phenyl)ethynyl)-3-hydroxy-1-methylpyrrolidin-2-one

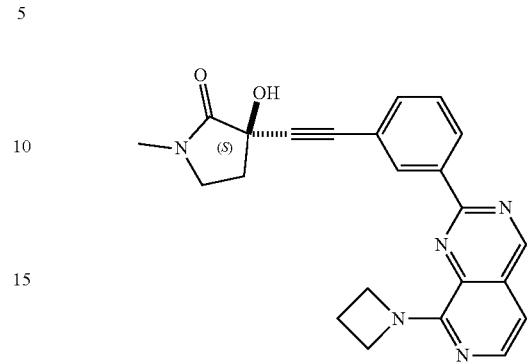

The title compound was prepared using analogous conditions described in Example 1 utilizing Intermediate 160 [8-(azetidin-1-yl)-2-(3-bromophenyl)pyrido[3,4-d]pyrimidine] and Intermediate 3 [(S)-3-ethynyl-3-hydroxy-1-methylpyrrolidin-2-one] to afford (S)-3-((3-(8-(azetidin-1-yl)pyrido[3,4-d]pyrimidin-2-yl)phenyl)ethynyl)-3-hydroxy-1-methylpyrrolidin-2-one (24 mg, 21%) as a colorless solid. MS (ESI): mass calcd. for $C_{23}H_{21}N_5O_2$, 399.17; m/z. found, 400.2 [M+H]$^+$. $^1$H NMR (400 MHz, DMSO-d$_6$) δ 9.51 (s, 1H), 8.48-8.44 (m, 1H), 8.43-8.38 (m, 1H), 8.10 (d, J=5.5 Hz, 1H), 7.61-7.53 (m, 2H), 7.05 (d, J=5.6 Hz, 1H), 6.52 (s, 1H), 4.56 (app s, 6H), 3.41-3.34 (m, 2H), 2.82 (s, 3H), 2.49-2.44 (m, 1H), 2.25-2.16 (m, 1H).

Example 249: (R)-3-((3-(5-Bromo-8-methyl-1,7-naphthyridin-2-yl)phenyl)ethynyl)-3-hydroxy-1-methylpyrrolidin-2-one

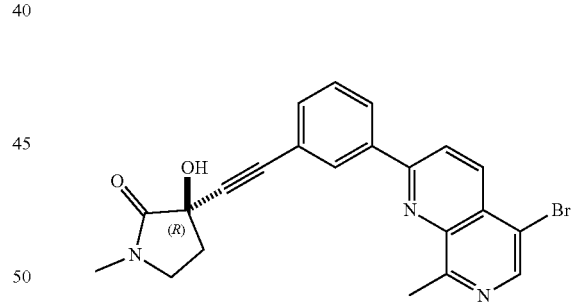

The title compound was prepared using analogous conditions described in Example 1 utilizing Intermediate 161 [5-bromo-2-(3-iodophenyl)-8-methyl-1,7-naphthyridine] to afford (R)-3-((3-(5-bromo-8-methyl-1,7-naphthyridin-2-yl)phenyl)ethynyl)-3-hydroxy-1-methylpyrrolidin-2-one (45.3 mg, 40%) as a white solid. MS (ESI): mass calcd. for $C_{22}H_{18}BrN_3O_2$ 435.1 m/z. found 436.0 [M+H]$^+$. $^1$H NMR (400 MHz, DMSO-d$_6$) δ 8.69 (s, 1H), 8.61-8.57 (m, 1H), 8.54-8.50 (m, 1H), 8.40-8.34 (m, 2H), 7.67-7.59 (m, 2H), 6.54 (s, 1H), 3.40-3.38 (m, 2H), 3.01 (s, 3H), 2.82 (s, 3H), 2.47-2.45 (m, 1H), 2.25-2.17 (m, 1H).

Example 250. (R)-3-((3-(4,8-Dimethylpyrido[3,2-d]pyrimidin-6-yl)phenyl)ethynyl)-3-hydroxy-1-methylpyrrolidin-2-one

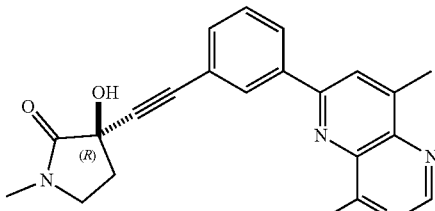

The title compound was prepared using analogous conditions described in Example 221 utilizing Intermediate 162 [6-chloro-4,8-dimethylpyrido[3,2-d]pyrimidine] to afford (R)-3-((3-(4,8-dimethylpyrido[3,2-d]pyrimidin-6-yl)phenyl)ethynyl)-3-hydroxy-1-methylpyrrolidin-2-one (80 mg, 33%) as a colorless solid. MS (ESI): mass calcd. for $C_{22}H_{20}N_4O_2$ 372.2 m/z. found 373.2 $[M+H]^+$. $^1$H NMR (400 MHz, DMSO-$d_6$) δ 9.19 (s, 1H), 8.58-8.54 (m, 1H), 8.37-8.31 (m, 2H), 7.65-7.58 (m, 2H), 6.54-6.52 (m, 1H), 3.41-3.38 (m, 2H), 3.05 (s, 3H), 2.83 (s, 3H), 2.78 (s, 3H), 2.48-2.45 (m, 1H), 2.27-2.18 (m, 1H).

Example 251: (R)-2-(3-((3-Hydroxy-1-methyl-2-oxopyrrolidin-3-yl)ethynyl)phenyl)-8-methyl-1,7-naphthyridine-5-carbonitrile

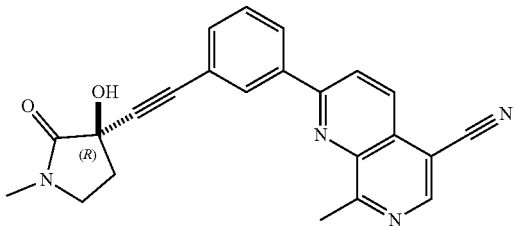

A vial was charged with Example 249 [(R)-3-((3-(5-Bromo-8-methyl-1,7-naphthyridin-2-yl)phenyl)ethynyl)-3-hydroxy-1-methylpyrrolidin-2-one (100 mg, 0.23 mmol)], $Zn(CN)_2$ (135 mg, 1.15 mmol), 2-dicyclohexylphosphino-2',4',6'-triisopropylbiphenyl (44 mg, 0.09 mmol), Zn dust (9.0 mg, 0.14 mmol), and DMF (5 mL). The resultant mixture was sparged with Ar for 5 min and then treated with $Pd_2(dba)_3$ (42 mg, 0.05 mmol). The mixture was sparged with Ar for another 5 min and then heated at 100° C. for 2 h before cooling to rt. The suspension was filtered, and the filter cake was washed with ethyl acetate (20 mL). The filtrate was dried over anhydrous $Na_2SO_4$, filtered and concentrated to dryness. The resulting residue was purified by FCC (10:1 to 0:1 gradient, petroleum ether/ethyl acetate) followed by purification by preparative reverse phase HPLC (Boston Prime NX-C18 150×30 mm×5 μm, eluent: 40% to 70% (v/v) $CH_3CN$ and $H_2O$ with 0.05% $NH_3H_2O+10$ mM $NH_4HCO_3$) to afford (R)-2-(3-((3-hydroxy-1-methyl-2-oxopyrrolidin-3-yl)ethynyl)phenyl)-8-methyl-1,7-naphthyridine-5-carbonitrile (25.5 mg, 29%) as a white solid. MS (ESI): mass calcd. for $C_{23}H_{18}N_4O_2$ 382.1 m/z. found 383.1 $[M+H]^+$. $^1$H NMR (400 MHz, CDCl$_3$) δ 8.84 (s, 1H), 8.50 (d, J=8.8 Hz, 1H), 8.30-8.20 (m, 3H), 7.63-7.58 (m, 1H), 7.55-7.46 (m, 1H), 3.75-3.70 (m, 1H), 3.58-3.49 (m, 1H), 3.46-3.39 (m, 1H), 3.24 (s, 3H), 3.00 (s, 3H), 2.75-2.66 (m, 1H), 2.48-2.38 (m, 1H).

Example 252. (R)-3-((3-(5,8-Dimethyl-1,7-naphthyridin-2-yl)phenyl)ethynyl)-3-hydroxy-1-methylpyrrolidin-2-one

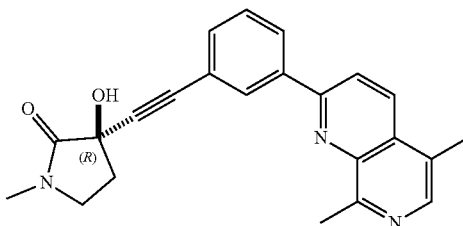

A vial was charged with Example 249 (R)-3-((3-(5-Bromo-8-methyl-1,7-naphthyridin-2-yl)phenyl)ethynyl)-3-hydroxy-1-methylpyrrolidin-2-one (70.0 mg, 0.16 mmol), 2,4,6-trimethyl-1,3,5,2,4,6-trioxatriborinane (0.05 mL, 50% in THF, 0.17 mmol), $K_2CO_3$ (0.40 mL, 2 M in water, 0.80 mmol), and 1,4-dioxane (5 mL). The mixture was sparged with Ar for 5 min and then treated with Pd(dppf)Cl$_2$·CH$_2$Cl$_2$ (13.0 mg, 0.02 mmol). The mixture was sparged with Ar for another 5 min and the resultant mixture was heated at 80° C. for 2 h before it was cooled to rt. The reaction mixture was poured into saturated aqueous NaHCO$_3$ (20 mL) and extracted with ethyl acetate (30 mL×3). The combined organic extracts was washed with brine, dried with anhydrous Na$_2$SO$_4$, filtered, and concentrated to dryness. The resulting residue was purified by FCC (0:1 to 1:1 gradient, petroleum ether/ethyl acetate) followed by further purification by preparative reverse phase HPLC (Boston Green ODS 150×30 mm, 5 μm column, eluent: 15% to 45% (v/v) CH$_3$CN and H$_2$O with 0.225% HCOOH) to afford (R)-3-((3-(5,8-dimethyl-1,7-naphthyridin-2-yl)phenyl)ethynyl)-3-hydroxy-1-methylpyrrolidin-2-one (12.1 mg, 20%) as a white solid. MS (ESI): mass calcd. for $C_{23}H_{21}N_3O_2$ 371.2 m/z found 372.2 $[M+H]^+$. $^1$H NMR (400 MHz, DMSO-$d_6$) δ 8.58-8.52 (m, 1H), 8.49-8.43 (m, 1H), 8.39-8.33 (m, 2H), 8.30 (s, 1H), 7.65-7.55 (m, 2H), 6.54 (s, 1H), 3.40-3.36 (m, 2H), 2.99 (s, 3H), 2.81 (s, 3H), 2.58 (s, 3H), 2.47-2.44 (m, 1H), 2.26-2.16 (m, 1H).

Example 253: (R)-3-((3-(4-Amino-8-bromopyrido[3,2-d]pyrimidin-6-yl)phenyl)ethynyl)-3-hydroxy-1-methylpyrrolidin-2-one

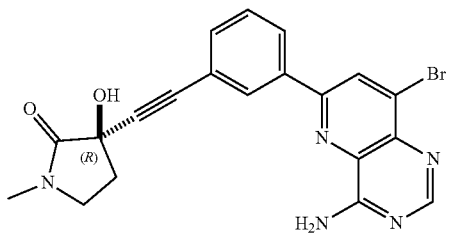

A vial was charged with Intermediate 163 [6,8-dibromopyrido[3,2-d]pyrimidin-4-amine (600 mg, 1.97 mmol)], 3-hydroxy-1-methyl-3-((3-(4,4,5,5-tetramethyl-1,3,2-dioxaborolan-2-yl)phenyl)ethynyl)pyrrolidin-2-one (337 mg, 0.988 mmol), $K_3PO_4$ (838 mg, 3.95 mmol], 1,4-dioxane (10 mL), and $H_2O$ (2 mL). The mixture was sparged with Ar for 5 min and then treated with $Pd(dppf)Cl_2CH_2Cl_2$ (161 mg, 0.197 mmol). The mixture was sparged with Ar for another 5 min and the resultant mixture was then subjected to microwave irradiation at 65° C. in for 1 h. After the reaction mixture was allowed to cool to rt and concentrated to dryness. The resulting residue was purified by FCC (1:0 to 0:1 gradient, petroleum ether/ethyl acetate) followed by further purification using preparative reverse phase HPLC (Phenomenex Gemini NX-C18 75×30 mm, 3 μm column, eluent: 40% to 80% (v/v) $CH_3CN$ and $H_2O$ with 0.05% $NH_3H_2O$) to afford racemic-3-((3-(4-amino-8-bromopyrido [3,2-d]pyrimidin-6-yl)phenyl)ethynyl)-3-hydroxy-1-methylpyrrolidin-2-one (30 mg, 3.4%) as a white solid. MS (ESI): mass calcd. for $C_{20}H_{16}BrN_5O_2$ 437.1 m/z. found 438.0 [M+H]$^+$. The enantiomers of racemic 3-((3-(4-Amino-8-bromopyrido[3,2-d]pyrimidin-6-yl)phenyl)ethynyl)-3-hydroxy-1-methylpyrrolidin-2-one (30 mg, 0.068 mmol) were separated by chiral SFC (DAICEL CHIRALCEL OD-H 250×30 mm, 5 μm (isocratic elution: EtOH (containing 0.1% of 25% aq. $NH_3$): supercritical $CO_2$, 50%: 50% to 50%: 50% (v/v)) to afford (R)-3-((3-(4-amino-8-bromopyrido[3,2-d]pyrimidin-6-yl)phenyl)ethynyl)-3-hydroxy-1-methylpyrrolidin-2-one (9.4 mg, 31%, >97% ee) as a white solid and (S)-3-((3-(4-amino-8-bromopyrido[3,2-d]pyrimidin-6-yl)phenyl)ethynyl)-3-hydroxy-1-methylpyrrolidin-2-one (Example 254, 6.0 mg, 20%, >97% ee). Data for (R)-3-((3-(4-amino-8-bromopyrido[3,2-d]pyrimidin-6-yl)phenyl)ethynyl)-3-hydroxy-1-methylpyrrolidin-2-one: MS (ESI): mass calcd. for $C_{20}H_{16}BrN_5O_2$ 437.05 m/z. found 438.0 [M+H]$^+$. $^1$H NMR (400 MHz, DMSO-$d_6$) δ 8.87 (s, 1H), 8.54-8.45 (m, 3H), 8.41 (br. s., 1H), 8.21 (br. s., 1H), 7.55 (d, J=5.0 Hz, 2H), 6.48 (br s, 1H), 3.41-3.36 (m, 2H), 2.82 (s, 3H), 2.48-2.46 (m, 1H), 2.25-2.18 (m, 1H).

Example 254: (S)-3-((3-(4-Amino-8-bromopyrido[3,2-d]pyrimidin-6-yl)phenyl)ethynyl)-3-hydroxy-1-methylpyrrolidin-2-one

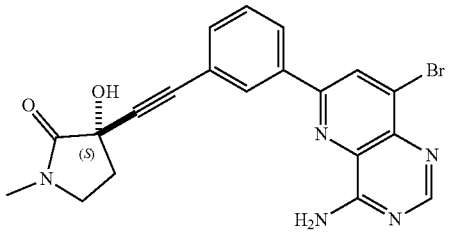

The chiral separation described in Example 253 provided (S)-3-((3-(4-amino-8-bromopyrido[3,2-d]pyrimidin-6-yl) phenyl)ethynyl)-3-hydroxy-1-methylpyrrolidin-2-one (6.0 mg, 20%, >97% ee) as a white solid. MS (ESI): mass calcd. for $C_{20}H_{16}BrN_5O_2$ 437.1 m/z. found 438.1 [M+H]$^+$. $^1$H NMR (400 MHz, DMSO-$d_6$) δ 8.87 (s, 1H), 8.53-8.43 (m, 3H), 8.40 (br. s., 1H), 8.20 (br. s., 1H), 7.54 (d, J=5.1 Hz, 2H), 6.48 (br s, 1H), 3.40-3.37 (m, 2H), 2.82 (s, 3H), 2.48-2.45 (m, 1H), 2.25-2.17 (m, 1H).

Example 255: (R)-3-((3-(4-Amino-8-(tetrahydro-2H-pyran-4-yl)pyrido[3,2-d]pyrimidin-6-yl)phenyl) ethynyl)-3-hydroxy-1-methylpyrrolidin-2-one

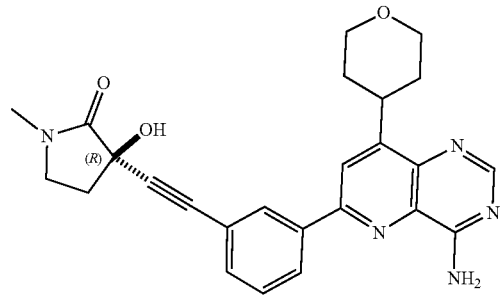

The title compound was prepared using analogous conditions described in Example 221 utilizing Intermediate 165 [6-chloro-8-(tetrahydro-2H-pyran-4-yl)pyrido[3,2-d]pyrimidin-4-amine] and purified by preparative reverse phase HPLC (Phenomenex Gemini-NX C18 150×30 mm, 5 μm column, eluent: 25% to 55% (v/v) $CH_3CN$ and $H_2O$ with 0.05% $NH_3H_2O+10$ mM $NH_4HCO_3$) to afford (R)-3-((3-(4-amino-8-(tetrahydro-2H-pyran-4-yl)pyrido[3,2-d]pyrimidin-6-yl)phenyl)ethynyl)-3-hydroxy-1-methylpyrrolidin-2-one (60 mg, 48%) as a white solid. MS (ESI): mass calcd. for $C_{25}H_{25}N_5O_3$ 443.2 m/z, found 444.1 [M+H]$^+$. $^1$H NMR (400 MHz, DMSO-$d_6$) δ 8.55-8.43 (m, 3H), 8.29 (s, 1H), 8.16 (br s, 1H), 7.96 (br s, 1H), 7.60-7.49 (m, 2H), 6.50 (s, 1H), 4.07-3.98 (m, 2H), 3.98-3.87 (m, 1H), 3.63-3.51 (m, 2H), 3.43-3.39 (m, 2H), 2.82 (s, 3H), 2.59-2.54 (m, 1H), 2.27-2.17 (m, 1H), 2.07-1.92 (m, 2H), 1.81-1.72 (m, 2H).

Example 256: (S)-3-((3-(4-Amino-8-(tetrahydro-2H-pyran-4-yl)pyrido[3,2-d]pyrimidin-6-yl)phenyl)ethynyl)-3-hydroxy-1-methylpyrrolidin-2-one

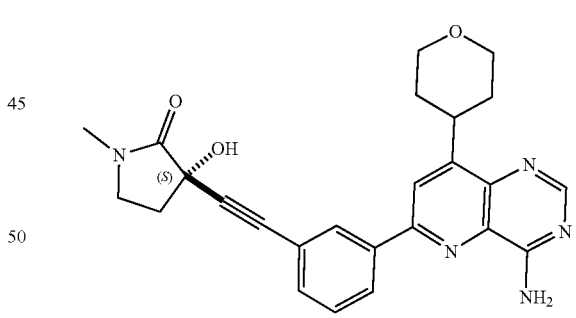

The title compound was prepared using analogous conditions described in Example 221 utilizing Intermediate 165 [6-chloro-8-(tetrahydro-2H-pyran-4-yl)pyrido[3,2-d]pyrimidin-4-amine] and Intermediate 5 [(S)-3-Hydroxy-1-methyl-3-((3-(4,4,5,5-tetramethyl-1,3,2-dioxaborolan-2-yl) phenyl)ethynyl)pyrrolidin-2-one] to afford (S)-3-((3-(4-amino-8-(tetrahydro-2H-pyran-4-yl)pyrido[3,2-d] pyrimidin-6-yl)phenyl)ethynyl)-3-hydroxy-1-methylpyrrolidin-2-one (10.1 mg, 16%) as a white solid. LCMS (ESI): mass calcd. for $C_{25}H_{25}N_5O_3$ 443.2 m/z. found 444.1 [M+H]$^+$. $^1$H NMR (400 MHz, DMSO-$d_6$) δ 8.55-8.43 (m, 3H), 8.29 (s, 1H), 8.16 (br s, 1H), 7.96 (br s, 1H), 7.60-7.49 (m, 2H), 6.50 (s, 1H), 4.07-3.98 (m, 2H), 3.98-

3.87 (m, 1H), 3.63-3.51 (m, 2H), 3.43-3.39 (m, 2H), 2.82 (s, 3H), 2.59-2.54 (m, 1H), 2.27-2.17 (m, 1H), 2.07-1.92 (m, 2H), 1.81-1.72 (m, 2H).

Example 257: (R)-3-Hydroxy-1-methyl-3-((3-(4-phenylpyrido[3,2-d]pyrimidin-6-yl)phenyl)ethynyl)pyrrolidin-2-one

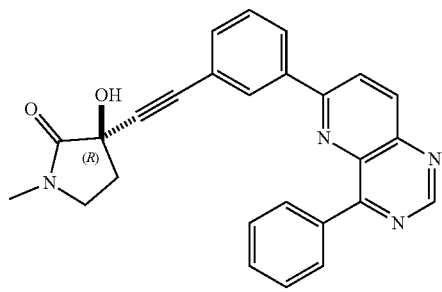

The title compound was prepared using analogous conditions described in Example 221 utilizing Intermediate 166 [6-chloro-4-phenylpyrido[3,2-d]pyrimidine] to afford (R)-3-hydroxy-1-methyl-3-((3-(4-phenylpyrido[3,2-d]pyrimidin-6-yl)phenyl)ethynyl)pyrrolidin-2-one (47.7 mg, 39%) as a yellow solid. MS (ESI): mass calcd. for $C_{26}H_{20}N_4O_2$ 420.2 m/z found 421.2 [M+H]$^+$. $^1$H NMR (400 MHz, DMSO-d$_6$) δ 9.44 (s, 1H), 8.72 (d, J=9.0 Hz, 1H), 8.56 (d, J=8.8 Hz, 1H), 8.42-8.37 (m, 2H), 8.33 (s, 1H), 8.32-8.27 (m, 1H), 7.68-7.63 (m, 3H), 7.62-7.57 (m, 2H), 6.53 (s, 1H), 3.42-3.36 (m, 2H), 2.83 (s, 3H), 2.48-2.44 (m, 1H), 2.26-2.18 (m, 1H).

Example 258: (R)—N-(6-(3-((3-Hydroxy-1-methyl-2-oxopyrrolidin-3-yl)ethynyl)phenyl)-2-methylpyrido[3,2-d]pyrimidin-4-yl)acetamide

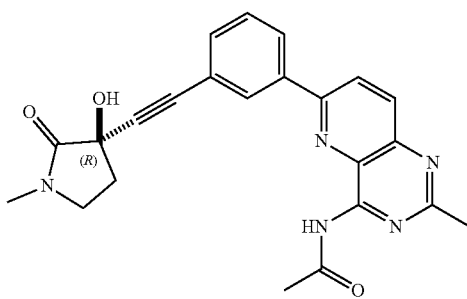

A flask was charged with Example 6 [(R)-3-((3-(4-amino-2-methylpyrido[3,2-d]pyrimidin-6-yl)phenyl)ethynyl)-3-hydroxy-1-methylpyrrolidin-2-one (200 mg, 0.54 mmol)], 1,4-dioxane (15 mL), pyridine (0.20 mL, 2.53 mmol), and acetic anhydride (0.10 mL, 1.07 mmol) at rt. After 5 h, the mixture was heated at 40° C. in an aluminum heating mantle. After 30 h, the contents were cooled to rt and concentrated to dryness. The resulting residue was purified by FCC (100% DCM increasing to 5% MeOH-DCM) to afford (R)—N-(6-(3-((3-hydroxy-1-methyl-2-oxopyrrolidin-3-yl)ethynyl)phenyl)-2-methylpyrido[3,2-d]pyrimidin-4-yl)acetamide (202 mg, 91%) as a white solid. MS (ESI): mass calcd. for $C_{23}H_{21}N_5O_3$, 415.2; m/z. found, 416.1 [M+H]$^+$.

$^1$H NMR (500 MHz, DMSO-d$_6$) δ 10.36 (s, 1H), 8.57 (d, J=8.9 Hz, 1H), 8.40-8.25 (m, 2H), 8.29 (d, J=8.8 1 H), 7.68-7.45 (m, 2H), 6.50 (s, 1H), 3.37-3.42 (m, 2H), 2.83 (s, 3H), 2.68 (s, 3H), 2.60 (s, 3H), 2.50-2.41 (m, 1H), 2.19-2.25 (m, 1H).

Example 259: (R)—N-(6-(3-((3-Hydroxy-1-methyl-2-oxopyrrolidin-3-yl)ethynyl)phenyl)pyrido[3,2-d]pyrimidin-4-yl-2-d)acetamide

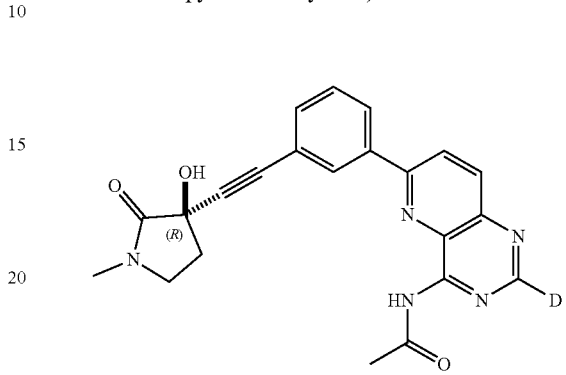

The title compound was prepared using analogous conditions described in Example 258 utilizing Example 8 [(R)-3-((3-(4-aminopyrido[3,2-d]pyrimidin-6-yl-2-d)phenyl)ethynyl)-3-hydroxy-1-methylpyrrolidin-2-one] to afford (R)—N-(6-(3-((3-hydroxy-1-methyl-2-oxopyrrolidin-3-yl)ethynyl)phenyl)pyrido[3,2-d]pyrimidin-4-yl-2-d)acetamide (58 mg, 65%) as a white solid. MS (ESI): mass calcd. for $C_{22}H_{19}N_5O_3$, 402.2; m/z. found, 403.1 [M+H]$^+$. $^1$H NMR (500 MHz, CD$_3$OD) δ 8.47 (d, J=8.9 Hz, 1H), 8.36 (br s, 1H), 8.33 (d, J=8.9 Hz, 1H), 8.26-8.29 (m, 1H), 7.58-7.62 (m, 1H), 7.52-7.56 (m, 1H), 3.57-3.41 (m, 2H), 2.94 (s, 3H), 2.69-2.56 (m, 4H), 2.30-2.36 (m 1H).

Example 260: (S)-3-((3-(4-Aminopyrido[3,2-d]pyrimidin-6-yl)-4-methylphenyl)ethynyl)-3-hydroxy-1-methylpyrrolidin-2-one

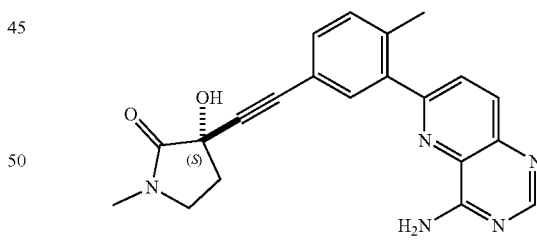

The title compound was prepared using analogous conditions described in Example 3 utilizing Intermediate 5 [(S)-3-hydroxy-1-methyl-3-((4-methyl-3-(4,4,5,5-tetramethyl-1,3,2-dioxaborolan-2-yl)phenyl)ethynyl)pyrrolidin-2-one] to afford (S)-3-((3-(4-aminopyrido[3,2-d]pyrimidin-6-yl)-4-methylphenyl)ethynyl)-3-hydroxy-1-methylpyrrolidin-2-one (61.2 mg, 27%) as a yellow solid. MS (ESI): mass calcd. for $C_{21}H_{19}N_5O_2$ 373.2 m/z. found 374.2 [M+H]$^+$. $^1$H NMR (400 MHz, DMSO-d$_6$) δ 8.44 (s, 1H), 8.13 (d, J=8.6 Hz, 1H), 7.98 (d, J=8.6 Hz, 1H), 7.96-7.84 (m, 2H), 7.56 (s, 1H), 7.45-7.36 (m, 2H), 6.46 (s, 1H), 3.33-3.30 (m, 2H), 2.79 (s, 3H), 2.45-2.38 (m, 4H), 2.22-2.12 (m, 1H).

Example 261: (3R,5R)-3-((3-(4-Aminopyrido[3,2-d]pyrimidin-6-yl-2-d)phenyl)ethynyl)-3-hydroxy-1,5-dimethylpyrrolidin-2-one

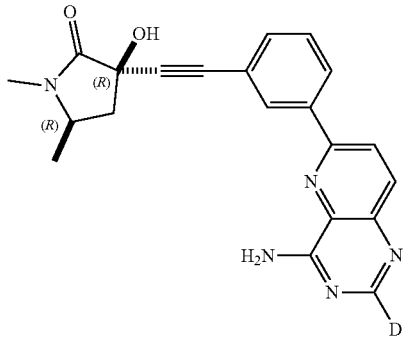

The title compound was prepared using analogous conditions described in Example 1 utilizing Intermediate 117 [6-(3-Iodophenyl)pyrido[3,2-d]pyrimidin-2-d-4-amine] and Intermediate 168 [(3R,5R)-3-ethynyl-3-hydroxy-1,5-dimethylpyrrolidin-2-one] to afford (3R,5R)-3-((3-(4-aminopyrido[3,2-d]pyrimidin-6-yl-2-d)phenyl)ethynyl)-3-hydroxy-1,5-dimethylpyrrolidin-2-one (600 mg, 56%) as a colorless solid. MS (ESI): mass calcd. for $C_{21}H_{18}DN_5O_2$, 374.16; m/z. found, 375.0 [M+H]$^+$. $^1$H NMR (500 MHz, DMSO-d$_6$) δ 8.47 (d, J=8.9 Hz, 1H), 8.45-8.41 (m, 2H), 8.20 (s, 1H), 8.14 (d, J=8.8 Hz, 1H), 7.99 (s, 1H), 7.60-7.50 (m, 2H), 6.49 (s, 1H), 3.67-3.59 (m, 1H), 2.79 (s, 3H), 2.74-2.65 (m, 1H), 1.87-1.65 (m, 1H), 1.26 (d, J=6.3 Hz, 3H).

Example 262: (3R,5S)-3-((3-(4-Aminopyrido[3,2-d]pyrimidin-6-yl-2-d)phenyl)ethynyl)-3-hydroxy-1,5-dimethylpyrrolidin-2-one

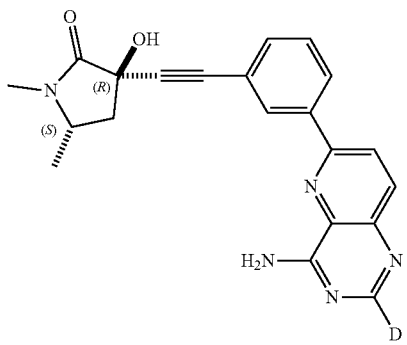

The title compound was prepared using analogous conditions described in Example 1 utilizing Intermediate 117 [6-(3-Iodophenyl)pyrido[3,2-d]pyrimidin-2-d-4-amine] and Intermediate 169 [(3R,5S)-3-ethynyl-3-hydroxy-1,5-dimethylpyrrolidin-2-one] to afford (3R,5S)-3-((3-(4-aminopyrido[3,2-d]pyrimidin-6-yl-2-d)phenyl)ethynyl)-3-hydroxy-1,5-dimethylpyrrolidin-2-one (18 mg, 17%) as a colorless solid. MS (ESI): mass calcd. for $C_{21}H_{18}DN_5O_2$, 374.16; m/z. found, 400.2 [M+H]$^+$. $^1$H NMR (500 MHz, DMSO-d$_6$) δ 8.49-8.38 (m, 3H), 8.19 (s, 1H), 8.13 (d, J=8.8 Hz, 1H), 7.97 (s, 1H), 7.58-7.51 (m, 2H), 6.45 (s, 1H), 3.69-3.58 (m, 1H), 2.77 (s, 3H), 2.47-2.40 (m, 1H), 2.12 (dd, J=13.2, 5.2 Hz, 1H), 1.28 (d, J=6.4 Hz, 3H).

Example 263: (3S,5S)-3-((3-(4-Aminopyrido[3,2-d]pyrimidin-6-yl-2-d)phenyl)ethynyl)-3-hydroxy-1,5-dimethylpyrrolidin-2-one

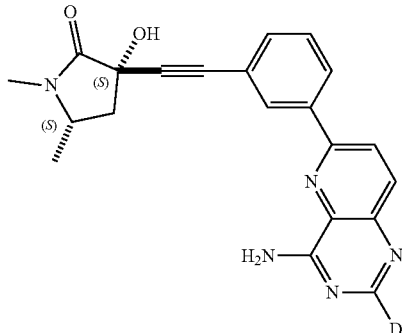

The title compound was prepared using analogous conditions described in Example 1 utilizing Intermediate 117 [6-(3-Iodophenyl)pyrido[3,2-d]pyrimidin-2-d-4-amine] and Intermediate 167 [(3S,5S)-3-ethynyl-3-hydroxy-1,5-dimethylpyrrolidin-2-one] to afford (3S,5S)-3-((3-(4-aminopyrido[3,2-d]pyrimidin-6-yl-2-d)phenyl)ethynyl)-3-hydroxy-1,5-dimethylpyrrolidin-2-one (27 mg, 25%) as a colorless solid. MS (ESI): mass calcd. for $C_{21}H_{18}DN_5O_2$, 374.16; m/z. found, 400.2 [M+H]$^+$. $^1$H NMR (500 MHz, DMSO-d$_6$) δ 8.47 (d, J=8.9 Hz, 1H), 8.45-8.41 (m, 2H), 8.20 (s, 1H), 8.14 (d, J=8.8 Hz, 1H), 7.99 (s, 1H), 7.60-7.50 (m, 2H), 6.49 (s, 1H), 3.67-3.59 (m, 1H), 2.79 (s, 3H), 2.74-2.65 (m, 1H), 1.87-1.65 (m, 1H), 1.26 (d, J=6.3 Hz, 3H).

Example 264: (3S,5R)-3-((3-(4-Aminopyrido[3,2-d]pyrimidin-6-yl-2-d)phenyl)ethynyl)-3-hydroxy-1,5-dimethylpyrrolidin-2-one

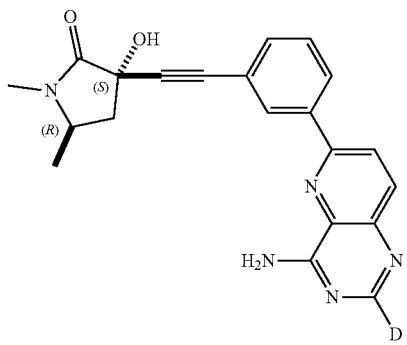

The title compound was prepared using analogous conditions described in Example 1 utilizing Intermediate 117 [6-(3-Iodophenyl)pyrido[3,2-d]pyrimidin-2-d-4-amine] and Intermediate 170 [(3S,5R)-3-ethynyl-3-hydroxy-1,5-dimethylpyrrolidin-2-one] to afford (3S,5R)-3-((3-(4-aminopyrido[3,2-d]pyrimidin-6-yl-2-d)phenyl)ethynyl)-3-hydroxy-1,5-dimethylpyrrolidin-2-one (23 mg, 22%) as a colorless solid. MS (ESI): mass calcd. for $C_{21}H_{18}DN_5O_2$, 374.16; m/z. found, 400.2 [M+H]$^+$. $^1$H NMR (500 MHz, DMSO-d$_6$) δ 8.49-8.38 (m, 3H), 8.19 (s, 1H), 8.13 (d, J=8.8 Hz, 1H), 7.97 (s, 1H), 7.58-7.51 (m, 2H), 6.45 (s, 1H), 3.69-3.58 (m, 1H), 2.77 (s, 3H), 2.47-2.40 (m, 1H), 2.12 (dd, J=13.2, 5.2 Hz, 1H), 1.28 (d, J=6.4 Hz, 3H).

Example 265: (3R,5R)-3-((3-(4-Amino-2-methylpyrido[3,2-d]pyrimidin-6-yl)phenyl)ethynyl)-3-hydroxy-1,5-dimethylpyrrolidin-2-one

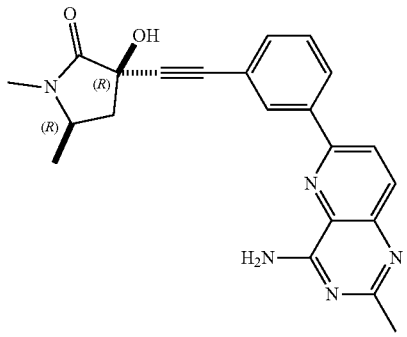

The title compound was prepared using analogous conditions described in Example 1 utilizing Intermediate 110 [6-(3-iodophenyl)-2-methylpyrido[3,2-d]pyrimidin-4-amine] and Intermediate 168 [(3R,5R)-3-ethynyl-3-hydroxy-1,5-dimethylpyrrolidin-2-one] to afford (3R,5R)-3-((3-(4-amino-2-methylpyrido[3,2-d]pyrimidin-6-yl)phenyl)ethynyl)-3-hydroxy-1,5-dimethylpyrrolidin-2-one (103 mg, 48%) as an orange solid. MS (ESI): mass calcd. for $C_{22}H_{21}N_5O_2$, 387.2; m/z. found, 388.1 [M+H]$^+$. $^1$H NMR (500 MHz, CD$_3$OD) δ 8.29 (br s, 1H), 8.24 (d, J=8.8 Hz, 1H), 8.15-8.19 (m, 1H), 7.99 (d, J=8.8 Hz, 1H), 7.55-7.41 (m, 2H), 3.80-3.66 (m, 1H), 2.90 (s, 3H), 2.80 (dd, J=12.8, 6.4 Hz, 1H), 2.53 (s, 3H), 1.90 (dd, J=12.8, 7.4 Hz, 1H), 1.35 (d, J=6.3 Hz, 3H).

Example 266: (3S,5S)-3-((3-(4-Amino-2-methylpyrido[3,2-d]pyrimidin-6-yl)phenyl)ethynyl)-3-hydroxy-1,5-dimethylpyrrolidin-2-one

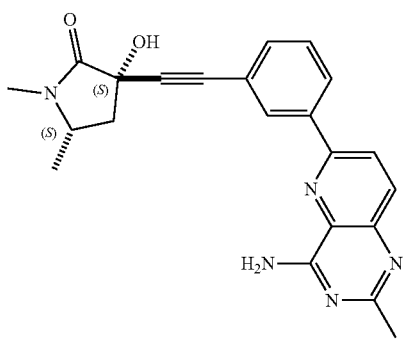

The title compound was prepared using analogous conditions described in Example 1 utilizing Intermediate 110 [6-(3-iodophenyl)-2-methylpyrido[3,2-d]pyrimidin-4-amine] and Intermediate 167 [(3S,5S)-3-ethynyl-3-hydroxy-1,5-dimethylpyrrolidin-2-one] to afford (3S,5S)-3-((3-(4-amino-2-methylpyrido[3,2-d]pyrimidin-6-yl)phenyl)ethynyl)-3-hydroxy-1,5-dimethylpyrrolidin-2-one (190 mg, 89%) as an orange solid. MS (ESI): mass calcd. for $C_{22}H_{21}N_5O_2$, 387.2; m/z. found, 388.0 [M+H]$^+$. $^1$H NMR (500 MHz, CD$_3$OD) δ 8.29 (br s, 1H), 8.24 (d, J=8.8 Hz, 1H), 8.15-8.19 (m, 1H), 7.99 (d, J=8.8 Hz, 1H), 7.55-7.41 (m, 2H), 3.80-3.66 (m, 1H), 2.90 (s, 3H), 2.80 (dd, J=12.8, 6.4 Hz, 1H), 2.53 (s, 3H), 1.90 (dd, J=12.8, 7.4 Hz, 1H), 1.35 (d, J=6.3 Hz, 3H).

Example 267: (3S,5R)-3-((3-(4-Amino-2-methylpyrido[3,2-d]pyrimidin-6-yl)phenyl)ethynyl)-3-hydroxy-1,5-dimethylpyrrolidin-2-one

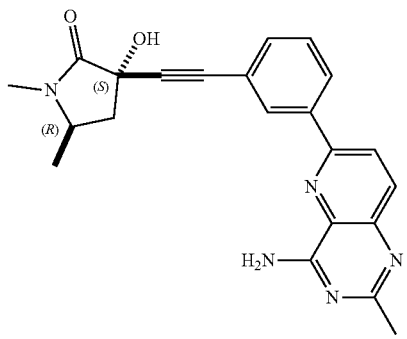

The title compound was prepared using analogous conditions described in Example 1 utilizing Intermediate 110 [6-(3-iodophenyl)-2-methylpyrido[3,2-d]pyrimidin-4-amine] and Intermediate 170 [(3S,5R)-3-ethynyl-3-hydroxy-1,5-dimethylpyrrolidin-2-one] to afford (3S,5R)-3-((3-(4-amino-2-methylpyrido[3,2-d]pyrimidin-6-yl)phenyl)ethynyl)-3-hydroxy-1,5-dimethylpyrrolidin-2-one (89 mg, 83%) as an orange solid. MS (ESI): mass calcd. for $C_{22}H_{21}N_5O_2$, 387.2; m/z. found, 388.1 [M+H]$^+$. $^1$H NMR (500 MHz, CD$_3$OD) δ 8.38 (d, J=1.8 Hz, 1H), 8.32 (d, J=8.9 Hz, 1H), 8.24 (dt, J=7.6, 1.5 Hz, 1H), 8.05 (d, J=8.9 Hz, 1H), 7.60-7.44 (m, 2H), 3.84-3.67 (m, 1H), 2.90 (s, 3H), 2.55 (s, 4H), 2.25 (dd, J=13.4, 4.9 Hz, 1H), 1.37 (d, J=6.3 Hz, 3H).

Example 268: (3R,5S)-3-((3-(4-Amino-2-methylpyrido[3,2-d]pyrimidin-6-yl)phenyl)ethynyl)-3-hydroxy-1,5-dimethylpyrrolidin-2-one

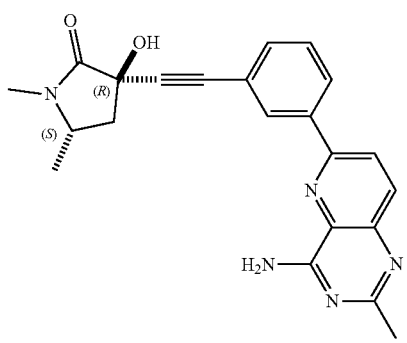

The title compound was prepared using analogous conditions described in Example 1 utilizing Intermediate 110 [6-(3-iodophenyl)-2-methylpyrido[3,2-d]pyrimidin-4-amine] and Intermediate 169 [(3R,5S)-3-ethynyl-3-hydroxy-1,5-dimethylpyrrolidin-2-one] to afford (3R,5S)-3-((3-(4-amino-2-methylpyrido[3,2-d]pyrimidin-6-yl)phenyl)ethynyl)-3-hydroxy-1,5-dimethylpyrrolidin-2-one (85 mg, 79%) as an orange solid. MS (ESI): mass calcd. for $C_{22}H_{21}N_5O_2$, 387.2; m/z. found, 388.1 [M+H]$^+$. $^1$H NMR (500 MHz, CD$_3$OD) δ 8.38 (d, J=1.8 Hz, 1H), 8.32 (d, J=8.9 Hz, 1H), 8.24 (dt, J=7.6, 1.5 Hz, 1H), 8.05 (d, J=8.9 Hz, 1H), 7.60-7.44 (m, 2H), 3.84-3.67 (m, 1H), 2.90 (s, 3H), 2.55 (s, 4H), 2.25 (dd, J=13.4, 4.9 Hz, 1H), 1.37 (d, J=6.3 Hz, 3H).

Example 269: (R)—N-(6-(3-((3-Hydroxy-1-methyl-2-oxopyrrolidin-3-yl)ethynyl)phenyl)pyrido[3,2-d]pyrimidin-4-yl-2-d)methanesulfonamide

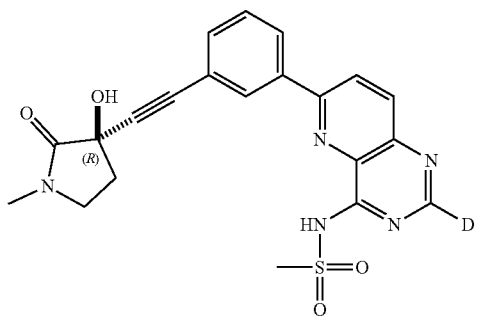

The title compound was prepared using analogous conditions described in Example 1 utilizing to afford Intermediate 171 [N-(6-(3-iodophenyl)pyrido[3,2-d]pyrimidin-4-yl-2-d)methanesulfonamide] to afford (R)—N-(6-(3-((3-hydroxy-1-methyl-2-oxopyrrolidin-3-yl)ethynyl)phenyl)pyrido[3,2-d]pyrimidin-4-yl-2-d)methanesulfonamide (30 mg, 42%) as a brown solid. MS (ESI): mass calcd. for C$_{21}$H$_{19}$N$_5$O$_4$S 438.1 m/z found 439.1 [M+H]$^+$. $^1$H NMR (500 MHz, CD$_3$OD) δ 8.34 (d, J=8.8 Hz, 1H), 8.28 (br s, 1H), 8.23-8.11 (m, 2H), 7.48-7.52 (m, 1H), 7.44 (t, J=7.7 Hz, 1H), 3.56-3.40 (m, 5H), 2.94 (s, 3H), 2.58-2.64 (m, 1H), 2.29-2.35 (m, 1H).

Example 270: (R)-3-((3-(4-Cyclopropylpyrido[3,2-d]pyrimidin-6-yl)phenyl)ethynyl)-3-hydroxy-1-methylpyrrolidin-2-one

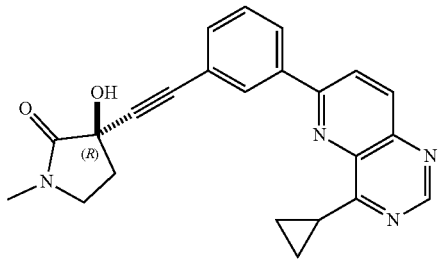

The title compound was prepared using analogous conditions described in Example 221 utilizing Intermediate 172 [6-chloro-4-cyclopropylpyrido[3,2-d]pyrimidine] to afford (R)-3-((3-(4-cyclopropylpyrido[3,2-d]pyrimidin-6-yl)phenyl)ethynyl)-3-hydroxy-1-methylpyrrolidin-2-one (37.4 mg, 28%) as a white solid. MS (ESI): mass calcd. for C$_{23}$H$_{20}$N$_4$O$_2$ 384.2 m/z found 385.2, [M+H]$^+$. $^1$H NMR (400 MHz, CDCl$_3$) δ 9.12 (s, 1H), 8.38-8.34 (m, 1H), 8.29 (s, 1H), 8.25 (d, J=8.8 Hz, 1H), 8.20 (d, J=7.7 Hz, 1H), 7.60-7.56 (m, 1H), 7.52-7.48 (m, 1H), 3.80-3.74 (m, 1H), 3.57-3.50 (m, 2H), 3.44-3.38 (m, 1H), 2.99 (s, 3H), 2.70 (ddd, J=2.4, 6.8, 12.6 Hz, 1H), 2.45-2.38 (m, 1H), 1.50-1.46 (m, 2H), 1.44-1.38 (m, 2H).

Example 271: (R)-3-((3-(4-Aminopyrido[3,2-d]pyrimidin-6-yl)-4-(trifluoromethoxy)phenyl)ethynyl)-3-hydroxy-1-methylpyrrolidin-2-one

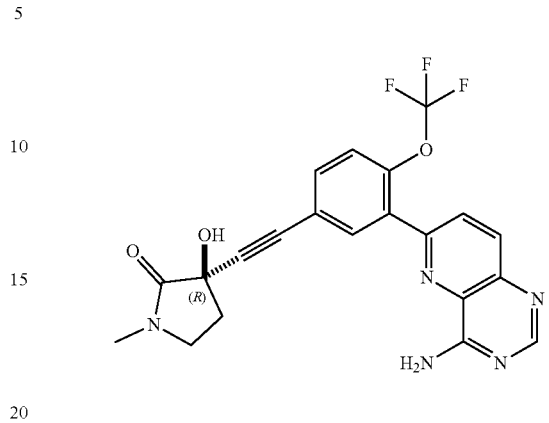

The title compound was prepared using analogous conditions described in Example 221 utilizing 6-chloropyrido[3,2-d]pyrimidin-4-amine and Intermediate 27 [(R)-3-hydroxy-1-methyl-3-((3-(4,4,5,5-tetramethyl-1,3,2-dioxaborolan-2-yl)-4-(trifluoromethoxy)phenyl)ethynyl)pyrrolidin-2-one] to afford (R)-3-((3-(4-aminopyrido[3,2-d]pyrimidin-6-yl)-4-(trifluoromethoxy)phenyl)ethynyl)-3-hydroxy-1-methylpyrrolidin-2-one (41.0 mg, 33%) as a colorless solid. MS (ESI): mass calcd. for C$_{21}$H$_{16}$F$_3$N$_5$O$_3$ 443.1 m/z, found 444.0 [M+H]$^+$. $^1$H NMR (400 MHz, DMSO-d$_6$) δ 8.47 (s, 1H), 8.24-8.16 (m, 1H), 8.15-8.00 (m, 4H), 7.73-7.65 (m, 1H), 7.63-7.55 (m, 1H), 6.56 (s, 1H), 3.36-3.33 (m, 2H), 2.81 (s, 3H), 2.49-2.42 (m, 1H), 2.25-2.15 (m, 1H). $^{19}$F NMR (376 MHz, DMSO-d$_6$) δ −56.35 (s, 3F).

Example 272: (R)-3-Hydroxy-3-((3-(4-isopropylpyrido[3,2-d]pyrimidin-6-yl)phenyl)ethynyl)-1-methylpyrrolidin-2-one

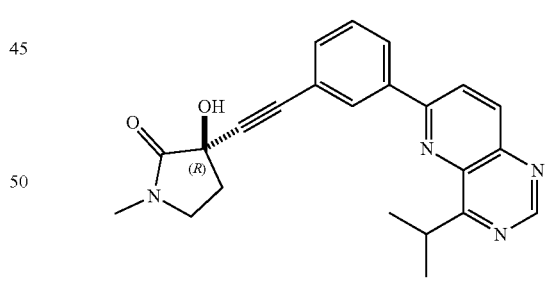

The title compound was prepared using analogous conditions described in Example 221 utilizing Intermediate 173 [6-chloro-4-isopropylpyrido[3,2-d]pyrimidine] to afford (R)-3-hydroxy-3-((3-(4-isopropylpyrido[3,2-d]pyrimidin-6-yl)phenyl)ethynyl)-1-methylpyrrolidin-2-one (27 mg, 20%) as a white solid. MS (ESI): mass calcd. for C$_{23}$H$_{22}$N$_4$O$_2$ 386.2 m/z found 387.1 [M+H]$^+$. $^1$H NMR (400 MHz, CDCl$_3$) δ 9.30 (s, 1H), 8.39 (d, J=8.8 Hz, 1H), 8.31-8.10 (m, 3H), 7.71-7.54 (m, 1H), 7.53-7.45 (m, 1H), 4.78-4.58 (m, 1H), 3.66 (s, 1H), 3.60-3.49 (m, 1H), 3.48-3.34 (m, 1H), 2.99 (s, 3H), 2.77-2.65 (m, 1H), 2.48-2.37 (m, 1H), 1.49 (d, J=6.8 Hz, 6H).

Example 273: (1R,4R,5S)-4-((3-(4-Amino-2-methylpyrido[3,2-d]pyrimidin-6-yl)phenyl)ethynyl)-4-hydroxy-2-methyl-2-azabicyclo[3.1.0]hexan-3-one

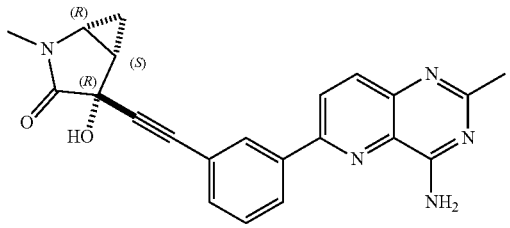

The title compound was prepared using analogous conditions described in Example 1 utilizing Intermediate 110 [6-(3-iodophenyl)-2-methylpyrido[3,2-d]pyrimidin-4-amine] and Intermediate 175 [(1R,4R,5S)-4-ethynyl-4-hydroxy-2-methyl-2-azabicyclo[3.1.0]hexan-3-one] to afford (1R,4R,5S)-4-((3-(4-amino-2-methylpyrido[3,2-d]pyrimidin-6-yl)phenyl)ethynyl)-4-hydroxy-2-methyl-2-azabicyclo[3.1.0]hexan-3-one (125 mg, 59%) as a white solid. MS (ESI): mass calcd. for $C_{22}H_{19}N_5O_2$, 385.2; m/z found, 386.1 [M+H]$^+$. $^1$H NMR (500 MHz, CDCl$_3$) δ 7.99 (d, J=8.8 Hz, 1H), 7.82 (ddd, J=10.7, 8.2, 2.1 Hz, 2H), 7.77 (s, 1H), 7.46-7.40 (m, 1H), 7.39-7.32 (m, 1H), 7.14 (s, 2H), 5.95 (s, 1H), 3.22 (ddd, J=7.0, 4.7, 2.5 Hz, 1H), 3.01 (s, 3H), 2.70 (s, 3H), 2.17 (ddd, J=8.6, 6.8, 4.8 Hz, 1H), 1.01 (ddd, J=8.6, 6.3, 4.7 Hz, 1H), 0.92 (ddt, J=7.0, 4.1, 1.4 Hz, 1H).

Example 274: (1 S,4S,5R)-4-((3-(4-Amino-2-methylpyrido[3,2-d]pyrimidin-6-yl)phenyl)ethynyl)-4-hydroxy-2-methyl-2-azabicyclo[3.1.0]hexan-3-one

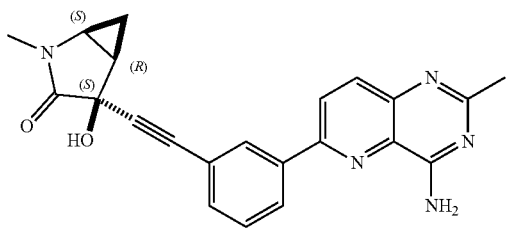

The title compound was prepared using analogous conditions described in Example 1 utilizing Intermediate 110 [6-(3-iodophenyl)-2-methylpyrido[3,2-d]pyrimidin-4-amine] and Intermediate 174 [(1 S,4S,5R)-4-ethynyl-4-hydroxy-2-methyl-2-azabicyclo[3.1.0]hexan-3-one] to afford (1 S,4S,5R)-4-((3-(4-amino-2-methylpyrido[3,2-d]pyrimidin-6-yl)phenyl)ethynyl)-4-hydroxy-2-methyl-2-azabicyclo[3.1.0]hexan-3-one (120 mg, 56%) as a white solid. MS (ESI): mass calcd. for $C_{22}H_{19}N_5O_2$, 385.2; m/z found, 386.1 [M+H]$^+$. $^1$H NMR (500 MHz, CDCl$_3$) δ 7.99 (d, J=8.8 Hz, 1H), 7.82 (ddd, J=10.7, 8.2, 2.1 Hz, 2H), 7.77 (s, 1H), 7.46-7.40 (m, 1H), 7.39-7.32 (m, 1H), 7.14 (s, 2H), 5.95 (s, 1H), 3.22 (ddd, J=7.0, 4.7, 2.5 Hz, 1H), 3.01 (s, 3H), 2.70 (s, 3H), 2.17 (ddd, J=8.6, 6.8, 4.8 Hz, 1H), 1.01 (ddd, J=8.6, 6.3, 4.7 Hz, 1H), 0.92 (ddt, J=7.0, 4.1, 1.4 Hz, 1H).

Example 275: (1 S,4S,5R)-4-((3-(4-Aminopyrido[3,2-d]pyrimidin-6-yl-2-d)phenyl)ethynyl)-4-hydroxy-2-methyl-2-azabicyclo[3.1.0]hexan-3-one

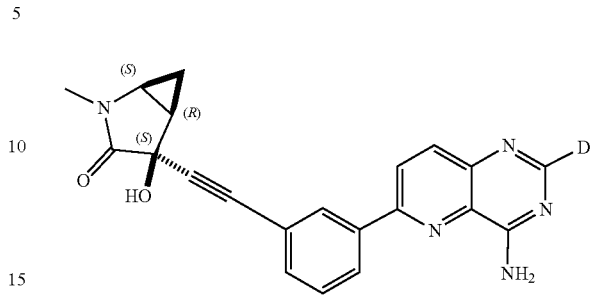

The title compound was prepared using analogous conditions described in Example 1 utilizing Intermediate 117 [6-(3-Iodophenyl)pyrido[3,2-d]pyrimidin-2-d-4-amine] and Intermediate 174 [(1 S,4S,5R)-4-ethynyl-4-hydroxy-2-methyl-2-azabicyclo[3.1.0]hexan-3-one] to afford (1 S,4S,5R)-4-((3-(4-aminopyrido[3,2-d]pyrimidin-6-yl-2-d)phenyl)ethynyl)-4-hydroxy-2-methyl-2-azabicyclo[3.1.0]hexan-3-one (97 mg, 47%) as a white solid. MS (ESI): mass calcd. for $C_{21}H_{17}N_5O_2$, 372.1; m/z found, 373.1 [M+H]$^+$. $^1$H NMR (400 MHz, CDCl$_3$) δ 8.05 (d, J=8.8 Hz, 1H), 7.80 (ddd, J=7.8, 1.9, 1.2 Hz, 1H), 7.75 (d, J=8.8 Hz, 1H), 7.61 (t, J=1.7 Hz, 1H), 7.43 (dt, J=7.8, 1.4 Hz, 1H), 7.33 (t, J=7.7 Hz, 1H), 7.14 (s, 2H), 3.20-3.25 (m, 1H), 3.02 (s, 3H), 2.16-2.22 (m, 1H), 1.09-0.88 (m, 2H).

Example 276: (1R,4R,5S)-4-((3-(4-Aminopyrido[3,2-d]pyrimidin-6-yl-2-d)phenyl)ethynyl)-4-hydroxy-2-methyl-2-azabicyclo[3.1.0]hexan-3-one

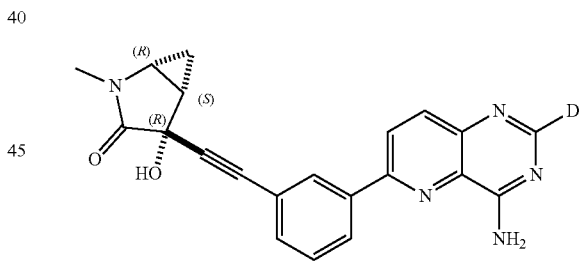

The title compound was prepared using analogous conditions described in Example 1 utilizing Intermediate 117 [6-(3-Iodophenyl)pyrido[3,2-d]pyrimidin-2-d-4-amine] and Intermediate 175 [(1R,4R,5S)-4-ethynyl-4-hydroxy-2-methyl-2-azabicyclo[3.1.0]hexan-3-one] to afford (1R,4R,5S)-4-((3-(4-aminopyrido[3,2-d]pyrimidin-6-yl-2-d)phenyl)ethynyl)-4-hydroxy-2-methyl-2-azabicyclo[3.1.0]hexan-3-one (102 mg, 50%) as white solid. MS (ESI): mass calcd. for $C_{21}H_{17}N_5O_2$, 372.1; m/z. found, 373.1 [M+H]$^+$. $^1$H NMR (400 MHz, CDCl$_3$) δ 8.05 (d, J=8.8 Hz, 1H), 7.80 (ddd, J=7.8, 1.9, 1.2 Hz, 1H), 7.75 (d, J=8.8 Hz, 1H), 7.61 (t, J=1.7 Hz, 1H), 7.43 (dt, J=7.8, 1.4 Hz, 1H), 7.33 (t, J=7.7 Hz, 1H), 7.14 (s, 2H), 3.20-3.25 (m, 1H), 3.02 (s, 3H), 2.16-2.22 (m, 1H), 1.09-0.88 (m, 2H).

Example 277: (R)-3-((3-(4-Amino-8-cyclopentylpyrido[3,2-d]pyrimidin-6-yl-2-d)phenyl)ethynyl)-3-hydroxy-1-methylpyrrolidin-2-one

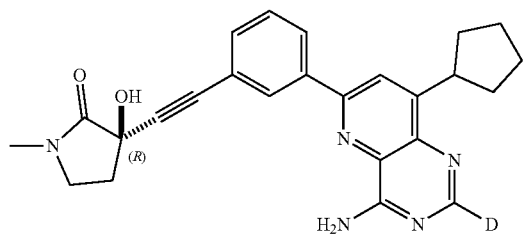

A vial was flushed with nitrogen and charged with Example 8 [(R)-3-((3-(4-aminopyrido[3,2-d]pyrimidin-6-yl-2-d)phenyl)ethynyl)-3-hydroxy-1-methylpyrrolidin-2-one (125 mg, 0.34 mmol)], 1,3-dioxoisoindolin-2-yl cyclopentanecarboxylate (0.13 g, 0.52 mmol), and [4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate (7.72 mg, 6.88 μmol). Then DMSO (2.55 mL) was added followed by trifluoroacetic acid (0.106 mL, 1.38 mmol). The reaction mixture was subjected to a 450 nm photoreactor with 1000 rpm stirring, 3500 rpm fan, and 100% LCD for 4 h. After which time, an additional 1,3-dioxoisoindolin-2-yl cyclopentanecarboxylate (44.6 mg, 0.17 mmol) was added and the resulting mixture was re-subjected to a 450 nm photoreactor (1000 rpm stirring, 3500 rpm fan 100% LCD) for 2 h. The resulting mixture was purified directly by preparative reverse phase HPLC (C18, 10-100% MeCN/H$_2$O) to afford (R)-3-((3-(4-amino-8-cyclopentylpyrido[3,2-d]pyrimidin-6-yl-2-d)phenyl)ethynyl)-3-hydroxy-1-methylpyrrolidin-2-one (25 mg, 17%) as a white solid. MS (ESI): mass calcd. for C$_{25}$H$_{24}$DN$_5$O$_2$, 428.21; m/z. found, 429.0 [M+H]$^+$. $^1$H NMR (500 MHz, DMSO-d$_6$) δ 8.44 (dt, J=7.0, 2.1 Hz, 1H), 8.43-8.41 (m, 1H), 8.25 (s, 1H), 8.09 (br s, 1H), 7.90 (br s, 1H), 7.58-7.50 (m, 2H), 6.47 (br s, 1H), 4.00 (tt, J=9.5, 7.4 Hz, 1H), 3.37 (dd, J=7.2, 5.8 Hz, 2H), 2.81 (s, 3H), 2.53-2.45 (m, 1H), 2.21 (dt, J=12.8, 7.1 Hz, 1H), 2.12-2.06 (m, 2H), 1.91-1.84 (m, 2H), 1.84-1.69 (m, 4H).

Example 278: (R)-3-Hydroxy-1-methyl-3-((3-(4-(trifluoromethyl)pyrido[3,2-d]pyrimidin-6-yl)phenyl)ethynyl)pyrrolidin-2-one

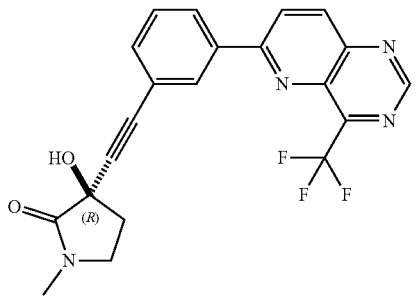

The title compound was prepared using analogous conditions described in Example 221 utilizing Intermediate 178 [6-chloro-4-(trifluoromethyl)pyrido[3,2-d]pyrimidine] to afford (R)-3-hydroxy-1-methyl-3-((3-(4-(trifluoromethyl)pyrido[3,2-d]pyrimidin-6-yl)phenyl)ethynyl)pyrrolidin-2-one (42.2 mg, 15%) as a white solid. MS (ESI): mass calcd. for C$_{21}$H$_{15}$F$_3$N$_4$O$_2$ 412.1 m/z found 413.0, [M+H]$^+$. $^1$H NMR (400 MHz, CDCl$_3$) δ 9.49 (s, 1H), 8.52 (d, J=9.0 Hz, 1H), 8.39 (d, J=9.0 Hz, 1H), 8.34-8.26 (m, 1H), 8.25-8.20 (m, 1H), 7.65-7.56 (m, 1H), 7.53-7.47 (m, 1H), 3.87 (s, 1H), 3.58-3.50 (m, 1H), 3.46-3.38 (m, 1H), 3.00 (s, 3H), 2.74-2.65 (m, 1H), 2.47-2.37 (m, 1H).

Example 279: (R)-6-(3-((3-Hydroxy-1-methyl-2-oxopyrrolidin-3-yl)ethynyl)phenyl)pyrido[3,2-d]pyrimidine-4-carbonitrile

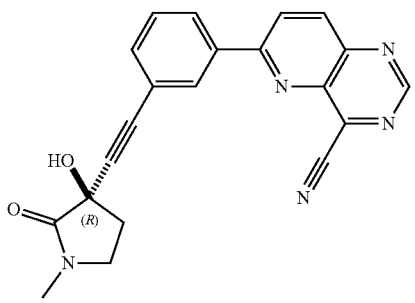

The title compound was prepared using analogous conditions described in Example 1 utilizing Intermediate 179 [6-(3-iodophenyl)pyrido[3,2-d]pyrimidine-4-carbonitrile] to afford (R)-6-(3-((3-hydroxy-1-methyl-2-oxopyrrolidin-3-yl)ethynyl)phenyl)pyrido[3,2-d]pyrimidine-4-carbonitrile (14.4 mg, 17%) as a brown solid. MS (ESI): mass calcd. for C$_{21}$H$_{15}$N$_5$O$_2$ 369.1 m/z found 370.0 [M+H]$^+$. $^1$H NMR (400 MHz, DMSO-d$_6$) δ 9.61 (s, 1H), 8.90 (d, J=9.0 Hz, 1H), 8.71 (d, J=9.0 Hz, 1H), 8.47-8.38 (m, 2H), 7.72-7.63 (m, 2H), 6.57 (s, 1H), 3.42-3.38 (m, 2H), 2.82 (s, 3H), 2.47-2.43 (m, 1H), 2.27-2.16 (m, 1H).

Example 280: (R)-3-Hydroxy-1-methyl-3-((3-(8-methyl-1,7-naphthyridin-2-yl)phenyl)ethynyl)pyrrolidin-2-one

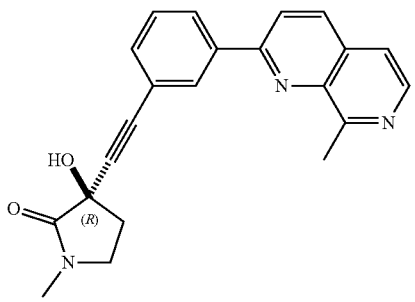

The title compound was prepared using analogous conditions described in Example 1 utilizing Intermediate 180 [2-(3-iodophenyl)-8-methyl-1,7-naphthyridine] to afford (R)-3-hydroxy-1-methyl-3-((3-(8-methyl-1,7-naphthyridin-2-yl)phenyl)ethynyl)pyrrolidin-2-one (45.9 mg, 30%) as a yellow solid. MS (ESI): mass calcd. for C$_{22}$H$_{19}$N$_3$O$_2$ 357.2 m/z. found 358.1 [M+H]$^+$. $^1$H NMR (400 MHz, DMSO-d$_6$): δ 8.52-8.47 (m, 1H), 8.47-8.41 (m, 2H), 8.37-8.33 (m, 2H), 7.77 (d, J=5.5 Hz, 1H), 7.65-7.55 (m, 2H), 6.56 (s, 1H), 3.38-3.36 (m, 2H), 3.04 (s, 3H), 2.82 (s, 3H), 2.48-2.45 (m, 1H), 2.26-2.17 (m, 1H).

Example 281: (1R,4R,5S)-4-((3-(4-Amino-8-methylpyrido[3,2-d]pyrimidin-6-yl)phenyl)ethynyl)-4-hydroxy-2-methyl-2-azabicyclo[3.1.0]hexan-3-one

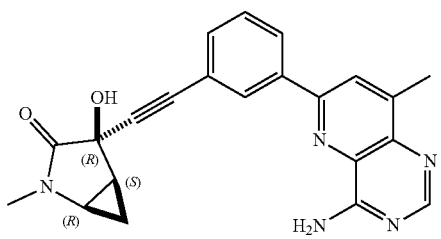

The title compound was prepared using analogous conditions described in Example 221 utilizing Intermediate 181 [6-chloro-8-methylpyrido[3,2-d]pyrimidin-4-amine] and Intermediate 182 [(1R,4R,5S)-4-hydroxy-2-methyl-4-((3-(4,4,5,5-tetramethyl-1,3,2-dioxaborolan-2-yl)phenyl)ethynyl)-2-azabicyclo[3.1.0]hexan-3-one] to afford (1R,4R,5S)-4-((3-(4-amino-8-methylpyrido[3,2-d]pyrimidin-6-yl)phenyl)ethynyl)-4-hydroxy-2-methyl-2-azabicyclo[3.1.0]hexan-3-one (15 mg, 15%) as a yellow solid. MS (ESI): mass calcd. for $C_{22}H_{19}N_5O_2$ 385.2 m/z. found 386.0 [M+H]$^+$. $^1$H NMR (400 MHz, DMSO-d$_6$) δ 8.49-8.44 (m, 1H), 8.44-8.40 (m, 2H), 8.39 (s, 1H), 8.14 (br. s, 1H), 7.91 (br. s, 1H), 7.60-7.51 (m, 2H), 6.42 (br. s, 1H), 3.32-3.21 (m, 1H), 2.82 (s, 3H), 2.65 (s, 3H), 2.12-2.03 (m, 1H), 0.89-0.83 (m, 1H), 0.68-0.61 (m, 1H).

Example 282: (R)-3-((3-(4-Amino-8-(aminomethyl)pyrido[3,2-d]pyrimidin-6-yl-2-d)phenyl)ethynyl)-3-hydroxy-1-methylpyrrolidin-2-one

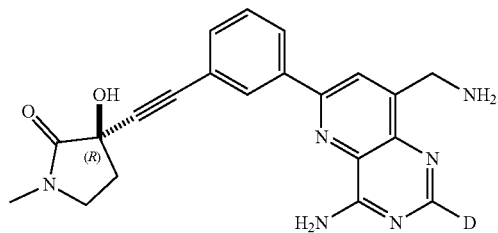

Step A: A vial was flushed with N$_2$ and charged with Example 8 [(R)-3-((3-(4-aminopyrido[3,2-d]pyrimidin-6-yl-2-d)phenyl)ethynyl)-3-hydroxy-1-methylpyrrolidin-2-one (200 mg, 0.551 mmol)], 1,3-dioxoisoindolin-2-yl (tert-butoxycarbonyl)glycinate (0.826 mmol), and [4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate (12.4 mg, 11.0 μmol). Then DMSO (3.06 mL, 0.180 M) was added followed by trifluoroacetic acid (0.170 mL, 2.20 mmol). The reaction mixture was subjected to a 450 nm photoreactor with 1000 rpm stirring, 3500 rpm fan, and 100% LCD for 4 h. After which time additional 1,3-dioxoisoindolin-2-yl (tert-butoxycarbonyl) glycinate (0.200 mmol) was added and the resulting mixture was re-subjected to a 450 nm photoreactor (1000 rpm stirring, 3500 rpm fan, 100% LCD) for 2 h. The resulting mixture was purified on reverse phase preparative HPLC (C18, 10% MeCN/H$_2$O for 2 min, 10-25% MeCN/H$_2$O for 2 min, 25-60% MeCN/H$_2$O for 15 min, 60-100% MeCN/H$_2$O for 4 min) to give tert-butyl (R)-((4-amino-6-(3-((3-hydroxy-1-methyl-2-oxopyrrolidin-3-yl)ethynyl)phenyl)pyrido[3,2-d]pyrimidin-8-yl-2-d)methyl)carbamate (15.0 mg, 5.57%) as a white solid. MS (ESI): mass calc'd. For $C_{26}H_{27}DN_6O_4$, 489.22; m/z. found, 490.0 [M+H]$^+$.

Step B: HCl (4M in dioxane) (0.306 mL, 4.0 M, 1.23 mmol) was added to a solution of tert-butyl (R)-((4-amino-6-(3-((3-hydroxy-1-methyl-2-oxopyrrolidin-3-yl)ethynyl)phenyl)pyrido[3,2-d]pyrimidin-8-yl-2-d)methyl)carbamate (15.0 mg, 30.6 μmol) in 1,4-dioxane (0.31 mL) at rt and stirred for 2 h. The resulting mixture was purified on reverse phase preparative HPLC (C18, 10-50% MeCN/H$_2$O, 15 min) to give (R)-3-((3-(4-amino-8-(aminomethyl)pyrido[3,2-d]pyrimidin-6-yl-2-d)phenyl)ethynyl)-3-hydroxy-1-methylpyrrolidin-2-one (9.40 mg, 78.8%) as a white solid. MS (ESI): mass calc'd. For $C_{21}H_{19}DN_6O_2$, 389.17; m/z. found, 390.1 [M+H]$^+$.

Example 283: (R)-3-((3-(4-Amino-8-isopropylpyrido[3,2-d]pyrimidin-6-yl-2-d)phenyl)ethynyl)-3-hydroxy-1-methylpyrrolidin-2-one

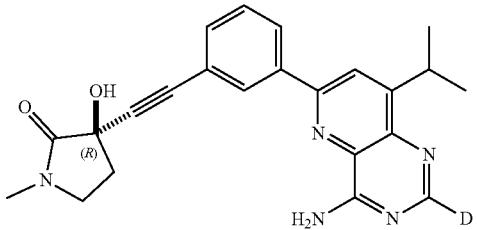

A vial was flushed with N$_2$ and charged with Example 8 [(R)-3-((3-(4-aminopyrido[3,2-d]pyrimidin-6-yl-2-d)phenyl)ethynyl)-3-hydroxy-1-methylpyrrolidin-2-one (200 mg, 0.551 mmol)], 1,3-dioxoisoindolin-2-yl isobutyrate (0.826 mmol), and [4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate (12.4 mg, 11.0 μmol). Then DMSO (3.06 mL, 0.180 M) was added followed by trifluoroacetic acid (0.170 mL, 2.20 mmol). The reaction mixture was subjected to a 450 nm photoreactor with 1000 rpm stirring, 3500 rpm fan, and 100% LCD for 4 h. After which time additional 1,3-dioxoisoindolin-2-yl isobutyrate (46.6 mg, 0.200 mmol) was added and the resulting mixture was re-subjected to a 450 nm photoreactor (1000 rpm stirring, 3500 rpm fan, 100% LCD) for 2 h. The resulting material was purified on a reverse phase preparative HPLC (C18, 10% MeCN/H$_2$O for 2 min, 10-25% MeCN/H$_2$O for 2 min, 25-60% MeCN/H$_2$O for 15 min, 60-100% MeCN/H$_2$O for 4 min) to give (R)-3-((3-(4-amino-8-isopropylpyrido[3,2-d]pyrimidin-6-yl-2-d)phenyl)ethynyl)-3-hydroxy-1-methylpyrrolidin-2-one (22.0 mg, 9.93%) as a white solid. MS (ESI): mass calc'd. For $C_{23}H_{22}DN_5O_2$, 402.19; m/z. found, 403.0 [M+H]$^+$.

Example 284: (R)-3-((3-(4-Amino-8-(trifluoromethyl)pyrido[3,2-d]pyrimidin-6-yl)phenyl)ethynyl)-3-hydroxy-1-methylpyrrolidin-2-one

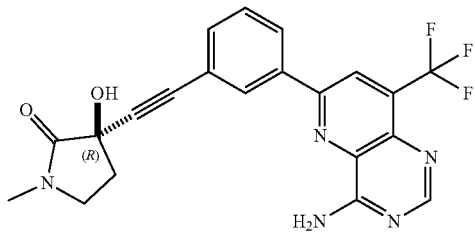

The title compound was prepared using analogous conditions described in Example 221 utilizing Intermediate 183 [6-chloro-8-(trifluoromethyl)pyrido[3,2-d]pyrimidin-4-amine] to afford (R)-3-((3-(4-amino-8-(trifluoromethyl)pyrido[3,2-d]pyrimidin-6-yl)phenyl)ethynyl)-3-hydroxy-1-methylpyrrolidin-2-one (42 mg, 35%) as a white solid. MS (ESI): mass calcd. for $C_{21}H_{16}F_3N_5O_2$ 427.1 m/z. found 428.1 [M+H]$^+$. $^1$H NMR (400 MHz, DMSO-d$_6$) δ 8.70 (s, 1H), 8.59-8.46 (m, 4H), 8.30 (br. s, 1H), 7.62-7.52 (m, 2H), 6.58 (br s, 1H), 3.54-3.46 (m, 2H), 2.82 (s, 3H), 2.48-2.39 (m, 1H), 2.27-2.16 (m, 1H). $^{19}$F NMR (376 MHz, DMSO-d$_6$) δ 60.75 (s, 3F).

Example 285: (R)-3-((3-(4-Amino-2,8-dimethylpyrido[3,2-d]pyrimidin-6-yl)phenyl)ethynyl)-3-hydroxy-1-methylpyrrolidin-2-one

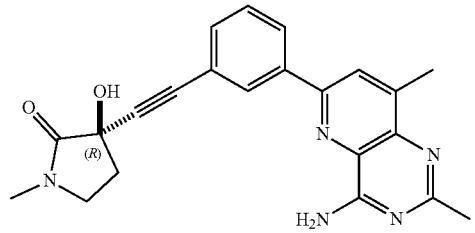

The title compound was prepared using analogous conditions described in Example 221 utilizing Intermediate 184 [6-chloro-2,8-dimethylpyrido[3,2-d]pyrimidin-4-amine] to afford (R)-3-((3-(4-amino-2,8-dimethylpyrido[3,2-d]pyrimidin-6-yl)phenyl)ethynyl)-3-hydroxy-1-methylpyrrolidin-2-one (23.3 mg, 17%) as a pink solid. MS (ESI): mass calcd. for $C_{22}H_{21}N_5O_2$ 387.2 m/z. found 388.1 [M+H]$^+$. $^1$H NMR (400 MHz, DMSO-d$_6$) δ 8.46-8.29 (m, 3H), 7.98 (br. s, 1H), 7.79 (br. s, 1H), 7.59-7.46 (m, 2H), 6.50 (br. s, 1H), 3.41-3.40 (m, 2H), 2.82 (s, 3H), 2.62 (s, 3H), 2.49-2.45 (m, 4H), 2.27-2.15 (m, 1H).

Example 286: (R)-3-((3-(4-Amino-8-(methyl-d$_3$)pyrido[3,2-d]pyrimidin-6-yl)phenyl)ethynyl)-3-hydroxy-1-methylpyrrolidin-2-one

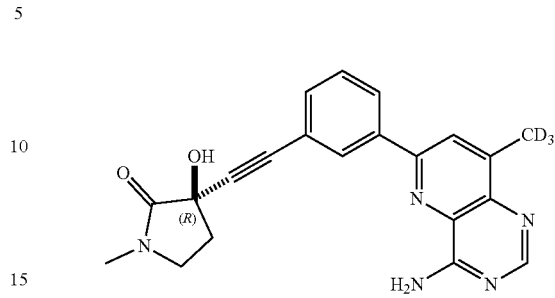

The title compound was prepared using analogous conditions described in Example 221 utilizing Intermediate 185 [6-chloro-8-(methyl-d$_3$)pyrido[3,2-d]pyrimidin-4-amine] to afford (R)-3-((3-(4-amino-8-(methyl-d$_3$)pyrido[3,2-d]pyrimidin-6-yl)phenyl)ethynyl)-3-hydroxy-1-methylpyrrolidin-2-one (48.3 mg, 36%) as a white solid. MS (ESI): mass calcd. for $C_{21}H_{16}D_3N_5O_2$ 376.2 m/z found 377.1 [M+H]$^+$. $^1$H NMR (400 MHz, DMSO-d$_6$) δ 8.49-8.34 (m, 4H), 8.13 (br s, 1H), 7.92 (br s, 1H), 7.59-7.49 (m, 2H), 6.51 (s, 1H), 3.43-3.39 (m, 2H), 2.82 (s, 3H), 2.49-2.44 (m, 1H), 2.26-2.17 (m, 1H).

Example 287: (R)-3-((3-(4-Amino-8-(piperidin-4-yl)pyrido[3,2-d]pyrimidin-6-yl-2-d)phenyl)ethynyl)-3-hydroxy-1-methylpyrrolidin-2-one

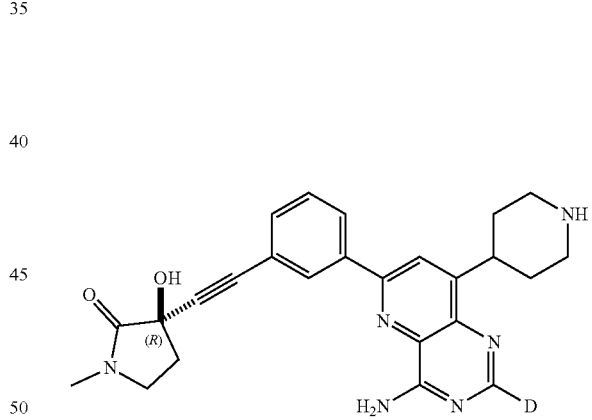

The title compound was prepared using analogous conditions described in Example 282 utilizing 1-(tert-butyl) 4-(1,3-dioxoisoindolin-2-yl) piperidine-1,4-dicarboxylate in Step A to afford (R)-3-((3-(4-amino-8-(piperidin-4-yl)pyrido[3,2-d]pyrimidin-6-yl-2-d)phenyl)ethynyl)-3-hydroxy-1-methylpyrrolidin-2-one (17.5 mg, 71.5%). MS (ESI): mass calc'd. For $C_{25}H_{25}DN_6O_2$, 443.22; m/z. found, 444.2 [M+H]$^+$.

Example 288: (R)-3-((3-(4-Amino-2-fluoropyrido[3,2-d]pyrimidin-6-yl)phenyl)ethynyl)-3-hydroxy-1-methylpyrrolidin-2-one

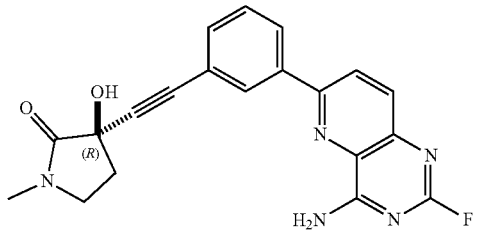

The title compound was prepared using analogous conditions described in Example 221 utilizing Intermediate 186 [6-chloro-2-fluoropyrido[3,2-d]pyrimidin-4-amine] to afford (R)-3-((3-(4-amino-2-fluoropyrido[3,2-d]pyrimidin-6-yl)phenyl)ethynyl)-3-hydroxy-1-methylpyrrolidin-2-one (23 mg, 42%) as a white solid. MS (ESI): mass calcd. for $C_{20}H_{16}FN_5O_2$ 377.1 m/z. found 378.0 [M+H]+. $^1$H NMR (400 MHz, DMSO-$d_6$) δ 8.77 (br s, 1H), 8.64 (br s, 1H), 8.50-8.42 (m, 3H), 8.11-8.03 (m, 1H), 7.60-7.51 (m, 2H), 6.51 (br s, 1H), 3.37-3.35 (m, 2H), 2.82 (s, 3H), 2.48-2.44 (m, 1H), 2.27-2.17 (m, 1H).

Example 289: (R)-3-((3-(4-Amino-8-(difluoromethyl)pyrido[3,2-d]pyrimidin-6-yl)phenyl)ethynyl)-3-hydroxy-1-methylpyrrolidin-2-one

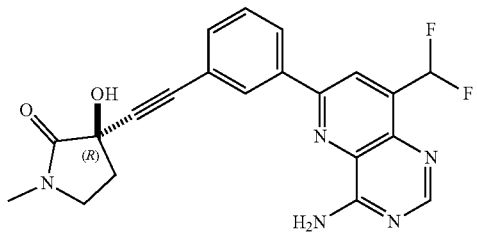

The title compound was prepared using analogous conditions described in Example 221 utilizing Intermediate 187 [6-chloro-8-(difluoromethyl)pyrido[3,2-d]pyrimidin-4-amine] to afford (R)-3-((3-(4-amino-8-(difluoromethyl)pyrido[3,2-d]pyrimidin-6-yl)phenyl)ethynyl)-3-hydroxy-1-methylpyrrolidin-2-one (9.3 mg, 12%) as a white solid. MS (ESI): mass calcd. for $C_{21}H_{17}F_2N_5O_2$ 409.1 m/z. found 410.0 [M+H]+. $^1$H NMR (400 MHz, DMSO-$d_6$) δ 8.59 (s, 1H), 8.54-8.41 (m, 4H), 8.23 (br s, 1H), 7.82-7.49 (m, 3H), 6.50 (s, 1H), 3.42-3.40 (m, 2H), 2.81 (s, 3H), 2.46-2.41 (m, 1H), 2.26-2.16 (m, 1H).

Example 290: (S)-3-((3-(4-Amino-8-(difluoromethyl)pyrido[3,2-d]pyrimidin-6-yl)phenyl)ethynyl)-3-hydroxy-1-methylpyrrolidin-2-one

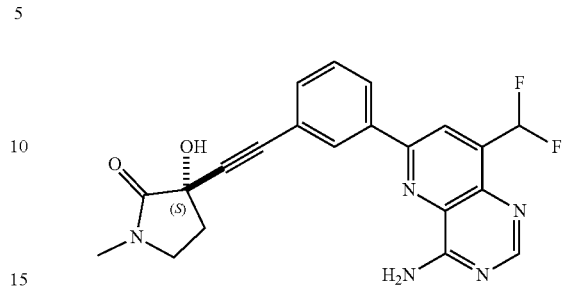

The title compound was prepared using analogous conditions described in Example 221 utilizing Intermediate 187 [6-chloro-8-(difluoromethyl)pyrido[3,2-d]pyrimidin-4-amine] and Intermediate 5 [(S)-3-hydroxy-1-methyl-3-((3-(4,4,5,5-tetramethyl-1,3,2-dioxaborolan-2-yl)phenyl)ethynyl)pyrrolidin-2-one] to afford (S)-3-((3-(4-amino-8-(difluoromethyl)pyrido[3,2-d]pyrimidin-6-yl)phenyl)ethynyl)-3-hydroxy-1-methylpyrrolidin-2-one (8.3 mg, 10%) as a white solid. MS (ESI): mass calcd. for $C_{21}H_{17}F_2N_5O_2$ 409.1 m/z. found 410.0 [M+H]+. $^1$H NMR (400 MHz, DMSO-$d_6$) δ 8.59 (s, 1H), 8.54-8.41 (m, 4H), 8.23 (br s, 1H), 7.82-7.49 (m, 3H), 6.50 (s, 1H), 3.42-3.40 (m, 2H), 2.81 (s, 3H), 2.46-2.41 (m, 1H), 2.26-2.16 (m, 1H).

Example 291: (3R,4S*)-3-((3-(4-Amino-2-methylpyrido[3,2-d]pyrimidin-6-yl)phenyl)ethynyl)-3-hydroxy-1,4-dimethylpyrrolidin-2-one

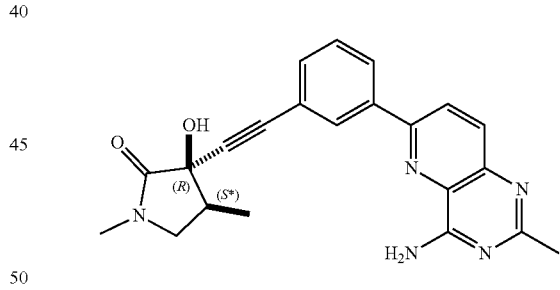

The title compound was prepared using analogous conditions described in Example 1 utilizing Intermediate 110 [6-(3-iodophenyl)-2-methylpyrido[3,2-d]pyrimidin-4-amine] and Intermediate 188 [(3R,4S*)-3-ethynyl-3-hydroxy-1,4-dimethylpyrrolidin-2-one] to afford (3R,4S*)-3-((3-(4-amino-2-methylpyrido[3,2-d]pyrimidin-6-yl)phenyl)ethynyl)-3-hydroxy-1,4-dimethylpyrrolidin-2-one (77 mg, 80%) as a white solid. MS (ESI): mass calcd. for $C_{22}H_{21}N_5O_2$ 387.2; m/z. found, 388.1 [M+H]+. $^1$H NMR (400 MHz, CDCl$_3$) δ 7.95 (d, J=8.7 Hz, 1H), 7.82-7.59 (m, 2H), 7.43-7.27 (m, 2H), 6.85-7.20 (m, 2H), 3.40-3.45 (m, 1H), 3.08-3.15 (m, 1H), 3.00 (s, 3H), 2.68 (s, 3H), 2.52-2.65 (m, 1H), 1.38 (d, J=6.8 Hz, 3H).

Example 292: (3R,4R*)-3-((3-(4-Amino-2-methylpyrido[3,2-d]pyrimidin-6-yl)phenyl)ethynyl)-3-hydroxy-1,4-dimethylpyrrolidin-2-one

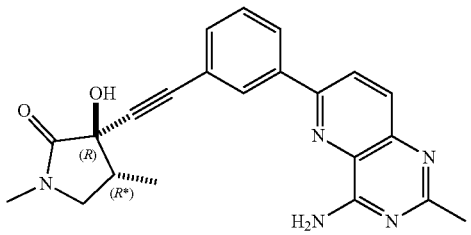

The title compound was prepared using analogous conditions described in Example 1 utilizing Intermediate 110 [6-(3-iodophenyl)-2-methylpyrido[3,2-d]pyrimidin-4-amine] and Intermediate 189 [(3R,4R*)-3-ethynyl-3-hydroxy-1,4-dimethylpyrrolidin-2-one] to afford (3R,4R*)-3-((3-(4-amino-2-methylpyrido[3,2-d]pyrimidin-6-yl)phenyl)ethynyl)-3-hydroxy-1,4-dimethylpyrrolidin-2-one (79 mg, 87%) as an amber solid. MS (ESI): mass calcd. for $C_{22}H_{21}N_5O_2$, 387.2; m/z. found, 388.1 [M+H]$^+$. $^1$H NMR (400 MHz, CDCl$_3$) δ 8.01-7.90 (m, 1H), 7.80-7.68 (m, 1H), 7.56-7.62 (m, 1H), 7.42-7.33 (m, 2H), 7.33-7.28 (m, 1H), 7.12 (br s, 1H), 3.61-3.46 (m, 1H), 3.16-3.22 (m, 1H), 2.99 (s, 3H), 2.65-2.75 (m, 4H), 1.28 (d, J=7.0 Hz, 3H).

Example 293: (3S,4S*)-3-((3-(4-Amino-2-methylpyrido[3,2-d]pyrimidin-6-yl)phenyl)ethynyl)-3-hydroxy-1,4-dimethylpyrrolidin-2-one

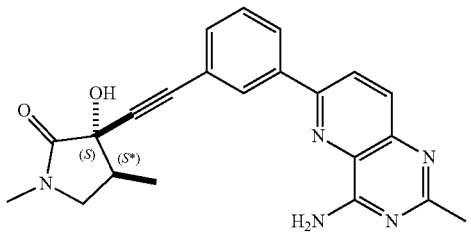

The title compound was prepared using analogous conditions described in Example 1 utilizing Intermediate 110 [6-(3-iodophenyl)-2-methylpyrido[3,2-d]pyrimidin-4-amine] and Intermediate 190 [(3S,4S*)-3-ethynyl-3-hydroxy-1,4-dimethylpyrrolidin-2-one] to afford (3S,4S*)-3-((3-(4-amino-2-methylpyrido[3,2-d]pyrimidin-6-yl)phenyl)ethynyl)-3-hydroxy-1,4-dimethylpyrrolidin-2-one (74 mg, 81%) as a white solid. MS (ESI): mass calcd. for $C_{22}H_{21}N_5O_2$, 387.2; m/z. found, 388.2 [M+H]$^+$. $^1$H NMR (400 MHz, CDCl$_3$) δ 8.01-7.90 (m, 1H), 7.80-7.68 (m, 1H), 7.56-7.62 (m, 1H), 7.42-7.33 (m, 2H), 7.33-7.28 (m, 1H), 7.12 (br s, 1H), 3.61-3.46 (m, 1H), 3.16-3.22 (m, 1H), 2.99 (s, 3H), 2.65-2.75 (m, 4H), 1.28 (d, J=7.0 Hz, 3H).

Example 294: (3S,4R*)-3-((3-(4-Amino-2-methylpyrido[3,2-d]pyrimidin-6-yl)phenyl)ethynyl)-3-hydroxy-1,4-dimethylpyrrolidin-2-one

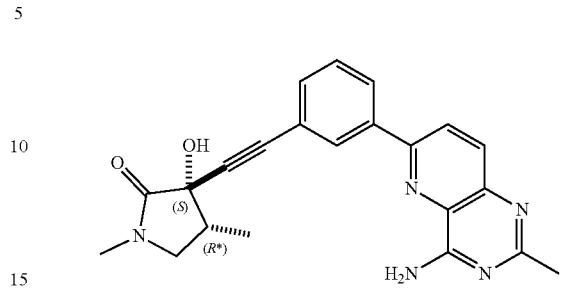

The title compound was prepared using analogous conditions described in Example 1 utilizing Intermediate 110 [6-(3-iodophenyl)-2-methylpyrido[3,2-d]pyrimidin-4-amine] and Intermediate 191 [(3S,4R*)-3-ethynyl-3-hydroxy-1,4-dimethylpyrrolidin-2-one] to afford (3S,4R*)-3-((3-(4-amino-2-methylpyrido[3,2-d]pyrimidin-6-yl)phenyl)ethynyl)-3-hydroxy-1,4-dimethylpyrrolidin-2-one (41 mg, 51%) as a white solid. MS (ESI): mass calcd. for $C_{22}H_{21}N_5O_2$, 387.2; m/z. found, 388.1 [M+H]$^+$. $^1$H NMR (400 MHz, CDCl$_3$) δ 7.95 (d, J=8.7 Hz, 1H), 7.82-7.59 (m, 2H), 7.43-7.27 (m, 2H), 6.85-7.20 (m, 2H), 3.40-3.45 (m, 1H), 3.08-3.15 (m, 1H), 3.00 (s, 3H), 2.68 (s, 3H), 2.52-2.65 (m, 1H), 1.38 (d, J=6.8 Hz, 3H).

Example 295: (R)-3-[2-[3-[4-Amino-8-(dimethylamino)pyrido[3,2-d]pyrimidin-6-yl]phenyl]ethynyl]-3-hydroxy-1-methyl-pyrrolidin-2-one

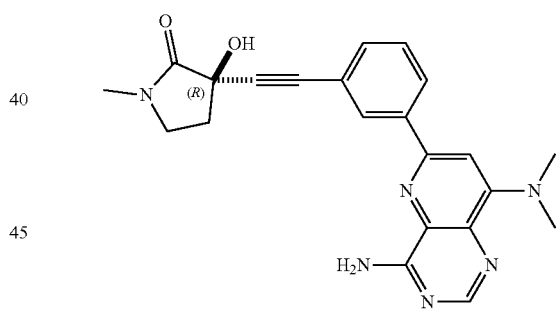

Step A: 6-Chloro-dimethylpyrido[3,2-d]pyrimidine-4,8-diamine. To a solution of 8-bromo-6-chloro-pyrido[3,2-d]pyrimidin-4-amine (100 mg, 0.385 mmol) in toluene (1 mL) was added sodium tert-butoxide (44 mg, 0.46 mmol), dimethylamine (0.23 mL, 0.46 mmol, 2.0 M solution in methanol), and (2'-amino-[1,1'-biphenyl]-2-yl)palladium(II) chloride dicyclohexyl(2',4',6'-triisopropyl-[1,1'-biphenyl]-2-yl)phosphane (30 mg, 0.039 mmol). The mixture was heated at 85° C. for 4 h. The mixture was cooled to rt, diluted with saturated aqueous NH$_4$Cl solution (1 mL), and extracted with ethyl acetate (3 mL×3). The combined organic layers were dried over MgSO$_4$, filtered, and concentrated to dryness. The resulting residue was purified on FCC (0 to 5% 2 M NH$_3$ in MeOH/CH$_2$Cl$_2$) to give 6-chloro-dimethylpyrido[3,2-d]pyrimidine-4,8-diamine (64 mg, 74%) as a white solid. MS (ESI): mass calcd. for $C_9H_{10}ClN_5$, 223.1; m/z. found, 224.1 [M+H]$^+$. $^1$H NMR (500 MHz, CD$_3$OD) δ 8.28 (s, 1H), 6.75 (s, 1H), 3.36 (s, 6H).

Step B: (R)-3-[2-[3-[4-Amino-8-(dimethylamino)pyrido[3,2-d]pyrimidin-6-yl]phenyl]ethynyl]-3-hydroxy-1-methyl-pyrrolidin-2-one. A sealable vial was charged with 6-chloro-dimethylpyrido[3,2-d]pyrimidine-4,8-diamine (39.0 mg, 0.18 mmol), Intermediate 4 [(R)-3-hydroxy-1-methyl-3-((3-(4,4,5,5-tetramethyl-1,3,2-dioxaborolan-2-yl)phenyl)ethynyl)pyrrolidin-2-one (60 mg, 0.17 mmol)], tri-tert-butylphosphine (35.0 mg, 0.17 mmol), tris(dibenzylideneacetone)dipalladium(0) (80.0 mg, 0.88 mmol), potassium fluoride (61.0 mg, 1.10 mmol), and dioxane/H$_2$O (1.4 mL/0.5 mL). The mixture was degassed for 10 min with nitrogen and then heated at 90° C. After 1.5 h, the mixture was cooled to rt and partitioned with H$_2$O (1 mL). The mixture was extracted with ethyl acetate (3×2 mL). The combined organic extracts were concentrated to dryness and the resulting residue was purified by FCC (5-10% gradient, MeOH/DCM) to afford (R)-3-[2-[3-[4-amino-8-(dimethylamino)pyrido[3,2-d]pyrimidin-6-yl]phenyl]ethynyl]-3-hydroxy-1-methyl-pyrrolidin-2-one (10 mg, 14%) as a white solid. MS (ESI): mass calcd. for C$_{22}$H$_{22}$N$_6$O$_2$, 402.2; m/z. found, 403.1 [M+H]$^+$. $^1$H NMR (500 MHz, CD$_3$OD) δ 8.37-8.24 (m, 2H), 8.22-8.09 (m, 1H), 7.57-7.44 (m, 2H), 7.30 (s, 1H), 3.55-3.42 (m, 2H), 3.37 (s, 6H), 2.94 (s, 3H), 2.69-2.53 (m, 1H), 2.37-2.27 (m, 1H).

Example 296: (R)-3-[2-[3-[4-Amino-8-(methylamino)pyrido[3,2-d]pyrimidin-6-yl]phenyl]ethynyl]-3-hydroxy-1-methyl-pyrrolidin-2-one

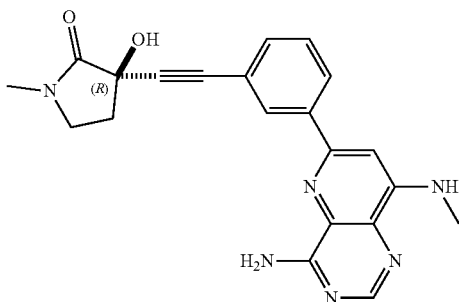

Step A: 6-Chloro-methylpyrido[3,2-d]pyrimidine-4,8-diamine. The title compound was prepared using analogous conditions described in Example 295 utilizing methylamine in Step A to afford 6-chloro-methylpyrido[3,2-d]pyrimidine-4,8-diamine (23 mg, 28%) as a white solid. MS (ESI): mass calcd. for C$_8$H$_8$ClN$_5$, 209.0; m/z. found, 210.1 [M+H]$^+$.

Step B: ((R)-3-[2-[3-[4-Amino-8-(methylamino)pyrido[3,2-d]pyrimidin-6-yl]phenyl]ethynyl]-3-hydroxy-1-methyl-pyrrolidin-2-one. A sealable vial was charged with 6-chloro-methylpyrido[3,2-d]pyrimidine-4,8-diamine (38.0 mg, 0.18 mmol), and Intermediate 4 [(R)-3-hydroxy-1-methyl-3-((3-(4,4,5,5-tetramethyl-1,3,2-dioxaborolan-2-yl)phenyl)ethynyl)pyrrolidin-2-one (93.0 mg, 0.27 mmol)], bis(triphenylphosphine)palladium(II) chloride (15 mg, 0.02 mmol), K$_2$CO$_3$ (0.41 mL, 0.81 mmol, 2 M in H$_2$O) and dioxane/EtOH (1 mL/1 mL). The mixture was degassed for 10 min with nitrogen and heated at 170° C. for 10 min. The mixture was cooled to rt and poured into ethyl acetate (2 mL) and H$_2$O (2 mL). The mixture was extracted with ethyl acetate (2 mL×3). The combined organics were dried over anhydrous Na$_2$SO$_4$, filtered, and concentrated to dryness. The resulting residue was purified by FCC (0 to 5% gradient, 2 M NH$_3$ in MeOH/DCM) to afford (30 mg, 43%) as a white solid. MS (ESI): mass calcd. for C$_{21}$H$_{20}$N$_6$O$_2$, 388.2; m/z. found, 389.1 [M+H]$^+$. $^1$H NMR (500 MHz, CD$_3$OD) δ 8.25 (s, 1H), 8.24-8.19 (m, 1H), 8.14-8.06 (m, 1H), 7.53-7.48 (m, 1H), 7.47-7.42 (m, 1H), 7.02 (s, 1H), 3.52-3.45 (m, 2H), 3.04 (s, 3H), 2.94 (s, 3H), 2.65-2.58 (m, 1H), 2.37-2.29 (m, 1H).

Example 297: (R)-3-[2-[3-[4-Amino-8-(isopropylamino)pyrido[3,2-d]pyrimidin-6-yl]phenyl]ethynyl]-3-hydroxy-1-methyl-pyrrolidin-2-one

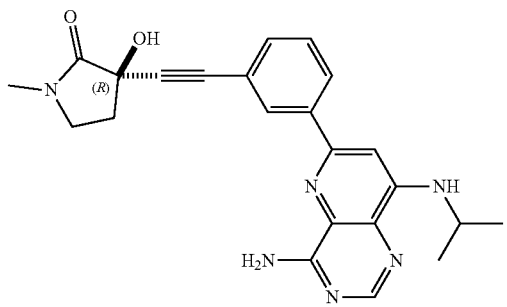

Step A: 6-Chloro-isopropylyrido[3,2-d]pyrimidine-4,8-diamine. To a solution of 6,8-dichloro-pyrido[3,2-d]pyrimidin-4-amine (100 mg, 0.46 mmol) in CH$_3$CN (1 mL) was added isopropylamine (41.0 mg, 0.70 mmol). The mixture was heated at 150° C. for 2 h. The mixture was cooled to rt and H$_2$O (10 mL) was added. The resulting solids were collected by filtration and dried under vacuum to afford 6-chloro-isopropylyrido[3,2-d]pyrimidine-4,8-diamine (80 mg, 72%). MS (ESI): mass calcd. for C$_{10}$H$_{12}$ClN$_5$, 237.1; m/z. found, 238.1 [M+H]$^+$. $^1$H NMR (500 MHz, CD$_3$OD) δ 8.28 (s, 1H), 6.64 (s, 1H), 3.82 (hept, J=6.4 Hz, 1H), 1.31 (d, J=6.4 Hz, 6H).

Step B: (R)-3-[2-[3-[4-Amino-8-(isopropylamino)pyrido[3,2-d]pyrimidin-6-yl]phenyl]ethynyl]-3-hydroxy-1-methyl-pyrrolidin-2-one was prepared using analogous conditions described in Example 296 in Step B to afford (R)-3-[2-[3-[4-amino-8-(isopropylamino)pyrido[3,2-d]pyrimidin-6-yl]phenyl]ethynyl]-3-hydroxy-1-methyl-pyrrolidin-2-one (41 mg, 29%) as a white solid. MS (ESI): mass calcd. for C$_{23}$H$_{24}$N$_6$O$_2$, 416.2; m/z. found, 417.1 [M+H]$^+$. $^1$H NMR (500 MHz, CD$_3$OD) δ 8.27 (s, 1H), 8.25-8.19 (m, 1H), 8.14-8.06 (m, 1H), 7.55-7.39 (m, 2H), 7.09 (s, 1H), 4.04-3.91 (m, 1H), 3.55-3.42 (m, 2H), 2.94 (s, 3H), 2.66-2.54 (m, 1H), 2.42-2.28 (m, 1H), 1.35 (d, J=6.4 Hz, 6H).

Example 298: (R)-3-[2-[3-[4-Amino-8-(cyclopropylamino)pyrido[3,2-d]pyrimidin-6-yl]phenyl]ethynyl]-3-hydroxy-1-methyl-pyrrolidin-2-one

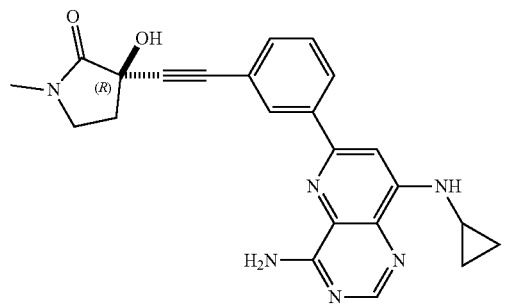

The title compound was prepared using analogous conditions described in Example 295 utilizing cyclopropylamine in Step A to afford (R)-3-[2-[3-[4-amino-8-(cyclopropylamino)pyrido[3,2-d]pyrimidin-6-yl]phenyl]ethynyl]-3-hydroxy-1-methyl-pyrrolidin-2-one (21 mg, 18%) as a white solid. MS (ESI): mass calcd. for $C_{23}H_{22}N_6O_2$, 414.2; m/z. found, 415.1 [M+H]$^+$. $^1$H NMR (500 MHz, CD$_3$OD) δ 8.32-8.20 (m, 2H), 8.17-8.09 (m, 1H), 7.57-7.45 (m, 2H), 7.43 (s, 1H), 3.57-3.44 (m, 2H), 2.94 (s, 3H), 2.71-2.65 (m, 1H), 2.65-2.56 (m, 1H), 2.38-2.28 (m, 1H), 1.00-0.90 (m, 2H), 0.71-0.62 (m, 2H).

Example 299: (R)-3-[2-[3-[4-Amino-8-(difluoromethoxy)pyrido[3,2-d]pyrimidin-6-yl]phenyl]ethynyl]-3-hydroxy-1-methyl-pyrrolidin-2-one

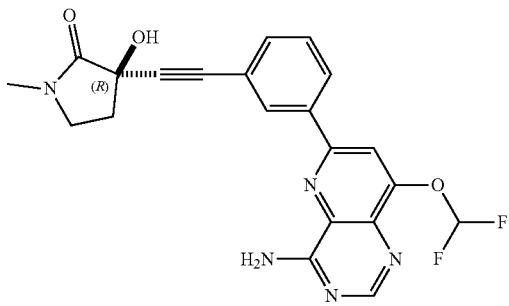

Step A: 6-Chloro-8-(difluoromethoxy)pyrido[3,2-d]pyrimidin-4-amine. A flask was charged with a solution of Intermediate 194 [6,8-dichloropyrido[3,2-d]pyrimidin-4-amine, (100 mg, 0.51 mmol)] in DMA (1 mL), followed by cesium acetate (107 mg, 0.56 mmol). The resulting mixture was heated at 100° C. for 16 h. After which time, the mixture was cooled to rt and a saturated aqueous solution of ammonium chloride (2 mL) was added and extracted with DCM (3 mL×2). The combined organic layers were concentrated to dryness to afford 4-amino-6-chloropyrido[3,2-d]pyrimidin-8-ol (100 mg, 0.509 mmol) which was added to DMA (1 mL), Cs$_2$CO$_3$ (497 mg, 1.50 mmol), and ethyl bromodifluoroacetate (158 mg, 0.763 mmol). This mixture was heated at 70° C. After 16 h, the resulting mixture was cooled to rt and saturated aqueous solution of ammonium chloride (2 mL) was added. The mixture was extracted with DCM (3 mL×2) and the combined organic layers were concentrated to dryness. The resulting residue was purified by FCC (0 to 5% 2 M NH$_3$ in MeOH/DCM) to afford 6-chloro-8-(difluoromethoxy)pyrido[3,2-d]pyrimidin-4-amine (20 mg, 16%). MS (ESI): mass calcd. for $C_8H_5ClF_2N_4O$, 246.0; m/z. found, 247.0 [M+H]$^+$. $^1$H NMR (400 MHz, CD$_3$OD) δ 8.42 (s, 1H), 7.71-7.15 (m, 2H).

Step B: (R)-3-[2-[3-[4-Amino-8-(difluoromethoxy)pyrido[3,2-d]pyrimidin-6-yl]phenyl]ethynyl]-3-hydroxy-1-methyl-pyrrolidin-2-one. (R)-3-[2-[3-[4-Amino-8-(difluoromethoxy)pyrido[3,2-d]pyrimidin-6-yl]phenyl]ethynyl]-3-hydroxy-1-methyl-pyrrolidin-2-one was prepared using analogous conditions described in Example 12 utilizing 6-chloro-8-(difluoromethoxy)pyrido[3,2-d]pyrimidin-4-amine and Intermediate 4 [(R)-3-hydroxy-1-methyl-3-((3-(4,4,5,5-tetramethyl-1,3,2-dioxaborolan-2-yl)phenyl)ethynyl)pyrrolidin-2-one] to afford (R)-3-[2-[3-[4-amino-8-(difluoromethoxy)pyrido[3,2-d]pyrimidin-6-yl]phenyl]ethynyl]-3-hydroxy-1-methyl-pyrrolidin-2-one (10 mg, 29%) as a white solid. MS (ESI): mass calcd. for $C_{21}H_{17}F_2N_5O_3$, 425.1; m/z. found, 426.1 [M+H]$^+$. $^1$H NMR (600 MHz, CD$_3$OD) δ 8.40 (s, 1H), 8.38-8.35 (m, 1H), 8.26-8.21 (m, 1H), 7.99 (s, 1H), 7.71-7.41 (m, 3H), 3.57-3.44 (m, 2H), 2.94 (s, 3H), 2.66-2.56 (m, 1H), 2.40-2.24 (m, 1H).

Example 300: (R)-3-[2-[3-[4-Amino-8-(3,3-difluoroazetidin-1-yl)pyrido[3,2-d]pyrimidin-6-yl]phenyl]ethynyl]-3-hydroxy-1-methyl-pyrrolidin-2-one

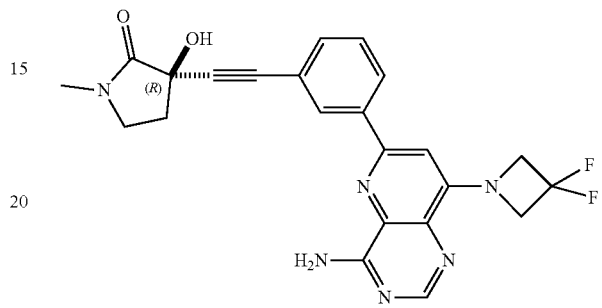

The title compound was prepared using analogous conditions described in Example 297 utilizing 3,3-difluoroazetidine in Step A to afford (R)-3-[2-[3-[4-amino-8-(3,3-difluoroazetidin-1-yl)pyrido[3,2-d]pyrimidin-6-yl]phenyl]ethynyl]-3-hydroxy-1-methyl-pyrrolidin-2-one (45 mg, 34%) as a white solid. MS (ESI): mass calcd. for $C_{23}H_{20}F_2N_6O_2$, 450.2; m/z. found, 451.1 [M+H]$^+$. $^1$H NMR (600 MHz, CD$_3$OD) δ 8.31-8.20 (m, 2H), 8.20-8.11 (m, 1H), 7.56-7.50 (m, 1H), 7.47 (t, J=7.7 Hz, 1H), 7.01 (s, 1H), 4.79 (t, J=12.1 Hz, 4H), 3.54-3.46 (m, 2H), 2.94 (s, 3H), 2.66-2.55 (m, 1H), 2.39-2.25 (m, 1H).

Example 301: (R)-3-[2-[3-(8-Amino-4-methyl-pyrimido[5,4-d]pyrimidin-2-yl)-4-methyl-phenyl]ethynyl]-3-hydroxy-1-methyl-pyrrolidin-2-one

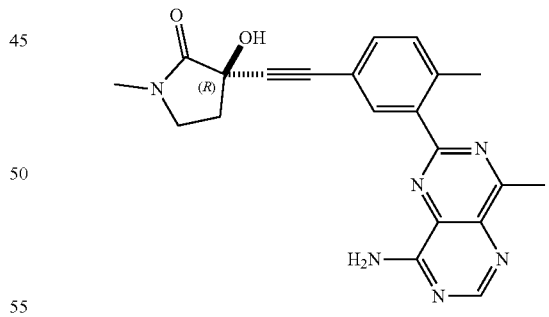

The title compound was prepared using analogous conditions described in Example 6 utilizing Intermediate 6 [(R)-3-hydroxy-1-methyl-3-((4-methyl-3-(4,4,5,5-tetramethyl-1,3,2-dioxaborolan-2-yl)phenyl)ethynyl)pyrrolidin-2-one] and Intermediate 24 [6-chloro-8-methylpyrimido[5,4-d]pyrimidin-4-amine] to afford (R)-3-[2-[3-(8-amino-4-methyl-pyrimido[5,4-d]pyrimidin-2-yl)-4-methyl-phenyl]ethynyl]-3-hydroxy-1-methyl-pyrrolidin-2-one (70 mg, 24%) as a white solid. MS (ESI): mass calcd. for $C_{21}H_{20}N_6O_2$, 388.2; m/z. found, 389.1 [M+H]$^+$. $^1$H NMR (500 MHz, CDCl$_3$) δ 8.60 (s, 1H), 7.74 (d, J=1.8 Hz, 1H), 7.31 (dd, J=7.9, 1.8 Hz, 1H), 7.16 (s, 1H), 6.87 (s, 2H), 5.00 (s, 1H), 3.52-3.32 (m, 2H), 2.94-2.86 (m, 6H), 2.64-2.55 (m, 1H), 2.49 (s, 3H), 2.40-2.29 (m, 1H).

Example 302: (R)-3-((3-(4-Amino-8-cyclopropylpyrido[3,2-d]pyrimidin-6-yl)phenyl)ethynyl)-3-hydroxy-1-methylpyrrolidin-2-one

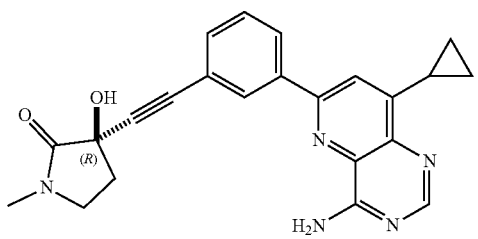

The title compound was prepared using analogous conditions described in Example 6 utilizing Intermediate 195 [6-chloro-8-cyclopropylpyrido[3,2-d]pyrimidin-4-amine] to afford (R)-3-((3-(4-amino-8-cyclopropylpyrido[3,2-d]pyrimidin-6-yl)phenyl)ethynyl)-3-hydroxy-1-methylpyrrolidin-2-one (63 mg, 74%) as a white solid. MS (ESI): mass calcd. for $C_{23}H_{21}N_5O_2$, 399.2; m/z. found, 400.2 [M+H]$^+$. $^1$H NMR (600 MHz, CD$_3$OD) δ 8.35 (s, 1H), 8.18-8.09 (m, 1H), 8.01 (ddd, J=7.9, 1.9, 1.2 Hz, 1H), 7.47-7.42 (m, 2H), 7.36 (t, J=7.7 Hz, 1H), 3.54-3.43 (m, 2H), 2.94 (s, 3H), 2.80-2.75 (m, 1H), 2.60 (ddd, J=13.0, 6.8, 4.4 Hz, 1H), 2.34 (ddd, J=13.0, 7.8, 7.0 Hz, 1H), 1.20 (ddd, J=8.5, 4.1, 2.3 Hz, 2H), 0.99-0.91 (m, 2H).

Example 303: (R)-3-[2-[3-(4-Amino-8-pyrazol-1-yl-pyrido[3,2-d]pyrimidin-6-yl)phenyl]ethynyl]-3-hydroxy-1-methyl-pyrrolidin-2-one

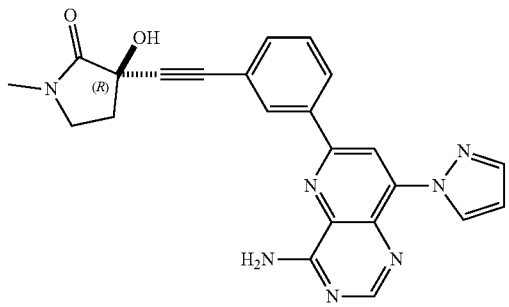

Step A: 6-Chloro-8-(1H-pyrazol-1-yl)pyrido[3,2-d]pyrimidin-4-amine. To a solution of 6,8-dichloro-pyrido[3,2-d]pyrimidin-4-amine (150 mg, 0.70 mmol) in DMA (1 mL) was added pyrazole (72 mg, 1.5 mmol) and Cs$_2$CO$_3$ (0.7 g, 2.1 mmol). The mixture was heated at 70° C. for 16 h. The mixture was cooled to rt and H$_2$O (10 mL) was added. The resulting solids were collected by filtration and dried under vacuum to afford 6-chloro-8-(1H-pyrazol-1-yl)pyrido[3,2-d] pyrimidin-4-amine (108 mg, 55%) as a white solid, which was used directly in the next step. MS (ESI): mass calcd. for $C_{10}H_7ClN_6$, 246.0; m/z. found, 247.0 [M+H]$^+$.

Step B: (R)-3-[2-[3-(4-Amino-8-pyrazol-1-yl-pyrido[3,2-d]pyrimidin-6-yl)phenyl]ethynyl]-3-hydroxy-1-methyl-pyrrolidin-2-one. (R)-3-[2-[3-(4-Amino-8-pyrazol-1-yl-pyrido[3,2-d]pyrimidin-6-yl)phenyl]ethynyl]-3-hydroxy-1-methyl-pyrrolidin-2-one was prepared with analogous conditions as described in Example 12 utilizing 6-chloro-8-(1H-pyrazol-1-yl)pyrido[3,2-d]pyrimidin-4-amine to afford (R)-3-[2-[3-(4-amino-8-pyrazol-1-yl-pyrido[3,2-d]pyrimidin-6-yl)phenyl]ethynyl]-3-hydroxy-1-methyl-pyrrolidin-2-one (31 mg, 18%) as a white solid. MS (ESI): mass calcd. for $C_{23}H_{19}N_7O_2$, 425.2; m/z. found, 426.1 [M+H]$^+$. $^1$H NMR (500 MHz, CD$_3$OD) δ 9.48 (dd, J=2.7, 0.6 Hz, 1H), 8.81 (s, 1H), 8.49 (s, 1H), 8.42 (t, J=1.8 Hz, 1H), 8.35-8.22 (m, 1H), 7.90 (dd, J=1.7, 0.6 Hz, 1H), 7.63-7.50 (m, 2H), 6.63 (dd, J=2.7, 1.7 Hz, 1H), 3.55-3.42 (m, 2H), 2.94 (s, 3H), 2.70-2.57 (m, 1H), 2.41-2.27 (m, 1H).

Example 304: (R)-3-[2-[3-[4-Amino-8-(cyclopropoxy)pyrido[3,2-d]pyrimidin-6-yl]phenyl]ethynyl]-3-hydroxy-1-methyl-pyrrolidin-2-one

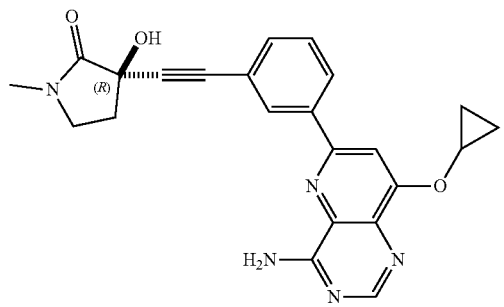

The title compound was prepared with analogous conditions described in Example 303 utilizing cyclopropyl alcohol in step A to afford (R)-3-[2-[3-[4-amino-8-(cyclopropoxy)pyrido[3,2-d]pyrimidin-6-yl]phenyl]ethynyl]-3-hydroxy-1-methyl-pyrrolidin-2-one (45 mg, 26%) as a white solid. MS (ESI): mass calcd. for $C_{23}H_{21}N_5O_3$, 415.2; m/z found, 416.1 [M+H]$^+$. $^1$H NMR (500 MHz, CDCl$_3$) δ 8.50 (s, 1H), 8.46-8.33 (m, 1H), 7.72-7.62 (m, 1H), 7.36-7.28 (m, 1H), 7.27-7.20 (m, 1H), 7.17-7.00 (m, 3H), 4.11-3.98 (m, 1H), 3.53-3.34 (m, 2H), 2.90 (s, 3H), 2.60-2.50 (m, 1H), 2.47-2.34 (m, 1H), 1.20-1.09 (m, 1H), 0.99-0.90 (m, 1H), 0.86-0.78 (m, 1H), 0.75-0.58 (m, 1H).

Example 305: (R)-3-[2-[3-[4-Amino-8-[1-(difluoromethyl)pyrazol-4-yl]oxy-pyrido[3,2-d]pyrimidin-6-yl]phenyl]ethynyl]-3-hydroxy-1-methyl-pyrrolidin-2-one

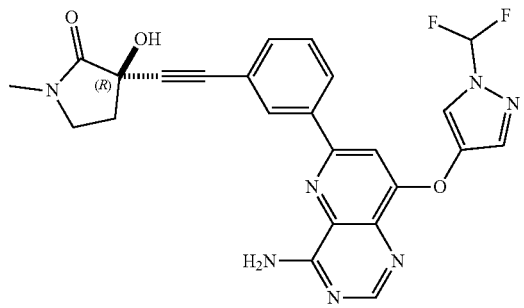

The title compound was prepared with analogous conditions described in Example 303 utilizing 1-(difluoromethyl)-1H-pyrazol-4-ol in Step A to afford (R)-3-[2-[3-[4-amino-8-[1-(difluoromethyl)pyrazol-4-yl]oxy-pyrido[3,2-d]pyrimidin-6-yl]phenyl]ethynyl]-3-hydroxy-1-methyl-pyrrolidin-2-one (110 mg, 70%) as a white solid. MS (ESI): mass calcd. for $C_{24}H_{19}F_2N_7O_3$, 491.2; m/z. found, 492.1 [M+H]$^+$. $^1$H NMR (500 MHz, CDCl$_3$) δ 8.80-8.65 (br s, 1H), 8.62 (s, 1H), 8.56 (s, 1H), 7.66 (s, 1H), 7.60-7.52 (m, 1H), 7.33-7.25 (m, 1H), 7.25-7.15 (m, 2H), 7.11-7.00 (broad, 1H), 6.77 (t, J=1.8 Hz, 1H), 6.67 (s, 1H), 3.52-3.40 (m, 2H), 2.91 (s, 3H), 2.60-2.49 (m, 1H), 2.44-2.33 (m, 1H).

Example 306: (R)-3-[2-[3-[4-Amino-8-(3,3,3-trifluoropropoxy)pyrido[3,2-d]pyrimidin-6-yl]phenyl]ethynyl]-3-hydroxy-1-methyl-pyrrolidin-2-one

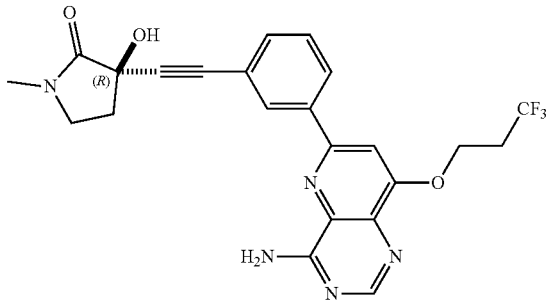

The title compound was prepared with analogous conditions described in Example 303 utilizing Intermediate 197 [6-chloro-8-(3,3,3-trifluoropropoxy)pyrido[3,2-d]pyrimidin-4-amine] to afford (R)-3-[2-[3-[4-amino-8-(3,3,3-trifluoropropoxy)pyrido[3,2-d]pyrimidin-6-yl]phenyl]ethynyl]-3-hydroxy-1-methyl-pyrrolidin-2-one (10 mg, 44%) as a white solid. MS (ESI): mass calcd. for $C_{23}H_{20}F_3N_5O_3$, 471.2; m/z. found, 472.1 [M+H]$^+$. $^1$H NMR (500 MHz, CDCl$_3$) δ 8.54 (s, 1H), 7.76 (d, J=7.7 Hz, 1H), 7.71-7.45 (m, 2H), 7.37 (d, J=7.6 Hz, 1H), 7.30 (t, J=7.8 Hz, 1H), 7.10-6.93 (m, 2H), 6.56-6.34 (broad, 1H), 4.56-4.46 (m, 1H), 4.36 (q, J=8.4, 7.9 Hz, 1H), 3.49-3.34 (m, 2H), 2.93 (s, 3H), 2.89-2.81 (m, 2H), 2.65-2.56 (m, 1H), 2.45-2.32 (m, 1H).

Example 307: (R)-3-[2-[3-[4-Amino-8-(2,2-difluoro-5-azaspiro[2.3]hexan-5-yl)pyrido[3,2-d]pyrimidin-6-yl]phenyl]ethynyl]-3-hydroxy-1-methyl-pyrrolidin-2-one

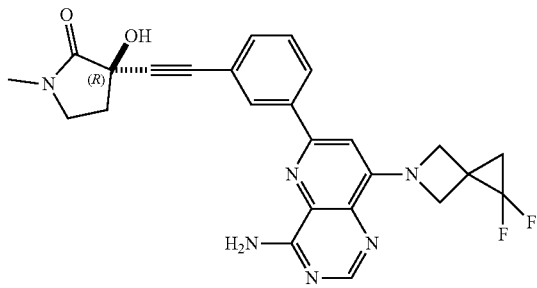

The title compound was prepared using analogous conditions described in Example 297 utilizing 1,1-difluoro-5-azaspiro[2.3]hexane in Step A to afford (R)-3-[2-[3-[4-amino-8-(2,2-difluoro-5-azaspiro[2.3]hexan-5-yl)pyrido[3,2-d]pyrimidin-6-yl]phenyl]ethynyl]-3-hydroxy-1-methyl-pyrrolidin-2-one (65 mg, 27%) as a white solid. MS (ESI): mass calcd. for $C_{25}H_{22}F_2N_6O_2$, 476.2; m/z. found, 477.1 [M+H]$^+$. $^1$H NMR (500 MHz, CDCl$_3$) δ 8.28 (s, 1H), 7.84-7.45 (m, 3H), 7.32-7.11 (m, 3H), 7.11-6.77 (broad, 1H), 6.09 (s, 1H), 4.68-4.29 (m, 4H), 3.49-3.36 (m, 2H), 2.92 (s, 3H), 2.61-2.50 (m, 1H), 2.44-2.27 (m, 1H), 1.60-1.44 (m, 2H).

Example 308: (R)-3-((3-(4-Amino-8-ethylpyrido[3,2-d]pyrimidin-6-yl-2-d)phenyl)ethynyl)-3-hydroxy-1-methylpyrrolidin-2-one, and its trifluoroacetate

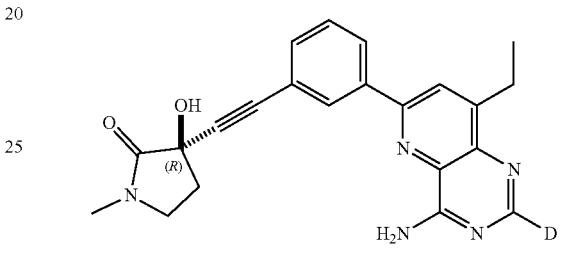

To a vial containing Example 8, [(R)-3-((3-(4-aminopyrido[3,2-d]pyrimidin-6-yl-2-d)phenyl)ethynyl)-3-hydroxy-1-methylpyrrolidin-2-one (0.30 g, 0.83 mmol)] was added DMSO (3.3 ml) and the solution was sparged for 20 min with nitrogen. To the solution was added 1,3-dioxoisoindolin-2-yl propionate (0.27 g, 1.24 mmol) followed by [4,4'-bis(1,1-dimethylethyl)-2,2'-bipyridine-N1,N1']bis[3,5-difluoro-2-[5-(trifluoromethyl)-2-pyridinyl-N]phenyl-C] Iridium(III) hexafluorophosphate (0.02 g, 0.02 mmol) and trifluoroacetic acid (0.25 mL, 3.30 mmol). The sealed vial was then illuminated under Blue LEDs (450 nm) for 4 h at rt. After this time, an additional amount of 1,3-dioxoisoindolin-2-yl propionate (0.20 g) was added and illuminated under Blue LEDs (450 nm) for an additional 2 h. The resulting mixture was directly injected onto preparative reverse phase HPLC (Welch Xtimate C18 10 μm, 250×50 mm; mobile phase: [water (0.1% TFA)-ACN]; B %: 10%-60%, 20 min, 100% 5 min. Detection, UV at λ=220-254 nM) to afford (R)-3-((3-(4-amino-8-ethylpyrido[3,2-d]pyrimidin-6-yl-2-d)phenyl)ethynyl)-3-hydroxy-1-methylpyrrolidin-2-one trifluoroacetate (16 mg, 4%) as a white solid. MS (ESI): mass calcd. for $C_{22}H_{20}DN_5O_2$, 388.2; m/z. found, 389.1 [M+H]$^+$. $^1$H NMR (500 MHz, CD$_3$OD) δ 8.10 (d, J=0.9 Hz, 1H), 7.74-7.69 (m, 1H), 7.64-7.59 (m, 2H), 7.58-7.49 (m, 1H), 3.47 (dd, J=7.5, 5.5 Hz, 2H), 2.94-2.88 (m, 5H), 2.58 (dt, J=12.9, 5.5 Hz, 1H), 2.32 (dt, J=12.9, 7.5 Hz, 1H), 1.23 (t, J=7.5 Hz, 3H). (R)-3-((3-(4-Amino-8-ethylpyrido[3,2-d]pyrimidin-6-yl-2-d)phenyl)ethynyl)-3-hydroxy-1-methylpyrrolidin-2-one trifluoroacetate can be converted to its respective free base, (R)-3-((3-(4-Amino-8-ethylpyrido[3,2-d]pyrimidin-6-yl-2-d)phenyl)ethynyl)-3-hydroxy-1-methylpyrrolidin-2-one, by partitioning (R)-3-((3-(4-Amino-8-ethylpyrido[3,2-d]pyrimidin-6-yl-2-d)phenyl)ethynyl)-3-hydroxy-1-methylpyrrolidin-2-one trifluoroacetate between saturated aqueous sodium bicarbonate and ethyl acetate. After the partitioning, the organic layer is then separated, and the aqueous layer is extracted twice with ethyl acetate. The combined organic extracts are washed with brine and concentrated to dryness.

Example 309: (R)-3-((3-(4-Amino-8-cyclobutylpyrido[3,2-d]pyrimidin-6-yl)phenyl)ethynyl)-3-hydroxy-1-methylpyrrolidin-2-one

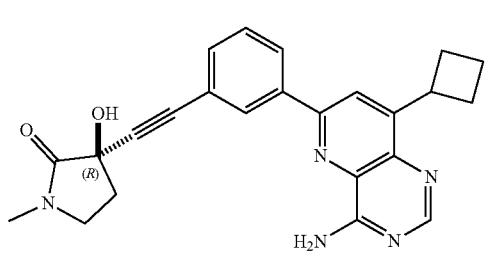

The title compound was prepared using analogous conditions described in Example 221 utilizing Intermediate 198 [6-chloro-8-cyclobutylpyrido[3,2-d]pyrimidin-4-amine] to afford (R)-3-((3-(4-amino-8-cyclobutylpyrido[3,2-d]pyrimidin-6-yl)phenyl)ethynyl)-3-hydroxy-1-methylpyrrolidin-2-one (48.0 mg, 40%) as a white solid. MS (ESI): mass calcd. for $C_{24}H_{25}N_5O_2$ 413.2 m/z. found 414.2 [M+H]$^+$. $^1$H NMR (400 MHz, DMSO-d$_6$) δ 8.54-8.44 (m, 2H), 8.41 (s, 1H), 8.28 (s, 1H), 8.11 (br s, 1H), 7.91 (br s, 1H), 7.60-7.49 (m, 2H), 6.51 (s, 1H), 4.44-4.32 (m, 1H), 3.48-3.40 (m, 2H), 2.82 (s, 3H), 2.49-2.46 (m, 1H), 2.44-2.30 (m, 4H), 2.27-2.17 (m, 1H), 2.16-2.03 (m, 1H), 1.97-1.85 (m, 1H).

Example 310: (R)-3-((3-(4-Amino-8-phenylpyrido[3,2-d]pyrimidin-6-yl)phenyl)ethynyl)-3-hydroxy-1-methylpyrrolidin-2-one, and its trifluoroacetate

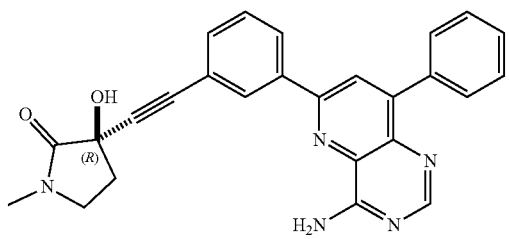

(R)-3-((3-(4-Amino-8-phenylpyrido[3,2-d]pyrimidin-6-yl)phenyl)ethynyl)-3-hydroxy-1-methylpyrrolidin-2-one was prepared using analogous conditions described in Example 6 utilizing Intermediate 199 [6-chloro-8-phenylpyrido[3,2-d]pyrimidin-4-amine] and purified by preparative reverse phase HPLC (Welch Xtimate C18 10 μm, 250×50 mm; mobile phase: [water (0.1% TFA)-ACN]; B %: 10%-60%, 20 min, 100% 5 min.

Detection, UV at λ=220-254 nM) to afford (R)-3-((3-(4-amino-8-phenylpyrido[3,2-d]pyrimidin-6-yl)phenyl)ethynyl)-3-hydroxy-1-methylpyrrolidin-2-one trifluoroacetate (50 mg, 82%) as a clear residue. MS (ESI): mass calcd. for $C_{26}H_{21}N_5O_2$, 435.2; m/z. found, 436.1 [M+H]$^+$. $^1$H NMR (500 MHz, DMSO-d$_6$) δ 8.57 (t, J=1.7 Hz, 1H), 8.53 (s, 1H), 8.49 (s, 1H), 8.39 (ddd, J=7.9, 2.0, 1.2 Hz, 1H), 7.71-7.61 (m, 6H), 7.57 (t, J=7.8 Hz, 1H), 3.51-3.47 (m, 2H), 2.94 (s, 3H), 2.61 (dt, J=13.0, 5.5 Hz, 1H), 2.34 (dt, J=13.0, 7.4 Hz, 1H).

Example 311: (R)-3-((3-(4-Amino-8-(thiophen-2-yl)pyrido[3,2-d]pyrimidin-6-yl)phenyl)ethynyl)-3-hydroxy-1-methylpyrrolidin-2-one, and its trifluoroacetate

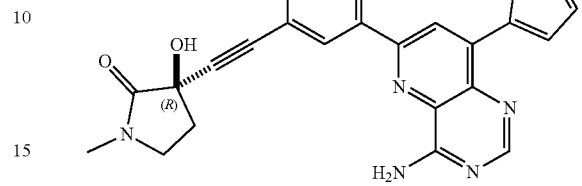

(R)-3-((3-(4-Amino-8-(thiophen-2-yl)pyrido[3,2-d]pyrimidin-6-yl)phenyl)ethynyl)-3-hydroxy-1-methylpyrrolidin-2-one was prepared using analogous conditions described in Example 6 utilizing Intermediate 200 [6-chloro-8-(thiophen-2-yl)pyrido[3,2-d]pyrimidin-4-amine trifluoroacetic acid salt]. It was then purified by preparative reverse phase HPLC (Welch Xtimate C18 10 μm, 250×50 mm; mobile phase: [water (0.1% TFA)-ACN]; B %: 10%-60%, 20 min, 100% 5 min. Detection, UV at λ=220-254 nM) to afford (R)-3-((3-(4-Amino-8-(thiophen-2-yl)pyrido[3,2-d]pyrimidin-6-yl)phenyl)ethynyl)-3-hydroxy-1-methylpyrrolidin-2-one trifluoroacetate (29 mg, 66%) as a white solid. MS (ESI): mass calcd. for $C_{24}H_{19}N_5O_2S$, 441.1; m/z. found, 442.1 [M+H]$^+$. $^1$H NMR (600 MHz, CD$_3$OD) δ 8.54-8.50 (m, 1H), 8.49-8.47 (m, 1H), 8.42-8.40 (m, 1H), 8.30-8.25 (m, 1H), 8.00-7.98 (m, 1H), 7.83-7.80 (m, 1H), 7.61-7.57 (m, 1H), 7.54-7.49 (m, 1H), 7.30-7.25 (m, 1H), 3.52 (dd, J=7.2, 5.7 Hz, 2H), 2.97 (s, 3H), 2.63 (dt, J=13.0, 5.7 Hz, 1H), 2.36 (dt, J=13.3, 7.2 Hz, 1H).

Example 312: (R)-3-((3-(4-Amino-8-(furan-2-yl)pyrido[3,2-d]pyrimidin-6-yl)phenyl)ethynyl)-3-hydroxy-1-methylpyrrolidin-2-one, and its trifluoroacetate

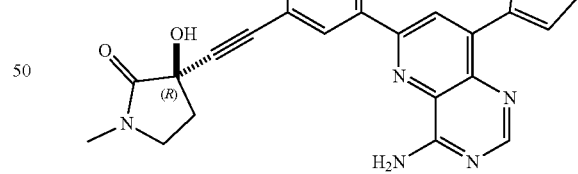

(R)-3-((3-(4-Amino-8-(furan-2-yl)pyrido[3,2-d]pyrimidin-6-yl)phenyl)ethynyl)-3-hydroxy-1-methylpyrrolidin-2-one was prepared using analogous conditions described in Example 6 utilizing Intermediate 201 [6-chloro-8-(furan-2-yl)pyrido[3,2-d]pyrimidin-4-amine as a trifluoroacetic acid salt]. It was then purified by preparative reverse phase HPLC (Welch Xtimate C18 10 μm, 250×50 mm; mobile phase: [water (0.1% TFA)-ACN]; B %: 10%-60%, 20 min, 100% 5 min. Detection, UV at λ=220-254 nM) to afford (R)-3-((3-(4-Amino-8-(furan-2-yl)pyrido[3,2-d]pyrimidin-6-yl)phenyl)ethynyl)-3-hydroxy-1-methylpyrrolidin-2-one trifluoroacetate (17 mg, 63%) as a white solid. MS (ESI): mass calcd.

for $C_{24}H_{19}N_5O_3$, 425.2; m/z. found, 426.1 [M+H]$^+$. $^1$H NMR (500 MHz, CD$_3$OD) δ 8.70 (s, 1H), 8.59 (s, 1H), 8.49 (t, J=1.7 Hz, 1H), 8.35 (ddd, J=7.9, 1.9, 1.2 Hz, 1H), 7.94 (dd, J=1.8, 0.7 Hz, 1H), 7.83 (d, J=3.6 Hz, 1H), 7.62 (dt, J=7.7, 1.4 Hz, 1H), 7.56 (t, J=7.8 Hz, 1H), 6.80 (dd, J=3.6, 1.8 Hz, 1H), 3.51 (dd, J=7.3, 5.6 Hz, 2H), 2.96 (s, 3H), 2.63 (dt, J=13.0, 5.5 Hz, 1H), 2.36 (dt, J=12.9, 7.3 Hz, 1H).

Example 313: (3R)-3-((3-(4-Amino-8-(azetidin-2-yl)pyrido[3,2-d]pyrimidin-6-yl-2-d)phenyl)ethynyl)-3-hydroxy-1-methylpyrrolidin-2-one, and its trifluoroacetate

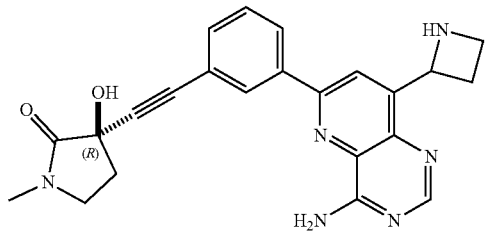

To a 20 mL vial containing Intermediate 202 [tert-butyl 2-(4-amino-6-(3-(((R)-3-hydroxy-1-methyl-2-oxopyrrolidin-3-yl)ethynyl)phenyl)pyrido[3,2-d]pyrimidin-8-yl-2-d)azetidine-1-carboxylate] and DCM (1.8 mL) was added TFA (0.18 mL) at rt. The solution was stirred for 2 h before additional TFA (0.20 mL) was added. After 3 h, the mixture was concentrated to dryness. The resulting residue was purified by preparative reverse phase HPLC (Welch Xtimate C18 10 µm, 250×50 mm; mobile phase: [water (0.1% TFA)-ACN]; B %: 10%-60%, 20 min, 100% 5 min. Detection, UV at λ=220-254 nM) to afford (3R)-3-((3-(4-amino-8-(azetidin-2-yl)pyrido[3,2-d]pyrimidin-6-yl-2-d)phenyl)ethynyl)-3-hydroxy-1-methylpyrrolidin-2-one trifluoroacetate as a mixture of diastereomers (20 mg, 21%) as a white solid. MS (ESI): mass calcd. for $C_{23}H_{21}DN_6O_2$, 415.2; m/z. found, 416.2 [M+H]$^+$. $^1$H NMR (500 MHz, CD$_3$OD) δ 8.48-8.39 (m, 1H), 8.34-8.30 (m, 2H), 7.62-7.51 (m, 2H), 6.22-6.15 (m, 1H), 4.34 (qd, J=9.4, 3.7 Hz, 1H), 4.08 (td, J=10.0, 4.9 Hz, 1H), 3.53-3.45 (m, 2H), 3.28-3.17 (m, 1H), 3.01 (ddt, J=8.8, 7.2, 4.4 Hz, 1H), 2.96-2.93 (m, 3H), 2.67-2.58 (m, 1H), 2.39-2.29 (m, 1H). (3R)-3-((3-(4-Amino-8-(azetidin-2-yl)pyrido[3,2-d]pyrimidin-6-yl-2-d)phenyl)ethynyl)-3-hydroxy-1-methylpyrrolidin-2-one trifluoroacetate is converted to its respective free base by partitioning between ethyl acetate and saturated aqueous sodium bicarbonate. The organic layer is separated, and the aqueous layer is extracted twice with ethyl acetate. The combined organic extracts are washed with brine and concentrated to dryness to provide (3R)-3-((3-(4-amino-8-(azetidin-2-yl)pyrido[3,2-d]pyrimidin-6-yl-2-d)phenyl)ethynyl)-3-hydroxy-1-methylpyrrolidin-2-one.

Example 314: (R)-3-((3-(4-Amino-8-vinylpyrido[3,2-d]pyrimidin-6-yl)phenyl)ethynyl)-3-hydroxy-1-methylpyrrolidin-2-one, and its trifluoroacetate

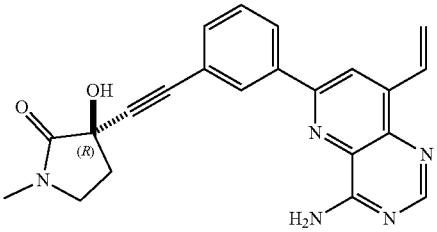

(R)-3-((3-(4-Amino-8-vinylpyrido[3,2-d]pyrimidin-6-yl)phenyl)ethynyl)-3-hydroxy-1-methylpyrrolidin-2-one was prepared using analogous conditions described in Example 6 utilizing Intermediate 203 [6-Chloro-8-vinylpyrido[3,2-d]pyrimidin-4-amine]. It was then purified by preparative reverse phase HPLC (Welch Xtimate C18 10 µm, 250×50 mm; mobile phase: [water (0.1% TFA)-ACN]; B %: 10%-60%, 20 min, 100% 5 min. Detection, UV at λ=220-254 nM) to afford (R)-3-((3-(4-Amino-8-vinylpyrido[3,2-d]pyrimidin-6-yl)phenyl)ethynyl)-3-hydroxy-1-methylpyrrolidin-2-one trifluoroacetate (30 mg, 80%) as a white solid. MS (ESI): mass calcd. for $C_{22}H_{19}N_5O_2$, 385.2; m/z. found, 386.2 [M+H]$^+$. $^1$H NMR (400 MHz, CD$_3$OD) δ 8.67 (s, 1H), 8.61 (s, 1H), 8.56-8.52 (m, 1H), 8.43-8.35 (m, 1H), 7.64 (dt, J=7.7, 1.4 Hz, 1H), 7.57 (t, J=7.7 Hz, 1H), 7.37 (dd, J=17.4, 11.4 Hz, 1H), 6.48 (d, J=17.4 Hz, 1H), 5.96 (d, J=11.4 Hz, 1H), 3.50 (dd, J=7.3, 5.6 Hz, 2H), 2.94 (s, 3H), 2.64-2.57 (m, 1H), 2.34 (dt, J=13.0, 7.7 Hz, 1H).

Example 315: (R)-3-[2-[3-[4-Amino-8-[3-(trifluoromethyl)azetidin-1-yl]pyrido[3,2-d]pyrimidin-6-yl]phenyl]ethynyl]-3-hydroxy-1-methyl-pyrrolidin-2-one

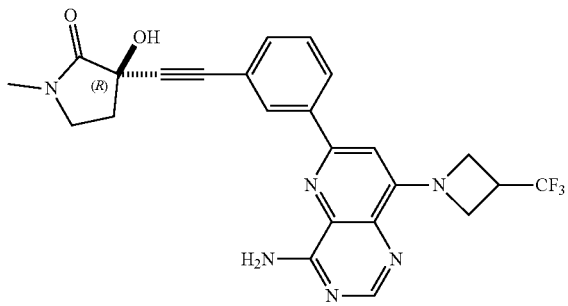

The title compound was prepared using analogous conditions described in Example 297 utilizing 3-(trifluoromethyl)azetidine to afford (R)-3-[2-[3-[4-amino-8-[3-(trifluoromethyl)azetidin-1-yl]pyrido[3,2-d]pyrimidin-6-yl]phenyl]ethynyl]-3-hydroxy-1-methyl-pyrrolidin-2-one (42 mg, 22%) as a white solid. MS (ESI): mass calcd. for $C_{24}H_{21}F_3N_6O_2$, 482.2; m/z. found, 483.1 [M+H]$^+$. $^1$H NMR (500 MHz, CD$_3$OD) δ 8.31-8.20 (m, 2H), 8.20-8.13 (m, 1H), 7.58-7.37 (m, 2H), 6.91 (s, 1H), 4.74-4.65 (m, 2H), 4.58-4.42 (m, 2H), 3.70-3.57 (m, 1H), 3.55-3.44 (m, 2H), 2.94 (s, 3H), 2.67-2.54 (m, 1H), 2.36-2.26 (m, 1H).

Example 316: (R)-3-[2-[3-[4-Amino-8-(azetidin-1-yl)pyrido[3,2-d]pyrimidin-6-yl]phenyl]ethynyl]-3-hydroxy-1-methyl-pyrrolidin-2-one

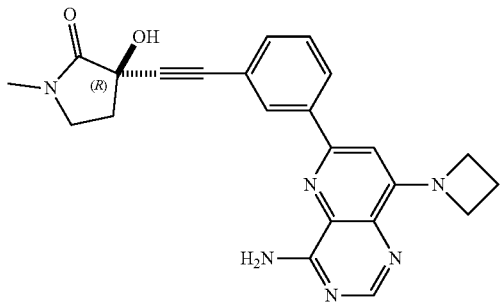

The title compound was prepared using analogous conditions described in Example 297 utilizing azetidine to afford (R)-3-[2-[3-[4-amino-8-(azetidin-1-yl)pyrido[3,2-d]pyrimidin-6-yl]phenyl]ethynyl]-3-hydroxy-1-methyl-pyrrolidin-2-one (45 mg, 39%) as a white solid. MS (ESI): mass calcd. for $C_{23}H_{22}N_6O_2$, 414.2; m/z. found, 415.1 [M+H]$^+$. $^1$H NMR (500 MHz, CD$_3$OD) δ 8.31-8.20 (m, 2H), 8.20-8.13 (m, 1H), 7.58-7.37 (m, 2H), 6.91 (s, 1H), 4.74-4.65 (m, 2H), 4.58-4.42 (m, 2H), 3.70-3.57 (m, 1H), 3.55-3.44 (m, 2H), 2.94 (s, 3H), 2.67-2.54 (m, 1H), 2.36-2.26 (m, 1H).

Example 317: (R)-3-((3-(4-Amino-8-((2,2,2-trifluoroethyl)amino)pyrido[3,2-d]pyrimidin-6-yl)phenyl)ethynyl)-3-hydroxy-1-methylpyrrolidin-2-one

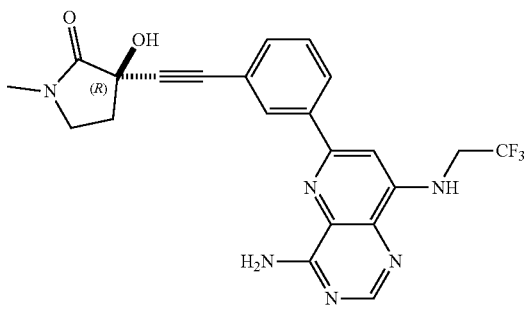

(R)-3-((3-(4-Amino-8-((2,2,2-trifluoroethyl)amino)pyrido[3,2-d]pyrimidin-6-yl)phenyl)ethynyl)-3-hydroxy-1-methylpyrrolidin-2-one was prepared using analogous conditions described in Example 297 utilizing 2,2,2-trifluoroethan-1-amine. MS (ESI): mass calcd. for $C_{22}H_{19}F_3N_6O_2$ 456.15 m/z found 457.3 [M+H]$^+$. $^1$H NMR (500 MHz, DMSO-d$_6$) δ 8.34 (s, 1H), 8.32 (s, 1H), 8.24-8.17 (m, 1H), 7.58-7.47 (m, 2H), 7.45 (s, 1H), 4.34-4.25 (m, 2H), 3.57-3.46 (m, 2H), 2.96 (s, 3H), 2.70-2.58 (m, 1H), 2.42-2.23 (m, 1H).

Example 318: (1R,4R,5S)-4-((3-(7-Aminothiazolo[5,4-d]pyrimidin-2-yl)-4-methylphenyl)ethynyl)-4-hydroxy-2-methyl-2-azabicyclo[3.1.0]hexan-3-one

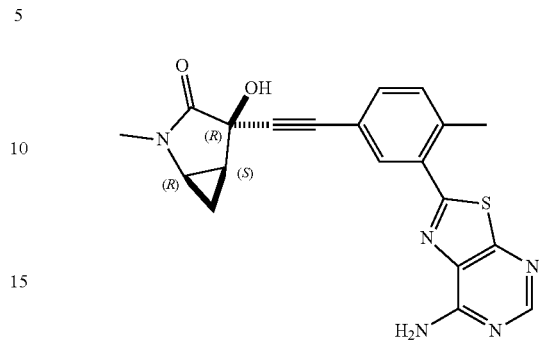

(1R,4R,5S)-4-((3-(7-Aminothiazolo[5,4-d]pyrimidin-2-yl)-4-methylphenyl)ethynyl)-4-hydroxy-2-methyl-2-azabicyclo[3.1.0]hexan-3-one was prepared using analogous conditions described in Example 10 utilizing Intermediate 9 [2-(5-iodo-2-methylphenyl)thiazolo[5,4-d]pyrimidin-7-amine] and Intermediate 175 [(1R,4R,5S)-4-ethynyl-4-hydroxy-2-methyl-2-azabicyclo[3.1.0]hexan-3-one]. MS (ESI): mass calcd. for $C_{20}H_{17}N_5O_2S$ 391.11 m/z found 392.0 [M+H]$^+$. $^1$H NMR (400 MHz, CDCl$_3$) δ 8.53 (s, 1H), 7.38-7.32 (m, 1H), 7.23-7.17 (m, 1H), 7.13 (s, 1H), 6.73-6.65 (m, 1H), 3.23-3.16 (m, 1H), 2.97 (s, 3H), 2.53 (s, 3H), 2.18-2.10 (m, 1H), 1.03-0.95 (m, 1H), 0.94-0.88 (m, 1H).

Example 319: (3R,5R)-3-((3-(7-Aminothiazolo[5,4-d]pyrimidin-2-yl)-4-methylphenyl)ethynyl)-3-hydroxy-1,5-dimethylpyrrolidin-2-one

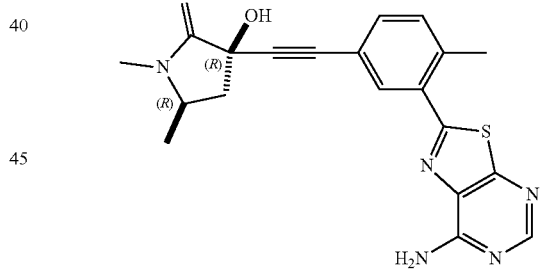

(3R,5R)-3-((3-(7-Aminothiazolo[5,4-d]pyrimidin-2-yl)-4-methylphenyl)ethynyl)-3-hydroxy-1,5-dimethylpyrrolidin-2-one was prepared using analogous conditions described in Example 10 utilizing Intermediate 9 [2-(5-iodo-2-methylphenyl)thiazolo[5,4-d]pyrimidin-7-amine] and Intermediate 168 [(3R,5R)-3-ethynyl-3-hydroxy-1,5-dimethylpyrrolidin-2-one]. MS (ESI): mass calcd. for $C_{20}H_{19}N_5O_2S$ 393.13 m/z found 394.0 [M+H]$^+$. $^1$H NMR (400 MHz, CDCl$_3$) δ 8.56 (s, 1H), 7.35-7.30 (m, 1H), 7.24-7.20 (m, 1H), 7.19-7.14 (m, 1H), 7.08-7.04 (m, 1H), 3.80-3.70 (m, 1H), 2.95 (s, 3H), 2.87-2.79 (m, 1H), 2.55 (s, 3H), 2.08-1.99 (m, 1H), 1.40 (d, J=6.3 Hz, 3H).

Compounds of the invention were tested in biological assays. The results of the assays are presented in Table 2 which is entitled Results of Biological Assays. The results are presented as an average of values obtained.

Assay 1

Inhibition of auto-phosphorylation of recombinant human NF-kappaB-inducing kinase (NIK/MAP3K14) activity (AlphaScreen®)

NIK/MAP3K14 auto-phosphorylation activity was measured using the AlphaScreen® (αscreen) format (Perkin Elmer). All compounds tested were dissolved in dimethyl sulfoxide (DMSO) and further dilutions were made in assay buffer. The final DMSO concentration was 0.7% (v/v) in assays. The assay buffer was 50 mM Tris pH 7.5 containing 1 mM EGTA (ethylene glycol tetraacetic acid), 1 mM DTT (dithiothreitol), 0.1 mM $Na_3VO_4$, 5 mM $MgCl_2$, and 0.01% Tween® 20. The assays were carried out in 384 well Proxiplates (Perkin Elmer). The incubations consisted of the compound, 5 μM Adenosine-5'-triphosphate (ATP), and 1 nM NIK/MAP3K14. Incubations were initiated by the addition of GST-tagged NIK/MAP3K14 enzyme, carried out for 2 h at 25° C. and terminated by addition of stop buffer containing anti-phospho-IKK Ser176/180 antibody. Protein A Acceptor and Glutathione-Donor beads were added before reading using an EnVision® Multilabel Plate Reader (Perkin Elmer). The signal obtained in the wells was normalized using high (full enzyme activity, 0.7% DMSO) and low controls (no enzyme activity, 0.7% DMSO, no ATP). $IC_{50}$'s were determined by fitting a sigmoidal curve to % inhibition of control versus $Log_{10}$ compound concentration.

Assay 2

Effect of Compounds on p-IKKα Levels in L363 (NIK Translocated Multiple Myeloma) Cells All compounds tested were dissolved and serially diluted in DMSO, 1:3 dilution for 11 points in an Echo compatible plate. 100% DMSO was added to columns 12 and 24 of the plate to serve as high and low signal controls. This compound plate was used to spot 20 nL of compound or DMSO into a Greiner 384 well TC plate (781080). The final DMSO concentration was 0.3% (v/v) in cell assays. Human L363 cells (ATCC) were cultured in RPMI1640 medium supplemented with GlutaMax, non-essential amino acids, sodium pyruvate and 10% fetal bovine serum. Cells were routinely maintained at densities of $0.2 \times 10^6$ cells per ml-$2 \times 10^6$ cells per mL at 37° C. in a humidified 5% $CO_2$ atmosphere incubator. Cells were passaged twice a week splitting back to obtain the low density. The day before the assay, cells were washed twice in HBSS (Hank's Balanced Salt Solution), resuspended in Dulbecco's Modified Eagle Medium (DMEM)+0.5% IgG and protease free BSA (Jackson Immuno Research Laboratories), +/−250 ng/ml recombinant human B-cell activating factor (BAFF/BLyS/TNFSF13B) and incubated overnight at 37° C. in a humidified 5% $CO_2$ atmosphere (bulk stimulation with or without BAFF). The next day, the cell concentration was adjusted to $1 \times 10^7$ cells/ml in DMEM+/−250 ng/ml BAFF+/−10 μM MG132 and plated at 10 μl/well into compound or DMSO spotted 384 well TC plates. Seeded cells were incubated at 37° C. in a humidified 5% $CO_2$ atmosphere for 6 h. After 6 h, the plates were removed from the incubator and cell lysis was achieved by the addition of 2.5 μl 5× lysis buffer containing protease and phosphatase inhibitors, followed by shaking on a plate shaker at room temperature for 15 min. At the end of this incubation, lysed cells were sequentially treated and incubated with acceptor and donor bead mixes according to the manufacturer's protocol for a 1 plate/2-incubation suspension cell assay (AlphaLISA SureFire Ultra p-IKKα (Ser 176/180) Assay Kit (Perkin Elmer). Plates were read using an EnVision® Multilabel Plate Reader (Perkin Elmer). Within an experiment, a concentration response curve for each compound was run in duplicate. The signal obtained in the test wells was normalized using high signal (BAFF stimulated cells, DMSO, MG132) and low signal (unstimulated cells, DMSO) controls. To determine the $IC_{50}$, a sigmoidal curve was fitted to the plot of % inhibition versus $Log_{10}$ compound concentration.

Table 2 below provides $IC_{50}$ data for certain compounds of the invention on NIK inhibition.

TABLE 2

Results of Biological Assays

| Example | Assay 1 $IC_{50}$ (nM) | Assay 2 $IC_{50}$ (nM) |
|---|---|---|
| 1 | ≤0.5 | 3.7 |
| 2 | 160 | >5000 |
| 3 | 0.7 | 28 |
| 4 | 0.8 | 5.4 |
| 5 | 230 | 1560 |
| 6 | 0.6 | 12 |
| 7 | 170 | 2300 |
| 8 | ≤0.5 | 3.3 |
| 9 | 72 | 670 |
| 10 | ≤0.5 | 8.1 |
| 11 | 83 | 2060 |
| 12 | ≤0.5 | 3 |
| 13 | ≤0.5 | 2.8 |
| 14 | ≤0.5 | 18 |
| 15 | 0.9 | 50 |
| 16 | 0.7 | 57 |
| 17 | ≤0.5 | 5.9 |
| 18 | 0.9 | 61 |
| 19 | ≤0.5 | 9.9 |
| 20 | 1.2 | 55 |
| 21 | 22 | 590 |
| 22 | 4.3 | 480 |
| 23 | 10 | 260 |
| 24 | 260 | 4030 |
| 25 | 2.1 | 180 |
| 26 | 1.2 | 58 |
| 27 | 7.8 | 240 |
| 28 | ≤0.5 | 0.7 |
| 29 | 4.1 | 45 |
| 30 | 60 | 1190 |
| 31 | 23 | 550 |
| 32 | ≤0.5 | 12 |
| 33 | 4.5 | 620 |
| 34 | ≤0.5 | 52 |
| 35 | 15 | 700 |
| 36 | 1.9 | 200 |
| 37 | 0.6 | 35 |
| 38 | 0.7 | 40 |
| 39 | ≤0.5 | 9 |
| 40 | 0.7 | 210 |
| 41 | 68 | >5000 |
| 42 | 1.3 | 29 |
| 43 | 0.9 | 60 |
| 44 | 43 | nt |
| 45 | ≤0.5 | 17 |
| 46 | 2030 | nt |
| 47 | 42 | 1600 |
| 48 | ≤0.5 | 16 |
| 49 | 2.5 | 130 |
| 50 | ≤0.5 | 17 |
| 51 | 1.0 | 480 |
| 52 | 2.5 | 110 |
| 53 | 2.0 | 49 |
| 54 | 10 | 280 |
| 55 | ≤0.5 | 29 |
| 56 | 2.0 | 36 |
| 57 | 1.3 | 35 |
| 58 | 0.7 | 15 |
| 59 | 740 | >5000 |
| 60 | 0.8 | 27 |
| 61 | 4.0 | 170 |
| 62 | ≤0.5 | 22 |
| 63 | 1.4 | 140 |
| 64 | 31 | 730 |
| 65 | 1.0 | 48 |
| 66 | ≤0.5 | 4.5 |

TABLE 2-continued

Results of Biological Assays

| Example | Assay 1 IC$_{50}$ (nM) | Assay 2 IC$_{50}$ (nM) |
|---|---|---|
| 67 | 11 | 350 |
| 68 | 55 | >5000 |
| 69 | 1.0 | 150 |
| 70 | 26 | 2210 |
| 71 | 4220 | >5000 |
| 72 | 8.0 | 910 |
| 73 | 1730 | >5000 |
| 74 | 56 | 2950 |
| 75 | 1.3 | 84 |
| 76 | 2.3 | 66 |
| 77 | >5000 | >5000 |
| 78 | 840 | >5000 |
| 79 | 590 | >5000 |
| 80 | 28 | 4000 |
| 81 | 11 | 1980 |
| 82 | 31 | 2000 |
| 83 | ≤0.5 | 3.2 |
| 84 | ≤0.5 | 5.5 |
| 85 | 0.7 | 6.1 |
| 86 | ≤0.5 | 7.7 |
| 87 | ≤0.5 | 6 |
| 88 | 4.7 | 400 |
| 89 | 2.3 | 590 |
| 90 | ≤0.5 | 70 |
| 91 | ≤0.5 | 17 |
| 92 | 6.6 | 480 |
| 93 | ≤0.5 | 6.5 |
| 94 | ≤0.5 | 4.2 |
| 95 | 0.8 | 28 |
| 96 | 29 | >5000 |
| 97 | 0.8 | 46 |
| 98 | 1.5 | 38 |
| 99 | ≤0.5 | 12 |
| 100 | ≤0.5 | 6.1 |
| 101 | 1.2 | 26 |
| 102 | ≤0.5 | 11 |
| 103 | ≤0.5 | 5.8 |
| 104 | 1.3 | 280 |
| 105 | 0.6 | 64 |
| 106 | 14 | 1450 |
| 107 | 52 | >5000 |
| 108 | 7.6 | >5000 |
| 109 | 13 | >5000 |
| 110 | ≤0.5 | 11 |
| 111 | 1.2 | 160 |
| 112 | ≤0.5 | 4.8 |
| 113 | ≤0.5 | 92 |
| 114 | ≤0.5 | 120 |
| 115 | ≤0.5 | 42 |
| 116 | 0.9 | 47 |
| 117 | ≤0.5 | 33 |
| 118 | ≤0.5 | 1.5 |
| 119 | 0.7 | 43 |
| 120 | ≤0.5 | 21 |
| 121 | 0.7 | 42 |
| 122 | ≤0.5 | 2.3 |
| 123 | ≤0.5 | 4 |
| 124 | ≤0.5 | 7.7 |
| 125 | ≤0.5 | 18 |
| 126 | 0.9 | 820 |
| 127 | ≤0.5 | 12 |
| 128 | 0.6 | 28 |
| 129 | ≤0.5 | 12 |
| 130 | 0.7 | 58 |
| 131 | ≤0.5 | 47 |
| 132 | 46 | 730 |
| 133 | 6.8 | 400 |
| 134 | ≤0.5 | 150 |
| 135 | 5.7 | 140 |
| 136 | 0.7 | 60 |
| 137 | ≤0.5 | 9.3 |
| 138 | ≤0.5 | 9.6 |
| 139 | 2.9 | 22 |
| 140 | ≤0.5 | 6.2 |
| 141 | 16 | 2450 |
| 142 | 350 | >5000 |
| 143 | 420 | >5000 |
| 144 | 2290 | >5000 |
| 145 | 3.6 | 280 |
| 146 | ≤0.5 | 2.7 |
| 147 | ≤0.5 | 14 |
| 148 | 1.4 | 370 |
| 149 | ≤0.5 | 17 |
| 150 | 4.7 | 320 |
| 151 | 0.7 | 28 |
| 152 | 3.8 | 200 |
| 153 | 0.8 | 47 |
| 154 | 620 | >5000 |
| 155 | ≤0.5 | 6.1 |
| 156 | 1.1 | 16 |
| 157 | 3790 | >5000 |
| 158 | 1930 | >5000 |
| 159 | 1.3 | 130 |
| 160 | 2.4 | 19 |
| 161 | 7.0 | 78 |
| 162 | >5000 | >5000 |
| 163 | 350 | >5000 |
| 164 | 0.7 | 78 |
| 165 | 120 | >5000 |
| 166 | 4700 | >5000 |
| 167 | 12 | 3470 |
| 168 | 2.2 | 4.2 |
| 169 | 1210 | >5000 |
| 170 | 0.8 | 22 |
| 171 | 4.0 | 180 |
| 172 | 20 | 400 |
| 173 | 12 | 180 |
| 174 | 830 | >5000 |
| 175 | 2.4 | 230 |
| 176 | 1.4 | 81 |
| 177 | 5.1 | 66 |
| 178 | 18 | 820 |
| 179 | 1170 | >5000 |
| 180 | 410 | >5000 |
| 181 | >5000 | >5000 |
| 182 | 1.2 | 74 |
| 183 | ≤0.5 | 6.6 |
| 184 | ≤0.5 | 9.9 |
| 185 | 11 | 1520 |
| 186 | 710 | >5000 |
| 187 | 3.8 | 190 |
| 188 | 1.0 | 23 |
| 189 | 1.8 | 71 |
| 190 | 1830 | >5000 |
| 191 | 15 | 2980 |
| 192 | 1110 | >5000 |
| 193 | 2370 | >5000 |
| 194 | 1.0 | 8.3 |
| 195 | 21 | 1130 |
| 196 | 4.4 | 250 |
| 197 | 6.3 | 380 |
| 198 | 1310 | >5000 |
| 199 | 1590 | >5000 |
| 200 | 29 | 3190 |
| 201 | 4030 | >5000 |
| 202 | 1.0 | 280 |
| 203 | 1.2 | 100 |
| 204 | 21 | 1060 |
| 205 | 4880 | >5000 |
| 206 | 3.5 | 160 |
| 207 | 180 | >5000 |
| 208 | ≤0.5 | 12 |
| 209 | 110 | >5000 |
| 210 | 0.8 | 45 |
| 211 | 2.2 | >5000 |
| 212 | 0.7 | 59 |
| 213 | 18 | 1080 |
| 214 | 320 | >5000 |
| 215 | 16 | 900 |
| 216 | ≤0.5 | 8.5 |
| 217 | 0.9 | 77 |
| 218 | 78 | >5000 |

TABLE 2-continued
Results of Biological Assays
| Example | Assay 1 IC$_{50}$ (nM) | Assay 2 IC$_{50}$ (nM) |
|---|---|---|
| 219 | 240 | >5000 |
| 220 | 1.3 | 65 |
| 221 | 630 | >5000 |
| 222 | 4.2 | 390 |
| 223 | 190 | >5000 |
| 224 | 250 | >5000 |
| 225 | 6.1 | 600 |
| 226 | 42 | 1400 |
| 227 | 23 | 540 |
| 228 | 4.8 | 300 |
| 229 | 110 | 1910 |
| 230 | 15 | 350 |
| 231 | 340 | >5000 |
| 232 | 5.7 | 210 |
| 233 | 520 | >5000 |
| 234 | 1800 | >5000 |
| 235 | 2950 | >5000 |
| 236 | 57 | 1370 |
| 237 | 9.2 | 240 |
| 238 | 34 | 73 |
| 239 | 1.5 | 69 |
| 240 | 21 | 570 |
| 241 | 56 | 930 |
| 242 | 7.4 | 320 |
| 243 | 14 | 670 |
| 244 | 4.9 | 240 |
| 245 | 40 | 1190 |
| 246 | 23 | 3790 |
| 247 | 850 | >5000 |
| 248 | 3340 | >5000 |
| 249 | 7.3 | 470 |
| 250 | 7.9 | 130 |
| 251 | 86 | 560 |
| 252 | 31 | >2000 |
| 253 | 0.4 | 5.1 |
| 254 | 230 | 1330 |
| 255 | 0.7 | 15 |
| 256 | 350 | 4150 |
| 257 | 44 | 2460 |
| 258 | 210 | 450 |
| 259 | 39 | 65 |
| 260 | 110 | 2740 |
| 261 | 0.7 | 7.7 |
| 262 | 7.9 | 220 |
| 263 | 600 | 4350 |
| 264 | 74 | 660 |
| 265 | 1.9 | 28 |
| 266 | 680 | 3700 |
| 267 | 385 | 2825 |
| 268 | 65 | 585 |
| 269 | 990 | 3850 |
| 270 | 26 | 1000 |
| 271 | 4.2 | 44 |
| 272 | 59 | 1960 |
| 273 | 2.7 | 27 |
| 274 | 1930 | >5000 |
| 275 | 300 | >5000 |
| 276 | ≤0.5 | 8.9 |
| 277 | 0.7 | 13 |
| 278 | 170 | >5000 |
| 279 | 1510 | >5000 |
| 280 | 45 | 720 |
| 281 | 0.9 | 7.7 |
| 282 | 5.6 | 205 |
| 283 | 0.6 | 1.4 |
| 284 | 0.7 | 2.8 |
| 285 | 1.7 | 12 |
| 286 | 0.9 | 3.1 |
| 287 | 44 | >5000 |
| 288 | 0.9 | 16 |
| 289 | 1.4 | nt |
| 290 | nt | nt |
| 291 | 54 | 1390 |
| 292 | 22 | 660 |
| 293 | >5000 | >5000 |
| 294 | 390 | 2460 |
| 295 | 3.1 | 18 |
| 296 | ≤0.5 | 6.9 |
| 297 | 1.9 | 31 |
| 298 | 0.8 | 24 |
| 299 | 1.7 | 12 |
| 300 | 1.2 | 39 |
| 301 | 4.5 | 48 |
| 302 | ≤0.5 | 4.5 |
| 303 | 0.9 | 11 |
| 304 | 0.6 | 15 |
| 305 | 2.2 | 64 |
| 306 | 1.9 | 26 |
| 307 | 1.6 | 40 |
| 308 | 6.8 | 190 |
| 309 | ≤0.5 | 9.7 |
| 310 | 0.7 | 13 |
| 311 | ≤0.5 | 3.6 |
| 312 | 0.8 | 11 |
| 313 | 3.1 | 231 |
| 314 | 2.9 | 14 |
| 315 | 5.0 | nt |
| 316 | 0.9 | 9.5 |
| 317 | 0.6 | nt |
| 318 | 1.0 | nt |
| 319 | 1.5 | nt |
nt indicates that the compound was not tested in that assay.
What is claimed:
1. A compound selected from the group consisting of:
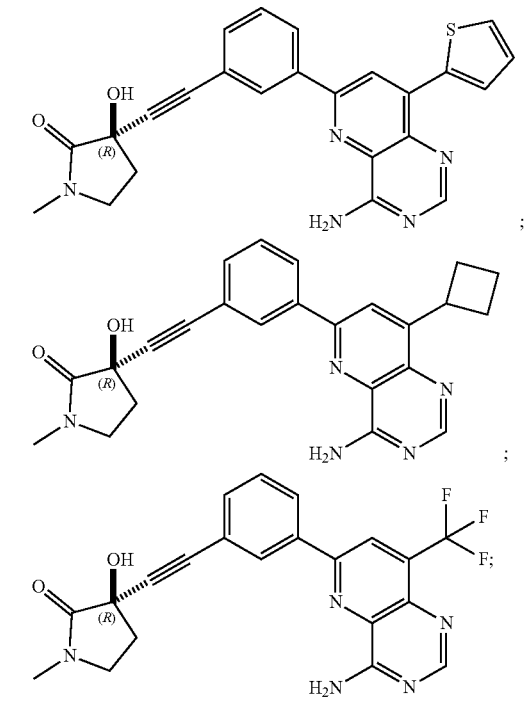

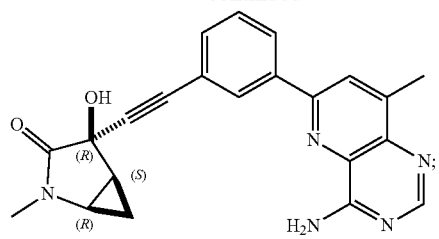
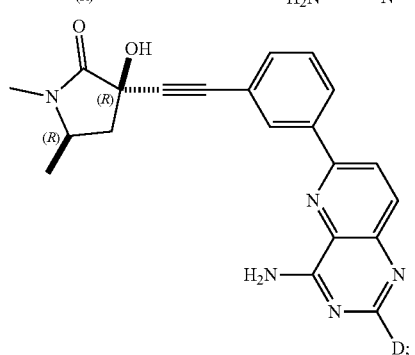
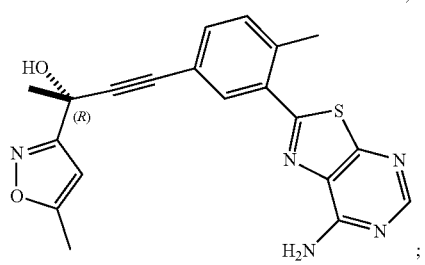
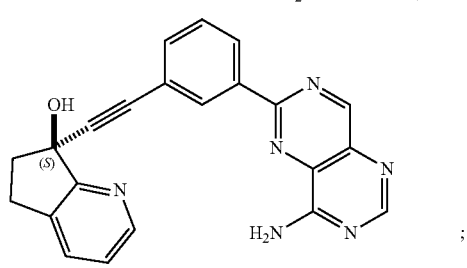
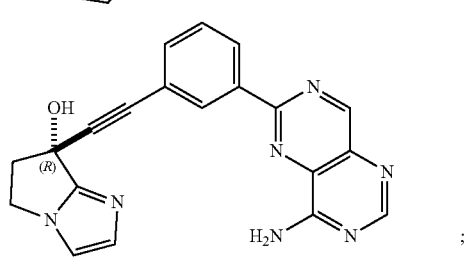
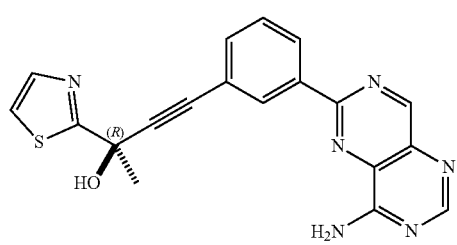
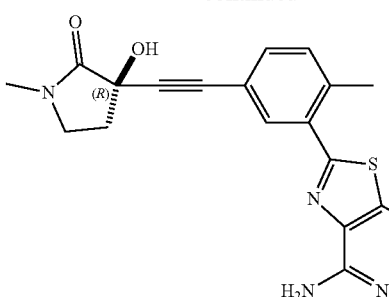
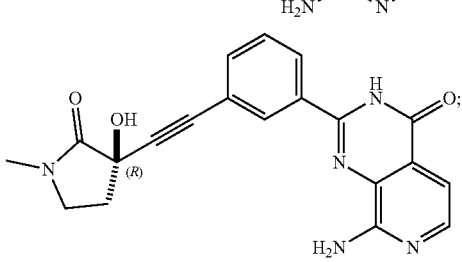
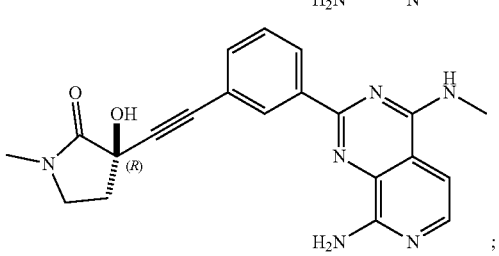
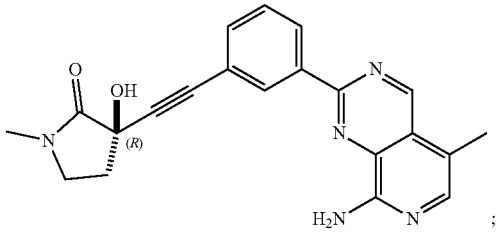
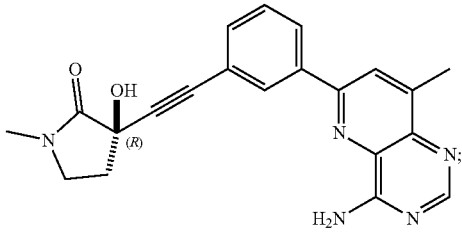
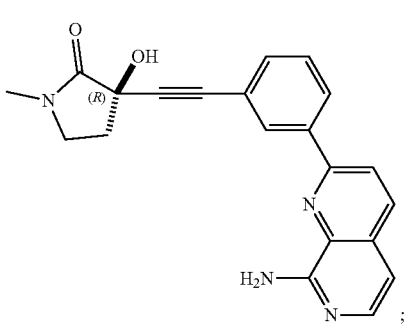

-continued

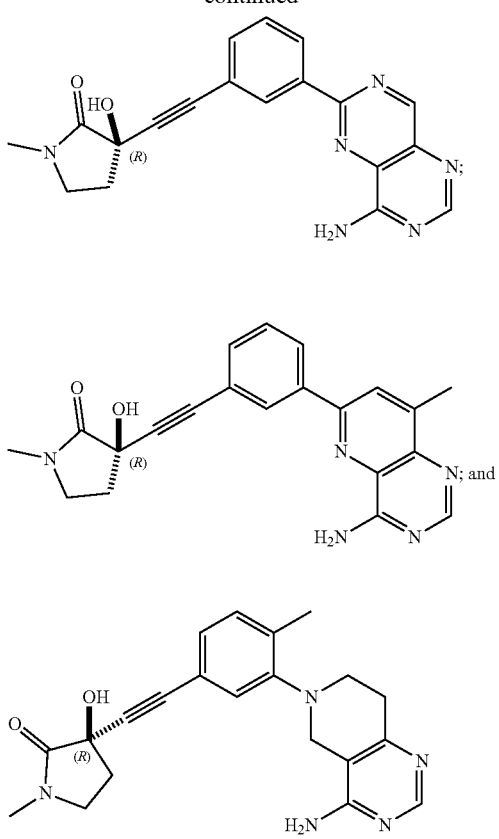

or a pharmaceutically acceptable salt thereof.

2. The compound of claim 1, having the following structure

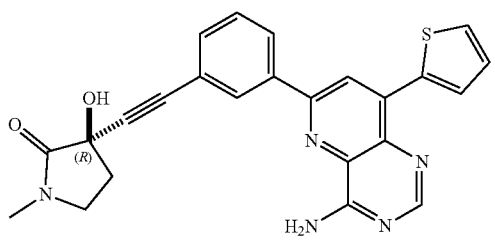

or a pharmaceutically acceptable salt thereof.

3. The compound of claim 1, having the following structure

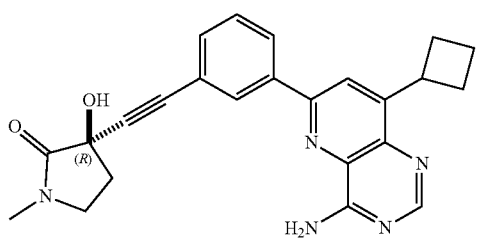

or a pharmaceutically acceptable salt thereof.

4. The compound of claim 1, having the following structure

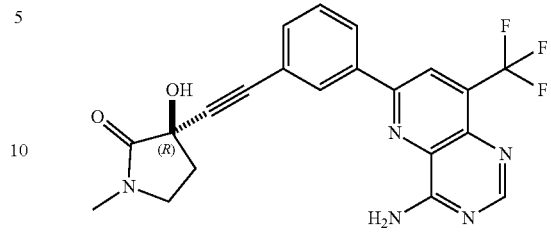

or a pharmaceutically acceptable salt thereof.

5. The compound of claim 1, having the following structure

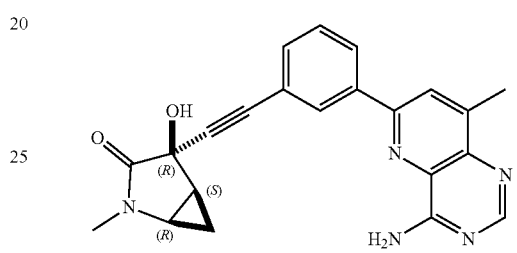

or a pharmaceutically acceptable salt thereof.

6. The compound of claim 1, having the following structure

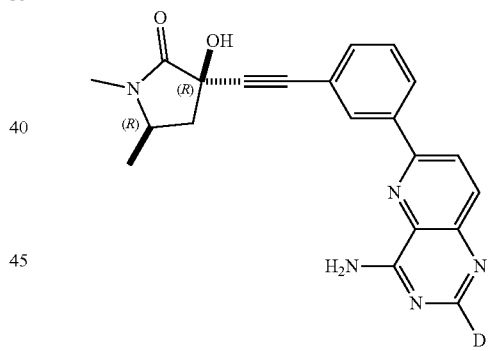

or a pharmaceutically acceptable salt thereof.

7. The compound of claim 1, having the following structure

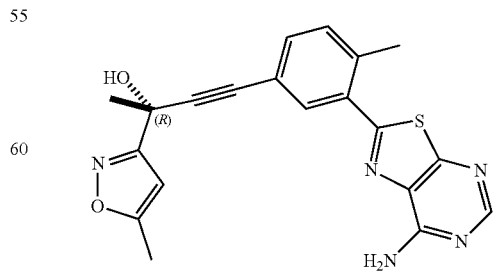

or a pharmaceutically acceptable salt thereof.

8. The compound of claim 1, having the following structure

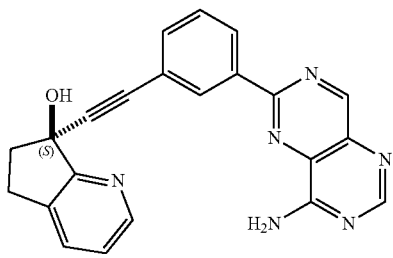

or a pharmaceutically acceptable salt thereof.

9. The compound of claim 1, having the following structure

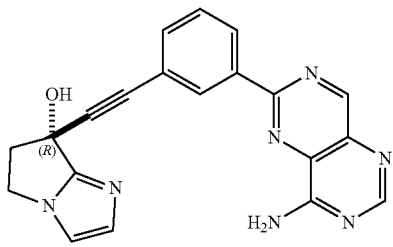

or a pharmaceutically acceptable salt thereof.

10. The compound of claim 1, having the following structure

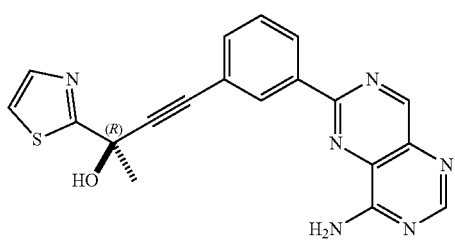

or a pharmaceutically acceptable salt thereof.

11. The compound of claim 1, having the following structure

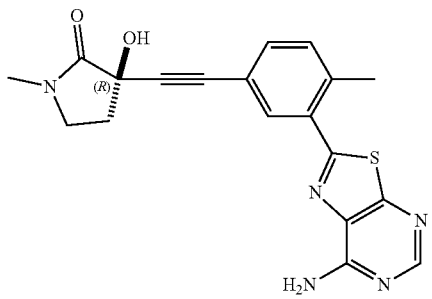

or a pharmaceutically acceptable salt thereof.

12. The compound of claim 1, having the following structure

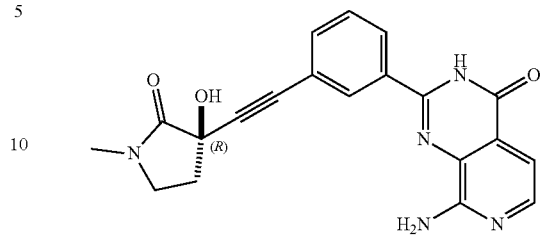

or a pharmaceutically acceptable salt thereof.

13. The compound of claim 1, having the following structure

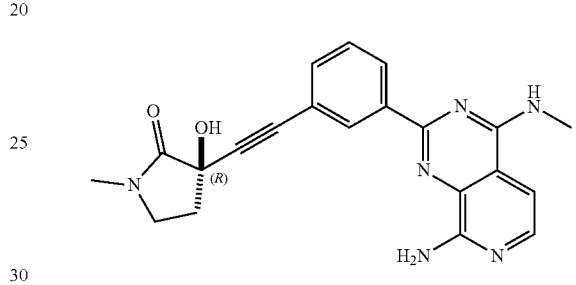

or a pharmaceutically acceptable salt thereof.

14. The compound of claim 1, having the following structure

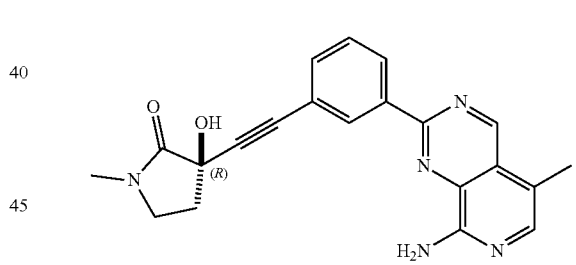

or a pharmaceutically acceptable salt thereof.

15. The compound of claim 1, having the following structure

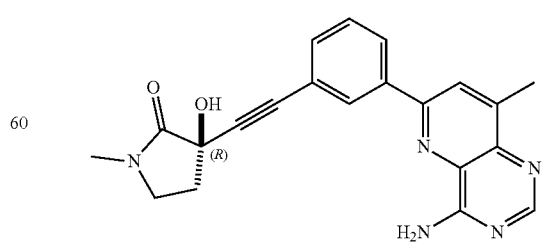

or a pharmaceutically acceptable salt thereof.

16. The compound of claim 1, having the following structure

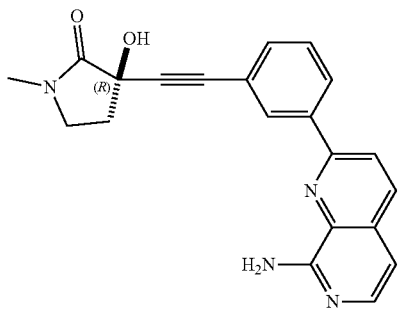

or a pharmaceutically acceptable salt thereof.

17. The compound of claim 1, having the following structure

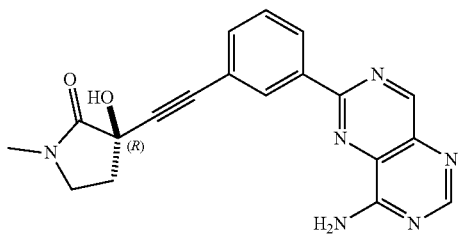

or a pharmaceutically acceptable salt thereof.

18. The compound of claim 1, having the following structure

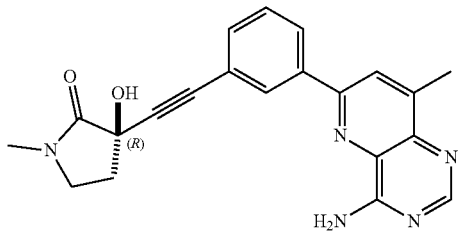

or a pharmaceutically acceptable salt thereof.

19. The compound of claim 1, having the following structure

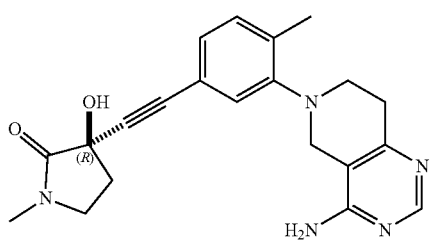

or a pharmaceutically acceptable salt thereof.

20. A pharmaceutical composition comprising a therapeutically effective amount of at least one compound or pharmaceutically acceptable salt thereof as claimed in claim 1.

21. The compound of claim 1, having the following structure

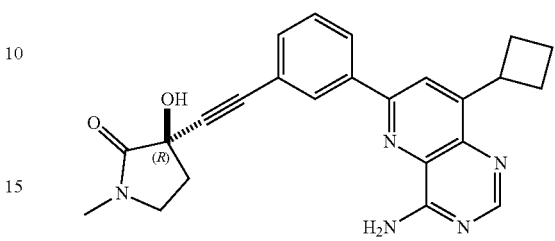

22. The compound of claim 1, having the following structure

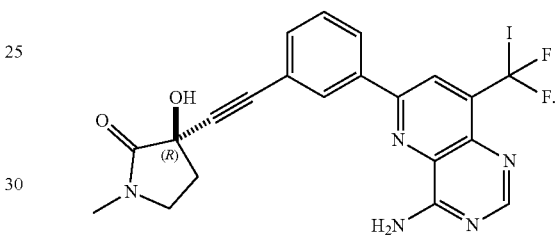

23. The compound of claim 1, having the following structure

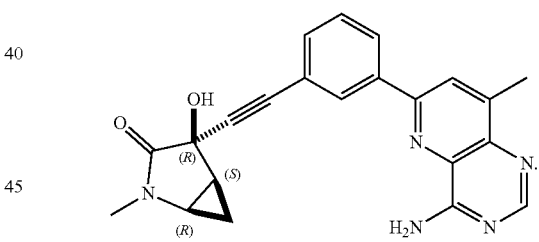

24. The compound of claim 1, having the following structure

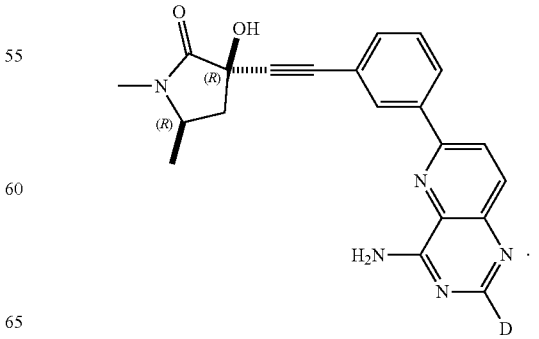

25. The compound of claim 1, having the following structure

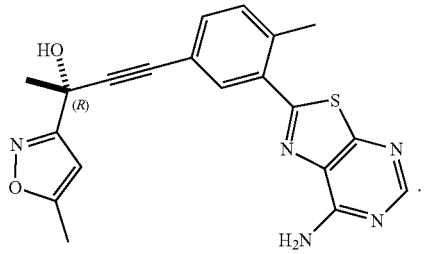

26. The compound of claim 1, having the following structure

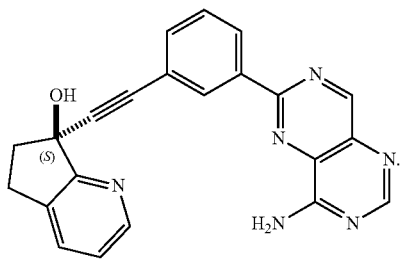

27. The compound of claim 1, having the following structure

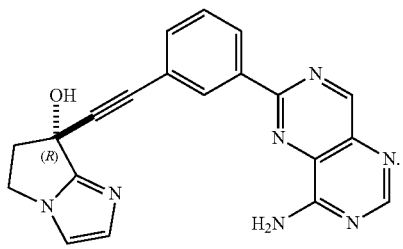

28. The compound of claim 1, having the following structure

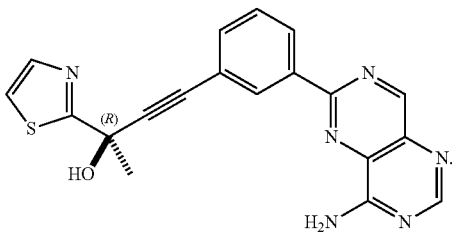

29. The compound of claim 1, having the following structure

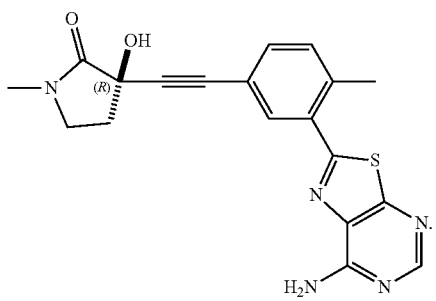

30. The compound of claim 1, having the following structure

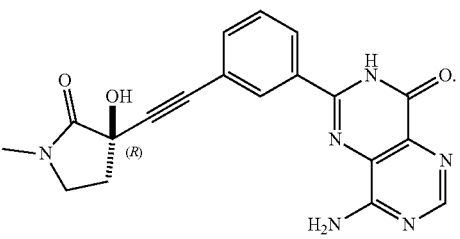

31. The compound of claim 1, having the following structure

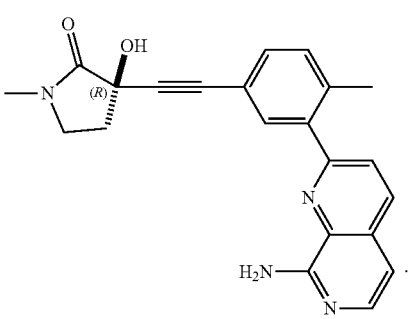

* * * * *